US012753408B2

(12) United States Patent
Aznarez et al.

(10) Patent No.: US 12,753,408 B2
(45) **Date of Patent: *Oct. 6, 2026**

(54) OPA1 ANTISENSE OLIGOMERS FOR TREATMENT OF CONDITIONS AND DISEASES

(71) Applicant: Stoke Therapeutics, Inc., Bedford, MA (US)

(72) Inventors: Isabel Aznarez, Boston, MA (US); Aditya Venkatesh, Natick, MA (US); Gene Liau, Wayland, MA (US)

(73) Assignee: STOKE THERAPEUTICS, INC., Bedford, MA (US)

( * ) Notice: Subject to any disclaimer, the term of this patent is extended or adjusted under 35 U.S.C. 154(b) by 58 days.

This patent is subject to a terminal disclaimer.

(21) Appl. No.: 18/483,333

(22) Filed: Oct. 9, 2023

(65) Prior Publication Data

US 2024/0102011 A1 Mar. 28, 2024

Related U.S. Application Data

(63) Continuation of application No. 18/304,878, filed on Apr. 21, 2023, now Pat. No. 11,814,622, which is a continuation of application No. 17/924,966, filed as application No. PCT/US2021/030254 on Apr. 30, 2021, now Pat. No. 12,338,437.

(60) Provisional application No. 63/023,013, filed on May 11, 2020, provisional application No. 63/112,458, filed on Nov. 11, 2020.

(51) Int. Cl.

*C12N 15/113* (2010.01)
*A61K 9/00* (2006.01)
*A61P 27/02* (2006.01)
*C12N 15/86* (2006.01)

(52) U.S. Cl.

CPC .......... *C12N 15/113* (2013.01); *A61K 9/0048* (2013.01); *A61P 27/02* (2018.01); *C12N 15/86* (2013.01); *C12N 2310/11* (2013.01); *C12N 2310/20* (2017.05); *C12N 2310/314* (2013.01); *C12N 2310/315* (2013.01); *C12N 2310/321* (2013.01); *C12N 2750/14143* (2013.01)

(58) Field of Classification Search

None

See application file for complete search history.

(56) References Cited

U.S. PATENT DOCUMENTS 4,476,116 A 10/1984 Anik
4,522,811 A 6/1985 Eppstein et al.
4,866,042 A 9/1989 Neuwelt
5,034,506 A 7/1991 Summerton et al.
5,142,047 A 8/1992 Summerton et al.
5,151,510 A 9/1992 Stec et al.
5,166,315 A 11/1992 Summerton et al.
5,185,444 A 2/1993 Summerton et al.
5,217,866 A 6/1993 Summerton et al.
5,506,337 A 4/1996 Summerton et al.
5,521,063 A 5/1996 Summerton et al.
5,656,612 A 8/1997 Monia
5,665,593 A 9/1997 Kole et al.
5,698,685 A 12/1997 Summerton et al.
5,914,396 A 6/1999 Cook et al.
5,916,808 A 6/1999 Kole et al.
5,976,879 A 11/1999 Kole et al.
6,083,482 A 7/2000 Wang
6,147,200 A 11/2000 Manoharan et al.
6,166,197 A 12/2000 Cook et al.
6,210,892 B1 4/2001 Bennett et al.
6,294,520 B1 9/2001 Naito
6,383,752 B1 5/2002 Agrawal et al.
6,391,452 B1 5/2002 Antonsen et al.
6,436,657 B1 8/2002 Famodu et al.
6,451,991 B1 9/2002 Martin et al.
6,485,960 B1 11/2002 Harris et al.
6,531,591 B1 3/2003 Fensholdt
6,573,073 B2 6/2003 Harris
6,605,611 B2 8/2003 Simmonds et al.
6,632,427 B1 10/2003 Finiels et al.
6,639,059 B1 10/2003 Kochkine et al.
6,670,461 B1 12/2003 Wengel et al.
(Continued)

FOREIGN PATENT DOCUMENTS

AU 2018355237 A1 5/2020
AU 2018322319 B2 8/2021
(Continued)

OTHER PUBLICATIONS

OPA1 genereviews—A comprehensive review of the OPA1 gene and its association with human diseases, pages Science of Bio Genetics, retrieved on-line Apr. 2, 2025 Genetics https://genethics.ca, pp. 1-47 (Year: 2023).*
Gagliardi et al. Biomedicines 9, 433. pp. 1-18 (Year: 2021).*
Ferenchak et al. Seminars in ophthalomogy 36:5-6, 452-457 (Year: 2021).*
Doench et al. Nat Biotechnol. 34:184-191 (Year: 2016).*
Sciezynska et al. Plos One, 12:e0183866, pp. 1-9 (Year: 2017).*
Aartsma-Rus et al.: Antisense-mediated exon skipping: a versatile tool with therapeutic and research applications. RNA 13(10):1609-24 (2007). Epub Aug. 7, 2007.
Aceti et al.: Syngap1 haploinsufficiency damages a postnatal critical period of pyramidal cell structural maturation linked to cortical circuit assembly, Biol Psychiatry 77(9):805-815 (2015).
(Continued)

*Primary Examiner* — Brian Whiteman
(74) *Attorney, Agent, or Firm* — Wilson Sonsini Goodrich & Rosati

(57) ABSTRACT

Alternative splicing events in genes can lead to non-productive mRNA transcripts which in turn can lead to aberrant protein expression, and therapeutic agents which can target the alternative splicing events in genes can modulate the expression level of functional proteins in patients and/or inhibit aberrant protein expression. Such therapeutic agents can be used to treat a condition or disease caused by protein deficiency and/or mitochondrial function deficit.

58 Claims, 67 Drawing Sheets

Specification includes a Sequence Listing.

(56) References Cited

U.S. PATENT DOCUMENTS 6,677,445 B1 1/2004 Innis et al.
6,734,291 B2 5/2004 Kochkine et al.
6,756,523 B1 6/2004 Kahn et al.
6,770,748 B2 8/2004 Imanishi et al.
6,794,499 B2 9/2004 Wengel et al.
6,846,921 B2 1/2005 Innis et al.
6,936,589 B2 8/2005 Naito
6,963,589 B1 11/2005 Sugata et al.
6,998,484 B2 2/2006 Koch et al.
7,015,315 B1 3/2006 Cook et al.
7,034,133 B2 4/2006 Wengel et al.
7,053,199 B2 5/2006 Imanishi et al.
7,053,207 B2 5/2006 Wengel
7,060,809 B2 6/2006 Wengel et al.
7,071,324 B2 7/2006 Preparata et al.
7,084,125 B2 8/2006 Wengel
7,101,993 B1 9/2006 Cook et al.
7,169,594 B2 1/2007 Guan
7,214,783 B2 5/2007 Jeon et al.
7,217,805 B2 5/2007 Imanishi et al.
7,314,923 B2 1/2008 Kaneko et al.
7,335,765 B2 2/2008 Kaneko et al.
7,368,549 B2 5/2008 Dempcy et al.
7,399,845 B2 7/2008 Seth et al.
7,432,249 B2 10/2008 Crooke
7,432,250 B2 10/2008 Crooke
7,547,684 B2 6/2009 Seth et al.
7,553,644 B2 6/2009 Germino et al.
7,569,575 B2 8/2009 Soerensen et al.
7,569,686 B1 8/2009 Bhat et al.
7,572,582 B2 8/2009 Wengel et al.
7,595,304 B2 9/2009 Zhao et al.
7,615,619 B2 11/2009 Imanishi et al.
7,662,946 B2 2/2010 Ginsburg et al.
7,662,948 B2 2/2010 Kurreck et al.
7,666,854 B2 2/2010 Seth et al.
7,687,617 B2 3/2010 Thrue et al.
7,696,345 B2 4/2010 Allerson et al.
7,741,457 B2 6/2010 Seth et al.
7,750,131 B2 7/2010 Seth et al.
7,816,333 B2 10/2010 Kaneko et al.
7,846,686 B2 12/2010 Kramer
7,951,934 B2 5/2011 Freier
7,994,145 B2 8/2011 Imanishi et al.
8,022,193 B2 9/2011 Seth et al.
8,030,467 B2 10/2011 Seth et al.
8,048,998 B2 11/2011 Rasmussen et al.
8,067,569 B2 11/2011 Iversen et al.
8,084,458 B2 12/2011 Soerensen et al.
8,088,746 B2 1/2012 Seth et al.
8,090,542 B2 1/2012 Khvorova et al.
8,110,674 B2 2/2012 Manoharan et al.
8,124,745 B2 2/2012 Allerson et al.
8,129,515 B2 3/2012 Esau et al.
8,168,605 B2 5/2012 Zhao et al.
8,258,109 B2 9/2012 Bennett et al.
8,268,980 B2 9/2012 Seth et al.
8,278,036 B2 10/2012 Kariko et al.
8,278,283 B2 10/2012 Seth et al.
8,278,425 B2 10/2012 Prakash et al.
8,278,426 B2 10/2012 Seth et al.
8,293,684 B2 10/2012 Mouritzen et al.
8,361,979 B2 1/2013 Aartsma-Rus et al.
8,383,792 B2 2/2013 Okamoto et al.
8,394,947 B2 3/2013 Bhat et al.
8,415,465 B2 4/2013 Freier
8,436,163 B2 5/2013 Iversen et al.
8,450,467 B2 5/2013 Manoharan et al.
8,461,124 B2 6/2013 Chattopadhyaya
8,492,390 B2 7/2013 Detlef et al.
8,501,703 B2 8/2013 Bennett et al.
8,501,805 B2 8/2013 Seth et al.
8,518,908 B2 8/2013 Hrdlicka et al.
8,530,640 B2 9/2013 Seth et al.
8,541,562 B2 9/2013 Obika et al.
8,546,556 B2 10/2013 Seth et al.
8,592,156 B2 11/2013 Liu et al.
8,637,478 B2 1/2014 Bennett
RE44,779 E 2/2014 Imanishi et al.
8,653,252 B2 2/2014 Elmen et al.
8,673,560 B2 3/2014 Leamon et al.
8,680,254 B2 3/2014 Lutz et al.
8,691,783 B2 4/2014 Thum et al.
8,703,728 B2 4/2014 Swayze et al.
8,710,021 B2 4/2014 Anro et al.
8,735,366 B2 5/2014 Bauer et al.
8,748,089 B2 6/2014 Kariko et al.
8,779,118 B2 7/2014 Allerson et al.
8,796,437 B2 8/2014 Swayze et al.
8,809,516 B2 8/2014 Manoharan et al.
8,846,386 B2 9/2014 Ambati et al.
8,846,637 B2 9/2014 Seth et al.
8,846,639 B2 9/2014 Swayze et al.
8,846,885 B2 9/2014 Hirai et al.
8,895,722 B2 11/2014 Iversen et al.
8,957,040 B2 2/2015 Bennett et al.
8,957,200 B2 2/2015 Seth et al.
8,957,201 B2 2/2015 Kaneko et al.
9,005,906 B2 4/2015 Swayze et al.
9,006,194 B2 4/2015 Katsikis et al.
9,006,415 B2 4/2015 Ren et al.
9,012,139 B2 4/2015 Collard et al.
9,029,335 B2 5/2015 Prakash et al.
9,045,518 B2 6/2015 Christensen et al.
9,045,754 B2 6/2015 Bhanot et al.
9,057,066 B2 6/2015 Hung et al.
9,109,001 B2 8/2015 Parsy et al.
9,127,272 B2 9/2015 Esau et al.
9,127,276 B2 9/2015 Prakash et al.
9,156,873 B2 10/2015 Prakash et al.
9,157,081 B2 10/2015 Bennett et al.
9,181,549 B2 11/2015 Prakash et al.
9,187,515 B2 11/2015 Mayes et al.
9,192,621 B2 11/2015 Mayes et al.
9,193,752 B2 11/2015 Migawa et al.
9,193,969 B2 11/2015 Montefeltro et al.
9,211,300 B2 12/2015 Mayes et al.
9,217,147 B2 12/2015 Singh et al.
9,221,864 B2 12/2015 Seth et al.
9,243,245 B2 1/2016 De Kimpe et al.
9,290,534 B2 3/2016 Seth et al.
9,296,778 B2 3/2016 Parsy et al.
9,309,275 B2 4/2016 Stewart et al.
9,315,535 B2 4/2016 Mitsuoka et al.
9,334,495 B2 5/2016 Khvorova et al.
9,339,541 B2 5/2016 Dousson et al.
9,347,068 B2 5/2016 Dhugga et al.
9,359,445 B2 6/2016 Finkbeiner et al.
9,359,603 B2 6/2016 Lutz et al.
9,359,609 B2 6/2016 Duffield et al.
9,410,155 B2 8/2016 Collard et al.
9,428,534 B2 8/2016 Christensen et al.
9,447,166 B2 9/2016 Ambati et al.
9,453,261 B2 9/2016 Lee et al.
9,464,292 B2 10/2016 Okumura et al.
9,499,818 B2 11/2016 Van Deutekom et al.
9,518,259 B2 12/2016 Rigo et al.
9,534,222 B2 1/2017 Ambati et al.
9,550,988 B2 1/2017 Swayze
9,714,422 B2 7/2017 Vorechovsky et al.
9,745,577 B2 8/2017 Vorechovsky et al.
9,771,579 B2 9/2017 Collard et al.
9,914,922 B2 3/2018 Freier et al.
9,976,143 B2 5/2018 Krainer et al.
10,119,168 B2 11/2018 Vaidya et al.
10,196,405 B2 2/2019 Breslin et al.
10,196,639 B2 2/2019 Vorechovsky et al.
10,517,853 B2 12/2019 Welch et al.
10,538,764 B2 1/2020 Vorechovsky et al.
10,583,128 B2 3/2020 Collard et al.
10,683,503 B2 6/2020 Aznarez et al.
10,696,969 B2 6/2020 Krainer et al.
10,906,931 B2 2/2021 Moghadam
10,913,947 B2 2/2021 Aznarez et al.

(56) References Cited

U.S. PATENT DOCUMENTS

| | | | |
|---|---|---|---|
| 10,941,405 | B2 | 3/2021 | Vorechovsky et al. |
| 11,083,745 | B2 | 8/2021 | Aznarez et al. |
| 11,096,956 | B2 | 8/2021 | Aznarez et al. |
| 11,390,869 | B2 | 7/2022 | Vorechovsky et al. |
| 11,702,660 | B2 | 7/2023 | Vorechovsky et al. |
| 11,814,622 | B2 | 11/2023 | Aznarez et al. |
| 11,873,490 | B2 | 1/2024 | Aznarez et al. |
| 11,891,605 | B2 | 2/2024 | Vorechovsky et al. |
| 12,338,437 | B2 | 6/2025 | Aznarez et al. |
| 2003/0087861 | A1 | 5/2003 | Iversen |
| 2003/0148974 | A1 | 8/2003 | Monia et al. |
| 2004/0063129 | A1 | 4/2004 | Gaarde et al. |
| 2004/0102401 | A1 | 5/2004 | Dean et al. |
| 2004/0219515 | A1 | 11/2004 | Bentwich |
| 2005/0221354 | A1 | 10/2005 | Mounts |
| 2005/0233327 | A1 | 10/2005 | Welch et al. |
| 2005/0244851 | A1 | 11/2005 | Blume et al. |
| 2006/0058253 | A1 | 3/2006 | Chabot et al. |
| 2006/0062790 | A1 | 3/2006 | Reinhard et al. |
| 2006/0134670 | A1 | 6/2006 | Piu |
| 2006/0166922 | A1 | 7/2006 | Eichler et al. |
| 2007/0009899 | A1 | 1/2007 | Mounts |
| 2007/0087376 | A1 | 4/2007 | Potashkin |
| 2007/0249538 | A1 | 10/2007 | Sazani et al. |
| 2008/0152650 | A1 | 6/2008 | Rosenberg et al. |
| 2008/0269123 | A1 | 10/2008 | Li et al. |
| 2009/0186846 | A1 | 7/2009 | Chabot et al. |
| 2009/0186946 | A1 | 7/2009 | Taketomi et al. |
| 2009/0264353 | A1 | 10/2009 | Orum et al. |
| 2009/0270332 | A1 | 10/2009 | Bare et al. |
| 2010/0016215 | A1 | 1/2010 | Moulton et al. |
| 2010/0088778 | A1 | 4/2010 | Mulley et al. |
| 2010/0111935 | A1 | 5/2010 | Bhagat et al. |
| 2010/0150839 | A1 | 6/2010 | Kelleher |
| 2010/0166784 | A1 | 7/2010 | Murphy et al. |
| 2011/0124591 | A1 | 5/2011 | Bennett |
| 2011/0229891 | A1 | 9/2011 | Michaud et al. |
| 2012/0157512 | A1 | 6/2012 | Ben-Chanoch et al. |
| 2012/0190728 | A1 | 7/2012 | Bennett et al. |
| 2012/0252877 | A1 | 10/2012 | Lo |
| 2013/0072671 | A1 | 3/2013 | Van Deutekom |
| 2013/0096183 | A1 | 4/2013 | Collard et al. |
| 2013/0109850 | A1 | 5/2013 | Prakash et al. |
| 2013/0136732 | A1 | 5/2013 | Wagner et al. |
| 2013/0184223 | A1 | 7/2013 | Land et al. |
| 2013/0253036 | A1 | 9/2013 | Collard et al. |
| 2013/0266560 | A1 | 10/2013 | Demopulos et al. |
| 2013/0289092 | A1 | 10/2013 | Rigo et al. |
| 2014/0011761 | A1 | 1/2014 | Hotamisligil et al. |
| 2014/0128449 | A1 | 5/2014 | Liu et al. |
| 2014/0154783 | A1 | 6/2014 | Rossomando et al. |
| 2014/0186839 | A1 | 7/2014 | Margulies et al. |
| 2014/0194610 | A1 | 7/2014 | Verdine et al. |
| 2014/0235605 | A1 | 8/2014 | Shiffman et al. |
| 2014/0309181 | A1 | 10/2014 | Collard et al. |
| 2014/0336238 | A1 | 11/2014 | Collin et al. |
| 2014/0343127 | A1 | 11/2014 | Kammler |
| 2014/0349290 | A1 | 11/2014 | Watnick et al. |
| 2014/0378526 | A1 | 12/2014 | Rossi et al. |
| 2014/0378527 | A1 | 12/2014 | Van Deutekom |
| 2014/0378533 | A1 | 12/2014 | Freier |
| 2015/0004217 | A1 | 1/2015 | Guild et al. |
| 2015/0018540 | A1 | 1/2015 | Prakash et al. |
| 2015/0184153 | A1 | 7/2015 | Freier et al. |
| 2015/0211006 | A1 | 7/2015 | Butler et al. |
| 2015/0211010 | A1 | 7/2015 | Kerem et al. |
| 2015/0232845 | A1 | 8/2015 | Ozsolak |
| 2015/0232858 | A1 | 8/2015 | Ozsolak |
| 2015/0238516 | A1 | 8/2015 | Dowdy et al. |
| 2015/0267192 | A1 | 9/2015 | Heartlein et al. |
| 2015/0291957 | A1 | 10/2015 | Smith |
| 2015/0329918 | A1 | 11/2015 | Kang et al. |
| 2015/0337310 | A1 | 11/2015 | Walker et al. |
| 2015/0361497 | A1 | 12/2015 | Rose |
| 2016/0017322 | A1 | 1/2016 | Vorechovsky et al. |
| 2016/0024500 | A1 | 1/2016 | Popplewell et al. |
| 2016/0046935 | A1 | 2/2016 | Bentwich et al. |
| 2016/0122767 | A1 | 5/2016 | Gouya et al. |
| 2016/0201063 | A1 | 7/2016 | Ozsolak |
| 2016/0201064 | A1 | 7/2016 | Ozsolak |
| 2016/0208264 | A1 | 7/2016 | Wilton et al. |
| 2016/0215291 | A1 | 7/2016 | Garcia et al. |
| 2016/0244762 | A1 | 8/2016 | Vorechovsky et al. |
| 2016/0244767 | A1 | 8/2016 | Hastings |
| 2016/0298121 | A1 | 10/2016 | Krainer et al. |
| 2017/0044540 | A1 | 2/2017 | Sætrom et al. |
| 2017/0101641 | A1 | 4/2017 | Vorechovsky et al. |
| 2017/0159049 | A9 | 6/2017 | Krainer et al. |
| 2017/0240904 | A1 | 8/2017 | Tallent et al. |
| 2018/0002694 | A1 | 1/2018 | Vorechovsky et al. |
| 2018/0201937 | A1 | 7/2018 | Gomez et al. |
| 2018/0296501 | A1 | 10/2018 | During |
| 2018/0346907 | A1 | 12/2018 | Crooke et al. |
| 2018/0362987 | A1 | 12/2018 | Krainer et al. |
| 2018/0369275 | A1 | 12/2018 | Arnarez et al. |
| 2019/0024118 | A1 | 1/2019 | Tagliatela et al. |
| 2019/0024119 | A1 | 1/2019 | Tagliatela et al. |
| 2019/0024120 | A1 | 1/2019 | Tagliatela et al. |
| 2019/0024121 | A1 | 1/2019 | Tagliatela et al. |
| 2019/0070213 | A1 | 3/2019 | Aznarez et al. |
| 2019/0192691 | A1 | 6/2019 | Barrett et al. |
| 2019/0218255 | A1 | 7/2019 | Chung et al. |
| 2019/0225939 | A1 | 7/2019 | Chambers et al. |
| 2019/0264211 | A1 | 8/2019 | Vorechovsky et al. |
| 2020/0024603 | A1 | 1/2020 | Aznarez et al. |
| 2020/0024606 | A1 | 1/2020 | Aznarez et al. |
| 2020/0085838 | A1 | 3/2020 | Martinez Botella et al. |
| 2020/0101174 | A1 | 4/2020 | Coller et al. |
| 2020/0231969 | A1 | 7/2020 | Vorechovsky |
| 2020/0399640 | A1 | 12/2020 | Gottesman et al. |
| 2021/0087238 | A1 | 3/2021 | Hoffmann et al. |
| 2021/0108208 | A1 | 4/2021 | Krainer et al. |
| 2021/0155936 | A1 | 5/2021 | Vorechovsky |
| 2021/0261963 | A1 | 8/2021 | Uno et al. |
| 2021/0268667 | A1 | 9/2021 | Aznarez et al. |
| 2021/0309996 | A1 | 10/2021 | Aznarez et al. |
| 2021/0317462 | A1 | 10/2021 | Petrou |
| 2022/0162605 | A1 | 5/2022 | Aznarez |
| 2022/0290142 | A1 | 9/2022 | Aznarez |
| 2023/0116704 | A1 | 4/2023 | Aznarez et al. |
| 2023/0183693 | A1 | 6/2023 | Vorechovsky et al. |
| 2023/0250429 | A1 | 8/2023 | Aznarez et al. |
| 2023/0287410 | A1 | 9/2023 | Aznarez et al. |
| 2023/0416756 | A1 | 12/2023 | Vorechovsky et al. |
| 2024/0033378 | A1 | 2/2024 | Aznarez et al. |
| 2024/0150760 | A1 | 5/2024 | Aznarez et al. |
| 2024/0254488 | A1 | 8/2024 | Aznarez et al. |
| 2024/0309377 | A1 | 9/2024 | Vorechovsky et al. |
| 2025/0059535 | A1 | 2/2025 | Aznarez et al. |
| 2025/0066781 | A1 | 2/2025 | Ticho et al. |
| 2025/0270563 | A1 | 8/2025 | Krainer et al. |

FOREIGN PATENT DOCUMENTS

| | | | |
|---|---|---|---|
| AU | 2016334804 | B2 | 3/2022 |
| AU | 2022204606 | A1 | 7/2022 |
| CN | 102171342 | A | 8/2011 |
| CN | 103667438 | A | 3/2014 |
| CN | 107109411 | A | 8/2017 |
| CN | 109312343 | A | 2/2019 |
| CN | 111278991 | A | 6/2020 |
| CN | 111518898 | A | 8/2020 |
| EP | 0549615 | A1 | 7/1993 |
| EP | 1281758 | A2 | 2/2003 |
| EP | 1201678 | B1 | 9/2004 |
| EP | 1409497 | B1 | 1/2005 |
| EP | 1579015 | A2 | 9/2005 |
| EP | 1007714 | B1 | 12/2005 |
| EP | 1334109 | B1 | 5/2006 |
| EP | 1178999 | B1 | 3/2007 |
| EP | 1203827 | B1 | 5/2007 |
| EP | 1501848 | B1 | 8/2007 |
| EP | 1569661 | B1 | 9/2009 |
| EP | 1161439 | B1 | 4/2010 |

(56) References Cited

FOREIGN PATENT DOCUMENTS

| | | | |
|---|---|---|---|
| EP | 1984381 | B1 | 9/2010 |
| EP | 2284269 | A2 | 2/2011 |
| EP | 1013661 | B1 | 1/2012 |
| EP | 2092065 | B1 | 1/2012 |
| EP | 2099461 | B1 | 3/2012 |
| EP | 2170917 | B1 | 6/2012 |
| EP | 2066684 | B1 | 7/2012 |
| EP | 2284269 | A3 | 8/2012 |
| EP | 2356129 | B1 | 4/2013 |
| EP | 2376516 | B1 | 4/2013 |
| EP | 2114981 | B1 | 5/2013 |
| EP | 2149605 | B1 | 7/2013 |
| EP | 2285819 | B1 | 10/2013 |
| EP | 2161038 | B1 | 12/2013 |
| EP | 1562971 | B1 | 2/2014 |
| EP | 2295441 | B1 | 5/2014 |
| EP | 2314594 | B1 | 7/2014 |
| EP | 2410053 | B1 | 10/2014 |
| EP | 2176280 | B2 | 6/2015 |
| EP | 2361921 | B1 | 6/2015 |
| EP | 2462153 | B1 | 7/2015 |
| EP | 1015469 | B2 | 11/2015 |
| EP | 2173760 | B2 | 11/2015 |
| EP | 1937312 | B1 | 6/2016 |
| EP | 2141233 | B1 | 10/2016 |
| EP | 2410054 | B1 | 1/2017 |
| EP | 3329909 | A1 | 6/2018 |
| EP | 3359685 | A1 | 8/2018 |
| EP | 2753317 | B1 | 2/2020 |
| EP | 3673080 | A1 | 7/2020 |
| EP | 3700570 | A1 | 9/2020 |
| EP | 3155124 | B1 | 11/2021 |
| EP | 4015648 | A1 | 6/2022 |
| EP | 4069256 | A1 | 10/2022 |
| GB | 1517937 | A | 7/1978 |
| GB | 2546719 | A | 8/2017 |
| JP | 2007534772 | A | 11/2007 |
| JP | 6923517 | B2 | 8/2021 |
| JP | 2021180669 | A | 11/2021 |
| KR | 20130026484 | A | 3/2013 |
| WO | WO-9402501 | A1 | 2/1994 |
| WO | WO-9426887 | A1 | 11/1994 |
| WO | WO-9747772 | A2 | 12/1997 |
| WO | WO-0010608 | A1 | 3/2000 |
| WO | WO-0107660 | A1 | 2/2001 |
| WO | WO-2005049651 | A2 | 6/2005 |
| WO | WO-2006107846 | A2 | 10/2006 |
| WO | WO-2007002390 | A2 | 1/2007 |
| WO | WO-2007048628 | A2 | 5/2007 |
| WO | WO-2007048629 | A2 | 5/2007 |
| WO | WO-2007056113 | A2 | 5/2007 |
| WO | WO-2008036127 | A2 | 3/2008 |
| WO | WO-2009003694 | A2 | 1/2009 |
| WO | WO-2009064920 | A2 | 5/2009 |
| WO | WO-2009084472 | A1 | 7/2009 |
| WO | WO-2009099942 | A2 | 8/2009 |
| WO | WO-2010051632 | A1 | 5/2010 |
| WO | WO-2010148249 | A1 | 12/2010 |
| WO | WO-2011057350 | A1 | 5/2011 |
| WO | WO-2011163499 | A2 | 12/2011 |
| WO | WO-2012168435 | A1 | 12/2012 |
| WO | WO-2012178146 | A1 | 12/2012 |
| WO | WO-2013036105 | A1 | 3/2013 |
| WO | WO-2013081755 | A1 | 6/2013 |
| WO | WO-2013106770 | A1 | 7/2013 |
| WO | WO-2013119916 | A2 | 8/2013 |
| WO | WO-2013119916 | A3 | 10/2013 |
| WO | WO-2014012081 | A2 | 1/2014 |
| WO | WO-201428459 | A1 | 2/2014 |
| WO | WO-2014028459 | A1 | 2/2014 |
| WO | WO-2014031575 | A1 | 2/2014 |
| WO | WO-2014049536 | A2 | 4/2014 |
| WO | WO-2014121287 | A2 | 8/2014 |
| WO | WO-2014172698 | A1 | 10/2014 |
| WO | WO-2014201413 | A1 | 12/2014 |
| WO | WO-2014209841 | A2 | 12/2014 |
| WO | WO-2015024876 | A2 | 2/2015 |
| WO | WO-2015035091 | A1 | 3/2015 |
| WO | WO-2014209841 | A3 | 10/2015 |
| WO | WO-2015190922 | A1 | 12/2015 |
| WO | WO-2015193651 | A1 | 12/2015 |
| WO | WO-2015198054 | A1 | 12/2015 |
| WO | WO-2016022914 | A1 | 2/2016 |
| WO | WO-2016027168 | A2 | 2/2016 |
| WO | WO-2015193651 | A4 | 3/2016 |
| WO | WO-2016027168 | A3 | 4/2016 |
| WO | WO-2016054615 | A2 | 4/2016 |
| WO | WO-2016061509 | A1 | 4/2016 |
| WO | WO-2016054615 | A3 | 5/2016 |
| WO | WO-2016077837 | A1 | 5/2016 |
| WO | WO-2016081885 | A2 | 5/2016 |
| WO | WO-2016087842 | A1 | 6/2016 |
| WO | WO-2016118697 | A1 | 7/2016 |
| WO | WO-2016128343 | A1 | 8/2016 |
| WO | WO-2016138534 | A2 | 9/2016 |
| WO | WO-2016161429 | A1 | 10/2016 |
| WO | WO-2016196386 | A1 | 12/2016 |
| WO | WO-2017053982 | A1 | 3/2017 |
| WO | WO-2017060731 | A1 | 4/2017 |
| WO | WO-2017106210 | A1 | 6/2017 |
| WO | WO-2017106211 | A1 | 6/2017 |
| WO | WO-2017106283 | A1 | 6/2017 |
| WO | WO-2017106292 | A1 | 6/2017 |
| WO | WO-2017106364 | A2 | 6/2017 |
| WO | WO-2017106370 | A1 | 6/2017 |
| WO | WO-2017106375 | A1 | 6/2017 |
| WO | WO-2017106377 | A1 | 6/2017 |
| WO | WO-2017106382 | A1 | 6/2017 |
| WO | WO-2017106383 | A1 | 6/2017 |
| WO | WO-2018007980 | A1 | 1/2018 |
| WO | WO-2018098446 | A1 | 5/2018 |
| WO | WO-2018187363 | A1 | 10/2018 |
| WO | WO-2018191482 | A2 | 10/2018 |
| WO | WO-2018206924 | A1 | 11/2018 |
| WO | WO-2019040923 | A1 | 2/2019 |
| WO | WO-2019084050 | A1 | 5/2019 |
| WO | WO-2019109051 | A1 | 6/2019 |
| WO | WO-2019191341 | A1 | 10/2019 |
| WO | WO-2019199867 | A1 | 10/2019 |
| WO | WO-2019224864 | A1 | 11/2019 |
| WO | WO-2019227096 | A1 | 11/2019 |
| WO | WO-2019236750 | A2 | 12/2019 |
| WO | WO-2019243430 | A1 | 12/2019 |
| WO | WO-2020041348 | A1 | 2/2020 |
| WO | WO-2020176776 | A1 | 9/2020 |
| WO | WO-2020237294 | A1 | 12/2020 |
| WO | WO-2021113541 | A1 | 6/2021 |
| WO | WO-2021119756 | A1 | 6/2021 |
| WO | WO-2021231107 | A1 | 11/2021 |
| WO | WO-2022067398 | A1 | 4/2022 |
| WO | WO-2023028575 | A2 | 3/2023 |
| WO | WO-2023086342 | | 5/2023 |
| WO | WO-2023141681 | A1 | 8/2023 |
| WO | WO-2023178386 | A1 | 9/2023 |
| WO | WO-2024026122 | A2 | 2/2024 |
| WO | WO-2024173582 | A2 | 8/2024 |
| WO | WO-2024249949 | | 12/2024 |
| WO | WO-2025024568 | A1 | 1/2025 |

OTHER PUBLICATIONS

Aceti et al.: "Syngap1 haploinsufficiency damages a postnatal critical period of pyramidal cell structural maturation linked to cortical circuit assembly" Biol Psychiatry (2015) 77(9): pp. 805-819.

Aizer et al.: Lack of reduction in racial disparities in cancer-specific mortality over a 20-year period. Cancer 120:1532-9 (2014).

Altschul et al.: Basic Local Alignment Search Tool. J Mol Biol 215(3):403-410 (1990).

Aly et al.: Extreme genetic risk for type 1A diabetes. Proc Natl Acad Sci U.S.A. 103(38): 14074-9 (2006). Epub Sep. 11, 2006.

(56) References Cited

OTHER PUBLICATIONS

Amarnath et al.: The PDL1-PD1 Axis Converts Human TH1 Cells into Regulatory T Cells. Science Translational Medicine 3(111):1-13 (2011).
Anders et al.: Detecting differential usage of exons from RNA-seq data. Genome Res. 22(10):2008-17 (2012). Epub Jun. 23, 2012. doi: gr.133744.111 [pii] 10.1101/gr.133744.111. PubMed PMID: 22722343.
AU 2018322319 Examination Report No. 1 dated Oct. 16, 2020.
Au et al.: Molecular Genetic Basis of Tuberous Sclerosis Complex: From Bench to Bedside. Journal of Child Neurology 19:9 (2004).
Audentes Therapeutics Announces Expansion of AAV Technology Platform and Pipeline with New Development Programs for Duchenne Muscular Dystrophy and Myotonic Dystrophy. PRNewswire Apr. 8, 2019 (7 pgs).
Aznarez et al.: TANGO-Targeted augmentation of nuclear gene output—for the treatment of genetic diseases [abstract]. In: 2018 Annual Meeting Abstract of the American Society of Gene and Cell Therapy, May 16-19, 2018, Chicago, IL (2018), Abstract No. 304.
Bakkenist et al.: DNA damage activates ATM through intermolecular autophosphorylation and dimer dissociation. Nature 421(6922):499-506 (2003). doi: 10.1038/nature01368. PubMed PMID: 12556884.
Balagurumoorthy et al.: Hairpin and parallel quartet structures for telomeric sequences. Nucleic Acids Res. 20(15):4061-7 (1992).
Balkwill et al.: Repression of translation of human estrogen receptor alpha by G-quadruplex formation. Biochemistry 48(48):11487-95 (2009). doi: 10.1021/bi901420k.
Barratt et al.: Remapping the insulin gene/IDDM2 locus in type 1 diabetes. Diabetes 53(7):1884-9 (2004).
Bassi et al.: A novel mutation in the ATP1A2 gene causes alternating hemiplegia of childhood. J. Med. Genet. 41:621-628 (2004).
Battistini et al.: A new CACNA1A gene mutation in acetazolamide-responsive familial hemiplegic migraine and ataxia. Neurology 53(1):38-43 (1999).
Baughan et al.: Delivery of bifunctional RNAs that target an intronic repressor and increase SMN levels in an animal model of spinal muscular atrophy. Hum Mol Genet. 18(9):1600-11 (2009). doi: 10.1093/hmg/ddp076. Epub Feb. 19, 2009.
Bauman et al.: Therapeutic potential of splice-switching oligonucleotides. Oligonucleotides 19.1:1-13 (2009).
Beaudoin et al.: 5'-UTR G-quadruplex structures acting as translational repressors. Nucleic Acids Res. 38(20):7022-36 (2010). doi: 10.1093/nar/gkq557. Epub Jun. 22, 2010.
Beli et al.: Proteomic investigations reveal a role for RNA processing factor THRAP3 in the DNA damage response. Mol Cell. 46(2):212-25 (2012). doi: 10.1016/j.molcel.2012.01.026. PubMed PMID: 22424773; PubMed Central PMCID: PMC3565437.
Berge et al.: Pharmaceutical Salts. J. Pharmaceutical Sciences 66(1):1-19 (1977).
Berger et al.: The molecular basis of human retinal and vitreoretinal diseases. Progress in Retinal and Eye Research 29:335-375 (2010).
Bethke et al.: Comprehensive analysis of the role of DNA repair gene polymorphisms on risk of glioma. Hum Mol Genet. 17(6):800-5 (2008). Epub Dec. 1, 2007.doi: ddm351 [pii] 10.1093/hmg/ddm351. PubMed PMID: 18048407.
Bicknell et al.: Introns in UTRs: why we should stop ignoring them. Bioessays 34(12):1025-34 (2012). doi: 10.1002/bies.201200073. Epub Oct. 26, 2012.
Blencowe, Benjamin: Reflections for the 20th anniversary issue of RNA journal. RNA Journal 21(4):573-575 (2015).
Blencowe BJ: Splicing regulation: the cell cycle connection. Curr. Biol. 13(4):R149-51 (2003). PubMed PMID: 12593819.
Bolognini et al.: Characterization of two novel intronic OPA1 mutations resulting in aberrant pre-mRNA splicing. BMC Medical Genetics 18:22 (2017).
Bonifert et al.: Antisense Oligonucleotide Mediated Splice Correction of a Deep Intronic Mutation in OPA1. Molecular Therapy—Nucleic Acids, vol. 5 (2016).
Bonifert et al.: Pure and syndromic optic atrophy explained by deep intronic OPA1 mutations and an intralocus modifier. Brain 137(8):2164-2177 (2014).
Bonnen et al.: Haplotypes at ATM identify coding-sequence variation and indicate a region of extensive linkage disequilibrium. Am J Hum Genet. 67(6):1437-51 (2000). Epub Nov. 15, 2000.doi: S0002-9297(07)63213-3 [pii] 10.1086/316908. PubMed PMID: 11078475.
Boothby et al.: Removal of Retained Introns Regulates Translation in the Rapidly Developing Gametophyte of Marsilea vestita. Developmental Cell 24:517-529 (2013).
Booy et al.: The RNA helicase Rhau (DHX36) unwinds a G4-quadruplex in human telomerase RNA and promotes the formation of the P1 helix template boundary. Nucleic Acids Res. (9):4110-24 (2012). doi: 10.1093/nar/gkr1306. Epub Jan. 11, 2012.
Boutz, et al.: Detained intron are a novel, widespread class of post-transcriptionally spliced introns, Genes & Development 29: 63-80.
Boutz et al.: Detained introns are a novel, widespread class of post-transcriptionally spliced introns. Genes Dev. 29(1):63-80 (2015). doi: 10.1101/gad.247361.114.
Braunschweig et al.: "Widespread intron retention in mammal functionally tunes transcriptomes", Chold Spring Harbor Laboratory Press, 2014 p. 1-14.
Braunschweig et al.: Widespread intron retention in mammals functionally tunes transcriptomes. Widespread intron retention in mammals functionally tunes transcriptomes. Genome Res. 24(11):1774-86 (2014). doi: 10.1101/gr.177790.114. Epub Sep. 25, 2014.
Braunschweig, Intron Retention, Supplemental Figure Legends.
Bravo-Gil et al.: Improving the management of Inherited Retinal Dystrophies by targeted sequencing of a population-specific gene panel. Scientific Reports 6:23910, 10 pages (2015).
Brooks et al.: A pan-cancer analysis of transcriptome changes associated with somatic mutations in U2AF1 reveals commonly altered splicing events. PLoS One. 9(1):e87361 (2014). Epub Feb. 6, 2014.doi: 10.1371/journal.pone.0087361 PONE-D-13-26905 [pii]. PubMed PMID: 24498085.
Buchman et al.: Comparison of intron-dependent and intron-independent gene expression. Mol Cell Biol. 8(10):4395-405 (1988).
Buckley et al.: Cytoplasmic intron retention, function, splicing, and the sentinel RNA hypothesis.WIREs RNA 5:223-2330 (2014).
Bugaut et al.: 5'-UTR RNA G-quadruplexes: translation regulation and targeting. Nucleic Acids Res. 40(11):4727-41 (2012). doi: 10.1093/nar/gks068. Epub Feb. 20, 2012.
Bugaut et al.: An RNA hairpin to G-quadruplex conformational transition. J Am Chem Soc. 134(49):19953-6 (2012). doi: 10.1021/ja308665g. Epub Nov. 29, 2012.
Buratti et al.: DBASS3 and DBASS5: databases of aberrant 3'- and 5'-splice sites. Nucleic Acids Res. 39(Database issue):D86-91 (2011). doi: 10.1093/nar/gkq887. Epub Oct. 6, 2010.
Buratti et al.: RNA folding affects the recruitment of SR proteins by mouse and human polypurinic enhancer elements in the fibronectin EDA exon. Mol Cell Biol. 24(3):1387-400 (2004).
Burnette et al.: Subdivision of large introns in *Drosophila* by recursive splicing at non-exonic elements. Genetics (2005).
Burns et al.: Connections between pre-mRNA processing and regulation of the eukaryotic cell cycle. Front Horm Res. 25:59-82 (1999).
Buschmann et al.: Chitosans for delivery of nucleic acids. Advanced drug delivery reviews 65.9:1234-1270 (2013).
Busslinger et al.: β+ Thalassemia: Aberrant splicing results from a single point mutation in an intron. Cell 27.2:289-298 (1981).
Callis et al. Introns increase gene expression in cultured maize cells. Genes Dev. 1(10):1183-200 (1987).
Catterall et al.: Nav1.1 channels and epilepsy. J Physiol. 1;588(Pt 11):1849-59 (2010).
Cavaloc et al.: The splicing factors 9G8 and SRp20 transactivate splicing through different and specific enhancers. RNA 5(3):468-83 (1999).
Cazzola et al.: Translational pathophysiology: a novel molecular mechanism of human disease. Blood 95(11):3280-8 (2000).
Chambers et al.: The INO80 chromatin remodeling complex prevents polyploidy and maintains normal chromatin structure at centromeres. Genes Dev. 26(23):2590-603 (2012). Epub Dec. 5, 2012.doi: 26/23/2590 [pii] 10.1101/gad.199976.112. PubMed PMID: 23207916.

(56) References Cited

OTHER PUBLICATIONS

Chen et al.: A functional single nucleotide polymorphism in promoter of ATM is associated with longevity. Mech Ageing Dev. 131:636-40 (2010).
Chen et al.: Chk1 kinase negatively regulates mitotic function of Cdc25A phosphatase through 14-3-3 binding. Mol Cell Biol. 23(21):7488-97 (2003). PubMed PMID: 14559997; PubMed Central PMCID: PMC207598.
Schimpf et al.: "Activation of cryptic splice sites is a frequent splicing defect mechanism caused by mutations in exon and intron sequences of the OPA1 gene, Human Genetics, 2006, vol. 118, No. 6, pp. 767-771".
Choi et al.: CHK2 kinase promotes pre-mRNA splicing via phosphorylating CDK11p110. Oncogene 33:108-15 (2014).
Colla et al.: Telomere dysfunction drives aberrant hematopoietic differentiation and myelodysplastic syndrome. Cancer Cell. 27(5):644-57 (2015). doi: 10.1016/j.ccell.2015.04.007. PubMed PMID: 25965571.
Collie et al.: The application of DNA and RNA G-quadruplexes to therapeutic medicines. Chem Soc Rev. 40(12):5867-92 (2011). doi: 10.1039/c1cs15067g. Epub Jul. 25, 2011.
Collin et al.: Antisense Oligonucleotide (AON)-based Therapy for Leber Congenital Amaurosis caused by a Frequent Mutation in CEP290. Molecular Therapy-Nucleic Acids, pp. 1-7 (2012).
Consortium. TGP. An integrated map of genetic variation from 1,092 human genomes. Nature (London). 491:56-65 (2012).
Corallini et al.: Transcriptional and Posttranscriptional Regulation of the CTNS Gene. Pediatric Research 70(2):130-135 (2011).
Corey et al.: A non-classical translocation involving 17q12 (retinoic acid receptor alpha) in acute promyelocytic leukemia (APML) with atypical features. Leukemia 8(8):1350-3 (1994). PubMed PMID: 8057672.
Cornille et al.: Reversible optic neuropathy with OPA1 exon 5b mutation. Annals of Neurology 63(5):667-671 (2008).
Corvelo et al.: Genome-wide association between branch point properties and alternative splicing. PLoS Comput Biol. 6(11):e1001016 (2010). Epub Dec. 3, 2010.doi: 10.1371/journal.pcbi.1001016. PubMed PMID: 21124863.
Coulombe-Huntington et al.: Fine-Scale Variation and Genetic Determinants of Alternative Splicing across Individuals. PLoS Genet. 5(12):e1000766 (2009). Epub Dec. 17, 2009.doi: 10.1371/journal.pgen.1000766. PubMed PMID: 20011102.
Coutinho et al.: Functional significance of a deep intronic mutation in the ATM gene and evidence for an alternative exon 28a. Hum Mutat. 25(2):118-24 (2005). Epub Jan. 12, 2005.doi: 10.1002/humu.20170. PubMed PMID: 15643608.
Creacy, et al.: G4 resolvase 1 binds both DNA and RNA tetramolecular quadruplex with high affinity and is the major source of tetramolecular quadruplex G4-DNA and G4-RNA resolving activity in HeLa cell lysates. J Biol Chem. 283(50):34626-34 (2008). doi: 10.1074/jbc.M806277200. Epub Oct. 7, 2008.
Creson, et al.: "Re-expression of SynGAP Protein in Adulthood Improves Translatable Measure of Brain Function and Behavior in a Model of Neurodevelopmental Disorders" BioRxiv (2018) pp. 1-27.
Creson et al.: Re-expression of SynGAP Protein in Adulthood Improves Translatable Measures of Brain Function and Behavior in a Model of Neurodevelopmental Disorders. Departments of Neuroscience and Molecular medicine, The Scripps Research Institute (2018).
Culler et al.: Functional selection and systematic analysis of intronic splicing elements identify active sequence motifs and associated splicing factors. Nucleic Acids Res. 38(15):5152-65 (2010). doi: 10.1093/nar/gkq248. Epub Apr. 12, 2010.
Database Geneseq [Online], Nov. 13, 2008 (Nov. 13, 2008), Dual label detection probe, QF probe 1, 5. 3.11, XP055572852, retrieved from EBI Accession No. GSN:ARK21623.
Davies et al.: A genome-wide search for human type 1 diabetes susceptibility genes. Nature 8;371(6493):130-6 (1994).
Decorsiere et al.: Essential role for the interaction between hnRNP H/F and a G quadruplex in maintaining p53 pre-mRNA 3'-end processing and function during DNA damage. Genes Dev. 25(3):220-5 (2011). doi: 10.1101/gad.607011.
Dedic et al.: Alagille Syndrome Mimicking Biliary Atresia in Early Infancy, PLOS OONE, 10(11):e0143939: pp. 1-7 (2015).
Deere et al.: AntisensePhosphorodiamidate Morpholino OligomerLengthand TargetPositionEffects on Gene-SpecificInhibitionin *Escherichia coli*. Antimicrobial Agents Andchemotherapy 49(1):249-255 (2005).
Del Dotto et al.: OPA1 Isoforms in the Hierarchical Organization of Mitochondrial Functions. Cell Reports 19(12):2557-2571 (2017).
Derecka et al.: Occurrence of a quadruplex motif in a unique insert within exon C of the bovine estrogen receptor alpha gene (ESR1). Biochemistry 49(35):7625-33 (2010). doi: 10.1021/bi100804f.
Dias et al.: Antisense oligonucleotides: basic concepts and mechanisms Mol. Cancer Ther. 1:347-355 ( 2002).
Didiot et al.: The G-quartet containing FMRP binding site in FMR1 mRNA is a potent exonic splicing enhancer. Nucleic Acids Res. Sep. 2008;36(15):4902-12. doi: 10.1093/nar/gkn472. Epub Jul. 24, 2008.
Ding, H. et al.: DeliveringPD-1 inhibitory signal concomitant with blocking ICOS co-stimulation suppresses lupus-like syndrome in autoimmune BXSB mice.Clinical Immunology, vol. 118, pp. 258-267, (2006).
Divina, P. et al.: Ab initio prediction of cryptic splice-site activation and exon skipping. Eur J Hum Genet. 2009; 17:759-65.
Dominski, et al.: Restoration of correct splicing in thalassemic pre-mRNA by antisense oligonucleotides. Proc Natl Acad Sci U S A. Sep. 15, 1993;90(18):8673-7.
Dredge, et al.: NeuN/Rbfox3 Nuclear and Cytoplasmic Isoforms Differentially Regulate Alternative Splicing and Nonsense-Mediated Decay of Rbfox2. PLoS One. 2011; 6(6): e21585.
Du, et al.: "Correction of prototypic ATM splicing utations and aberrant ATM function with antisense morpholino oligonucleotides" (2007) PNAS, vol. 104, No. 14, pp. 6007-6012.
Du, et al.: "Downregulation of neuronal sodium channel subunits Nav. 1. and Nav1.6 in the sinoatrial node from volume-overloaded heart failure rat", Pflugers Arch—Eur J Physiol (2007) 454:451-459.
Ducros et al.Recurrence of the T666M calcium channel CACNA1A gene mutation in familial hemiplegic migraine with progressive cerebellar ataxia.Am J Hum Genet. vol. 64, No. 1, pp. 89-98 (Jan. 1999).
Duikers, et al. "Antisense Oligonucleotide-Based Splicing Correction in Individuals with Leber Congenital Amaurosis due to Compound Heterozygosity for the c.2991+1655AG Mutation in CEP290" (2018) International Journal of Molecular Sciences, 19, 753, pp. 1-12.
Dulla, et al.: "Splice-Modulating Oligonucleotide QR-110 Restores CEP290 mRNA and Function in Human c.2991+1655AG LCA10 Models" (2018) Molecular Therapy: Nucleic Acids, vol., pp. 730-740.
Duryagina R, et al. Overexpression of Jagged-1 and its intracellular domain in human mesenchymal stromal cells differentially affect the interaction with hematopoietic stem and progenitor cells.Stem Cells Dev. vol. 22, No. 20, pp. 2736-2750 (2013).
Dutertre, M., et al. et al. DNA damage: RNA-binding proteins protect from near and far. Trends Biochem Sci. 2014; 39(3):141-9. Epub Feb. 19, 2014.doi: S0968-0004(14)00015-2 [pii] 10.1016/j.tibs.2014.01.003. PubMed PMID: 24534650.
Eddy, et al. G4 motifs correlate with promoter-proximal transcriptional pausing in human genes. Nucleic Acids Res. Jul. 2011;39(12):4975-83. doi: 10.1093/nar/gkr079. Epub Mar. 3, 2011.
El Bougrini et al.: PML positively regulates interferon gamma signaling. Biochimie. 2011; 93(3):389-98. doi: 10.1016/j.biochi.2010.11.005. PubMed PMID: 21115099.
Emerick, et al. Multivariate analysis and visualization of splicing correlations in single-gene transcriptomes. BMC Bioinformatics. Jan. 18, 2007;8:16.
EP 15846242.4 Partial Supplementary Search Report and Search Opinion dated May 2, 2018.
EP 16876621.0 Extended European Search Report and Search Opinion dated Mar. 7, 2019.
EP15729929.8 Office Action dated Dec. 22, 2017.
EP15729929.8 Office Action dated Oct. 30, 2018.

(56) References Cited

OTHER PUBLICATIONS

EP15846242.4 Extended European Search Report dated Aug. 21, 2018.
EP16781187.6 Office Action dated May 20, 2019.
EP16876499.1 Extended Search Report dated Jun. 14, 2019.
EP168766061.1 Extended Search Report dated May 24, 2019.
Escayg et al.: Sodium channel SCN1A and epilepsy: mutations and mechanisms, Epilepsia, Sep. 2010, vol. 51, No. 9, pp. 1-16.
Fairbrother, W.G., et al.: Predictive identification of exonic splicing enhancers in human genes. Science. 2002; 297(5583):1007-13. PubMed PMID: 12114529.
Fededa, et al.: A polar mechanism coordinates different regions of alternative splicing within a single gene. Mol Cell. Aug. 5, 2005;19(3):393-404.
Ferreira, P.G., et al.: Transcriptome characterization by RNA sequencing identifies a major molecular and clinical subdivision in chronic lymphocytic leukemia. Genome Res. 2014; 24:212-26.
Fletcher, Sue et al.: Antisense suppression of donor splice site mutations in the dystrophin gene transcript.Molecular Genetics & Genomic Medicine, vol. 1, No. 3, pp. 162-173, Jun. 13, 2013.
Fred et al.: The human insulin mRNA is partly translated via a cap- and eIF4A-independent mechanism. Biochem Biophys Res Commun. Sep. 9, 2011;412(4):693-8. doi: 10.1016/j.bbrc.2011.08.030. Epub Aug. 16, 2011.
Friedman, et al.: "Correction of Aberrant Splicing of the Cystic Fibrosis Transmembrane conductance Regulator (CFTR) Gene by Antisense Oligonucleotides" (1999) The Journal of Biological Chemistry, vol. 274, No. 51, pp. 36193-36199.
Friend, KL et al.: Detection of a novel missense mutation and second recurrent mutation in the CACNA1A gene in individuals with EA-2 and FHM. Hum Genet. vol. 105(3):261-5 (Sep. 1999).
Furukawa & Kish 2008, GeneReviews Pagon Ra et al.: eds. Univ. of WA Seattle, NCBI Bookshelf ID NBK1437.
Galante, et al.: Detection and evaluation of intron retention events in the human transcriptome. RNA. May 2004;10(5):757-65.
Gallus, G. N. et al.: "Alu-element insertion in an OPA1 intron sequence associated with autosomal dominant optic atrophy, Molecular vision, 2010, vol. 16, pp. 178-183".
Garanto, et al.: "In vitro and in vivo rescue of aberrant splicing in CEP290-associted LCA by antisense oligonucleotide delivery" (2016) Human Molecular Genetics, vol. 25, No. 12, pp. 2552-2563.
Garner, et al.: Selectivity of small molecule ligands for parallel and anti-parallel DNA G-quadruplex structures. Org Biomol Chem. Oct. 21, 2009;7(20):4194-200. doi: 10.1039/b910505k. Epub Aug. 14, 2009.
Geary et al.: Absolute Bioavailability of 29-O-(2-Methoxyethyl)-Modified Antisense Oligonucleotides following Intraduodenal Instillation in Rats. J Pharmacal Exp Ther. vol. 296, No. 3, pp. 898-904 (Mar. 2001).
Geary, et al.: "Pharmacokinetics, biodistribution and cell uptake of antisense oligonucleotides", (2015) Advance Drug Delivery Reviews.
Geary, RS et al.: Pharmacokinetic properties of 2'-O-(2-methoxyethyl)-modified oligonucleotide analogs in ratsJ Pharmacal Exp Ther. vol. 296, No. 3, pp. 890-897 (Mar. 2001).
Gerard, et al.: "AON-mediated Exon Skipping Restores ciliation in Fibroblasts Harboring the Common Leber Congenital Amaurosis CEP290 Mutation" (2012) Molecular Therapy-Nucleic Acids, pp. 1-9.
Gianchecchi et al.: Recent insights into the role of the PD-1/PD-L1 pathway in immunological tolerance and autoimmunity. Autoimmunity Reviews 12:1091-1100 (2013).
Gibson, G.: Hints of hidden heritability in GWAS. Nat Genet. 2010; 42(7):558-60. Epub Jun. 29, 2010.doi: ng0710-558 [pii] 10.1038/ng0710-558. PubMed PMID: 20581876.
Gohring, J. et al.: Imaging of Endogenous MessengerRNA Splice Variants in Living Cells Reveals Nuclear Retention of Transcripts Inaccessible to Nonsense-Mediated Decay in *Arabidopsis*. The Plant Cell.vol. 26, pp. 754-764.(Feb. 2014).
Gomes et al.: Translating chitosan to clinical delivery of nucleic acid-based drugs. MRS bulletin 39.1 (2014): 60-70.
Gomez, et al.: Telomerase downregulation induced by the G-quadruplex ligand 12459 in A549 cells is mediated by hTERT RNA alternative splicing. Nucleic Acids Res. Jan. 16, 2004;32(1):371-9. Print 2004.
Goncharova et al.: Tuberin regulates p70 S6 kinase activation and ribosomal protein S6 phosphorylation. A role for the TSC2 tumor suppressor gene in pulmonary lymphangioleiomyomatosis (LAM). J. Biol. Chem. (Aug. 23, 2002) 277(34);30958-67. EPub Jun. 3, 2002.
Gonzalez-Santos, et al.: Mutation in the splicing factor Hprp3p linked to retinitis pigmentosa impairs interactions within the U4/U6 snRNP pigmentosa impairs interactions within the U4/U6 snRNP complex, PubMed Central Canada , Author Manuscript, 29 pages.
Goto et al.: "Targeted skipping of a Single Exon Harboring a Premature termination Codon Mutation: Implications and Potential for Gene Correction Therapy for Selective Dystrophic Epiderolysis Bullosa Patients" (2006) Journal of Investigative Dermatology, vol. 126, pp. 2614-262.
Goyenvalie et al.: Therapeutic approaches to muscular dystrophy. Hum Mol Genet. Apr. 15, 2011;20(R1):R69-78. doi: 10.1093/hmg/ddr105. Epub Mar. 24, 2011.
Gozani, O. et al.: A potential role for U2AF-SAP 155 interactions in recruiting U2 snRNP to the branch site. Mol Cell Biol. 1998; 18(8):4752-60. PubMed PMID: 9671485.
Graveley, B.R. The haplo-spliceo-transcriptome: common variations in alternative splicing in the human population. Trends Genet. 2008; 24(1):5-7. Epub Dec. 7, 2007.doi: S0168- 9525(07)00349-6 [pii] 10.1016/j.tig.2007.10.004. PubMed PMID: 18054116.
Gutell, R.R., et al. A story: unpaired adenosine bases in ribosomal RNAs. J Mol Biol. 2000; 304(3):335-54. Epub Nov. 25, 2000.doi: 10.1006/jmbi.2000.4172 S0022-2836(00)94172-X [pii]. PubMed PMID: 11090278.
Guth, S., et al. Dual function for U2AF(35) in AG-dependent pre-mRNA splicing. Mol Cell Biol. 2001;21(22):7673-81. PubMed PMID: 11604503.
Guy et al. A mouse Mecp2-null mutation causes neurological symptoms that mimic Rett syndrome. Nat Genet 27:322-326 (2001).
Hai, et al.: A G-tract element in apoptotic agents-induced alternative splicing. Nucleic Acids Res. Jun. 2008;36(10):3320-31. doi: 10.1093/nar/gkn207. Epub Apr. 24, 2008.
Hamdan, et al.: "Mutations in SYNGAP1 in autosomal nonsyndromic mental retardation, New England Journal of Medicine, 2009, vol. 360, No. 6, pp. 599-605".
Hamdan, F. F. et al. De Novo SYNGAP1 Mutations in Nonsyndromic Intellectual Disability and Autism, Biol. Psychiatry, 69:898-901 (2011).
Hammond, et al "Genetic therapies for RNA mis-splicing diseases" (2011) Cell Press 10 pages.
Han, et al.: "Antisense oligonucleotides increase Scn1a expression and reduce seizures and SUDEP incidence in a mouse model of Dravet syndrome" (2020) Science Translational Medicine, 12, pp. 1-14.
Han, et al.: "Antisense oligonucleotides increase Son1a expression and reduce seizures and SUDEP incidence in a mouse model of Dravet syndrome" Science Translational Medicine 12 (2020) pp. 1-14.
Han, et al.: "TANGO—Targeted Augmentation of Nuclear Gene Output for the Treatment of Genetic Diseases" Poster.
Han, et al. TANGO-Targeted augmentation of nuclear gene output for the treatment of genetic diseases. Poster session presented at the American Society of Gene and Cell Therapy, Chicago, IL. (May 2018).
Han Zhou et al: "Antisense-Mediated Increase of SCN1A Expression Using TANGO Technology for the Treatment of Dravet Syndrome", Molecular Therapy, vol. 27, No. 4, Suppl. 1, Apr. 22, 2019 (Apr. 22, 2019), pp. 304-305.
Hargous, et al. Molecular basis of RNA recognition and TAP binding by the SR proteins SRp20 and 9G8. EMBO J. Nov. 1, 2006;25(21):5126-37. Epub Oct. 12, 2006.
Harkin, et al. The spectrum of SCN1A-related infantile epileptic encephalopathies. Brain. Mar. 2007;130(Pt 3):843-52.
Hastings, M.L., et al. Control of pre-mRNA splicing by the general splicing factors PUF60 and U2AF. PLoS ONE. 2007;2:e538. PubMed PMID: 17579712.

(56) References Cited

OTHER PUBLICATIONS

Havens, et al.: "Targeting RNA Splicing forDisease Therapy" (2013) Wiley Interdiscip Rev RNA , 4(3): 247-266.
He, Y.H., et al. Association of the insulin-like growth factor binding protein 3 (IGFBP-3) polymorphism with longevity in Chinese nonagenarians and centenarians. Aging (Milano). 2014;6:944-56.
Hegele et al.: Dynamic protein-protein interaction wiring of the human spliceosome. Mol Cell. Feb. 24, 2012;45(4):567-80. doi: 10.1016/j.molcel.2011.12.034.
Hernan, I. et al. : Cellular Expression and siRNA-Mediated Interference of Rhodopsin cis-Acting Splicing Mutants Associated with Autosomal Dominant Retinitis Pigmentosa, Invest Ophthalmol. Vis. Sci. (2011) 52:3723-3729.
Heyn, P. et al.: Introns and gene expression: Cellular constraints, transcriptional regulation, and evolutionary consequences. Bioessays vol. 37, pp. 148-154 (2014).
Hiller et al. Pre-mRNA secondary structures influence exon recognition. PLoS genetics 3.11 (2007): e204.
Hirata et al.Prevention of Experimental Autoimmune Encephalomyelitis by Transfer of Embryonic Stem Cell-Derived Dendritic Cells Expressing Myelin Oligodendrocyte Glycoprotein Peptide along with TRAIL or Programmed Death-1 Ligand.J. Immunology vol. 174 pp. 1888-1897 (2005).
Hishida, A. et al.: Polymorphisms in PPAR Genes (PPARD, PPARG, and PPARGC1A) and the Risk of Chronic Kidney Disease in Japanese: Cross-Sectional Data from the J-MICC Study. PPAR 2013; 980471 pp. 1-8.
*Homo sapiens* pre-mRNA processing factor 3 (PRPF3), mRNA, NCBI Reference Sequence: NM_004698.2 Accessed Apr. 6, 2017.
Hua, et al.: Antisense correction of SMN2 splicing in the CNS rescues necrosis in a type III SMA mouse model. Genes Dev. Aug. 1, 2010;24(15):1634-44. doi: 10.1101/gad.1941310. Epub Jul. 12, 2010.
Hua et al.: Antisense masking of an hnRNP A1/A2 intronic splicing silencer corrects SMN2 splicing in transgenic mice. Am. J. Hum. Genet. 82:834-848 (Mar. 27, 2008).
Hua, Y., et al. Enhancement of SMN2 exon 7 inclusion by antisense oligonucleotides targeting the exon. PLoS Biol. 2007;5(4):e73. Epub Mar. 16, 2007.doi: 06-PLBI-RA-1492R3 [pii] 10.1371/journal.pbio.0050073. PubMed PMID: 17355180.
Hug, et al.: "Mechanism and regulation of the nonsense-mediated decay pathway", Nucleic Acids Research, 2016, vol. 44, No. 4 1483-1495.
Hunt, et al. Negligible impact of rare autoimmune-locus coding-region variants on missing heritability. Nature. Jun. 13, 2013;498(7453):232-5. doi: 10.1038/nature12170. Epub May 22, 2013.
Huynh, K.D., et al. BCoR, a novel corepressor involved in BCL-6 repression. Genes Dev. 2000;14(14):1810-23. PubMed PMID: 10898795; PubMed Central PMCID: PMC316791.
International Application No. PCT/GB2015/051756 International Preliminary Report on Patentability, Dec. 26, 2016.
International Application No. PCT/GB2015/051756 International Search Report and Written Opinion Mailed Nov. 30, 2015.
International Application No. PCT/GB2016/053136 International Search Report and Written Opinion Mailed Mar. 6, 2017.
International Application No. PCT/GB2016/053136 Partial International Search Report Mailed Jan. 19, 2017.
International Application No. PCT/US16/66576 International Search Report and Written Opinion Mailed May 4, 2017.
International Application No. PCT/US16/66691 International Search Report and Written Opinion Mailed May 10, 2017.
International Application No. PCT/US16/66708 International Search Report and Written Opinion Mailed May 8, 2017.
International Application No. PCT/US16/66721 International Search Report and Written Opinion mailed May 1, 2017.
International Application No. PCT/US2015/053896 International Preliminary Report on Patentability Mailed Apr. 4, 2017.
International Application No. PCT/US2015/53896 International Search Report and Written Opinion dated Mar. 3, 2016.
International Application No. PCT/US2016/066414 International Search Report and Written Opinion Mailed Apr. 19, 2017.
International Application No. PCT/US2016/066417 International Search Report and Written Opinion Mailed Apr. 19, 2017.
International Application No. PCT/US2016/066564 International Search Report and Written Opinion Mailed May 4, 2017.
International Application No. PCT/US2016/066705 International Search Report and Written Opinion Mailed Apr. 24, 2017.
International Application No. PCT/US2018/048031 International Search Report and Written Opinion Mailed Jan. 22, 2019.
International Preliminary Report on Patentability issued in PCT/US2021/030254, dated Nov. 15, 2022.
International search report and written opinion dated Jun. 5, 2017 for PCT Application No. PCT/US2016/066684.
International search report and written opinion dated Jun. 26, 2020 for PCT Application No. PCT/US20/20175.
International Search Report and Written Opinion for corresponding PCT application PCT/GB2016/053136 issued Jan. 19, 2017.
International Search Report and Written Opinion issued in PCT/US2021/030254, mailed Jul. 28, 2021.
International Search Report and Written Opinion dated Mar. 28, 2019 for PCT/US2018/057165.
Itoh et al.: Methyl CpG-binding Protein Isoform MeCP2_e2 Is Dispensable for Rett Syndrome Phenotypes but Essential for Embryo Viability and Placenta Development. J Biol Chem 287:13859-13867 (2012).
Iwamoto, et al.: Transcription-dependent nucleolar cap localization and possible nuclear function of DExH RNA helicase RHAU. Exp Cell Res. Apr. 1, 2008;314(6):1378-91. doi: 10.1016/j.yexcr.2008.01.006. Epub Jan. 16, 2008.
Jacob et al.: Intron retention as a component of regulated gene expression programs. Hum Genet 136:1043-1057 (2017).
Jarver, P. et al.: "A Chemical View of Oligonucleotides for Exon Skipping and Related Drug Applications," Nucleic Acid Therapeutics, 2014, vol. 24, No. 1, pp. 37-47.
Jearawiriyapaisarn et al. Sustained Dystrophin Expression Induced by Peptide-conjugated Morpholino Oligomers in the Muscles of mdx Mice. Mol Ther. 16(9): 1624-1629 (2008).
JP 2018-529250 Notice of Reasons for Rejection dated Nov. 19, 2020.
Jurka et al. Identification of new medium reiteration frequency repeats in the genomes of Primates, Rodentia and Lagomorpha. Genetica98.3 (1996): 235-247.
Jurkiewicz, D. et al.: Spectrum of JAG1 gene mutations in Polish patients with Alagille syndrome J. Appl. Genetics vol. 55, pp. 329-336, (2014).
Kach et al. A novel antisense oligonucleotide approach to treat eye diseases by increasing target gene expression. No. 3423-A0194 ARVO Poster Apr. 19, 2019 (1 pg.).
Kamakari, S. et al.: "First report of OPA1 screening in Greek patients with autosomal dominant optic atrophy and identification of a previously undescribed OPA1 mutation, Molecular Vision, 2014, vol. 20, pp. 691-703".
Kaminker, P.G., et al. A novel form of the telomere-associated protein TIN2 localizes to the nuclear matrix. Cell Cycle. 2009;8(6):931-9. PubMed PMID: 19229133; PubMed Central PMCID: PMC2751576.
Kang et al. Up-regulation of luciferase gene expression with antisense oligonucleotides: implications and applications in functional assay development. Biochemistry 37.18 (1998): 6235-6239.
Kaplan et al. Medium reiteration frequency repetitive sequences in the human genome. Nucleic acids research 19.17 (1991): 4731-4738.
Katsani, K.R. et al.: Functional Genomics Evidence Unearths New Moonlighting Roles of Outer Ring Coat Nucleoporins Scientific Reports vol. 4, No. 4655 (Apr. 11, 2014).
Kawamata, N., et al. Genetic differences between Asian and Caucasian chronic lymphocytic leukemia. Int J Oncol. 2013;43(2):561-5. doi: 10.3892/ijo.2013.1966. PubMed PMID: 23708256; PubMed Central PMCID: PMC3775563.
Ke, et al.: Quantitative evaluation of all hexamers as exonic splicing elements. Genome Res. Aug. 2011;21(8):1360-74. doi: 10.1101/gr.119628.110. Epub Jun. 9, 2011.

(56) References Cited

OTHER PUBLICATIONS

Keir, M.E. et al.: PD-1 and Its Ligands in Tolerance and Immunity. Annu. Rev. Immunol. vol. 26, pp. 677-704 (2008).
Kervestin et al. NMD: a multifaceted response to premature translational termination. Nature reviews Molecular cell biology13.11 (2012): 700.
Kikin, et al.: QGRS Mapper: a web-based server for predicting G-quadruplexes in nucleotide sequences. Nucleic Acids Res. Jul. 1, 2006;34(Web Server issue):W676-82.
Kim, E., et al. SRSF2 Mutations Contribute to Myelodysplasia by Mutant-Specific Effects on Exon Recognition. Cancer Cell. 2015;27(5):617-30. doi: 10.1016/j.ccell.2015.04.006. PubMed PMID: 25965569; PubMed Central PMCID: PMC4429920.
Kim et al.: ChimerDB 2.0—a knowledgebase for fusion genes updated. Nucleic Acids Res. 2009;38(Database issue):D81-5. Epub Nov. 13, 2009.doi: gkp982 [pii] 10.1093/nar/gkp982. PubMed PMID: 19906715.
Kim, et al. "Reduced Sodium Channel nav1.1 Levels in BACE1-NULL Mice", JBC (2010) 1-21.
Kim et al. The role of synaptic GTPase-activating protein in neuronal development and synaptic plasticity. J. Neurosci. 23(4):1119-1124 (Feb. 15, 2003).
Kim et al.: The splicing factor U2AF65 stabilizes TRF1 protein by inhibiting its ubiquitin-dependent proteolysis. Biochem Biophys Res Commun. 2014;443(3):1124-30. doi: 10.1016/j.bbrc.2013.12.118. PubMed PMID: 24389012.
Knudsen et al. Increased skewing of X chromosome inactivation in Rett syndrome patients and their mothers. Eur J Hum Genet 14:1189-1194 (2006).
Kole, et al. RNA therapeutics: beyond RNA interference and antisense oligonucleotides. Nat Rev Drug Discov. Jan. 20, 2012;11(2):125-40. doi: 10.1038/nrd3625.
Kralovicova, et al.: "Optimal antisense target reducing INS intron 1 retention is adjacent to a parallel G quadruplex" (2014) Nucleic Acids Research, v. 42, n. 12, p. 8161-8173.
Kralovicova, et al.: Allele-specific recognition of the 3' splice site of INS intron 1. Hum Genet. Oct. 2010;128(4):383-400. doi: 10.1007/s00439-010-0860-1. Epub Jul. 14, 2010.
Kralovicova, et al.: Compensatory signals associated with the activation of human GC 5' splice sites. Nucleic Acids Res. Sep. 1, 2011;39(16):7077-91. doi: 10.1093/nar/gkr306. Epub May 23, 2011.
Kralovicova, et al.: "Exon-Centric Regulation of ATM expression is population-dependent and amenable to antisense modification by pseudoexon targeting", Scientific Reports (2016) p. 1-13.
Kralovicova et al.: Exon-centric regulation of ATM expression is population-dependent and amenable to antisense modification by pseudoexon targeting, Scientific Reports, 6:18741, doi:10.1038/srep18741, Jan. 6, 2016, 13 pages.
Kralovicova, et al.: "Global control of aberrant splice-site activation by auxiliary splicing sequences: evidence for a gradient in exon and intron definition", (2007) Nucleic Acids Research, v. 35, n. 19, p. 6399-6413.
Kralovicova, et al. Global control of aberrant splice-site activation by auxiliary splicing sequences: evidence for a gradient in exon and intron definition. Nucleic Acids Res. Oct. 2007; 35(19): 6399-6413.
Kralovicova, et al. Identification of U2AF(35)-dependent exons by RNA-Seq reveals a link between 3' splice-site organization and activity of U2AF-related proteins. Nucleic Acids Res. Apr. 20, 2015;43(7):3747-63. doi: 10.1093/nar/gkv194. Epub Mar. 16, 2015.
Kralovicova, et al. Optimal antisense target reducing INS intron 1 retention is adjacent to a parallel G quadruplex. Nucleic Acids Res. Jul. 2014;42(12):8161-73. doi: 10.1093/nar/gku507. Epub Jun. 17, 2014.
Kralovicova, et al. Phenotypic consequences of branch point substitutions. Hum Mutat. Aug. 2006;27(8):803-13.
Kralovicova, et al. Position-dependent repression and promotion of DQB1 intron 3 splicing by GGGG motifs. J Immunol. Feb. 15, 2006;176(4):2381-8.
Kralovicova, et al.: Variants in the human insulin gene that affect pre-mRNA splicing: is −23Hphl a functional single nucleotide polymorphism at IDDM2? Diabetes. Jan. 2006;55(1):260-4.
Kralovicova, et al. Antisense Oligonucleotides Modulating Activation of a Nonsense-Mediated RNA Decay Switch Exon in the ATM Gene.Nucleic Acid Ther. Dec. 1, 2016; 26(6): 392-400.
Kralovicova, J. et al. Branch sites haplotypes that control alternative splicing. Hum Mol Genet. 2004;13:3189-202.
Kralovicova, J. et al. The role of short RNA loops in recognition of a single-hairpin exon derived from a mammalian-wide interspersed repeat. RNA Biol. 2015;12(1):54-69. doi: 10.1080/15476286.2015.1017207. PubMed PMID: 25826413.
Kriaucionis et al.: The major form of MeCP2 has a novel N-terminus generated by alternative splicing. Nucleic Acids Res 32:1818-1823 (2004).
Krishnaraj et al. RettBASE: Rett syndrome database update. Hum Mutat 38:922-931 (2017).
Kwong et al. Identification of SCN1A and PCDH19 Mutations in Chinese Children with Dravet Syndrome. PloS one, vol. 7, Issue, 7, Jul. 2012: e41802.
Laceerra, et al.: "Restoration of hemoglobin A synthesis in erythroid cells from peripheral blood of thalassemic patients" (2000) PNAS, vol. 97, No. 17, pp. 9591-9596.
Lander, et al. Initial sequencing and analysis of the human genome. Nature 409:860-921 (Feb. 15, 2001).
Laplanche, L.A. et al.: "Phosphorothioate-modified oligodeoxyribonucleotides. III. NMR and UV spectroscoptc studies of the Rp-Rp, Sp-Sp, and Rp-Sp duplexes, [d(GGSAATTCC)]2, derived from diastereomeric O-ethyl phosphorothioates," Nucleic Acids Res., 1986, vol. 14, No. 22, pp. 9081-9083.
Le Gal, et al.: "A case of SUDEP in a patient with Dravet syndrome with SCNIA mutation" (2010) Epilepsia, 5199): 1915-1918.
Le Hir, et al. How introns influence and enhance eukaryotic gene expression. Trends Biochem Sci. Apr. 2003;28(4):215-20.
Lee et al.: The Consensus 5' Splice Site Motif Inhibits mRNA Nuclear Export.PLoS One vol. 10, No. 3, p. e0122743 (Mar. 31, 2015).
Lee, J., et al.: Metastasis of neuroendocrine tumors are characterized by increased cell proliferation and reduced expression of the ATM gene. PLoS ONE. 2012;7:e34456.
Lefave, et al.: "Splicing factor hnRNPH drives an oncogenic splicing switch in gliomas",(2011) The EMBO Journal, vol. 30, No. 19, pp. 4084-4097.
Le Hir, H. et al.: 5'-End RET Splicing: Absence of Variants in Normal Tissues and Intron Retention in Pheochromocytomas, Oncology 63:84-91 (2002).
Lei et al. Exonization of Alu Ya5 in the human ACE gene requires mutations in both 3' and 5' splice sites and is facilitated by a conserved splicing enhancer. Nucleic acids research 33.12 (2005): 3897-3906.
Lei, et al.: Identification of splicing silencers and enhancers in sense Alus: a role for pseudoacceptors in splice site repression. Mol Cell Biol. Aug. 2005;25(16):6912-20.
Lemaire, M., et al. CDC25B phosphorylation by p38 and MK-2. Cell Cycle. 2006;5(15):1649-53. PubMed PMID: 16861915.
Lenaers, G. et al.: "Dominant optic atrophy," Orphanet J Rare Diseases, 2012, vol. 7, No. 46, pp. 1-12.
Levin, et al.: "Treating Disease at the RNA Level with Oligonucleotides" (2019) The New England Journal of Medicine 380:57-70.
Lev-Maor et al. Intronic Alus influence alternative splicing. PLoS genetics 4.9 (2008): e1000204.
Lev-Maor et al. The birth of an alternatively spliced exon: 3'splice-site selection in Alu exons. Science 300.5623 (2003): 1288-1291.
Levy et al.TranspoGene and microTranspoGene: transposed elements influence on the transcriptome of seven vertebrates and invertebrates. Nucleic acids research 36.suppl_1 (2007): D47-D52.
Li et al. JAG1 Mutation Spectrum and Origin in Chinese Children with Clinical Features of Alagille Syndrome. PLoS One 10(6):e0130355 (2015).
Li et al. PD-L1-Driven Tolerance Protects Neurogenin3-Induced Islet Neogenesis to Reverse Established Type 1 Diabetes in NOD Mice.Diabetes vol. 64, pp. 529-540 (Feb. 2015; epub Oct. 20, 2014).

(56) References Cited

OTHER PUBLICATIONS

Liang et al. Short intronic repeat sequences facilitate circular RNA production. Genes & development (2014): gad-251926.
Liang, et al.: "Translation efficiency of mRNAs is increased by antisense oligonucleotides targeting upstream open reading frames" (2016) Nature Biotechnology, V. 34, N. 8, p. 875-882.
Liang, Xue-Hai et al.: Translation efficiency of mRNAs is increased by antisense oligonucleotides targeting upstream open reading frames, Nature Biotechnology, 34(8):875-882 (Aug. 2016).
Lianoglou, S., et al. Ubiquitously transcribed genes use alternative polyadenylation to achieve tissue-specific expression. Genes Dev. 2013;27(21):2380-96. Epub Oct. 23, 2013.doi: gad.229328.113 [pii] 10.1101/gad.229328.113. PubMed PMID: 24145798.
Lim et al. A computational analysis of sequence features involved in recognition of short introns. Proceedings of the National Academy of Sciences98.20 (2001): 11193-11198.
Lim, et al.: "Antisense oligonucleotide modulation of non-productive alternative splicing upregulates gene expression" (2020) Nature Communication.
Litchfield, D.W., et al. Pin1: Intimate involvement with the regulatory protein kinase networks in the global phosphorylation landscape. Biochem Biophys Acta. 2015. doi: 10.1016/j.bbagen.2015.02.018. PubMed PMID: 25766872.
Liu et al. Alternative splicing and retinal degeneration. Clinical Genetics 84(2):142-149 (2013).
Llorian et al. Position-dependent alternative splicing activity revealed by global profiling of alternative splicing events regulated by PTB. Nature structural & molecular biology 17.9 (2010): 1114.
Lo, et al.: "ATM polymorphisms and risk of lung cancer among never smokers", (2010) Lund Cancer 69, p. 148-154.
Lo, YL et al. ATM Polymorphisms and risk of lung cancer among never smokers, Lung Cancer 69(2):148-154 (2010).
Long et al.: Correction of diverse muscular dystrophy mutations in human engineered heart muscle by single-site genome editing. Sci Adv 4:eaap9004 (2018).
Lorenz, et al. 2D meets 4G: G-Quadruplexes in RNA Secondary Structure Prediction. IEEE/ACM Trans Comput Biol Bioinform. Jul.-Aug. 2013;10(4):832-44. doi: 10.1109/TCBB.2013.7.
Lu, F.: Conditional JAG1 Mutation Shows the Developing Heart Is More Sensitive Than Developing Liver to JAG1 Dosage. Am. J. Hum. Genet. vol. 72, pp. 1065-1070 (2003).
Ludecke et al. Recessively inherited L-DOPA-responsive parkinsonism in infancy caused by a point mutation (L205P) in the tyrosine hydroxylase gene Hum. Mol. Genet. vol. 5, pp. 1023-1028, (1996).
Luo et al.: Palmitic Acid Suppresses Apolipoprotein M Gene Expression via the Pathway of PPARb/d in HepG2 Cells. Biochemical and Biophysical Research Communications, 445(1):203-207 (Feb. 2014).
Magi-Galuzzi, C. et al. TMPRSS2-ERG gene fusion prevalence and class are significantly difference in prostate cancer of Caucasian, African-American and Japanese patients. The Prostate. 2011;71:489-97.
Makishima, et al. Mutations in the spliceosome machinery, a novel and ubiquitous pathway in leukemogenesis. Blood. Apr. 5, 2012;119(14):3203-10. doi: 10.1182/blood-2011-12-399774. Epub Feb. 9, 2012.
Maniatis et al. An extensive network of coupling among gene expression machines. Nature 416.6880 (2002): 499.
Mansouri, S. et al.: Epstein-Barr Virus EBNA1 Protein Regulates Viral Latency through Effects on let-7 MicroRNA and Dicer. Journal of Virology, vol. 88, No. 19, pp. 11166-11177, (Oct. 2014).
Mantegazza et al.: Identification of a Nav1.1 sodium channel (SCN1A) loss-of-function mutation associated with familial simple febrile seizures, PNAS, Dec. 13, 2005, vol. 102, No. 50, p. 18177-18182.
Marcel, et al. G-quadruplex structures in TP53 intron 3: role in alternative splicing and in production of p53 mRNA isoforms. Carcinogenesis. Mar. 2011;32(3):271-8. doi: 10.1093/carcin/bgq253. Epub Nov. 26, 2010.
Marquez, Y. et al. Unmasking alternative splicing inside protein-coding exons defines exitrons and their role inproteome plasticity. Genome vol. 25, pp. 995-1007 (2015).
Martinez-Losa, et al. "Nav1.1-Overexpressing Interneuron Transplants Restore Brain Tyhthms and Cognition in a Mouse Model of Alzheimer's Disease", Neuron. Apr. 4, 2018; 98(1): 75-89.
Matsuoka et al. ATM and ATR substrate analysis reveals extensive protein networks responsive to DNA damage. Science 316(5828):1160-1166 (2007).
Matsuoka, S., et al. Ataxia telangiectasia-mutated phosphorylates Chk2 in vivo and in vitro. Proc Natl Acad Sci USA. 2000;97:10389-94.
Mayeda, et al. Surveying cis-acting sequences of pre-mRNA by adding antisense 2'-O-methyl oligoribonucleotides to a splicing reaction. J Biochem. Sep. 1990;108(3):399-405.
Mckie et al. Mutations in the pre-mRNA splicing factor gene PRPC8 in autosomal dominant retinitis pigmentosa (RP13). Human Molecular Genetics 10(15):1555-1562 (2001).
Melhuish, et al. The Tgif2 gene contains a retained intron within the coding sequence, BMC Molecular Biology 7(2);1-10 (2006).
Melko, et al. Functional characterization of the AFF (AF4/FMR2) family of RNA-binding proteins: insights into the molecular pathology of FRAXE intellectual disability. Hum Mol Genet. May 15, 2011;20(10):1873-85. doi: 10.1093/hmg/ddr069. Epub Feb. 17, 2011.
Mendell, J.T., ap Rhys CM, Dietz HC. Separable roles for rent1/hUpf1 in altered splicing and decay of nonsense transcripts. Science. 2002;298(5592):419-22. Epub Sep. 14, 2002.doi: 10.1126/science.1074428 1074428 [pii]. PubMed PMID: 12228722.
Menzi, et al.: "Towards Improved Oligonucleotide Therapeutics Through Faster Target Binding Kinetics", (2017) ChemPubSoc Europe, 23, p. 14221-14230.
Merendino, L., et al. Inhibition of msl-2 splicing by Sex-lethal reveals interaction between U2AF35 and the 3' splice site AG. Nature. 1999;402(6763):838-41. PubMed PMID: 10617208.
Michael, et al. Mfold web server for nucleic acid folding and hybridization prediction. Nucleic Acids Research. 31 (2003): 3406-3415.
Miller at al. 1993-2015 GeneReviews Eds. Pagon RA et al. Seattle (WA); University of WA, Seattle Bookshelf ID NBK1318.
Millevoi, et al. G-quadruplexes in RNA biology. Wiley Interdiscip Rev RNA. Jul.-Aug. 2012;3(4):495-507. doi: 10.1002/wrna.1113. Epub Apr. 4, 2012.
Min et al. Optimization of a novel series of ataxia-telangiectasia mutated kinase inhibitors as potential radiosensitizing agents. Journal of medicinal chemistry 59.2 (2016): 559-577.
Mirey, G., et al. CDC25B phosphorylated by pEg3 localizes to the centrosome and the spindle poles at mitosis. Cell Cycle. 2005;4(6):806-11. PubMed PMID: 15908796.
Mitelman, F., et al. The impact of translocations and gene fusions on cancer causation. Nat Rev Cancer. 2007;7(4):233-45. Epub Mar. 16, 2007.
Mnatzakanian et al. A previously unidentified MECP2 open reading frame defines a new protein isoform relevant to Rett syndrome. Nat Genet 36:339-341 (2004).
Mochizuki, T. et al. PKD2, a gene for polycystic kidney disease that encodes an integral membrane protein.Science vol. 272, pp. 1339-1342 (1996).
Montecucco, A., et al. Pre-mRNA processing factors meet the DNA damage response. Front Genet. 2013;4:102. doi: 10.3389/fgene.2013.00102. PubMed PMID: 23761808; PubMed Central PMCID: PMC3674313.
Moreno et al. Delivery of splice switching oligonucleotides by amphiphilic chitosan-based nanoparticles. Molecular pharmaceutics 13.2 (2016): 344-356.
Morris, et al. An RNA G-quadruplex is essential for cap-independent translation initiation in human VEGF IRES. J Am Chem Soc. Dec. 22, 2010;132(50):17831-9. doi: 10.1021/ja106287x. Epub Nov. 24, 2010.
Morrison, A.J., et al. Mec1/Tel1 phosphorylation of the INO80 chromatin remodeling complex influences DNA damage checkpoint responses. Cell. 2007;130(3):499-511. doi: 10.1016/j.cell.2007.06.010. PubMed PMID: 17693258.

(56) References Cited

OTHER PUBLICATIONS

Moskowitz, et al.: Mutation in Scheie syndrome (MPS IS): a G-->A transition creates new splice site in intron 5 of one IDUA allele, Hum. Mutat. 2(2):141-144 (1993).
Mulley et al. A new molecular mechanism for severe myoclonic epilepsy of infancy: Exonic deletions in SCN1A.Neurol. vol. 67, pp. 1094-1095 (2006).
Mulley et al. SCN1A mutations and epilepsy. Hum. Muta. vol. 25, pp. 535-542 (2005).
Murray, S.F. et al. Allele-Specific Inhibition of Rhodopsin with an Antisense Oligonucleotide Slows Photoreceptor Cell Degeneration, Invest Ophthalmol. Vis. Sci. 56:6362-6375 (Oct. 2015).
Neidle, S. and Balasubramanian, S. (2006) Quadruplex Nucleic Acids. RSC Biomolecular Sciences, Cambridge, UK.
Nemeroff et al. Identification of cis-acting intron and exon regions in influenza virus NS1 mRNA that inhibit splicing and cause the formation of aberrantly sedimenting presplicing complexes. Molecular and cellular biology 12.3 (1992): 962-970.
Nguyen, L.A., et al. Physical and functional link of the leukemia-associated factors AML1 and PML. Blood. 2005;105(1):292-300. doi: 10.1182/blood-2004-03-1185. PubMed PMID: 15331439.
Nishi, M. et al. Insulin gene mutations and diabetes. Journal of Diabetes Investigation vol. 2 Issue 2 (Apr. 2011).
Nishida, A. et al. Tissue- and Case-specific retention of intron 40 in mature dystrophin mRNA, Journal of Human Genetic 60;327-333 (2015).
Nisole, S., et al. Differential Roles of PML Isoforms. Front Oncol. 2013;3:125. doi: 10.3389/fonc.2013.00125. PubMed PMID: 23734343; PubMed Central PMCID: PMC3660695.
Nomakuchi et al. Antisense-oligonucleotide-directed inhibition of nonsense-mediated mRNA decay. Nat. Biotechnol. 34(2):164-166 (Feb. 2016).
Nozu et al. Alport syndrome caused by a COL4A5 deletion and exonization of an adjacent AluY. Molecular genetics & genomic medicine 2.5 (2014): 451-453.
Nussinov. Conserved quartets near 5' intron junctions in primate nuclear pre-mRNA. J Theor Biol. Jul. 8, 1988;133(1):73-84.
Oda, T. et al. Identification and cloning of the human homolog (JAG) of the rat Jagged1 gene from the Alagille syndrome critical region at 20p12.Genomics vol. 43, No. 3, pp. 376-379 (1997).
Office Action issued in European Patent Application No. 18871437.2 dated Sep. 12, 2023.
Ogiwara et al. Nav1.1 Localizes to Axons of Parvalbumin-Positive Inhibitory Interneurons: A Circuit Basis for Epileptic Seizures in Mice Carrying an Scn1a Gene Mutation. The Journal of Neuroscience 27(22):5903-5914 (May 30, 2007).
Okazaki, T. et al. PD-1 and PD-1 ligands: from discovery to clinical application. International Immunology(The Japanese Society for Immunology), vol. 19, No. 7, pp. 813-824, (2007).
Oustric, V. et al. Antisense oligonucleotide-based therapy in human erythropoietic protoporphyria. Am J Hum Genet. 2014;94(4):611-7. doi: 10.1016/j.ajhg.2014.02.010. PubMed PMID: 24680888; PubMed Central PMCID: PMC3980518.
Pacheco, et al. Diversity of vertebrate splicing factor U2AF35: identification of alternatively spliced U2AF1 mRNAS. J Biol Chem. Jun. 25, 2004;279(26):27039-49. Epub Apr. 19, 2004.
Pacheco, et al. RNA interference knockdown of hU2AF35 impairs cell cycle progression and modulates alternative splicing of Cdc25 transcripts. Mol Biol Cell. Oct. 2006; 17(10):4187-99. Epub Jul. 19, 2006.
Page-Mccaw, P.S., et al. PUF60: a novel U2AF65-related splicing activity. RNA. 1999;5(12):1548-60. PubMed PMID: 10606266.
Palazzo et al. Non-coding RNA: what is functional and what is junk?. Frontiers in genetics 6 (2015): 2.
Pandit et al. Genome-wide analysis reveals SR protein cooperation and competition in regulated splicing. Molecular cell 50.2 (2013): 223-235.
Papaemmanuil, et al. Clinical and biological implications of driver mutations in myelodysplastic syndromes. Blood. Nov. 21, 2013;122(22):3616-27; quiz 3699. doi: 10.1182/blood-2013-08-518886. Epub Sep. 12, 2013.
Parihar, et al.: "The SCN1A gene variants and epileptic encephalophathies", Journal of Human Genetics (2013) 58, 573-580.
Passamonti, C. et al. A novel inherited SCN1A mutation associated with different neuropsychological phenotypes: Is there a common core deficit? Epilepsy & Behavior 43:89-92 (2015).
Pastor, et al. Interaction of hnRNPA1/A2 and DAZAP1 with an Alu-derived intronic splicing enhancer regulates ATM aberrant splicing. PLoS One. 2011;6(8):e23349. doi: 10.1371/journal.pone.0023349. Epub Aug. 8, 2011.
Pastor, F., et al. Induction of tumour immunity by targeted inhibition of nonsense-mediated mRNA decay. Nature. 2010;465(7295):227-30. doi: 10.1038/nature08999. PubMed PMID: 20463739; PubMed Central PMCID: PMC3107067.
Paz, A., et al. SPIKE: a database of highly curated human signaling pathways. Nucleic Acids Res. 2011;39(Database issue):D793-9. doi: 10.1093/nar/gkq1167. PubMed PMID: 21097778; PubMed Central PMCID: PMC3014840.
PCT/US2021/030254 International Search Report and Written Opinion dated Jul. 28, 2023.
Pear, Warren S.: New roles for Notch in tuberous sclerosis, Journal of Clinical Investigation, 120(1):84-87 (Jan. 4, 2010).
Pecarelli et al. Regulation of natural mRNAs by the nonsense-mediated mRNA decay pathway. Eukaryotic cell(2014): EC-00090.
Pellagatti, A., et al. Deregulated gene expression pathways in myelodysplastic syndrome hematopoietic stem cells. Leukemia. 2010;24(4):756-64. doi: 10.1038/leu.2010.31. PubMed PMID: 20220779.
Peng, et al. Functional importance of different patterns of correlation between adjacent cassette exons in human and mouse. BMC Genomics. Apr. 26, 2008;9:191. doi: 10.1186/1471-2164-9-191.
Penton, A.L.Notch signaling in humandevelopment and disease. Seminars in Cell & Developmental Biology. vol. 23, pp. 450-457 (2012).
Perdiguero, E., et al. Regulation of Cdc25C activity during the meiotic G2/M transition. Cell Cycle. 2004;3(6):733-7. PubMed PMID: 15136768.
Piaceri, I., et al. Ataxia-telangiectasia mutated (ATM) genetic variant in Italian centenarians. Neurophysiology. 2013;34:573-5.
Pilia et al. Jagged-1 mutation analysis in Italian Alagille syndrome patients. Hum Mut 14(5):394-400 (1999).
Pomentel et al. A dynamic intron retention program enriched in RNA processing genes regulates gene expression during terminal erythropoiesis. Nucleic acids research 44.2 (2015): 838-851.
Precursor mRNA-Processing Factor 3, S. Cerevisiae, Homolog Of; PRPF3m, 3 pages.
Przychodzen, B., et al. Patterns of missplicing due to somatic U2AF1 mutations in myeloid neoplasms. Blood. 2013;122:999-1006. Epub Jun. 19, 2013.doi: blood-2013-01-480970 [pii] 10.1182/blood-2013-01-480970. PubMed PMID: 23775717.
Pugliese, et al. The insulin gene is transcribed in the human thymus and transcription levels correlated with allelic variation at the Ins VNTR-IDDM2 susceptibility locus for type 1 diabetes. Nat Genet. Mar. 1997;15(3):293-7.
Raghavan, et al.: "The spliceosomal U1 snRNP component Mud1 is autoregulated by promoting premature cleavage and polyadenylation of its own transcript, The Nineteenth Annual Meeting of the RNA Society".
Rainey et al. Transient inhibition of ATM kinase is sufficient to enhance cellular sensitivity to ionizing radiation. Cancer research68. 18 (2008): 7466-7474.
Ramocki et al. The MECP2 duplication syndrome. Am J Med Genet A 152A:1079-1088 (2010).
Rangasamy et al.: Reduced neuronal size and mTOR pathway activity in the Mecp2 A140V Rett syndrome mouse model. F1000research 5:2269 (2016).
Ray, D. et al. A compendium of RNA-binding motifs for decoding gene regulation. Nature. vol. 499, No. 7457, pp. 172-177 (Jul. 11, 2013).

(56) References Cited

OTHER PUBLICATIONS

Reineke, E.L., et al. Degradation of the tumor suppressor PML by Pin1 contributes to the cancer phenotype of breast cancer MDA-MB-231 cells. Mol Cell Biol. 2008;28(3):997-1006. doi: 10.1128/MCB.01848-07. PubMed PMID: 18039859; PubMed Central PMCID: PMC2223389.
Rendu, J. et al. Hum Gene Ther. Exon skipping as a therapeutic strategy applied to an RYR1 mutation with pseudo-exon inclusion causing a severe core myopathy. Jul. 2013;24(7):702-13. doi: 10.1089/hum.2013.052.
Reynolds, DM et al.Aberrant Splicing in the PKD2 Gene as a Cause of Polycystic Kidney Disease.Am. Soc. Nephrol. vol. 10, pp. 2342-2351 (1999).
Ritprajak et al. Keratinocyte-Associated B7-H1 Directly Regulates Cutaneous Effector CD8+ T Cell Responses.J Immunology vol. 184, pp. 4918-4925 (2010).
RNA 2-14 The Nineteenth Annual Meeting of the RNA Society. Quebec City, Canada. (Jun. 3-8, 2014).
Roberts, Jennifer et al. Efficient and Persistent Splice Switching by Systemically Delivered LNA Oligonucleotides in Mice. Molecular Therapy, Nature Publishing, vol. 14, No. 4, pp. 471-475, Oct. 1, 2006.
Romero, P.R., et al. Alternative splicing in concert with protein intrinsic disorder enables increased functional diversity in multicellular organisms. Proc Natl Acad Sci USA. 2006;103(22):8390-5. Epub 2006/05/24.doi: 0507916103 [pii] 10.1073/pnas.0507916103. PubMed PMID: 16717195.
Rosenbloom et al. The UCSC Genome Browser database: 2015 Update. Nucleic Acids Research 43, Database Issue doi:101093/nar/gku1177.
Ruchlemer, R. et al.: Geography, ethnicity and "roots" in chronic lymphocytic leukemia. Leuk Lymphoma. 2013;54(6):1142-50. doi: 10.3109/10428194.2012.740670. PubMed PMID: 23121522.
Rudd, M.F., et al. Variants in the ATM-BRCA2-CHEK2 axis predispose to chronic lymphocytic leukemia. Blood. 2006;108(2):638-44. Epub 2006/04/01.doi: 2005-12-5022 [pii] 10.1182/blood-2005-12-5022. PubMed PMID: 16574953.
Ruskin, et al. A factor, U2AF, is required for U2 snRNP binding and splicing complex assembly. Cell. Jan. 29, 1988;52(2):207-19.
Sadleir, et al. Not all SCN1A epileptic encephalopathies are Dravet syndrome. Neurology. Sep. 5, 2017; 89(10): 1-8.
Sahashi et al. Pathological impact of SMN2 mis-splicing in adult SMA mice. EMBO Mol. Med. 5(10):1586-601 (Oct. 2013).
Sahashi et al. TSUNAMI: an antisense method to phenocopy splicing-associated diseases in animals. Genes Dev. 26(16):1874-1884 (Aug. 15, 2012).
Sakabe, et al. Sequence features responsible for intron retention in human. BMC Genomics. Feb. 26, 2007;8:59.
Samatanga, et al. The high kinetic stability of a G-quadruplex limits hnRNP F qRRM3 binding to G-tract RNA. Nucleic Acids Res. Feb. 1, 2013;41(4):2505-16. doi: 10.1093/nar/gks1289. Epub Dec. 28, 2012.
Sazani, et al.: "Therapeutic potential of antisense oligonucleotides as modulators of alternative splicing" (2003) The Journal of clinical Investigation, 112(4):481-486.
Schanen et al.: A Severely Affected Male Born into a Rett Syndrome Kindred Supports X-Linked Inheritance and Allows Extension of the Exclusion Map. Am J Hum Genetics 63:267-269 (1998).
Scheffer, et al.: "SCN1A-related pehnotypes: Epilepsy and beyond" Epilepsia (2019);60(s3):S17-S24.
Schwarze, et al. Redefinition of exon 7 in the COL1A1 gene of type I collagen by an intron 8 splice-donor-site mutation in a form of osteogenesis imperfecta: influence of intron splice order on outcome of splice-site mutation. Am J Hum Genet. Aug. 1999;65(2):336-44.
Scott, S.P., et al. Missense mutations but not allelic variants alter the function of ATM by dominant interference in patients with breast cancer. Proc Natl Acad Sci USA. 2002;99:925-30.
SG 11201702682P Search Report and Written Opinion dated Apr. 9, 2018.
Shao, C., et al. Mechanisms for U2AF to define 3' splice sites and regulate alternative splicing in the human genome. Nat Struct Mol Biol. 2014;doi: 10.1038/nsmb.2906.
Shcherbakova, I., et al. Alternative spliceosome assembly pathways revealed by single-molecule fluorescence microscopy. Cell Rep. 2013;5(1):151-65. Epub Oct. 1, 2013.doi: S2211-1247(13)00467-1 [pii] 10.1016/j.celrep.2013.08.026. PubMed PMID: 24075986.
Shen, M., et al. Characterization and cell cycle regulation of the related human telomeric proteins Pin2 and TRF1 suggest a role in mitosis. Proc Natl Acad Sci USA. 1997;94(25):13618-23. PubMed PMID: 9391075; PubMed Central PMCID: PMC28355.
Shiloh, Y., et al The ATM protein kinase: regulating the cellular response to genotoxic stress, and more. Nat Rev Mol Cell Biol. 2013;14(4):197-210. doi: 10.1038/nrm3546. PubMed PMID: 23486281.
Shiria, C.L. et al. Mutant U2AF1 Expression Alters Hematopoiesis and Pre-mRNA Splicing In Vivo. Cancer Cell. 2015;27(5):631-43. doi: 10.1016/j.ccell.2015.04.008. PubMed PMID: 25965570; PubMed Central PMCID: PMC4430854.
Shirley, M.H., et al Incidence of haematological malignancies by ethnic group in England, 2001-7. Br J Haematol. 2013;163(4):465-77. doi: 10.1111/bjh.12562. PubMed PMID: 24033296.
Sierakowska, H et al. Repair of thalassemic human beta-globin mRNA in mammalian cells by antisense oligonucleotides. Proc Natl Acad Sci U S A. Nov. 12, 1996;93(23):12840-4.
Singh, et al. An antisense microwalk reveals critical role of an intronic position linked to a unique long-distance interaction in pre-mRNA splicing. RNA. Jun. 2010;16(6):1167-81. doi: 10.1261/rna.2154310. Epub Apr. 22, 2010.
Sirand-Pugnet, et al.: An intronic (A/U)GGG repeat enhances the splicing of an alternative intron of the chicken beta-tropomyosin pre-mRNA. Nucleic Acids Res. Sep. 11, 1995;23(17):3501-7.
Skjevik et al. The N-Terminal Sequence of Tyrosine Hydroxylase Is a Conformationally Versatile Motif That Binds 14-3-3 Proteins and Membranes. J. Mol. Bio. vol. 426, pp. 150-168 (2014).
Smith, C.W., et al. Scanning and competition between AGs are involved in 3' splice site selection in mammalian introns. Mol Cell Biol. 1993;13(8):4939-52. PubMed PMID: 8336728.
Smith, et al.: Alternative pre-mRNA splicing: the logic of combinatorial control. Trends Biochem Sci. 25(8):381-8 (2000).
Smith, et al.: Nonsense-mediated RNA decay-a switch and dial for regulating gene expression. Bioessays 37(6): 612-623 (2015).
Smith, P.J., et al. An increased specificity score matrix for the prediction of SF2/ASF-specific exonic splicing enhancers. Hum Mol Genet. 2006;15(16):2490-508. PubMed PMID: 16825284.
Soo, R.A., et al.: Ethnic differences in survival outcome in patients with advanced stage non-small cell lung cancer. J Thorac Oncol. 2011;6:1030-8.
Sorek et al. Minimal conditions for exonization of intronic sequences: 5' splice site formation in alu exons. Molecular cell 14.2 (2004): 221-231.
Soutar et al. Mechanisms of disease: genetic causes of familial hpercholesterolemia. Nat. Clin. Pract. Cardiovasc. Med. 4:214-255 (Apr. 1, 2007).
Spellman et al. Regulation of alternative splicing by PTB and associated factors. (2005): 457-460.
Spinner et al. Jagged1 mutations in alagille syndrome. Hum Mutat 17(1):18-33 (2001).
Stamm, S.: Regulation of alternative splicing by reversible protein phosphorylation. J Biol Chem. 2008;283(3):1223-7. PubMed PMID: 18024427.
Stankovic, T., et al.: Inactivation of ataxia telangiectasia mutated gene in B-cell chronic lymphocytic leukaemia. Lancet. 1999;353(9146):26-9. doi: 10.1016/S0140-6736(98)10117-4. PubMed PMID: 10023947.
Staropoli et al. Rescue of gene-expression changes in an induced mouse model of spinal muscular atrophy by an antisense oligonucleotide that promotes inclusion of SMN2 exon 7. Genomics 105:220-228 (2015).
Stead, et al. Global haplotype diversity in the human insulin gene region. Genome Res. Sep. 2003;13(9):2101-11.

(56) References Cited

OTHER PUBLICATIONS

Stec, W.J. et al.: "Automated solid-phase synthesis, separation, and stereochemistry of phosphorothioate analogs of oligodeoxyribonucleotides," J. Am. Chem. Soc., 1984, vol. 106, No. 20, pp. 6077-6079.
Stein, C.A. et al.: "Physicochemical properties of phosphorothioate oligodeoxynucleotides," Nucleic Acids Res., 1988, vol. 16, No. 8, pp. 3209-3221.
Stein et al.: FDA-Approved Oligonucleotide Therapies in 2017. Mol Ther 25:1069-1075 (2017).
Story, M.D. et al. ATM has a major role in the double-stand break repair pathway dysregulation in sporadic breast carcinomas and is an independent prognostic marker at both mRNA and protein levels, Breast Diseases: A Yearbook Quarterly, 26(4);297-299 (Mar. 17, 2015).
Strausfeld, U., et al. Activation of p34cdc2 protein kinase by microinjection of human cdc25C into mammalian cells. Requirement for prior phosphorylation of cdc25C by p34cdc2 on sites phosphorylated at mitosis. J Biol Chem. 1994;269(8):5989-6000. PubMed PMID: 8119945.
Suarez, F. et al. Incidence, presentation, and prognosis of malignancies in ataxia-telangiectasia: a report from the French national registry of primary immune deficiencies. J Clin Oncol. 2015;33(2):202-8. doi: 10.1200/JCO.2014.56.5101. PubMed PMID: 25488969.
Summerton, James. Morpholino Antisense Oligos: Applications in Biopharmaceutical Research Morpholinos constitute a radical redesign of DNA, providing decisive advantages over the more conventional oligo types used for modulating gene expression. Innovations in Pharmaceutical Technology Issue No. 17 (2005).
Sun, H., et al.: Multiple splicing defects in an intronic false exon. Mol Cell Biol. 2000;20(17):6414-25. PubMed PMID: 10938119.
Supplementary European Search Report dated Apr. 18, 2019 for EP16876615.2.
Svasti, et al. RNA repair restores hemoglobin expression in IVS2-654 thalassemic mice. Proc Natl Acad Sci U S A. Jan. 27, 2009; 106(4): 1205-1210.
Swaans, RJM et al. Four novel mutations in the Tyrosine Hydroxylase gene in patients with infantile parkinsonism Annals of Human Genetic, vol. 64, No. 1, pp. 25-31, (Jan. 2000).
Tabrez, S. et al.: A Synopsis of the Role of Tyrosine Hydroxylase in Parkinson's Disease. CNS & Neurological Disorders—Drug Targets vol. 11, No. 4 (2012).
Takahashi et al. Skewed X chromosome inactivation failed to explain the normal phenotype of a carrier female with MECP2 mutation resulting in Rett syndrome. Clin Genet 73:257-261 (2008).
Tavanez, J.P., et al. hnRNP A1 proofreads 3' splice site recognition by U2AF. Mol Cell. 2012;45(3):314-29. Epub Feb. 14, 2012. doi: S1097-2765(12)00032-9 [pii] 10.1016/j.molcel.2011.11.033. PubMed PMID: 22325350.
Taylor, A.M., et al. Ataxia telangiectasia: more variation at clinical and cellular levels. Clin Genet. 2015;87(3):199-208. doi: 10.1111/cge.12453. PubMed PMID: 25040471.
Taylor, A.M., et al.: Leukemia and lymphoma in ataxia telangiectasia. Blood. 1996;87(2):423-38. PubMed PMID: 8555463.
Thisted, et al. Optimized RNA targets of two closely related triple KH domain proteins, heterogeneous nuclear ribonucleoprotein K and alphaCP-2KL, suggest Distinct modes of RNA recognition. J Biol Chem. May 18, 2001;276(20):17484-96. Epub Feb. 2, 2001.
Tilgner, H. et al.: "Deep sequencing of subcellular RNA fractions shows splicing to be predominantly co-transcriptional in the human genome but inefficient for IncRNAs," Genome Research, 2012, vol. 22, No. 9, pp. 1616-1625.
Tillotson et al. Radically truncated MeCP2 rescues Rett syndrome-like neurological defects. Nature 550:398 (2017).
Torres, V.E. et al. Autosomal dominant polycystic kidney disease: the last 3 years. Kidney International vol. 76, pp. 149-168 (May 20, 2009).
Trabattoni et al.: Costimulatory Pathways in Multiple Disease Sclerosis: Distinctive Expression of PD-1 and PD-L1 in Patients with Different Patterns of Disease. J. Immunol. vol. 183, pp. 4984-4993 (2009).
Trapnell, C. et al. Differential gene and transcript expression analysis of RNA-seq experiments with Top Hat and Cufflinks. Nat Protoc. 2012;7(3):562-78. Epub Mar. 3, 2012.doi: nprot.2012.016 [pii] 10.1038/nprot.2012.016. PubMed PMID: 22383036.
Turnpenny, P.D. et al. Alagille syndrome: pathogenesis, diagnosis and management.European Journal of Human Genetics vol. 20, pp. 251-257 (2012.
Uhlmann, E. et al.: "Antisense oligonucleotides: a new therapeutic principle," Chemical Reviews, 1990, vol. 90, No. 4, pp. 543-584.
U.S. Appl. No. 14/741,071 Non-Final Office Action mailed Dec. 1, 2016.
U.S. Appl. No. 14/874,420 Non-Final Office Action Mailed Mar. 21, 2017.
U.S. Appl. No. 16/561,960 Pre-Interview First Office Action Mailed Dec. 19, 2019.
U.S. Appl. No. 14/874,420 Office Action dated Oct. 24, 2017.
U.S. Appl. No. 15/619,984 Office Action dated Dec. 17, 2018.
U.S. Appl. No. 15/949,902 Office Action dated Mar. 1, 2019.
U.S. Appl. No. 15/288,415 Office Action dated Jun. 26, 2018.
Vacher, et al.: "ATM has a major role in the double-strand break repair pathway dysregulation in sporadic breast carcinomas and is an independent prognostic marker at both mRNA and protein levels", (2015), Br J Cancer 112: 1059-1066.
Vafiadis, et al. Insulin expression in human thymus is modulated by INS VNTR alleles at the IDDM2 locus. Nat Genet. Mar. 1997;15(3):289-92.
Van Nostrand et al. Robust transcriptome-wide discovery of RNA-binding protein binding sites with enhanced CLIP (eCLIP). Nature methods 13.6 (2016): 508.
Van Wart, et al.: "Impaired Firing an dCell-Specific compensation in Neurons Lacking Navv1.6 sodium Channels" The Journal of Neuroscience, (2006), 26(27):7172-7180.
Venkatesh, A. et al.: "Antisense oligonucleotide mediated increase of OPA1 expression using TANGO technology for the treatment of autosomal dominant optic atrophy," Molecular Therapy, 2020, vol. 28, No. 4S1.
Venkatesh, A. et al.: "Antisense oligonucleotide mediated increase of OPA1 expression using TANGO technology for the treatment of autosomal dominant optic atrophy," ARVO Annual Meeting (Abrstract), 2020, vol. 61, No. 2755.
Verhaart, I.E.C. AON-Mediated Exon Skipping for Duchenne Muscular Dystrophy. Chapter 3. pp. 1-26 (Aug. 1, 2012).
Verret et al.: Inhibitory Interneuron Deficit Links Altered Network Activity and Cognitive Dysfunction in Alzheimer Model, Cell, 149(3): 708-721 (2012).
Vickers, et al.: "Fully modified 2' MOE oligonucleotides redirect polyadenylation", Isis Pharmaceuticals, Department of Molecular and Structural Biology, Nucleic Acids Research, 2001, vol. 29, No. 6 p. 1293-1299.
Vieira, N. et al.: Jagged 1Rescues the Duchenne Muscular Dystrophy Phenotype. Cell vol. 163, pp. 1204-1213 (Nov. 19, 2015).
Voelker, et al. A comprehensive computational characterization of conserved mammalian intronic sequences reveals conserved motifs associated with constitutive and alternative splicing. Genome Res. Jul. 2007;17(7):1023-33. Epub May 24, 2007.
Vorechovsky Correspondence Pediatric Research 2010.
Vorechovsky, I. Letter to the Editor: MER91B-assisted cryptic exon activation in Gitelman syndrome. Pediatric research 67.4 (2010): 444-445.
Vorechovsky, "Modulating Splicing-Mediated gene expression using antisense technology", Southhampton.sc.uk/business.
Vorechovsky Transposable elements in disease-associated cryptic exons. Human genetics 127.2 (2010): 135-154.
Wahl, et al. The spliceosome: design principles of a dynamic RNP machine. Cell. Feb. 20, 2009;136(4):701-18. doi: 10.1016/j.cell.2009.02.009.
Wan, W.B. et al.: "Synthesis, biophysical properties and biological activity of second generation antisense oligonucleotides containing

(56) References Cited

OTHER PUBLICATIONS chiral phosphorothioate linkages," Nucleic Acids Research, 2014, vol. 42, No. 22, pp. 13456-13468.
Wang, et al. A complex network of factors with overlapping affinities represses splicing through intronic elements. Nat Struct Mol Biol. Jan. 2013;20(1):36-45. doi: 10.1038/nsmb.2459. Epub Dec. 16, 2012.
Wang et al. Alternative isoform regulation in human tissue transcriptomes. Nature. 2008;456(November):470-476.
Wang et al. Human Adenovirus Type 36 Enhances Glucose Uptake in Diabetic and Nondiabetic Human Skeletal Muscle Cells Independent of Insulin Signaling. Diabetes vol. 57, pp. 1861-1869 (2008).
Wang, et al.: Intronic splicing enhancers, cognate splicing factors and context-dependent regulation rules. Nat Struct Mol Biol. Oct. 2012;19(10):1044-52. doi: 10.1038/nsmb.2377. Epub Sep. 16, 2012.
Wang, et al.: Regulation of insulin preRNA splicing by glucose. Proc Natl Acad Sci U S A. Apr. 29, 1997;94(9):4360-5.
Wang, Z. et al.: Systematic identification and analysis of exonic splicing silencers. Cell. 2004;119(6):831-45. PubMed PMID: 15607979.
Warf, M.B., et al.: Role of RNA structure in regulating pre-mRNA splicing. Trends Biochem Sci. 2010;35(3):169-78. Epub Dec. 5, 2009.doi: S0968-0004(09)00196-0 [pii].
Weiss, et al.: "Sodium channels SCN1A, SCN2A, SCN3A in familial autism", (2003) 8, p. 186-194.
Wieland, et al.: RNA quadruplex-based modulation of gene expression. Chem Biol. Jul. 2007;14(7):757-63.
Wilton, et al. Splice modification to restore functional dystrophin synthesis in Duchenne muscular dystrophy. Current pharmaceutical design 16.8 (2010): 988-1001.
Wong et al. Orchestrated intron retention regulates normal granulocyte differentiation. Cell 154.3 (2013): 583-595.
Wu et al. AT-AC Pre-mRNA Splicing Mechanisms and Conservation of Minor Introns in Voltage-Gated Ion Channel Genes. Molecular and Cellular Biology 19(5): 3225-3236 (May 1999).
Wu et al.: Functional recognition of the 3' splice site AG by the splicing factor U2AF35.Nature. 1999;402(6763):832-5. PubMed PMID: 10617206.
Wu et al.: MRE11-RAD50-NBS1 and ATM function as co-mediators of TRF1 in telomere length control. Nat Struct Mol Biol. 2007;14(9):832-40. doi: 10.1038/nsmb1286. PubMed PMID: 17694070.
Wu, J.Y., et al.: Specific interactions between proteins implicated in splice site selection and regulated alternative splicing. Cell. 1993;75(6):1061-70. Epub Dec. 17, 1993.doi: 0092-8674(93)90316-1 [pii]. PubMed PMID: 8261509.
Xia, Y. et al.: Frequencies of SF3B1, NOTCH1, MYD88, BIRC3 and IGHV mutations and TP53 disruptions in Chinese with chronic lymphocytic leukemia: disparities with Europeans. Oncotarget. 2015;6(7):5426-34. PubMed PMID: 25605254.
Xing, et al.: The multiassembly problem: reconstructing multiple transcript isoforms from EST fragment mixtures. Genome Res. Mar. 2004;14(3):426-41. Epub Feb. 12, 2004.
Yamamoto et al. Mib-Jag1-Notch signalling regulates patterning and structural roles of the notochord by controlling cell-fate decisions. Development 137(15):2527-2537 (2010).
Yamamoto, Y., et al. BCOR as a novel fusion partner of retinoic acid receptor alpha in a t(X;17)(p11;q12) variant of acute promyelocytic leukemia. Blood. 2010;116(20):4274-83. doi: 10.1182/blood-2010-01-264432. PubMed PMID: 20807888.
Yan, et al. Systematic discovery of regulated and conserved alternative exons in the mammalian brain reveals NMD modulating chromatin regulators. Proc Natl Acad Sci U S A. Mar. 17, 2015; 112(11): 3445-3450.
Yang et al.: Biophysical analysis and small-angle X-ray scattering-derived structures of MeCP2-nucleosome complexes. Nucleic Acids Res 39:4122-4135 (2011).
Yang, S. et al. PML-dependent apoptosis after DNA damage is regulated by the checkpoint kinase hCds1/Chk2. Nat Cell Biol. 2002;4(11):865-70. doi: 10.1038/ncb869. PubMed PMID: 12402044.
Yang, S., et al. Promyelocytic leukemia activates Chk2 by mediating Chk2 autophosphorylation. J Biol Chem. 2006;281(36):26645-54. doi: 10.1074/jbc.M604391200. PubMed PMID: 16835227.
Yang, Y. et al. Oligomerization of the polycystin-2 C-terminal tail and effects on its Ca2+binding properties. J. Bio. Chem. vol. 290, No. 16, pp. 10544-10554 (2015).
Yeo, et al.: Discovery and analysis of evolutionarily conserved intronic splicing regulatory elements. PLoS Genet. May 25, 2007;3(5):e85. Epub Apr. 13, 2007.
Yoshida, et al. Frequent pathway mutations of splicing machinery in myelodysplasia. Nature. Sep. 11, 2011;478(7367):64-9. doi: 10.1038/nature10496.
Yoshida, K., et al. Splicing factor mutations and cancer. Wiley Interdiscip Rev RNA. 2014;5(4):445-59. doi: 10.1002/wrna.1222. PubMed PMID: 24523246.
Young et al. 915—a GABA-Selective AAV Vector-Based Approach to Up-Regulate Endogenous Scn1a Expression reverses key Phenotypes in a Mouse Model of Dravet Syndrome. 22nd Annual Meeting American Society of Gene & Cell Therapy. Washington, D.C. Apr. 29-May 2, 2019 (Abstract).
Yu, E.Y., et al. Regulation of telomere structure and functions by subunits of the INO80 chromatin remodeling complex. Mol Cell Biol. 2007;27(16):5639-49. doi: 10.1128/MCB.00418-07. PubMed PMID: 17562861; PubMed Central PMCID: PMC1952117.
Yuan et al. Brain localization and neurotoxicity evaluation of polysorbate 80-modified chitosan nanoparticles in rats. PloS one 10.8 (2015): e0134722.
Yuan X., et al. Nuclear protein profiling of Jurkat cells during heat stress-induced apoptosis by 2-DE and MS/MS. Electrophoresis. 2007;28(12):2018-26. doi: 10.1002/elps.200600821. PubMed PMID: 17523140.
Zammarchi, et al. "Antitumorigenic potential of STAT3 alternative splicing modulation", (2011) PNAS, vol. 108, No. 43, pp. 17779-17784.
Zamore, P.D., et al. Identification, purification, and biochemical characterization of U2 small nuclear ribonucleoprotein auxiliary factor. Proc Natl Acad Sci USA. 1989;86(23):9243-7. PubMed PMID: 2531895.
Zarnack K., et al. Direct competition between hnRNP C and U2AF65 protects the transcriptome from the exonization of Alu elements. Cell. 2013;152(3):453-66. Epub Feb. 5, 2013.doi: S0092-8674(12)01545-0 [pii] 10.1016/j.cell.2012.12.023. PubMed PMID: 23374342.
Zhang C., et al. RNA landscape of evolution for optimal exon and intron discrimination. Proc Natl Acad Sci USA. 2008;105(15):5797-802. Epub 2008/04/09.doi: 0801692105 [pii] 10.1073/pnas.0801692105. PubMed PMID: 18391195.
Zhang et al.: Computational definition of sequence motifs governing constitutive exon splicing. Genes Dev. 2004;18:1241-50. PubMed PMID: 15145827.
Zhang, et al. Insulin as an autoantigen in NOD/human diabetes. Curr Opin Immunol. Feb. 2008;20(1):111-8. doi: 10.1016/j.coi.2007.11.005.
Zhang, et al.: The kinetics and folding pathways of intramolecular G-quadruplex nucleic acids. J Am Chem Soc. Nov. 21, 2012;134(46):19297-308. doi: 10.1021/ja309851t. Epub Nov. 12, 2012.
Zhang, J. et al.: "PowerBlast: A network application for automated analysis of large genomic sequences," Genome Methods, 1997, vol. 7, pp. 649-656.
Zimrin et al. An Antisense Oligonucleotide to the Notch Ligand Jagged Enhances Firbroblast Growth Factor-induced Angiogenesis in Vitro. J. Biol. Chem. 271(51):32499-502 (Dec. 20, 1996).
Zon et al. Phosphorothioate oligonucleotides: chemistry, purification, analysis, scale-up and future directions. Anti-Cancer Drug Design vol. 6, No. 6, pp. 539-568 (1991).
Zon et al. (1991) In Eckstein,F. (ed.), Oligonucleotides and Analogues: A Practical Approach. Oxford University Press, Oxford, UK, pp. 87-108.
Zorio, D.A., et al. Both subunits of U2AF recognize the 3' splice site in Caenorhabditis elegans. Nature. 1999;402(6763):835-8. PubMed PMID: 10617207.

(56) References Cited

OTHER PUBLICATIONS

Zuker, M. Mfold web server for nucleic acid folding and hybridization prediction. Nucleic Acids Res. 31, 3406-3415 (2003).
Arzimanoglou, A. et al.: A Review of the New Antiepileptic Drugs for Focal-Onset Seizures in Pediatrics: Role of Extrapolation, Pediatr. Drugs 20(3):249-64 (2018).
Berecki, G. et al.: SCN1A Gain of Function in Early Infantile Encephalopathy. Ann Neurol. 85:514-25 (2019).
Carvill, et al., "Aberrant Inclusion of a Poison Exon Causes Dravet Syndrome and Related SCN1A-Associated Genetic Epilepsies", The American Journal of Human Genetics, Vo. 103, No. 6, pp. 1022-1029 (2018).
"Cestele, S. et al., "Nonfunctional NaV1.1 familial hemiplegic migraine mutant transformed into gain of function by partial rescue of folding defects," Proc. Natl. Acad. Sci., 2013, vol. 110, No. 43, pp. 17546-51".
"Cheah, C. S. et al., "Correlations in timing of sodium channel expression, epilepsy, and sudden death in Dravet syndrome," Channels, 2013, vol. 7, No. 6, pp. 468-472".
"Cheah, C. S. et al., "Specific deletion of NaV1.1 sodium channels in inhibitory interneurons causes seizures and premature death in a mouse model of Dravet syndrome," PNAS, 2012, vol. 109, No. 36, pp. 14646-14651".
De-Lange et al.: Influence of contraindicated medication use on cognitive outcome in Dravet syndrome and age at first afebrile seizure as a clinical predictor in SCN1A-related seizure phenotypes, Epilepsia 59:1154-65 (2018).
"Depienne, C. et al., "Spectrum of SCN1A gene mutations associated with Dravet syndrome: analysis of 333 patients," J. Med Genet., 2009, vol. 46, pp. 183-191".
"Dhifallah, S. et al., "Gain of Function for the SCN1A/hNav1.1-L1670W Mutation Responsible for Familial Hemiplegic Migraine," Front Mol. Neurosci., 2018, vol. 11, No. 232, pp. 1-14".
"Djemie, T. et al., "Pitfalls in genetic testing: the story of missed SCN1A mutations," Mol Genet Genomic Med., 2016, vol. 4, No. 4, pp. 457-464".
European Patent Application No. 21209655.6 Search Report dated May 23, 2022.
"Fan, C. et al., "Early-onset familial hemiplegic migraine due to a novel SCN1A mutation," Cephalalgia, 2016, vol. 36, No. 13, pp. 1238-1247".
"Gataullina, S. et al., "From genotype to phenotype in Dravet disease," Seizure, 2017, vol. 44, pp. 58-64".
"Genton, P. et al., "Dravet syndrome: the long-term outcome," Epilepsia, 2011, vol. 52, Suppl 2, pp. 44-49".
Hsiao, J. et al., "Upregulation of Haploinsufficient Gene Expression in the Brain by Targeting a Long Non-coding RNA Improves Seizure Phenotype in a Model of Dravet Syndrome," EBioMedicine, 2016, vol. 9, pp. 257-277.
Khorkova et al., Oligonucleotide therapies for disorders of the nervous system. Nat Biotechnol. Mar. 2017;35(3):249-263. doi: 10.1038/nbt.3784. Epub Feb. 27, 2017. PMID: 28244991; PMCID: PMC6043900.
"Lagae, L. et al., "Quality of life and comorbidities associated with Dravet syndrome severity: a multinational cohort survey," Dev. Med. Child Neurol., 2018, vol. 60, No. 1, pp. 63-72".
"Liu, Y. et al., "Dravet syndrome patient-derived neurons suggest a novel epilepsy mechanism," Ann Neurol., 2013, vol. 74, No. 1, pp. 128-139".
Maljevic, et al., "Models for discovery of targeted therapy in genetic epileptic encephalopathies", Journal of Neurochemistry (2017) Vo. 143, No. 1, pp. 30-48.
"Meng, H. et al., "The SCN1A Mutation Database: Updating Information and Analysis of the Relationships among Genotype, Functional Alteration, and Phenotype," Hum Mutation, 2015, vol. 36, No. 6, pp. 573-580".
Minn; Alexandra H. et al.: Insulinomas and expression of an insulin splice variant. Lancet 363(9406):363-367 (2004). doi: 10.1016/S0140-6736(04)15438-X. Abstract.
Palhais, Bruno et al.: Splice-shifting oligonucleotide (SSO) mediated blocking of an exonic splicing enhancer (ESE) created by the prevalent c.903+469TC MTRR mutation corrects splicing and restores enzyme activity in patient cells. Nucleic Acids Research 43(9):4627. 4639 (2015). https://doi.org/10.1093/nar/gkv275.
"Ragona, F. et al., "Cognitive development in Dravet syndrome: A retrospective, multicenter study of 26 patients," Epilepsia, 2011, vol. 52, No. 2, pp. 386-392,".
Sazani, et al., "Splice Switching Oligonucleotides as Potential Therapeutics", Antisense Drug Technology, Second Edition, p. 90-114.
Sierakowska, et al., Repair of thalassemic human B-globin mRNA in mammalian cells by antisense oligonucleotides. PNAS 93: 12840-4 (1996).
Supplemental European Search Report issued in corresponding EP application No. 18848036 issued Apr. 15, 2021.
Takeshima Y et al.: Modulation of in vitro splicing of the upstream intron by modifying an intra-exon sequence which is deleted from the dystrophin gene in dystrophin Kobe. The Journal of Clinical Investigation 95(2):515-20 (1995). doi: 10.1172/JCI117693.
Tsuchiya, Teizo et al.: Evidence for the Essential Role of Myosin Subfragment-2 in the ATP-Dependent Actin-Myosin Sliding in Muscle Contraction. The Japanese Journal of Physiology 48(5):383-387 (1998). https://doi.org/10.2170/jjphysiol.48.383.
Abramova, Tatyana V. et al. Novel Oligonucleotide Analogues Based on Morpholino Nucleoside Subunits Antisense Technologies: New Chemical Possibilities. Indian Journal of Chemistry 48B:1721-1726 (2009).
Alanis, Eugenio F., et al., An exon-specific U1 small nuclear RNA (snRNA) strategy to correct splicing defects. Human Molecular Genetics 21(11):2389-2398 (2012). https://doi.org/10.1093/hmg/dds045.
Araujo et al.: Before It Gets Started: Regulating Translation at the 5' UTR. Comp Funct Genomics. 2012:475731 (2012) doi: 10.1155/2012/475731.
Boisguerin, P. et al. Delivery of therapeutic oligonucleotides with cell penetrating peptides. Advanced Drug Delivery Reviews 87:56-27 (2015).
Co-pending U.S. Appl. No. 18/658,390, inventors Aznarez; Isabel et al., filed May 8, 2024.
Co-pending U.S. Appl. No. 18/672,649, filed May 23, 2024.
EP16781187.6 European Second Office Action dated Feb. 24, 2023.
EP20763143.3 Extended European Search Report dated Nov. 13, 2023.
European Supplementary Search Report dated Sep. 20, 2023 issued in European Patent Application No. 20897381.
Gadgil, Ankur, et al., U7 snRNA: A tool for gene therapy. The Journal of Gene Medicine 23(4):e3321 (2021). https://doi.org/10.1002/jgm.3321.
Gong, Q. et al. Inhibition of nonsense-mediated mRNA decay by antisense morpholino oligonucleotides restores functional expression of hERG nonsense and frameshift mutations in long-QT syndrome. J Mol Cell Cardiol. 50(1):223-9 (2011).
Han et al.: Antisense-Mediated Increase of SCN1A Expression Using TANGO Technology for the Treatment of Dravet Syndrome. Molecular Therapy 22nd Annual Meeting of the American Society of Gene and Cell Therapy (ASGCT) 27(4):304-305 (2019).
Harris, et al. Single-molecule DNA sequencing of a viral genome. Science 320(5872):106-9 (2008).
Huppert et al.: Prevalence of quadruplexes in the human genome. Nucleic Acids Res. 33(9):2908-16 (2005).
Koizumi, Makoto. ENA Oligonucleotides as Therapeutics. Current Opinion in Molecular Therapeutics 8(2):144-149 (2006).
Kuzmiak, HA. et al. Applying nonsense-mediated mRNA decay research to the clinic: progress and challenges. Trends Mol Med. 12(7):306-16 (2006).
Lochmann, D. et al. Drug delivery of oligonucleotides by peptides. European Journal of Pharmaceutics and Biopharmaceutics 58: 237-251 (2004).
Margulies et al.: Genome sequencing in microfabricated high-density picolitre reactors. Nature. 437(7057):376-380 (2005).

(56) References Cited

OTHER PUBLICATIONS

Martin, L et al. Identification and characterization of small molecules that inhibit nonsense-mediated RNA decay and suppress nonsense p53 mutations. Cancer Res. 74(11):3104-13 (2014).
Meyer et al.: Antisense Derivatives of U7 Small Nuclear RNA as Modulators of Pre-mRNA Splicing. Alternative pre-mRNA Splicing: Theory and Protocols (2012). https://doi.org/10.1002/9783527636778.ch45.
Michaels, W. et al. Antisense oligonucleotide-mediated correction of CFTR splicing improves chloride secretion in cystic fibrosis patient-derived bronchial epithelial cells. Nucleic Acids Research 48(13): 7454-7467 (2020).
Mishra et al.: G4IPDB: A database for G-quadruplex structure forming nucleic acid interacting proteins. Sci Rep. 6:38144 pp. 1-9 (2016).
Obika, et al. "Synthesis of 2'-0,4'-C-methyleneuridine and -cytidine. Novel bicyclic nucleosides having a fixed C3, -endo sugar puckering". Tetrahedron Letters 38 (50): 8735 (1997).
PCT/US2016/066708 International Preliminary Report on Patentability dated Jun. 28, 2018.
PCT/US2020/063157 International Search Report and Written Opinion dated Mar. 10, 2021.
PCT/US2022/049318 International Search Report and Written Opinion dated Mar. 4, 2024 (Pub. No. WO2023086342).
PCT/US2023/029040 International Search Report and Written Opinion dated Feb. 16, 2024.
PCT/US2024/015838 International Search Report and Written Opinion dated Sep. 3, 2024.
Popp, MW et al. Attenuation of nonsense-mediated mRNA decay facilitates the response to chemotherapeutics. Nat Commun. 6(6632): 1-32 (2015).
Scheffer, Ingrid E. Diagnosis and Long-term Course of Dravet Syndrome. European Journal of Paediatric Neurology 16(Suppl 1):S5-S8 (2012).
Singh et al. Encyclopedia of Pharmaceutical Technology 2nd Ed. pp. 751-753 (2002).
Stefanovic et al.: Assemble, nuclear import and function of U7 snRNPs studied by microinjection of synthetic U7 RNA into Xenopus oocytes. Nucleic Acids Research 23(16):3141-3151 (1995). https://doi.org/10.1093/nar/23.16.3141.
Stoke Therapeutics Presents Data from the Phase 1/2a MONARCH Study of STK-001 in Children and Adolescents with Dravet Syndrome at the American Epilepsy Society (AES) 2021 Annual Meeting. Stoke Therapeutics. American Epilepsy Society (AES) 2021 Annual Meeting: 1-3 (2021).
The AON based uORF blockage in the expression of OPA1—a pre-clinical development of therepy for OPA1-linked optic atrophy, Wissinger Lab, Molecular Genetics Laboratory, Web page http://www.eye-tuebingen.de/wissinger/lab/members/ting-xiao/, 3 pages, Oct. 22, 20109, retrieved from Internet Archive Wayback Machine https://web.archive.org/web/20191022233241/ http://www.eye-tuebingen.de/wissinger/lab/members/ting-xiao/ on Jun. 7, 2022.
Todd et al.: Highly prevalent putative quadruplex sequence motifs in human DNA. Nucleic Acids Res. 33(9):2901-7 (2005).
U.S. Appl. No. 17/924,966 Restriction Requirement dated Jun. 27, 2024.
Venkatesh, Aditya: Antisense oligonucleotide mediated increase of OPA1 expression using TANGO technology for the treatment of autosomal dominant optic atrophy. Stoke Therapeutics. Association for Research in Vision & Ophthalmology Meeting 2020.
Wagnon, J. TANGO With SCNIA: Can This Molecular Dance Defeat Dravet Syndrome? Epilpesy Currents 21(1):60-61 (2021).
Wang, AG et al, OPA1 expression in the human retina and optic nerve,. Exp Eye Res 83(5): 1171-1178 (2006).
Wang, W. et al. The developmental changes of Na(v)1.1 and Na(v)1.2 expression in the human hippocampus and temporal lobe, Brain Res 1389:61-70 (2011).
Wu, Y. et al. Incidence of Dravet Syndrome in a US Population. Pediatrics 136(5): e1310-e1315 (2015).
Biliouris, K. et al., A Semi-Mechanistic Population Pharmacokinetic Model of Nusinersen: An Antisense Oligonucleotide for the Treatment of Spinal Muscular Atrophy. CPT Pharmacometrics Syst Pharmacol 7(9):581-592 (2018).
Brown, P., Pharmacology Review (Nusinersen), Center for Drug Evaluation and Research. Available at URL: https://www.accessdata.fda.gov/drugsatfda_docs/nda/2016/209531Orig1s000PharmR.pdf pp. 1-90 (2016).
Co-pending U.S. Appl. No. 19/035,483, inventor Aznarez; Isabel, filed Jan. 23, 2025.
Co-pending U.S. Appl. No. 19/236,584, inventors Vorechovsky; Igor et al., filed Jun. 12, 2025.
FDA. Integrated review (Tofersen). Available at URL: https://www.accessdata.fda.gov/drugsatfda_docs/nda/2023/215887Orig1s000IntegratedR.pdf pp. 1-135 (2023).
Griffey, Richard H. et al. 2'-O-aminopropyl Ribonucleotides: A Zwitterionic Modification that Enhances the Exonuclease Resistance and Biological Activity of Antisense Oligonucleotides. Journal of Medicinal Chemistry 39(26):5100-5109 (1997).
Hinnebusch, Alan G., et al. Translational control by 5'-untranslated regions of eukaryotic mRNAs. Science 352.6292: 1413-1416. (2016).
Jeong, J.H. et al. Anti-GAD antibody targeted non-viral gene delivery to islet beta cells. J Control Release. 107(3): 562-700 (2005).
Kosei, T. et al., Physiological Function Analysis by Antisense Oligonucleotides. Molecular Biology for Physiologists 60:383-400 (1998).
Kouzehgarani, G. et al., Harnessing cerebrospinal fluid circulation for drug delivery to brain tissues. Adv Drug Deliv Rev 173:20-59 (2021).
Lebedeva, I. et al., Phosphorothioate oligodeoxynucleotides as inhibitors of gene expression: antisense and non-antisense effects. Applications of antisense therapies to restenosis. Boston, MA: Springer 99-101 (1999).
Leppek, Kathrin, et al. Functional 5' UTR mRNA structures in eukaryotic translation regulation and how to find them. Nature Reviews, Molecular Cell Biology: pp. 1-17. (2017).
Liang, Xue-hai, et al. Antisense oligonucleotides targeting translation inhibitory elements in 5' UTRs can selectively increase protein levels. Nucleic acids research 45.16: 9528-9546. (2017).
Madocsai, C. et al., Correction of SMN2 Pre-mRNA splicing by antisense U7 small nuclear RNAs. Molecular therapy 12(6):1013-1022 (2005).
Metz, T. et al., Biodistribution of Radioactively Labeled Splice Modulating Antisense Oligonucleotides After Intracerebroventricular and Intrathecal Injection in Mice. Nucleic Acid Ther 34(1):26-34 (2024).
Mignot, Cyril et al.: Genetic and neurodevelopmental spectrum of SYNGAP1-associated intellectual disability and epilepsy. J. Med. Genet. 53:511-522 (2016). doi:10.1136/jmedgenet-2015-103451.
Monine, M. et al., A physiologically-based pharmacokinetic model to describe antisense oligonucleotide distribution after intrathecal administration. Journal of Pharmacokinetics and Pharmacodynamics 48:639-654 (2021).
Parker, D. et al. Pharmacogenetics of antiepileptic drugs: A brief review. The mental health clinician 6(1):28-34 (2016).
PCT/US2024/032131 International Search Report mailed Jan. 10, 2025.
PCT/US2024/039369 International Search Report and Written Opinion dated Dec. 26, 2024.
PCT/US2025/021022 Invitation to Pay Additional Fees dated May 14, 2025.
Phillips, M., Antisense inhibition and adeno-associated viral vector delivery for reducing hypertension. Hypertension 29(1):177-187 (1997).
Prchalova, Darina et al.: Analysis of 31-year-old patient with SYNGAP1 gene defect points to importance of variants in broader splice regions and reveals developmental trajectory of SYNGAP1-associated phenotype: case report. BMC Medical Genetics 18:62 (2017). DOI 10.1186/s12881-017-0425-4.

(56) References Cited

OTHER PUBLICATIONS

Rigo, F. et al., Pharmacology of a central nervous system delivered 2'-O-methoxyethyl-modified survival of motor neuron splicing oligonucleotide in mice and nonhuman primates. J Pharmacol Exp Ther 350(1):46-55 (2014).
Romagnoli, M. et al. Idebenone increases chance of stabilization/recovery of visual acuity in OPA1-dominant optic atrophy. Annals of Clinical and Translational Neurology 7(4): 590-594 (2020).
Soni, G. et al. Progress toward ultrafast DNA sequencing using solid-state nanopores. Clin Chem. 53(11): 1996-2001 (2007).
U.S. Appl. No. 16/696,635 Office Action dated Sep. 17, 2021.
U.S. Appl. No. 16/696,635 Office Action dated Feb. 23, 2021.
U.S. Appl. No. 17/412,664 Office Action dated Jun. 4, 2025.
U.S. Appl. No. 17/412,664 Office Action dated Nov. 1, 2024.
U.S. Appl. No. 17/924,966 Notice of Allowance dated Mar. 26, 2025.
U.S. Appl. No. 17/924,966 Office Action dated Oct. 18, 2024.
Vuillemenot, B. et al., Safety Evaluation of CNS Administered Biologics-Study Design, Data Interpretation, and Translation to the Clinic. Toxicol Sci 152(1):3-9 (2016).
World Health Organization, WHO Drug Information. 35(2):270-604 (2021); relevant page is p. 576.
Yamamoto, Y. et al., Development of a population pharmacokinetic model to characterize the pharmacokinetics of intrathecally administered tominersen in cerebrospinal fluid and plasma. CPT Pharmacometrics Syst Pharmacol 12(9):1213-1226 (2023).
Yin, W. et al., Targeting RNA: A Transformative Therapeutic Strategy. Clin Transl Sci 12(2):98-112 (2019).
Zhang, Y. et al., Pharmacological characterization of an antisense knockdown zebrafish model of Dravet syndrome: inhibition of epileptic seizures by the serotonin agonist fenfluramine. PloS one 10(5):e0125898, 1-19 (2015).
Burki, et al., Development and Application of an Ultrasensitive Hybridization-Based ELISA Method for the Determination of Peptide-Conjugated Phosphorodiamidate Morpholino Oligonucleotides, Nucleic Acid Ther., 25(5): 275-84 (2015).
Co-pending U.S. Appl. No. 19/403,531, inventors Aznarez; Isabel et al., filed Nov. 28, 2025.
Co-pending U.S. Appl. No. 19/456,908, inventors Vorechovsky; Igor et al., filed Jan. 22, 2026.
Disterer, Petra et al. Development of therapeutic splice-switching oligonucleotides. Human gene therapy 25(7): 587-598 (2014).
Fu, et al. "Context-dependent control of alternative splicing by RNA-binding proteins" Genetics, vol. 15, (2014) p. 689-701.
Gerard et al.: Intravitreal Injection of Splice-switching Oligonucleotides to Manipulate Splicing in Retinal Cells. Molecular Therapy Nucleic Acids 4:E250 (2015). DOI:https://doi.org/10.1038/mtna.2015.24.
Havens, Mallory A., and Michelle L. Hastings. Splice-switching antisense oligonucleotides as therapeutic drugs. Nucleic Acids Research 44(14):6549-6563 (2016).
Kralovicova, J. et al., Global control of aberrant splice-site activation by auxiliary splicing sequences: evidence for a gradient in exon and intron definition. Nucleic Acids Research 35(19):6399-6413 (2007). https://doi.org/10.1093/nar/gkm680.
Lim, et al. TANGO (Targeted Augmentation of Nuclear Gene Output) for the Treatment of Genetic Diseases. Cold Spring Harbor Meeting on Eukaryotic mRNA Processing, Aug. 20-24, 2019 (Abstract).
Lim, K.H. et al.: Antisense oligonucleotide modulation of non-productive alternative splicing upregulates gene expression. Nature Communication 11(3501): 1-13 (2020).
Mcgiincy, Nicholas J. and Christopher W. J. Smith. Alternative splicing resulting in nonsense-mediated mRNA decay: what is the meaning of nonsense?. Trends in Biochemical Sciences 33(8):385-393 (2008).
No Author "Stoke Therapeutics Announces Publication of Data in the Journal Nature Communications That Support the Company's Proprietary Approach to Addressing Severe Genetic Diseases by Precisely Upregulating Protein Expression" Retrieved from https://www.businesswire.com/news/home/20200709005385/en/Stoke-Therapeutics-Announces-Publication-of-Data-in-the-Journal-Nature-Communications-That-Support-the-Company%E2%80%99s-Proprietary-Approach-to-Addressing-Severe-Genetic-Diseases-by-Precisely-Upregulating-Protein-Expression, 2020 pp. 1-4.
PCT/US2024/032131 International Preliminary Report on Patentability dated Dec. 11, 2025.
Perez, Belen. et al. Antisense mediated splicing modulation for inherited metabolic diseases: challenges for delivery. Nucleic acid therapeutics 24(1):48-56 (2014).
Sazani, Peter et al., Abstract: Splice Switching Oligonucleotides as Potential Therapeutics. Antisense Drug Technology, Edition 2nd Edition. CRC Press, chapter 4, 26 Pages (2007). Accessed at https://www.taylorfrancis.com/books/edit/10.1201/9780849387951/antisense-drug-technology-stanley-crooke?refld=7edadcf9-9c8f-44bc-9672-37385a26bac2&context=ubx.
Sibley et al.: Lessons from non-canonical splicing. Nat Rev Genet. 17(7):407-421 (2016). doi: 10.1038/nrg.2016.46. Epub May 31, 2016.
Straarup, E et al., Short locked nucleic acid antisense oligonucleotides potently reduce apolipoprotein B mRNA and serum cholesterol in mice and non-human primates. Nucleic Acids Res. 38(20): 7100-11 (2010).
U.S. Appl. No. 18/299,509 Office Action dated Dec. 22, 2025.
U.S. Appl. No. 18/299,956 Office Action dated Jan. 21, 2026.
Wang et al.: Mechanism of alternative splicing and its regulation. Biomedical Reports 3(2):152-158 (2014).

* cited by examiner

| Group | N | Treatment | Dose (ug/eye) | Final conc. expected in vitreous* (uM) | Dose volume (uL/eye) | Dose and regimen | Matrices collected (OU) |
|---|---|---|---|---|---|---|---|
| 1 | 3 | Vehicle (PBS) | NA | N/A | | | Retinae split along the nasal-temporal axes, temporal half used for RNA, nasal for protein |
| 2 | 3 | NT ASO | 110 | 12 | | | |
| 3 | 3 | Test ASO – Low Dose | 39 | 4 | 30 | IVT OU on Day 1 | |
| 4 | 3 | Test ASO – High Dose | 116 | 12 | | | |

| | | Chemistry | |
|---|---|---|---|
| Compound ID No.: | Sequence (5'-3') | (All MOE unless otherwise noted; G-LNA, C-5MeC-MOE) | |
| 1 | AGGCCATTCTGAAATTCT | AGGCCATTCTGAAATTCT | |
| 2 | CATTGAGGCCATTCTGAA | CATTGAGGCCATTCTGAA | |
| 3 | TAAGGCATTGAGGCCATT | TAAGGCATTGAGGCCATT | |
| 4 | CCTATTAAGGCATTGAGG | CCTATTAAGGCATTGAGG | |
| 5 | TTCTTCCTATTAAGGCAT | TTCTTCCTATTAAGGCAT | |
| 6 | AGTATTTCTTCCTATTAA | AGTATTTCTTCCTATTAA | |
| 7 | TTTCAAGTATTTCTTCCT | TTTCAAGTATTTCTTCCT | |
| 8 | AAAAATTTCAAGTATTTC | AAAAATTTCAAGTATTTC | |
| 9 | AATTTAAAAATTTCAAGT | AATTTAAAAATTTCAAGT | |
| 10 | GCCCTAATTTAAAAATTT | GCCCTAATTTAAAAATTT | |
| 11 | ACCAAGCCCTAATTTAAA | ACCAAGCCCTAATTTAAA | |
| 12 | ACAAAACCAAGCCCTAAT | ACAAAACCAAGCCCTAAT | |
| 13 | TCCTCACAAAACCAAGCC | TCCTCACAAAACCAAGCC | |
| 14 | CTAGCTCCTCACAAAACC | CTAGCTCCTCACAAAACC | |
| 15 | CTTTACTAGCTCCTCACA | CTTTACTAGCTCCTCACA | |
| 16 | AAAACCTTTACTAGCTCC | AAAACCTTTACTAGCTCC | |
| 17 | AGAGAAAAACCTTTACTA | AGAGAAAAACCTTTACTA | |
| 18 | CTGAAAGAGAAAAACCTT | CTGAAAGAGAAAAACCTT | |
| 19 | AAGCTGAAAGAGAAAAAC | AAGCTGAAAGAGAAAAAC | |
| 20 | CTAAAGCTGAAAGAGAAA | CTAAAGCTGAAAGAGAAA | |

FIG. 15

| | | Chemistry |
|---|---|---|
| Compound ID No.: | Sequence (5'-3') | (All MOE unless otherwise noted; G-LNA, C-5MeC-MOE) |
| 21 | AAGCTAAAGCTGAAAGAG | AAGCTAAAGCTGAAAGAG |
| 22 | AACAAGCTAAAGCTGAAA | AACAAGCTAAAGCTGAAA |
| 23 | AGAAACAAGCTAAAGCTG | AGAAACAAGCTAAAGCTG |
| 24 | CGCAGAAACAAGCTAAAG | CGCAGAAACAAGCTAAAG |
| 25 | TCCTCCGCAGAAACAAGC | TCCTCCGCAGAAACAAGC |
| 26 | CGGAATCCTCCGCAGAAA | CGGAATCCTCCGCAGAAA |
| 27 | AAGAGCGGAATCCTCCGC | AAGAGCGGAATCCTCCGC |
| 28 | GGAGAAAGAGCGGAATCC | GGAGAAAGAGCGGAATCC |
| 29 | CTGATGGAGAAAGAGCGG | CTGATGGAGAAAGAGCGG |
| 30 | TGAAACTGATGGAGAAAG | TGAAACTGATGGAGAAAG |
| 31 | GGCTATGAAACTGATGGA | GGCTATGAAACTGATGGA |
| 32 | TCCAGGGCTATGAAACTG | TCCAGGGCTATGAAACTG |
| 33 | ACAATTCCAGGGCTATGA | ACAATTCCAGGGCTATGA |
| 34 | TTTCTACAATTCCAGGGC | TTTCTACAATTCCAGGGC |
| 35 | GAGCTTTTCTACAATTCC | GAGCTTTTCTACAATTCC |
| 36 | AACCAGAGCTTTTCTACA | AACCAGAGCTTTTCTACA |
| 37 | CTTGAAACCAGAGCTTTT | CTTGAAACCAGAGCTTTT |
| 38 | ATGGTCTTGAAACCAGAG | ATGGTCTTGAAACCAGAG |
| 39 | TATCAATGGTCTTGAAAC | TATCAATGGTCTTGAAAC |
| 40 | ATGGATATCAATGGTCTT | ATGGATATCAATGGTCTT |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 41 | CAGAAATGGATATCAATG | CAGAAATGGATATCAATG | |
| 42 | CCTGACAGAAATGGATAT | CCTGACAGAAATGGATAT | |
| 43 | CACCCTGACAGAAATGGA | CACCCTGACAGAAATGGA | |
| 44 | ACTCACCCTGACAGAAAT | ACTCACCCTGACAGAAAT | |
| 45 | AAAACTCACCCTGACAGA | AAAACTCACCCTGACAGA | |
| 46 | TTTAAAACTCACCCTGAC | TTTAAAACTCACCCTGAC | |
| 47 | AAATTTAAAACTCACCCT | AAATTTAAAACTCACCCT | |
| 48 | AATAAATTTAAAACTCAC | AATAAATTTAAAACTCAC | |
| 49 | CATGAAATAAATTTAAAA | CATGAAATAAATTTAAAA | |
| 50 | TGCATCATGAAATAAATT | TGCATCATGAAATAAATT | |
| 51 | TTGTTTGCATCATGAAAT | TTGTTTGCATCATGAAAT | |
| 52 | ATATATTGTTTGCATCAT | ATATATTGTTTGCATCAT | |
| 53 | GTTCAATATATTGTTTGC | GTTCAATATATTGTTTGC | |
| 54 | CTGTTGTTCAATATATTG | CTGTTGTTCAATATATTG | |
| 55 | ATGTCCTGTTGTTCAATA | ATGTCCTGTTGTTCAATA | |
| 56 | AGTTCATGTCCTGTTGTT | AGTTCATGTCCTGTTGTT | |
| 57 | GAACAAGTTCATGTCCTG | GAACAAGTTCATGTCCTG | |
| 58 | AACAAGAACAAGTTCATG | AACAAGAACAAGTTCATG | |
| 59 | CTTACAACAAGAACAAGT | CTTACAACAAGAACAAGT | |
| 60 | AGCCACTTACAACAAGAA | AGCCACTTACAACAAGAA | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 61 | AATTCAGCCACTTACAAC | AATTCAGCCACTTACAAC | |
| 62 | GATAAAATTCAGCCACTT | GATAAAATTCAGCCACTT | |
| 63 | TTACTGATAAAATTCAGC | TTACTGATAAAATTCAGC | |
| 64 | GTGCTTTACTGATAAAAT | GTGCTTTACTGATAAAAT | |
| 65 | TTGATGTGCTTTACTGAT | TTGATGTGCTTTACTGAT | |
| 66 | TGGAGAAAGAGCGGAATC | TGGAGAAAGAGCGGAATC | |
| 67 | ATGGAGAAAGAGCGGAAT | ATGGAGAAAGAGCGGAAT | |
| 68 | GATGGAGAAAGAGCGGAA | GATGGAGAAAGAGCGGAA | |
| 69 | TGATGGAGAAAGAGCGGA | TGATGGAGAAAGAGCGGA | |
| 70 | ACTGATGGAGAAAGAGCG | ACTGATGGAGAAAGAGCG | |
| 71 | AACTGATGGAGAAAGAGC | AACTGATGGAGAAAGAGC | |
| 72 | AAACTGATGGAGAAAGAG | AAACTGATGGAGAAAGAG | |
| 73 | GAAACTGATGGAGAAAGA | GAAACTGATGGAGAAAGA | |
| 74 | ATGAAACTGATGGAGAAA | ATGAAACTGATGGAGAAA | |
| 75 | TATGAAACTGATGGAGAA | TATGAAACTGATGGAGAA | |
| 76 | CTATGAAACTGATGGAGA | CTATGAAACTGATGGAGA | |
| 77 | GCTATGAAACTGATGGAG | GCTATGAAACTGATGGAG | |
| 78 | GGGCTATGAAACTGATGG | GGGCTATGAAACTGATGG | |
| 79 | AGGGCTATGAAACTGATG | AGGGCTATGAAACTGATG | |
| 80 | CAGGGCTATGAAACTGAT | CAGGGCTATGAAACTGAT | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 81 | CCAGGGCTATGAAACTGA | CCAGGGCTATGAAACTGA | |
| 82 | CTGATGGAGAAAGAGCGGAATC | CTGATGGAGAAAGAGCGGAATC | |
| 83 | CTGATGGAGAAAGAGCGGAA | CTGATGGAGAAAGAGCGGAA | |
| 84 | AACTGATGGAGAAAGAGCGGAA | AACTGATGGAGAAAGAGCGGAA | |
| 85 | AACTGATGGAGAAAGAGCGG | AACTGATGGAGAAAGAGCGG | |
| 86 | GAAACTGATGGAGAAAGAGCGG | GAAACTGATGGAGAAAGAGCGG | |
| 87 | GGCTATGAAACTGATGGAGAAA | GGCTATGAAACTGATGGAGAAA | |
| 88 | GGCTATGAAACTGATGGAGA | GGCTATGAAACTGATGGAGA | |
| 89 | AGGGCTATGAAACTGATGGAGA | AGGGCTATGAAACTGATGGAGA | |
| 90 | AGGGCTATGAAACTGATGGA | AGGGCTATGAAACTGATGGA | |
| 91 | CCAGGGCTATGAAACTGATGGA | CCAGGGCTATGAAACTGATGGA | |
| 92 | TTCTTACCCATTTAATTA | TTCTTACCCATTTAATTA | |
| 93 | TGCTTCTTACCCATTTAA | TGCTTCTTACCCATTTAA | |
| 94 | TAATGCTTCTTACCCATT | TAATGCTTCTTACCCATT | |
| 95 | AGATAATGCTTCTTACCC | AGATAATGCTTCTTACCC | |
| 96 | CAGATAATGCTTCTTACC | CAGATAATGCTTCTTACC | |
| 97 | CCCTTCAGATAATGCTTC | CCCTTCAGATAATGCTTC | |
| 98 | CTACTCCCTTCAGATAAT | CTACTCCCTTCAGATAAT | |
| 99 | AGCTCCTACTCCCTTCAG | AGCTCCTACTCCCTTCAG | |
| 100 | TTCACAGCTCCTACTCCC | TTCACAGCTCCTACTCCC | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 101 | TAAAATTCACAGCTCCTA | TAAAATTCACAGCTCCTA | |
| 102 | AAATCTAAAATTCACAGC | AAATCTAAAATTCACAGC | |
| 103 | GAATAAAATCTAAAATTC | GAATAAAATCTAAAATTC | |
| 104 | GATGGGAATAAAATCTAA | GATGGGAATAAAATCTAA | |
| 105 | GCTGTGATGGGAATAAAA | GCTGTGATGGGAATAAAA | |
| 106 | TAGAGGCTGTGATGGGAA | TAGAGGCTGTGATGGGAA | |
| 107 | AAAGATAGAGGCTGTGAT | AAAGATAGAGGCTGTGAT | |
| 108 | AAAAGAAAGATAGAGGCT | AAAAGAAAGATAGAGGCT | |
| 109 | GACCTAAAAGAAAGATAG | GACCTAAAAGAAAGATAG | |
| 110 | ATAAAGACCTAAAAGAAA | ATAAAGACCTAAAAGAAA | |
| 111 | GAGATATAAAGACCTAAA | GAGATATAAAGACCTAAA | |
| 112 | GGCTGTGATGGGAATAAA | GGCTGTGATGGGAATAAA | |
| 113 | AGGCTGTGATGGGAATAA | AGGCTGTGATGGGAATAA | |
| 114 | GAGGCTGTGATGGGAATA | GAGGCTGTGATGGGAATA | |
| 115 | AGAGGCTGTGATGGGAAT | AGAGGCTGTGATGGGAAT | |
| 116 | ATAGAGGCTGTGATGGGA | ATAGAGGCTGTGATGGGA | |
| 117 | GATAGAGGCTGTGATGGG | GATAGAGGCTGTGATGGG | |
| 118 | AGATAGAGGCTGTGATGG | AGATAGAGGCTGTGATGG | |
| 119 | AAGATAGAGGCTGTGATG | AAGATAGAGGCTGTGATG | |
| 120 | TAGAGGCTGTGATGGGAATAAA | TAGAGGCTGTGATGGGAATAAA | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 121 | ATAGAGGCTGTGATGGGAATAA | ATAGAGGCTGTGATGGGAATAA | |
| 122 | GATAGAGGCTGTGATGGGAATA | GATAGAGGCTGTGATGGGAATA | |
| 123 | AGATAGAGGCTGTGATGGGAAT | AGATAGAGGCTGTGATGGGAAT | |
| 124 | AAGATAGAGGCTGTGATGGGAA | AAGATAGAGGCTGTGATGGGAA | |
| 125 | GAGGCTGTGATGGGAATAAA | GAGGCTGTGATGGGAATAAA | |
| 126 | AGAGGCTGTGATGGGAATAA | AGAGGCTGTGATGGGAATAA | |
| 127 | TAGAGGCTGTGATGGGAATA | TAGAGGCTGTGATGGGAATA | |
| 128 | ATAGAGGCTGTGATGGGAAT | ATAGAGGCTGTGATGGGAAT | |
| 129 | GATAGAGGCTGTGATGGGAA | GATAGAGGCTGTGATGGGAA | |
| 130 | AGATAGAGGCTGTGATGGGA | AGATAGAGGCTGTGATGGGA | |
| 131 | AAGATAGAGGCTGTGATGGG | AAGATAGAGGCTGTGATGGG | |
| 132 | CTGTGATGGGAATAAA | CTGTGATGGGAATAAA | |
| 133 | GCTGTGATGGGAATAA | GCTGTGATGGGAATAA | |
| 134 | GGCTGTGATGGGAATA | GGCTGTGATGGGAATA | |
| 135 | AGGCTGTGATGGGAAT | AGGCTGTGATGGGAAT | |
| 136 | GAGGCTGTGATGGGAA | GAGGCTGTGATGGGAA | |
| 137 | AGAGGCTGTGATGGGA | AGAGGCTGTGATGGGA | |
| 138 | TAGAGGCTGTGATGGG | TAGAGGCTGTGATGGG | |
| 139 | ATAGAGGCTGTGATGG | ATAGAGGCTGTGATGG | |
| 140 | GATAGAGGCTGTGATG | GATAGAGGCTGTGATG | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 141 | AGATAGAGGCTGTGAT | AGATAGAGGCTGTGAT | |
| 142 | AAGATAGAGGCTGTGA | AAGATAGAGGCTGTGA | |
| 143 | AGGCTGTGATGTGAATAA | AGGCTGTGATGTGAATAA | |
| 144 | AGGCTGTGATGTGAATAA | AGGCTGTGATGTGAATAA | |
| 145 | AGGCTGTGATGTGAATAA | AGGCTGTGATGTGAATAA | |
| 146 | AGAGGCTGTGATGTGAAT | AGAGGCTGTGATGTGAAT | |
| 147 | AGAGGCTGTGATGTGAAT | AGAGGCTGTGATGTGAAT | |
| 148 | AGAGGCTGTGATGTGAAT | AGAGGCTGTGATGTGAAT | |
| 149 | TAGAGGCTGTGATGTGAA | TAGAGGCTGTGATGTGAA | |
| 150 | TAGAGGCTGTGATGTGAA | TAGAGGCTGTGATGTGAA | |
| 151 | TAGAGGCTGTGATGTGAA | TAGAGGCTGTGATGTGAA | |
| 152 | GATAGAGGCTGTGATTGG | GATAGAGGCTGTGATTGG | |
| 153 | GATAGAGGCTGTGATTGG | GATAGAGGCTGTGATTGG | |
| 154 | GATAGAGGCTGTGATTGG | GATAGAGGCTGTGATTGG | |
| 155 | AGATAGAGGCTGTGATGG | AGATAGAGGCTGTGATGG | |
| 156 | GGCTGTGATGTGAATA | GGCTGTGATGTGAATA | |
| 157 | GGCTGTGATGTGAATA | GGCTGTGATGTGAATA | |
| 158 | GGCTGTGATGTGAATA | GGCTGTGATGTGAATA | |
| 159 | GAGGCTGTGATGTGAA | GAGGCTGTGATGTGAA | |
| 160 | GAGGCTGTGATGTGAA | GAGGCTGTGATGTGAA | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 161 | GAGGCTGTGATGTGAA | gAggcTgtgatGtGAa | |
| 162 | TAGAGGCTGTGATTGG | tagaggctgtgattgg | |
| 163 | TAGAGGCTGTGATTGG | tAgagGctgtGattGg | |
| 164 | TAGAGGCTGTGATTGG | tAgagGctgtGaTtGg | |
| 165 | ATAGAGGCTGTGATGG | aTagaGgctgTgatGg | |
| 166 | GATAGAGGCTGTGATG | gAtagAggctGtgatg | |
| 167 | AGATAGAGGCTGTGAT | aGataGaggcTgtgAt | |
| 168 | GGCTATGAAACTGATGGAGA | gGctaTgaaactgaTggaGa | |
| 169 | CTATGAAACTGATGGAGA | cTatgAaactgaTggaGa | |
| 170 | GCTATGAAACTGATGGAG | gCtatGaaactgAtggAg | |
| 171 | GGCTATGAAACTGATGGA | gGctaTgaaactGatgGa | |
| 172 | ATGAAACTGATGGAGA | aTgaAactgatGgaGa | |
| 173 | ATGAAACTGATGGAGA | aTgaAacTGatGgaGa | |
| 174 | CTATGAAACTGATGGA | cTatGaaactgAtgGa | |
| 175 | CTATGAAACTGATGGA | cTatGaaACtgAtgGa | |
| 176 | GGCTATGAAACTGATG | gGctAtgaaacTgaTg | |
| 177 | GGCTATGAAACTGATG | gGctAtgAAacTgaTg | |
| 178 | GAAACTGATGGAGA | gAaaCtGAtGgaGa | |
| 179 | ATGAAACTGATGGA | aTgaAaCTgAtgGa | |
| 180 | CTATGAAACTGATG | cTatGaAAcTgaTg | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 181 | GGCTATGAAACTGA | GGCTATGAAACTGA | |
| 182 | TAGAGGCTGTGATGGGAATAAA | TAGAGGCTGTGATGGGAATAAA | PMO |
| 183 | TAGAGGCTGTGATGGGAATAAAAT | TAGAGGCTGTGATGGGAATAAAAT | PMO |
| 184 | ATAGAGGCTGTGATGGGAATAA | ATAGAGGCTGTGATGGGAATAA | PMO |
| 185 | ATAGAGGCTGTGATGGGAATAAAA | ATAGAGGCTGTGATGGGAATAAAA | PMO |
| 186 | ATAGAGGCTGTGATGGGAATAAAAT | ATAGAGGCTGTGATGGGAATAAAAT | PMO |
| 187 | AAAGATAGAGGCTGTGATGGGAATA | AAAGATAGAGGCTGTGATGGGAATA | PMO |
| 188 | GGCTATGAAACTGATGGAGAA | GGCTATGAAACTGATGGAGAA | PMO |
| 189 | GGCTATGAAACTGATGGAGAAA | GGCTATGAAACTGATGGAGAAA | PMO |
| 190 | GGCTATGAAACTGATGGAGAAAGA | GGCTATGAAACTGATGGAGAAAGA | PMO |
| 191 | AGGGCTATGAAACTGATGGAGAAAG | AGGGCTATGAAACTGATGGAGAAAG | PMO |
| 192 | CATTTAATTAAATTATAT | CATTTAATTAAATTATAT | |
| 193 | CCATTTAATTAAATTATA | CCATTTAATTAAATTATA | |
| 194 | CCCATTTAATTAAATTAT | CCCATTTAATTAAATTAT | |
| 195 | ACCCATTTAATTAAATTA | ACCCATTTAATTAAATTA | |
| 196 | TACCCATTTAATTAAATT | TACCCATTTAATTAAATT | |
| 197 | TTACCCATTTAATTAAAT | TTACCCATTTAATTAAAT | |
| 198 | CTTACCCATTTAATTAAA | CTTACCCATTTAATTAAA | |
| 199 | TCTTACCCATTTAATTAA | TCTTACCCATTTAATTAA | |
| 200 | GATAGAGGCTGTGATGG | GATAGAGGCTGTGATGG | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 201 | GGCTGTGAAACTGATGGA | GGCTGTGAAACTGATGGA | |
| 202 | GGCTGTGAAACTGATGGAGA | GGCTGTGAAACTGATGGAGA | |
| 203 | CTATGAAACTGATGGA | CTATGAAACTGATGGA | |
| 204 | GCTATGAAACTGATGG | GCTATGAAACTGATGG | |
| 205 | GGCTATGAAACTGATG | GGCTATGAAACTGATG | |
| 206 | ATGAAACTGATGGA | ATGAAACTGATGGA | |
| 207 | TATGAAACTGATGG | TATGAAACTGATGG | |
| 208 | CTATGAAACTGATG | CTATGAAACTGATG | |
| 209 | GCTATGAAACTGAT | GCTATGAAACTGAT | |
| 210 | GGCTATGAAACTGA | GGCTATGAAACTGA | |
| 211 | GCTGTGAAACTGATGGAGAA | GCTGTGAAACTGATGGAGAA | |
| 212 | GGGCTGTGAAACTGATGGAG | GGGCTGTGAAACTGATGGAG | |
| 213 | TGTGAAACTGATGGAGAA | TGTGAAACTGATGGAGAA | |
| 214 | CTGTGAAACTGATGGAGA | CTGTGAAACTGATGGAGA | |
| 215 | GCTGTGAAACTGATGGAG | GCTGTGAAACTGATGGAG | |
| 216 | GGGCTGTGAAACTGATGG | GGGCTGTGAAACTGATGG | |
| 217 | TGAAACTGATGGAGAA | TGAAACTGATGGAGAA | |
| 218 | GTGAAACTGATGGAGA | GTGAAACTGATGGAGA | |
| 219 | TGTGAAACTGATGGAG | TGTGAAACTGATGGAG | |
| 220 | CTGTGAAACTGATGGA | CTGTGAAACTGATGGA | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 221 | GCTGTGAAACTGATGG | GCTGTGAAACTGATGG | |
| 222 | GGCTGTGAAACTGATG | GGCTGTGAAACTGATG | |
| 223 | GGGCTGTGAAACTGAT | GGGCTGTGAAACTGAT | |
| 224 | CGGTCCAGGAATGAC | CGGTCCAGGAATGAC | |
| 225 | CCGGTCCAGGAATGA | CCGGTCCAGGAATGA | |
| 226 | CCCGGTCCAGGAATG | CCCGGTCCAGGAATG | |
| 227 | TCCCGGTCCAGGAAT | TCCCGGTCCAGGAAT | |
| 228 | CTCCCGGTCCAGGAA | CTCCCGGTCCAGGAA | |
| 229 | GCTCCCGGTCCAGGA | GCTCCCGGTCCAGGA | |
| 230 | GGCTCCCGGTCCAGG | GGCTCCCGGTCCAGG | |
| 231 | CGGGAGCCCCCGTGT | CGGGAGCCCCCGTGT | |
| 232 | GCGGGAGCCCCCGTG | GCGGGAGCCCCCGTG | |
| 233 | CGCGGGAGCCCCCGT | CGCGGGAGCCCCCGT | |
| 234 | ACGCGGGAGCCCCCG | ACGCGGGAGCCCCCG | |
| 235 | CACGCGGGAGCCCCC | CACGCGGGAGCCCCC | |
| 236 | CCACGCGGGAGCCCC | CCACGCGGGAGCCCC | |
| 237 | GCCACGCGGGAGCCC | GCCACGCGGGAGCCC | |
| 238 | GGCCACGCGGGAGCC | GGCCACGCGGGAGCC | |
| 239 | CGGCCACGCGGGAGC | CGGCCACGCGGGAGC | |
| 240 | ACGGCCACGCGGGAG | ACGGCCACGCGGGAG | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 241 | GACGGCCACGCGGGA | GACGGCCACGCGGGA | |
| 242 | AGACGGCCACGCGGG | AGACGGCCACGCGGG | |
| 243 | GCTAGGGAGGGATGGTTA | GCTAGGGAGGGATGGTTA | |
| 244 | TGTAAGCTAGGGAGGGAT | TGTAAGCTAGGGAGGGAT | |
| 245 | ACAGATGTAAGCTAGGGA | ACAGATGTAAGCTAGGGA | |
| 246 | AAGGAACAGATGTAAGCT | AAGGAACAGATGTAAGCT | |
| 247 | CAACAAAGGAACAGATGT | CAACAAAGGAACAGATGT | |
| 248 | GGGTGCAACAAAGGAACA | GGGTGCAACAAAGGAACA | |
| 249 | ACCAAGGGTGCAACAAAG | ACCAAGGGTGCAACAAAG | |
| 250 | GTTAAACCAAGGGTGCAA | GTTAAACCAAGGGTGCAA | |
| 251 | ATAATGTTAAACCAAGGG | ATAATGTTAAACCAAGGG | |
| 252 | GGAGAATAATGTTAAACC | GGAGAATAATGTTAAACC | |
| 253 | GGGGAGGAGAATAATGTT | GGGGAGGAGAATAATGTT | |
| 254 | AAATTGGGGAGGAGAATA | AAATTGGGGAGGAGAATA | |
| 255 | AGAGGAAATTGGGGAGGA | AGAGGAAATTGGGGAGGA | |
| 256 | GGAGAAGAGGAAATTGGG | GGAGAAGAGGAAATTGGG | |
| 257 | AATGAGGAGAAGAGGAAA | AATGAGGAGAAGAGGAAA | |
| 258 | TTCACAATGAGGAGAAGA | TTCACAATGAGGAGAAGA | |
| 259 | ACGAGTTCACAATGAGGA | ACGAGTTCACAATGAGGA | |
| 260 | CTGCCACGAGTTCACAAT | CTGCCACGAGTTCACAAT | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 261 | AGACCCTGCCACGAGTTC | AGACCCTGCCACGAGTTC | |
| 262 | CAAGCAGACCCTGCCACG | CAAGCAGACCCTGCCACG | |
| 263 | CTCACCAAGCAGACCCTG | CTCACCAAGCAGACCCTG | |
| 264 | GAGCTCACCAAGCAGACC | GAGCTCACCAAGCAGACC | |
| 265 | AGAATGAGCTCACCAAGC | AGAATGAGCTCACCAAGC | |
| 266 | GTAAGAGAATGAGCTCAC | GTAAGAGAATGAGCTCAC | |
| 267 | TTGTTGTAAGAGAATGAG | TTGTTGTAAGAGAATGAG | |
| 268 | ATTTGTTGTTGTAAGAGA | ATTTGTTGTTGTAAGAGA | |
| 269 | CTTGAATTTGTTGTTGTA | CTTGAATTTGTTGTTGTA | |
| 270 | ATGCTCTTGAATTTGTTG | ATGCTCTTGAATTTGTTG | |
| 271 | TCTTCATGCTCTTGAATT | TCTTCATGCTCTTGAATT | |
| 272 | CTTCCTCTTCATGCTCTT | CTTCCTCTTCATGCTCTT | |
| 273 | GCGCGCTTCCTCTTCATG | GCGCGCTTCCTCTTCATG | |
| 274 | GCTCTGCGCGCTTCCTCT | GCTCTGCGCGCTTCCTCT | |
| 275 | GGCCAGCGGCTCTGCGCG | GGCCAGCGGCTCTGCGCG | |
| 276 | ATATTGGCCAGCGGCTCT | ATATTGGCCAGCGGCTCT | |
| 277 | GTGCTATATTGGCCAGCG | GTGCTATATTGGCCAGCG | |
| 278 | AGCTCGTGCTATATTGGC | AGCTCGTGCTATATTGGC | |
| 279 | GGCATAGCTCGTGCTATA | GGCATAGCTCGTGCTATA | |
| 280 | TGTTGGGCATAGCTCGTG | TGTTGGGCATAGCTCGTG | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 281 | GCTTCTGTTGGGCATAGC | GCTTCTGTTGGGCATAGC | |
| 282 | CTTGCGCTTCTGTTGGGC | CTTGCGCTTCTGTTGGGC | |
| 283 | CACCTTGCGCTTCTGTTG | CACCTTGCGCTTCTGTTG | |
| 284 | TCCATCACCTTGCGCTTC | TCCATCACCTTGCGCTTC | |
| 285 | AACCATCCATCACCTTGC | AACCATCCATCACCTTGC | |
| 286 | CCTTAAACCATCCATCAC | CCTTAAACCATCCATCAC | |
| 287 | AGCCCCCTTAAACCATCC | AGCCCCCTTAAACCATCC | |
| 288 | TCGGTAGCCCCCTTAAAC | TCGGTAGCCCCCTTAAAC | |
| 289 | ATGTATCGGTAGCCCCCT | ATGTATCGGTAGCCCCCT | |
| 290 | TGTGAATGTATCGGTAGC | TGTGAATGTATCGGTAGC | |
| 291 | ATTAGTGTGAATGTATCG | ATTAGTGTGAATGTATCG | |
| 292 | GGCTGATTAGTGTGAATG | GGCTGATTAGTGTGAATG | |
| 293 | GAAATGGCTGATTAGTGT | GAAATGGCTGATTAGTGT | |
| 294 | TGGCAGAAATGGCTGATT | TGGCAGAAATGGCTGATT | |
| 295 | GATCTTGGCAGAAATGGC | GATCTTGGCAGAAATGGC | |
| 296 | GACATGATCTTGGCAGAA | GACATGATCTTGGCAGAA | |
| 297 | GAGGTGACATGATCTTGG | GAGGTGACATGATCTTGG | |
| 298 | AGATTGAGGTGACATGAT | AGATTGAGGTGACATGAT | |
| 299 | TGAACAGATTGAGGTGAC | TGAACAGATTGAGGTGAC | |
| 300 | GTCCATGAACAGATTGAG | GTCCATGAACAGATTGAG | |

FIG. 15 cont.

| | | Chemistry | |
|---|---|---|---|
| Compound ID No.: | Sequence (5'-3') | (All MOE unless otherwise noted; G-LNA, C-5MeC-MOE) | |
| 301 | TTGGAGTCCATGAACAGA | TTGGAGTCCATGAACAGA | |
| 302 | TGTATTTGGAGTCCATGA | TGTATTTGGAGTCCATGA | |
| 303 | TTTCTTGTATTTGGAGTC | TTTCTTGTATTTGGAGTC | |

FIG. 15 cont.

MinION Sequencing Data in HEK293 cells transfected with ASO-14

| Isoform | Exons | Mock | ASO-14 |
|---|---|---|---|
| 1 | 6-7-8 | 60.1% | 49.0% |
| 2 | 6-8 | 35.8% | 47.3% |
| 3* | 6a-8 | 1.2% | 1.3% |
| 4* | 6-7x-8 | n.d. | n.d. |
| 5* | 6-7-7x-8 | 0.6% | 0.0% |

OPA1 ANTISENSE OLIGOMERS FOR TREATMENT OF CONDITIONS AND DISEASES

CROSS-REFERENCE

This application is a continuation of U.S. patent application Ser. No. 18/304,878, filed Apr. 21, 2023, now issued as U.S. Pat. No. 11,814,622, which is continuation of U.S. patent application Ser. No. 17/924,966, filed Nov. 11, 2022, now issued as U.S. Pat. No. 12,338,437, which is U.S. National Stage entry of International Patent Application No. PCT/US2021/030254, filed Apr. 30, 2021, which claims the benefit of U.S. Provisional Application No. 63/023,013, filed May 11, 2020, and U.S. Provisional Application No. 63/112,458, filed Nov. 11, 2020, each of which is incorporated herein by reference in its entirety.

SEQUENCE LISTING

The instant application contains a Sequence Listing which has been submitted electronically in XML format and is hereby incorporated by reference in its entirety. Said XML copy, created on Mar. 16, 2023, is named 47991-731_301.xml and is 971,903 bytes in size.

BACKGROUND

Alternative splicing events in genes can lead to non-productive mRNA transcripts which in turn can lead to aberrant or reduced protein expression, and therapeutic agents which can target the alternative splicing events in genes can modulate the expression level of functional proteins in patients and/or inhibit aberrant protein expression. Such therapeutic agents can be used to treat a condition or disease caused by the protein deficiency.

Autosomal dominant optic atrophy (ADOA) is one of the most commonly diagnosed optic neuropathies. This optic nerve disease is associated with structural and functional mitochondrial deficits that lead to degeneration of the retinal ganglion cells and progressive, irreversible loss of vision. A majority of ADOA patients carry mutations in OPA1 and most mutations lead to haploinsufficiency (Lenaers G. et al. Orphanet J Rare Dis 2012). OPA1 encodes a mitochondrial GTPase with a critical role in mitochondrial fusion, ATP synthesis and apoptosis. Currently, there is no approved disease-modifying treatment for ADOA patients and there is a need for such treatments.

SUMMARY

Described herein, in some aspects, is a method of modulating expression of an OPA1 protein in a cell having a pre-mRNA that is transcribed from an OPA1 gene and that comprises a non-sense mediated RNA decay-inducing exon (NMD exon), the method comprising contacting an agent or a vector encoding the agent to the cell, whereby the agent modulates splicing of the NMD exon from the pre-mRNA, thereby modulating a level of processed mRNA that is processed from the pre-mRNA, and modulating the expression of the OPA1 protein in the cell, wherein the agent comprises an antisense oligomer with at least 80% sequence identity to a sequence selected from the group consisting of SEQ ID NOs: 6-275 and 280-299.

In some embodiments, the agent: (a) binds to a targeted portion of the pre-mRNA; (b) modulates binding of a factor involved in splicing of the NMD exon; or (c) a combination of (a) and (b). In some embodiments, the agent interferes with binding of the factor involved in splicing of the NMD exon to a region of the targeted portion. In some embodiments, the targeted portion of the pre-mRNA is proximal to the NMD exon. In some embodiments, the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of 5' end of the NMD exon. In some embodiments, the targeted portion of the pre-mRNA is at least about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides upstream of 5' end of the NMD exon. In some embodiments, the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of 3' end of the NMD exon. In some embodiments, the targeted portion of the pre-mRNA is at least about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides downstream of 3' end of the NMD exon. In some embodiments, the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of genomic site GRCh38/hg38: chr3 193628509. In some embodiments, the targeted portion of the pre-mRNA is about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of genomic site GRCh38/hg38: chr3 193628509. In some embodiments, the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of genomic site GRCh38/hg38: chr3 193628616. In some embodiments, the targeted portion of the pre-mRNA is about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of genomic site GRCh38/hg38: chr3 193628616. In some embodiments, the targeted portion of the pre-mRNA is located in an intronic region between two canonical exonic regions of the pre-mRNA, and wherein the intronic region contains the NMD exon. In some embodiments, the targeted portion of the pre-mRNA at least partially overlaps with the NMD exon. In some embodiments, the targeted portion of the pre-mRNA at least partially overlaps with an intron upstream or downstream of the NMD exon. In some embodiments, the targeted portion of the pre-mRNA comprises 5' NMD exon-intron junction or 3' NMD exon-intron junction. In some embodiments, the targeted portion of the pre-mRNA is within the NMD exon. In some embodiments, the targeted portion of the pre-mRNA comprises about 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

In some embodiments, the NMD exon comprises a sequence with at least 80%, at least 90%, or 100% sequence identity to SEQ ID NO: 279. In some embodiments, the NMD exon comprises a sequence of SEQ ID NO: 279. In some embodiments, the targeted portion of the pre-mRNA is within the non-sense mediated RNA decay-inducing exon GRCh38/hg38: chr3 193628509 to 193628616. In some embodiments, the targeted portion of the pre-mRNA is upstream or downstream of the non-sense mediated RNA decay-inducing exon GRCh38/hg38: chr3 193628509 to 193628616. In some embodiments, the targeted portion of the pre-mRNA comprises an exon-intron junction of exon GRCh38/hg38: chr3 193628509 to 193628616. In some embodiments, the OPA1 protein expressed from the processed mRNA is a full-length OPA1 protein or a wild-type OPA1 protein. In some embodiments, the OPA1 protein expressed from the processed mRNA is a functional OPA1 protein. In some embodiments, the OPA1 protein expressed from the processed mRNA is at least partially functional as compared to a wild-type OPA1 protein. In some embodiments, the OPA1 protein expressed from the processed mRNA is at least partially functional as compared to a full-length wild-type OPA1 protein. In some embodiments, the OPA1 protein expressed from the processed mRNA is an OPA1 protein that lacks an amino acid sequence encoded by a nucleic acid sequence with at least 80% sequence identity to SEQ ID NO: 277.

In some embodiments, the method promotes exclusion of the NMD exon from the pre-mRNA. In some embodiments, the exclusion of the NMD exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the method results in an increase in the level of the processed mRNA in the cell. In some embodiments, the level of the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the method results in an increase in the expression of the OPA1 protein in the cell. In some embodiments, a level of the OPA1 protein expressed from the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

In some embodiments, the agent comprises an antisense oligomer with at least 80%, at least 90%, or 100% sequence identity to a sequence selected from the group consisting of SEQ ID NOs: 36, 236, 242, 250, 280-283, 288, and 290-292. In some embodiments, the agent further comprises a gene editing molecule. In some embodiments, the gene editing molecule comprises CRISPR-Cas9.

Described herein, in some aspects, is a method of modulating expression of an OPA1 protein in a cell having a pre-mRNA that is transcribed from an OPA1 gene, wherein the pre-mRNA comprises a coding exon, the method comprising contacting an agent or a vector encoding the agent to the cell, whereby the agent promotes exclusion of the coding exon from the pre-mRNA, thereby increasing a level of a processed mRNA that is processed from the pre-mRNA and that lacks the coding exon in the cell. In some embodiments, the agent: (a) binds to a targeted portion of the pre-mRNA; (b) modulates binding of a factor involved in splicing of the coding exon; or (c) a combination of (a) and (b). In some embodiments, the agent interferes with binding of the factor involved in splicing of the coding exon to a region of the targeted portion. In some embodiments, the targeted portion of the pre-mRNA is proximal to the coding exon. In some embodiments, the targeted portion of the pre-mRNA is located in an intronic region immediately upstream of the coding exon. In some embodiments, the targeted portion of the pre-mRNA is within a region spanning from 100 to 50, from 90 to 50, from 80 to 50, from 70 to 50, from 60 to 50, from 60 to 40, from 60 to 30, from 60 to 20, from 60 to 10, from 49 to 1, from 39 to 1, from 29 to 1, or from 19 to 1 nucleotides upstream of 5' end of the coding exon. In some embodiments, the targeted portion of the pre-mRNA is within a region spanning from 49 to 1, from 39 to 1, from 29 to 1, or from 19 to 1 nucleotides upstream of 5' end of the coding exon. In some embodiments, the targeted portion of the pre-mRNA is located in an intronic region immediately downstream of the coding exon. In some embodiments, the targeted portion of the pre-mRNA is within a region spanning from 1 to 49, from 1 to 39, from 1 to 29, from 1 to 19, from 10 to 60, from 20 to 60, from 30 to 60, from 40 to 60, from 50 to 60, from 50 to 70, from 50 to 80, from 50 to 90, or from 50 to 100 nucleotides downstream of 3' end of the coding exon. In some embodiments, the targeted portion of the pre-mRNA is within a region spanning from 1 to 49, from 1 to 39, from 1 to 29, or from 1 to 19 nucleotides downstream of 3' end of the coding exon. In some embodiments, the targeted portion of the pre-mRNA at least partially overlaps with the coding exon. In some embodiments, the targeted portion of the pre-mRNA at least partially overlaps with an intron immediately upstream or immediately downstream of the coding exon. In some embodiments, the targeted portion of the pre-mRNA comprises 5' coding exon-intron junction or 3' coding exon-intron junction. In some embodiments, the targeted portion is within the coding exon of the pre-mRNA. In some embodiments, the coding exon is an alternatively spliced exon.

In some embodiments, the coding exon comprises a sequence with at least 80%, at least 90%, or 100% sequence identity to SEQ ID NO: 277. In some embodiments, the coding exon comprises SEQ ID NO: 277. In some embodiments, the targeted portion of the pre-mRNA is immediately upstream of the coding exon GRCh38/hg38: chr3 193626092 to 193626202. In some embodiments, the targeted portion of the pre-mRNA is within a region spanning from 49 to 1, from 39 to 1, from 29 to 1, or from 19 to 1 nucleotides upstream of genomic site GRCh38/hg38: chr3 193626092. In some embodiments, the targeted portion of the pre-mRNA is immediately downstream of the coding exon GRCh38/hg38: chr3 193626092 to 193626202. In some embodiments, the targeted portion of the pre-mRNA is within a region spanning from 1 to 49, from 1 to 39, from 1 to 29, or from 1 to 19 nucleotides downstream of genomic site GRCh38/hg38: chr3 193626202. In some embodiments, the targeted portion of the pre-mRNA is within the coding exon GRCh38/hg38: chr3 193626092 to 193626202. In some embodiments, the targeted portion of the pre-mRNA comprises an exon-intron junction of exon GRCh38/hg38: chr3 193626092 to 193626202. In some embodiments, the targeted portion comprises about 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the coding exon. In some embodiments, the targeted portion of the pre-mRNA comprises a sequence with at least 80%, 85%, 90%, 95%, 97%, or 100% sequence identity to a region comprising at least 8 contiguous nucleic acids of SEQ ID NO: 277.

In some embodiments, the exclusion of the coding exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the method results in an increase in expression of the OPA1 protein in the cell. In some embodiments, a level of the OPA1 protein expressed from the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, a level of the OPA1 protein expressed from the processed mRNA in the cell contacted with the agent is increased by at least about 1.5-fold compared to in the absence of the agent.

In some embodiments, the OPA1 protein expressed from the processed mRNA is a functional OPA1 protein. In some embodiments, the OPA1 protein expressed from the processed mRNA is at least partially functional as compared to a wild-type OPA1 protein. In some embodiments, the OPA1 protein expressed from the processed mRNA is at least partially functional as compared to a full-length wild-type OPA1 protein. In some embodiments, the agent promotes exclusion of a non-sense mediated RNA decay-inducing exon (NMD exon) from the pre-mRNA. In some embodiments, the NMD exon comprises a sequence with at least 80%, at least 90%, or 100% sequence identity to SEQ ID NO: 279. In some embodiments, the NMD exon comprises a sequence of SEQ ID NO: 279. In some embodiments, the OPA1 protein expressed from the processed mRNA comprises fewer proteolytic cleavage sites than an OPA1 protein encoded by a corresponding mRNA containing the coding exon.

In some embodiments, the agent comprises an antisense oligomer with at least 80%, at least 90%, or 100% sequence identity to a sequence selected from the group consisting of SEQ ID NOs: 227-242, 250, 280-283, 288, and 290-292. In some embodiments, the agent comprises a gene editing molecule. In some embodiments, the gene editing molecule comprises CRISPR-Cas9.

Described herein, in some aspects, is a method of modulating expression of an OPA1 protein in a cell having a pre-mRNA that is transcribed from an OPA1 gene, wherein the pre-mRNA comprises a coding exon, the method comprising contacting an agent or a vector encoding the agent to the cell, wherein the agent comprises an antisense oligomer that binds to: (a) a targeted portion of the pre-mRNA within an intronic region immediately upstream of a 5' end of the coding exon of the pre-mRNA; or (b) a targeted portion of the pre-mRNA within an intronic region immediately downstream of a 3' end of the coding exon of the pre-mRNA; whereby the agent increases a level of a processed mRNA that is processed from the pre-mRNA and that contains the coding exon in the cell.

In some embodiments, the coding exon is an alternatively spliced exon. In some embodiments, the method promotes inclusion of the coding exon in the processed mRNA during splicing of the pre-mRNA in the cell. In some embodiments, the target portion of the pre-mRNA is within a region spanning from 100 to 50, from 100 to 60, from 100 to 70, from 100 to 80, or from 100 to 90 nucleotides upstream of a 5' end of the coding exon. In some embodiments, the target portion of the pre-mRNA is within a region spanning from 40 to 100, from 50 to 100, from 60 to 100, from 70 to 100, from 80 to 100, or from 90 to 100 nucleotides downstream of a 3' end of the coding exon. In some embodiments, the coding exon comprises a sequence with at least 80%, at least 90%, or 100% sequence identity to SEQ ID NO: 277. In some embodiments, the coding exon comprises SEQ ID NO: 277. In some embodiments, the targeted portion of the pre-mRNA is within a region spanning from 100 to 50, from 100 to 60, from 100 to 70, from 100 to 80, or from 100 to 90 nucleotides upstream of genomic site GRCh38/hg38: chr3 193626092. In some embodiments, the targeted portion of the pre-mRNA is within a region spanning from 40 to 100, from 50 to 100, from 60 to 100, from 70 to 100, from 80 to 100, or from 90 to 100 nucleotides downstream of genomic site GRCh38/hg38: chr3 193626202. In some embodiments, the inclusion of the coding exon in the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the agent comprises an antisense oligomer with at least 80%, at least 90%, or 100% sequence identity to SEQ ID NO: 267.

Described herein, in some aspects, is a method of modulating expression of a target protein in a cell having a pre-mRNA transcribed from a gene that encodes the target protein, wherein the pre-mRNA comprises a coding exon and a non-sense mediated RNA decay-inducing exon (NMD exon), the method comprising contacting an agent or a vector encoding the agent to the cell, wherein the agent promotes exclusion of both the coding exon and the NMD exon from the pre-mRNA, thereby increasing a level of a processed mRNA that is processed from the pre-mRNA and that lacks both the NMD exon and the coding exon in the cell.

In some embodiments, the agent: (a) binds to a targeted portion of the pre-mRNA; (b) modulates binding of a factor involved in splicing of the coding exon, the NMD exon, or both; or (c) a combination of (a) and (b). In some embodiments, the agent interferes with binding of the factor involved in splicing of the coding exon, the NMD exon, or both, to a region of the targeted portion. In some embodiments, the NMD exon is within an intronic region adjacent to the coding exon. In some embodiments, the NMD exon is within an intronic region immediately upstream of the coding exon. In some embodiments, the NMD exon is within an intronic region immediately downstream of the coding exon. In some embodiments, the targeted portion of the pre-mRNA is proximal to the coding exon. In some embodiments, the targeted portion of the pre-mRNA is located in an intronic region immediately upstream of the coding exon. In some embodiments, the targeted portion of the pre-mRNA is located in an intronic region immediately downstream of the coding exon. In some embodiments, the targeted portion of the pre-mRNA is located within the coding exon. In some embodiments, the targeted portion of the pre-mRNA is within a region spanning from 49 to 1, from 39 to 1, from 29 to 1, or from 19 to 1 nucleotides upstream of 5' end of the coding exon. In some embodiments, the targeted portion of the pre-mRNA is within a region spanning from 100 nucleotides upstream of the coding exon to 100 nucleotides downstream of the coding exon. In some embodiments, the coding exon is an alternatively spliced exon. In some embodiments, the coding exon comprises a sequence with at least 80%, at least 90%, or 100% sequence identity to SEQ ID NO: 277.

In some embodiments, the coding exon comprises SEQ ID NO: 277. In some embodiments, the targeted portion of the pre-mRNA is immediately upstream of the coding exon GRCh38/hg38: chr3 193626092 to 193626202. In some embodiments, the targeted portion of the pre-mRNA is immediately downstream of the coding exon GRCh38/hg38: chr3 193626092 to 193626202. In some embodiments, the targeted portion of the pre-mRNA is within a region spanning from 49 to 1, from 39 to 1, from 29 to 1, or from 19 to 1 nucleotides upstream of GRCh38/hg38: chr3 193626092. In some embodiments, the targeted portion of the pre-mRNA is within a region spanning from 100 nucleotides upstream of genomic site GRCh38/hg38: chr3 193626092. to 100 nucleotides downstream of genomic site GRCh38/hg38: chr3 193626202. In some embodiments, the targeted portion of the pre-mRNA is within the coding exon GRCh38/hg38: chr3 193626092 to 193626202. In some embodiments, the targeted portion of the pre-mRNA comprises an exon-intron junction of the coding exon GRCh38/hg38: chr3 193626092 to 193626202. In some embodiments, the targeted portion comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the coding exon. In some embodiments, the targeted portion of the pre-mRNA is proximal to the NMD exon. In some embodiments, the targeted portion of the pre-mRNA is located in an intronic region immediately upstream of the NMD exon. In some embodiments, the targeted portion of the pre-mRNA is located in an intronic region immediately downstream of the NMD exon. In some embodiments, the targeted portion of the pre-mRNA is located within the NMD exon. In some embodiments, the targeted portion of the pre-mRNA is within a region spanning from 100 nucleotides upstream of the NMD exon to 100 nucleotides downstream of the NMD exon. In some embodiments, the NMD exon comprises a sequence with at least 80%, at least 90%, or 100% sequence identity to SEQ ID NO: 279. In some embodiments, the NMD exon comprises SEQ ID NO: 279. In some embodiments, the targeted portion of the pre-mRNA is immediately upstream of the NMD exon GRCh38/hg38: chr3 193628509 to 193628616. In some embodiments, the targeted portion of the pre-mRNA is immediately downstream of the NMD exon GRCh38/hg38: chr3 193628509 to 193628616. In some embodiments, the targeted portion of the pre-mRNA is within a region spanning from 100 nucleotides upstream of genomic site GRCh38/hg38: chr3 193628509 to 100 nucleotides downstream of genomic site GRCh38/hg38: chr3 193628616. In some embodiments, the targeted portion of the pre-mRNA is within the NMD exon GRCh38/hg38: chr3 193628509 to 193628616. In some embodiments, the targeted portion of the pre-mRNA comprises an exon-intron junction of the NMD exon GRCh38/hg38: chr3 193628509 to 193628616. In some embodiments, the targeted portion comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

In some embodiments, the exclusion of the coding exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the exclusion of the NMD exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the agent results in an increase in the level of the processed mRNA in the cell. In some embodiments, the level of the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the method results in an increase in expression of the target protein in the cell. In some embodiments, a level of the target protein expressed from the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the target protein is an OPA1 protein. In some embodiments, a level of the OPA1 protein expressed from the processed mRNA in the cell contacted with the agent is increased by at least about 1.5-fold compared to in the absence of the agent. In some embodiments, the OPA1 protein expressed from the processed mRNA is a functional OPA1 protein.

In some embodiments, the OPA1 protein expressed from the processed mRNA is at least partially functional as compared to a wild-type OPA1 protein. In some embodiments, the OPA1 protein expressed from the processed mRNA is at least partially functional as compared to a full-length wild-type OPA1 protein.

In some embodiments, the agent comprises an antisense oligomer with at least 80%, at least 90%, or 100% sequence identity to a sequence selected from the group consisting of SEQ ID NOs: 236, 242, 250, 280-283, 288, and 290-292. In some embodiments, the agent comprises a gene editing molecule. In some embodiments, the gene editing molecule comprises CRISPR-Cas9.

In some embodiments, the agent is an antisense oligomer (ASO) and wherein the antisense oligomer comprises a backbone modification comprising a phosphorothioate linkage or a phosphorodiamidate linkage. In some embodiments, the agent is an antisense oligomer (ASO) and wherein the antisense oligomer comprises a phosphorodiamidate morpholino, a locked nucleic acid, a peptide nucleic acid, a 2'-O-methyl moiety, a 2'-Fluoro moiety, or a 2'-O-methoxyethyl moiety. In some embodiments, the therapeutic agent is an antisense oligomer (ASO) and wherein the antisense oligomer comprises at least one modified sugar moiety. In some embodiments, each sugar moiety is a modified sugar moiety. In some embodiments, the agent is an antisense oligomer (ASO) and wherein the antisense oligomer consists of from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases. In some embodiments, the vector comprises a viral vector encoding the agent. In some embodiments, the viral vector comprises an adenoviral vector, adeno-associated viral (AAV) vector, lentiviral vector, Herpes Simplex Virus (HSV) viral vector, or retroviral vector.

In some embodiments, the method further comprises assessing mRNA level or expression level of the OPA1 protein. In some embodiments, the agent is a therapeutic agent.

Described herein, in some aspects, is a pharmaceutical composition comprising the therapeutic agent as disclosed herein or a vector encoding the therapeutic agent as disclosed herein, and a pharmaceutically acceptable excipient.

Described herein, in some aspects, is a pharmaceutical composition, comprising a therapeutic agent or a vector encoding a therapeutic agent, and a pharmaceutically acceptable excipient, wherein the therapeutic agent comprises an antisense oligomer with at least 80% sequence identity to a sequence selected from the group consisting of SEQ ID NOs: 6-275 and 280-299. In some embodiments, the therapeutic agent comprises an antisense oligomer with at least 80%, at least 90%, or 100% sequence identity to a sequence selected from the group consisting of SEQ ID NOs: 36, 236, 242, 250, 280-283, 288, and 290-292. In some embodiments, the therapeutic agent comprises an antisense oligomer with at least 80%, at least 90%, or 100% sequence identity to a sequence selected from the group consisting of SEQ ID NOs: 227-242, 250, 280-283, 288, and 290-292. In some embodiments, the therapeutic agent comprises an antisense oligomer with at least 80%, at least 90%, or 100% sequence identity to SEQ ID NO: 267. In some embodiments, the therapeutic agent comprises an antisense oligomer with at least 80%, at least 90%, or 100% sequence identity to a sequence selected from the group consisting of SEQ ID NOs: 236, 242, 250, 280-283, 288, and 290-292.

Described herein, in some aspects, is a composition, comprising an antisense oligomer with at least 80% sequence identity to a sequence selected from the group consisting of SEQ ID NOs: 6-275 and 280-299, wherein the antisense oligomer comprises a backbone modification, a sugar moiety modification, or a combination thereof. In some embodiments, the antisense oligomer has at least 80%, at least 90%, or 100% sequence identity to a sequence selected from the group consisting of SEQ ID NOs: 36, 236, 242, 250, 280-283, 288, and 290-292. In some embodiments, the antisense oligomer has at least 80%, at least 90%, or 100% sequence identity to a sequence selected from the group consisting of SEQ ID NOs: 227-242, 250, 280-283, 288, and 290-292. In some embodiments, the antisense oligomer has at least 80%, at least 90%, or 100% sequence identity to SEQ ID NO: 267. In some embodiments, the antisense oligomer has at least 80%, at least 90%, or 100% sequence identity to a sequence selected from the group consisting of SEQ ID NOs: 236, 242, 250, 280-283, 288, and 290-292.

Described herein, in some aspects, is a pharmaceutical composition, comprising a therapeutic agent or a vector encoding the therapeutic agent, and a pharmaceutically acceptable excipient, wherein the therapeutic agent promotes exclusion of a coding exon from a pre-mRNA, thereby increasing a level of a processed mRNA that is processed from the pre-mRNA and that lacks the coding exon in a cell, wherein the pre-mRNA is transcribed from an OPA1 gene and that comprises the coding exon.

Described herein, in some aspects, is a pharmaceutical composition, comprising a therapeutic agent or a vector encoding the therapeutic agent, and a pharmaceutically acceptable excipient, wherein the therapeutic agent comprises an antisense oligomer that binds to a pre-mRNA that is transcribed from an OPA1 gene in a cell, wherein the antisense oligomer binds to: (a) a targeted portion of the pre-mRNA within an intronic region immediately upstream of a 5' end of the coding exon of the pre-mRNA; or (b) a targeted portion of the pre-mRNA within an intronic region immediately downstream of a 3' end of the coding exon of the pre-mRNA; whereby the therapeutic agent increases a level of a processed mRNA that is processed from the pre-mRNA and that contains the coding exon in the cell.

Described herein, in some aspects, is a pharmaceutical composition, comprising a therapeutic agent or a vector encoding the therapeutic agent, and a pharmaceutically acceptable excipient, wherein the therapeutic agent promotes exclusion of both a coding exon and a non-sense mediated RNA decay-inducing exon (NMD exon) from a pre-mRNA, thereby increasing a level of a processed mRNA that is processed from the pre-mRNA and that lacks the coding exon and the NMD exon in a cell, wherein the pre-mRNA is transcribed from an OPA1 gene in the cell and comprises the coding exon and the NMD exon.

In some embodiments, the pharmaceutical composition is formulated for intracerebroventricular injection, intraperitoneal injection, intramuscular injection, intrathecal injection, subcutaneous injection, oral administration, synovial injection, intravitreal administration, subretinal injection, topical application, implantation, or intravenous injection. In some embodiments, the pharmaceutical composition is formulated for intravitreal injection. In some embodiments, the pharmaceutical composition further comprises a second therapeutic agent. In some embodiments, the second therapeutic agent comprises a small molecule. In some embodiments, the second therapeutic agent comprises an antisense oligomer. In some embodiments, the second therapeutic agent corrects intron retention. In some embodiments, the antisense oligomer is selected from the group consisting of Compound ID NOs: 1-303.

Described herein, in some aspects, is a method of treating or reducing the likelihood of developing a disease or condition in a subject in need thereof by modulating expression of an OPA1 protein in a cell of the subject, comprising contacting to cells of the subject the therapeutic agent as disclosed herein. In some embodiments, the disease or condition is associated with a loss-of-function mutation in an OPA1 gene. In some embodiments, the disease or condition is associated with haploinsufficiency of the OPA1 gene, and wherein the subject has a first allele encoding a functional OPA1 protein, and a second allele from which the OPA1 protein is not produced or produced at a reduced level, or a second allele encoding a nonfunctional OPA1 protein or a partially functional OPA1 protein. In some embodiments, the disease or condition comprises an eye disease or condition. In some embodiments, the disease or condition comprises ADOA-plus syndrome; a mitochondrial disorder; glaucoma; normal tension glaucoma; Charcot-Marie-Tooth disease; mitochondria dysfunction; diabetic retinopathy; age-related macular degeneration; retinal ganglion cell death; mitochondrial fission-mediated mitochondrial dysfunction; progressive external ophthalmoplegia; deafness; ataxia; motor neuropathy; sensory neuropathy; myopathy; Behr syndrome; brain dysfunction; encephalopathy; peripheral neuropathy; fatal infantile mitochondrial encephalomyopathy; hypertrophic cardiomyopathy; spastic ataxic syndrome; sensory motor peripheral neuropathy; hypotonia; gastrointestinal dysmotility and dysphagia; optic atrophy; optic atrophy plus syndrome; Mitochondrial DNA depletion syndrome 14; late-onset cardiomyopathy; diabetic cardiomyopathy; Alzheimer's Disease; focal segmental glomerulosclerosis; kidney disease; Huntington's Disease; cognitive function decline in healthy aging; Prion diseases; late onset dementia and parkinsonism; mitochondrial myopathy; Leigh syndrome; Friedreich's ataxia; Parkinson's disease; MELAS (Mitochondrial encephalomyopathy, lactic acidosis, and stroke-like episodes); pyruvate dehydrogenase complex deficiency; chronic kidney disease; Leber's hereditary optic neuropathy; obesity; age-related systemic neurodegeneration; skeletal muscle atrophy; heart and brain ischemic damage; or massive liver apoptosis. In some embodiments, the disease or condition comprises Optic atrophy type 1. In some embodiments, the disease or condition comprises autosomal dominant optic atrophy (ADOA). In some embodiments, the disease or condition is associated with an autosomal recessive mutation of OPA1 gene, wherein the subject has a first allele encoding from which: (i) OPA1 protein is not produced or produced at a reduced level compared to a wild-type allele; or (ii) the OPA1 protein produced is nonfunctional or partially functional compared to a wild-type allele, and a second allele from which: (iii) the OPA1 protein is produced at a reduced level compared to a wild-type allele and the OPA1 protein produced is at least partially functional compared to a wild-type allele; or (iv) the OPA1 protein produced is partially functional compared to a wild-type allele.

In some embodiments, the subject is a human. In some embodiments, the subject is a non-human animal. In some embodiments, the subject is a fetus, an embryo, or a child. In some embodiments, the cells that the methods and compositions described herein are applicable to are ex vivo. In some embodiments, the therapeutic agent is administered by intracerebroventricular injection, intraperitoneal injection, intramuscular injection, intrathecal injection, subcutaneous injection, oral administration, synovial injection, intravitreal administration, subretinal injection, topical application, implantation, or intravenous injection. In some embodiments, the therapeutic agent is administered by intravitreal injection. In some embodiments, the method disclosed herein treats the disease or condition.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A shows a cell divided into nuclear and cytoplasmic compartments. In the nucleus, a pre-mRNA transcript of a target gene undergoes splicing to generate mRNA, and this mRNA is exported to the cytoplasm and translated into target protein. For this target gene, some fraction of the mRNA contains a nonsense-mediated mRNA decay-inducing exon (NMD exon mRNA) that is degraded in the cytoplasm, thus leading to no target protein production. FIG. 1B shows an example of the same cell divided into nuclear and cytoplasmic compartments. Treatment with a therapeutic agent, such as an antisense oligomer (ASO), promotes the exclusion of the nonsense-mediated mRNA decay-inducing exon and results in an increase in mRNA, which is in turn translated into higher levels of target protein. FIG. 1C shows an example schematic of a Novel NMD exon inclusion event (Exon X) identified in the OPA1 gene which leads to the introduction of a premature termination codon (PTC) resulting in a non-productive mRNA transcript degraded by non-sense mediated decay (NMD).

FIG. 2 discloses SEQ ID NO: 300.

FIG. 3 discloses SEQ ID NO: 301.

FIG. 5 discloses SEQ ID NOS 302-304, respectively, in order of appearance.

FIG. 9A confirms expression of OPA1 transcripts containing the NMD exon in these cells.

FIG. 15 illustrates exemplary OPA1 ASOs of this disclosure. The right two columns in the chart illustrate the chemical modifications of the exemplary ASOs. Each nucleotide of all the ASOs has 2'-O-methoxyethyl (2'MOE) modification ("MOE") unless otherwise noted, for instance, letters of larger font size (e.g., G) are locked nucleic acids ("LNA"), underlined letters (e.g., C) are 5' methyl-cytosines that have 2'-MOE moiety ("SMeC-MOE"), and some ASOs are noted as phosphorodiamidate morpholino oligomers ("PMO"). FIG. 15 discloses SEQ ID NOS 6-148, 148, 148, 149, 149, 149, 150, 150, 150-151, 151, 151, 123, 152, 152, 152-153, 153, 153-154, 154, 154, 144-146, 93, 81-82, 36, 155, 155-156, 156-157, 157-161, 125, 162, 126, 163-166, 92, 167-179, 156, 180, 157, 159, 181, 160, 182, 161, 183-275, and 305-607 respectively, in order of column.

FIG. 18D summarizes the Ct values for the qPCR reactions, and FIG. 18E summarizes the relative amounts.

FIG. 24B shows the immunoblot gel images of OPA1 and β-actin proteins, and FIG. 24C is a histogram that summarizes quantification of the immunoblot results.

in wildtype (WT) fibroblast cells and fibroblast cells from diagnosed patients that have haploinsufficient mutation in OPA1 gene.

Figure 26B:
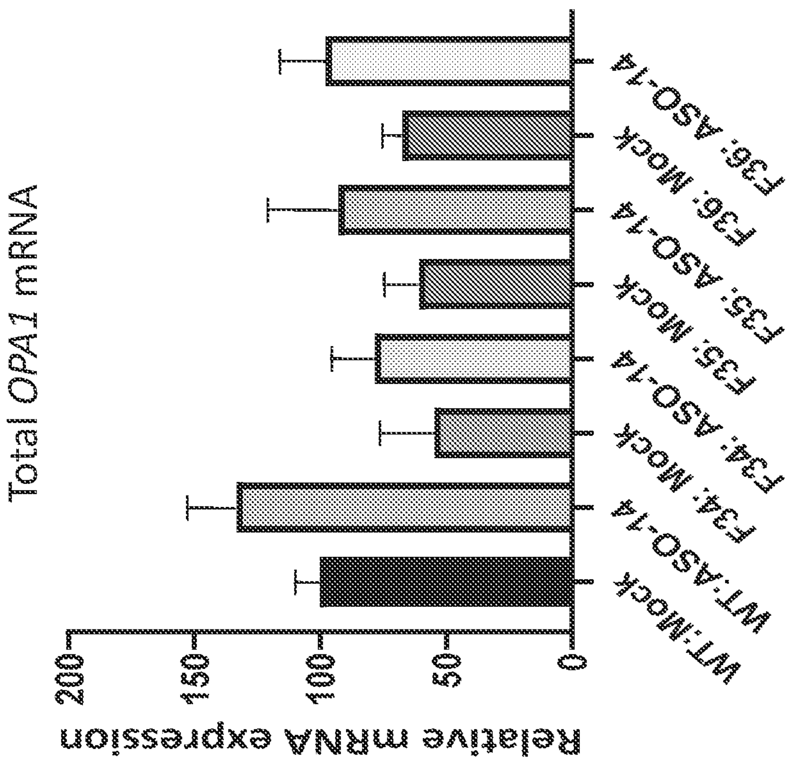
FIGS. 26A, 26B, and 26D show histograms that demonstrate exemplary antisense oligomer, ASO-14, decreased OPA1 NMD exon inclusion (FIG. 26A), increased OPA1 total mRNA level (FIG. 26B), and protein level (FIG. 26D)
Figure 26A:
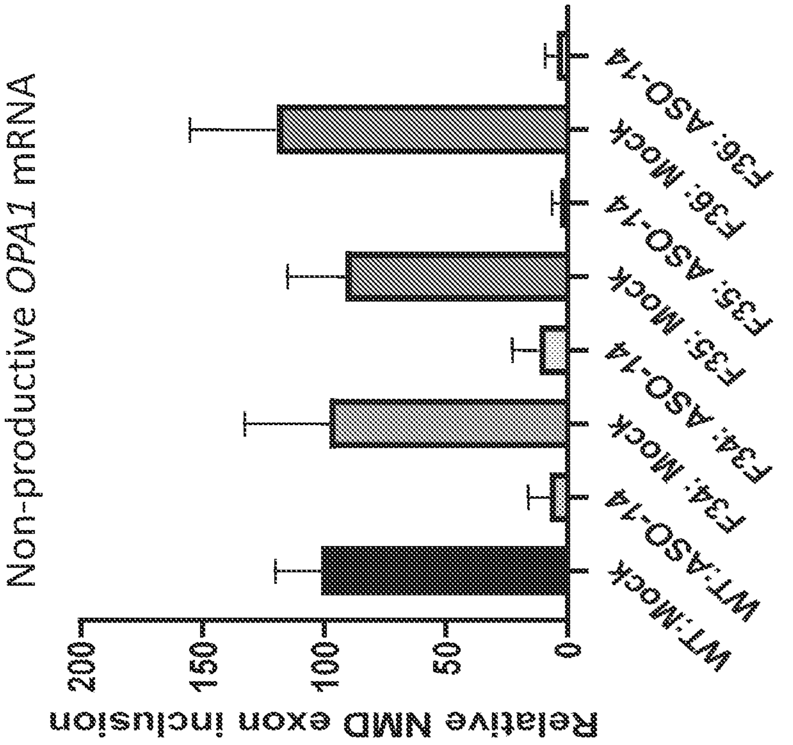
Figure 26C:
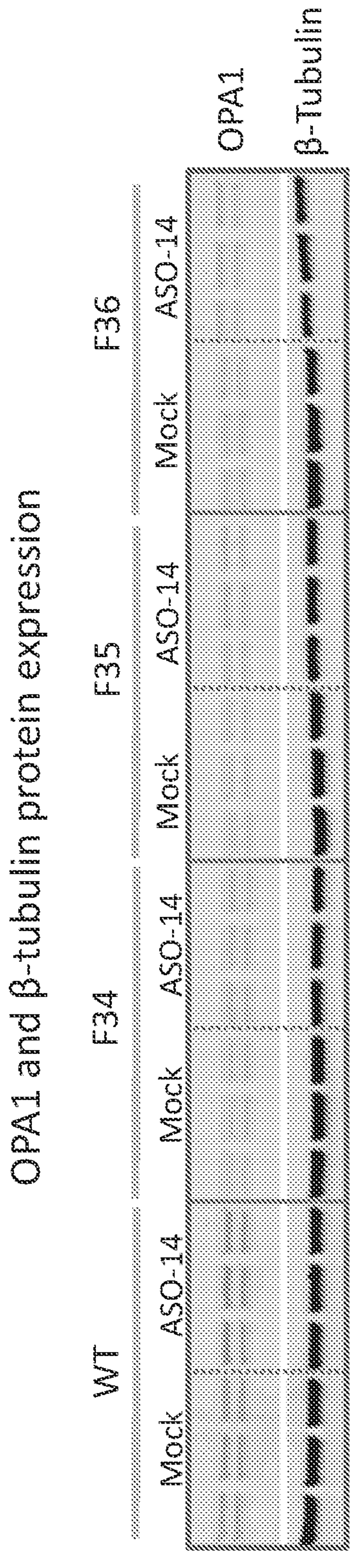

FIG. 26C shows representative immunoblot images of OPA1 protein and loading control 13-Tubulin under all types of conditions.

Figure 27A:
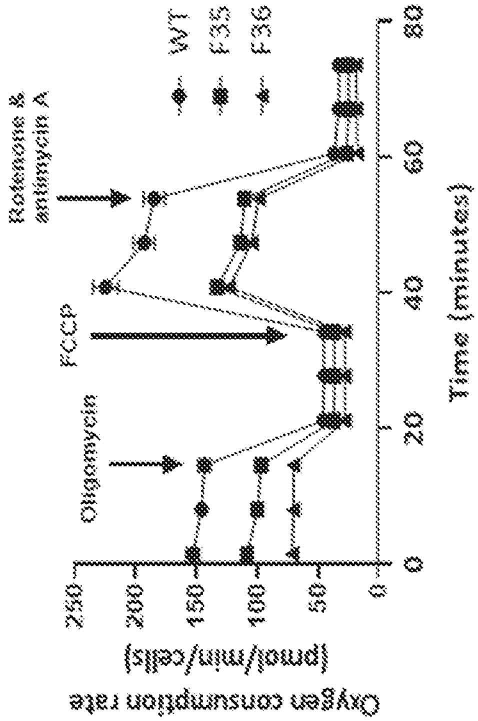
Figure 27B:
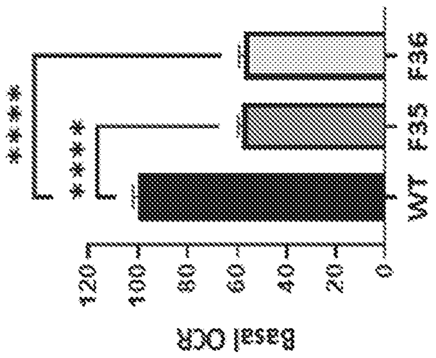
Figure 27C:
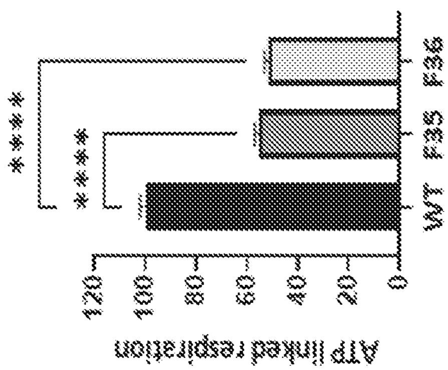
Figure 27D:
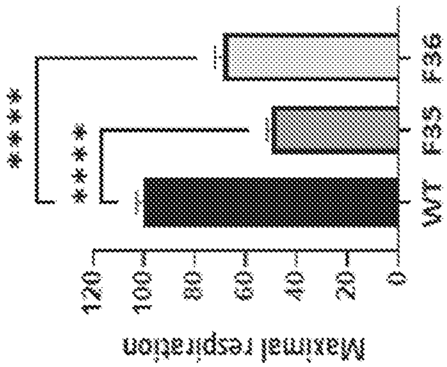
Figure 27E:
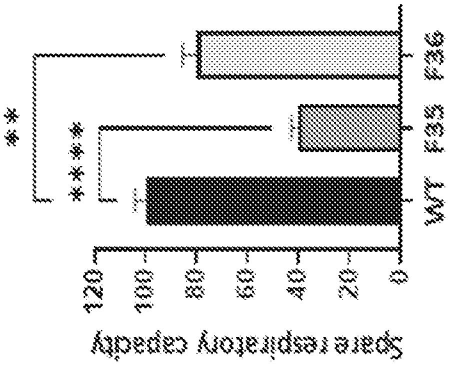

FIGS. 27A-27E demonstrate that patient fibroblast cells (cell lines F35 and F36) show deficiencies in mitochondrial bioenergetics. FIG. 27A shows representative time courses of the oxygen consumption rate of WT cells, F35 cells, and F36 cells at baseline level and when challenged sequentially with oligomycin, FCCP, rotenone and antimycin A. FIGS. 27B-27E show histograms demonstrating that patient fibroblast cells, F35 and F36 cells had reduced basal oxygen consumption rate (FIG. 27B), ATP linked respiration (FIG. 27C), maximal respiration (FIG. 27D), and spare respiratory capacity (FIG. 27E), as compared to WT fibroblast cells.

FIGS. 28A-28D show histograms demonstrating that treatment of ASO-14 at 20 nM, 40 nM, and 60 nM increased basal oxygen consumption rate (FIG. 28A), ATP linked respiration (FIG. 28B), maximal respiration (FIG. 28C), and spare respiratory capacity (FIG. 28D) of F35 patient cells in a dose-dependent manner.

FIGS. 29A-29D show histograms demonstrating that treatment of ASO-14 at 20 nM, 40 nM, and 60 nM increased basal oxygen consumption rate (FIG. 29A), ATP linked respiration (FIG. 29B), maximal respiration (FIG. 29C), and spare respiratory capacity (FIG. 29D) of F36 patient cells in a dose-dependent manner.

DETAILED DESCRIPTION

Alternative splicing events in the OPA1 gene can lead to non-productive mRNA transcripts which in turn can lead to aberrant protein expression, and therapeutic agents which can target the alternative splicing events in the OPA1 gene can modulate the expression level of functional proteins in DS patients and/or inhibit aberrant protein expression. Such therapeutic agents can be used to treat a condition caused by OPA1 protein deficiency.

One of the alternative splicing events that can lead to non-productive mRNA transcripts is the inclusion of an extra exon in the mRNA transcript that can induce non-sense mediated mRNA decay. The present disclosure provides compositions and methods for modulating alternative splicing of OPA1 to increase the production of protein-coding mature mRNA, and thus, translated functional OPA1 protein. These compositions and methods include antisense oligomers (ASOs) that can cause exon skipping, e.g., pseudoexon skipping, and promote constitutive splicing of OPA1 pre-mRNA. In various embodiments, functional OPA1 protein can be increased using the methods of the disclosure to treat a condition caused by OPA1 protein deficiency.

mRNA Splicing

Intervening sequences in RNA sequences or introns are removed by a large and highly dynamic RNA-protein complex termed the spliceosome, which orchestrates complex interactions between primary transcripts, small nuclear RNAs (snRNAs) and a large number of proteins. Spliceosomes assemble ad hoc on each intron in an ordered manner, starting with recognition of the 5' splice site (5'ss) by U1 snRNA or the 3'splice site (3'ss) by the U2 pathway, which involves binding of the U2 auxiliary factor (U2AF) to the 3'ss region to facilitate U2 binding to the branch point sequence (BPS). U2AF is a stable heterodimer composed of a U2AF2-encoded 65-kD subunit (U2AF65), which binds the polypyrimidine tract (PPT), and a U2AF1-encoded 35-kD subunit (U2AF35), which interacts with highly conserved AG dinucleotides at 3'ss and stabilizes U2AF65 binding. In addition to the BPS/PPT unit and 3'ss/5'ss, accurate splicing requires auxiliary sequences or structures that activate or repress splice site recognition, known as intronic or exonic splicing enhancers or silencers. These elements allow genuine splice sites to be recognized among a vast excess of cryptic or pseudo-sites in the genome of higher eukaryotes, which have the same sequences but outnumber authentic sites by an order of magnitude. Although they often have a regulatory function, the exact mechanisms of their activation or repression are poorly understood.

The decision of whether to splice or not to splice can be typically modeled as a stochastic rather than deterministic process, such that even the most defined splicing signals can sometimes splice incorrectly. However, under normal conditions, pre-mRNA splicing proceeds at surprisingly high fidelity. This is attributed in part to the activity of adjacent cis-acting auxiliary exonic and intronic splicing regulatory elements (ESRs or ISRs). Typically, these functional elements are classified as either exonic or intronic splicing enhancers (ESEs or ISEs) or silencers (ESSs or ISSs) based on their ability to stimulate or inhibit splicing, respectively. Although there is now evidence that some auxiliary cis-acting elements may act by influencing the kinetics of spliceosome assembly, such as the arrangement of the complex between U1 snRNP and the 5'ss, it seems very likely that many elements function in concert with trans-acting RNA-binding proteins (RBPs). For example, the serine- and arginine-rich family of RBPs (SR proteins) is a conserved family of proteins that have a key role in defining exons. SR proteins promote exon recognition by recruiting components of the pre-spliceosome to adjacent splice sites or by antagonizing the effects of ESSs in the vicinity. The repressive effects of ESSs can be mediated by members of the heterogeneous nuclear ribonucleoprotein (hnRNP) family and can alter recruitment of core splicing factors to adjacent splice sites. In addition to their roles in splicing regulation, silencer elements are suggested to have a role in repression of pseudo-exons, sets of decoy intronic splice sites with the typical spacing of an exon but without a functional open reading frame. ESEs and ESSs, in cooperation with their cognate trans-acting RBPs, represent important components in a set of splicing controls that specify how, where and when mRNAs are assembled from their precursors.

Alternative splicing is a regulated process during gene expression that can result in multiple isoforms of mature mRNA transcripts that are processed from a single primary mRNA transcript that is transcribed from a single gene, and the resultant multiple proteins that are translated from at least some of the multiple mature mRNA isoforms. In this process, particular exons of a gene may be included within or excluded from the final, processed mRNA produced from that gene. Consequently, the proteins translated from alternatively splices mRNAs will contain differences in their amino acid sequence and, in some cases, in their biological functions.

As described herein, an "alternatively spliced exon" can refer to an exon of a gene that can be either included or excluded naturally from a mature mRNA transcript, thus resulting in different protein products that are translated from the different mature mRNA transcripts. The inclusion or skipping of an alternatively spliced exon can take place naturally in a cell, either randomly, or in a regulated manner, e.g., subject to regulation by external physiological or pathological stimuli, or intracellular signaling. In some cases, the production of alternatively spliced mRNAs, e.g., the splicing of the alternatively spliced exon, is regulated by a system of trans-acting proteins that bind to cis-acting sites on the primary transcript itself. In some cases, an alternatively spliced exon is a coding exon, e.g., an exon that, when included in the mature mRNA transcript, is translated into an amino acid sequence as part of the protein product translated from the mature mRNA transcript. In some cases, the inclusion of an alternatively spliced exon in the mature mRNA transcript would maintain the canonical open reading frame as compared to a mature mRNA transcript without the alternatively spliced exon, e.g., the number of nucleotides in the alternatively spliced exon is divisible by 3.

The sequences marking the exon-intron boundaries are degenerate signals of varying strengths that can occur at high frequency within human genes. In multi-exon genes, different pairs of splice sites can be linked together in many different combinations, creating a diverse array of transcripts from a single gene. This is commonly referred to as alternative pre-mRNA splicing. Although most mRNA isoforms produced by alternative splicing can be exported from the nucleus and translated into functional polypeptides, different mRNA isoforms from a single gene can vary greatly in their translation efficiency. Those mRNA isoforms with premature termination codons (PTCs) at least 50 bp upstream of an exon junction complex are likely to be targeted for degradation by the nonsense-mediated mRNA decay (NMD) pathway. Mutations in traditional (BPS/PPT/3'ss/5'ss) and auxiliary splicing motifs can cause aberrant splicing, such as exon skipping or cryptic (or pseudo-) exon inclusion or splice-site activation, and contribute significantly to human morbidity and mortality. Both aberrant and alternative splicing patterns can be influenced by natural DNA variants in exons and introns.

Given that exon-intron boundaries can occur at any of the three positions of a codon, it is clear that only a subset of alternative splicing events can maintain the canonical open reading frame. For example, only exons that are evenly divisible by 3 can be skipped or included in the mRNA without any alteration of reading frame. Splicing events that do not have compatible phases will induce a frame-shift. Unless reversed by downstream events, frame-shifts can certainly lead to one or more PTCs, probably resulting in subsequent degradation by NMD. NMD is a translation-coupled mechanism that eliminates mRNAs containing PTCs. NMD can function as a surveillance pathway that exists in all eukaryotes. NMD can reduce errors in gene expression by eliminating mRNA transcripts that contain premature stop codons. Translation of these aberrant mRNAs could, in some cases, lead to deleterious gain-of-function or dominant-negative activity of the resulting proteins. NMD targets not only transcripts with PTCs but also a broad array of mRNA isoforms expressed from many endogenous genes, suggesting that NMD is a master regulator that drives both fine and coarse adjustments in steady-state RNA levels in the cell.

A NMD-inducing exon ("NIE" or "NMD exon") is an exon or a pseudo-exon that is a region within an intron and can activate the NMD pathway if included in a mature RNA transcript. In constitutive splicing events, the intron containing an NMD exon is usually spliced out, but the intron or a portion thereof (e.g. NMD exon) may be retained during alternative or aberrant splicing events. Mature mRNA transcripts containing such an NMD exon may be non-productive due to frame shifts which induce the NMD pathway. Inclusion of a NMD exon in mature RNA transcripts may downregulate gene expression. mRNA transcripts containing an NMD exon may be referred to as "NIE-containing mRNA" or "NMD exon mRNA" in the current disclosure.

Cryptic (or pseudo-splice sites) have the same splicing recognition sequences as genuine splice sites but are not used in splicing reactions. They outnumber genuine splice sites in the human genome by an order of a magnitude and are normally repressed by thus far poorly understood molecular mechanisms. Cryptic 5' splice sites have the consensus NNN/GUNNNN or NNN/GCNNNN where N is any nucleotide and/is the exon-intron boundary. Cryptic 3' splice sites have the consensus NAG/N. Their activation is positively influenced by surrounding nucleotides that make them more similar to the optimal consensus of authentic splice sites, namely MAG/GURAGU and YAG/G, respectively, where M is C or A, R is G or A, and Y is C or U.

Splice sites and their regulatory sequences can be readily identified by a skilled person using suitable algorithms publicly available, listed for example in Kralovicova, J. and Vorechovsky, I. (2007) Global control of aberrant splice site activation by auxiliary splicing sequences: evidence for a gradient in exon and intron definition. *Nucleic Acids Res.,* 35, 6399-6413 (www.ncbi.nlm.nih.gov/pmc/articles/PMC2095810/pdf/gkm680.pdf).

The cryptic splice sites or splicing regulatory sequences may compete for RNA-binding proteins, such as U2AF, with a splice site of the NMD exon. In some embodiments, an agent may bind to a cryptic splice site or splicing regulatory sequence to prevent binding of RNA-binding proteins and thereby favor binding of RNA-binding proteins to the NMD exon splice sites.

In some embodiments, the cryptic splice site may not comprise the 5' or 3' splice site of the NMD exon. In some embodiments, the cryptic splice site may be at least 10 nucleotides, at least 20 nucleotides, at least 50 nucleotides, at least 100 nucleotides or at least 200 nucleotides upstream of the NMD exon 5' splice site. In some embodiments, the cryptic splice site may be at least 10 nucleotides, at least 20 nucleotides, at least 50 nucleotides, at least 100 nucleotides, at least 200 nucleotides downstream of the NMD exon 3' splice site.

Target Transcripts

In some embodiments, the methods and compositions of the present disclosure exploit the presence of NMD exon in the pre-mRNA transcribed from the OPA1 gene. Splicing of the identified OPA1 NMD exon pre-mRNA species to produce functional mature OPA1 mRNA may be induced using an agent such as an ASO that stimulates exon skipping of an NMD exon. Induction of exon skipping may result in inhibition of an NMD pathway. The resulting mature OPA1 mRNA can be translated normally without activating NMD pathway, thereby increasing the amount of OPA1 protein in the patient's cells and alleviating symptoms of a condition or disease associated with OPA1 deficiency, such as an eye disease or condition, Optic atrophy type 1, autosomal dominant optic atrophy (ADOA), ADOA-plus syndrome; a mitochondrial disorder; glaucoma; normal tension glaucoma; Charcot-Marie-Tooth disease; mitochondria dysfunction; diabetic retinopathy; age-related macular degeneration; retinal ganglion cell death; mitochondrial fission-mediated mitochondrial dysfunction; progressive external ophthalmoplegia; deafness; ataxia; motor neuropathy; sensory neuropathy; myopathy; Behr syndrome; brain dysfunction; encephalopathy; peripheral neuropathy; fatal infantile mitochondrial encephalomyopathy; hypertrophic cardiomyopathy; spastic ataxic syndrome; sensory motor peripheral neuropathy; hypotonia; gastrointestinal dysmotility and dysphagia; optic atrophy; optic atrophy plus syndrome; Mitochondrial DNA depletion syndrome 14; late-onset cardiomyopathy; diabetic cardiomyopathy; Alzheimer's Disease; focal segmental glomerulosclerosis; kidney disease; Huntington's Disease; cognitive function decline in healthy aging; Prion diseases; late onset dementia and parkinsonism; mitochondrial myopathy; Leigh syndrome; Friedreich's ataxia; Parkinson's disease; MELAS (Mitochondrial encephalomyopathy, lactic acidosis, and stroke-like episodes); pyruvate dehydrogenase complex deficiency; chronic kidney disease; Leber's hereditary optic neuropathy; obesity; age-related systemic neurodegeneration; skeletal muscle atrophy; heart and brain ischemic damage; or massive liver apoptosis.

In some embodiments, the methods and compositions of the present disclosure exploit the alternative splicing of the pre-mRNA transcribed from the OPA1 gene. In some cases, splicing of a coding exon, e.g., an alternatively spliced exon, e.g., OPA1 exon 7 (or an exon encoded by genomic region spanning from GRCh38/hg38: chr3 193626092 to 193626202), can modulate the level of OPA1 protein expressed from the OPA1 gene. As described herein, the term "OPA1 exon 7" or grammatically equivalents thereof, is used interchangeably with the term "exon (GRCh38/hg38: chr3 193626092 to 193626202)" or "an exon encoded by genomic region spanning from GRCh38/hg38: chr3 193626092 to 193626202." Without wishing to be bound by a certain theory, the presence or absence of an amino acid sequence encoded by exon 7 or exon (GRCh38/hg38: chr3 193626092 to 193626202) can modulate the stability of the OPA1 protein. For instance, in some cases, the OPA1 protein encoded by a mature mRNA transcript that lacks exon 7 can have fewer proteolytic cleavage sites as compared to an OPA1 protein encoded by a corresponding mature mRNA transcript that has contains exon 7. In some cases, the OPA1 protein an OPA1 protein encoded by a corresponding mature mRNA transcript that has contains encoded by a mature mRNA transcript that lacks exon 7 is a functional protein. The OPA1 protein encoded by a mature mRNA transcript that lacks exon 7 can be at least partially functional as compared to an OPA1 protein encoded by a corresponding mature mRNA transcript that has contains exon 7. In some cases, the OPA1 protein encoded by a mature mRNA transcript that lacks exon 7 is at least partially functional as compared to a full-length wild-type OPA1 protein. In some cases, increase of OPA1 protein encoded by a mature mRNA transcript that lacks exon 7 in a cell can result in more functional OPA1 protein in the cell, due to the higher stability of the OPA1 protein lacking exon 7 and its at least partial functional equivalence.

In other embodiments, a coding exon of OPA1 pre-mRNA other than exon 7 is targeted by an agent disclosed herein, which promotes exclusion of the coding exon other than exon 7. In these other embodiments, the agent that promotes exclusion of the coding exon other than exon 7 increases expression of OPA1 protein encoded by a mature mRNA transcript that lacks the excluded exon.

Alternative splicing of the OPA1 pre-mRNA species, e.g., skipping of a coding exon, e.g., an alternatively spliced exon, e.g., exon 7, to produce functional mature OPA1 protein may be induced using an agent such as an ASO that stimulates the exon skipping. Induction of exon skipping may result in modulation of levels of different alternatively spliced mRNA transcripts. The resulting mature OPA1 mRNA can be translated into different OPA1 proteins, thereby modulating the amount of OPA1 protein in the patient's cells and alleviating symptoms of a condition or disease associated with OPA1 deficiency, such as an eye disease or condition, Optic atrophy type 1, autosomal dominant optic atrophy (ADOA), ADOA-plus syndrome; a mitochondrial disorder; glaucoma; normal tension glaucoma; charcot-Marie-tooth disease; mitochondria dysfunction; diabetic retinopathy; age-related macular degeneration; retinal ganglion cell death; mitochondrial fission-mediated mitochondrial dysfunction; progressive external ophthalmoplegia; deafness; ataxia; motor neuropathy; sensory neuropathy; myopathy; Behr syndrome; brain dysfunction; encephalopathy; peripheral neuropathy; fatal infantile mitochondrial encephalomyopathy; hypertrophic cardiomyopathy; spastic ataxic syndrome; sensory motor peripheral neuropathy; hypotonia; gastrointestinal dysmotility and dysphagia;

optic atrophy; optic atrophy plus syndrome; Mitochondrial DNA depletion syndrome 14; late-onset cardiomyopathy; diabetic cardiomyopathy; Alzheimer's Disease; focal segmental glomerulosclerosis; kidney disease; Huntington's Disease; cognitive function decline in healthy aging; Prion diseases; late onset dementia and parkinsonism; mitochondrial myopathy; Leigh syndrome; Friedreich's ataxia; Parkinson's disease; MELAS (Mitochondrial encephalomyopathy, lactic acidosis, and stroke-like episodes); pyruvate dehydrogenase complex deficiency; chronic kidney disease; Leber's hereditary optic neuropathy; obesity; age-related systemic neurodegeneration; skeletal muscle atrophy; heart and brain ischemic damage; or massive liver apoptosis.

In some embodiments, the diseases or conditions that can be treated or ameliorated using the method or composition disclosed herein are not directly associated with the target protein (gene) that the therapeutic agent targets. In some embodiments, a therapeutic agent provided herein can target a protein (gene) that is not directly associated with a disease or condition, but the modulation of expression of the target protein (gene) can treat or ameliorate the disease or condition.

In various embodiments, the present disclosure provides a therapeutic agent which can target OPA1 mRNA transcripts to modulate splicing or protein expression level. The therapeutic agent can be a small molecule, polynucleotide, or polypeptide. In some embodiments, the therapeutic agent is an ASO. Various regions or sequences on the OPA1 pre-mRNA can be targeted by a therapeutic agent, such as an ASO. In some embodiments, the ASO targets an OPA1 pre-mRNA transcript containing an NMD exon. In some embodiments, the ASO targets a sequence within an NMD exon of an OPA1 pre-mRNA transcript. In some embodiments, the ASO targets a sequence upstream (or 5') from the 5' end of an NMD exon (3'ss) of an OPA1 pre-mRNA transcript. In some embodiments, the ASO targets a sequence downstream (or 3') from the 3' end of an NMD exon (5'ss) of an OPA1 pre-mRNA transcript. In some embodiments, the ASO targets a sequence that is within an intron flanking on the 5' end of the NMD exon of an OPA1 pre-mRNA transcript. In some embodiments, the ASO targets a sequence that is within an intron flanking the 3' end of the NMD exon of an OPA1 pre-mRNA transcript. In some embodiments, the ASO targets a sequence comprising an NMD exon-intron boundary of an OPA1 pre-mRNA transcript. An NMD exon-intron boundary can refer to the junction of an intron sequence and an NMD exon region. The intron sequence can flank the 5' end of the NMD exon, or the 3' end of the NMD exon. In some embodiments, the ASO targets a sequence within an exon of an OPA1 pre-mRNA transcript. In some embodiments, the ASO targets a sequence within an intron of an OPA1 pre-mRNA transcript.

In some embodiments, the ASO targets a sequence comprising both a portion of an intron and a portion of an exon of an OPA1 pre-mRNA transcript.

In some embodiments, the ASO targets a sequence about 4 to about 300 nucleotides upstream (or 5') from the 5' end of the NMD exon. In some embodiments, the ASO targets a sequence about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, or about 250 to about 300 nucleotides upstream (or 5') from the 5' end of the NMD exon region. In some embodiments, the ASO may target a sequence more than 300 nucleotides upstream from the 5' end of the NMD exon. In some embodiments, the ASO targets a sequence about 4 to about 300 nucleotides downstream (or 3') from the 3' end of the NMD exon. In some embodiments, the ASO targets a sequence about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, or about 250 to about 300 nucleotides downstream from the 3' end of the NMD exon. In some embodiments, the ASO targets a sequence more than 300 nucleotides downstream from the 3' end of the NMD exon.

In some embodiments, the OPA1 NMD exon-containing pre-mRNA transcript is encoded by a genetic sequence with at least about 80%, 85%, 90%, 95%, 96%, 97%, 98%, 99% or 100% sequence identity to SEQ ID NO. 1. In some embodiments, the OPA1 NMD exon pre-mRNA transcript comprises a sequence with at least about 80%, 85%, 90%, 95%, 96%, 97%, 98%, 99% or 100% sequence identity to any one of SEQ ID NOs: 2-5.

In some embodiments, the OPA1 NMD exon-containing pre-mRNA transcript (or NMD exon mRNA) comprises a sequence with at least about 80%, 85%, 90%, 95%, 97%, or 100% sequence identity to any one of SEQ ID NOs: 2-5. In some embodiments, OPA1 NMD exon-containing pre-mRNA transcript (or NMD exon mRNA) is encoded by a sequence with at least about 80%, 85%, 90%, 95%, 97%, or 100% sequence identity to any one of SEQ ID NOs: 2-5. In some embodiments, the targeted portion of the NMD exon mRNA comprises a sequence with at least 80%, 85%, 90%, 95%, 97%, or 100% sequence identity to a region comprising at least 8 contiguous nucleic acids of any one of SEQ ID NOs: 2-5.

In some embodiments, the ASO targets exon 6x of an OPA1 NMD exon-containing pre-mRNA comprising NIE exon 6, exon 7x of an OPA1 NMD exon-containing pre-mRNA comprising NIE exon 7, or exon 28x of an OPA1 NMD exon-containing pre-mRNA comprising NIE exon 28. In some embodiments, the ASO targets exon (GRCh38/hg38: chr3 193628509 193628616) of OPA1 pre-mRNA; or exon (GRCh38/hg38: chr3 193603500 193603557) of OPA1. In some embodiments, the ASO targets an NMD exon of OPA1 pre-mRNA other than NMD exon (GRCh38/hg38: chr3 193628509 193628616).

In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from the 5' end of exon 6x of OPA1, exon 7x of OPA1, or exon 28x of OPA1. In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from GRCh38/hg38: chr3 193628509 of OPA1; or GRCh38/hg38: chr3 193603500 of OPA1.

In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from the 5' end of exon 6x of OPA1, exon 7x of OPA1, or exon 28x of OPA1. In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from GRCh38/hg38: chr3 193628509 of OPA1; or GRCh38/hg38: chr3 193603500 of OPA1.

In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from the 3' end of exon 6x of OPA1, exon 7x of OPA1, or exon 28x of OPA1. In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from GRCh38/hg38: chr3 193628616 of OPA1; or GRCh38/hg38: chr3 193603557 of OPA1.

In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from the 3' end of exon 6x of OPA1, exon 7x of OPA1, or exon 28x of OPA1. In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from GRCh38/hg38: chr3 193628616 of OPA1; or GRCh38/hg38: chr3 193603557 of OPA1.

In some embodiments, the ASO has a sequence complementary to the targeted portion of the NMD exon mRNA according to any one of SEQ ID NOs: 2-5, or 279.

In some embodiments, the ASO targets a sequence upstream from the 5' end of an NMD exon. For example, ASOs targeting a sequence upstream from the 5' end of an NMD exon (exon 6x of OPA1, exon 7x of OPA1, or exon 28x of OPA1) comprises a sequence that is at least about 80%, 85%, 90%, 95%, 97%, or 100% complimentary to at least 8 contiguous nucleic acids of SEQ ID NO: 2 or 3. For example, ASOs targeting a sequence upstream from the 5' end of an NMD exon (e.g., exon (GRCh38/hg38: chr3 193628509 to 193628616) of OPA1; or exon (GRCh38/hg38: chr3 193603500 193603557) of OPA1) can comprise a sequence with at least 80%, 85%, 90%, 95%, 97%, or 100% sequence identity to SEQ ID NO: 4 or 5.

In some embodiments, the ASOs target a sequence containing an exon-intron boundary (or junction). For example, ASOs targeting a sequence containing an exon-intron boundary can comprise a sequence that is at least about 80%, 85%, 90%, 95%, 97%, or 100% complimentary to at least 8 contiguous nucleic acids of any one of SEQ ID NOs: 2-5. In some embodiments, the ASOs target a sequence downstream from the 3' end of an NMD exon. For example, ASOs targeting a sequence downstream from the 3' end of an NMD exon (e.g., exon 6x of OPA1, exon 7x of OPA1, or exon 28x of OPA1) can comprise a sequence with at least 80%, 85%, 90%, 95%, 97%, or 100% sequence identity to SEQ ID NO: 2 or 3, or at least 8 contiguous nucleic acids of SEQ ID NO: 2 or 3. For example, ASOs targeting a sequence downstream from the 3' end of an NMD exon (e.g., exon (GRCh38/hg38: chr3 193628509 to 193628616) of OPA1; or exon (GRCh38/hg38: chr3 193603500 to 193603557) of OPA1) can comprise a sequence with at least 80%, 85%, 90%, 95%, 97%, or 100% sequence identity to SEQ ID NO: 4 or 5, or at least 8 contiguous nucleic acids of SEQ ID NO: 4 or 5. In some embodiments, ASOs target a sequence within an NMD exon.

In some embodiments, the ASO targets exon 6x of an OPA1 NMD exon-containing pre-mRNA comprising NIE exon 6, exon 7x of an OPA1 NMD exon-containing pre-mRNA comprising NIE exon 7, or exon 28x of an OPA1 NMD exon-containing pre-mRNA comprising NIE exon 28. In some embodiments, the ASO targets a sequence downstream (or 3') from the 5' end of exon 6x, exon 7x, or exon 28x of an OPA1 pre-mRNA. In some embodiments, the ASO targets a sequence upstream (or 5') from the 3' end of exon 6x, exon 7x, or exon 28x of an OPA1 pre-mRNA.

In some embodiments, the targeted portion of the OPA1 NMD exon-containing pre-mRNA is in intron 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, hybridization of an ASO to the targeted portion of the NMD exon pre-mRNA results in exon skipping of at least one of NMD exon within intron 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and subsequently increases OPA1 protein production. In some embodiments, the targeted portion of the OPA1 NMD exon-containing pre-mRNA is in intron 6 of OPA1, or intron 28 of OPA1. In some embodiments, the targeted portion of the OPA1 NMD exon-containing pre-mRNA is intron (GRCh38/hg38: chr3 193626203 to 193631611) of OPA1; or intron (GRCh38/hg38: chr3 193593374 to 193614710) of OPA1.

In some embodiments, the methods and compositions of the present disclosure are used to increase the expression of OPA1 by inducing exon skipping of a pseudo-exon of an OPA1 NMD exon-containing pre-mRNA. In some embodiments, the pseudo-exon is a sequence within any of introns 1-50. In some embodiments, the pseudo-exon is a sequence within any of introns 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, the pseudo-exon can be an OPA1 intron or a portion thereof. In some embodiments, the pseudo-exon is within intron 6 of OPA1, or intron 28 of OPA1. In some embodiments, the pseudo-exon is within intron (GRCh38/hg38: chr3 193626203 to 193631611) of OPA1; or intron (GRCh38/hg38: chr3 193593374 to 193614710) of OPA1.

In some embodiments, the ASO targets an OPA1 pre-mRNA transcript to induce exon skipping of a coding exon, e.g., an alternatively spliced exon. In some embodiments, the ASO targets a sequence within a coding exon, e.g., an alternatively spliced exon, of an OPA1 pre-mRNA transcript. In some embodiments, the ASO targets a sequence upstream (or 5') from the 5' end of a coding exon (3'ss) of an OPA1 pre-mRNA transcript. In some embodiments, the ASO targets a sequence downstream (or 3') from the 3' end of a coding exon (5'ss) of an OPA1 pre-mRNA transcript. In some embodiments, the ASO targets a sequence that is within an intron flanking on the 5' end of the coding exon of an OPA1 pre-mRNA transcript. In some embodiments, the ASO targets a sequence that is within an intron flanking the 3' end of the coding exon of an OPA1 pre-mRNA transcript. In some embodiments, the ASO targets a sequence comprising an exon-intron boundary of an OPA1 pre-mRNA transcript. An exon-intron boundary can refer to the junction of an intron sequence and an exon sequence. The intron sequence can flank the 5' end of the coding exon, or the 3' end of the coding exon. In some embodiments, the ASO targets a sequence within an exon of an OPA1 pre-mRNA transcript. In some embodiments, the ASO targets a sequence within an intron of an OPA1 pre-mRNA transcript. In some embodiments, the ASO targets a sequence comprising both a portion of an intron and a portion of an exon of an OPA1 pre-mRNA transcript.

In some embodiments, the ASO targets a sequence about 4 to about 300 nucleotides upstream (or 5') from the 5' end of the coding exon, e.g., alternatively spliced exon. In some embodiments, the ASO targets a sequence about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, or about 250 to about 300 nucleotides upstream (or 5') from the 5' end of the coding exon region. In some embodiments, the ASO may target a sequence more than 300 nucleotides upstream from the 5' end of the coding exon. In some embodiments, the ASO targets a sequence about 4 to about 300 nucleotides downstream (or 3') from the 3' end of the coding exon. In some embodiments, the ASO targets a sequence about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, or about 250 to about 300 nucleotides downstream from the 3' end of the coding exon. In some embodiments, the ASO targets a sequence more than 300 nucleotides downstream from the 3' end of the coding exon.

In some embodiments, the OPA1 pre-mRNA transcript is encoded by a genetic sequence with at least about 80%, 85%, 90%, 95%, 96%, 97%, 98%, 99% or 100% sequence identity to SEQ ID NO. 1. In some embodiments, the OPA1 pre-mRNA transcript comprises a sequence with at least about 80%, 85%, 90%, 95%, 96%, 97%, 98%, 99% or 100% sequence identity to any one of SEQ ID NOs: 2-5.

In some embodiments, the OPA1 pre-mRNA transcript (or NMD exon mRNA) comprises a sequence with at least about 80%, 85%, 90%, 95%, 97%, or 100% sequence identity to any one of SEQ ID NOs: 2-5. In some embodiments, OPA1 pre-mRNA transcript (or NMD exon mRNA) is encoded by a sequence with at least about 80%, 85%, 90%, 95%, 97%, or 100% sequence identity to any one of SEQ ID NOs: 2-5. In some embodiments, the targeted portion of the OPA1 pre-mRNA comprises a sequence with at least 80%, 85%, 90%, 95%, 97%, or 100% sequence identity to a region comprising at least 8 contiguous nucleic acids of any one of SEQ ID NOs: 2-5.

In some embodiments, the ASO targets exon 7 of an OPA1 pre-mRNA, i.e., the ASO targets exon (GRCh38/hg38: chr3 193626092 to 193626202) of OPA1 pre-mRNA.

In some embodiments, the ASO targets a coding exon of an OPA1 pre-mRNA other than exon 7, i.e., the ASO targets an exon of OPA1 pre-mRNA other than exon defined by (GRCh38/hg38: chr3 193626092 to 193626202).

In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from the 5' end of exon 7 of OPA1. In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from GRCh38/hg38: chr3 193626092 of OPA1.

In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from the 5' end of exon 7 of OPA1. In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from GRCh38/hg38: 193626092 of OPA1.

In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from the 3' end of exon 7 of OPA1. In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from GRCh38/hg38: chr3 193626202 of OPA1.

In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from the 3' end of exon 7 of OPA1. In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from GRCh38/hg38: chr3 193626202 of OPA1.

In some embodiments, the ASO has a sequence complementary to the targeted portion of the NMD exon mRNA according to any one of SEQ ID NOs: 2-5, or 277.

In some embodiments, the ASO targets a sequence upstream from the 5' end of a coding exon, e.g., an alternatively spliced exon. For example, ASOs targeting a sequence upstream from the 5' end of a coding exon (e.g., exon 7 of OPA1) comprises a sequence that is at least about 80%, 85%, 90%, 95%, 97%, or 100% complimentary to at least 8 contiguous nucleic acids of SEQ ID NO: 2 or 3. For example, ASOs targeting a sequence upstream from the 5' end of a coding exon (e.g., exon (GRCh38/hg38: 193626092 to 193626202) of OPA1) can comprise a sequence with at least 80%, 85%, 90%, 95%, 97%, or 100% sequence identity to SEQ ID NO: 4 or 5.

In some embodiments, the ASOs target a sequence containing an exon-intron boundary (or junction). For example, ASOs targeting a sequence containing an exon-intron boundary can comprise a sequence that is at least about 80%, 85%, 90%, 95%, 97%, or 100% complimentary to at least 8 contiguous nucleic acids of any one of SEQ ID NOs: 2-5. In some embodiments, the ASOs target a sequence downstream from the 3' end of a coding exon, e.g., an alternatively spliced exon. For example, ASOs targeting a sequence downstream from the 3' end of a coding exon (e.g., exon 7 of OPA1) can comprise a sequence with at least 80%, 85%, 90%, 95%, 97%, or 100% sequence identity to SEQ ID NO: 2 or 3, or at least 8 contiguous nucleic acids of SEQ ID NO: 2 or 3. For example, ASOs targeting a sequence downstream from the 3' end of a coding exon (e.g., exon 7 of OPA1) can comprise a sequence with at least 80%, 85%, 90%, 95%, 97%, or 100% sequence identity to SEQ ID NO: 4 or 5, or at least 8 contiguous nucleic acids of SEQ ID NO: 4 or 5. In some embodiments, ASOs target a sequence within a coding exon, e.g., an alternatively spliced exon.

Protein Expression

In some embodiments, the methods described herein are used to increase the production of a functional OPA1 protein or RNA. As used herein, the term "functional" refers to the amount of activity or function of an OPA1 protein or RNA that is necessary to eliminate any one or more symptoms of a treated condition or disease, e.g., Optic atrophy type 1. In some embodiments, the methods are used to increase the production of a partially functional OPA1 protein or RNA. As used herein, the term "partially functional" refers to any amount of activity or function of the OPA1 protein or RNA that is less than the amount of activity or function that is necessary to eliminate or prevent any one or more symptoms of a disease or condition. In some embodiments, a partially functional protein or RNA will have at least 10%, at least 20%, at least 30%, at least 40%, at least 50%, at least 60%, at least 70%, at least 75%, at least 80%, at least 85%, at least 90%, or at least 95% less activity relative to the fully functional protein or RNA.

In some embodiments, the method is a method of increasing the expression of the OPA1, protein by cells of a subject having an OPA1 pre-mRNA, wherein the subject has a disease or condition, e.g., Optic atrophy type 1, caused by a deficient amount of activity of OPA1 protein, and wherein the deficient amount of the OPA1 protein is caused by haploinsufficiency of the OPA1 protein. In such an embodiment, the subject has a first allele encoding a functional OPA1 protein, and a second allele from which the OPA1 protein is not produced. In another such embodiment, the subject has a first allele encoding a functional OPA1 protein, and a second allele encoding a nonfunctional OPA1 protein. In another such embodiment, the subject has a first allele encoding a functional OPA1 protein, and a second allele encoding a partially functional OPA1 protein. In any of these embodiments, the antisense oligomer binds to a targeted portion of the OPA1 pre-mRNA transcribed from the second allele, thereby inducing exon skipping of the pseudo-exon from the pre-mRNA, and causing an increase in the level of mature mRNA encoding functional OPA1 protein, and an increase in the expression of the OPA1 protein in the cells of the subject.

In some embodiments, the method is a method of increasing the expression of the OPA1 protein by cells of a subject having an OPA1 pre-mRNA, wherein the subject has a disease or condition caused by a deficient amount of activity of OPA1 protein, and wherein the deficient amount of the OPA1 protein is caused by autosomal recessive inheritance.

In some embodiments, the method is a method of increasing the expression of the OPA1 protein by cells of a subject having an OPA1 pre-mRNA, wherein the subject has a disease or condition, e.g., Optic atrophy type 1, caused by a deficient amount of activity of OPA1, protein, and wherein the deficient amount of the OPA1 protein is caused by autosomal dominant inheritance.

In related embodiments, the method is a method of using an ASO to increase the expression of a protein or functional RNA. In some embodiments, an ASO may be used to increase the expression of OPA1 protein in cells of a subject having an OPA1 pre-mRNA, wherein the subject has a deficiency, e.g., Optic atrophy type 1; in the amount or function of an OPA1 protein.

In some embodiments, the pre-mRNA transcript that encodes the protein that is causative of the disease or condition is targeted by the agent, e.g., the oligonucleotides, described herein. In some cases, it is the NMD exon-containing pre-mRNA transcript targeted by the agent, e.g., the oligonucleotides, described herein. In some cases, the agent, e.g., the oligonucleotides, described herein, are designed to target a coding exon of the pre-mRNA. In some cases, the agent, e.g., the oligonucleotides, described herein can induce skipping of the NMD exon, a coding exon, or both. In some embodiments, a NMD exon-containing pre-mRNA transcript that encodes a protein that is not causative of the disease is targeted by the ASOs. For example, a disease that is the result of a mutation or deficiency of a first protein in a particular pathway may be ameliorated by targeting a pre-mRNA that encodes a second protein, thereby increasing production of the second protein. In some embodiments, the function of the second protein is able to compensate for the mutation or deficiency of the first protein (which is causative of the disease or condition).

In some embodiments, the subject has:

(a) a first mutant allele from which
   (i) the OPA1 protein is produced at a reduced level compared to production from a wild-type allele,
   (ii) the OPA1 protein is produced in a form having reduced function compared to an equivalent wild-type protein, or
   (iii) the OPA1 protein or functional RNA is not produced; and
(b) a second mutant allele from which
   (i) the OPA1 protein is produced at a reduced level compared to production from a wild-type allele,
   (ii) the OPA1 protein is produced in a form having reduced function compared to an equivalent wild-type protein, or
   (iii) the OPA1 protein is not produced, and wherein the NMD exon-containing pre-mRNA is transcribed from the first allele and/or the second allele. In these embodiments, the ASO binds to a targeted portion of the NMD exon-containing pre-mRNA transcribed from the first allele or the second allele, thereby inducing exon skipping of the pseudo-exon from the NMD exon-containing pre-mRNA, and causing an increase in the level of mRNA encoding OPA1 protein and an increase in the expression of the target protein or functional RNA in the cells of the subject. In these embodiments, the target protein or functional RNA having an increase in expression level resulting from the exon skipping of the pseudo-exon from the NMD exon-containing pre-mRNA may be either in a form having reduced function compared to the equivalent wild-type protein (partially-functional), or having full function compared to the equivalent wild-type protein (fully-functional).

In some embodiments, the subject has:

(a) a first mutant allele from which
   (i) the OPA1 protein is produced at a reduced level compared to production from a wild-type allele,
   (ii) the OPA1 protein is produced in a form having reduced function compared to an equivalent wild-type protein, or
   (iii) the OPA1 protein or functional RNA is not produced; and
(b) a second mutant allele from which
   (i) the OPA1 protein is produced at a reduced level compared to production from a wild-type allele,
   (ii) the OPA1 protein is produced in a form having reduced function compared to an equivalent wild-type protein, or
   (iii) the OPA1 protein is not produced, and wherein the OPA1 pre-mRNA is transcribed from the first allele and/or the second allele. In these embodiments, the ASO binds to a targeted portion of the OPA1 pre-mRNA transcribed from the first allele or the second allele, thereby inducing exon skipping of a coding exon from the OPA1 pre-mRNA, and causing an increase in the expression of the target OPA1 protein in the cells of the subject. In these embodiments, the target OPA1 protein having an increase in expression level resulting from the exon skipping of the coding exon from the OPA1 pre-mRNA may be either in a form having reduced function compared to the equivalent full-length wild-type protein (partially-functional), or having full function compared to the equivalent full-length wild-type protein (fully-functional).

In some embodiments, the level of mRNA encoding OPA1 protein is increased 1.1 to 10-fold, when compared to the amount of mRNA encoding OPA1 protein that is produced in a control cell, e.g., one that is not treated with the antisense oligomer or one that is treated with an antisense oligomer that does not bind to the targeted portion of the OPA1 pre-mRNA.

In some embodiments, a subject treated using the methods of the present disclosure expresses a partially functional OPA1 protein from one allele, wherein the partially functional OPA1 protein may be caused by a frameshift mutation, a nonsense mutation, a missense mutation, or a partial gene deletion. In some embodiments, a subject treated using the methods of the disclosure expresses a nonfunctional OPA1 protein from one allele, wherein the nonfunctional OPA1 protein may be caused by a frameshift mutation, a nonsense mutation, a missense mutation, a partial gene deletion, in one allele. In some embodiments, a subject treated using the methods of the disclosure has an OPA1 whole gene deletion, in one allele.

Exon Inclusion

As used herein, a "NMD exon-containing pre-mRNA" is a pre-mRNA transcript that contains at least one pseudo-exon. Alternative or aberrant splicing can result in inclusion of the at least one pseudo-exon in the mature mRNA transcripts. The terms "mature mRNA," and "fully-spliced mRNA," are used interchangeably herein to describe a fully processed mRNA. Inclusion of the at least one pseudo-exon can be non-productive mRNA and lead to NMD of the mature mRNA. NMD exon-containing mature mRNA may sometimes lead to aberrant protein expression.

In some embodiments, the included pseudo-exon is the most abundant pseudo-exon in a population of NMD exon-containing pre-mRNAs transcribed from the gene encoding the target protein in a cell. In some embodiments, the included pseudo-exon is the most abundant pseudo-exon in a population of NMD exon-containing pre-mRNAs transcribed from the gene encoding the target protein in a cell, wherein the population of NMD exon-containing pre-mRNAs comprises two or more included pseudo-exons. In some embodiments, an antisense oligomer targeted to the most abundant pseudo-exon in the population of NMD exon-containing pre-mRNAs encoding the target protein induces exon skipping of one or two or more pseudo-exons in the population, including the pseudo-exon to which the antisense oligomer is targeted or binds. In some embodiments, the targeted region is in a pseudo-exon that is the most abundant pseudo-exon in a NMD exon-containing pre-mRNA encoding the OPA1 protein.

The degree of exon inclusion can be expressed as percent exon inclusion, e.g., the percentage of transcripts in which a given pseudo-exon is included. In brief, percent exon inclusion can be calculated as the percentage of the amount of RNA transcripts with the exon inclusion, over the sum of the average of the amount of RNA transcripts with exon inclusion plus the average of the amount of RNA transcripts with exon exclusion.

In some embodiments, an included pseudo-exon is an exon that is identified as an included pseudo-exon based on a determination of at least about 5%, at least about 10%, at least about 15%, at least about 20%, at least about 25%, at least about 30%, at least about 35%, at least about 40%, at least about 45%, or at least about 50%, inclusion. In embodiments, a included pseudo-exon is an exon that is identified as a included pseudo-exon based on a determination of about 5% to about 100%, about 5% to about 95%, about 5% to about 90%, about 5% to about 85%, about 5% to about 80%, about 5% to about 75%, about 5% to about 70%, about 5% to about 65%, about 5% to about 60%, about 5% to about 55%, about 5% to about 50%, about 5% to about 45%, about 5% to about 40%, about 5% to about 35%, about 5% to about 30%, about 5% to about 25%, about 5% to about 20%, about 5% to about 15%, about 10% to about 100%, about 10% to about 95%, about 10% to about 90%, about 10% to about 85%, about 10% to about 80%, about 10% to about 75%, about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 15% to about 100%, about 15% to about 95%, about 15% to about 90%, about 15% to about 85%, about 15% to about 80%, about 15% to about 75%, about 15% to about 70%, about 15% to about 65%, about 15% to about 60%, about 15% to about 55%, about 15% to about 50%, about 15% to about 45%, about 15% to about 40%, about 15% to about 35%, about 15% to about 30%, about 15% to about 25%, about 20% to about 100%, about 20% to about 95%, about 20% to about 90%, about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 25% to about 100%, about 25% to about 95%, about 25% to about 90%, about 25% to about 85%, about 25% to about 80%, about 25% to about 75%, about 25% to about 70%, about 25% to about 65%, about 25% to about 60%, about 25% to about 55%, about 25% to about 50%, about 25% to about 45%, about 25% to about 40%, or about 25% to about 35%, inclusion. ENCODE data (described by, e.g., Tilgner, et al., 2012, "Deep sequencing of subcellular RNA fractions shows splicing to be predominantly co-transcriptional in the human genome but inefficient for lncRNAs," Genome Research 22(9):1616-25) can be used to aid in identifying exon inclusion.

In some embodiments, contacting cells with an ASO that is complementary to a targeted portion of an OPA1 pre-mRNA transcript results in an increase in the amount of OPA1 protein produced by at least 10, 20, 30, 40, 50, 60, 80, 100, 150, 200, 250, 300, 350, 400, 450, 500, or 1000%, compared to the amount of the protein produced by a cell in the absence of the ASO/absence of treatment. In some embodiments, the total amount of OPA1 protein produced by the cell to which the antisense oligomer is contacted is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 10%, at least about 20%, at least about 50%, at least about 100%, at least about 150%, at least about 200%, at least about 250%, or at least about 300%, compared to the amount of target protein produced by a control compound. In some embodiments, the total amount of OPA1 protein produced by the cell to which the antisense oligomer is contacted is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the amount of target protein produced by a control compound. A control compound can be, for example, an oligonucleotide that is not complementary to a targeted portion of the pre-mRNA.

In some embodiments, contacting cells with an ASO that is complementary to a targeted portion of an OPA1 pre-mRNA transcript results in an increase in the amount of mRNA encoding OPA1, including the mature mRNA encoding the target protein. In some embodiments, the amount of mRNA encoding OPA1 protein, or the mature mRNA encoding the OPA1 protein, is increased by at least 10, 20, 30, 40, 50, 60, 80, 100, 150, 200, 250, 300, 350, 400, 450, 500, or 1000%, compared to the amount of the protein produced by a cell in the absence of the ASO/absence of treatment. In some embodiments, the total amount of the mRNA encoding OPA1 protein, or the mature mRNA encoding OPA1 protein produced in the cell to which the antisense oligomer is contacted is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 10%, at least about 20%, at least about 50%, at least about 100%, at least about 150%, at least about 200%, at least about 250%, or at least about 300%, compared to the amount of mature RNA produced in an untreated cell, e.g., an untreated cell or a cell treated with a control compound. In some embodiments, the total amount of the mRNA encoding OPA1 protein, or the mature mRNA encoding OPA1 protein produced in the cell to which the antisense oligomer is contacted is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold compared to the amount of mature RNA produced in an untreated cell, e.g., an untreated cell or a cell treated with a control compound. A control compound can be, for example, an oligonucleotide that is not complementary to a targeted portion of the OPA1 NMD exon-containing pre-mRNA.

The NMD exon can be in any length. In some embodiments, the NMD exon comprises a full sequence of an intron, in which case, it can be referred to as intron retention. In some embodiments, the NMD exon can be a portion of the intron. In some embodiments, the NMD exon can be a 5' end portion of an intron including a 5'ss sequence. In some embodiments, the NMD exon can be a 3' end portion of an intron including a 3'ss sequence. In some embodiments, the NMD exon can be a portion within an intron without inclusion of a 5'ss sequence. In some embodiments, the NMD exon can be a portion within an intron without inclusion of a 3'ss sequence. In some embodiments, the NMD exon can be a portion within an intron without inclusion of either a 5'ss or a 3'ss sequence. In some embodiments, the NMD exon can be from 5 nucleotides to 10 nucleotides in length, from 10 nucleotides to 15 nucleotides in length, from 15 nucleotides to 20 nucleotides in length, from 20 nucleotides to 25 nucleotides in length, from 25 nucleotides to 30 nucleotides in length, from 30 nucleotides to 35 nucleotides in length, from 35 nucleotides to 40 nucleotides in length, from 40 nucleotides to 45 nucleotides in length, from 45 nucleotides to 50 nucleotides in length, from 50 nucleotides to 55 nucleotides in length, from 55 nucleotides to 60 nucleotides in length, from 60 nucleotides to 65 nucleotides in length, from 65 nucleotides to 70 nucleotides in length, from 70 nucleotides to 75 nucleotides in length, from 75 nucleotides to 80 nucleotides in length, from 80 nucleotides to 85 nucleotides in length, from 85 nucleotides to 90 nucleotides in length, from 90 nucleotides to 95 nucleotides in length, or from 95 nucleotides to 100 nucleotides in length. In some embodiments, the NMD exon can be at least 10 nucleotides, at least 20 nucleotides, at least 30 nucleotides, at least 40 nucleotides, at least 50 nucleotides, at least 60 nucleoids, at least 70 nucleotides, at least 80 nucleotides in length, at least 90 nucleotides, or at least 100 nucleotides in length. In some embodiments, the NMD exon can be from 100 to 200 nucleotides in length, from 200 to 300 nucleotides in length, from 300 to 400 nucleotides in length, from 400 to 500 nucleotides in length, from 500 to 600 nucleotides in length, from 600 to 700 nucleotides in length, from 700 to 800 nucleotides in length, from 800 to 900 nucleotides in length, from 900 to 1,000 nucleotides in length. In some embodiments, the NMD exon may be longer than 1,000 nucleotides in length.

Inclusion of a pseudo-exon can lead to a frameshift and the introduction of a premature termination codon (PIC) in the mature mRNA transcript rendering the transcript a target of NMD. Mature mRNA transcript containing NMD exon can be non-productive mRNA transcript which does not lead to protein expression. The PIC can be present in any position downstream of an NMD exon. In some embodiments, the PIC can be present in any exon downstream of an NMD exon. In some embodiments, the PIC can be present within the NMD exon. For example, inclusion of exon 6x of OPA1, exon 7x of OPA1, or exon 28x of OPA1, in an mRNA transcript encoded by the OPA1 gene can induce a PIC in the mRNA transcript. For example, inclusion of exon (GRCh38/hg38: chr3 193628509 193628616) of OPA1; or exon (GRCh38/hg38: chr3 193603500 193603557) of OPA1 in an mRNA transcript encoded by the OPA1.

In some aspects, provided herein is a method of modulating expression of an OPA1 protein by promoting inclusion of a coding exon. The method can comprise contacting an agent to a cell having an OPA1 pre-mRNA, wherein the agent comprises an oligonucleotide that binds to: (a) a targeted portion of the pre-mRNA within an intronic region immediately upstream of a 5' end of the coding exon of the pre-mRNA; or (b) a targeted portion of the pre-mRNA within an intronic region immediately downstream of a 3' end of the coding exon of the pre-mRNA; whereby the agent increases a level of a processed mRNA that is processed from the pre-mRNA and that contains the coding exon in the cell. In some cases, the coding exon to be included is an alternatively spliced exon. In some cases, the method promotes inclusion of the coding exon in the processed mRNA during splicing of the pre-mRNA in the cell.

In some of these embodiments for inclusion of coding exon, the target portion of the pre-mRNA is within a region spanning from 100 to 50, from 100 to 60, from 100 to 70, from 100 to 80, or from 100 to 90 nucleotides upstream of a 5' end of the coding exon. In some cases, the target portion of the pre-mRNA is within a region spanning from 40 to 100, from 50 to 100, from 60 to 100, from 70 to 100, from 80 to 100, or from 90 to 100 nucleotides downstream of a 3' end of the coding exon. In some cases, the coding exon is exon 7 of OPA1. In some cases, the coding exon comprises a sequence with at least 80%, at least 90%, or 100% sequence identity to SEQ ID NO: 277. In some cases, the coding exon comprises SEQ ID NO: 277. The targeted portion of the pre-mRNA can be within a region spanning from 100 to 50, from 100 to 60, from 100 to 70, from 100 to 80, or from 100 to 90 nucleotides upstream of genomic site GRCh38/hg38: chr3 193626092. In some cases, the targeted portion of the pre-mRNA is within a region spanning from 40 to 100, from 50 to 100, from 60 to 100, from 70 to 100, from 80 to 100, or from 90 to 100 nucleotides downstream of genomic site GRCh38/hg38: chr3 193626202.

In some cases, the inclusion of the coding exon in the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Exclusion of Both NMD Exon and Coding Exon

In some embodiments, provided herein is a method of modulating expression of a target protein by targeting a pre-mRNA and modulating exclusion of both a coding exon and a non-sense mediated RNA decay-inducing exon (NMD exon) from the pre-mRNA. In some cases, the method comprises contacting an agent to the cell, and the agent promotes exclusion of both the coding exon and the NMD exon from the pre-mRNA, thereby increasing level of a processed mRNA that is processed from the pre-mRNA and lacks both the coding exon and the NMD exon. In some cases, the agent binds to a targeted portion of the pre-mRNA, or modulates binding of a factor involved in splicing of the coding exon, the NMD exon, or both. In some cases, the agent interferes with binding of the factor involved in splicing of the coding exon, the NMD exon, or both, to a region of the targeted portion. In some cases, the NMD exon is within an intronic region adjacent to the coding exon. In some cases, the NMD exon is within an intronic region immediately upstream of the coding exon. In some cases, the NMD exon is within an intronic region immediately downstream of the coding exon. In some cases, the coding exon is an alternatively spliced exon.

In some cases, the targeted portion of the pre-mRNA is proximal to the coding exon. The targeted portion of the pre-mRNA can be located in an intronic region immediately upstream of the coding exon. The targeted portion of the pre-mRNA can be located in an intronic region immediately downstream of the coding exon. In some cases, the targeted portion of the pre-mRNA can be located within the coding exon. In some cases, the targeted portion of the pre-mRNA is within a region spanning from 49 to 1, from 39 to 1, from 29 to 1, or from 19 to 1 nucleotides upstream of 5' end of the coding exon. In some cases, the targeted portion of the pre-mRNA is within a region spanning from 100 nucleotides upstream of the coding exon to 100 nucleotides downstream of the coding exon. In some cases, the targeted portion comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the coding exon.

In some cases, the targeted portion of the pre-mRNA is proximal to the NMD exon. In some cases, the targeted portion of the pre-mRNA is located in an intronic region immediately upstream of the NMD exon. In some cases, the targeted portion of the pre-mRNA is located in an intronic region immediately downstream of the NMD exon. In some cases, the targeted portion of the pre-mRNA is located within the NMD exon. In some cases, the targeted portion of the pre-mRNA is within a region spanning from 100 nucleotides upstream of the NMD exon to 100 nucleotides downstream of the NMD exon.

In some embodiments, the method described herein is applicable to modulation of expression of OPA1 protein by modulating exclusion of both exon 7 and an NMD exon (e.g., exon 7x) of OPA1 pre-mRNA that contains both exon 7 and exon 7x. In some cases, the coding exon comprises a sequence with at least 80%, at least 90%, or 100% sequence identity to SEQ ID NO: 277. In some cases, the coding exon comprises SEQ ID NO: 277. In some cases, the targeted portion of the pre-mRNA is immediately upstream of the coding exon GRCh38/hg38: chr3 193626092 to 193626202. In some cases, the targeted portion of the pre-mRNA is immediately downstream of the coding exon GRCh38/hg38: chr3 193626092 to 193626202. In some cases, the targeted portion of the pre-mRNA is within a region spanning from 49 to 1, from 39 to 1, from 29 to 1, or from 19 to 1 nucleotides upstream of GRCh38/hg38: chr3 193626092. In some cases, the targeted portion of the pre-mRNA is within a region spanning from 100 nucleotides upstream of genomic site GRCh38/hg38: chr3 193626092 to 100 nucleotides downstream of genomic site GRCh38/hg38: chr3 193626202. In some cases, the targeted portion of the pre-mRNA is within the coding exon GRCh38/hg38: chr3 193626092 to 193626202. In some cases, the targeted portion of the pre-mRNA comprises an exon-intron junction of the coding exon GRCh38/hg38: chr3 193626092 to 193626202. In some cases, the NMD exon comprises a sequence with at least 80%, at least 90%, or 100% sequence identity to SEQ ID NO: 279. In some cases, the NMD exon comprises SEQ ID NO: 279. In some cases, the targeted portion of the pre-mRNA is immediately upstream of the NMD exon GRCh38/hg38: chr3 193628509 to 193628616. In some cases, the targeted portion of the pre-mRNA is immediately downstream of the NMD exon GRCh38/hg38: chr3 193628509 to 193628616. In some cases, the targeted portion of the pre-mRNA is within a region spanning from 100 nucleotides upstream of genomic site GRCh38/hg38: chr3 193628509 to 100 nucleotides downstream of genomic site GRCh38/hg38: chr3 193628616.

In some cases, the targeted portion of the pre-mRNA is within the NMD exon GRCh38/hg38: chr3 193628509 to 193628616. In some cases, the targeted portion of the pre-mRNA comprises an exon-intron junction of the NMD exon GRCh38/hg38: chr3 193628509 to 193628616. In some cases, the targeted portion comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

In some cases, the exclusion of the coding exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of contacting with the agent. In some cases, the exclusion of the NMD exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of contacting with the agent. In some cases, the method results in an increase in the level of the processed mRNA in the cell. The level of the processed mRNA in the cell contacted with the agent can be increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of contacting with the agent.

In some cases, the method results in an increase in expression of the OPA1 protein in the cell. A level of the OPA1 protein expressed from the processed mRNA in the cell contacted with the agent can be increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of contacting with the agent.

In some cases, a level of the OPA1 protein expressed from the processed mRNA in the cell contacted with the agent is increased by at least about 1.5-fold compared to in the absence of contacting with the agent.

In some cases, the OPA1 protein expressed from the processed mRNA that lacks exon 7 and exon 7x is a functional OPA1 protein. The OPA1 protein expressed from the processed mRNA that lacks exon 7 and exon 7x can be at least partially functional as compared to a wild-type OPA1 protein. The OPA1 protein expressed from the processed mRNA that lacks exon 7 and exon 7x can be at least partially functional as compared to a full-length wild-type OPA1 protein.

Therapeutic Agents

In various embodiments of the present disclosure, compositions and methods comprising a therapeutic agent are provided to modulate protein expression level of OPA1. In some embodiments, provided herein are compositions and methods to modulate alternative splicing of OPA1 pre-mRNA. In some embodiments, provided herein are compositions and methods to induce exon skipping in the splicing of OPA1 pre-mRNA, e.g., to induce skipping of a pseudo-exon during splicing of OPA1 pre-mRNA. In other embodiments, therapeutic agents may be used to induce the inclusion of an exon in order to decrease the protein expression level.

A therapeutic agent disclosed herein can be a NIE repressor agent. A therapeutic agent may comprise a polynucleic acid polymer.

According to one aspect of the present disclosure, provided herein is a method of treatment or prevention of a condition or disease associated with a functional OPA1 protein deficiency, comprising administering a NIE repressor agent to a subject to increase levels of functional OPA1 protein, wherein the agent binds to a region of the pre-mRNA transcript to decrease inclusion of the NMD exon in the mature transcript. For example, provided herein is a method of treatment or prevention of a condition associated with a functional OPA1 protein deficiency, comprising administering a NIE repressor agent to a subject to increase levels of functional OPA1 protein, wherein the agent binds to a region of an intron containing an NMD exon (e.g., exon 6x of OPA1, exon 7x of OPA1, or exon 28x of OPA1) of the pre-mRNA transcript or to a NMD exon-activating regulatory sequence in the same intron. For example, provided herein is a method of treatment or prevention of a condition associated with a functional OPA1 protein deficiency, comprising administering a NIE repressor agent to a subject to increase levels of functional OPA1 protein, wherein the agent binds to a region of an intron containing an NMD exon (e.g., exon (GRCh38/hg38: chr3 193628509 193628616) of OPA1; or exon (GRCh38/hg38: chr3 193603500 193603557) of OPA1) of the pre-mRNA transcript or to a NMD exon-activating regulatory sequence in the same intron. In some embodiments, the method comprises administering a NIE repressor agent to a subject to increase levels of functional OPA1 protein, wherein the agent binds to a region of an intron containing an NMD exon (e.g., exon of OPA1 other than exon 7x defined by (GRCh38/hg38: chr3 193628509 193628616) or exon defined by (GRCh38/hg38: chr3 193603500 193603557)) of the pre-mRNA transcript or to a NMD exon-activating regulatory sequence in the same intron. In some embodiments, the therapeutic agent promotes exclusion of an NMD exon of OPA1 pre-mRNA other than exon 7x defined by (GRCh38/hg38: chr3 193628509 193628616) or exon defined by (GRCh38/hg38: chr3 193603500 193603557). In some embodiments, the composition disclosed herein includes an agent that promotes exclusion of an NMD exon of OPA1 pre-mRNA other than exon 7x defined by (GRCh38/hg38: chr3 193628509 193628616) or exon defined by (GRCh38/hg38: chr3 193603500 193603557).

Where reference is made to reducing NMD exon inclusion in the mature mRNA, the reduction may be complete, e.g., 100%, or may be partial. The reduction may be clinically significant. The reduction/correction may be relative to the level of NMD exon inclusion in the subject without treatment, or relative to the amount of NMD exon inclusion in a population of similar subjects. The reduction/correction may be at least 10% less NMD exon inclusion relative to the average subject, or the subject prior to treatment. The reduction may be at least 20% less NMD exon inclusion relative to an average subject, or the subject prior to treatment. The reduction may be at least 40% less NMD exon inclusion relative to an average subject, or the subject prior to treatment. The reduction may be at least 50% less NMD exon inclusion relative to an average subject, or the subject prior to treatment. The reduction may be at least 60% less NMD exon inclusion relative to an average subject, or the subject prior to treatment. The reduction may be at least 80% less NMD exon inclusion relative to an average subject, or the subject prior to treatment. The reduction may be at least 90% less NMD exon inclusion relative to an average subject, or the subject prior to treatment.

According to one aspect of the present disclosure, provided herein is a method of treatment or prevention of a condition or disease associated with a functional OPA1 protein deficiency, comprising administering an agent to a subject to increase levels of functional OPA1 protein, wherein the agent binds to a region of the pre-mRNA transcript to decrease inclusion of a coding exon (e.g., exon 7) in the mature transcript. For example, provided herein is a method of treatment or prevention of a condition associated with a functional OPA1 protein deficiency, comprising administering an agent to a subject to increase levels of functional OPA1 protein, wherein the agent binds to a region containing a coding exon (e.g., exon 7 of OPA1) of the pre-mRNA transcript. For example, provided herein is a method of treatment or prevention of a condition associated with a functional OPA1 protein deficiency, comprising administering an agent to a subject to increase levels of functional OPA1 protein, wherein the agent binds to a region containing a coding exon (e.g., exon (GRCh38/hg38: chr3 193626092 to 193626202) of OPA1) of the pre-mRNA transcript. In some embodiments, the method comprises administering an agent to a subject to increase levels of functional OPA1 protein, wherein the agent binds to a region containing a coding exon (e.g., exon of OPA1 other than exon 7 defined by (GRCh38/hg38: chr3 193626092 to 193626202)) of the pre-mRNA transcript. In some embodiments, the therapeutic agent promotes exclusion of a coding exon of OPA1 pre-mRNA other than exon 7 defined by (GRCh38/hg38: chr3 193626092 to 193626202). In some embodiments, the composition disclosed herein includes an agent that promotes exclusion of a coding exon of OPA1 pre-mRNA other than exon 7 defined by (GRCh38/hg38: chr3 193626092 to 193626202).

Where reference is made to increasing active OPA1 protein levels, the increase may be clinically significant. The increase may be relative to the level of active OPA1 protein in the subject without treatment, or relative to the amount of active OPA1 protein in a population of similar subjects. The increase may be at least 10% more active OPA1 protein relative to the average subject, or the subject prior to treatment. The increase may be at least 20% more active OPA1 protein relative to the average subject, or the subject prior to treatment. The increase may be at least 40% more active OPA1 protein relative to the average subject, or the subject prior to treatment. The increase may be at least 50% more active OPA1 protein relative to the average subject, or the subject prior to treatment. The increase may be at least 80% more active OPA1 protein relative to the average subject, or the subject prior to treatment. The increase may be at least 100% more active OPA1 protein relative to the average subject, or the subject prior to treatment. The increase may be at least 200% more active OPA1 protein relative to the average subject, or the subject prior to treatment. The increase may be at least 500% more active OPA1 protein relative to the average subject, or the subject prior to treatment.

In embodiments wherein the NIE repressor agent comprises a polynucleic acid polymer, the polynucleic acid polymer may be about 50 nucleotides in length. The polynucleic acid polymer may be about 45 nucleotides in length. The polynucleic acid polymer may be about 40 nucleotides in length. The polynucleic acid polymer may be about 35 nucleotides in length. The polynucleic acid polymer may be about 30 nucleotides in length. The polynucleic acid polymer may be about 24 nucleotides in length. The polynucleic acid polymer may be about 25 nucleotides in length. The polynucleic acid polymer may be about 20 nucleotides in length. The polynucleic acid polymer may be about 19 nucleotides in length. The polynucleic acid polymer may be about 18 nucleotides in length. The polynucleic acid polymer may be about 17 nucleotides in length. The polynucleic acid polymer may be about 16 nucleotides in length. The polynucleic acid polymer may be about 15 nucleotides in length. The polynucleic acid polymer may be about 14 nucleotides in length. The polynucleic acid polymer may be about 13 nucleotides in length. The polynucleic acid polymer may be about 12 nucleotides in length. The polynucleic acid polymer may be about 11 nucleotides in length. The polynucleic acid polymer may be about 10 nucleotides in length. The polynucleic acid polymer may be between about 10 and about 50 nucleotides in length. The polynucleic acid polymer may be between about 10 and about 45 nucleotides in length. The polynucleic acid polymer may be between about 10 and about 40 nucleotides in length. The polynucleic acid polymer may be between about 10 and about 35 nucleotides in length. The polynucleic acid polymer may be between about 10 and about 30 nucleotides in length. The polynucleic acid polymer may be between about 10 and about 25 nucleotides in length. The polynucleic acid polymer may be between about 10 and about 20 nucleotides in length. The polynucleic acid polymer may be between about 15 and about 25 nucleotides in length. The polynucleic acid polymer may be between about 15 and about 30 nucleotides in length. The polynucleic acid polymer may be between about 12 and about 30 nucleotides in length.

The sequence of the polynucleic acid polymer may be at least 50%, 55%, 60%, 65%, 70%, 75%, 80%, 85%, 90%, 91%, 92%, 93%, 94%, 95%, 96%, 97%, 98%, 99%, or 99.5% complementary to a target sequence of an mRNA transcript, e.g., a partially processed mRNA transcript. The sequence of the polynucleic acid polymer may be 100% complementary to a target sequence of a pre-mRNA transcript.

The sequence of the polynucleic acid polymer may have 4 or fewer mismatches to a target sequence of the pre-mRNA transcript. The sequence of the polynucleic acid polymer may have 3 or fewer mismatches to a target sequence of the pre-mRNA transcript. The sequence of the polynucleic acid polymer may have 2 or fewer mismatches to a target sequence of the pre-mRNA transcript. The sequence of the polynucleic acid polymer may have 1 or fewer mismatches to a target sequence of the pre-mRNA transcript. The sequence of the polynucleic acid polymer may have no mismatches to a target sequence of the pre-mRNA transcript.

The polynucleic acid polymer may specifically hybridize to a target sequence of the pre-mRNA transcript. For example, the polynucleic acid polymer may have 91%, 92%, 93%, 94%, 95%, 96%, 97%, 98%, 99%, 99.5% or 100% sequence complementarity to a target sequence of the pre-mRNA transcript. The hybridization may be under high stringent hybridization conditions.

The polynucleic acid polymer comprising a sequence with at least 50%, 55%, 60%, 65%, 70%, 75%, 80%, 85%, 90%, 91%, 92%, 93%, 94%, 95%, 96%, 97%, 98%, 99%, or 99.5% sequence identity to a sequence selected from the group consisting of SEQ ID NOs: 2-5. The polynucleic acid polymer may comprise a sequence with 100% sequence identity to a sequence selected from the group consisting of SEQ ID NOs: 2-5.

Where reference is made to a polynucleic acid polymer sequence, the skilled person will understand that one or more substitutions may be tolerated, optionally two substitutions may be tolerated in the sequence, such that it maintains the ability to hybridize to the target sequence; or where the substitution is in a target sequence, the ability to be recognized as the target sequence. References to sequence identity may be determined by BLAST sequence alignment using standard/default parameters. For example, the sequence may have 99% identity and still function according to the present disclosure. In other embodiments, the sequence may have 98% identity and still function according to the present disclosure. In another embodiment, the sequence may have 95% identity and still function according to the present disclosure. In another embodiment, the sequence may have 90% identity and still function according to the present disclosure.

Antisense Oligomers

Provided herein is a composition comprising an antisense oligomer that induces exon skipping by binding to a targeted portion of an OPA1 pre-mRNA, e.g., an OPA1 NMD exon-containing pre-mRNA. As used herein, the terms "ASO" and "antisense oligomer" are used interchangeably and refer to an oligomer such as a polynucleotide, comprising nucleobases that hybridizes to a target nucleic acid (e.g., an OPA1 pre-mRNA, e.g., an OPA1 NMD exon-containing pre-mRNA) sequence by Watson-Crick base pairing or wobble base pairing (G-U). The ASO may have exact sequence complementary to the target sequence or near complementarity (e.g., sufficient complementarity to bind the target sequence and enhancing splicing at a splice site). ASOs are designed so that they bind (hybridize) to a target nucleic acid (e.g., a targeted portion of a pre-mRNA transcript) and remain hybridized under physiological conditions. Typically, if they hybridize to a site other than the intended (targeted) nucleic acid sequence, they hybridize to a limited number of sequences that are not a target nucleic acid (to a few sites other than a target nucleic acid). Design of an ASO can take into consideration the occurrence of the nucleic acid sequence of the targeted portion of the pre-mRNA transcript or a sufficiently similar nucleic acid sequence in other locations in the genome or cellular pre-mRNA or transcriptome, such that the likelihood the ASO will bind other sites and cause "off-target" effects is limited. Any antisense oligomers known in the art (for example, in PCT Application No. PCT/US2014/054151, published as WO 2015/035091, titled "Reducing Nonsense-Mediated mRNA Decay," incorporated by reference herein), can be used to practice the methods described herein.

In some embodiments, ASOs "specifically hybridize" to or are "specific" to a target nucleic acid or a targeted portion of an OPA1 pre-mRNA, e.g., a NMD exon-containing pre-mRNA. Typically such hybridization occurs with a $T_m$ substantially greater than 37 °C, preferably at least 50 °C, and typically between 60 °C to approximately 90 °C. Such hybridization preferably corresponds to stringent hybridization conditions. At a given ionic strength and pH, the $T_m$ is the temperature at which 50% of a target sequence hybridizes to a complementary oligonucleotide.

Oligomers, such as oligonucleotides, are "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree to which one polynucleotide is complementary with another) is quantifiable in terms of the proportion (e.g., the percentage) of bases in opposing strands that are expected to form hydrogen bonds with each other, according to generally accepted base-pairing rules. The sequence of an antisense oligomer (ASO) need not be 100% complementary to that of its target nucleic acid to hybridize. In certain embodiments, ASOs can comprise at least 70%, at least 75%, at least 80%, at least 85%, at least 90%, at least 95%, at least 96%, at least 97%, at least 98%, or at least 99% sequence complementarity to a target region within the target nucleic acid sequence to which they are targeted. For example, an ASO in which 18 of 20 nucleobases of the oligomeric compound are complementary to a target region, and would therefore specifically hybridize, would represent 90 percent complementarity. In this example, the remaining noncomplementary nucleobases may be clustered together or interspersed with complementary nucleobases and need not be contiguous to each other or to complementary nucleobases. Percent complementarity of an ASO with a region of a target nucleic acid can be determined routinely using BLAST programs (basic local alignment search tools) and PowerBLAST programs known in the art (Altschul, et al., J. Mol. Biol., 1990, 215, 403-410; Zhang and Madden, Genome Res., 1997, 7, 649-656).

An ASO need not hybridize to all nucleobases in a target sequence and the nucleobases to which it does hybridize may be contiguous or noncontiguous. ASOs may hybridize over one or more segments of a pre-mRNA transcript, such that intervening or adjacent segments are not involved in the hybridization event (e.g., a loop structure or hairpin structure may be formed). In certain embodiments, an ASO hybridizes to noncontiguous nucleobases in a target pre-mRNA transcript. For example, an ASO can hybridize to nucleobases in a pre-mRNA transcript that are separated by one or more nucleobase(s) to which the ASO does not hybridize.

The ASOs described herein comprise nucleobases that are complementary to nucleobases present in a target portion of an OPA1 pre-mRNA, e.g., a NMD exon-containing pre-mRNA. The term ASO embodies oligonucleotides and any other oligomeric molecule that comprises nucleobases capable of hybridizing to a complementary nucleobase on a target mRNA but does not comprise a sugar moiety, such as a peptide nucleic acid (PNA). The ASOs may comprise naturally-occurring nucleotides, nucleotide analogs, modified nucleotides, or any combination of two or three of the preceding. The term "naturally occurring nucleotides" includes deoxyribonucleotides and ribonucleotides. The term "modified nucleotides" includes nucleotides with modified or substituted sugar groups and/or having a modified backbone. In some embodiments, all of the nucleotides of the ASO are modified nucleotides. Chemical modifications of ASOs or components of ASOs that are compatible with the methods and compositions described herein will be evident to one of skill in the art and can be found, for example, in U.S. Pat. No. 8,258,109 B2, U.S. Pat. No. 5,656,612, U.S. Patent Publication No. 2012/0190728, and Dias and Stein, Mol. Cancer Ther. 2002, 347-355, herein incorporated by reference in their entirety.

One or more nucleobases of an ASO may be any naturally occurring, unmodified nucleobase such as adenine, guanine, cytosine, thymine and uracil, or any synthetic or modified nucleobase that is sufficiently similar to an unmodified nucleobase such that it is capable of hydrogen bonding with a nucleobase present on a target pre-mRNA. Examples of modified nucleobases include, without limitation, hypoxanthine, xanthine, 7-methylguanine, 5, 6-dihydrouracil, 5-methylcytosine, and 5-hydroxymethoylcytosine.

The ASOs described herein also comprise a backbone structure that connects the components of an oligomer. The term "backbone structure" and "oligomer linkages" may be used interchangeably and refer to the connection between monomers of the ASO. In naturally occurring oligonucleotides, the backbone comprises a 3'-5' phosphodiester linkage connecting sugar moieties of the oligomer. The backbone structure or oligomer linkages of the ASOs described herein may include (but are not limited to) phosphorothioate, phosphorodithioate, phosphoroselenoate, phosphorodiselenoate, phosphoroanilothioate, phosphoraniladate, phosphoramidate, and the like. See, e.g., LaPlanche, et al., Nucleic Acids Res. 14:9081 (1986); Stec, et al., J. Am. Chem. Soc. 106:6077 (1984), Stein, et al., Nucleic Acids Res. 16:3209 (1988), Zon, et al., Anti-Cancer Drug Design 6:539 (1991); Zon, et al., Oligonucleotides and Analogues: A Practical Approach, pp. 87-108 (F. Eckstein, Ed., Oxford University Press, Oxford England (1991)); Stec, et al., U.S. Pat. No. 5,151,510; Uhlmann and Peyman, Chemical Reviews 90:543 (1990). In some embodiments, the backbone structure of the ASO does not contain phosphorous but rather contains peptide bonds, for example in a peptide nucleic acid (PNA), or linking groups including carbamate, amides, and linear and cyclic hydrocarbon groups. In some embodiments, the backbone modification is a phosphorothioate linkage. In some embodiments, the backbone modification is a phosphoramidate linkage.

In some embodiments, the stereochemistry at each of the phosphorus internucleotide linkages of the ASO backbone is random. In some embodiments, the stereochemistry at each of the phosphorus internucleotide linkages of the ASO backbone is controlled and is not random. For example, U.S. Pat. App. Pub. No. 2014/0194610, "Methods for the Synthesis of Functionalized Nucleic Acids," incorporated herein by reference, describes methods for independently selecting the handedness of chirality at each phosphorous atom in a nucleic acid oligomer. In some embodiments, an ASO used in the methods of the disclosure, including, but not limited to, any of the ASOs set forth herein in Tables 5 and 6, comprises an ASO having phosphorus internucleotide linkages that are not random. In some embodiments, a composition used in the methods of the disclosure comprises a pure diastereomeric ASO. In some embodiments, a composition used in the methods of the disclosure comprises an ASO that has diastereomeric purity of at least about 90%, at least about 91%, at least about 92%, at least about 93%, at least about 94%, at least about 95%, at least about 96%, at least about 97%, at least about 98%, at least about 99%, about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, or about 99% to about 100%.

In some embodiments, the ASO has a nonrandom mixture of Rp and Sp configurations at its phosphorus internucleotide linkages. For example, it has been suggested that a mix of Rp and Sp is required in antisense oligonucleotides to achieve a balance between good activity and nuclease stability (Wan, et al., 2014, "Synthesis, biophysical properties and biological activity of second generation antisense oligonucleotides containing chiral phosphorothioate linkages," Nucleic Acids Research 42(22): 13456-13468, incorporated herein by reference). In some embodiments, an ASO used in the methods of the disclosure, including, but not limited to, any of the ASOs set forth herein in SEQ ID NOs: 2-5, comprises about 5-100% Rp, at least about 5% Rp, at least about 10% Rp, at least about 15% Rp, at least about 20% Rp, at least about 25% Rp, at least about 30% Rp, at least about 35% Rp, at least about 40% Rp, at least about 45% Rp, at least about 50% Rp, at least about 55% Rp, at least about 60% Rp, at least about 65% Rp, at least about 70% Rp, at least about 75% Rp, at least about 80% Rp, at least about 85% Rp, at least about 90% Rp, or at least about 95% Rp, with the remainder Sp, or about 100% Rp. In some embodiments, an ASO used in the methods of the disclosure, including, but not limited to, any of the ASOs set forth herein comprise a sequence with at least about 80%, 85%, 90%, 95%, 97%, or 100% sequence identity to a region comprising at least 8 contiguous nucleic acids of any one of SEQ ID NOs: 2-5, comprises about 10% to about 100% Rp, about 15% to about 100% Rp, about 20% to about 100% Rp, about 25% to about 100% Rp, about 30% to about 100% Rp, about 35% to about 100% Rp, about 40% to about 100% Rp, about 45% to about 100% Rp, about 50% to about 100% Rp, about 55% to about 100% Rp, about 60% to about 100% Rp, about 65% to about 100% Rp, about 70% to about 100% Rp, about 75% to about 100% Rp, about 80% to about 100% Rp, about 85% to about 100% Rp, about 90% to about 100% Rp, or about 95% to about 100% Rp, about 20% to about 80% Rp, about 25% to about 75% Rp, about 30% to about 70% Rp, about 40% to about 60% Rp, or about 45% to about 55% Rp, with the remainder Sp.

In some embodiments, an ASO used in the methods of the disclosure, including, but not limited to, any of the ASOs set forth herein comprise a sequence with at least about 80%, 85%, 90%, 95%, 97%, or 100% sequence identity to a region comprising at least 8 contiguous nucleic acids of any one of SEQ ID NOs: 2-5, comprises about 5-100% Sp, at least about 5% Sp, at least about 10% Sp, at least about 15% Sp, at least about 20% Sp, at least about 25% Sp, at least about 30% Sp, at least about 35% Sp, at least about 40% Sp, at least about 45% Sp, at least about 50% Sp, at least about 55% Sp, at least about 60% Sp, at least about 65% Sp, at least about 70% Sp, at least about 75% Sp, at least about 80% Sp, at least about 85% Sp, at least about 90% Sp, or at least about 95% Sp, with the remainder Rp, or about 100% Sp. In embodiments, an ASO used in the methods of the disclosure, including, but not limited to, any of the ASOs set forth herein comprise a sequence with at least about 80%, 85%, 90%, 95%, 97%, or 100% sequence identity to a region comprising at least 8 contiguous nucleic acids of any one of SEQ ID NOs: 2-5, comprises about 10% to about 100% Sp, about 15% to about 100% Sp, about 20% to about 100% Sp, about 25% to about 100% Sp, about 30% to about 100% Sp, about 35% to about 100% Sp, about 40% to about 100% Sp, about 45% to about 100% Sp, about 50% to about 100% Sp, about 55% to about 100% Sp, about 60% to about 100% Sp, about 65% to about 100% Sp, about 70% to about 100% Sp, about 75% to about 100% Sp, about 80% to about 100% Sp, about 85% to about 100% Sp, about 90% to about 100% Sp, or about 95% to about 100% Sp, about 20% to about 80% Sp, about 25% to about 75% Sp, about 30% to about 70% Sp, about 40% to about 60% Sp, or about 45% to about 55% Sp, with the remainder Rp.

Any of the ASOs described herein may contain a sugar moiety that comprises ribose or deoxyribose, as present in naturally occurring nucleotides, or a modified sugar moiety or sugar analog, including a morpholine ring. Non-limiting examples of modified sugar moieties include 2' substitutions such as 2'-O-methyl (2'-O-Me), 2'-O-methoxyethyl (2'MOE), 2'-O-aminoethyl, 2'F; N3'->P5' phosphoramidate, 2'dimethylaminooxyethoxy, 2'dimethylaminoethoxyethoxy, 2'-guanidinidium, 2'-O-guanidinium ethyl, carbamate modified sugars, and bicyclic modified sugars. In some embodiments, the sugar moiety modification is selected from 2'-O-Me, 2'F, and 2'MOE. In some embodiments, the sugar moiety modification is an extra bridge bond, such as in a locked nucleic acid (LNA). In some embodiments the sugar analog contains a morpholine ring, such as phosphorodiamidate morpholino (PMO). In some embodiments, the sugar moiety comprises a ribofuransyl or 2'deoxyribofuransyl modification. In some embodiments, the sugar moiety comprises 2'4'-constrained 2'O-methyloxyethyl (cMOE) modifications. In some embodiments, the sugar moiety comprises cEt 2', 4' constrained 2'-O ethyl BNA modifications. In some embodiments, the sugar moiety comprises tricycloDNA (tcDNA) modifications. In some embodiments, the sugar moiety comprises ethylene nucleic acid (ENA) modifications. In some embodiments, the sugar moiety comprises MCE modifications. Modifications are known in the art and described in the literature, e.g., by Jarver, et al., 2014, "A Chemical View of Oligonucleotides for Exon Skipping and Related Drug Applications," Nucleic Acid Therapeutics 24(1): 37-47, incorporated by reference for this purpose herein.

In some embodiments, each monomer of the ASO is modified in the same way, for example each linkage of the backbone of the ASO comprises a phosphorothioate linkage or each ribose sugar moiety comprises a 2'O-methyl modification. Such modifications that are present on each of the monomer components of an ASO are referred to as "uniform modifications." In some examples, a combination of different modifications may be desired, for example, an ASO may comprise a combination of phosphorodiamidate linkages and sugar moieties comprising morpholine rings (morpholinos). Combinations of different modifications to an ASO are referred to as "mixed modifications" or "mixed chemistries."

In some embodiments, the ASO comprises one or more backbone modifications. In some embodiments, the ASO comprises one or more sugar moiety modification. In some embodiments, the ASO comprises one or more backbone modifications and one or more sugar moiety modifications. In some embodiments, the ASO comprises a 2'MOE modification and a phosphorothioate backbone. In some embodiments, the ASO comprises a phosphorodiamidate morpholino (PMO). In some embodiments, the ASO comprises a peptide nucleic acid (PNA). Any of the ASOs or any component of an ASO (e.g., a nucleobase, sugar moiety, backbone) described herein may be modified in order to achieve desired properties or activities of the ASO or reduce undesired properties or activities of the ASO. For example, an ASO or one or more components of any ASO may be modified to enhance binding affinity to a target sequence on a pre-mRNA transcript; reduce binding to any non-target sequence; reduce degradation by cellular nucleases (i.e., RNase H); improve uptake of the ASO into a cell and/or into the nucleus of a cell; alter the pharmacokinetics or pharmacodynamics of the ASO; and/or modulate the half-life of the ASO.

In some embodiments, the ASOs are comprised of 2'-O-(2-methoxyethyl) (MOE) phosphorothioate-modified nucleotides. ASOs comprised of such nucleotides are especially well-suited to the methods disclosed herein; oligomers having such modifications have been shown to have significantly enhanced resistance to nuclease degradation and increased bioavailability, making them suitable, for example, for oral delivery in some embodiments described herein. See e.g., Geary, et al., J Pharmacol Exp Ther. 2001; 296(3):890-7; Geary, et al., J Pharmacol Exp Ther. 2001; 296(3):898-904.

Methods of synthesizing ASOs will be known to one of skill in the art. Alternatively or in addition, ASOs may be obtained from a commercial source.

Unless specified otherwise, the left-hand end of single-stranded nucleic acid (e.g., pre-mRNA transcript, oligonucleotide, ASO, etc.) sequences is the 5' end and the left-hand direction of single or double-stranded nucleic acid sequences is referred to as the 5' direction. Similarly, the right-hand end or direction of a nucleic acid sequence (single or double stranded) is the 3' end or direction. Generally, a region or sequence that is 5' to a reference point in a nucleic acid is referred to as "upstream," and a region or sequence that is 3' to a reference point in a nucleic acid is referred to as "downstream." Generally, the 5' direction or end of an mRNA is where the initiation or start codon is located, while the 3' end or direction is where the termination codon is located. In some aspects, nucleotides that are upstream of a reference point in a nucleic acid may be designated by a negative number, while nucleotides that are downstream of a reference point may be designated by a positive number. For example, a reference point (e.g., an exon-exon junction in mRNA) may be designated as the "zero" site, and a nucleotide that is directly adjacent and upstream of the reference point is designated "minus one," e.g., "−1," while a nucleotide that is directly adjacent and downstream of the reference point is designated "plus one," e.g., "+1."

In some embodiments, the ASOs are complementary to (and bind to) a targeted portion of an OPA1 pre-mRNA, e.g., an OPA1 NMD exon-containing pre-mRNA, that is downstream (in the 3' direction) of the 5' splice site (or 3' end of the NMD exon) of the included exon in an OPA1 pre-mRNA (e.g., the direction designated by positive numbers relative to the 5' splice site). In some embodiments, the ASOs are complementary to a targeted portion of the OPA1 pre-mRNA, e.g., the OPA1 NMD exon-containing pre-mRNA that is within the region about +1 to about +500 relative to the 5' splice site (or 3' end) of the included exon. In some embodiments, the ASOs may be complementary to a targeted portion of an OPA1 pre-mRNA, e.g., an OPA1 NMD exon-containing pre-mRNA, that is within the region between nucleotides +6 and +40,000 relative to the 5' splice site (or 3' end) of the included exon. In some aspects, the ASOs are complementary to a targeted portion that is within the region about +1 to about +40,000, about +1 to about +30,000, about +1 to about +20,000, about +1 to about +15,000, about +1 to about +10,000, about +1 to about +5,000, about +1 to about +4,000, about +1 to about +3,000, about +1 to about +2,000, about +1 to about +1,000, about +1 to about +500, about +1 to about +490, about +1 to about +480, about +1 to about +470, about +1 to about +460, about +1 to about +450, about +1 to about +440, about +1 to about +430, about +1 to about +420, about +1 to about +410, about +1 to about +400, about +1 to about +390, about +1 to about +380, about +1 to about +370, about +1 to about +360, about +1 to about +350, about +1 to about +340, about +1 to about +330, about +1 to about +320, about +1 to about +310, about +1 to about +300, about +1 to about +290, about +1 to about +280, about +1 to about +270, about +1 to about +260, about +1 to about +250, about +1 to about +240, about +1 to about +230, about +1 to about +220, about +1 to about +210, about +1 to about +200, about +1 to about +190, about +1 to about +180, about +1 to about +170, about +1 to about +160, about +1 to about +150, about +1 to about +140, about +1 to about +130, about +1 to about +120, about +1 to about +110, about +1 to about +100, about +1 to about +90, about +1 to about +80, about +1 to about +70, about +1 to about +60, about +1 to about +50, about +1 to about +40, about +1 to about +30, or about +1 to about +20 relative to 5' splice site (or 3' end) of the included exon. In some aspects, the ASOs are complementary to a targeted portion that is within the region from about +1 to about +100, from about +100 to about +200, from about +200 to about +300, from about +300 to about +400, or from about +400 to about +500 relative to 5' splice site (or 3' end) of the included exon.

In some embodiments, the ASOs are complementary to (and bind to) a targeted portion of an OPA1 pre-mRNA, e.g., an OPA1 NMD exon-containing pre-mRNA, that is upstream (in the 5' direction) of the 5' splice site (or 3' end) of the included exon in an OPA1 pre-mRNA, e.g., an OPA1 NMD exon-containing pre-mRNA (e.g., the direction designated by negative numbers relative to the 5' splice site). In some embodiments, the ASOs are complementary to a targeted portion of the OPA1 pre-mRNA, e.g., the OPA1 NMD exon-containing pre-mRNA, that is within the region about −4 to about −270 relative to the 5' splice site (or 3'end) of the included exon. In some embodiments, the ASOs may be complementary to a targeted portion of an OPA1 pre-mRNA, e.g., an OPA1 NMD exon-containing pre-mRNA, that is within the region between nucleotides −1 and −40,000 relative to the 5' splice site (or 3' end) of the included exon. In some aspects, the ASOs are complementary to a targeted portion that is within the region about −1 to about −40,000, about −1 to about −30,000, about −1 to about −20,000, about −1 to about −15,000, about −1 to about −10,000, about −1 to about −5,000, about −1 to about −4,000, about −1 to about −3,000, about −1 to about −2,000, about −1 to about −1,000, about −1 to about −500, about −1 to about −490, about −1 to about −480, about −1 to about −470, about −1 to about −460, about −1 to about −450, about −1 to about −440, about −1 to about −430, about −1 to about −420, about −1 to about −410, about −1 to about −400, about −1 to about −390, about −1 to about −380, about −1 to about −370, about −1 to about −360, about −1 to about −350, about −1 to about −340, about −1 to about −330, about −1 to about −320, about −1 to about −310, about −1 to about −300, about −1 to about −290, about −1 to about −280, about −1 to about −270, about −1 to about −260, about −1 to about −250, about −1 to about −240, about −1 to about −230, about −1 to about −220, about −1 to about −210, about −1 to about −200, about −1 to about −190, about −1 to about −180, about −1 to about −170, about −1 to about −160, about −1 to about −150, about −1 to about −140, about −1 to about −130, about −1 to about −120, about −1 to about −110, about −1 to about −100, about −1 to about −90, about −1 to about −80, about −1 to about −70, about −1 to about −60, about −1 to about −50, about −1 to about −40, about −1 to about −30, or about −1 to about −20 relative to 5' splice site (or 3' end) of the included exon.

In some embodiments, the ASOs are complementary to a targeted region of an OPA1 pre-mRNA, e.g., an OPA1 NMD exon-containing pre-mRNA, that is upstream (in the 5' direction) of the 3' splice site (or 5' end) of the included exon in an OPA1 pre-mRNA (e.g., in the direction designated by negative numbers). In some embodiments, the ASOs are complementary to a targeted portion of the OPA1 pre-mRNA, e.g., the OPA1 NMD exon-containing pre-mRNA, that is within the region about −1 to about −500 relative to the 3' splice site (or 5' end) of the included exon. In some embodiments, the ASOs are complementary to a targeted portion of the OPA1 pre-mRNA that is within the region −1 to −40,000 relative to the 3' splice site of the included exon. In some aspects, the ASOs are complementary to a targeted portion that is within the region about −1 to about −40,000, about −1 to about −30,000, −1 to about −20,000, about −1 to about −15,000, about −1 to about −10,000, about −1 to about −5,000, about −1 to about −4,000, about −1 to about −3,000, about −1 to about −2,000, about −1 to about −1,000, about −1 to about −500, about −1 to about −490, about −1 to about −480, about −1 to about −470, about −1 to about −460, about −1 to about −450, about −1 to about −440, about −1 to about −430, about −1 to about −420, about −1 to about −410, about −1 to about −400, about −1 to about −390, about −1 to about −380, about −1 to about −370, about −1 to about −360, about −1 to about −350, about −1 to about −340, about −1 to about −330, about −1 to about −320, about −1 to about −310, about −1 to about −300, about −1 to about −290, about −1 to about −280, about −1 to about −270, about −1 to about −260, about −1 to about −250, about −1 to about −240, about −1 to about −230, about −1 to about −220, about −1 to about −210, about −1 to about −200, about −1 to about −190, about −1 to about −180, about −1 to about −170, about −1 to about −160, about −1 to about −150, about −1 to about −140, about −1 to about −130, about −1 to about −120, about −1 to about −110, about −1 to about −100, about −1 to about −90, about −1 to about −80, about −1 to about −70, about −1 to about −60, about −1 to about −50, about −1 to about −40, about −1 to about −30, or about −1 to about −20 relative to 3' splice site of the included exon. In some aspects, the ASOs are complementary to a targeted portion that is within the region from about −1 to about −100, from about −100 to about −200, from about −200 to about −300, from about −300 to about −400, or from about −400 to about −500 relative to 3' splice site of the included exon.

In some embodiments, the ASOs are complementary to a targeted region of an OPA1 pre-mRNA, e.g., an OPA1 NMD exon-containing pre-mRNA, that is downstream (in the 3' direction) of the 3' splice site (5' end) of the included exon in an OPA1 pre-mRNA, e.g., an OPA1 NMD exon-containing pre-mRNA (e.g., in the direction designated by positive numbers). In some embodiments, the ASOs are complementary to a targeted portion of the OPA1 pre-mRNA that is within the region of about +1 to about +40,000 relative to the 3' splice site of the included exon. In some aspects, the ASOs are complementary to a targeted portion that is within the region about +1 to about +40,000, about +1 to about +30,000, about +1 to about +20,000, about +1 to about +15,000, about +1 to about +10,000, about +1 to about +5,000, about +1 to about +4,000, about +1 to about +3,000, about +1 to about +2,000, about +1 to about +1,000, about +1 to about +500, about +1 to about +490, about +1 to about +480, about +1 to about +470, about +1 to about +460, about +1 to about +450, about +1 to about +440, about +1 to about +430, about +1 to about +420, about +1 to about +410, about +1 to about +400, about +1 to about +390, about +1 to about +380, about +1 to about +370, about +1 to about +360, about +1 to about +350, about +1 to about +340, about +1 to about +330, about +1 to about +320, about +1 to about +310, about +1 to about +300, about +1 to about +290, about +1 to about +280, about +1 to about +270, about +1 to about +260, about +1 to about +250, about +1 to about +240, about +1 to about +230, about +1 to about +220, about +1 to about +210, about +1 to about +200, about +1 to about +190, about +1 to about +180, about +1 to about +170, about +1 to about +160, about +1 to about +150, about +1 to about +140, about +1 to about +130, about +1 to about +120, about +1 to about +110, about +1 to about +100, about +1 to about +90, about +1 to about +80, about +1 to about +70, about +1 to about +60, about +1 to about +50, about +1 to about +40, about +1 to about +30, or about +1 to about +20, or about +1 to about +10 relative to 3' splice site of the included exon.

In some embodiments, the targeted portion of the OPA1 pre-mRNA, e.g., the OPA1 NMD exon-containing pre-mRNA, is within the region +100 relative to the 5' splice site (3' end) of the included exon to −100 relative to the 3' splice site (5' end) of the included exon. In some embodiments, the targeted portion of the OPA1 NMD exon-containing pre-mRNA is within the NMD exon. In some embodiments, the target portion of the OPA1 NMD exon-containing pre-mRNA comprises a pseudo-exon and intron boundary.

The ASOs may be of any length suitable for specific binding and effective enhancement of splicing. In some embodiments, the ASOs consist of 8 to 50 nucleobases. For example, the ASO may be 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, or 50 nucleobases in length. In some embodiments, the ASOs consist of more than 50 nucleobases. In some embodiments, the ASO is from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, 12 to 15 nucleobases, 13 to 50 nucleobases, 13 to 40 nucleobases, 13 to 35 nucleobases, 13 to 30 nucleobases, 13 to 25 nucleobases, 13 to 20 nucleobases, 14 to 50 nucleobases, 14 to 40 nucleobases, 14 to 35 nucleobases, 14 to 30 nucleobases, 14 to 25 nucleobases, 14 to 20 nucleobases, 15 to 50 nucleobases, 15 to 40 nucleobases, 15 to 35 nucleobases, 15 to 30 nucleobases, 15 to 25 nucleobases, 15 to 20 nucleobases, 20 to 50 nucleobases, 20 to 40 nucleobases, 20 to 35 nucleobases, 20 to 30 nucleobases, 20 to 25 nucleobases, 25 to 50 nucleobases, 25 to 40 nucleobases, 25 to 35 nucleobases, or 25 to 30 nucleobases in length. In some embodiments, the ASOs are 18 nucleotides in length. In some embodiments, the ASOs are 15 nucleotides in length. In some embodiments, the ASOs are 25 nucleotides in length.

In some embodiments, two or more ASOs with different chemistries but complementary to the same targeted portion of the pre-mRNA, e.g., NMD exon-containing pre-mRNA, are used. In some embodiments, two or more ASOs that are complementary to different targeted portions of the pre-mRNA, e.g., the NMD exon-containing pre-mRNA, are used.

In some embodiments, the antisense oligonucleotides of the disclosure are chemically linked to one or more moieties or conjugates, e.g., a targeting moiety or other conjugate that enhances the activity or cellular uptake of the oligonucleotide. Such moieties include, but are not limited to, a lipid moiety, e.g., as a cholesterol moiety, a cholesteryl moiety, an aliphatic chain, e.g., dodecandiol or undecyl residues, a polyamine or a polyethylene glycol chain, or adamantane acetic acid. Oligonucleotides comprising lipophilic moieties and preparation methods have been described in the published literature. In embodiments, the antisense oligonucleotide is conjugated with a moiety including, but not limited to, an abasic nucleotide, a polyether, a polyamine, a polyamide, a peptides, a carbohydrate, e.g., N-acetylgalactosamine (GalNAc), N-Ac-Glucosamine (GluNAc), or mannose (e.g., mannose-6-phosphate), a lipid, or a polyhydrocarbon compound. Conjugates can be linked to one or more of any nucleotides comprising the antisense oligonucleotide at any of several positions on the sugar, base or phosphate group, as understood in the art and described in the literature, e.g., using a linker. Linkers can include a bivalent or trivalent branched linker. In embodiments, the conjugate is attached to the 3' end of the antisense oligonucleotide. Methods of preparing oligonucleotide conjugates are described, e.g., in U.S. Pat. No. 8,450,467, "Carbohydrate conjugates as delivery agents for oligonucleotides," incorporated by reference herein.

In some embodiments, the nucleic acid to be targeted by an ASO is an OPA1 pre-mRNA, e.g., NMD exon-containing pre-mRNA expressed in a cell, such as a eukaryotic cell. In some embodiments, the term "cell" may refer to a population of cells. In some embodiments, the cell is in a subject. In some embodiments, the cell is isolated from a subject. In some embodiments, the cell is ex vivo. In some embodiments, the cell is a condition or disease-relevant cell or a cell line. In some embodiments, the cell is in vitro (e.g., in cell culture).

Pharmaceutical Compositions

Pharmaceutical compositions or formulations comprising the agent, e.g., antisense oligonucleotide, of the described compositions and for use in any of the described methods can be prepared according to conventional techniques well known in the pharmaceutical industry and described in the published literature. In embodiments, a pharmaceutical composition or formulation for treating a subject comprises an effective amount of any antisense oligomer as described herein, or a pharmaceutically acceptable salt, solvate, hydrate or ester thereof. The pharmaceutical formulation comprising an antisense oligomer may further comprise a pharmaceutically acceptable excipient, diluent or carrier.

Pharmaceutically acceptable salts are suitable for use in contact with the tissues of humans and lower animals without undue toxicity, irritation, allergic response, etc., and are commensurate with a reasonable benefit/risk ratio. (See, e.g., S. M. Berge, et al., J. Pharmaceutical Sciences, 66: 1-19 (1977), incorporated herein by reference for this purpose. The salts can be prepared in situ during the final isolation and purification of the compounds, or separately by reacting the free base form with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other documented methodologies such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

In some embodiments, the compositions are formulated into any of many possible dosage forms such as, but not limited to, tablets, capsules, gel capsules, liquid syrups, soft gels, suppositories, and enemas. In embodiments, the compositions are formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers. In embodiments, a pharmaceutical formulation or composition of the present disclosure includes, but is not limited to, a solution, emulsion, microemulsion, foam or liposome-containing formulation (e.g., cationic or noncationic liposomes).

The pharmaceutical composition or formulation described herein may comprise one or more penetration enhancers, carriers, excipients or other active or inactive ingredients as appropriate and well known to those of skill in the art or described in the published literature. In embodiments, liposomes also include sterically stabilized liposomes, e.g., liposomes comprising one or more specialized lipids. These specialized lipids result in liposomes with enhanced circulation lifetimes. In embodiments, a sterically stabilized liposome comprises one or more glycolipids or is derivatized with one or more hydrophilic polymers, such as a polyethylene glycol (PEG) moiety. In some embodiments, a surfactant is included in the pharmaceutical formulation or compositions. The use of surfactants in drug products, formulations and emulsions is well known in the art. In embodiments, the present disclosure employs a penetration enhancer to effect the efficient delivery of the antisense oligonucleotide, e.g., to aid diffusion across cell membranes and/or enhance the permeability of a lipophilic drug. In some embodiments, the penetration enhancers are a surfactant, fatty acid, bile salt, chelating agent, or non-chelating nonsurfactant.

In some embodiments, the pharmaceutical formulation comprises multiple antisense oligonucleotides. In embodiments, the antisense oligonucleotide is administered in combination with another drug or therapeutic agent.

Combination Therapies

In some embodiments, the ASOs disclosed in the present disclosure can be used in combination with one or more additional therapeutic agents. In some embodiments, the one or more additional therapeutic agents can comprise a small molecule. For example, the one or more additional therapeutic agents can comprise a small molecule described in WO2016128343A1, WO2017053982A1, WO2016196386A1, WO201428459A1, WO201524876A2, WO2013119916A2, and WO2014209841A2, which are incorporated by reference herein in their entirety. In some embodiments, the one or more additional therapeutic agents comprise an ASO that can be used to correct intron retention.

Treatment of Subjects

Any of the compositions provided herein may be administered to an individual. "Individual" may be used interchangeably with "subject" or "patient." An individual may be a mammal, for example a human or animal such as a non-human primate, a rodent, a rabbit, a rat, a mouse, a horse, a donkey, a goat, a cat, a dog, a cow, a pig, or a sheep. In embodiments, the individual is a human. In embodiments, the individual is a fetus, an embryo, or a child. In other embodiments, the individual may be another eukaryotic organism, such as a plant. In some embodiments, the compositions provided herein are administered to a cell ex vivo.

In some embodiments, the compositions provided herein are administered to an individual as a method of treating a disease or disorder. In some embodiments, the individual has a genetic disease, such as any of the diseases described herein. In some embodiments, the individual is at risk of having a disease, such as any of the diseases described herein. In some embodiments, the individual is at increased risk of having a disease or disorder caused by insufficient amount of a protein or insufficient activity of a protein. If an individual is "at an increased risk" of having a disease or disorder caused insufficient amount of a protein or insufficient activity of a protein, the method involves preventative or prophylactic treatment. For example, an individual may be at an increased risk of having such a disease or disorder because of family history of the disease. Typically, individuals at an increased risk of having such a disease or disorder benefit from prophylactic treatment (e.g., by preventing or delaying the onset or progression of the disease or disorder). In embodiments, a fetus is treated in utero, e.g., by administering the ASO composition to the fetus directly or indirectly (e.g., via the mother).

In some cases, the subject pharmaceutical composition and method are applicable for treatment of a condition or disease associated with OPA1 deficiency. In some cases, the subject pharmaceutical composition and method are applicable for treatment of an eye disease or condition. In some cases, the subject pharmaceutical composition and method are applicable for treatment of Optic atrophy type 1, autosomal dominant optic atrophy (ADOA), ADOA-plus syndrome; a mitochondrial disorder; glaucoma; normal tension glaucoma; Charcot-Marie-Tooth disease; mitochondria dysfunction; diabetic retinopathy; age-related macular degeneration; retinal ganglion cell death; mitochondrial fission-mediated mitochondrial dysfunction; progressive external ophthalmoplegia; deafness; ataxia; motor neuropathy; sensory neuropathy; myopathy; Behr syndrome; brain dysfunction; encephalopathy; peripheral neuropathy; fatal infantile mitochondrial encephalomyopathy; hypertrophic cardiomyopathy; spastic ataxic syndrome; sensory motor peripheral neuropathy; hypotonia; gastrointestinal dysmotility and dysphagia; optic atrophy; optic atrophy plus syndrome; Mitochondrial DNA depletion syndrome 14; late-onset cardiomyopathy; diabetic cardiomyopathy; Alzheimer's Disease; focal segmental glomerulosclerosis; kidney disease; Huntington's Disease; cognitive function decline in healthy aging; Prion diseases; late onset dementia and parkinsonism; mitochondrial myopathy; Leigh syndrome; Friedreich's ataxia; Parkinson's disease; MELAS (Mitochondrial encephalomyopathy, lactic acidosis, and stroke-like episodes); pyruvate dehydrogenase complex deficiency; chronic kidney disease; Leber's hereditary optic neuropathy;

obesity; age-related systemic neurodegeneration; skeletal muscle atrophy; heart and brain ischemic damage; or massive liver apoptosis.

Autosomal dominant optic atrophy (ADOA) is the most common inherited optic nerve disorder and is characterized by retinal ganglion cell loss. In some cases, 65-90% of ADOA cases are caused by mutations in one allele of the OPA1 gene. OPA1 gene encodes an OPA1 protein that is a mitochondrial GTPase, which can have a critical maintenance role in mitochondria structure and function. Most OPA1 mutations can lead to a haploinsufficiency, resulting in about a 50% decrease of normal OPA1 protein levels. Approximately 1 out of 30,000 people are affected globally with a higher incidence of −1 out of 10,000 in Denmark due to a founder effect. ADOA can present within the first decade of life. 80% of ADOA patients are symptomatic before 10 years of age. The disease can cause progressive and irreversible vision loss and up to 46% of patients are registered as legally blind.

In some cases, a therapeutic agent comprises an oligonucleotide. In some cases, a therapeutic agent comprises a vector, e.g., a viral vector, expressing a oligonucleotide that binds to the targeted region of a pre-mRNA the encodes the target peptide sequence. The methods provided herein can be adapted to contacting a vector that encodes an agent, e.g., an oligonucleotide, to a cell, so that the agent binds to a pre-mRNA in the cell and modulates the processing of the pre-mRNA. In some cases, the viral vector comprises an adenoviral vector, adeno-associated viral (AAV) vector, lentiviral vector, Herpes Simplex Virus (HSV) viral vector, retroviral vector, or any applicable viral vector. In some cases, a therapeutic agent comprises a gene editing tool that is configured to modify a gene encoding the target peptide sequence such that a gene region that encodes the inefficient translation region is deleted. In some cases, a gene editing tool comprises vector, e.g., viral vector, for gene editing based on CRISPR-Cas9, TALEN, Zinc Finger, or other applicable technologies.

Suitable routes for administration of ASOs of the present disclosure may vary depending on cell type to which delivery of the ASOs is desired. Multiple tissues and organs are affected by ADOA, with the eye being the most significantly affected tissue. The ASOs of the present disclosure may be administered to patients parenterally, for example, by intravitreal injection, intrathecal injection, intracerebroventricular injection, intraperitoneal injection, intramuscular injection, subcutaneous injection, or intravenous injection.

In embodiments, the antisense oligonucleotide is administered with one or more agents capable of promoting penetration of the subject antisense oligonucleotide across the blood-brain barrier by any method known in the art. For example, delivery of agents by administration of an adenovirus vector to motor neurons in muscle tissue is described in U.S. Pat. No. 6,632,427, "Adenoviral-vector-mediated gene transfer into medullary motor neurons," incorporated herein by reference. Delivery of vectors directly to the brain, e.g., the striatum, the thalamus, the hippocampus, or the substantia nigra, is described, e.g., in U.S. Pat. No. 6,756,523, "Adenovirus vectors for the transfer of foreign genes into cells of the central nervous system particularly in brain," incorporated herein by reference.

In some embodiments, the antisense oligonucleotides are linked or conjugated with agents that provide desirable pharmaceutical or pharmacodynamic properties. In embodiments, the antisense oligonucleotide is coupled to a substance, known in the art to promote penetration or transport across the blood-brain barrier, e.g., an antibody to the transferrin receptor. In embodiments, the antisense oligonucleotide is linked with a viral vector, e.g., to render the antisense compound more effective or increase transport across the blood-brain barrier. In embodiments, osmotic blood brain barrier disruption is assisted by infusion of sugars, e.g., meso erythritol, xylitol, D(+) galactose, D(+) lactose, D(+) xylose, dulcitol, myo-inositol, L(−) fructose, D(−) mannitol, D(+) glucose, D(+) arabinose, D(−) arabinose, cellobiose, D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose, or amino acids, e.g., glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 9,193,969, "Compositions and methods for selective delivery of oligonucleotide molecules to specific neuron types," U.S. Pat. No. 4,866,042, "Method for the delivery of genetic material across the blood brain barrier," U.S. Pat. No. 6,294,520, "Material for passage through the blood-brain barrier," and U.S. Pat. No. 6,936,589, "Parenteral delivery systems," each incorporated herein by reference.

In some embodiments, subjects treated using the methods and compositions are evaluated for improvement in condition using any methods known and described in the art.

Methods of Identifying Additional ASOs that Induce Exon Skipping

Also within the scope of the present disclosure are methods for identifying or determining ASOs that induce exon skipping of an OPA1 NMD exon-containing pre-mRNA. For example, a method can comprise identifying or determining ASOs that induce pseudo-exon skipping of an OPA1 NMD exon-containing pre-mRNA. ASOs that specifically hybridize to different nucleotides within the target region of the pre-mRNA may be screened to identify or determine ASOs that improve the rate and/or extent of splicing of the target intron. In some embodiments, the ASO may block or interfere with the binding site(s) of a splicing repressor(s)/silencer. Any method known in the art may be used to identify (determine) an ASO that when hybridized to the target region of the exon results in the desired effect (e.g., pseudo-exon skipping, protein or functional RNA production). These methods also can be used for identifying ASOs that induce exon skipping of the included exon by binding to a targeted region in an intron flanking the included exon, or in a non-included exon. An example of a method that may be used is provided below.

A round of screening, referred to as an ASO "walk" may be performed using ASOs that have been designed to hybridize to a target region of a pre-mRNA. For example, the ASOs used in the ASO walk can be tiled every 5 nucleotides from approximately 100 nucleotides upstream of the 3' splice site of the included exon (e.g., a portion of sequence of the exon located upstream of the target/included exon) to approximately 100 nucleotides downstream of the 3' splice site of the target/included exon and/or from approximately 100 nucleotides upstream of the 5' splice site of the included exon to approximately 100 nucleotides downstream of the 5' splice site of the target/included exon (e.g., a portion of sequence of the exon located downstream of the target/included exon). For example, a first ASO of 15 nucleotides in length may be designed to specifically hybridize to nucleotides +6 to +20 relative to the 3' splice site of the target/included exon. A second ASO may be designed to specifically hybridize to nucleotides +11 to +25 relative to the 3' splice site of the target/included exon. ASOs are designed as such spanning the target region of the pre-mRNA. In embodiments, the ASOs can be tiled more closely, e.g., every 1, 2, 3, or 4 nucleotides. Further, the ASOs can be tiled from 100 nucleotides downstream of the 5' splice site, to 100 nucleotides upstream of the 3' splice site. In some embodiments, the ASOs can be tiled from about 1,160 nucleotides upstream of the 3' splice site, to about 500 nucleotides downstream of the 5' splice site. In some embodiments, the ASOs can be tiled from about 500 nucleotides upstream of the 3' splice site, to about 1,920 nucleotides downstream of the 3' splice site.

One or more ASOs, or a control ASO (an ASO with a scrambled sequence, sequence that is not expected to hybridize to the target region) are delivered, for example by transfection, into a disease-relevant cell line that expresses the target pre-mRNA (e.g., a NMD exon-containing pre-mRNA described herein). The exon skipping effects of each of the ASOs may be assessed by any method known in the art, for example by reverse transcriptase (RT)-PCR using primers that span the splice junction, as described in Example 4. A reduction or absence of a longer RT-PCR product produced using the primers spanning the region containing the included exon (e.g. including the flanking exons of the NMD exon) in ASO-treated cells as compared to in control ASO-treated cells indicates that splicing of the target NMD exon has been enhanced. In some embodiments, the exon skipping efficiency (or the splicing efficiency to splice the intron containing the NMD exon), the ratio of spliced to unspliced pre-mRNA, the rate of splicing, or the extent of splicing may be improved using the ASOs described herein. The amount of protein or functional RNA that is encoded by the target pre-mRNA can also be assessed to determine whether each ASO achieved the desired effect (e.g., enhanced functional protein production). Any method known in the art for assessing and/or quantifying protein production, such as Western blotting, flow cytometry, immunofluorescence microscopy, and ELISA, can be used.

A second round of screening, referred to as an ASO "micro-walk" may be performed using ASOs that have been designed to hybridize to a target region of a pre-mRNA. The ASOs used in the ASO micro-walk are tiled every 1 nucleotide to further refine the nucleotide acid sequence of the pre-mRNA that when hybridized with an ASO results in exon skipping (or enhanced splicing of NMD exon).

Regions defined by ASOs that promote splicing of the target intron are explored in greater detail by means of an ASO "micro-walk", involving ASOs spaced in 1-nt steps, as well as longer ASOs, typically 18-25 nt.

As described for the ASO walk above, the ASO micro-walk is performed by delivering one or more ASOs, or a control ASO (an ASO with a scrambled sequence, sequence that is not expected to hybridize to the target region), for example by transfection, into a disease-relevant cell line that expresses the target pre-mRNA. The splicing-inducing effects of each of the ASOs may be assessed by any method known in the art, for example by reverse transcriptase (RT)-PCR using primers that span the NMD exon, as described herein (see, e.g., Example 4). A reduction or absence of a longer RT-PCR product produced using the primers spanning the NMD exon in ASO-treated cells as compared to in control ASO-treated cells indicates that exon skipping (or splicing of the target intron containing an NMD exon) has been enhanced. In some embodiments, the exon skipping efficiency (or the splicing efficiency to splice the intron containing the NMD exon), the ratio of spliced to unspliced pre-mRNA, the rate of splicing, or the extent of splicing may be improved using the ASOs described herein. The amount of protein or functional RNA that is encoded by the target pre-mRNA can also be assessed to determine whether each ASO achieved the desired effect (e.g., enhanced functional protein production). Any method known in the art for assessing and/or quantifying protein production, such as Western blotting, flow cytometry, immunofluorescence microscopy, and ELISA, can be used.

ASOs that when hybridized to a region of a pre-mRNA result in exon skipping (or enhanced splicing of the intron containing a NMD exon) and increased protein production may be tested in vivo using animal models, for example transgenic mouse models in which the full-length human gene has been knocked-in or in humanized mouse models of disease. Suitable routes for administration of ASOs may vary depending on the disease and/or the cell types to which delivery of the ASOs is desired. ASOs may be administered, for example, by intravitreal injection, intrathecal injection, intracerebroventricular injection, intraperitoneal injection, intramuscular injection, subcutaneous injection, or intravenous injection. Following administration, the cells, tissues, and/or organs of the model animals may be assessed to determine the effect of the ASO treatment by for example evaluating splicing (e.g., efficiency, rate, extent) and protein production by methods known in the art and described herein. The animal models may also be any phenotypic or behavioral indication of the disease or disease severity.

Also within the scope of the present disclosure is a method to identify or validate an NMD-inducing exon in the presence of an NMD inhibitor, for example, cycloheximide. An exemplary method is provided in Example 2.

SPECIFIC EMBODIMENTS (A)

Embodiment A1. A method of treating Optic atrophy type 1 in a subject in need thereof, by increasing the expression of a target protein or functional RNA by a cell of the subject, wherein the cell has an mRNA that contains a non-sense mediated RNA decay-inducing exon (NMD exon mRNA), and wherein the NMD exon mRNA encodes the target protein or functional RNA, the method comprising contacting the cell of the subject with a therapeutic agent that binds to a targeted portion of the NMD exon mRNA encoding the target protein or functional RNA, whereby the non-sense mediated RNA decay-inducing exon is excluded from the NMD exon mRNA encoding the target protein or functional RNA, thereby increasing the level of mRNA encoding the target protein or functional RNA, and increasing the expression of the target protein or functional RNA in the cell of the subject.

Embodiment A2. The method of embodiment A1, wherein the target protein is OPA1.

Embodiment A3. A method of increasing expression of OPA1 protein by a cell having an mRNA that contains a non-sense mediated RNA decay-inducing exon (NMD exon mRNA) and encodes OPA1 protein, the method comprising contacting the cell with an agent that binds to a targeted portion of the NMD exon mRNA encoding OPA1 protein, whereby the non-sense mediated RNA decay-inducing exon is excluded from the NMD exon mRNA encoding OPA1 protein, thereby increasing the level of mRNA encoding OPA1 protein, and increasing the expression of OPA1 protein in the cell.

Embodiment A4. The method of any one of embodiments A1 to A3, wherein the non-sense mediated RNA decay-inducing exon is spliced out from the NMD exon mRNA encoding the target protein or functional RNA.

Embodiment A5. The method of any one of embodiments A1 to A4, wherein the target protein does not comprise an amino acid sequence encoded by the non-sense mediated RNA decay-inducing exon.

Embodiment A6. The method of any one of embodiments A1 to A5, wherein the target protein is a full-length target protein.

Embodiment A7. The method of any one of embodiments A1 to A6, wherein the agent is an antisense oligomer (ASO) complementary to the targeted portion of the NMD exon mRNA.

Embodiment A8. The method of any one of embodiments A1 to A7, wherein the mRNA is pre-mRNA.

Embodiment A9. The method of any one of embodiments A1 to A8, wherein the contacting comprises contacting the therapeutic agent to the mRNA, wherein the mRNA is in a nucleus of the cell.

Embodiment A10. The method of any one of embodiments A1 to A9, wherein the target protein or the functional RNA corrects a deficiency in the target protein or functional RNA in the subject.

Embodiment A11. The method of any one of embodiments A1 to A10, wherein the cells are in or from a subject with a condition caused by a deficient amount or activity of an OPA1 protein.

Embodiment A12. The method of any one of embodiments A1 to A11, wherein the deficient amount of the target protein is caused by haploinsufficiency of the target protein, wherein the subject has a first allele encoding a functional target protein, and a second allele from which the target protein is not produced, or a second allele encoding a nonfunctional target protein, and wherein the antisense oligomer binds to a targeted portion of a NMD exon mRNA transcribed from the first allele.

Embodiment A13. The method of any one of embodiments A1 to A11, wherein the subject has a condition caused by a disorder resulting from a deficiency in the amount or function of the target protein, wherein the subject has (a) a first mutant allele from which
  (i) the target protein is produced at a reduced level compared to production from a wild-type allele,
  (ii) the target protein is produced in a form having reduced function compared to an equivalent wild-type protein, or
  (iii) the target protein is not produced, and
(b) a second mutant allele from which
  (i) the target protein is produced at a reduced level compared to production from a wild-type allele,
  (ii) the target protein is produced in a form having reduced function compared to an equivalent wild-type protein, or
  (iii) the target protein is not produced, and wherein when the subject has a first mutant allele (a)(iii)., the second mutant allele is (b)(i) or (b)(ii) and wherein when the subject has a second mutant allele (b)(iii), the first mutant allele is (a)(i) or (a)(ii), and wherein the NMD exon mRNA is transcribed from either the first mutant allele that is (a)(i) or (a)(ii), and/or the second allele that is (b)(i) or (b)(ii).

Embodiment A14. The method of embodiment A13, wherein the target protein is produced in a form having reduced function compared to the equivalent wild-type protein.

Embodiment A15. The method of embodiment A13, wherein the target protein is produced in a form that is fully-functional compared to the equivalent wild-type protein.

Embodiment A16. The method of any one of embodiments A1 to A15, wherein the targeted portion of the NMD exon mRNA is within the non-sense mediated RNA decay-inducing exon.

Embodiment A17. The method of any one of embodiments A1 to A15, wherein the targeted portion of the NMD exon mRNA is either upstream or downstream of the non-sense mediated RNA decay-inducing exon.

Embodiment A18. The method of any one of embodiments A1 to A17, wherein the NMD exon mRNA comprises a sequence with at least about 80%, 85%, 90%, 95%, 97%, or 100% sequence identity to SEQ ID NO: 2 or 3.

Embodiment A19. The method of any one of embodiments A1 to A17, wherein the NMD exon mRNA is encoded by a genetic sequence with at least about 80%, 85%, 90%, 95%, 97%, or 100% sequence identity to SEQ ID NO: 1.

Embodiment A20. The method of any one of embodiments A1 to A17, wherein the targeted portion of the NMD exon mRNA comprises a sequence with at least 80%, 85%, 90%, 95%, 97%, or 100% sequence identity to a region comprising at least 8 contiguous nucleic acids of SEQ ID NO: 2 or 3.

Embodiment A21. The method of any one of embodiments A1 to A20, wherein the agent is an antisense oligomer (ASO) and wherein the ASO comprises a sequence that is at least about 80%, 85%, 90%, 95%, 97%, or 100% complementary to at least 8 contiguous nucleic acids of SEQ ID NO: 2 or 3.

Embodiment A22. The method of any one of embodiments A1 to A15, wherein the targeted portion of the NMD exon mRNA is within the non-sense mediated RNA decay-inducing exon 6x of OPA1, exon 7x of OPA1, or exon 28x of OPA1.

Embodiment A23. The method of any one of embodiments A1 to A15, wherein the targeted portion of the NMD exon mRNA is upstream or downstream of the non-sense mediated RNA decay-inducing exon 6x of OPA1, exon 7x of OPA1, or exon 28x of OPA1.

Embodiment A24. The method of any one of embodiments A1 to A15, wherein the targeted portion of the NMD exon mRNA comprises an exon-intron junction exon 6x of OPA1, exon 7x of OPA1, or exon 28x of OPA1.

Embodiment A25. The method of any one of embodiments A1 to A24, wherein the target protein produced is full-length protein, or wild-type protein.

Embodiment A26. The method of any one of embodiments A1 to A25, wherein the total amount of the mRNA encoding the target protein or functional RNA produced in the cell contacted with the antisense oligomer is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the total amount of the mRNA encoding the target protein or functional RNA produced in a control cell.

Embodiment A27. The method of any one of embodiments A1 to A25, wherein the total amount of the mRNA encoding the target protein or functional RNA produced in the cell contacted with the antisense oligomer is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 10%, at least about 20%, at least about 50%, at least about 100%, at least about 150%, at least about 200%, at least about 250%, or at least about 300%, compared to the total amount of the mRNA encoding the target protein or functional RNA produced in a control cell.

Embodiment A28. The method of one any of embodiments A1 to A25, wherein the total amount of target protein produced by the cell contacted with the antisense oligomer is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the total amount of target protein produced by a control cell.

Embodiment A29. The method of one any of embodiments A1 to A25, wherein the total amount of target protein produced by the cell contacted with the antisense oligomer is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 10%, at least about 20%, at least about 50%, at least about 100%, at least about 150%, at least about 200%, at least about 250%, or at least about 300%, compared to the total amount of target protein produced by a control cell.

Embodiment A30. The method of any one of embodiments A1 to 29, wherein the agent is an antisense oligomer (ASO) and wherein the antisense oligomer comprises a backbone modification comprising a phosphorothioate linkage or a phosphorodiamidate linkage.

Embodiment A31. The method of any one of embodiments A1 to A30, wherein the agent is an antisense oligomer (ASO) and wherein the antisense oligomer comprises a phosphorodiamidate morpholino, a locked nucleic acid, a peptide nucleic acid, a 2'-O-methyl, a 2'-Fluoro, or a 2'-O-methoxyethyl moiety.

Embodiment A32. The method of any one of embodiments A1 to A31, wherein the agent is an antisense oligomer (ASO) and wherein the antisense oligomer comprises at least one modified sugar moiety.

Embodiment A33. The method of embodiment A32, wherein each sugar moiety is a modified sugar moiety.

Embodiment A34. The method of any one of embodiments A1 to A33, wherein the agent is an antisense oligomer (ASO) and wherein the antisense oligomer consists of from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases.

Embodiment A35. The method of any one of embodiments A1 to A34, wherein the agent is an antisense oligomer (ASO) and wherein the antisense oligomer is at least 80%, at least 85%, at least 90%, at least 95%, at least 98%, at least 99%, or 100%, complementary to the targeted portion of the NMD exon mRNA encoding the protein.

Embodiment A36. The method of any one of embodiments A1 to A35, wherein the method further comprises assessing OPA1 mRNA or protein expression.

Embodiment A37. The method of any one of embodiments A1 to A36, wherein Optic atrophy type 1 is treated and wherein the antisense oligomer binds to a targeted portion of an OPA1 NMD exon mRNA, wherein the targeted portion is within SEQ ID NO: 2 or 3.

Embodiment A38. The method of any one of embodiments A1 to A37, wherein the subject is a human.

Embodiment A39. The method of any one of embodiments A1 to A38, wherein the subject is a non-human animal.

Embodiment A40. The method of any one of embodiments A1 to A39, wherein the subject is a fetus, an embryo, or a child.

Embodiment A41. The method of any one of embodiments A1 to A40, wherein the cells are ex vivo.

Embodiment A42. The method of any one of embodiments A1 to A41, wherein the therapeutic agent is administered by intrathecal injection, intracerebroventricular injection, intraperitoneal injection, intramuscular injection, subcutaneous injection, or intravenous injection of the subject.

Embodiment A43. The method of any of embodiments A1 to A42, wherein the method further comprises administering a second therapeutic agent to the subject.

Embodiment A44. The method of embodiment A43, wherein the second therapeutic agent is a small molecule.

Embodiment A45. The method of embodiment A43, wherein the second therapeutic agent is an ASO.

Embodiment A46. The method of any one of embodiments A43 to A45, wherein the second therapeutic agent corrects intron retention.

Embodiment A47. An antisense oligomer as used in a method of any of embodiments A1 to A46.

Embodiment A48. An antisense oligomer comprising a sequence with at least about 80%, 85%, 90%, 95%, 97%, or 100% sequence identity to a region comprising at least 8 contiguous nucleic acids of SEQ ID NO: 2 or 3.

Embodiment A49. A pharmaceutical composition comprising the antisense oligomer of embodiment A47 or A48 and an excipient.

Embodiment A50. A method of treating a subject in need thereof, comprising administering the pharmaceutical composition of embodiment A49 to the subject, wherein the administering is by intravitreal injection, intrathecal injection, intracerebroventricular injection, intraperitoneal injection, intramuscular injection, subcutaneous injection, or intravenous injection.

Embodiment A51. A composition comprising a therapeutic agent for use in a method of increasing expression of a target protein or a functional RNA by cells to treat Optic atrophy type 1 in a subject in need thereof, associated with a deficient protein or deficient functional RNA, wherein the deficient protein or deficient functional RNA is deficient in amount or activity in the subject, wherein the target protein is:

(a) the deficient protein; or (b) a compensating protein which functionally augments or replaces the deficient protein or in the subject;

and wherein the functional RNA is:

(c) the deficient RNA; or (d) a compensating functional RNA which functionally augments or replaces the deficient functional RNA in the subject;

wherein the therapeutic agent enhances exclusion of the non-sense mediated RNA decay-inducing exon from the NMD exon mRNA encoding the target protein or functional RNA, thereby increasing production or activity of the target protein or the functional RNA in the subject.

Embodiment A52. A composition comprising a therapeutic agent for use in a method of treating a condition associated with OPA1 protein in a subject in need thereof, the method comprising the step of increasing expression of OPA1 protein by cells of the subject, wherein the cells have an mRNA that contains a non-sense mediated RNA decay-inducing exon (NMD exon mRNA) and encodes OPA1 protein, the method comprising contacting the cells with the therapeutic agent, whereby the non-sense mediated RNA decay-inducing exon is excluded from the NMD exon mRNA that encodes OPA1 protein, thereby increasing the level of mRNA encoding OPA1 protein, and increasing the expression of OPA1 protein in the cells of the subject.

Embodiment A53. The composition of embodiment A52, wherein the condition is a disease or disorder.

Embodiment AM. The composition of embodiment A53, wherein the disease or disorder is Optic atrophy type 1.

Embodiment A55. The composition of any one of embodiments A52 to 54, wherein the OPA1 protein and NMD exon mRNA are encoded by the OPA1 gene.

Embodiment A56. The composition of any one of embodiments A51 to A55, wherein the non-sense mediated RNA decay-inducing exon is spliced out from the NMD exon mRNA encoding the OPA1 protein.

Embodiment A57. The composition of any one of embodiments A51 to A56, wherein the OPA1 protein does not comprise an amino acid sequence encoded by the non-sense mediated RNA decay-inducing exon.

Embodiment A58. The composition of any one of embodiments A51 to A57, wherein the OPA1 protein is a full-length OPA1 protein.

Embodiment A59. The composition of any one of embodiments A51 to A58, wherein the therapeutic agent is an antisense oligomer (ASO) complementary to the targeted portion of the NMD exon mRNA.

Embodiment A60. The composition of any of embodiments A51 to A59, wherein the therapeutic agent is an antisense oligomer (ASO) and wherein the antisense oligomer targets a portion of the NMD exon mRNA that is within the non-sense mediated RNA decay-inducing exon.

Embodiment A61. The composition of any of embodiments A51 to A59, wherein the therapeutic agent is an antisense oligomer (ASO) and wherein the antisense oligomer targets a portion of the NMD exon mRNA that is upstream or downstream of the non-sense mediated RNA decay-inducing exon.

Embodiment A62. The composition of any one of embodiments A51 to A61, wherein the target protein is OPA1.

Embodiment A63. The composition of embodiment A62, wherein the NMD exon mRNA comprises a sequence with at least about 80%, 85%, 90%, 95%, 97%, or 100% sequence identity to SEQ ID NO: 2 or 3.

Embodiment A64. The composition of embodiment A62, wherein the NMD exon mRNA is encoded by a genetic sequence with at least about 80%, 85%, 90%, 95%, 97%, or 100% sequence identity to SEQ ID NO: 1.

Embodiment A65. The composition of embodiment A62, wherein the targeted portion of the NMD exon mRNA comprises a sequence with at least 80%, 85%, 90%, 95%, 97%, or 100% sequence identity to a region comprising at least 8 contiguous nucleic acids of SEQ ID NO: 2 or 3.

Embodiment A66. The composition of any one of embodiments A62 to A65, wherein the targeted portion of the NMD exon mRNA is within the non-sense mediated RNA decay-inducing exon 6x of OPA1, exon 7x of OPA1, or exon 28x of OPA1.

Embodiment A67. The composition of any one of embodiments A62 to A65, wherein the targeted portion of the NMD exon mRNA is upstream or downstream of the non-sense mediated RNA decay-inducing exon 6x of OPA1, exon 7x of OPA1, or exon 28x of OPA1.

Embodiment A68. The composition of any one of embodiments A62 to A65, wherein the targeted portion of the NMD exon mRNA comprises an exon-intron junction of exon 6x of OPA1, exon 7x of OPA1, or exon 28x of OPA1.

Embodiment A69. The composition of any one of embodiments A62 to A68, wherein the therapeutic agent is an antisense oligomer (ASO) and wherein the ASO comprises a sequence that is at least about 80%, 85%, 90%, 95%, 97%, or 100% complementary to a region comprising at least 8 contiguous nucleic acids of SEQ ID NO: 2 or 3.

Embodiment A70. The composition of any one of embodiments A51 to A69, wherein the mRNA encoding the target protein or functional RNA is a full-length mature mRNA, or a wild-type mature mRNA.

Embodiment A71. The composition of any one of embodiments A51 to A70, wherein the target protein produced is full-length protein, or wild-type protein.

Embodiment A72. The composition of any one of embodiments A51 to A71, wherein the therapeutic agent is an antisense oligomer (ASO) and wherein the antisense oligomer comprises a backbone modification comprising a phosphorothioate linkage or a phosphorodiamidate linkage.

Embodiment A73. The composition of any of embodiments A51 to A72, wherein the therapeutic agent is an antisense oligomer (ASO) and wherein said antisense oligomer is an antisense oligonucleotide.

Embodiment A74. The composition of any of embodiments A51 to A73, wherein the therapeutic agent is an antisense oligomer (ASO) and wherein the antisense oligomer comprises a phosphorodiamidate morpholino, a locked nucleic acid, a peptide nucleic acid, a 2'-O-methyl, a 2'-Fluoro, or a 2'-O-methoxyethyl moiety.

Embodiment A75. The composition of any of embodiments A51 to A74, wherein the therapeutic agent is an antisense oligomer (ASO) and wherein the antisense oligomer comprises at least one modified sugar moiety.

Embodiment A76. The composition of embodiment A75, wherein each sugar moiety is a modified sugar moiety.

Embodiment A77. The composition of any of embodiments A51 to A76, wherein the therapeutic agent is an antisense oligomer (ASO) and wherein the antisense oligomer consists of from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases.

Embodiment A78. A pharmaceutical composition comprising the therapeutic agent of any of the compositions of embodiments A51 to A77, and an excipient.

Embodiment A79. A method of treating a subject in need thereof, comprising administering the pharmaceutical composition of embodiment A78 to the subject, wherein the administering is by intravitreal injection, intrathecal injection, intracerebroventricular injection, intraperitoneal injection, intramuscular injection, subcutaneous injection, or intravenous injection.

Embodiment A80. The method of any of embodiments A51 to A79, wherein the method further comprises administering a second therapeutic agent to the subject.

Embodiment A81. The method of embodiment A80, wherein the second therapeutic agent is a small molecule.

Embodiment A82. The method of embodiment A80, wherein the second therapeutic agent is an ASO.

Embodiment A83. The method of any one of embodiments A80 to A82, wherein the second therapeutic agent corrects intron retention.

Embodiment A84. A pharmaceutical composition comprising: an antisense oligomer that hybridizes to a target sequence of an OPA1 mRNA transcript, wherein the OPA1 mRNA transcript comprises a non-sense mediated RNA decay-inducing exon, wherein the antisense oligomer induces exclusion of the non-sense mediated RNA decay-inducing exon from the OPA1 mRNA transcript; and a pharmaceutical acceptable excipient.

Embodiment A85. The pharmaceutical composition of embodiment A84, wherein the OPA1 mRNA transcript is an OPA1 NMD exon mRNA transcript.

Embodiment A86. The pharmaceutical composition of embodiment A84 or A85, wherein the targeted portion of the NMD exon mRNA is within the non-sense mediated RNA decay-inducing exon 6x of OPA1, exon 7x of OPA1, or exon 28x of OPA1.

Embodiment A87. The pharmaceutical composition of embodiment A84 or A85, wherein the targeted portion of the NMD exon mRNA is upstream or downstream of the non-sense mediated RNA decay-inducing exon 6x of OPA1, exon 7x of OPA1, or exon 28x of OPA1.

Embodiment A88. The pharmaceutical composition of embodiment A84 or A85, wherein the targeted portion of the NMD exon mRNA comprises an exon-intron junction exon 6x of OPA1, exon 7x of OPA1, or exon 28x of OPA1.

Embodiment A89. The pharmaceutical composition of any one of embodiments A84 to A88, wherein the OPA1 NMD exon mRNA transcript is encoded by a genetic sequence with at least about 80%, 85%, 90%, 95%, 96%, 97%, 98%, 99% or 100% sequence identity to SEQ ID NO: 1.

Embodiment A90. The pharmaceutical composition of embodiment A84 or A88, wherein the OPA1 NMD exon mRNA transcript comprises a sequence with at least about 80%, 85%, 90%, 95%, 96%, 97%, 98%, 99% or 100% sequence identity to SEQ ID NO: 2 or 3.

Embodiment A91. The pharmaceutical composition of embodiment A84, wherein the antisense oligomer comprises a backbone modification comprising a phosphorothioate linkage or a phosphorodiamidate linkage.

Embodiment A92. The pharmaceutical composition of embodiment A84, wherein the antisense oligomer is an antisense oligonucleotide.

Embodiment A93. The pharmaceutical composition of embodiment A84, wherein the antisense oligomer comprises a phosphorodiamidate morpholino, a locked nucleic acid, a peptide nucleic acid, a 2'-O-methyl, a 2'-Fluoro, or a 2'-O-methoxyethyl moiety.

Embodiment A94. The pharmaceutical composition of embodiment A84, wherein the antisense oligomer comprises at least one modified sugar moiety.

Embodiment A95. The pharmaceutical composition of embodiment A84, wherein the antisense oligomer comprises from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases.

Embodiment A96. The pharmaceutical composition of embodiment A84 or A85, wherein the antisense oligomer is at least 80%, at least 85%, at least 90%, at least 95%, at least 98%, at least 99%, or is 100% complementary to a targeted portion of the OPA1 NMD exon mRNA transcript.

Embodiment A97. The pharmaceutical composition of embodiment A84 or A85, wherein the targeted portion of the OPA1 NMD exon mRNA transcript is within SEQ ID NO: 2 or 3.

Embodiment A98. The pharmaceutical composition of embodiment A84, wherein the antisense oligomer comprises a nucleotide sequence that is at least about 80%, 85%, 90%, 91%, 92%, 93%, 94%, 95%, 96%, 97%, 98%, or 99% sequence identity to a region comprising at least 8 contiguous nucleic acids of SEQ ID NO: 2 or 3.

Embodiment A99. The pharmaceutical composition of embodiment A84, wherein the antisense oligomer comprises a nucleotide sequence that is identical a region comprising at least 8 contiguous nucleic acids SEQ ID NO: 2 or 3.

Embodiment A100. The pharmaceutical composition of any one of the embodiments A84 to A99, wherein the pharmaceutical composition is formulated for intravitreal injection, intrathecal injection, intracerebroventricular injection, intraperitoneal injection, intramuscular injection, subcutaneous injection, or intravenous injection.

Embodiment A101. The method of any of embodiments A84 to A100, wherein the method further comprises administering a second therapeutic agent to the subject.

Embodiment A102. The method of embodiment A101, wherein the second therapeutic agent is a small molecule.

Embodiment A103. The method of embodiment A101, wherein the second therapeutic agent is an ASO.

Embodiment A104. The method of any one of embodiments A101 to A103, wherein the second therapeutic agent corrects intron retention.

Embodiment A105. A method of inducing processing of a deficient OPA1 mRNA transcript to facilitate removal of a non-sense mediated RNA decay-inducing exon to produce a fully processed OPA1 mRNA transcript that encodes a functional form of an OPA1 protein, the method comprising:

(a) contacting an antisense oligomer to a target cell of a subject;
(b) hybridizing the antisense oligomer to the deficient OPA1 mRNA transcript,
wherein the deficient OPA1 mRNA transcript is capable of encoding the functional form of an OPA1 protein and comprises at least one non-sense mediated RNA decay-inducing exon;
(c) removing the at least one non-sense mediated RNA decay-inducing exon from the deficient OPA1 mRNA transcript to produce the fully processed OPA1 mRNA transcript that encodes the functional form of OPA1 protein; and
(d) translating the functional form of OPA1 protein from the fully processed OPA1 mRNA transcript.

Embodiment A106. A method of treating a subject having a condition caused by a deficient amount or activity of OPA1 protein comprising administering to the subject an antisense oligomer comprising a nucleotide sequence with at least about 80%, 85%, 90%, 91%, 92%, 93%, 94%, 95%, 96%, 97%, 98%, or 99% sequence identity to a region comprising at least 8 contiguous nucleic acids of SEQ ID NO: 2 or 3.

Embodiment A107. A method of treating Optic atrophy type 1 in a subject in need thereof, by increasing the expression of a target protein or functional RNA by a cell of the subject, wherein the cell has an mRNA that contains a non-sense mediated RNA decay-inducing exon (NMD exon mRNA), and wherein the NMD exon mRNA encodes the target protein or functional RNA, the method comprising contacting the cell of the subject with a therapeutic agent that modulates splicing of the NMD exon mRNA encoding the target protein or functional RNA, whereby the non-sense mediated RNA decay-inducing exon is excluded from the NMD exon mRNA encoding the target protein or functional RNA, thereby increasing the level of mRNA encoding the target protein or functional RNA, and increasing the expression of the target protein or functional RNA in the cell of the subject.

Embodiment A108. A method of increasing expression of OPA1 protein by a cell having an mRNA that contains a non-sense mediated RNA decay-inducing exon (NMD exon mRNA) and encodes OPA1 protein, the method comprising contacting the cell with an agent that modulates splicing of the NMD exon mRNA encoding OPA1 protein, whereby the non-sense mediated RNA decay-inducing exon is excluded from the NMD exon mRNA encoding OPA1 protein, thereby increasing the level of mRNA encoding OPA1 protein, and increasing the expression of OPA1 protein in the cell.

Embodiment A109. The method of embodiment A107 or A108, wherein the agent (a) binds to a targeted portion of the NMD exon mRNA encoding the target protein or functional RNA;
(b) binds to one or more components of a spliceosome; or
(c) a combination of (a) and (b).

Embodiment B1. A method of modulating expression of a target protein, by a cell having an mRNA that comprises a non-sense mediated RNA decay-inducing exon (NMD exon) and encodes the target protein, the method comprising contacting a therapeutic agent to the cell, whereby the therapeutic agent modulates splicing of the NMD exon from the mRNA, thereby modulating level of processed mRNA encoding the target protein, and modulating the expression of the target protein in the cell, wherein the target protein is selected from the group consisting of: OPA1 proteins.

Embodiment B2. A method of treating a disease or condition in a subject in need thereof by modulating expression of a target protein in a cell of the subject, comprising: contacting the cell of the subject with a therapeutic agent that modulates splicing of a non-sense mediated mRNA decay-inducing exon (NMD exon) from an mRNA in the cell, wherein the mRNA comprises the NMD exon and encodes the target protein, thereby modulating level of processed mRNA encoding the target protein, and modulating expression of the target protein in the cell of the subject, wherein the target protein is selected from the group consisting of: OPA1 proteins.

Embodiment B3. The method of embodiment B1 or B2, wherein the therapeutic agent (a) binds to a targeted portion of the mRNA encoding the target protein;
(b) modulates binding of a factor involved in splicing of the NMD exon; or
(c) a combination of (a) and (b).

Embodiment B4. The method of embodiment B3, wherein the therapeutic agent interferes with binding of the factor involved in splicing of the NMD exon to a region of the targeted portion.

Embodiment B5. The method of embodiment B3 or B4, wherein the targeted portion is proximal to the NMD exon.

Embodiment B6. The method of any one of embodiments B3 to B5, wherein the targeted portion is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of 5' end of the NMD exon.

Embodiment B7. The method of any one of embodiments B3 to B6, wherein the targeted portion is at least about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides upstream of 5' end of the NMD exon.

Embodiment B8. The method of any one of embodiments B3 to B5, wherein the targeted portion is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of 3' end of the NMD exon.

Embodiment B9. The method of any one of embodiments B3 to B5 or B8, wherein the targeted portion is at least about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides downstream of 3' end of the NMD exon.

Embodiment B10. The method of any one of embodiments B3 to B5, wherein the targeted portion is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of genomic site selected from the group consisting of: GRCh38/hg38: chr3 193628509; and GRCh38/hg38: chr3 193603500.

Embodiment B11. The method of any one of embodiments B3 to B5 or B10, wherein the targeted portion is about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of genomic site selected from the group consisting of: GRCh38/hg38: chr3 193628509; and GRCh38/hg38: chr3 193603500.

Embodiment B12. The method of any one of embodiments B3 to B5, wherein the targeted portion is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of genomic site selected from the group consisting of: GRCh38/hg38: chr3 193628616; and GRCh38/hg38: chr3 193603557.

Embodiment B13. The method of any one of embodiments B3 to B5 or B12, wherein the targeted portion is about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of genomic site selected from the group consisting of: GRCh38/hg38: chr3 193628616; and GRCh38/hg38: chr3 193603557.

Embodiment B14. The method of any one of embodiments B3 to B13, wherein the targeted portion is located in an intronic region between two canonical exonic regions of the mRNA encoding the target protein, and wherein the intronic region contains the NMD exon.

Embodiment B15. The method of any one of embodiments B3 to B14, wherein the targeted portion at least partially overlaps with the NMD exon.

Embodiment B16. The method of any one of embodiments B3 to B15, wherein the targeted portion at least partially overlaps with an intron upstream or downstream of the NMD exon.

Embodiment B17. The method of any one of embodiments B3 to B16, wherein the targeted portion comprises 5' NMD exon-intron junction or 3' NMD exon-intron junction.

Embodiment B18. The method of any one of embodiments B3 to B16, wherein the targeted portion is within the NMD exon.

Embodiment B19. The method of any one of embodiments B1 to B18, wherein the targeted portion comprises about 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

Embodiment B20. The method of any one of embodiments B1 to B19, wherein the mRNA encoding the target protein comprises a sequence with at least about 80%, 85%, 90%, 95%, 97%, or 100% sequence identity to SEQ ID NO: 4 or 5.

Embodiment B21. The method of any one of embodiments B1 to B20, wherein the mRNA encoding the target protein is encoded by a genetic sequence with at least about 80%, 85%, 90%, 95%, 97%, or 100% sequence identity to SEQ ID NO: 1.

Embodiment B22. The method of any one of embodiments B3 to B21, wherein the targeted portion of the mRNA comprises a sequence with at least 80%, 85%, 90%, 95%, 97%, or 100% sequence identity to a region comprising at least 8 contiguous nucleic acids of SEQ ID NO: 4 or 5.

Embodiment B23. The method of any one of embodiments B1 to B22, wherein the agent is an antisense oligomer (ASO) and wherein the ASO comprises a sequence that is at least about 80%, 85%, 90%, 95%, 97%, or 100% complementary to at least 8 contiguous nucleic acids of SEQ ID Ns: 4 or 5.

Embodiment B24. The method of any one of embodiments B3 to B23, wherein the targeted portion of the mRNA is within the non-sense mediated RNA decay-inducing exon selected from the group consisting of: GRCh38/hg38: chr3 193628509 193628616; and GRCh38/hg38: chr3 193603500 193603557;

Embodiment B25. The method of any one of embodiments B3 to B23, wherein the targeted portion of the mRNA is upstream or downstream of the non-sense mediated RNA decay-inducing exon selected from the group consisting of: GRCh38/hg38: chr3 193628509 193628616; and GRCh38/hg38: chr3 193603500 193603557.

Embodiment B26. The method of any one of embodiments B3 to B23, wherein the targeted portion of the mRNA comprises an exon-intron junction of exon selected from the group consisting of: GRCh38/hg38: chr3 193628509 193628616; and GRCh38/hg38: chr3 193603500 193603557.

Embodiment B27. The method of any one of embodiments B1 to B26, wherein the target protein produced is a full-length protein or a wild-type protein.

Embodiment B28. The method of any one of embodiments B1 to B27, wherein the therapeutic agent promotes exclusion of the NMD exon from the pre-mRNA encoding the target protein.

Embodiment B29. The method of embodiment B28, wherein exclusion of the NMD exon from the pre-mRNA encoding the target protein in the cell contacted with the therapeutic agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to exclusion of the NMD exon from the pre-mRNA encoding the target protein in a control cell.

Embodiment B30. The method of embodiment B28 or B29, wherein the therapeutic agent increases the level of the processed mRNA encoding the target protein in the cell.

Embodiment B31. The method of any one of embodiments B28 to B30, wherein the level of the processed mRNA encoding the target protein produced in the cell contacted with the therapeutic agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to a level of the processed mRNA encoding the target protein in a control cell.

Embodiment B32. The method of any one of embodiments B28 to B31, wherein the therapeutic agent increases the expression of the target protein in the cell.

Embodiment B33. The method of any one of embodiments B28 to B32, wherein a level of the target protein produced in the cell contacted with the therapeutic agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to a level of the target protein produced in a control cell.

Embodiment B34. The method of any one of embodiments B2 to B33, wherein the disease or condition is induced by a loss-of-function mutation in the target protein.

Embodiment B35. The method of embodiment B34, wherein the disease or condition is associated with haploinsufficiency of a gene encoding the target protein, and wherein the subject has a first allele encoding a functional target protein, and a second allele from which the target protein is not produced or produced at a reduced level, or a second allele encoding a nonfunctional target protein or a partially functional target protein.

Embodiment B36. The method of any one of embodiments B2 to B35, wherein the disease or condition is selected from the group consisting of: Optic atrophy type 1.

Embodiment B37. The method of any one of embodiments B34 to B36, wherein the therapeutic agent promotes exclusion of the NMD exon from the pre-mRNA encoding the target protein and increases the expression of the target protein in the cell.

Embodiment B38. The method of any one of embodiments B1 to B27, wherein the therapeutic agent inhibits exclusion of the NMD exon from the pre-mRNA encoding the target protein.

Embodiment B39. The method of embodiment B38, wherein exclusion of the NMD exon from the pre-mRNA encoding the target protein in the cell contacted with the therapeutic agent is decreased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to exclusion of the NMD exon from the pre-mRNA encoding the target protein in a control cell.

Embodiment B40. The method of embodiment B38 or B39, wherein the therapeutic agent decreases the level of the processed mRNA encoding the target protein in the cell.

Embodiment B41. The method of any one of embodiments B38 to B40, wherein the level of the processed mRNA encoding the target protein in the cell contacted with the therapeutic agent is decreased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to a level of the processed mRNA encoding the target protein in a control cell.

Embodiment B42. The method of any one of embodiments B38 to B41, wherein the therapeutic agent decreases the expression of the target protein in the cell.

Embodiment B43. The method of any one of embodiments B38 to B42, wherein a level of the target protein produced in the cell contacted with the therapeutic agent is decreased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to a level of the target protein produced in a control cell.

Embodiment B44. The method of any one of embodiments B2 to B27 or B38 to B43, wherein the disease or condition is induced by a gain-of-function mutation in the target protein Embodiment B45. The method of embodiment B44, wherein the subject has an allele from which the target protein is produced at an increased level, or an allele encoding a mutant target protein that exhibits increased activity in the cell.

Embodiment B46. The method of embodiment B44 or B45, wherein the therapeutic agent inhibits exclusion of the NMD exon from the pre-mRNA encoding the target protein and decreases the expression of the target protein in the cell.

Embodiment B47. The method of any one of embodiments B1 to B46, wherein the therapeutic agent is an antisense oligomer (ASO) and wherein the antisense oligomer comprises a backbone modification comprising a phosphorothioate linkage or a phosphorodiamidate linkage.

Embodiment B48. The method of any one of embodiments B1 to B47, wherein the therapeutic agent is an antisense oligomer (ASO) and wherein the antisense oligomer comprises a phosphorodiamidate morpholino, a locked nucleic acid, a peptide nucleic acid, a 2'-O-methyl, a 2'-Fluoro, or a 2'-O-methoxyethyl moiety.

Embodiment B49. The method of any one of embodiments B1 to B48, wherein the therapeutic agent is an antisense oligomer (ASO) and wherein the antisense oligomer comprises at least one modified sugar moiety.

Embodiment B50. The method of embodiment B49, wherein each sugar moiety is a modified sugar moiety.

Embodiment B51. The method of any one of embodiments B1 to B50, wherein the therapeutic agent is an antisense oligomer (ASO) and wherein the antisense oligomer consists of from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases.

Embodiment B52. The method of any one of embodiments B3 to B51, wherein the therapeutic agent is an antisense oligomer (ASO) and wherein the antisense oligomer is at least 80%, at least 85%, at least 90%, at least 95%, at least 98%, at least 99%, or 100%, complementary to the targeted portion of the mRNA.

Embodiment B53. The method of any one of embodiments B1 to B52, wherein the method further comprises assessing mRNA level or expression level of the target protein.

Embodiment B54. The method of any one of embodiments B1 to B53, wherein the subject is a human.

Embodiment B55. The method of any one of embodiments B1 to B53, wherein the subject is a non-human animal.

Embodiment B56. The method of any one of embodiments B2 to B54, wherein the subject is a fetus, an embryo, or a child.

Embodiment B57. The method of any one of embodiments B1 to B56, wherein the cells are ex vivo.

Embodiment B58. The method of any one of embodiments B2 to B56, wherein the therapeutic agent is administered by intravitreal injection, intrathecal injection, intracerebroventricular injection, intraperitoneal injection, intramuscular injection, subcutaneous injection, intravitreal, or intravenous injection of the subject.

Embodiment B59. The method of any one of embodiments B2 to B56 or B58, wherein the method further comprises administering a second therapeutic agent to the subject.

Embodiment B60. The method of any one of embodiments B1 to B59, wherein the second therapeutic agent is a small molecule.

Embodiment B61. The method of any one of embodiments B1 to B59, wherein the second therapeutic agent is an antisense oligomer.

Embodiment B62. The method of any one of embodiments B1 to B61, wherein the second therapeutic agent corrects intron retention.

Embodiment B63. The method of any one of embodiments B2 to B62, wherein the disease or condition is Optic atrophy type 1.

FURTHER SPECIFIC EMBODIMENTS

Embodiment 1. A method of modulating expression of an OPA1 protein in a cell having a pre-mRNA that is transcribed from an OPA1 gene and that comprises a non-sense mediated RNA decay-inducing exon (NMD exon), the method comprising contacting an agent or a vector encoding the agent to the cell, whereby the agent modulates splicing of the NMD exon from the pre-mRNA, thereby modulating a level of processed mRNA that is processed from the pre-mRNA, and modulating the expression of the OPA1 protein in the cell, wherein the agent comprises an antisense oligomer with at least 80% sequence identity to a sequence selected from the group consisting of SEQ ID NOs: 6-275 and 280-299.

Embodiment 2. The method of embodiment 1, wherein the agent:

(a) binds to a targeted portion of the pre-mRNA;

(b) modulates binding of a factor involved in splicing of the NMD exon; or (c) a combination of (a) and (b).

Embodiment 3. The method of embodiment 2, wherein the agent interferes with binding of the factor involved in splicing of the NMD exon to a region of the targeted portion Embodiment 4. The method of embodiment 2, wherein the targeted portion of the pre-mRNA is proximal to the NMD exon.

Embodiment 5. The method of embodiment 2, wherein the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of 5' end of the NMD exon.

Embodiment 6. The method of embodiment 2, wherein the targeted portion of the pre-mRNA is at least about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides upstream of 5' end of the NMD exon.

Embodiment 7. The method of embodiment 2, wherein the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of 3' end of the NMD exon.

Embodiment 8. The method of embodiment 2, wherein the targeted portion of the pre-mRNA is at least about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides downstream of 3' end of the NMD exon.

Embodiment 9. The method of embodiment 2, wherein the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of genomic site GRCh38/hg38: chr3 193628509.

Embodiment 10. The method of embodiment 2, wherein the targeted portion of the pre-mRNA is about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of genomic site GRCh38/hg38: chr3 193628509.

Embodiment 11. The method of embodiment 2, wherein the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of genomic site GRCh38/hg38: chr3 193628616.

Embodiment 12. The method of embodiment 2, wherein the targeted portion of the pre-mRNA is about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of genomic site GRCh38/hg38: chr3 193628616.

Embodiment 13. The method of embodiment 2, wherein the targeted portion of the pre-mRNA is located in an intronic region between two canonical exonic regions of the pre-mRNA, and wherein the intronic region contains the NMD exon.

Embodiment 14. The method of embodiment 2, wherein the targeted portion of the pre-mRNA at least partially overlaps with the NMD exon.

Embodiment 15. The method of embodiment 2, wherein the targeted portion of the pre-mRNA at least partially overlaps with an intron upstream or downstream of the NMD exon.

Embodiment 16. The method of embodiment 2, wherein the targeted portion of the pre-mRNA comprises 5' NMD exon-intron junction or 3' NMD exon-intron junction.

Embodiment 17. The method of embodiment 2, wherein the targeted portion of the pre-mRNA is within the NMD exon.

Embodiment 18. The method of embodiment 2, wherein the targeted portion of the pre-mRNA comprises about 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

Embodiment 19. The method of any one of embodiments 1 to 18, wherein the NMD exon comprises a sequence with at least 80%, at least 90%, or 100% sequence identity to SEQ ID NO: 279.

Embodiment 20. The method of any one of embodiments 1 to 18, wherein the NMD exon comprises a sequence of SEQ ID NO: 279.

Embodiment 21. The method of embodiment 2, wherein the targeted portion of the pre-mRNA is within the non-sense mediated RNA decay-inducing exon GRCh38/hg38: chr3 193628509 to 193628616.

Embodiment 22. The method of embodiment 2, wherein the targeted portion of the pre-mRNA is upstream or downstream of the non-sense mediated RNA decay-inducing exon GRCh38/hg38: chr3 193628509 to 193628616.

Embodiment 23. The method of embodiment 2, wherein the targeted portion of the pre-mRNA comprises an exon-intron junction of exon GRCh38/hg38: chr3 193628509 to 193628616.

Embodiment 24. The method of any one of embodiments 1 to 23, wherein the OPA1 protein expressed from the processed mRNA is a full-length OPA1 protein or a wild-type OPA1 protein.

Embodiment 25. The method of any one of embodiments 1 to 23, wherein the OPA1 protein expressed from the processed mRNA is a functional OPA1 protein.

Embodiment 26. The method of any one of embodiments 1 to 23, wherein the OPA1 protein expressed from the processed mRNA is at least partially functional as compared to a wild-type OPA1 protein.

Embodiment 27. The method of any one of embodiments 1 to 23, wherein the OPA1 protein expressed from the processed mRNA is at least partially functional as compared to a full-length wild-type OPA1 protein.

Embodiment 28. The method of any one of embodiments 1 to 23, or 25 to 27, wherein the OPA1 protein expressed from the processed mRNA is an OPA1 protein that lacks an amino acid sequence encoded by a nucleic acid sequence with at least 80% sequence identity to SEQ ID NO: 277.

Embodiment 29. The method of any one of embodiments 1 to 28, wherein the method promotes exclusion of the NMD exon from the pre-mRNA.

Embodiment 30. The method of embodiment 29, wherein the exclusion of the NMD exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 31. The method of any one of embodiments 1 to 30, wherein the method results in an increase in the level of the processed mRNA in the cell.

Embodiment 32. The method of embodiment 31, wherein the level of the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 33. The method of any one of embodiments 1 to 32, wherein the method results in an increase in the expression of the OPA1 protein in the cell.

Embodiment 34. The method of embodiment 33, wherein a level of the OPA1 protein expressed from the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 35. The method of any one of embodiments 1 to 34, wherein the agent comprises an antisense oligomer with at least 80%, at least 90%, or 100% sequence identity to a sequence selected from the group consisting of SEQ ID NOs: 36, 236, 242, 250, 280-283, 288, and 290-292.

Embodiment 36. The method of any one of embodiments 1 to 34, wherein the agent further comprises a gene editing molecule.

Embodiment 37. The method of embodiment 36, wherein the gene editing molecule comprises CRISPR-Cas9.

Embodiment 38. A method of modulating expression of an OPA1 protein in a cell having a pre-mRNA that is transcribed from an OPA1 gene, wherein the pre-mRNA comprises a coding exon, the method comprising contacting an agent or a vector encoding the agent to the cell, whereby the agent promotes exclusion of the coding exon from the pre-mRNA, thereby increasing a level of a processed mRNA that is processed from the pre-mRNA and that lacks the coding exon in the cell.

Embodiment 39. The method of embodiment 38, wherein the agent:

(a) binds to a targeted portion of the pre-mRNA;
(b) modulates binding of a factor involved in splicing of the coding exon; or
(c) a combination of (a) and (b).

Embodiment 40. The method of embodiment 39, wherein the agent interferes with binding of the factor involved in splicing of the coding exon to a region of the targeted portion.

Embodiment 41. The method of embodiment 39, wherein the targeted portion of the pre-mRNA is proximal to the coding exon.

Embodiment 42. The method of embodiment 39, wherein the targeted portion of the pre-mRNA is located in an intronic region immediately upstream of the coding exon.

Embodiment 43. The method of embodiment 39, wherein the targeted portion of the pre-mRNA is within a region spanning from 100 to 50, from 90 to 50, from 80 to 50, from 70 to 50, from 60 to 50, from 60 to 40, from 60 to 30, from 60 to 20, from 60 to 10, from 49 to 1, from 39 to 1, from 29 to 1, or from 19 to 1 nucleotides upstream of 5' end of the coding exon.

Embodiment 44. The method of embodiment 39, wherein the targeted portion of the pre-mRNA is within a region spanning from 49 to 1, from 39 to 1, from 29 to 1, or from 19 to 1 nucleotides upstream of 5' end of the coding exon.

Embodiment 45. The method of embodiment 39, wherein the targeted portion of the pre-mRNA is located in an intronic region immediately downstream of the coding exon.

Embodiment 46. The method of embodiment 39, wherein the targeted portion of the pre-mRNA is within a region spanning from 1 to 49, from 1 to 39, from 1 to 29, from 1 to 19, from 10 to 60, from 20 to 60, from 30 to 60, from 40 to 60, from 50 to 60, from 50 to 70, from 50 to 80, from 50 to 90, or from 50 to 100 nucleotides downstream of 3' end of the coding exon.

Embodiment 47. The method of embodiment 39, wherein the targeted portion of the pre-mRNA is within a region spanning from 1 to 49, from 1 to 39, from 1 to 29, or from 1 to 19 nucleotides downstream of 3' end of the coding exon.

Embodiment 48. The method of embodiment 39, wherein the targeted portion of the pre-mRNA at least partially overlaps with the coding exon.

Embodiment 49. The method of embodiment 39, wherein the targeted portion of the pre-mRNA at least partially overlaps with an intron immediately upstream or immediately downstream of the coding exon.

Embodiment 50. The method of embodiment 39, wherein the targeted portion of the pre-mRNA comprises 5' coding exon-intron junction or 3' coding exon-intron junction.

Embodiment 51. The method of embodiment 39, wherein the targeted portion is within the coding exon of the pre-mRNA.

Embodiment 52. The method of any one of embodiments 39 to 51, wherein the coding exon is an alternatively spliced exon.

Embodiment 53. The method of any one of embodiments 39 to 52, wherein the coding exon comprises a sequence with at least 80%, at least 90%, or 100% sequence identity to SEQ ID NO: 277.

Embodiment 54. The method of any one of embodiments 39 to 52, wherein the coding exon comprises SEQ ID NO: 277.

Embodiment 55. The method of embodiment 39, wherein the targeted portion of the pre-mRNA is immediately upstream of the coding exon GRCh38/hg38: chr3 193626092 to 193626202.

Embodiment 56. The method of embodiment 39, wherein the targeted portion of the pre-mRNA is within a region spanning from 49 to 1, from 39 to 1, from 29 to 1, or from 19 to 1 nucleotides upstream of genomic site GRCh38/hg38: chr3 193626092.

Embodiment 57. The method of embodiment 39, wherein the targeted portion of the pre-mRNA is immediately downstream of the coding exon GRCh38/hg38: chr3 193626092 to 193626202.

Embodiment 58. The method of embodiment 39, wherein the targeted portion of the pre-mRNA is within a region spanning from 1 to 49, from 1 to 39, from 1 to 29, or from 1 to 19 nucleotides downstream of genomic site GRCh38/hg38: chr3 193626202.

Embodiment 59. The method of embodiment 39, wherein the targeted portion of the pre-mRNA is within the coding exon GRCh38/hg38: chr3 193626092 to 193626202.

Embodiment 60. The method of embodiment 39, wherein the targeted portion of the pre-mRNA comprises an exon-intron junction of exon GRCh38/hg38: chr3 193626092 to 193626202.

Embodiment 61. The method of embodiment 39, wherein the targeted portion comprises about 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the coding exon.

Embodiment 62. The method of embodiment 39, wherein the targeted portion of the pre-mRNA comprises a sequence with at least 80%, 85%, 90%, 95%, 97%, or 100% sequence identity to a region comprising at least 8 contiguous nucleic acids of SEQ ID NO: 277.

Embodiment 63. The method of any one of embodiments 38 to 62, wherein the exclusion of the coding exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 64. The method of any one of embodiments 38 to 63, wherein the method results in an increase in expression of the OPA1 protein in the cell.

Embodiment 65. The method of embodiment 64, wherein a level of the OPA1 protein expressed from the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 66. The method of embodiment 64, wherein a level of the OPA1 protein expressed from the processed mRNA in the cell contacted with the agent is increased by at least about 1.5-fold compared to in the absence of the agent.

Embodiment 67. The method of any one of embodiments 64 to 66, wherein the OPA1 protein expressed from the processed mRNA is a functional OPA1 protein.

Embodiment 68. The method of any one of embodiments 64 to 66, wherein the OPA1 protein expressed from the processed mRNA is at least partially functional as compared to a wild-type OPA1 protein.

Embodiment 69. The method of any one of embodiments 64 to 66, wherein the OPA1 protein expressed from the processed mRNA is at least partially functional as compared to a full-length wild-type OPA1 protein.

Embodiment 70. The method of any one of embodiments 64 to 69, wherein the OPA1 protein expressed from the processed mRNA comprises fewer proteolytic cleavage sites than an OPA1 protein encoded by a corresponding mRNA containing the coding exon.

Embodiment 71. The method of any one of embodiments 38 to 70, wherein the agent promotes exclusion of a non-sense mediated RNA decay-inducing exon (NMD exon) from the pre-mRNA.

Embodiment 72. The method of embodiment 71, wherein the NMD exon comprises a sequence with at least 80%, at least 90%, or 100% sequence identity to SEQ ID NO: 279.

Embodiment 73. The method of embodiment 71, wherein the NMD exon comprises a sequence of SEQ ID NO: 279.

Embodiment 74. The method of any one of embodiments 64 to 73, wherein the OPA1 protein expressed from the processed mRNA comprises fewer proteolytic cleavage sites than an OPA1 protein encoded by a corresponding mRNA containing the coding exon.

Embodiment 75. The method of any one of embodiments 38 to 74, wherein the agent comprises an antisense oligomer with at least 80%, at least 90%, or 100% sequence identity to a sequence selected from the group consisting of SEQ ID NOs: 227-242, 250, 280-283, 288, and 290-292.

Embodiment 76. The method of any one of embodiments 38 to 74, wherein the agent comprises a gene editing molecule.

Embodiment 77. The method of embodiment 76, wherein the gene editing molecule comprises CRISPR-Cas9.

Embodiment 78. A method of modulating expression of an OPA1 protein in a cell having a pre-mRNA that is transcribed from an OPA1 gene, wherein the pre-mRNA comprises a coding exon, the method comprising contacting an agent or a vector encoding the agent to the cell, wherein the agent comprises an antisense oligomer that binds to:

(a) a targeted portion of the pre-mRNA within an intronic region immediately upstream of a 5' end of the coding exon of the pre-mRNA; or (b) a targeted portion of the pre-mRNA within an intronic region immediately downstream of a 3' end of the coding exon of the pre-mRNA;

whereby the agent increases a level of a processed mRNA that is processed from the pre-mRNA and that contains the coding exon in the cell.

Embodiment 79. The method of embodiments 78, wherein the coding exon is an alternatively spliced exon.

Embodiment 80. The method of embodiments 78 or 79, wherein the method promotes inclusion of the coding exon in the processed mRNA during splicing of the pre-mRNA in the cell.

Embodiment 81. The method of any one of embodiments 78 to 80, wherein the target portion of the pre-mRNA is within a region spanning from 100 to 50, from 100 to 60, from 100 to 70, from 100 to 80, or from 100 to 90 nucleotides upstream of a 5' end of the coding exon.

Embodiment 82. The method of any one of embodiments 78 to 80, wherein the target portion of the pre-mRNA is within a region spanning from 40 to 100, from 50 to 100, from 60 to 100, from 70 to 100, from 80 to 100, or from 90 to 100 nucleotides downstream of a 3' end of the coding exon.

Embodiment 83. The method of any one of embodiments 78 to 80, wherein the coding exon comprises a sequence with at least 80%, at least 90%, or 100% sequence identity to SEQ ID NO: 277.

Embodiment 84. The method of any one of embodiments 78 to 80, wherein the coding exon comprises SEQ ID NO: 277.

Embodiment 85. The method of any one of embodiments 78 to 80, wherein the targeted portion of the pre-mRNA is within a region spanning from 100 to 50, from 100 to 60, from 100 to 70, from 100 to 80, or from 100 to 90 nucleotides upstream of genomic site GRCh38/hg38: chr3 193626092.

Embodiment 86. The method of any one of embodiments 78 to 80, wherein the targeted portion of the pre-mRNA is within a region spanning from 40 to 100, from 50 to 100, from 60 to 100, from 70 to 100, from 80 to 100, or from 90 to 100 nucleotides downstream of genomic site GRCh38/hg38: chr3 193626202.

Embodiment 87. The method of any one of embodiments 78 to 86, wherein the inclusion of the coding exon in the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 88. The method of any one of embodiments 78 to 87, wherein the agent comprises an antisense oligomer with at least 80%, at least 90%, or 100% sequence identity to SEQ ID NO: 267.

Embodiment 89. A method of modulating expression of a target protein in a cell having a pre-mRNA transcribed from a gene that encodes the target protein, wherein the pre-mRNA comprises a coding exon and a non-sense mediated RNA decay-inducing exon (NMD exon), the method comprising contacting an agent or a vector encoding the agent to the cell, wherein the agent promotes exclusion of both the coding exon and the NMD exon from the pre-mRNA, thereby increasing a level of a processed mRNA that is processed from the pre-mRNA and that lacks both the NMD exon and the coding exon in the cell.

Embodiment 90. The method of embodiment 89, wherein the agent:

(a) binds to a targeted portion of the pre-mRNA;

(b) modulates binding of a factor involved in splicing of the coding exon, the NMD exon, or both; or (c) a combination of (a) and (b).

Embodiment 91. The method of embodiment 90, wherein the agent interferes with binding of the factor involved in splicing of the coding exon, the NMD exon, or both, to a region of the targeted portion.

Embodiment 92. The method of any one of embodiments 89 to 91, wherein the NMD exon is within an intronic region adjacent to the coding exon.

Embodiment 93. The method of embodiment 92, wherein the NMD exon is within an intronic region immediately upstream of the coding exon.

Embodiment 94. The method of embodiment 92, wherein the NMD exon is within an intronic region immediately downstream of the coding exon.

Embodiment 95. The method of any one of embodiments 90 to 94, wherein the targeted portion of the pre-mRNA is proximal to the coding exon.

Embodiment 96. The method of any one of embodiments 90 to 94, wherein the targeted portion of the pre-mRNA is located in an intronic region immediately upstream of the coding exon.

Embodiment 97. The method of any one of embodiments 90 to 94, wherein the targeted portion of the pre-mRNA is located in an intronic region immediately downstream of the coding exon.

Embodiment 98. The method of any one of embodiments 90 to 94, wherein the targeted portion of the pre-mRNA is located within the coding exon.

Embodiment 99. The method of any one of embodiments 90 to 94, wherein the targeted portion of the pre-mRNA is within a region spanning from 49 to 1, from 39 to 1, from 29 to 1, or from 19 to 1 nucleotides upstream of 5' end of the coding exon.

Embodiment 100. The method of any one of embodiments 90 to 94, wherein the targeted portion of the pre-mRNA is within a region spanning from 100 nucleotides upstream of the coding exon to 100 nucleotides downstream of the coding exon.

Embodiment 101. The method of any one of embodiments 89 to 100, wherein the coding exon is an alternatively spliced exon.

Embodiment 102. The method of any one of embodiments 89 to 101, wherein the coding exon comprises a sequence with at least 80%, at least 90%, or 100% sequence identity to SEQ ID NO: 277.

Embodiment 103. The method of any one of embodiments 89 to 101, wherein the coding exon comprises SEQ ID NO: 277.

Embodiment 104. The method of embodiment 90, wherein the targeted portion of the pre-mRNA is immediately upstream of the coding exon GRCh38/hg38: chr3 193626092 to 193626202.

Embodiment 105. The method of embodiment 90, wherein the targeted portion of the pre-mRNA is immediately downstream of the coding exon GRCh38/hg38: chr3 193626092 to 193626202.

Embodiment 106. The method of any one of embodiments 90 to 94, wherein the targeted portion of the pre-mRNA is within a region spanning from 49 to 1, from 39 to 1, from 29 to 1, or from 19 to 1 nucleotides upstream of GRCh38/hg38: chr3 193626092.

Embodiment 107. The method of embodiment 90, wherein the targeted portion of the pre-mRNA is within a region spanning from 100 nucleotides upstream of genomic site GRCh38/hg38: chr3 193626092. to 100 nucleotides downstream of genomic site GRCh38/hg38: chr3 193626202.

Embodiment 108. The method of embodiment 90, wherein the targeted portion of the pre-mRNA is within the coding exon GRCh38/hg38: chr3 193626092 to 193626202.

Embodiment 109. The method of embodiment 90, wherein the targeted portion of the pre-mRNA comprises an exon-intron junction of the coding exon GRCh38/hg38: chr3 193626092 to 193626202.

Embodiment 110. The method of embodiment 90, wherein the targeted portion comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the coding exon.

Embodiment 111. The method of embodiment 90, wherein the targeted portion of the pre-mRNA is proximal to the NMD exon.

Embodiment 112. The method of embodiment 90, wherein the targeted portion of the pre-mRNA is located in an intronic region immediately upstream of the NMD exon.

Embodiment 113. The method of embodiment 90, wherein the targeted portion of the pre-mRNA is located in an intronic region immediately downstream of the NMD exon.

Embodiment 114. The method of embodiment 90, wherein the targeted portion of the pre-mRNA is located within the NMD exon.

Embodiment 115. The method of embodiment 90, wherein the targeted portion of the pre-mRNA is within a region spanning from 100 nucleotides upstream of the NMD exon to 100 nucleotides downstream of the NMD exon.

Embodiment 116. The method of any one of embodiments 89 to 115, wherein the NMD exon comprises a sequence with at least 80%, at least 90%, or 100% sequence identity to SEQ ID NO: 279.

Embodiment 117. The method of embodiment 89, wherein the NMD exon comprises SEQ ID NO: 279.

Embodiment 118. The method of embodiment 90, wherein the targeted portion of the pre-mRNA is immediately upstream of the NMD exon GRCh38/hg38: chr3 193628509 to 193628616.

Embodiment 119. The method of embodiment 90, wherein the targeted portion of the pre-mRNA is immediately downstream of the NMD exon GRCh38/hg38: chr3 193628509 to 193628616.

Embodiment 120. The method of embodiment 90, wherein the targeted portion of the pre-mRNA is within a region spanning from 100 nucleotides upstream of genomic site GRCh38/hg38: chr3 193628509 to 100 nucleotides downstream of genomic site GRCh38/hg38: chr3 193628616.

Embodiment 121. The method of embodiment 90, wherein the targeted portion of the pre-mRNA is within the NMD exon GRCh38/hg38: chr3 193628509 to 193628616.

Embodiment 122. The method of embodiment 90, wherein the targeted portion of the pre-mRNA comprises an exon-intron junction of the NMD exon GRCh38/hg38: chr3 193628509 to 193628616.

Embodiment 123. The method of embodiment 90, wherein the targeted portion comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

Embodiment 124. The method of any one of embodiments 89 to 123, wherein the exclusion of the coding exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 125. The method of any one of embodiments 89 to 124, wherein the exclusion of the NMD exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 126. The method of any one of embodiments 89 to 125, wherein the agent results in an increase in the level of the processed mRNA in the cell.

Embodiment 127. The method of embodiment 126, wherein the level of the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 128. The method of any one of embodiments 89 to 127, wherein the method results in an increase in expression of the target protein in the cell.

Embodiment 129. The method of embodiment 128, wherein a level of the target protein expressed from the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 130. The method of any one of embodiments 89 to 128, wherein the target protein is an OPA1 protein.

Embodiment 131. The method of embodiment 130, wherein a level of the OPA1 protein expressed from the processed mRNA in the cell contacted with the agent is increased by at least about 1.5-fold compared to in the absence of the agent.

Embodiment 132. The method of embodiment 130, wherein the OPA1 protein expressed from the processed mRNA is a functional OPA1 protein.

Embodiment 133. The method of embodiment 130, wherein the OPA1 protein expressed from the processed mRNA is at least partially functional as compared to a wild-type OPA1 protein.

Embodiment 134. The method of embodiment 130, wherein the OPA1 protein expressed from the processed mRNA is at least partially functional as compared to a full-length wild-type OPA1 protein.

Embodiment 135. The method of any one of embodiments 89 to 127, wherein the agent comprises an antisense oligomer with at least 80%, at least 90%, or 100% sequence identity to a sequence selected from the group consisting of SEQ ID NOs: 236, 242, 250, 280-283, 288, and 290-292.

Embodiment 136. The method of any one of embodiments 78 to 135, wherein the agent comprises a gene editing molecule.

Embodiment 137. The method of embodiment 136, wherein the gene editing molecule comprises CRISPR-Cas9.

Embodiment 138. The method of any one of embodiments 1 to 75 or 78 to 135, wherein the agent is an antisense oligomer (ASO) and wherein the antisense oligomer comprises a backbone modification comprising a phosphorothioate linkage or a phosphorodiamidate linkage.

Embodiment 139. The method of any one of embodiments 1 to 75 or 78 to 138, wherein the agent is an antisense oligomer (ASO) and wherein the antisense oligomer comprises a phosphorodiamidate morpholino, a locked nucleic acid, a peptide nucleic acid, a 2'-O-methyl moiety, a 2'-Fluoro moiety, or a 2'-O-methoxyethyl moiety.

Embodiment 140. The method of any one of embodiments 1 to 75 or 78 to 139, wherein the therapeutic agent is an antisense oligomer (ASO) and wherein the antisense oligomer comprises at least one modified sugar moiety.

Embodiment 141. The method of embodiment 140, wherein each sugar moiety is a modified sugar moiety.

Embodiment 142. The method of any one of embodiments 1 to 75 or 78 to 141, wherein the agent is an antisense oligomer (ASO) and wherein the antisense oligomer consists of from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases.

Embodiment 143. The method of any one of embodiments 1 to 142, wherein the vector comprises a viral vector encoding the agent.

Embodiment 144. The method of embodiment 143, wherein the viral vector comprises an adenoviral vector, adeno-associated viral (AAV) vector, lentiviral vector, Herpes Simplex Virus (HSV) viral vector, or retroviral vector.

Embodiment 145. The method of any one of embodiments 1 to 144, wherein the method further comprises assessing mRNA level or expression level of the OPA1 protein.

Embodiment 146. The method of any one of embodiments 1 to 145, wherein the agent is a therapeutic agent.

Embodiment 147. A pharmaceutical composition comprising the therapeutic agent of embodiment 146 or a vector encoding the therapeutic agent of embodiment 146, and a pharmaceutically acceptable excipient.

Embodiment 148. A pharmaceutical composition, comprising a therapeutic agent or a vector encoding a therapeutic agent, and a pharmaceutically acceptable excipient, wherein the therapeutic agent comprises an antisense oligomer with at least 80% sequence identity to a sequence selected from the group consisting of SEQ ID NOs: 6-275 and 280-299.

Embodiment 149. The pharmaceutical composition of embodiment 148, wherein the therapeutic agent comprises an antisense oligomer with at least 80%, at least 90%, or 100% sequence identity to a sequence selected from the group consisting of SEQ ID NOs: 227-242 and 250.

Embodiment 150. The pharmaceutical composition of embodiment 148, wherein the therapeutic agent comprises an antisense oligomer with at least 80%, at least 90%, or 100% sequence identity to SEQ ID NO: 267.

Embodiment 151. The pharmaceutical composition of embodiment 148, wherein the therapeutic agent comprises an antisense oligomer with at least 80%, at least 90%, or 100% sequence identity to a sequence selected from the group consisting of SEQ ID NOs: 36, 236, 242, 250, and 280-299.

Embodiment 152. A composition, comprising an antisense oligomer with at least 80% sequence identity to a sequence selected from the group consisting of SEQ ID NOs: 6-275 and 280-299, wherein the antisense oligomer comprises a backbone modification, a sugar moiety modification, or a combination thereof.

Embodiment 153. The composition of embodiment 152, wherein the antisense oligomer has at least 80%, at least 90%, or 100% sequence identity to a sequence selected from the group consisting of SEQ ID NOs: 227-242 and 250.

Embodiment 154. The composition of embodiment 152, wherein the antisense oligomer has at least 80%, at least 90%, or 100% sequence identity to SEQ ID NO: 267.

Embodiment 155. The composition of embodiment 152, wherein the antisense oligomer has at least 80%, at least 90%, or 100% sequence identity to a sequence selected from the group consisting of SEQ ID NOs: 36, 236, 242, 250, and 280-299.

Embodiment 156. A pharmaceutical composition, comprising a therapeutic agent or a vector encoding the therapeutic agent, and a pharmaceutically acceptable excipient, wherein the therapeutic agent promotes exclusion of a coding exon from a pre-mRNA, thereby increasing a level of a processed mRNA that is processed from the pre-mRNA and that lacks the coding exon in a cell, wherein the pre-mRNA is transcribed from an OPA1 gene and that comprises the coding exon.

Embodiment 157. A pharmaceutical composition, comprising a therapeutic agent or a vector encoding the therapeutic agent, and a pharmaceutically acceptable excipient, wherein the therapeutic agent comprises an antisense oligomer that binds to a pre-mRNA that is transcribed from an OPA1 gene in a cell, wherein the antisense oligomer binds to:

(a) a targeted portion of the pre-mRNA within an intronic region immediately upstream of a 5' end of the coding exon of the pre-mRNA; or (b) a targeted portion of the pre-mRNA within an intronic region immediately downstream of a 3' end of the coding exon of the pre-mRNA;

whereby the therapeutic agent increases a level of a processed mRNA that is processed from the pre-mRNA and that contains the coding exon in the cell.

Embodiment 158. A pharmaceutical composition, comprising a therapeutic agent or a vector encoding the therapeutic agent, and a pharmaceutically acceptable excipient, wherein the therapeutic agent promotes exclusion of both a coding exon and a non-sense mediated RNA decay-inducing exon (NMD exon) from a pre-mRNA, thereby increasing a level of a processed mRNA that is processed from the pre-mRNA and that lacks the coding exon and the NMD exon in a cell, wherein the pre-mRNA is transcribed from an OPA1 gene in the cell and comprises the coding exon and the NMD exon.

Embodiment 159. The pharmaceutical composition of any one of embodiments 147 to 158, wherein the pharmaceutical composition is formulated for intracerebroventricular injection, intraperitoneal injection, intramuscular injection, intrathecal injection, subcutaneous injection, oral administration, synovial injection, intravitreal administration, subretinal injection, topical application, implantation, or intravenous injection.

Embodiment 160. The pharmaceutical composition of any one of embodiments 147 to 158, wherein the pharmaceutical composition is formulated for intravitreal injection.

Embodiment 161. The pharmaceutical composition of any one of embodiments 147 to 160, wherein the pharmaceutical composition further comprises a second therapeutic agent.

Embodiment 162. The pharmaceutical composition of embodiment 161, wherein the second therapeutic agent comprises a small molecule.

Embodiment 163. The pharmaceutical composition of embodiment 161, wherein the second therapeutic agent comprises an antisense oligomer.

Embodiment 164. The pharmaceutical composition of embodiment 161, wherein the second therapeutic agent corrects intron retention.

Embodiment 165. The pharmaceutical composition or composition of any one of embodiments 147 to 160, wherein the antisense oligomer is selected from the group consisting of Compound ID NOs: 1-303.

Embodiment 166. A method of treating or reducing the likelihood of developing a disease or condition in a subject in need thereof by modulating expression of an OPA1 protein in a cell of the subject, comprising contacting to cells of the subject the therapeutic agent of any one of embodiments 147 to 165.

Embodiment 167. The method of embodiment 166, wherein the disease or condition is associated with a loss-of-function mutation in an OPA1 gene.

Embodiment 168. The method of embodiment 166 or 167, wherein the disease or condition is associated with haploinsufficiency of the OPA1 gene, and wherein the subject has a first allele encoding a functional OPA1 protein, and a second allele from which the OPA1 protein is not produced or produced at a reduced level, or a second allele encoding a nonfunctional OPA1 protein or a partially functional OPA1 protein.

Embodiment 169. The method of any one of embodiments 166 to 168, wherein the disease or condition comprises an eye disease or condition.

Embodiment 170. The method of any one of embodiments 166 to 168, wherein the disease or condition comprises ADOA-plus syndrome; a mitochondrial disorder; glaucoma; normal tension glaucoma; Charcot-Marie-Tooth disease; mitochondria dysfunction; diabetic retinopathy; age-related macular degeneration; retinal ganglion cell death; mitochondrial fission-mediated mitochondrial dysfunction; progressive external ophthalmoplegia; deafness; ataxia; motor neuropathy; sensory neuropathy; myopathy; Behr syndrome; brain dysfunction; encephalopathy; peripheral neuropathy; fatal infantile mitochondrial encephalomyopathy; hypertrophic cardiomyopathy; spastic ataxic syndrome; sensory motor peripheral neuropathy; hypotonia; gastrointestinal dysmotility and dysphagia; optic atrophy; optic atrophy plus syndrome; Mitochondrial DNA depletion syndrome 14; late-onset cardiomyopathy; diabetic cardiomyopathy; Alzheimer's Disease; focal segmental glomerulosclerosis; kidney disease; Huntington's Disease; cognitive function decline in healthy aging; Prion diseases; late onset dementia and parkinsonism; mitochondrial myopathy; Leigh syndrome; Friedreich's ataxia; Parkinson's disease; MELAS (Mitochondrial encephalomyopathy, lactic acidosis, and stroke-like episodes); pyruvate dehydrogenase complex deficiency; chronic kidney disease; Leber's hereditary optic neuropathy; obesity; age-related systemic neurodegeneration; skeletal muscle atrophy; heart and brain ischemic damage; or massive liver apoptosis.

Embodiment 171. The method of any one of embodiments 166 to 168, wherein the disease or condition comprises Optic atrophy type 1.

Embodiment 172. The method of any one of embodiments 166 to 168, wherein the disease or condition comprises autosomal dominant optic atrophy (ADOA).

Embodiment 173. The method of embodiment 166 or 167, wherein the disease or condition is associated with an autosomal recessive mutation of OPA1 gene, wherein the subject has a first allele encoding from which:

(i) OPA1 protein is not produced or produced at a reduced level compared to a wild-type allele; or (ii) the OPA1 protein produced is nonfunctional or partially functional compared to a wild-type allele, and a second allele from which:

(iii) the OPA1 protein is produced at a reduced level compared to a wild-type allele and the OPA1 protein produced is at least partially functional compared to a wild-type allele; or (iv) the OPA1 protein produced is partially functional compared to a wild-type allele.

Embodiment 174. The method of any one of embodiments 166 to 173, wherein the subject is a human.

Embodiment 175. The method of any one of embodiments 166 to 173, wherein the subject is a non-human animal.

Embodiment 176. The method of any one of embodiments 166 to 173, wherein the subject is a fetus, an embryo, or a child.

Embodiment 177. The method of any one of embodiments 166 to 173, wherein the cells are ex vivo.

Embodiment 178. The method of any one of embodiments 166 to 173, wherein the therapeutic agent is administered by intracerebroventricular injection, intraperitoneal injection, intramuscular injection, intrathecal injection, subcutaneous injection, oral administration, synovial injection, intravitreal administration, subretinal injection, topical application, implantation, or intravenous injection.

Embodiment 179. The method of any one of embodiments 166 to 173, wherein the therapeutic agent is administered by intravitreal injection.

Embodiment 180. The method of any one of embodiments 166 to 179, wherein the method treats the disease or condition.

EXAMPLES

The present disclosure will be more specifically illustrated by the following Examples. However, it should be understood that the present disclosure is not limited by these examples in any manner.

Figure 2:
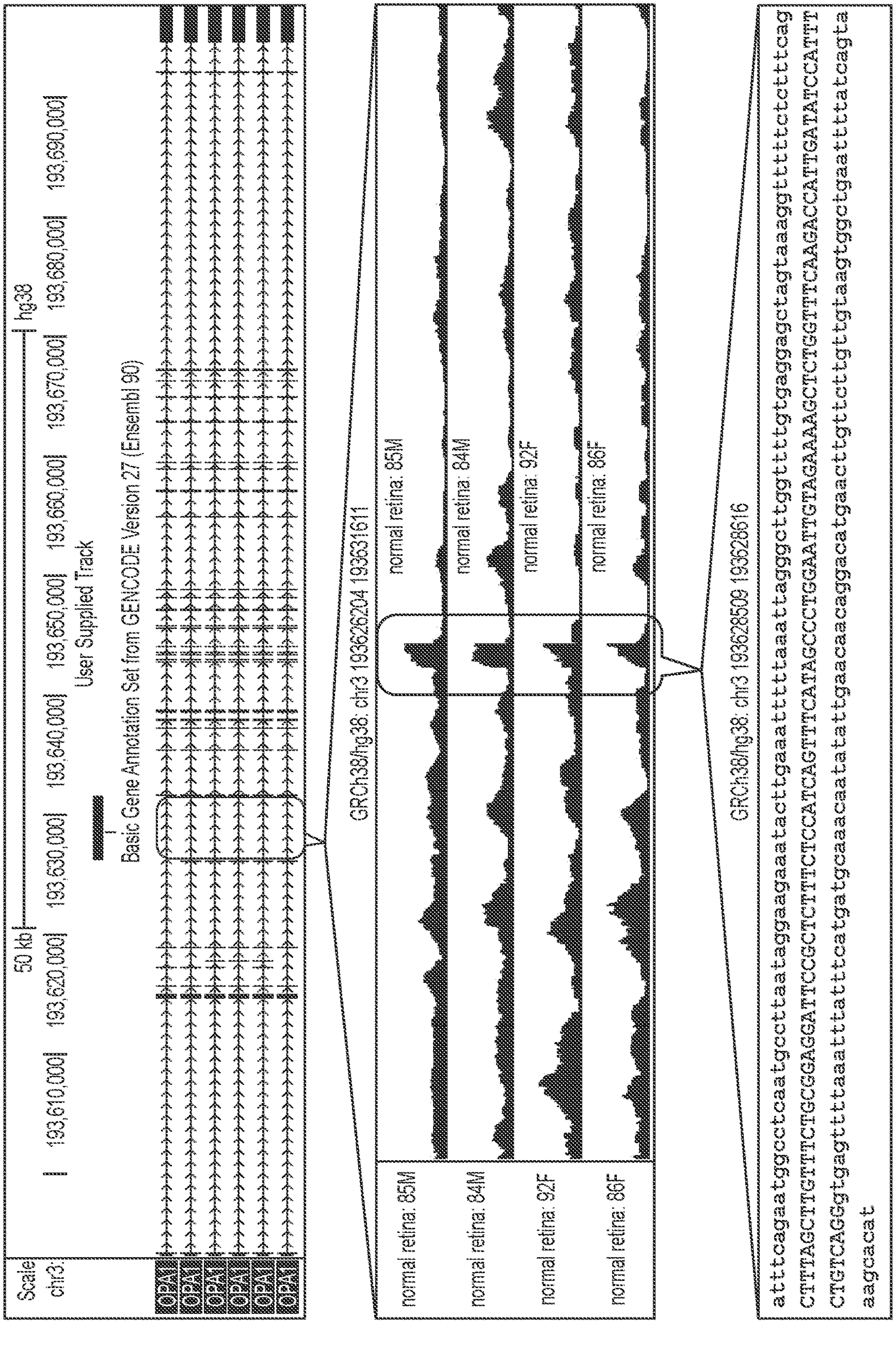
FIG. 2 depicts identification of an exemplary nonsense-mediated mRNA decay (NMD)-inducing exon in the OPA1 gene. The identification of the NMD-inducing exon in the OPA1 gene using RNA sequencing is shown, visualized in the UCSC genome browser. The upper panel shows a graphic representation of the OPA1 gene to scale. Peaks corresponding to RNA sequencing reads were identified in intron GRCh38/hg38: chr3 193626204 to 193631611, shown in the middle panel. Bioinformatic analysis identified an exon-like sequence (bottom panel, sequence highlighted in uppercase; GRCh38/hg38: chr3 193628509 to 193628616) flanked by 3' and 5' splice sites. Inclusion of this exon leads to the introduction of a premature termination codon rendering the transcript a target of NMD.
Figure 3:
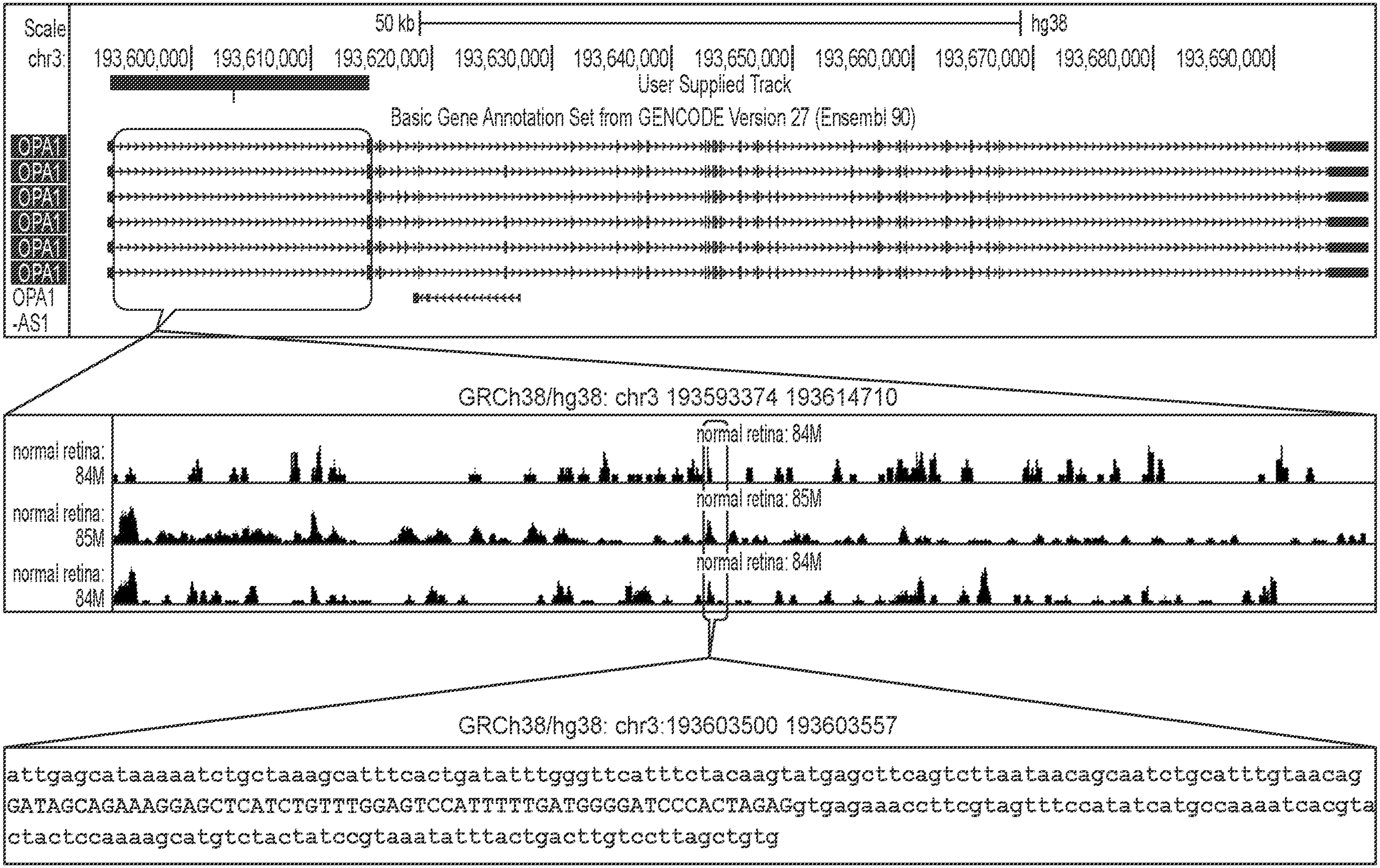
FIG. 3 depicts identification of an exemplary nonsense-mediated mRNA decay (NMD)-inducing exon in the OPA1 gene. The identification of the NMD-inducing exon in the OPA1 gene using RNA sequencing is shown, visualized in the UCSC genome browser. The upper panel shows a graphic representation of the OPA1 gene to scale. Peaks corresponding to RNA sequencing reads were identified in intron GRCh38/hg38: chr3 193593374 to 193614710, shown in the middle panel. Bioinformatic analysis identified an exon-like sequence (bottom panel, sequence highlighted in uppercase; GRCh38/hg38: chr3 193603500 to 193603557) flanked by 3' and 5' splice sites. Inclusion of this exon leads to the introduction of a premature termination codon rendering the transcript a target of NMD.

Example 1: Identification of NMD-Inducing Exon Inclusion Events in Transcripts by RNAseq Using Next Generation Sequencing Whole transcriptome shotgun sequencing is carried out using next generation sequencing to reveal a snapshot of transcripts produced by the genes described herein to identify NMD exon inclusion events. For this purpose, polyA+ RNA from nuclear and cytoplasmic fractions of human cells is isolated and cDNA libraries are constructed using Illumina's TruSeq Stranded mRNA library Prep Kit. The libraries are pair-end sequenced resulting in 100-nucleotide reads that are mapped to the human genome (February 2009, GRCh37/hg19 assembly). FIGS. 2 and 3 depict identification of different exemplary nonsense-mediated mRNA decay (NMD)-inducing exons in various genes.

Exemplary genes and intron sequences are summarized in Table 1 and Table 2 (SEQ ID NOs indicate the corresponding nucleotide sequences represented by the Gene ID Nos). The sequence for each intron is summarized in Table 3 and Table 4. Table 5 lists sequences of OPA1 antisense oligomers of this disclosure.

TABLE 1

List of exemplary target gene sequences.

| Gene Symbol | Gene ID No. | SEQ ID No. | Disease | OMIM | Genetics | Introns |
|---|---|---|---|---|---|---|
| OPA1 | 4976 | 1 | Optic atrophy type 1; Autosomal dominant optic atrophy (ADOA) | 165500 | Haploinsufficient | ENST00000361908.7:6<br>ENST00000361908.7:28 |

TABLE 2

List of exemplary target gene sequences.

| Gene Symbol | Gene ID No. | SEQ ID No. | Disease | OMIM | Genetics | Introns |
|---|---|---|---|---|---|---|
| OPA1 | 4976 | 1 | Optic atrophy type 1; Autosomal dominant optic atrophy (ADOA) | 165500 | Haploinsufficient | GRCh38/<br>hg38: chr3<br>193626203<br>193631611<br>GRCh38/<br>hg38: chr3<br>193593374<br>193614710 |

TABLE 3

Sequences of exemplary target introns in pre-mRNA transcripts.

| Gene | SEQ ID NO. | Intron |
|---|---|---|
| OPA1 | 2 | Intron 6:<br>gtgatggatggtttaagggggctaccgata<br>cattcacactaatcagccatttctgccaag<br>atcatgtcacctcaatctgttcatggactc<br>caaatacaagaaattaatttgacaaagtga |

TABLE 3-continued

Sequences of exemplary target introns in pre-mRNA transcripts.

| Gene | SEQ ID NO. | Intron |
|---|---|---|
| | | aaatataaaagatgcatcatataaatatgt<br>aacttttctggagtgggtagtataggtaaa<br>gccaaaagaaacaaattcaagcagaggaat<br>tttggtttctgaaaattaggttgtctgtag<br>ggtccctgtatttatacttagaacaaaatt<br>aggaatttctgtttatgtggtccagttatt<br>gagtcaccctaagtttgtaggcatcttacc<br>tacctacttgctccccaagtttttatttct<br>aaaatgaaaagcattgctgtagatgaccag<br>tttacactaaagaataacatttatttattt<br>gttttagctaaagtatatggacagggaaca<br>ttcatattcttgtagaagaaaattattttg<br>acttttgggcaaaagcatgtagttcttata<br>cactttgacaaactcattgcgtacattttt<br>cacattaatcaaagtcagcacaaataaatt<br>ttcaccttggaccacggagggtttgaacac<br>tggaaatttgatataattctggttgctaaa<br>gaacaagttctaataaaagcttaagtgtat<br>accaatatgtggctgttggtgcaatcagca<br>ggtccgtaaaaatatgattttaatggttag<br>gtaatcccacaacggagatcccaaagttca<br>tgtttggaagagacttttgggtcaaagtga<br>aatcagtgtaatgaatttaaaattatactc<br>tgagatcttgaaatcagctaattatgttac<br>atcttattagctcagaaaagttttgaagtt<br>atatacaaatgctagtcaggaaaaaagatt |

TABLE 3-continued

Sequences of exemplary target introns in pre-mRNA transcripts.

| Gene | SEQ ID NO. | Intron |
|---|---|---|
| | | cagtcatgtaattcttgtacattctactat<br>ttaaatcaaccaatattatagattatgatt<br>tagtgcagtaattctgctggctaaccttat<br>ctcatttggtggtggttagtacttcagagt<br>actcaccatagtttcatttatgttttcagc |

TABLE 3-continued

Sequences of exemplary target introns in pre-mRNA transcripts.

| Gene | SEQ ID NO. | Intron |
|---|---|---|
| | | atcacttcctggtttttctcaattccatgg |
| | | ctgtggaatcaattcatatgtatatttagc |
| | | ttcggtgagcaaaaacatagctagaaaaag |
| | | aaaagaagtgagtttcctacctggttaaat |
| | | taaagtcgatgtgttaagccaaggaggact |
| | | tcttttgaatggtactttaacaatccctgt |
| | | tctgtatactgtgaatatatcatttaaata |
| | | gcctaataaattggatgcttaggctgagcc |
| | | acctatactttagttttgttatggaaagaa |
| | | gggagaggagcaagtatgttcttatatgtt |
| | | acttagaaataagaatgtagctgtagttac |
| | | acattgttcttaagtttttttcgtaagaca |
| | | acttgaaatgagtcccataggcctgctatt |
| | | taacattctaagatatgacttaaggttaat |
| | | gatgagcttttgaatctgacaattcaagag |
| | | atatccataatgaatactgattcattttct |
| | | acattgctgaaagctaatgttcattttaag |
| | | cctactttagtagcctttatttgggcttag |
| | | agatgttattcctctttctgatatttattg |
| | | ggttatctgtttaacccttttatatctccc |
| | | tttcccgatttgtaaattagagactggcaa |
| | | gactttttaccctgagtagagcaccaaaca |
| | | tggcttgtttctgcccacactgtagttacc |
| | | ttgaggggaagtaaatgggactttaaaagc |
| | | aatttatgctcttttatagtgaaattatcc |
| | | ctcttactatcccgaaagactgttacctta |
| | | caatatcctccactcctttccccctgtagt |
| | | tactatagagatgacttttcggttcttcac |
| | | tgccataatgatcaaaatcctaattcatga |
| | | gatttttatcattccaggcatgtgaggttt |
| | | acttgatgcataaaaccgcaagtacttttt |
| | | gttgtttttaattgtttttctctcttat |
| | | cttcttgaaagtctaagtagatcatcattt |
| | | ttgatgtcttattagtagcaactaataaat |
| | | tttccctgtatcttctcagcaaaagaactc |
| | | aagcagagacagaagattagaactaccatt |
| | | ggtagttttgcttcctatggatatgttcac |
| | | atacatagaaatttttacaatgaccttttt |
| | | atatatgtatttcagaatttcagaatggcc |
| | | tcaatgccttaataggaagaaatacttgaa |
| | | atttttaaattagggcttggttttgtgagg |
| | | agctagtaaaggtttttctctttcagcttt |
| | | agcttgtttctgcggaggattccgctcttt |
| | | ctccatcagtttcatagccctggaattgta |
| | | gaaaagctctggtttcaagaccattgatat |
| | | ccatttctgtcagggtgagttttaaattta |
| | | tttcatgatgcaaacaatatattgaacaac |
| | | aggacatgaacttgttcttgttgtaagtgg |
| | | ctgaattttatcagtaaagcacatcaaaat |
| | | aaaatataccccaattgctagttaagacct |
| | | agagtgacagattgaaaatagcttgtgtta |
| | | ttctcttaagaaaatatataaaaattatca |
| | | tctcatcaatctttaatgtttgttttataa |
| | | atctaaatgttttatattgtttcctagga |
| | | aatattaggtctaatttttttactttaccac |
| | | cagctgtcttttattttactcttttttga |
| | | gacggagtttcgctcttgttgcttaggcta |
| | | gagtgcagtggcactatctcagctcactgc |
| | | gacctctgcctcccgggttcaagcgattct |
| | | cctgcctcagtctcccgagtagctgggatt |
| | | acaggcacatgccactacaccaggctaatt |
| | | ttgtatttttagtagagacggggtttcttc |
| | | atgttggtcaggctggtctcgaactcccga |
| | | cctcaggtgatccgcctgcctcggcctccc |
| | | agagtgctgggattacaggcatgagccacc |
| | | gcacctggccagctgtcttttaatataaca |
| | | ttatgattaattgtgatgttccattaaact |
| | | aagcggagaggaaacatgctggtaaaccat |
| | | gtgtgagttattcattgtaccagaaaggca |
| | | aatgatacattttatcctaaaattcaaatt |
| | | tataaacatcttaacacttgtgatcattaa |
| | | atactactaatctagcatataaattatatt |
| | | tgtaggcggggcacggtggctcacgcctgt |
| | | aatcccagcactttgggaggctgaggtggg |
| | | cagatcacgaggtcaggagatcgagaccat |
| | | cctggctaacatggtgaaaccccatctcta |
| | | ctaaaaatacaaaaaaaattagctgggtgt |
| | | gctggcgggcacctgtagtcccagctactt |
| | | gggaggctgaggcaggagaatggcgtgacc |
| | | ccaggaggcagagcttccagcctgggcgac |
| | | tccgtctcaaaaaaaaagaaaaaagaaatt |
| | | atatttgtaatattctactaaccttatatc |
| | | attttaactttttatataactttttattt |
| | | taccaaattaagttaaccttttatagccct |
| | | tggcttatactaaacatcctaactttttg |
| | | tttaattgtattagtttttaagttattgcc |
| | | ccagatgtcaagtaatgttggattttctat |
| | | aataatttaggatatattgcatgaagtcag |
| | | ttagtatttacatttaaaactaaaacaatt |
| | | tatactaatacagtttatacatttcatact |
| | | aatttagctacagttggataaatatttaat |
| | | ggaacaaagtaaatcaaagtaccttttcaa |
| | | atgaattggaaattaaatccacataacaat |
| | | tttttatgaccacactattacagtgtgatg |
| | | gcatgccaaatgatcataatgtggaattat |
| | | gtatttcttcattggctttcaagattctgt |
| | | tctttagtttgtgggctcctctccaacttg |
| | | cttgtctcctcacagtttaggcgactgttt |
| | | ataattcttgtccatcctgcataaacacac |
| | | acagtcaaaatgaaaaaaagcttctatcag |
| | | cagatctgtgcttgctgtacagaaatggga |
| | | aaacaattgaagtttgcattatctttttttc |
| | | taattaccagatcgtttttggagctattta |
| | | ggcatacgcttttaaggaaaaaagaaaaaa |
| | | agagtgtaccttttgtttctaacaaaggtt |
| | | gttatctatattattgaaataaaaaattgg |
| | | ggatagttatgacaaagtatttagaaatag |
| | | gaattaaaatcttaaaataacttttcatag |
| | | catggacaagacttattaatgtctacctca |
| | | ataagcaaatcatttaaaaatttttcatgt |
| | | atatttgctgccatgatgtgttgtgattgc |
| | | ttaaataaccaatgaatgaagatcaacaag |
| | | gatttaaatgaagaagaatatggatttaac |
| | | tattttctcctgtgaaataagttcatattt |
| | | acaagttttgattttcagaaattagacaat |
| | | tatttttaaaggctgggatgacaacttctg |
| | | cctcttaccaagaagtcaaagcacagttat |
| | | gtgaattcatcataaatcacatcattttta |
| | | ttatattttgtatttataattgtattgtga |
| | | ctactttaaaacctgttataaaataaaatt |
| | | gtttttttaatattttattttagaattatta |
| | | gcattaataacaatttgaagtagtttacac |
| | | aatacctgtgagttttatttttgttttata |
| | | ttgaaattaattttagttgctttacttggc |
| | | ttcattgctatggatgcattctctgtgtta |
| | | cgagttagcagatctttccttggaactgaa |
| | | tttaaaagcaagcatttggctccacttaaa |
| | | tctctgaaaatgcaacttgttctttgcatt |
| | | tattacataattcgctacttatggtacaga |
| | | aatggatacaatacaaaaatatttccttat |
| | | aagatacactgtgaccaatgagctttttaa |
| | | atagctgtaatcagtaacatgtatttgact |
| | | tttcaaaacacatttctggagggatatcac |
| | | tcttgtttttctaactagtctttcataaga |
| | | aatgactagaatagcaacagggaaatgatt |
| | | gccttttaaggtttttgtttctcaatataa |
| | | aattttggtgaaccatttttattgataaat |
| | | acaggtatttttactttcttaaatcacttg |
| | | atttaaaattactttgattaaatatgcata |
| | | taaagtcagttgtttttaactctcaatact |
| | | tatcaaaaaaatttaacttgctgtacattc |
| | | tgtataaacctaattctattcaactaaaat |
| | | tattttaaacatttag |
| | 3 | Intron 28: |
| | | gtgagtagttcttactgccctctaccttac |
| | | tacctttccacctttcccatttccatttgt |
| | | ttgttgatccatttaatctcaaacttacag |

TABLE 3-continued

Sequences of exemplary target introns in pre-mRNA transcripts.

| Gene | SEQ ID NO. | Intron |
|---|---|---|
| | | aaaagttacaaggaactgggctgagcacgg |
| | | tggctcacgcttgtaatcccagcactttgg |
| | | gaggccaagatgggtggaaaacaaggtcag |
| | | aagatcaagaccatcctggctaacacagtg |
| | | aaaccccgtctctactaaaaatacaaaaaa |
| | | cttagccaggtgtggtggtgggtgcctata |
| | | gtcccagctacttgggaggctgaggcagga |
| | | gaatggtgtgaacccgggaggcggagcttg |
| | | cggtgagccaagatcctgccactgcactcc |
| | | agcctgagcgacagggcgagattctgtctc |
| | | aaaaaaaaaaaaaaaaaaaaagttacaagg |
| | | aattttttcttctctgaagtatttgagag |
| | | taagttgctgaccttaagtcctatcacttc |
| | | caagtaggttcatgtatagttcttagaaac |
| | | agattttctcatagcaaccgaacattgata |
| | | aattacaatatctaattctcagacccctt |
| | | caagtttcacccgttgtcccagtattatcc |
| | | ctccatataacaagatgttccaggctcaat |
| | | acctgacccagcttccttttttgaagaat |
| | | ggtgtttagaaatggagacctagaaattat |
| | | atatgctgttattggaatatcactgttccc |
| | | tggtttctcagtggaaagagctaggaacta |
| | | agtgttgtgaatgtttgtgtgtgtgcaggt |
| | | gaatatacacacactgacatctgtattcct |
| | | aaatcatgtgtatatttatttattaaaaac |
| | | tgtgagttgatgctgatacttcccatttta |
| | | atccagcattacaaggtttgttctagtgtt |
| | | ctccctttcgatatttgtcacttgctttcc |
| | | tgatagaaaacgggcttctagtatccttaa |
| | | tatattttcatattttggtcagtcctccta |
| | | tacgtaacccaacttgaatgaagatatgtc |
| | | cttttccattgcagaaatgttcttttttccc |
| | | cagctcggactcaacactacacaccaggcc |
| | | accacatggcgccgcacccagcattgacac |
| | | ttcttttaccttgtctgggctctgacatcc |
| | | gtgccaggttgctcttcgtcatggagtccc |
| | | ttttactgagctctgctctgacgctttgtg |
| | | ccaggtgcctcttgtggagataccctcttt |
| | | accctgcctgtgcttcgccagcctgcacca |
| | | ggccaccctcctgcacagatactctcctca |
| | | gtactggaccaggctaccaacagccccatg |
| | | tgaacccattgtaacccaggtcaggcatta |
| | | acacctgcagtaggctaccatggcttcccc |
| | | ttcccaccccccctagcttggccctactaat |
| | | aatcactttgtcactgtttggggttgatat |
| | | ttggttgtttcttgtaggttcctagcttta |
| | | agataggattgcatactaaaatttacttag |
| | | atctttgagaactcaaggaaatcagtgaaa |
| | | cattattgttattaaataaaaataaaatac |
| | | ctgtagttggtacctctgtttgagcctgcc |
| | | ttgttacaagtttcactgacttcagcttcg |
| | | tgtaacaaagtatctttttctttcaacgtg |
| | | tacttaaatttcctgtcttattagttttct |
| | | gatatctaaaaggaaaaaaagcagatatcg |
| | | ttaataaattagaaagaagttctgcaaatt |
| | | taaaagtgccttctaagctgagttgtagga |
| | | ttacagtacaatccatagggttatcctgaa |
| | | gaagccaggcagggctcttctgtgttacac |
| | | cctgtgcctgcgcagcatgctcaccccttg |
| | | ccatcagcgcttgcggccccattctctccc |
| | | tctagtaataatctaagttctgcattgctt |
| | | tctcctttcctttttcttttcttcctttaaat |
| | | attcttctttcgagacatatctcattttaa |
| | | cttttattttcattttctgtcacttttggt |
| | | ttttctcatgccaccttggcaatgtagtta |
| | | agtttgtgctaacgtagaagattagtgctc |
| | | aaatctgaattgccatttactactagctgt |
| | | gtcatcttcggcagggaatctcccagagcc |
| | | ttagcttctttatttgtaaaatgactatta |
| | | tagtggttatttctcaggattgttagaatt |
| | | acttccgcaaacatttgcaagtccctggtt |
| | | cataatttcatgctaaattagtaccgttac |
| | | aggaagtggtatatcattgtcacagtgtat |
| | | acaaatatatttcttttatatccctcgtga |

TABLE 3-continued

Sequences of exemplary target introns in pre-mRNA transcripts.

| Gene | SEQ ID NO. | Intron |
|---|---|---|
| | | tataattatcaagacagtgaaacaattcaa |
| | | tgaattttaccagcataacacatttttaag |
| | | tgattggaaaatcataagtatcttttctta |
| | | tgtttttagtagaggctttgcaaccccatt |
| | | actctccgctcccaatttgattatttaaag |
| | | gaagtggattactaactcagatatgtacac |
| | | tgtcaagccaagttctatgttctactgctg |
| | | gtttcctgagaaagcagtcatataactcc |
| | | cttgaaatgatttactacttttgtacatat |
| | | aaaattataatggtgttaatgtaccaaata |
| | | atgtccttggaagcaagggttttgccagta |
| | | actcagctgcatcagtcaccctcaaggaga |
| | | tgagccatgactttgttcattagttggaaa |
| | | agagtctggagagtgccttttcgttactgt |
| | | ttatctttggtctgacacttgggaataggg |
| | | tcatggatacttcagccagaaaactttcca |
| | | aatttaagttattaatgtattataaggatc |
| | | aaagtttctagtatagcctgttcaattaga |
| | | acatagtgtgttggttgattggatttggag |
| | | aaagggaggcaatcaaatttttactacagt |
| | | ttcagcctgttacagaatattgtatagagt |
| | | gttaaaatgttgatgcattcatatttttgc |
| | | cagttttaagcttgtacgattttaaatcat |
| | | ttccttaccttggagacttcccccccacct |
| | | ttttttttttttttgagatggagtctcgct |
| | | gtgtcgcccaggctagagtgcagtggcacg |
| | | atctcggctcactgcaaggtggttctccca |
| | | cctctgcctcccgagtagctggggctacag |
| | | gcgcccgccaccatgcctggcttatttttt |
| | | gtatttttagtagagacggggtttccccat |
| | | gttagccaggatggtctcgatctcctgacc |
| | | tcatgatccgcccgcctcggcctcccaaag |
| | | tgctggaattataggcatgagccaccatgc |
| | | ccagccctgactgccctttaagatgagtac |
| | | ataagtagtagtagtacatttttctttcac |
| | | atcctggagaagatatactgtgttcactat |
| | | tgaaatgaaaccataaagctagagttagga |
| | | agattgaagaaatgaaaaaggagctcacat |
| | | gattttgtctcaggagaggctcttccagga |
| | | ttctttggagatatggtagattccatagct |
| | | ggagcagggaaaggacaggatgagcctgtg |
| | | ggtgtagaaaggaagggagtgcttgaaaga |
| | | tgatgaggagatgtcagcaggtcacagaaa |
| | | ccctctgaaggaggctccaactggccaggc |
| | | tggggacaattgggccccaaaataatgac |
| | | agtaacaaattgtaactcattgaatgaaat |
| | | aggaatccatacattggtaattatataaat |
| | | aagggaataaaaccatgatgcaaaaaggga |
| | | tgtttatgtcatcacgcaaaatatgttcac |
| | | agaaaatatgtactaattaaaagagggaaa |
| | | agagtaactttacagtggatgaagcctggc |
| | | aatcatcactttaagcaagtggtcagagtt |
| | | aatattatcagtaatggtcaaatcaaaacc |
| | | atatgcaagaagactctaaaatgcaagaag |
| | | actcctgaagtacttcttaccaaagatgta |
| | | gaacttaaattcagtcataacaatacatga |
| | | gacaaacccaagttagagcacagtctgcaa |
| | | aataactggcctgtaatcttcaaatgcatc |
| | | aagatcatgaaagacaaggaaagagtgaag |
| | | agctgctccagttggaagagacttaaaact |
| | | aaatgcaatgtatgatcctagattggatct |
| | | ttttgctctaaggacattaatgggccagtt |
| | | agtgatatttgaaggggatccgagggttcc |
| | | attgtagtaatatatcagtgttaattttta |
| | | aatttttattaggttgggattattttggaa |
| | | aataccattattcatagcgaatacaaagta |
| | | gaatatttggggatgataatgcatgattac |
| | | aacaaatgtttcaggagaaatatgatcttt |
| | | gtagtggtcttgcaacttttctgtaagtct |
| | | gaaattgtttatgcataaaaggttaaaaaa |
| | | aggttaaattttgtttttataactaataat |
| | | ggattagggtcatgtgaaagtactttagag |
| | | gaaatgagactttttgagaacatcatccctg |
| | | aagacgttgaaacactgagttacctcatgg |

TABLE 3-continued

Sequences of exemplary target introns in pre-mRNA transcripts.

| Gene | SEQ ID NO. | Intron |
|---|---|---|
| | | ataatttaataggatatgcagctgattttt |
| | | ctaccttaatttcttgtttgcagtatctac |
| | | ccatacttagaattgtctggtgttaaaata |
| | | tgcccactgggactttcatgaaattctttt |
| | | gattttctagaaaattcagtttcaaaggat |
| | | tttttaaatagatattttaagtttggtgtc |
| | | aacttagataaaatctgtttggagtcccag |
| | | tgtaagttttagtaatgtgtccaatctgtt |
| | | tattgaaatagtataactttagaatacttt |
| | | ctttggagagatgaagattggtatgttata |
| | | gttcaattcaaagttgttctttctattatg |
| | | atctattttataattcataaaatctatctt |
| | | atgattgtcatcataagtgcaatttgtttt |
| | | ttgccccattctacctcagaaactaagtat |
| | | ctgggcatcaataacaattggtagtagtgt |
| | | ttgctgctaagccaagtttcaccagtacag |
| | | tgtggaattattttattgtttttctgtga |
| | | acattgtatctgctgttactaggttattgt |
| | | gaggtattgggccttcatagaaattgcctg |
| | | gaacccttgttcactaaagcctgttacact |
| | | ttttattctctgtgcgtgtaatcagagact |
| | | tattgatactgacacattcaaggggcatta |
| | | ttgatcatttagattgctctaagacctaag |
| | | gagtcttggccggatgcggtgcctcacgcc |
| | | tgtaatcccagcactatgggaggccgaggc |
| | | gggtggatcacctgaggtcaggagttcgag |
| | | atcagcctggccaacatggtgaaaccccgt |
| | | ctctactaaaaatgcgaaaattagctgggc |
| | | atggtggcaggcgcctgtaattccagctac |
| | | tcgggaggctgagacaggagaatcgcctga |
| | | acccgggaggcagaggttgcagtgagccaa |
| | | gactgtgccattgcattccagcctgggtaa |
| | | cagagcgagactccatctcaaaaaaaaaaa |
| | | aaaaacgaaaaacaaaaacctaaggagtct |
| | | tttctccttattttacaataaattcctttt |
| | | gattttgtgtaaaaacttgaaactgtttat |
| | | gaatgtaaaataacatttgaatacttttct |
| | | tgtgccagatattaggttaaatgctttatg |
| | | tgaattttcatttgattctcacaactttg |
| | | agttaggtagttatttttctcatttacag |
| | | atgaaatggagggttaggaactcgtaggta |
| | | gtagatgctgaagctgagatttgggcctgg |
| | | gtcttttcactactgtgccagaatcatttg |
| | | ggagggagtaaaaactcaagcctttggaaa |
| | | atatgatgacataaaattgtcctttatatt |
| | | gagaagcttccatagttaccagtgtccttc |
| | | acagggttgatcggaaagacatacatgtta |
| | | gtgatgatgataatgatgaagataatcatt |
| | | attaccacaggtacttcctataatataagc |
| | | atctttcaaattgtatgagaactttcatag |
| | | aacatctgagtaaatgaacagtacagtgtg |
| | | catgaaaccactaagcaaaccaagggaagt |
| | | taattttctttatatgaattgtaaacatgt |
| | | ctctagatatcctttatcagattccaccat |
| | | gcgtaagtagtgtctaagttgccccatatt |
| | | tagagtttttcaatgaggttgtgttcctac |
| | | ttagaatcctaaagttcagctataacagat |
| | | atattaataaaatctgtggaatctttaatt |
| | | gagcataatggtggctgttattttaacttg |
| | | aggctttttgttgagctggattggaagtgc |
| | | aacttattagaaattacagtgtatttattc |
| | | ctatttcttgttctttatgtgagagaagat |
| | | atactttagtagactgaatacttcagagct |
| | | gtatctcatttaccaataaaatgtgaaaac |
| | | agtggtaaattccttcacttgggctaccat |
| | | tgtacaggcctattttaatggtatagtttg |
| | | atatccttaatgttaaaagcaatatagctt |
| | | aaagaggctggtaaattagaattttccaat |
| | | atcctcagctttttttcctctcacagttaa |
| | | tttgctctgctgactccctacgcgaggtgg |
| | | caacagctggcccttttactggagcttgtg |
| | | gggattagagagtcgggctcgcagcagcgt |
| | | gctcggcctcttgcctctgttgactgttct |
| | | ttattgtttgatgcctgagcatctcccaga |

TABLE 3-continued

Sequences of exemplary target introns in pre-mRNA transcripts.

| Gene | SEQ ID NO. | Intron |
|---|---|---|
| | | cagcgagcaattgtttctggaaacttaaag |
| | | tttgtttctcttgggagtagacaatgcttt |
| | | tggggcttgtctttgtgtttcttcacttca |
| | | tgagattctaaaacttagaagtataggcta |
| | | tagatgaaagtttctttttcagtaagcca |
| | | cctcagtaacaaatcatgttttaaatgaaa |
| | | actttgttcttcataatatcatttagtgag |
| | | agaaaacaaatgcatgagtgcattttgaa |
| | | attatggtactaaaagggagcagcagcaag |
| | | gtgacctaatactgccattttaaaagctag |
| | | gattagaaatgtatcataactgcttaaatc |
| | | taaaaagattctttcactgaatccaaaata |
| | | tagttctaatttataggatagttataagaa |
| | | atctctatgccatgtggaaacatgaataaa |
| | | aagtagtcagaacatagctaaatagaaccc |
| | | tgaggtaggcagaatgattttattcttcac |
| | | atttagaaaagaaaacatcaaggtaccctg |
| | | gaacttaatttctacagtgacttcacattc |
| | | cgacacttctcccatacctgccataccctt |
| | | gagtgttgttacggatgagaatatcgtctg |
| | | tgaagtagtatgagatggaaattttcctag |
| | | aaagattattgtactcggaatttggaactg |
| | | aaaagtgtagaaaggggaagtgatgtgttt |
| | | aaaactgtttgcggaggtggggctctgcca |
| | | tgtgtattttgacaaagctacacaggtgat |
| | | tcttgccatccccgattaccgtgtacccgc |
| | | ctgcccctgagctggcactccaaagagttc |
| | | tttcagtgcatagcaagacaattttcatg |
| | | ctattaattgggataaaattgacatacatt |
| | | catttgtagagtctgagacacaacgtcact |
| | | ttggaaaatttggtgagcaatttgaactgc |
| | | atctgcactggtgtgttctttttgtttctg |
| | | tagacttaaccaaagaaaatgaactttaaa |
| | | gggactttaaaggcatctgcactggtgtgt |
| | | tctttttgtttctgtagacttaaccaaaga |
| | | aaatgaattttaaaggaagagagggtgata |
| | | ccaagttgtagaattctaggtatgtaggtt |
| | | cagaggagattttttttttttaagaaaaaa |
| | | aaaaaaaaaaaaaaaaacacccaatcaaga |
| | | agaatagagcagggtgtcccgaagagaacg |
| | | tgtgagctcgaagcatcccggcagcatctt |
| | | tcatatctcagtactgttgctctgtttctt |
| | | gggctcacaacaccatttcctctctcctgg |
| | | cttttaacacatctcgaggcaacctttcc |
| | | ctttctttttatgcacttctctcactgcgt |
| | | ctcttctatatcatcatcacttcaacctaa |
| | | cccagtattttatcccacctgcttattta |
| | | ccttccttcagtgactaaaaaccttactca |
| | | gatactgccagtgttgtttaattgagcaga |
| | | atagaggcttctcactataggcaactgtaa |
| | | atcaatgaaaataaccatttaaagaagaaa |
| | | aacattttcatgtctatcacggtcgatccc |
| | | ttctgccaaagtgatttggttcattcataa |
| | | attccccatacctcgtgtgttacatattgt |
| | | actgtacacatttactgaatgttcgattgt |
| | | gatcttgtaatacagactgttcattagccc |
| | | ccttctcttgacttaaaaagttgggggaa |
| | | ctaactcttttcatcccaaggaaactttct |
| | | tctactctgtcttgccagaaagttactgct |
| | | catttctcttgtagagcagcttgcctgtgt |
| | | ggcattcactcctgttctgcccactccctt |
| | | cctaatatcgtgcagtctggctttcatcta |
| | | tatcaaaaccacttattgatagatcaccaa |
| | | tgatttcctaatgccagtctacccagttca |
| | | ccaggaaactttaataactttttatgttta |
| | | ttaggaatttttaagttcattggaatacat |
| | | tcaagtactttttggaatgattatatgatg |
| | | tagaaatgtgtatgtttgagagacagaaaa |
| | | attgattttttttcctcttcactacagaa |
| | | taaataatgtatttgttttatggtagcaat |
| | | acttgaactctttaaggcatcttttcatgg |
| | | taaatctggcaattttaaaaatctgggctt |
| | | tgtaaaataattttttttatagtaaggcag |
| | | ttaacacattaaagcaactaggaaagatag |

TABLE 3-continued

| Sequences of exemplary target introns in pre-mRNA transcripts. | | |
|---|---|---|
| Gene | SEQ ID NO. | Intron |
| | | tgaagaattatttttaccttgagtctgtat |
| | | agatgaagtaggctctgctttgtgttggaa |
| | | cagaacaaacaaacaaaaaaacctgagttg |
| | | atacaaagataaagtaatcctcaaggaaag |
| | | tcctctctgttagagaagtggttatttaca |
| | | cacagaattccacatgacaacgcctgagtg |
| | | gtgtggtttccaggttattgatgagaaaat |
| | | cgagactcaaaatgggtcttttagaatgaa |
| | | gtacatttttcatggcctaagtctgtcttt |
| | | aaaagtcaccgttgtggccgggtgtggtgg |
| | | ctcacgcctgtaatcccagcactttaggag |
| | | gccaaggtgggcggatcacaaggtcaggag |
| | | atccagaccatcctggctaacacagtgaaa |
| | | ccccgtctctactaaaaatacaaaaaattt |
| | | agccaggcgtggtggcgggcgcctgtagtc |
| | | ccagctgctggggaggctgaggcaggagaa |
| | | tggcgtgaacctgggaggcggagcttgcgg |
| | | tgagccgagatcgcgccactgcactccagc |
| | | ctgggtgacagagcaagactcgtctcaaaa |
| | | aaaaaaaaaaaaaaaaaaaaagtcactgtt |
| | | gaagaatatcaataaattagtacaagcgta |
| | | aaagaacatttcttttctataatattata |
| | | catgctgctggtaatcaacactttactagc |
| | | aagtatattcttttgctttaaactcaagtt |
| | | ttaactgattaagaataaagacaagaatgt |
| | | tctctacaataatgtatggattgaatttgc |
| | | catttatcattttaatgtaggttttactta |
| | | tatactattgtgaaaatactcttaatgtat |
| | | tcaaaaggccagtgcacaattttttttttct |
| | | tttacttcttttttttttctttagaaagag |
| | | tgtcacttgc |
| | | tgcccaggctagagtgcagtggtgtgatca |
| | | tggctcactgcagccttgaactcctgggct |
| | | caagtgatctaatacctttaaagttgggaa |
| | | taaactttatcttaagcgtttttattttta |
| | | aattatgtttttgcatatttgatagaaaaa |
| | | gtagaatgtagtaattgaaaacctaatcac |
| | | aaaacaattcattggactctgcaacagtat |
| | | ataaaaaataaaattaaacgagataggaaa |
| | | tcttaagggattggtggattgatgcacatg |
| | | aaactggtaacctctgttaagtacagttct |
| | | ccaggtagttggagaaattagttaaatgtg |
| | | aagagaattttaattttgcactattttgta |
| | | catttctaaactgtgtctcccacagccctt |
| | | ctcccccagtgagcacgattcagaattact |
| | | ttgaaatgttgtagtcttaattatcctatt |
| | | catggaaatgacgaagctaatacacgatgt |
| | | gctctatcttaaaagtaacagatattttcc |
| | | caagtaacctactgctggttgtgatgctga |
| | | gggacatttcatgggactgcatggtcgttg |
| | | ctcatcgtgataccatcctcagtggttggg |
| | | ggattcacagtgaattctcatatcctgtaa |
| | | ctatgcatcatggatctatcatctgaaaat |
| | | aaatcaaaatctttgttgaactcacagttt |
| | | ccacacttgtatcacccatttaagattgtt |
| | | tcattgttacctcctgtgtacagaatattt |
| | | catttcaatttctcttagaacagctcattc |
| | | atctattctctagtttcaatattctgagca |
| | | gtagaagtttgctgttttgattaacttcag |
| | | ttagatctcttttctgggccaagaattaaa |
| | | gccattttatctttagtctctccttttgtt |
| | | ggcactgcttcatagactgtgtcatatata |
| | | cagatctgtctttagactgatctttaccaa |
| | | agtacactactggaatttgagggtttttt |
| | | ttttaacatccttttcattatgagagagct |
| | | agtgtatatgcattgtgggaaattagaaac |
| | | tatagatggcaaaattttaaaaaataattg |
| | | ccaccacccagagattgcactgtagtttaa |
| | | gacacttttgaatgtggtcctagggacata |
| | | atttctggaacacatttttcgtgaagaggt |
| | | ctcaggttggcttcttatacccacagctcg |
| | | ttgtcattgccccctagttttaatttcccat |
| | | cgctcagtgggctagattttttttcatttt |
| | | cttcatataaacttatttcagaaatgttca |

TABLE 3-continued

| Sequences of exemplary target introns in pre-mRNA transcripts. | | |
|---|---|---|
| Gene | SEQ ID NO. | Intron |
| | | ttaagaggaataagcagcattagtaaaaat |
| | | gaaacctatggtacccattactttatatag |
| | | ttcaagtattctggaagccatattgtagca |
| | | tagcatgtactgaaaatcactctcctttga |
| | | acagtaatcccatacctgtatttgggacct |
| | | ggccttcctttgtgtgcttgtgtattcatt |
| | | atatcccctttctctcttcaaagatgctca |
| | | agtcattctcatcttaaaactaatgggttg |
| | | aaccttccatgcagtctagtagctactgtg |
| | | aactctaatctctattacaaaggttagctc |
| | | tttgagtctcacttctactgaagttgtttt |
| | | tttttcccaagattactgaaaatttaagag |
| | | aaaataatggcccaggcatgcattcaggac |
| | | tagaaaatacttccatgtacagaaaaccaa |
| | | acaccacatgttctcactcataagtgggaa |
| | | ttgaacattgagaacacatggacacaggga |
| | | ggggaacagcatacgccagggcctgttggg |
| | | gcgtgggggcgaggggagggaacttagag |
| | | gacttaagtgcagcagaccaccatggcaca |
| | | cgtatacctgtgtagcctgcacattctgca |
| | | catagagcccgcttttgtttttgtttttgt |
| | | ttttaagaagaaataacggggaaaaaaaag |
| | | gtttcaaaactcataaagaaagagaaagag |
| | | agggagggagggagggaagaaaatgcttcc |
| | | atgtaactgcatcatttggtactttggagt |
| | | ccatatcctacttgaaactctaggatctgg |
| | | ccctcacatttatgtagtgctttattttac |
| | | agtttacaaaacttctgcttgtccatgtgt |
| | | gtctgtaaagtcatatgaggcattatgccc |
| | | attgttcagatagagaaattaacgttcatt |
| | | gacataaatggttaagcccatta |
| | | tgtaaatatttatggcaaagctggggctaa |
| | | tcatatgtgttacagataggacttttttta |
| | | aagaattgtttaggtattctgttcatcatt |
| | | agtctctgggtttgtgtttgtggtaaccat |
| | | agacaaccaagttcatataatttggcttct |
| | | tttttatgtgatttttgatacgtgttaagg |
| | | atctataacaatgaatttgcctcctaaaga |
| | | ggtacataatgttttcattcctccaaaaag |
| | | ataattctaggtttataaatctatgtatgc |
| | | tcagtgccagttgaattttgtgattgttca |
| | | atagaaaagaaattgtgacttaaaggtgat |
| | | tttccagtttaatggaataaatgaaattag |
| | | tttagaagttatttttatttttctgagcct |
| | | gattctcactcagttgtgataaacagcacc |
| | | tctgtaagataaactcggtgataaaccgag |
| | | aacttctgaaatcagcctaacatgaatacc |
| | | tgttcttcttgtgctaagtttcataatgct |
| | | ttatcctaatacaccatttttttaagaaat |
| | | ggaacttgtatttcattttgctttcatct |
| | | cacctaattcataattttattaaaacctac |
| | | gattttaatttctttttttatgaatttttt |
| | | agtttggtgtataaatcagaattacattct |
| | | ctgatcttttacttttaaaattacagtgat |
| | | gaactgactgtttaagaatcattctcatga |
| | | ttcattcgtctgttatgcctccttttttaaa |
| | | gcttcagcactgaaggtcttttgacaaacc |
| | | aatatttataacagtttgacagcaggatga |
| | | ggaacagcgtttgtctttgtaacagcttga |
| | | agaaagaccctttccaggacccagtcatgc |
| | | agttacaatcttgacctctttcttatgctg |
| | | ggaacatgcatacagcagcacctcccatgt |
| | | gttttcttgtcccattgactgtccattcac |
| | | ttcccatctgttttgcagtcttaaaggaac |
| | | agaaggggccttcttataaatctgtctttg |
| | | caggtgataaatgatgcctacctctttaag |
| | | agctgcctgggtggttttcctttttcttaga |
| | | acatttctgctttcctcctaactaaatcag |
| | | ggaaaaatacaattttaggaataagagaaa |
| | | aagaagaaaagatgaatttttaaagcattt |
| | | aattgactaagaatattttactgatctttt |
| | | ttaatcttcccaattaattgcctaaatcat |
| | | atttttaaaatgtattatcgatatttaga |
| | | tttttgtcagggagtaaaatgaatgtattc |

TABLE 3-continued

Sequences of exemplary target introns in pre-mRNA transcripts.

| Gene | SEQ ID NO. | Intron |
|---|---|---|
| | | attttgaaataatgtaactctttttttgaga |
| | | aaacaaagccatgtatcattaatgagttaa |
| | | catataaaataacttttttaagtttttttgtg |
| | | ataatttaagtgtggagcatcttatgtatt |
| | | ggatacaaaagtaaaatatttcagagtaaa |
| | | tcattgtaatcttatggtaaaatctattca |
| | | tttttacatttaaaaagatgatcataaat |
| | | cccataaacatttatgcttttacttctgtt |
| | | gctgaaaataagtattgtaggaatagatat |
| | | tgatatcattgggttttctaagaattcagc |
| | | agaaataaaaataatttacttttttctccca |
| | | tgcagaaattatttatgcaaggttttatgt |
| | | aacaaatattgtccctctatggccctgcag |
| | | aatattcttaaattactgatttaaaaacta |
| | | ttaccagtataaaatgaccacttttagaat |
| | | attgtggtgtattatgtgaatcagctggct |
| | | aataatatatcttctgtggactagcttgtt |
| | | agtttgtttattaattccctggcatattcc |
| | | aaaaggaatttgaggcagcttacatatatc |
| | | ctacgcaaaagataaaactacttaagtgaa |
| | | aaatttgggttgaaagaaaaggaaaatcca |
| | | ggcaagtgaaataaagtaaactttcagata |
| | | aaattggtgcccctcaaagtgcatgctcaa |
| | | gggttctacgtacaggcagacctcattgta |
| | | ttgcatgtcactttattgcacttcacagtt |
| | | attgcatttttaacaatagaagttttgtgg |
| | | caaccctgcattgaacaagcctgttggcac |
| | | tattttcccaacagccatgtgctcacctca |
| | | tgtcactgtcacattttggtaattcttgca |
| | | atatttcaaatttttccattattattctgt |
| | | ctgtcatggtgatctttgatgtttgtattg |
| | | tagctattttgggtaccactaactgtgccc |
| | | atattagtcagtgaccttaatcagtaaacg |
| | | tgtgtattctggctgttccaccaactagac |
| | | attccctgtctctctcctcctcttcaggcc |
| | | tccctattccataggacacaacaatattga |
| | | aatttggccagctaataaccctacaatggc |
| | | ctctacatgttcaagtgaaagaaagagtgc |
| | | catatttcactttaaatcaacaactagaaa |
| | | tgattaagcttagtaaaggaggtttgttga |
| | | aagccaaaatgggctattagccaaattgtg |
| | | aatgcaaaagaaaagttcttgaaggaaatt |
| | | aaaagtgttattccagtgaacacacgaatg |
| | | ataaagcagaacagccttattgcctgagac |
| | | gcaggaagtttcactggtctggatagaaga |
| | | tcaaaccagccataacattcccttaagcta |
| | | aaacctaatccagagcaagttcctaactct |
| | | attcaattctccgaaagctgagaggtgagg |
| | | aagctgcagaataaaatttgaagctagcaa |
| | | agtttggttcataaggtttaagaggaaaaa |
| | | agccattctgcaacatgaaagtgcaaggtg |
| | | ctgatgtagcagctgcagcaagttatcaag |
| | | aatatctaactaagataattgatgaaggtg |
| | | attatactaaacaacagattcttgatgcag |
| | | atgaagtagctgtctattggaagacgatgc |
| | | catctagtaatttaatagctagagagaagt |
| | | caatgcccagcttcgaggcttcgaaagaga |
| | | ggctatcccctcatttgggtgccaatgca |
| | | gcaggtgcctttaagttgaagccaacctaa |
| | | agaatttaccattctgaaaatcctagggcc |
| | | cttaaggattatgctaagtctatcctgctt |
| | | gttttctaaaagtggaacaaaaagcctgga |
| | | tgacagcacatctgtttacagcatggttta |
| | | ctgaatattataactctcgagacctgctca |
| | | gaaaagttttctttcaaaatattactgctc |
| | | attgacaatgcatctggtcaagcaagagtt |
| | | ctgagggagatgtacaaggagatttatgtt |
| | | gtttttgtgcctgctagcacaacatccatt |
| | | ctgcagcccatggatcaaggaatactttca |
| | | accttgaagtcttattattttaaaaatacg |
| | | tgtcttaaggccctagctgccatagatagt |
| | | gattcctctgatggatttaggagaaaaaaa |
| | | aaggaaaagcttctggaaaggactcaccat |
| | | tttagatgctgttaagaccattcaggattc |

TABLE 3-continued

Sequences of exemplary target introns in pre-mRNA transcripts.

| Gene | SEQ ID NO. | Intron |
|---|---|---|
| | | atgggaggaggtcagaatgtcaccattaac |
| | | agtttggaagaagttgattccaaccctcat |
| | | ggatgactttgaagagtttgggacttaaga |
| | | ggaggaagtaactgcagatatggtagagac |
| | | agcaatagaactagaattagttctgttgta |
| | | atatgataaaacttgaacagatgaaacatt |
| | | gctttttatggacaagcaaagaaagtggtt |
| | | tctttttttttttttttttttttggcagtct |
| | | cagtttgaagaaagtggtttcttgagatgg |
| | | aatctgttcctggtgaagatgctgtgaaca |
| | | ttgttgaaatggcagtaaaggatttagaat |
| | | attacataaacttagtagataaagcagctg |
| | | cagggtttgagaagatagtgtcccaatttt |
| | | taaagaagaaaaatttgagtaaatttgggt |
| | | aaaatttacccaaaattacctattgtgggt |
| | | aaaatgctatcagacagcatcacatcctac |
| | | tgtgaaatctttcatgaaaggaagaatcaa |
| | | tcagtgcagcaaactacaattgttgtctta |
| | | ttttaagaaattgccatagccaccgtaacc |
| | | tgcaacagccaccaccctgatcagtcagca |
| | | gccatcaacgtcagggccagaccctccacc |
| | | agcaaaaagattatgacttgctgaaggctc |
| | | aggtgatccttagcatttgttagcaataaa |
| | | gtacttttaaataagttatgtacattgtct |
| | | ttttagacataatgctattacacacttaat |
| | | atattacagtatactgtaaacgtaacttaa |
| | | acgcaccggaaaaccaaaaaaccttatgtg |
| | | actcactttattgtgatatacgctttattg |
| | | tggcagtctagaaccaaacttgcatatctc |
| | | ccaagtatgctgggactttgctagaggtaa |
| | | gctgcaaatttagccctcagtttcctggtg |
| | | gctggcagttacaaaatggaaagcagaggt |
| | | cattccatcattcatggtggccatcagaca |
| | | acaacacagcagttgcttaggagaagcatg |
| | | ggtcttcttcgtacgcacaactgagagaaa |
| | | tttcccttaaagtggacactgagttagatg |
| | | atacaatgaatctaatggctacacataatc |
| | | atgaaaatcatggggccctttattgtaatg |
| | | tttctcatgcgggctaacatgcgtagttct |
| | | agggaaaatatgatgctgtccaaacataca |
| | | gctatttggtttggcttatctaaagataaa |
| | | atacatagtatccagagaaatagatgaact |
| | | gtatgtcctccatacagtctcccataaata |
| | | ttatttctttttgcagctgatccttttagt |
| | | aaatatcaggtagccagaagttcaagattt |
| | | tacactcattgacattgacaagcacctgga |
| | | atggtactaccttttttttttttttttttt |
| | | tttgagacagagtcttgctctgtcacccag |
| | | gctggagtgcagtggcatgatcttggctca |
| | | ctacaacctccgcctcctggattcaagtga |
| | | ttctcctgcctcagcctcccaggtagctgg |
| | | gattacaggcgcccgccactacgcccggct |
| | | aatttttgtatttttagtagagatgggttt |
| | | tcgccatgttggccagggtgatcttgaact |
| | | cctgacctcatgtgatccacccgcctcggc |
| | | ctcccaaagtgctgggattacaggcgtgag |
| | | ccactgcgcccagccaagtactatttttat |
| | | tagttaagtcagagccataatcattataac |
| | | tgagctgaaattagaattgccatccactta |
| | | agaaagttgagtggtctaacaagtataaaa |
| | | gcctaaatataaggctaattcatgttcata |
| | | ctgaagccttttggggaataggccttaaaa |
| | | tatgtagaaagtatttgaagcggttttaat |
| | | tgtactagccaaaaggagcctagtagaaat |
| | | gcttgtgttataagagtttatttttttaaaa |
| | | agctgaatttatctgaccaggcgcggtggt |
| | | tcacgcctgtaatcccagcactttgggagg |
| | | ccaaggcaggtggatcacgaggtcaggagt |
| | | ttgagaccagcctagccaatatggtgaaac |
| | | cccatcactactaaaaatacaaaaaaattg |
| | | gccaggcatggtgatgcctgcctgtagtcc |
| | | cagctactccggaggctgaggcagaagaat |
| | | catttgaaaccgggaggcggaggttgcagt |
| | | gagccgagattgcgccactgcactccagcc |

TABLE 3-continued

Sequences of exemplary target introns in pre-mRNA transcripts.

| Gene | SEQ ID NO. | Intron |
|---|---|---|
| | | tggacgacagagcgagactccatctcaaaa |
| | | aaaaaaaaagctgaatttatcaacaaattg |
| | | ctgtggagtttttatatattcagcaggca |
| | | tcagttgtaatttacctcacagactttctt |
| | | aaggttgctttctttctaaattatacttta |
| | | tgggggtcacaaaatagcaatttttaaata |
| | | atcacctttaatgattaagtattgtttaag |
| | | tcagatcactcaactatgaatgcatgaata |
| | | ttcatggacatctattacatagcaagcagt |
| | | gctatgctgggccgagtgattttaaatgac |
| | | agacttttggtaagtagagaatttaccca |
| | | agcagtccttgctgttctccacattaatgc |
| | | tcagaaaaaatacattataaaaatgatctt |
| | | tccaaaatgaattatgaagccccatgagaa |
| | | tgatatggcaatttgtggttacatatttta |
| | | ctagaggattaatatccaataaataaaaag |
| | | atactaaggaataaacaaaaaaaatttaaa |
| | | agatgaagtatataatgaattagaacaata |
| | | cattttaatcataagttttaaattagtgtg |
| | | gactttgaattctcctggacagattccttc |
| | | atttatagataaagctaggactgtgactt |
| | | atccagttatgaggttaacggcgaatacaa |
| | | cattgtcatatattttaaatgacacacatt |
| | | acaacatgttctctgctttataaaaatcat |
| | | atcaaataattgccccatagattattaaag |
| | | gtgttagactagggattcttaaaaaaaatt |
| | | ttcatcaaatgtttctttcattattaatcc |
| | | catgaagtccatgttacagaagattttgtc |
| | | tacaacagtgcagttacattcttctcgtta |
| | | gaaatacaaccaccagttagagttcctaat |
| | | cagtataaggaagtagttgttaggagaggg |
| | | gatgggtttcttgtccaaatgaagttttcc |
| | | atttgagtttttgaagtagtgaaactaacc |
| | | cagcgtttacaggccccagaaatctgggaa |
| | | cctcagctttcaaagtactgtaccagtctt |
| | | taacagttttcctggacgtgtgaattgatg |
| | | cctccttctgtaacatgcaggagtgttctg |
| | | tctgtcttcattgagtgttaaaaaataatc |
| | | atgcctatttcaaggaaaaaatctacagaa |
| | | ctaagatgcagaagataagtgctagattta |
| | | atcatattccttcatctatctgtttggttc |
| | | aacctttcatcaactaaaagatgcaccttt |
| | | tttcttgtgctaactctaagattttagcta |
| | | cagttttgagaatcttgagtgtagtctctt |
| | | gtttaccttttttcctttttttgtttcccc |
| | | cacaccctagattcatttaaatactgaact |
| | | tctaaagggcaagtatatagtgtagtttaa |
| | | taaaaagcaaaccttttcatgaacaatata |
| | | tattacataataagaagcgttcctttactt |
| | | ttcagtactctagtgaatagctttctacag |
| | | tagaatctcacttagagggtgtcttaaagc |
| | | ttaacaccaagtgctcaggcagcatgttat |
| | | acaacagttccattaaggtacatttggatc |
| | | tttggatgtgtggtttgcttaaagtacact |
| | | gcattagtaagttggcagcttgctttcttt |
| | | aaaaacatcaaaagttttaaaaggtttatt |
| | | tcagggcatgtgttagtgttttgtgtgtgg |
| | | ttctttgttcctgttctaaactgttattaa |
| | | ccactgaagtgaaccttctcccgggtttgg |
| | | ccttttggtattcacagtgtattcaaaacc |
| | | taattacagattagtctatatttgagactt |
| | | ttagagcaagtatcagaagacccaaaaaga |
| | | aaatgagagtagcagtatcatttcatgtag |
| | | agataaagagacccaaaacatgaatgggtg |
| | | tcaagtcagctgaagaaaagaaaaaagaga |
| | | aggaacttcattcactgagacggtttatga |
| | | gttggggattatgggaatattcatgactca |
| | | atcaagaagcacagtgaattgatgtttgaa |
| | | atagctcatcttttaagtaaacattggata |
| | | aatggaaagtagactcagtattcactacac |
| | | gtagaaatagctatttctgtatagcagaaa |
| | | tagcagtttgttaatcccttcctgagttgg |
| | | tttaatttaccaagtaaatcacaaatttta |
| | | ttctttatttgtgaatatttaattcaaata |

TABLE 3-continued

Sequences of exemplary target introns in pre-mRNA transcripts.

| Gene | SEQ ID NO. | Intron |
|---|---|---|
| | | tttaatggaaatatgagtttgctttataat |
| | | tagtcatgctgatccatacacgtatttctg |
| | | agagaaagcaatttctaatggtgaaatagt |
| | | tacaataatatttttgaaatttgaaagcac |
| | | cgtgatactgaagcattaatctgaaggatc |
| | | ggaaagtagggagtttttgttgccaacatt |
| | | taacttcattgtttatggataacttggttt |
| | | tctgggcagccagatggcacagttagtata |
| | | cagacattcttggaaacttgtatcaaaatt |
| | | taaaatgaatgaatttatgagaaataattc |
| | | tgcttattatttgtaatgtagctttcttga |
| | | aaagcaagaaatcggaatgtagtttctaaa |
| | | gctgcaagtgaatatgtatacatagccagc |
| | | tctttcagccttgataataaggtgcaacca |
| | | ttaagatgaagggattttttttcccactt |
| | | gtgtttttgggcccgagtatcctgatctgt |
| | | gttgcttgtctggttcaggtgtgagccacc |
| | | agctttctttgactttcattatctatgtgt |
| | | atcttgcctcctgttcccaggcttgctcta |
| | | gctcttctgatcctgtcttcctccctcttg |
| | | atcactagtgtagtattcatgaagccagct |
| | | aagttagtttttccctttgaaaaccacagc |
| | | ccttatcttctgtgccatattttgggcaac |
| | | ttcgtttatcattgattgaccgtacgcagt |
| | | gatcaggccttgttctagacactgaagact |
| | | ctgagcatttttgggcccattttgtactcc |
| | | tgtattgttctccaggggcttctccaagtg |
| | | tgcgtcaatttagtcttctcaagagggcat |
| | | cattttcatcagaatatgatagcatattat |
| | | ggagtgtccggtcatccttaggcatagact |
| | | acttaggaggtgtaactgttttgttccctg |
| | | atttttactgaaatgggtcttttcttttt |
| | | ttttttttgagacagagtctcgctat |
| | | gtcaccaggctggagtgcagtggcatgatc |
| | | tcagctcactgcaacctccgcctcccgatt |
| | | ctccctgaaatgcgtcttattttaagtcaa |
| | | aggtaatacttaaaaaagaccaaagagact |
| | | taaaataacagcatttgcttcgtcactatg |
| | | agctttgttattatgagttaacatacagta |
| | | gcagactgggtgtagtagctcacgccctgt |
| | | aattccagcagtttgtgaagccgagtgggg |
| | | aggattgcttgaggccaagacttcgagacc |
| | | agcctgggcaacatagtgagacccccatct |
| | | tgacaaaaaaaattgttttaaattagccag |
| | | gtgtggtgctgcatgcctgtggtcccagct |
| | | acttggaaggctaaggtaggagaatcgctt |
| | | gagcctgggaggtcgaggctgtagtgagcc |
| | | gtgtttgcatcactgcactcctgggtgaca |
| | | gtgcaagactctgcgtcagacaaacaaaca |
| | | tcgtagcagatgtgtttcttaatcagagaa |
| | | gtgtagacaaggctaactccaggctttaat |
| | | gtcctcatatttagcaatgatacctgcaag |
| | | gttgtatgagaaccaaatgaaacgccaaat |
| | | ttggaaatacatagtagatacatcatagca |
| | | gagtaagccaggaatgcttctcaaaggtag |
| | | gatatcatctgtgtcctcatatcactttat |
| | | gaagtacattgtgaaagtgaaagaacaaag |
| | | aaataaatgtttttttagttaatgtttaaag |
| | | gatacatttatcataattgctcttttaaca |
| | | ctcacctccagtctcccctccgttcacacc |
| | | tcctacccccattacttcctggtaacttag |
| | | ttaagtgtcctttgtcattcctgaggtttc |
| | | aaggcatggtagtactgtgtcctgatattc |
| | | taatcgtaaatatttaagggaaattcggca |
| | | ttttttcattttgtggttttcatattaaag |
| | | tacattaaatagtctttttgcttttattta |
| | | ggaaaaaaactgcttacctgttaattttag |
| | | aaaaatctgattttcatttagaccttacag |
| | | ggtgagacacctgcatcagggtggctcttg |
| | | gtatctttcaattcaattggatcttctctg |
| | | aatagtctcttgtagggagtgaggctgctg |
| | | taccacctccctgcagtagtccatccagct |
| | | taagatgggggtcaccagtaggccaaaaga |
| | | atgggtagacctggccatgcactgccctat |

TABLE 3-continued

Sequences of exemplary target introns in pre-mRNA transcripts.

| Gene | SEQ ID NO. | Intron |
|---|---|---|
| | | tgtactcaaatcgtgtatcaaatggagttg |
| | | gatttcttctcttcatacagtacagcattt |
| | | ccaagtagaaatatttctcaatgaaatgtg |
| | | gagagaagcacccgtttgagattcccgtgt |
| | | gttgtgtgatttaagttagatggtttttta |
| | | agaccacattcatttccagcattctaggta |
| | | acaatttagaaaatgtctttctcctaacct |
| | | ccccacttttaaaaatcctccaactgatg |
| | | aactgatgtgaaactttcttacattcactg |
| | | aaaaaaaaaaaaaaataggttaagctgtttc |
| | | taagcaactagatgaattaatttttaaact |
| | | aagaatgtggccttattttgggaaaacaag |
| | | aatatttacttgtttgtctgctgtttaaaa |
| | | aatggaagtcagcctaccaaaaaattgaga |
| | | ctcaacttctaggagatgggttaggatttt |
| | | tttttttaagtttctctagtttaattttat |
| | | atataaggggttaatgctaccttcataata |
| | | actattatcatattttctcaatacatagct |
| | | tgattaaaacaactggactcccccccacc |
| | | ccaccccacacacacacagattttatatca |
| | | gtctgaatctaatgcctagaataagaagtg |
| | | cttcagccaggcatagtggcactcacctgt |
| | | agtctcagctactcaggaggctgaggcagc |
| | | aggatcaattgagcccaggagtctgagtct |
| | | agcctgggcaacatagtgagacctagaagt |
| | | tttaaattactggaaaaataatatgaaaag |
| | | aataaattactggaaaaagaatatgaaaat |
| | | gttacgttctttatatccaaccgtggtagg |
| | | ctttttttgagttcctgcaatgctaataaga |
| | | attcataaaaaggacaattcttcattttct |
| | | tgggtactcatcactaatagctgcctcgct |
| | | ggtaaaaaggaatacatgtatcttcaattg |
| | | cagattatttacttttaaatataaaagata |
| | | taaatgtcaaatattaaatgcatcttacat |
| | | ggttttcctacatagtgaaagtagaatgct |
| | | tgccagttttgcctctaggtcactcacttt |
| | | gaaccagccaacccaccttaattgatcatt |
| | | tccactaatatgttaaattaccttaaaaga |
| | | acaaaaatatttatcatgcttactataacc |
| | | tgtgttttaaaataggaggccaggcacagt |

TABLE 3-continued

Sequences of exemplary target introns in pre-mRNA transcripts.

| Gene | SEQ ID NO. | Intron |
|---|---|---|
| | | ggctcacacctgtaatcccaggactttggg |
| | | aggccaaggcaggaggatcacttgagccca |
| | | ggtgttcaggaccagcctgggcaacaaagt |
| | | gagatcctatctccacaaaaaaattaaaaa |
| | | taaaaacttagccaggcgtggtggcacgtg |
| | | cctgtggtcttagctacgtgggaggccaag |
| | | gcgggaggatcacctgagctcaggaggttg |
| | | aggctgcagtaagccctgccaacaccactg |
| | | cacgccaacctgggcgacagagtaggaccc |
| | | ccatctcagaatataaaataaagtaggagg |
| | | tgcatgtgaagtagtatagatcatgacttt |
| | | tccaattttaagaggggattggcatgtact |
| | | atgagcagttcacatttgtggaggaaatct |
| | | acatttcagagagtatatatttcatttgga |
| | | agtctataaacatgaaaacctaaaataaat |
| | | aatgtaaatctacctctagtggctctggta |
| | | tttttaaacttatttatagctggcaaagta |
| | | ctttttttgtatgtatttttatagcaccatt |
| | | gcacttctcatgtttgttgcaagcatctcc |
| | | cacagcttcctttgtcttttaattttatga |
| | | catataaataaaagtatacatttcaatatg |
| | | gccatattgattgatcttttcctttgtaac |
| | | tcttactactttatatttaaaaagtcattt |
| | | cccagtctaaggccacctctattttctttt |
| | | agtttttttaaaatggtttcattgttttata |
| | | tttgcctatgatccagacattagtaactgt |
| | | gggttcttaattgggcttcagagaatctga |
| | | gaattccttaaaattctctacataattgta |
| | | catgtacttaatacatgctttttttccatgt |
| | | taagagtccagagtttttgttagatcctca |
| | | aaggggtcagtcagtctctcctcccacttc |
| | | caaaaaatgtctgagacctactactataat |
| | | ccatctggactttatttgggtaaaaggtgg |
| | | tatggtgagactcatatttttcttttcccc |
| | | gcaaatagttaagtataccaaccatttagt |
| | | aaataattacctcctgatttgtgatacctt |
| | | tgaaaaataaatgtttttctttatttttat |
| | | ctccacag |

TABLE 4

Exemplary target gene intron sequences

SEQ ID NO: 4

Gene: OPA1
Intron: GRCh38/hg38: chr3 193626203 to 193631611
Intron Sequence:
gtgatggatggtttaaggggctaccgatacattcacactaatcagccatttctgccaagatcatgtcacctcaatctgttcatggactcca
aatacaagaaattaatttgacaaagtgaaaatataaaagatgcatcatataaatatgtaacttttctggagtgggtagtataggtaaagcca
aaagaaacaaattcaagcagaggaattttggtttctgaaaattaggttgtctgtagggtccctgtatttatacttagaacaaaattaggaattt
ctgtttatgtggtccagttattgagtcaccctaagtttgtaggcatcttacctacctacttgctccccaagtttttatttctaaaatgaaaagcat
tgctgtagatgaccagtttacactaaagaataacatttatttatttgttttagctaaagtatatggacagggaacattcatattcttgtagaaga
aaattattttgacttttgggcaaaagcatgtagttcttatacactttgacaaactcattgcgtacatttttcacattaatcaaagtcagcacaaat
aaattttcaccttggaccacggagggtttgaacactggaaatttgatataattctggttgctaaagaacaagttctaataaaagcttaagtgt
ataccaatatgtggctgttggtgcaatcagcaggtccgtaaaaatatgatttaatggttaggtaatcccacaacggagatcccaaagttc
atgtttggaagagacttttgggtcaaagtgaaatcagtgtaatgaatttaaaattatactctgagatcttgaaatcagctaattatgttacatct
tattagctcagaaaagttttgaagttatatacaaatgctagtcaggaaaaaagattcagtcatgtaattcttgtacattctactatttaaatcaa
ccaatattatagattatgatttagtgcagtaattctgctggctaaccttatctcatttggtggtggttagtacttcagagtactcaccatagtttc
atttatgttttcagcatcacttcctggtttttctcaattccatggctgtggaatcaattcatatgtatatttagcttcggtgagcaaaaacatagct
agaaaaagaaaagaagtgagtttcctacctggttaaattaaagtcgatgtgttaagccaaggaggacttcttttgaatggtactttaacaat
ccctgttctgtatactgtgaatatatcatttaaatagcctaataaattggatgcttaggctgagccacctatactttagttttgttatggaaaga
agggagaggagcaagtatgttcttatatgttacttagaaataagaatgtagctgtagttacacattgttcttaagtttttttcgtaagacaactt
gaaatgagtcccataggcctgctatttaacattctaagatatgacttaaggttaatgatgagcttttgaatctgacaattcaagagatatccat
aatgaatactgattcattttctacattgctgaaagctaatgttcattttaagcctactttagtagcctttatttgggcttagagatgttattcctcttt
ctgatatttattgggttatctgtttaacccttttatatctccctttcccgatttgtaaattagagactggcaagactttttaccctgagtagagcac
caaacatggcttgtttctgcccacactgtagttaccttgaggggaagtaaatgggactttaaaagcaatttatgctcttttatagtgaaattat
ccctcttactatcccgaaagactgttaccttacaatatcctccactcctttccccctgtagttactatagagatgacttttcggttcttcactgc
cataatgatcaaaatcctaattcatgagatttttatcattccaggcatgtgaggtttacttgatgcataaaaccgcaagtactttttgttgtttttt
aattgtttttctctcttatcttcttgaaagtctaagtagatcatcattttgatgtcttattagtagcaactaataaattttccctgtatcttctcagc
aaaagaactcaagcagagacagaagattagaactaccattggtagttttgcttcctatggatatgttcacatacatagaaatttttacaatga TABLE 4-continued

| Exemplary target gene intron sequences |
| --- |
| cctttttatatatgtatttcagaatttcagaatggcctcaatgccttaataggaagaaatacttgaaatttttaaattagggcttggttttgtgag<br>gagctagtaaaggtttttctctttcagctttagcttgtttctgcggaggattccgctctttctccatcagtttcatagccctggaattgtagaaa<br>agctctggtttcaagaccattgatatccatttctgtcagggtgagttttaaatttatttcatgatgcaaacaatatattgaacaacaggacatg<br>aacttgttcttgttgtaagtggctgaattttatcagtaaagcacatcaaaataaaatataccccaattgctagttaagacctagagtgacaga<br>ttgaaaatagcttgtgttattctcttaagaaaatatataaaaattatcatctcatcaatctttaatgtttgttttataaatctaaatgtttttatattgttt<br>cctaggaaatattaggtctaatttttactttaccaccagctgtcttttatttactctttttttgagacggagtttcgctcttgttgcttaggctaga<br>gtgcagtggcactatctcagctcactgcgacctctgcctcccgggttcaagcgattctcctgcctcagtctcccgagtagctgggattac<br>aggcacatgccactacaccaggctaattttgtatttttagtagagacggggtttcttcatgttggtcaggctggtctcgaactcccgacctc<br>aggtgatccgcctgcctcggcctcccagagtgctgggattacaggcatgagccaccgcacctggccagctgtcttttaatataacattat<br>gattaattgtgatgttccattaaactaagcggagaggaaacatgctggtaaaccatgtgtgagttattcattgtaccagaaaggcaaatga<br>tacattttatcctaaaattcaaatttataaacatcttaacacttgtgatcattaaatactactaatctagcatataaattatatttgtaggcggggc<br>acggtggctcacgcctgtaatcccagcactttgggaggctgaggtgggcagatcacgaggtcaggagatcgagaccatcctggctaa<br>catggtgaaaccccatctctactaaaaatacaaaaaaaattagctgggtgtgctggcgggcacctgtagtcccagctacttgggaggct<br>gaggcaggagaatggcgtgacccaggaggcagagcttccagcctgggcgactccgtctcaaaaaaaaagaaaaaagaaattatat<br>ttgtaatattctactaaccttatatcattttaacttttatataactttttattttaccaaattaagttaacctttatagcccttggcttatactaaaca<br>tcctaactttttgtttaattgtattagttttaagttattgccccagatgtcaagtaatgttggattttctataataatttaggatatattgcatgaag<br>tcagttagtatttacatttaaaactaaaacaatttatactaatacagtttatacatttcatactaatttagctacagttggataaatatttaatggaa<br>caaagtaaatcaaagtaccttttcaaatgaattggaaattaaatccacataacaatttttatgaccacactattacagtgtgatggcatgcc<br>aaatgatcataatgtggaattatgtatttcttcattggctttcaagattctgttctttagtttgtgggctcctctccaacttgcttgtctcctcacag<br>tttaggcgactgtttataattcttgtccatcctgcataaacacacacagtcaaaatgaaaaaaagcttctatcagcagatctgtgcttgctgt<br>acagaaatgggaaaacaattgaagtttgcattatctttttttctaattaccagatcgtttttggagctatttaggcatacgcttttaaggaaaaaa<br>gaaaaaaagagtgtaccttttgtttctaacaaaggttgttatctatattattgaaataaaaaattggggatagttatgacaaagtatttagaaat<br>aggaattaaaatcttaaaataacttttcatagcatggacaagacttattaatgtctacctcaataagcaaatcatttaaaaatttttcatgtatat<br>ttgctgccatgatgtgttgtgattgcttaaataaccaatgaatgaagatcaacaaggatttaaatgaagaagaatatggatttaactattttct<br>cctgtgaaataagttcatatttacaagttttgattttcagaaattagacaattatttttaaaggctgggatgacaacttctgcctcttaccaaga<br>agtcaaagcacagttatgtgaattcatcataaatcacatcatttttattatatttgtatttataattgtattgtgactactttaaaacctgttataaa<br>ataaaattgtttttaatatttatttagaattattagcattaataacaatttgaagtagtttacacaatacctgtgagttttatttttgttttatattga<br>aattaattttagttgctttacttggcttcattgctatggatgcattctctgtgttacgagttagcagatctttccttggaactgaatttaaaagcaa<br>gcatttggctccacttaaatctctgaaaatgcaacttgttctttgcatttattacataattcgctacttatggtacagaaatggatacaatacaa<br>aaatatttccttataagatacactgtgaccaatgagctttttaaatagctgtaatcagtaacatgtatttgacttttcaaaacacatttctggag<br>ggatatcagtgctttatttccccaaatatctgaatccctatgctttagtacaaaacaacttctgaagaatttagtaaccatatgtgttgatctctt<br>gtttttctaactagtctttcataagaaatgactagaatagcaacagggaaatgattgccttttaaggttttgtttctcaatataaaatttggtga<br>accattttattgataaatacaggtatttttactttcttaaatcacttgatttaaaattactttgattaaatatgcatataaagtcagttgtttttaactc<br>tcaatacttatcaaaaaaatttaacttgctgtacattctgtataaacctaattctattcaactaaaattattttaaacatttag |
| SEQ ID NO: 5<br>Gene: OPA1<br>Intron: GRCh38/hg38: chr3 193593374 to 193614710<br>Intron Sequence:<br>gtaagtgcaggctctaatctggccccgttaattctggggcctcttgagagtggggctgtcttatctctatctccaaaaatgtgcaggtgact<br>ctcaggccaggccgacggcagttggagaattcccagatgttcttgaggacccagaatgacaggagccctggctgggcttacgttcgg<br>agccggcttcaatactggccctttctctggccctacccaacccgaaaattctggacgcctctcaatcttggcccgtctctattgtccttttgt<br>ctctgccctttacacccttgtgtcttcagtgttctgtctgtctctggttgcctcttttgcctttttctgtcctctccctgccaggtttggctctgtcc<br>atgagtcacctctctccacatttctcctaactctcggtgtcttctttttcttccatttccacgccatgtgtacattgcatcttcaggtacctgggct<br>cttctatcggggaaaggggcgtccgtctctttccctagcccgctgatagaagtcagaactagagcaatgacgcacacggtgtcagaga<br>cggtgattcgagatgccctttcaatagcagctttttctgtgtttcgggagggagacttacttttgatgcaaggtcgtgaacgtggcacca<br>cctttctaatctcaatcattgttgccctggggtggtttaattctaaatagaaaatcatagaaatcttttcatttctgtgcgttactatatgcattgta<br>atgagattaaattggattttataggaaattttgttctagtatcattagataccttcaagcttagctcattgttgcaggcatttgataggaagtaa<br>gatgcatcaagcaaaattggaaaaacgtggttttcctgaattaacttctaagcagttgttttgaatttttccagaccttttaagtggtatagat<br>aatttatcgtgtttataaggaatggaatgcattcgttagtttgtttttgttttgttttgagacggagtcttgctctgtcgtccaggctggagtgca<br>gtagcgctatctcggctcactgcaacctccgcctcccaggttcaagcaattctcctgtctccgcctccggagtagctggaattacaggca<br>cgcgccagcacgcctagctaattttgtatttttagtagagaggggtttcaccattttggccaggctggtctcgaactcctgacctcatgt<br>gatccaccctcctcgacttcccaaagtgctgggattacaaccgtgagccaccgcgcccggcccaatttgttttatataggttaactggagt<br>ccaaaatacagaactagatgagataacaatagttaacagtgttagtcagttagaattattgcataggtattttaatctcatggaattttagtct<br>ttgagtaagttcacagcccttggtattaaagtaagttatttacaacccttgcatttctacttctcaatatttagtgaggaaacatatctgatttct<br>ttaaataaaaagagaaaagactgcagaagatagcattctctgttggagcaattaagatgtataagaagaactacaaagacggagttttaa<br>aacaaactgatttataagtggtatttatttaattggctgtcattgggctaaattatttctaaagttaccatggatgccattgagtcatggcttaaa<br>aatgtctcctggtgatggcacagtttagctacctaaagaagtagagatgtgggaagccagaagccccaagctctgcagttttcttttgct<br>atagttcctttgcatgttgtgaaagaatacagttaaattcctgctccctaacagatgagagcataagcatttctttgggcatacatatgtaaat<br>acatgctcatggacatgtgaaaagatcaatactaacatttgggtgcaataaataattgtgtaaaattatttttaaaagaattacatattaggaa<br>atgatatattgattaaaagtgatagtcaatgaacaagagagtagatttctgggggaaacctatttgcatcatacttgattttagttttgactg<br>aatattgaagtctatattcaaaattcttttcctttagaactgtaaaggcattgctgcattttcttctaatgtaattgtttattgctgctgagaattctt<br>atgacaatctgatttttcatcttcatgattatcttgtttttcccttcatggaatctgttagggtcttgactttatcctttatcctaaatttctcaaggc<br>ttggaccaggtgtgggtttggttttgttttcttttgctactcatttgacttggcacactcagtgggcctttccctttatctttcttcatttctgagac<br>gtttttctctcttatttttattatcttcctttcattttcctgtccttttttctttctagacatctcttaggaggatagtggtcctcttagattgatatgttat<br>gtccgtgatttccaaagtaagatttgtactcgtcgtctgttaaaaggaaaagcatacatatacctatgtatatatgcacactttttattttttaa<br>attatatatgtatctgtactaattatttacattgtaagtcaaccctaacataatcttaaaggataagatacaaaacatactgcatctagaagctt<br>cagtactttcttcctgaatcccagtagatccttttgttcatcccacgggatgcattccgcccccatcctcccactccctttggataccacatta<br>ccacagctctgcatcacttaactttcctcttatgttttcaccttttttttttttttttttttttgcattttatgtcctggggaatttccttaattcatttcatgg<br>ttttactgttgatttttttaatattggccatcgcaactttttcttttcttttcctttcctttcctttcctttcctttcctttcttttcttttcttttcttttct<br>taattttcttttcttttcttttcttttctgttcttttcttttcttttcttttcttttctttcacacaggatcttggcgtgttgtccaggctggcctcgaactcct<br>gggctcaggtaatcctctcaccttggcctcccaaaatgccaggattacaggcgtgcgccactgcatttggcggcaacttaatttttttattttttatttt<br>tccttttagaggacacctagcactgagcattgcaacttttcatttccatgaacttttaagaaaactcttaaagacatgtttaattctgtacacttt<br>ctattgttctttgattgctgtttttgaataacaacaaggagtacgccttagcattttgatggtatcctcttaatagtcgcaataatagtccccttg<br>gcgctctgtatactctcaagtcttaaatgttttgtatgcagctgtacgttgacagttgaatggtctcgctccaagtggatcagcaagaacata<br>aagaatcatttaactggtacaggctgcggcttgtgaattccctattaacaccaaagaagacgtgtgagactccgtactgaaactaaagac<br>gacttgtgagttccacactgagatcaaataagtctttatgatggtgacagagagtggtgtcaacgcctaaagttttggttaatctctctaaat<br>tgaggggctgaccaaaaggggaacttaactgtattagacataattttgagaaacatgggtatgtggatggtaatggaggaaatgggtg |

TABLE 4-continued

| Exemplary target gene intron sequences |
| --- |
| tagatgagattgcctagggagagtgagaagtaggttaggtctaagccttgatgagttcccaacatttccaagggtagttgaggatactga<br>aaatgagtggccagtgagatagaggtaaagctagagactgcccaggggagaggaattttcaacaatgaggaggtgtcaacattgtca<br>ggtattgctgagaggtcagataaaaccagaattgagcaaaatggccattggaagcctatggtgccctccgtaagagctgtttcgctgaa<br>gtgatagaaacggaaatcaggctgggcacagtggctcactcctgtaatcccagcactttgggaggccgaggtgggcggatcacctga<br>ggttaggagttcgagaccagcctggccaacatggtgaaaccctgtctctactaaaaatacaaaaagtagccaggtgtggtggcaggtc<br>cctgtaatcccagctactcaggaggctgaggcaggagaatcgcttgagccccagaggcggaggttgcagtgagcagagatcgagcc<br>actgcactccaacctgggtgacagagcaagactccgtttcaaaaaaaaaaaaaaaaaaaagaaatggaaatcaggatggtttggcttta<br>ttttaataaaatagctagagcagggaaatggggtactttttttcccccttttaagatgagacatagccaggtgcagtggcttacacctgtaat<br>cccaacactttgaaagggagggtcgcttgagctcaggagtttgagaccagcctaggcaacatagcaagaccttgtctctactaaaattc<br>aaaaaaaattaactgggcatgctggcacacacctctagtcccagctatttatgaagctgaggcaggaggatcacacttgagcccagata<br>cgtggggctgcagtgagccctgataatgccattgcactccacgttgggcaacagagcaagacttcgtctcaaaaataaataaataccct<br>gtctcaaaaataaaaaataaatatgggaggagagatttgacttagattcctcaaagggcaggaggaaagagaattccaaacagtgattc<br>acctttaatgggagaaagatcgcttaattttacatgaggaagaagaggattggtggagatacagtaggtgaacagtttttgtatgaggaa<br>gttgaacatgtgtcattctaatagcttccattctctgtgaagtagagggcaaggtcatctactgagagttggggaggtcaagagagataa<br>ggggagattagaagagctcttctagcagagagtggaagaatgaattgctaagagagatgaagtaggattgttaagtagttttgagggcc<br>ctgttgagatgtgcttccagttgggtgtgattttctccagtagtgctttatttccctgggtacaggcagagagaaaaacaataaggctcatgt<br>agggtttgtattttgttggacaagtcaaacagaaaagtcagaggacgagggagtttagaatgtttgcaaaagagttattgaaacgatgaa<br>ccgcataatctaaggtggtaagtgggtgaatagataaggaggatgtgaataggtaaggagaagaaagaaatatcagattattgattattg<br>atggcgactctctaatacagctattatgccattttaaccgattaagaaactaaggctttagaaaattcataatttgccctaactgcacagcta<br>gtaagcagtggaaatgtgattggaaccagagttcttctgactcaatagactaaatggatgtaaggatgtagttgaaagaagggtgagcta<br>aacgttgtggaaccatgagctctttctctggttgatatccctctctgtaagtgataacatgggtcacgctggataaaaccttgtggtgattgg<br>tgactttcctttgtccttcctcctgtgcctagtctggcgagtatctgcctttccctttcctttctcattgctgccacctaactttaggctcttcccct<br>tacatctgggtaactgaaataagatcaccttttttgttccccttctgatttactttgacctaacattatctttactattttctttaaattaatgtttcatta<br>gtcttattctactcaggaactctgtagttccccattgcctacgaaaaaaagttaagcctcagccttatattcagtgactcttcaattggatattc<br>agtccagttttactcctcctatgagccttctatgccagctccttgggtctcttgccctttcattgtctcagctctgcacccttctttctctttttttatt<br>cttttttttttttgtactttttttggttttcttttttggtttcttttttttgttttatttattaaacctccatcacacttcatcctatggagttttgaaccacagcaa<br>ggtgcagtatcatcctggggctctggaggaagtggcagggagtccaaaatgtcaccttagcttcttatctggggccacatgtatttctgc<br>atctgctgcttcccacactcttgcccacaagtgtcgcttgtggaaataatttgagatttactgtctggctgaccctagtttcaatctcttttcca<br>ccatttgctaatcattctaccttgggcaaaacatagaattaaaagaaaacttcagacaagttaaatttgatggagtttaattgagcaaagaa<br>aaaaaatgatccacaaattgggcagtctccagaatcaccgcagattcagagagactccaggggtgcctcgtggtcagaacaaatttata<br>gacagaaaaggtaaagtgacctacaggaatcagaattgagacatagaaacagtgagattggttacagctcggcgtttgccttatttgaa<br>cgcagtttgaacactcagcagtctatgagtggttgaagtatggccgctgggattggccaacactcagctgttattacagatgcatactact<br>aagttaggttttcgattttgtctgcctatttgagctaggttacagttcgtccacaaggactcaaatataaaagtacggagtcctcttcgggcc<br>atatttagttcgctttaacaattccccctttggtcagcccctcaatttagagagattgaccaaaactttaggcgttgacaccactctctgtca<br>ccatcataaagacttatttggtctcagtgtggaactcacaagtcgtctttagtttcagtatggagtctcacacatcttctttggtgttaataggg<br>aattcacaagttgcaactttgtaccagctaaatgattctttatgttcttgctgatccagttggagtaagaccattcaactgtcaatgtacagct<br>gcatacaaaacatttaagacttgagagtatacagtgcaccaaggggactattattatgactgttaagaggacaccgtcaaaatgctaagg<br>tgtactccttaataaaagttcttatgaaatgaactgaaccaaatcagccaagttaaggttcagacaatataagcagttcagcagtattgggg<br>tctgattggtcagagtcttcagttggagtatgatagtgattaaggatcatagttcgctgtaaagtagcttgacttaaagaggtgctcgttttca<br>ttgttaccttgttaatacaagtcataataacttgaaaacctgctagaagagatataaagattagaaacccttggaaaacccaagcttgccat<br>tcaccacttaggatgcctgcaaaccaactgttagttgctcctataaacatatcgtgggttcctttctcttgagagatttctttattgtacttggtg<br>gcagtgtctaaggaaacagcagtatcagccacctttaaattaagcttttttgtagtaacagaatcaggggagggattagtacaaaattcag<br>ttttgtttaacaccaaacataggcctccagcttgagcaaaaagaagatctaagactgcatgatcttccattaagtgttttcgttgaatatgtat<br>gttgtcatgtgcctttctgagagtagcttctacccatctgaaaccctgggaggtctgattggctaccaaatccaagaattttcccaatataca<br>aattagttttaaattccgtacaaatggtacttcactaccaccaagagtgagcccccaggaaccccagtggaatctttccccggtagaaact<br>agcttatcctcgtctatttcgaggctagtgctaatttcagttattgatcattttggcctccaagtataagggctatcatgagaattttcaggggga<br>agcaattcgaaaggcaggagcaggccaggccagataacaagaaccaaaccaaccaaggaggcagaacagaatatgcagattctcc<br>acagacccaatagagaccctcaggggttggaaaagggggccacctagttgtatttgagcagggatcattcaggtttgttcgaccatgaa<br>tctgtagctcctgaataacatccagtgggaaatttacttttctatggcccctttgtagtgtgttgtaagggtgtataaccacatctagtaaaaa<br>gagaccctactggatatacaagcaatcacttgtactaacataagtaattcccaaatcttgagtatgtgatgcctgcaagcacaatatacgtt<br>ttgtaggcatcatttggatttgtttttttatatttggtgtgatcgactttatcagttgaaaaagagtgttgtttttagtgagtgtaggaaagcaagta<br>ctagtgatgtttagagtatcaagaatagctttccattcttcccttggggtttcagggtgactcattgggaaacgtggaggggcactggcac<br>ccttggaatcatttcctgatttttttggcattagcccacaaacccaacagttaccctggttttgtgctagagcataagcttgagctgaagccat<br>ccactgattatggtcccatggattttcatgtaaggaaaaggaaaggattagggaaaaaaataaggaaaacagaaaaacacataaggctt<br>tcatggtggtagagaagtcttgatctgtgatctagggaaagctgtctgtaaccaggatgctgtctgcttctgggaagagatttccctggtc<br>agctttaccttaaagtctccaacgggtatatagtaccaggagtctgaggggggcccttttgaattgtgagatgtggacccatggttcaaagc<br>cctgaagcttctctgcactgtgggtggtaagaaggacttggtatggtcccatccaacgaggttcaagagtgatcttcttctgatgtcatttc<br>cggaaggcccagtctccaaattccagaccatggagggtttgattgtcctcagttggtggatcttgaaatgcttcctttacctggtggaagt<br>atactttggcgtaatacattaaagccttgcagtatttagtcatatcagagtttaagagagcaggagaagcatgagatgctattattagggac<br>atgggcctcccagtgactatttcataaggggtcaatttatgttttccaacaggattgaatctgattgccattaaaaccaaaaggtagtacctt<br>tggccaaggcaactcaattgattcagttaacttggacagtttcagttttcaaatgccatttgttctttcaagctttcctgaagactgagggtaa<br>taaggacaatggtaatgcaactgtgtcagtaacaccttatttaactgctttataacttgctcagtaaaatgagttcctctatcactggagactt<br>ttagagggatcccccataaaggaaaaacattttctaataatttcttagctatggtcacagcatcagctttcctacatgggaaggcctttatcc<br>aaccagaaaacatgcaaactattacaagaacatactgataccccattgagggtggtaactgaatgaagtccatctgtaaatgttcaaatg<br>gtccatcaggtggtggaaatatactgcctctagtttttctgggattatgagtttgacaagtcaaacattgattataagccattttagtaatgtca<br>gaatagtcaccccaccagtatttttttcataatttggatcactttgtctgttccatgatgagctgtggagagctttcaataatggaagcttcaaa<br>gattcaggaaggaccaggcggccgtccgggccctttgtgagtctttgcttcacgttaaatttacatccttttagataccagtttgtttttgca<br>aatcagatgcgttgcactgtttattaaataggtcatcgtaaggaaattggcttggattaatcttatggagttcattcagattgcgtatcttgatg<br>gttccagcactagctgattgagcataaaaatctgctaaagcatttcactgatatttgggttcatttctacaagtatgagcttcagtcttaataa<br>cagcaatctgcatttgtaacaggatagcagaaaggagctcatctgtttggagtccatttttgatggggatcccactagaggtgagaaacc<br>ttcgtagtttccatatcatgccaaaatcacgtactactccaaaagcatgtctactatccgtaaatatttactgacttgtccttagctgtgtgaca<br>tgttcaggtaagggcagaaagttctgcaggttgggctgacttgacttgaagagttcgcttctctattaactcattttgggtggtaacagcat<br>atcctgactgatattttttttttctgagttttggcataggacccatcaacaaaaagtgttaattcaggattatccagtggagtatcttgtatagca<br>acacgaggggccactatttctgatactacactcacaccgttgtggtcttcaccatcatcaggcagagataacagagtagcagcattaagt<br>agattacagccttttagatgaagataagaaggagataggagaagtaattcataagatgttagtctactcactgaaaaatgctgggtttgatt<br>ggaatttaatagactttccacagcgtgtgggacttgcaaattaagttcatttcctaaaaccagatctgatgaagcttctaccagcttggctgc<br>tgctactgcttttaaacaattaggatatgccttagagactgggcctaattgcaggctatagtatgcagtggtcctatgtttagcaccgtgttc<br>ctgattattacattcatgaacaaacaaagtgaaaggtttagtgtaatttggaagtcctaaagctgggggctgttgtaaggccaacttcatttg |

TABLE 4-continued

| Exemplary target gene intron sequences |
|---|
| gctaaaagcctgctcatgactgtcttcccaaggtaaaggctctggtacagcatttttagtgagctcatacagtggtgaagctattaaggaa<br>aaatttggaacccaggatctgcaatatcctgcaagcctaagaaagccttttgtcttttggttgcaggtcgaggaaaactttaaataggtttta<br>tcctctcaggtaagagggaaatcccttcagcagccaagtcatgtcccaaatagtggactttttcttttgaaaattgaagttttggccaggca<br>tggtggctaacgcctgtaatcccagcactttgggaggctgaggcaggcggatcacctgaggtcgggagttcaaggacagcctgacca<br>acatggagaaaccctgtctctactaaaaatacaaaattagccaggcgtggtggtgcatgcctgtaatcccagctactcgggaggctgag<br>gcaggagaatcgcttgaacccaggaggcagaggttgtggtgagccagtatcacaccattgcactccagcctgggcaacaagagtga<br>aactccatctcaaaaaaaaaaaaaaagaaaaaagaaaagaaaaaattgaagtttttccattgaagccctgtgacctttatatgcaagttgc<br>tgtaaaaggtaaactgagtcaatttccgggcactccttaataggagagcataacaataagttatctacatactgaatgagagtagaattttg<br>aggaaactgtagtgtcattaactcctgatgcagtgcctggggaaaatatgaaggggcttcagtaaacccttgtggcattacactccaggt<br>gtattgctgatttttccaagtaaaggcaaacaagtattgactttctttatggaatgctagagaaggctgagccaagatctattactgtggaca<br>acttggaatcagtgggtacattaggttataaagtattaggatttgggactacaggaaatcttggtattacaattttattaattgcctgtaaatct<br>ggaacaaatctccagtctcatccatttgtttttaactggtaggattggagtgttacaggggctggtgcatggaattatgagtccttgtttaat<br>taaatcttctacaattggtgagagcccttaaattgcttcaggttttagtggatattgtggtaattaggcaaaggtttagaatgatctgttagtac<br>ttttataggttctacacttttaattcttcctatatcagttgggaagaggcccataaacattaggtgttttcgaaagatcaggggtattacaggct<br>tgagtttcgatcttatcaatttctgcctgtagacagcataacaattctagttcaggagaatcaggaaaactcttaagattatttctgtttctgag<br>gaaaatttaggtgcccttttagctttgaaagtaaatcttgccctaccaagtttactggaacagtatcacgtagtaaaaaactgtgtttttctga<br>aagggggctcagagttaattggatgggttcagatatgggaacctctggaacttgatttgaaacccctgtcacagaaatgacctttttactct<br>aagggatttgttggcttattaaggtggggtttatggtagatagagtagccctggtatccataaggactatacacaactccctatttattttaac<br>ctctgtttccccatgttcctttaaaggtattacggggagcaatccactggagaatcccttagagcctcctttaagttgaatattgtcaggagg<br>actaaggtctcttgggctccctctagtggtgaaacagtttggcctagagggaggtttatcagccgacaatcccttttccagtgccctggtt<br>gtttgcaatacaggcagacatcttggggtaaagaaattcttgttctgggacctcttgatttgatttttttaatatataattttaaaaatattttcca<br>aagtgtgacttaaaaaaattttttttattatactttaagttttagggtacatgtgcacaacgtgcaggtttgttacatatgtatacatgtgccatg<br>ttggtgtgctgcacccattaactcatcatttacattaggtatatctcctaatgctatccctccccctcccccaaccccacaacaggcccca<br>gtgtgtgatgttccccttcctgtgtccaagtgttctcactgttcagttcccacctacgagtgagaacatgcggtgtttggtttttttgtccttgtg<br>atagtttgctgagaatgatggtttccagcttcatccatgtccctacaaaggacattaactcatcatttttttatggctccatagtattccatggtg<br>tatatatgccacattttcttaatccagtctatcattgttggacatttgtgttggttccaagtctttgctattgtgaatagtgctgcaataaacatac<br>gtgtgcatgtgtctttatagcagcatgatttataatcctttgggtatatacccagtaatgggatggctgggtcaaacggtatttctagttctag<br>atccctgaggaattgccacactgacttccacaatggttgaactagtttacagtcccaccaacagtgtaaaagtgttcctatttctccacatc<br>ctctccagcacctgttgtttcctgacttttaatgattgccattctaactggtgtgagttggtatctcattgtggttttgatttgcatttctctgatg<br>gccagtgatgatgagcatttttcatgtgtcttttggctgcataaatgtcttcttttgagaagtgtctgttcatatccttcacccacttgttgatgg<br>ggttgtttgtttttctcttgtaagtttgtttgagttctttgtagattctggatattagccctttgtcagatgagaagtttcagaaattttctcccattct<br>gtaggttgcctgttcactctgatggtagtttcttttgctgtgcagaagctctttactttaatgagatcccatttgtcaattttggcttttgttgccat<br>tgcttttggtgtttagacatgaagtccttggccatgcctatgtcctgaatggtattgcctaggttttcttctaggattttatggtttaggtctaa<br>attaagtctttaatctatcttgaattaattttgtataaggtgtaaggaagggatccagtttcagctttctacatatggctagccagttttcccag<br>caccatttattaaatagggaatcgtttccccgtttcttgttttgtcaggtttgtcaaagatcagatagttgtagatatgcggcgttatttctgag<br>ggctctgttctgttccattggcctatatctctgttttggtaccagtaccatgctgttttggtgactgtagccttgtatagtttgaagtcaggtagc<br>gtgatgcctccagctttgttctttggcttaggattgacttggcaatgcaggctctttttggttccatatgaactttaaagtagtttttccaattct<br>gtgaagaaagtctttggtagcttgatggggatggcattgaatctataaattaccctgggcagtatggccattttcacgatattgattcttccta<br>cccatgagcatggaatgttcttccatttgtttgtatcctcttttatttccttgagcagtggtttgtagttctccttgaagaggtctttcacatccctt<br>gtatgttggattcctaggtattttattctctttgaagcaattgtgaatgagagttcactcatgatttggctctctgtttgtctgttattggtatataa<br>gaatgctctcttttgttctttgttagtcttgctagcggtctatcaatttgttgatcttttcgaaaaaccagttactggattcattgatttttgaagg<br>gtttttgtgtctctatctccttcagttctgctctggtcttatttatttcttgccttctgctggcttttgaatgtgtttgctcttgcttctctagttctttta<br>attgtgacgttagggtgtcaattttagatctttcctactttctcttgtgggcatttagtgctataaatttccctctacacactgctttgaatgtgtcc<br>cagagattctggtatgttgtgtctttgttctcattggtttcaaagaacatctttacttctgccttcatttcgttatgtacccagtagtcattcagga<br>gcaggttgttcagtttccatgtagttgagcagttttgagtgagtttcttaatcctgagttctagtttgattccactgtggtctgagagacagttt<br>gttataatttgtattctttacatttctgaggagagctttatttccaactatgtggtcaattttggaataagtgcagtgtggtgctaagaagaac<br>gtatgttctgttgatttggggtggagagttctgtagatgtgtattaggtccgcttggtgcagagctgagttgaattcctggatatccttgttaa<br>ctttctgtctcgttggtctgtctaatgttgacagtggggtgttaaagtctcccattattgttgtgtgggagtctgagtctctttgtaggtcactca<br>gggcttgctttatgaatctgggtgctcctgtattggttgcatatatatttaggatagttagctcttcttgttgaattgatccctttaccattatgtaa<br>tggccttctttgtctctttgatctttgttggtttaaagtctgttttaccagagactaggattgaaacccctgcctttttttgttttccatttgcttggt<br>agatcttcctccatccctttatttgagcctatgtgtgactctgcacgtgagatgggtttcctgaatacagcacactgatgggtcttgactcttt<br>atccaatttgccagtccgtgtcttttaattggagcatttagcccatttacatttaaggttaatattgttatgtgtgaatttgatcctgtcattctctc<br>aacatttgcttgtctgtaaaggattttatttctccttcacttatgaagcttagtttggctggatatgaaattctgggttgaaaattcttttctttaag<br>aatgttgaatattggcctccactctcttctggcgtgtagagtttctgccgagagatcagctgttggtctgatgggcttccctttgtgggtaac<br>ctgacctttctctctagctgccattaacatttttccttcatttcaactttggtgaatctgacaattatgtgtcttggagttgctcttttcgaggagt<br>atctttgtggcattctctgtgtttcctgaatttgaatgttggcctgccttgctagattggggaagttctcctggataatatcctgcagagtgtttt<br>ccaacttggttccattcttcccgtcactttcaggtacaccaatcagacgtagatttggtcttttcacatagtcccatatttcttggaggctttgtt<br>cgtttctttttattctttttctctaaacttctcttcccgcttcatttcattgatttgatcttccatcactgataccctttcttccagttgatcgaatcgg<br>ctactgaggcttgtgcatccgtcacgtagttctcgtgccttggttttcagctccatcaggtcctttaaggacttctctgcattagttattctagtt<br>agccgttcgtcgaatttttttcaaggttttaacttctttgccatgggttcgaacttcctcctttagcttggatagtttgattgtctgaagtcttcttc<br>tctcagctcgtcaaagtcattctctgtccagctttgttccgttgctggtgaggagctgcattcctttggaggaggagaggtgctctgatttta<br>gaattttcagtattttgctctgtttcttccccatctttgtggttttgtctacctttggtctttgatgatggtgatgtacagatgggtttttggtgtgg<br>atgtcctttctgtttgttagttttccttctaacagtcaggaccctcagctgcaggtctattggagtttgctggaggtccactccagaccatgttt<br>gcctgggtatcagcagcggaggctgcagaacaacgaatattggtgaacagcagatgttgctgcctgatcgttcctctggaagttttgtct<br>cagaggggtacccggccatgtgaggtgtcagtctgcccctactgggggtgcctcccagttaggctattcgggggtcagggacccac<br>ttgaggaggcagtctgtctgttctcagatctcaagctgtgtgctgggagaaccactgctctcttccaagctgtcagacagggacatttaag<br>tctgcagaggtttctgctgccttttgttcggctatgccctgcctgcagaggtggagtctacagaggaaggcaggcctccttgagctgcag<br>tgggctccacccagttcgagcttcccagctgctttttttacctgctcaagcctccgcaatgggggcacccctcccccagcctcgctgcc<br>accttgcagtttgatctcagactgctgtgctagcaatgagcgaggctccatgggcataggacccgctgagccaggcgcgggatatagt<br>ctcctggtgtgctgtttgctaagaccatcggaaaagcgcagtattagggtgggagtgacccaattttccaggtgctgtctgtcacccctttt<br>ccttggctaggaaagggaattccctgaccccttgtgcttcctgggtgaggcgatgcctcgccctgctttggctcatgctcggtgcgctgc<br>acccactgtcctgcacccactgtctgacaatccccagtgagatgaacccagtacctcagttggaaatgcagaaatcacccgttttctgcg<br>tcgctcaagctgggagctgtagactggagctgttcctatttggccatcttggaaccgcccgattgtgatttaaaatgagaacgagatggtc<br>cctttggttcctggtccctgtaactgttgcaattgaaggggcataagcttattagccttttgaggttttttttgctctagagtcttctcaaaatgc<br>ttagctaggttgggcacgatggctcacgcctgtaatcccagcactttggaaggccaaggtgggaggatcacgaggtcaggagatcaa<br>gaccatcctggctaagatggtgaaatcccatctctactaaaaatacacagattagctgggcatggtggcacacgcctgtagtcgcagct<br>actcgggaggctgaggcaagagaattgcttgaacctgggaggcagaggttgcagtgagccgagattgcgccactacactctagcctg<br>ggtgacagagcaagactccacctcaaaaaaaaaaaaaaaaaaaaaaaaagttcagctaaggccaccaattcagtcacatctctaactt |

TABLE 4-continued

| Exemplary target gene intron sequences |
|---|

cccattgcaacttatgttttttagttaaactgctaagttcaggatggagtccatttataagtaaagcagttaatgctgtttcagcccctgcagg
gaatactccttgctgtactttgagcccaggatgtttcacaaatatttctaagcgacttctgtaatctgaaactggttcatctttcttttcttttttttt
tgcttacaagattgtatgatggaccaatttttgtggaaaaatttaggaactgaatgttaaaaggttttcagcgattttctagctatttttggtc
cttcttgtgaggagctcttagagggccctttaaaatgtcctcctcaggtttgtcccattctgctgctgccatccatttctgagcttcaccagcc
cccagtatcatatgaataaattggtaaattcatgaagtcctggatcgtaagctcctattaggattctaaattcctcagtaaatttttgagactttt
ccccttggaccagggaagtccttcacaatggggctaagctcagttttagaccatggagtgaaagtagttacagcaggcaggcctggctg
atataaggtctcactttgtaagacatctgtctaacttcctttttttttttttttttttttttaaatcatcttcagggtgaaagtgtaatttaacaaaaagtt
tagtggactcagagtatgtaggtagagatggacaaagaaggaacagtccgagttagatcagtcaaagtacagtcctctttcttcatgtcct
tggtctgttgcttaagcttttcatttggtttttgcaaagaatcttttaaggaggcacttttgattcacttagtctttttggaggcctttgcgtatcca
tgagacaatacatcccactgtatttgtggggggctttgatcccctttttctaatatgccttgcaaacaattttatccaaattaaaacttctccattg
tggccattttaattctaagttttctttagtgaggttaacccatttttactgaaaatgcacatgttctgggcccataattttatacgtaaaattagct
ggagtccctgaagatggagtcccagactccttggattgagatgatcccattattaaataaggtacttatcagaggtctgaggcctctaact
gaatccaatccagttaattatcaaatccaatttgatcttggatccagtccaggctaagtattgcttgagtaaactcggagagctcaaaacac
aagttagtggagctcggaatctgagagaaaactcacccatgacctccagttacaatcaagagaccagtgagagcaacggcctcagtg
ggtacctcaccaggtcacctggtgttccagggggttgccagagttttttcttcaaatcccacttctgacaccagatctgttaaaagaaaactt
cagacaagttaaatttgatggagtttaattaagcaaggaaaataaacactttgcaaatcaggcagcctccagaattgaatgcagtttgaac
acttagcagtctattagtgcttgaagtatggccactgggattggccaacactcagctattattacagatgcatactactcaggttttccatttt
gtctgcctattgtgctaggttatggtttgtccacaagaacacaaatatagaagtatggagtccttctcaggccatatttagtttgctttaacaa
tacttaaaaaaaaaaatttgtaaaataaggatacttaaccttactcggtgtttctgagagttaacatttatatagttatgctgtagtgaaaacagc
tagcgtaatgtctggtatgtataggaacacaagagataccgcttttcccatatccccataccattcttcacagcattgctcctgtcttccttga
ttcctcctcctccttctttgtttttttttttgtttgtttgtttgtttttttttggaggtggagtctcactctgttgcccaggctggagtgcagtggtgtga
tctcagcttactgcaacctctgcctcctgggttcaagtgattctcctgcctcagcctcctgaatagctgggattacaggcacacaccaaca
cactcagctaattttgtatttttagtagggatggggtttcaccatgttggccaggctggtcttgaactcctgacctcaggtgattcacccac
ctcagcctcccaaagtgctgggattacaggtgtgagccaccacaccctgcctccttcttaagaagtttccagtcccttgtaattaaaggaa
ttaatatttttaactacttagaatcagactggccctgattattagtaagcaactaatagtaagcaagcaactatgtatgcaactatgagtgtat
gttaagatatggttgttggtaacctttcattctcttcaggaagaagaagagggtggagctctacagtcaatgtgtacatttaaattctgttccc
tttcgagctttttttgctactttcattcttctggggatccaggtgcttgagttgggattgattaacttccttaatttccacccctgtgctgtcaggat
cgggagacatagatgaaggtgttctaaactgctagaaatttgtttttgaaagcaaaagtttgcatgcattttgttttcaactttacttacagt
gaatagtagttaataaaataagtccctgcctttctctctttggtttcaattcctgagaccaggatcatagcccacatattagagtggagtccc
actgctttggtttgaatcatgcctttgtttcttatgtcagtgtgactttgggcaagttatttaagtctttgcaccacatttcctcatctgtaaaatg
aggataatactagtactttctacatgggattgttagcaggattaaatgagatagcacatactgtaaccatgtctggcacatagtcaatggtt
agtaaatgtgaactattgtgtgacattgtggttagtcacgtatggggctgtgtttcctttagtatattgctcttttaatgtcatttcctttgtactgtt
accctctctgatctttcttccatattca

SEQ ID NO: 276

Gene: OPA1
Intron: GRCh38/hg38: chr3 193618937 to 193626091
Intron Sequence:
gtaagtgtaaaagagaattgttcatgtaggtagtcttgaaagatttttttaaagtttttacttctttggaagatttaaaatgataacatctgagaa
gcaaatacaaaaacatccaagtagagatatcgttactaatcttagtgcaaagtacaaggtattacgtggcagttctggaaatataattgag
aagcccatttctttcacatatgtccagtgaagcattagtttcgagggttgtccccaagaaagagttgtgttgttaagtgtgtggggggagaa
aggctcgtttagacaaggcaagcggacttcttttcttccctaggacctctcatactgtaatatactcatgcgcattgtgaatttccaaggag
tcaaagcatacagtgttttcccaaattatttatcaacagaacccttttgctcatggaacgtcgtatagggactagatttcactttggggaaact
agaaagggaatagga attgggttattaggaaataaatcaattccctgatattgatagttaacaaagttatgtatggggttatttatggtatgtt
attttcaacacatattcattaacaaaatccatatgaaagttataggagaattgctgaggtagaataacatactttgtttgtatttataatactcat
atatttacctgacgttttctgagtcttcactttttcattcttttggaattggtaaaataactgattccttgaaagtttttttctaaataatacctagat
aatagatttatagaaaaaatattgtatgaatgttttaacattcatgtaatatggaacatgtaatttttatactggaggttattatagttttaatacat
caaagaaataatgtttattttggaagcagaaagaagaaataatttctatgaatgaggttttcatctctttccttgttcttcaactttgaactttttata
ttccaaattttaattatatttcaaaagatttttttctttgccttttaatttttatcttttggagaaaaatgtatgtcaaaatgtatgtacgtgtatttgtct
tttgatttgatctttttttgaccctcttttgcattgacattattttaaccaaaggacactcttgattgttcatgctactgggggaaaaaaaaaataagt
agaaattagcctaatagttgtggcttattttgagtgaaggccttagccctaaggcaattaaatttactgtggagagaagagctaatctaatg
gggagaaggagcctttgttacaggtgtggtagtgtggttctttgagtgacaagatttctgtttgccagattggttaggagaagtctgtgtgt
ctgctttctctcttatggcctaggatcactgtggtgaatgaaaaacctgtctcagggcctgactcagataattcccttaaaacccggctaag
gtcatagatgaatataatcagtaattgaacagaagctctgcaatagaaaagaagccagataattatttttggaaatttaattatatttacagatttt
attttatacagtagacatggaattaaatttattacattatgttctaatttactctttgcttgttttgatttgcttgtttgacaatacatgtccttgtaaa
ctatttcctttaacttttctcaatttatggtgcttattttccccattaaagacttaccaattttttttaactatttgttacacatactgaatctagag
ttgtaattaagctactttcattactggttaagtcaaattatagcaaatgctactataaaaatttactatccaaaaatgtgtctcaagccccaact
gatggtttcaaattctgttattaataatatgcagcattgtgtttgcaaagcttggctgttacttgtgatgcttgagaatgatgagtcactcagct
aaactgagtgattttgagacttgtgtacaaattgatggttgaatgtaagcatgcaaagagagaccttagcttagcagtacccttttttgaaatc
actctgacatcaagtttgaaaatgtgggcaataatcagaggtggtaaggtggccaggctttagctgaatactttttttaactggttcagtctg
agggctgaaagccccagatttaaacagtatttagaatttgaagcagtcaagtattagtttaatggttgtcaggtttgtaacaaagtttctggc
tagacttctactagaaatgtaaaagtgcatgtgaatcagctttttaaaaaagtaataataattgaaaaacatttctacaactagaactaaaga
aaagatttgtcctttctaataggaaaacacatctggagaagtgctggcaactagcagaacagttaggaccattcagaatcaactgaagtg
aaagtgacggggagctgaggggaacacagatagtttgacttcagtcagacagaataaacatgatgaaccgataacctgtgattcccag
cctggggttactactggagttttaggtgtcctggaaagttataataccggtcttcaaaaagtctacagaaagcatagatttccacataatgc
tgcacaggctaacgaattaatcaagtttcttttggtttggcctggatttatatccattcagtttgtggacactactgaattatttatgtcatgttgat
caaaagttctgatatgatttgattaatgaaacattgaaaaaaatagtaaaaccaaccatttttaaccttacactactatcttgaggtatgattga
catacattaaaaccacctcttaataaatgcttcttgttaatcaaaaatttgaaaacgtatgtccactggaggaaaaaagacatagccctgga
tgtgaactgaatattactgagactcggagaccttcagaactacctgaagatgaatcgaagtgctgcctactttagagaattggactaattta
atttgggagtcagcagattgctgtatatcagtcatcatatataccggtgacaagaccacttagttcattcccttttttagattctgtaagattatt
gtgttccagtgaaattgatttgcaaaatgagacattttatttctgtgcttttgttctatcatgtttctgattggtcataagcatctcacagaagta
agaaatatggcgattcagaaggcaacaagcacatttataatttatagaaaatatttgaaggactttttcatggcccaaatcatgaaaagtag
tagtattgttttaagtataattattaaattataatacattaatgttctttcttgcaacatattactctcattcttttttttttttttttttttttgagacggagtc
tcactctgtcacccggctggagtacagtggtacgatcttggcccactgcaacctctgcctcccgggttcaagcgattctcctgcctcagc
ctcccaagtagctgggattacaggctcctgccaccacgcctagctaatttttgtatttttagtagagacagggtttcaccaggttggccag
gatggtcttgatctcttgacctcatggtccgtccacctctgcctcccaaagtgttgggattacaggcgtgagccacccagcagtctgattc
ttaattttatagtttatgttgtacctccccagctgaagtatctcttttcttttttcccgcgtgtttagtgttcactcatctttatagcatagctcaattg
tcacttcatgaagccttccataacctttgtagctccattaattatattcttctgagtgtttaaaacacttgccatatgaaacactatttactttggc TABLE 4-continued

| Exemplary target gene intron sequences |
| --- |
| ttacattcttactatctaatcggccatttctgttactaaatctttttctcagagcacctgggatagtcttgtgtcttagtaaaatcagttgattgatt<br>taactcggtagagtagaggctgattaaagtaaataaatctggttgatgccaacaaaattttggtcccctcaatttttttgctctcattacctgca<br>aattctccctggccttcatatttggcaaccattgaggagaacaaggctgtaaaagtagttcatgtacttgatattctgaattggaattaagca<br>gagttgcttaagtaggacttgcttttctgggatttcttatgcaacaaataatgtagtaactggaaatccaagttcaagacactggcagattcg<br>atgtcttttgaggacccttggcttcatagatgatgccttctccctatatccttacatagcaaaaggggccaggcagctctggccttttttttgta<br>aggccaataactccagaaacctcatgacctcatcacctcccaaaggccccacctctcaatactatcacattgtgaggctaggtttcaaca<br>tatgaattgtgggagacaaaaattcagaccatagtataatatttcaagattacttaaactcttctctaccaaactcattaacttttaggttagca<br>cagtattttcattgatattttggtttctggagttattactaatttttcttgatctgatgttataattaaaaaaaaacaggactttgtacgtgaaatgag<br>actgagataaggaagctgattcagagatggagatttaaaaaaagagagatgagagattgagatctgcagtgtcaaactgacaatagcc<br>aggagtcaggagatattaagagactatatcatctgtgattgttaatgattatttattgttatttataaatactactgtattttatatattatatacatt<br>gttttaaaaattatttttgtaccatttcttgaaagaaaaatgtctaagcttgggaaaatatttattgaaaaatgtggtttgtacatctgaggagtg<br>tatcttgcacagtaggtgcatagatttcttcctcttcctgttccacatggccttagcttagaggctgtgtggccatcacttggtatttagggta<br>agactggtgcacaaaatcaaagacaggtaaccttggtataagtgtagtatcatgtaaatagcttttctatgtctaattcttgttttcttcctactt<br>tttcaggaggtcaatttcagttcatttcaactatctttacataatagtgctttagtaacaggcatggaaggaaagagacatgtccctagagtg<br>ttttcttgaaatctaatagatgattggagtatttaccatgcagttgtgtatatacataagcagtgaattcgagaggaattttttaagctgtaaaaa<br>aaagcattgtgtgccttatagacgcgagtgagaaatgtggaatatggctgatccaaagggaatgagttatctcaattgattaatcacagtc<br>agttacagattgaactctttgttctactctttgccccccttctcactattgctcttgactagtcttaagaaagaaatgtggaatattttctcacggc<br>tttgggattttataaattagaatactagtggtatgtaaatacagcaggtacactactgtataaaccaacataggaagccttctttaaagggaa<br>ttgtttgagaaatttgaacacttggataatttgaataaaggattgtgataaatgatcaaatgaaagaaaataaatcaggttactcttctttctgc<br>ttgataaagcaataatttttttaaaggtaaaaattatgagaatgatgaggatagtagttagcattgtctttctttgataggtttgttaatgatcat<br>aaaactgatttatttaaagacatgtctttttataactattttatactgttgtatctggaaacaaatattgaatttcatttgtcatgtggaagaaatca<br>actagttttaacctttgatttataataaatcaaccactttcatttattgtctaatactggcaatgaacacagcctaatgtatcaaaactaacaga<br>ataaaaattctccaagttatatccagactttaagacactttctaattatataaaataaaatatttgggcagtcatttttaactctgaaactattta<br>aaactcctaatttagaatatcttaataaataccatttcctctttttattttataacttggtaaaaattgagtccattgttttcccagaacgctgtt<br>cttaaacaaatggttacctccttcattagaactttactttttttaggatttctaattaagaaaacattaggcttgtaacattgtcaaatcttggtgg<br>tctttcttccacgtttttttgaggtcgattatctaagaggccatcagttaataaagctatgcaggaaatgacatcatgccacatgtgaatatcct<br>gtattaaaaattgtatcaatatactattttataattatgaagtggaatgaattttagaaatagaaaaggtgatttttttgtgcataggtccaaactg<br>tgttttgttttcatttcagaatttcataatactatattgtctccatatcttaattgtgtttttttatagcactttttgtttagtaatttgtatatgcttggct<br>gtattctcagaggctgtttctatttaatgttgtcaaaacagctcataaaaagtgaaaattcggtcagactagttatttgatattatatatgaaatc<br>aaaacaacctgaaacattatcttttaatttaaataaagaaccccaaattttaatcaaatgtatgcaaaggcacatagaatatatgacttaatgt<br>acaacctttattaacttgatgatggaaacctgttcctagggacctttacttgaataaatgaaatatcaagaaaaaatactaacttaagaataa<br>taatttaataagtaagtaagctattatgatcttcaatcagtcctgagagaatcatggttgagaattagaaaatttagaccagtaagatcaaca<br>ctgttaaaaaaaaaaaaaaaatcagtatttttttctccatatttttatatatctggatcatttatttagcacttattattgcactttccttttcactttta<br>aactatgctgttttattttttctgagacatctgatttactgaggaggaaaatggaaatgcggtacagagcccaagggtatgacggctttaaat<br>gagtttccatttctgttttaagttaaccatccctccctagcttacatctgttcctttgttgcacccttggtttaacattattctcctccccaatttcct<br>cttctccctcattgtgaactcgtggcag |

SEQ ID NO: 277

Gene: OPA1
Exon: GRCh38/hg38: chr3 193626092 to 193626202
Exon Sequence:
GGTCTGCTTGGTGAGCTCATTCTCTTACAACAACAAATTCAAGAGCATGAAGAGG
AAGCGCGCAGAGCCGCTGGCCAATATAGCACGAGCTATGCCCAACAGAAGCGCA
AG

SEQ ID NO: 278

Gene: OPA1
Intron: GRCh38/hg38: chr3 193626203 to 193631611
Intron Sequence:
gtgatggatggtttaaggggggctaccgatacattcacactaatcagccatttctgccaagatcatgtcacctcaatctgttcatggactcca
aatacaagaaattaatttgacaaagtgaaaatataaaagatgcatcatataaatatgtaacttttctggagtgggtagtataggtaaagcca
aaagaaacaaattcaagcagaggaattttggtttctgaaaattaggttgtctgtagggtccctgtatttatacttagaacaaaattaggaattt
ctgtttatgtggtccagttattgagtcaccctaagtttgtaggcatcttacctacctacttgctccccaagtttttatttctaaaatgaaaagcat
tgctgtagatgaccagtttacactaaagaataacatttatttatttgttttagctaaagtatatggacagggaacattcatattcttgtagaaga
aaattattttgacttttgggcaaaagcatgtagttcttatacactttgacaaactcattgcgtacatttttcacattaatcaaagtcagcacaaat
aaattttcaccttggaccacggagggtttgaacactggaaatttgatataattctggttgctaaagaacaagttctaataaaagcttaagtgt
ataccaatatgtggctgttggtgcaatcagcaggtccgtaaaaatatgattttaatggttaggtaatcccacaacggagatcccaaagttc
atgtttggaagagacttttgggtcaaagtgaaatcagtgtaatgaatttaaaattatactctgagatcttgaaatcagctaattatgttacatct
tattagctcagaaaagttttgaagttatatacaaatgctagtcaggaaaaaaagattcagtcatgtaattcttgtacattctactatttaaatcaa
ccaatattatagattatgatttagtgcagtaattctgctggctaaccttatctcatttggtggtggttagtacttcagagtactcaccatagtttc
atttatgttttcagcatcacttcctggttttttctcaattccatggctgtggaatcaattcatatgtatatttagcttcggtgagcaaaaacatagct
agaaaaagaaaagaagtgagtttcctacctggttaaattaaagtcgatgtgttaagccaaggaggacttcttttgaatggtactttaacaat
ccctgttctgtatactgtgaatatatcatttaaatagcctaataaattggatgcttaggctgagccacctatactttagttttgttatggaaaga
agggagaggagcaagtatgttcttatatgttacttagaaataagaatgtagctgtagttacacattgttcttaagttttttcgtaagacaactt
gaaatgagtcccataggcctgctatttaacattctaagatatgacttaaggttaatgatgagcttttgaatctgacaattcaagagatatccat
aatgaatactgattcattttctacattgctgaaagctaatgttcatttaagcctactttagtagcctttatttgggcttagagatgttattcctcttt
ctgatatttattgggttatctgtttaacccttttatatctccctttcccgatttgtaaattagagactggcaagactttttaccctgagtagagcac
caaacatggcttgtttctgcccacactgtagttaccttgaggggaagtaaatgggactttaaaagcaatttatgctcttttatagtgaaattat
ccctcttactatcccgaaagactgttaccttacaatatcctccactcctttccccctgtagttactatagagatgacttttcggttcttcactgc
cataatgatcaaaatcctaattcatgagatttttatcattccaggcatgtgaggtttacttgatgcataaaaccgcaagtacttttttgttgtttttt
aattgtttttttctctcttatcttcttgaaagtctaagtagatcatcatttttgatgtcttattagtagcaactaataaattttccctgtatcttctcagc
aaaagaactcaagcagagacagaagattagaactaccattggtagttttgcttcctatggatatgttcacatacatagaaattttttacaatga
ccttttttatatatgtatttcagaatttcagaatggcctcaatgccttaataggaagaaatacttgaaatttttaaattagggcttggttttgtgag
gagctagtaaaggtttttctctttcagctttagcttgtttctgcggaggattccgctctttctcccatcagtttcatagccctggaattgtagaaa
agctctggtttcaagaccattgatatccatttctgtcagggtgagttttaaatttatttcatgatgcaaacaatatattgaacaacaggacatg
aacttgttcttgttgtaagtggctgaattttatcagtaaagcacatcaaaataaaatataccccaattgctagttaagacctagagtgacaga
ttgaaaatagcttgtgttattctcttaagaaaatatataaaaattatcatctcatcaatctttaatgtttgttttataaatctaaatgtttttatattgttt
cctaggaaatattaggtctaattttttactttaccaccagctgtcttttatttactcttttttgagacggagtttcgctcttgttgcttaggctaga TABLE 4-continued

| Exemplary target gene intron sequences |
|---|
| gtgcagtggcactatctcagctcactgcgacctctgcctcccgggttcaagcgattctcctgcctcagtctcccgagtagctgggattac<br>aggcacatgccactacaccaggctaatttgtatttttagtagagacggggtttcttcatgttggtcaggctggtctcgaactcccgacctc<br>aggtgatccgcctgcctcggcctcccagagtgctgggattacaggcatgagccaccgcacctggccagctgtcttttaatataacattat<br>gattaattgtgatgttccattaaactaagcggagaggaaacatgctggtaaaccatgtgtgagttattcattgtaccagaaaggcaaatga<br>tacattttatcctaaaattcaaatttataaacatcttaacacttgtgatcattaaatactactaatctagcatataaattatatttgtaggcggggc<br>acggtggctcacgcctgtaatcccagcactttgggaggctgaggtgggcagatcacgaggtcaggagatcgagaccatcctggctaa<br>catggtgaaaccccatctctactaaaaatacaaaaaaaattagctgggtgtgctggcgggcacctgtagtcccagctacttgggaggct<br>gaggcaggagaatggcgtgaccccaggaggcagagcttccagcctgggcgactccgtctcaaaaaaaaagaaaaaagaaattatat<br>ttgtaatattctactaaccttatatcattttaacttttatataactttttattttaccaaattaagttaaccttttatagcccttggcttatactaaaca<br>tcctaactttttgtttaattgtattagttttaagttattgccccagatgtcaagtaatgttggattttctataataatttaggatatattgcatgaag<br>tcagttagtatttacatttaaaactaaaacaatttatactaatacagtttatacatttcatactaatttagctacagttggataaatatttaatggaa<br>caaagtaaatcaaagtaccttttcaaatgaattggaaattaaatccacataacaatttttatgaccacactattacagtgtgatggcatgcc<br>aaatgatcataatgtggaattatgtatttcttcattggctttcaagattctgttctttagtttgtgggctcctctccaacttgcttgtctcctcacag<br>tttaggcgactgtttataattcttgtccatcctgcataaacacacacagtcaaaatgaaaaaaagcttctatcagcagatctgtgcttgctgt<br>acagaaatgggaaaacaattgaagtttgcattatctttttctaattaccagatcgtttttggagctatttaggcatacgcttttaaggaaaaaa<br>gaaaaaaagagtgtaccttttgtttctaacaaaggttgttatctatattattgaaataaaaaattggggatagttatgacaaagtatttagaaat<br>aggaattaaaatcttaaaataacttttcatagcatggacaagacttattaatgtctacctcaataagcaaatcatttaaaaatttttcatgtatat<br>ttgctgccatgatgtgttgtgattgcttaaataaccaatgaatgaagatcaacaaggatttaaatgaagaagaatatggatttaactattttct<br>cctgtgaaataagttcatatttacaagttttgattttcagaaattagacaattatttttaaaggctgggatgacaacttctgcctcttaccaaga<br>agtcaaagcacagttatgtgaattcatcataaatcacatcatttttattatatttgtatttataattgtattgtgactactttaaaacctgttataaa<br>ataaaattgtttttaatattttattttagaattattagcattaataacaatttgaagtagtttacacaatacctgtgagttttattttgttttatattga<br>aattaatttagttgctttacttggcttcattgctatggatgcattctctgtgttacgagttagcagatctttccttggaactgaatttaaaagcaa<br>gcatttggctccacttaaatctctgaaaatgcaacttgttctttgcatttattacataattcgctacttatggtacagaaatggatacaatacaa<br>aaatatttccttataagatacactgtgaccaatgagctttttaaatagctgtaatcagtaacatgtatttgacttttcaaaacacatttctggag<br>ggatatcagtgctttatttccccaaatatctgaatccctatgctttagtacaaaacaacttctgaagaatttagtaaccatatgtgttgatctctt<br>gtttttctaactagtctttcataagaaatgactagaatagcaacagggaaatgattgccttttaaggttttgtttctcaatataaaattttggtga<br>accatttttattgataaatacaggtatttttactttcttaaatcacttgatttaaaattactttgattaaatatgcatataaagtcagttgtttttaactc<br>tcaatacttatcaaaaaaatttaacttgctgtacattctgtataaacctaattctattcaactaaaattattttaaacatttag |
| SEQ ID NO: 279<br>Gene: OPA1<br>NMD Exon: GRCh38/hg38: chr3 193628509 to 193628616<br>NMD Exon Sequence:<br>CTTTAGCTTGTTTCTGCGGAGGATTCCGCTCTTTCTCCATCAGTTTCATAGCCCTG<br>GAATTGTAGAAAAGCTCTGGTTTCAAGACCATTGATATCCATTTCTGTCAGG |

Example 2: Confirmation of NMD Exon Via Cycloheximide Treatment

Figure 4:
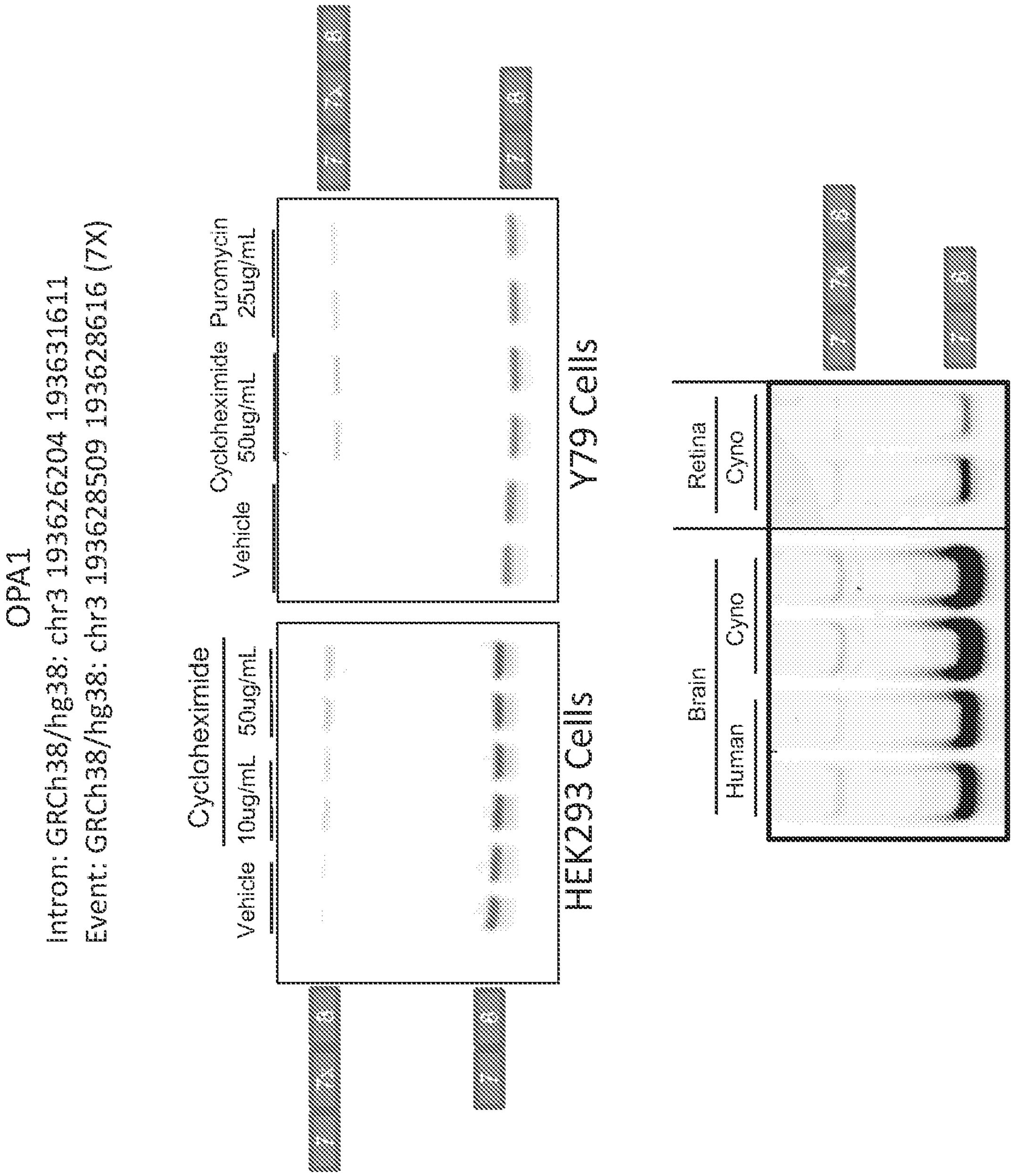
FIG. 4 depicts confirmation of NMD-inducing exon via puromycin or cycloheximide treatment in various cell lines, as well as the confirmation of NMD-inducing exon in brain and retina samples. RT-PCR analysis using total RNA from water-treated, DMSO-treated, puromycin-treated, or cycloheximide-treated cells confirmed the presence of a band corresponding to the NMD-inducing exon 7x (GRCh38/hg38: chr3 193628509 to 193628616) of OPA1 gene

RT-PCR analysis using cytoplasmic RNA from DMSO-treated or puromycin or cycloheximide-treated human cells and primers in exons was used to confirm the presence of a band corresponding to an NMD-inducing exon. The identity of the product was confirmed by sequencing. Densitometry analysis of the bands was performed to calculate percent NMD exon inclusion of total transcript. Treatment of cells with cycloheximide or puromycin to inhibit NMD can lead to an increase of the product corresponding to the NMD-inducing exon in the cytoplasmic fraction. FIG. 4 depicts confirmation of exemplary NMD exons in OPA1 gene transcripts using cycloheximide or puromycin treatment, respectively.

Example 3: NMD Exon Region ASO Walk

Figure 5:
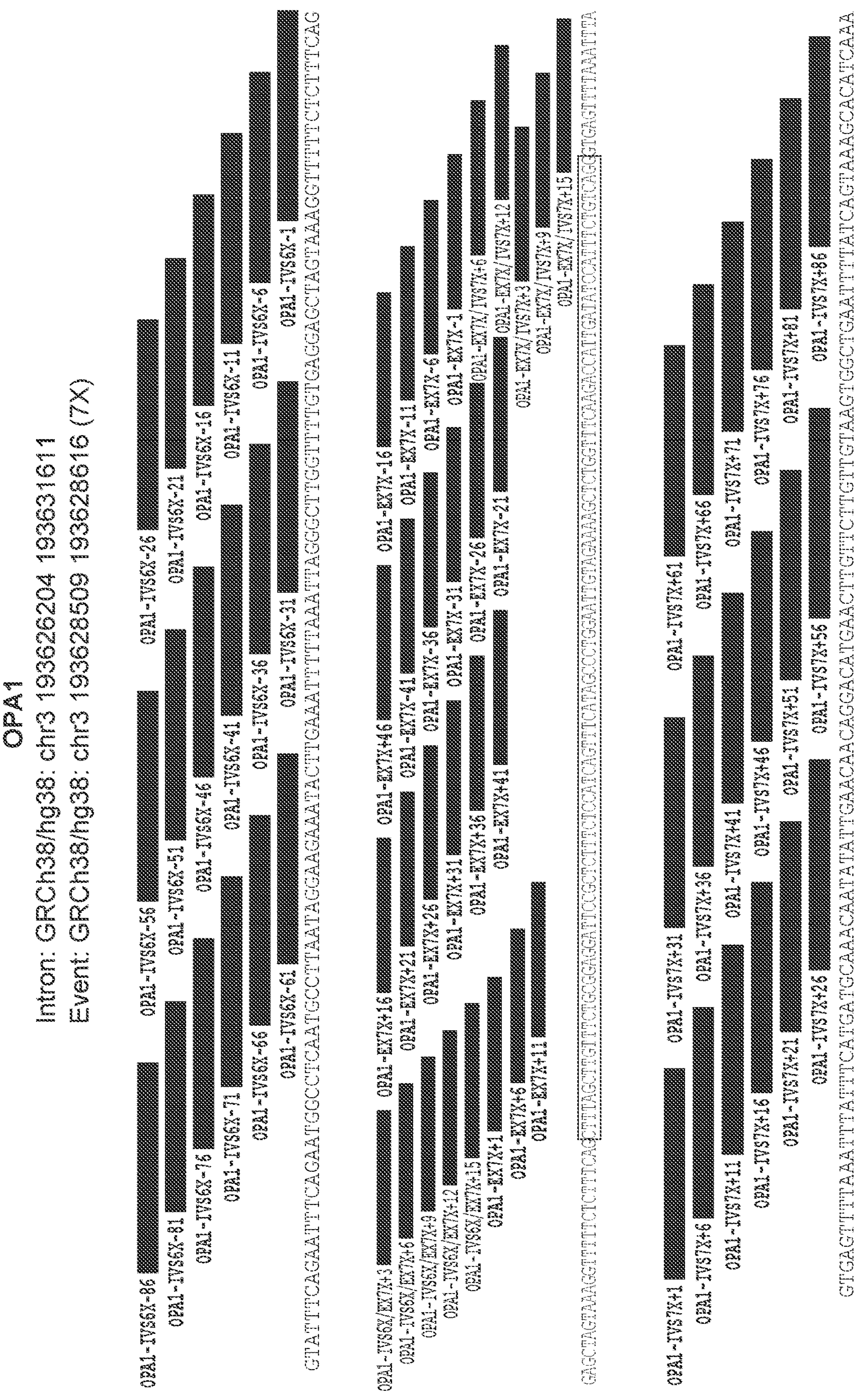
FIG. 5 depicts an exemplary ASO walk around OPA1 exon 7x (GRCh38/hg38: chr3 193628509 193628616) region. A graphic representation of an ASO walk performed for around OPA1 exon 7x (GRCh38/hg38: chr3 193628509 193628616) region targeting sequences upstream of the 3' splice site, across the 3'splice site, exon 7x, across the 5' splice site, and downstream of the 5' splice site is shown. ASOs were designed to cover these regions by shifting 5 nucleotides at a time or 3 nucleotides across the splice site regions.

An ASO walk was performed for NMD exon region targeting sequences immediately upstream of the 3' splice site, across the 3'splice site, the NMD exon, across the 5' splice site, and downstream of the 5' splice site using 2'-MOE ASOs, PS backbone. ASOs were designed to cover these regions by shifting 5 nucleotides at a time. FIG. 5 depicts an ASO walk for an exemplary OPA1 NMD exon region.

Example 4: NMD Exon Region ASO Walk Evaluated by RT-PCR

Figure 6:
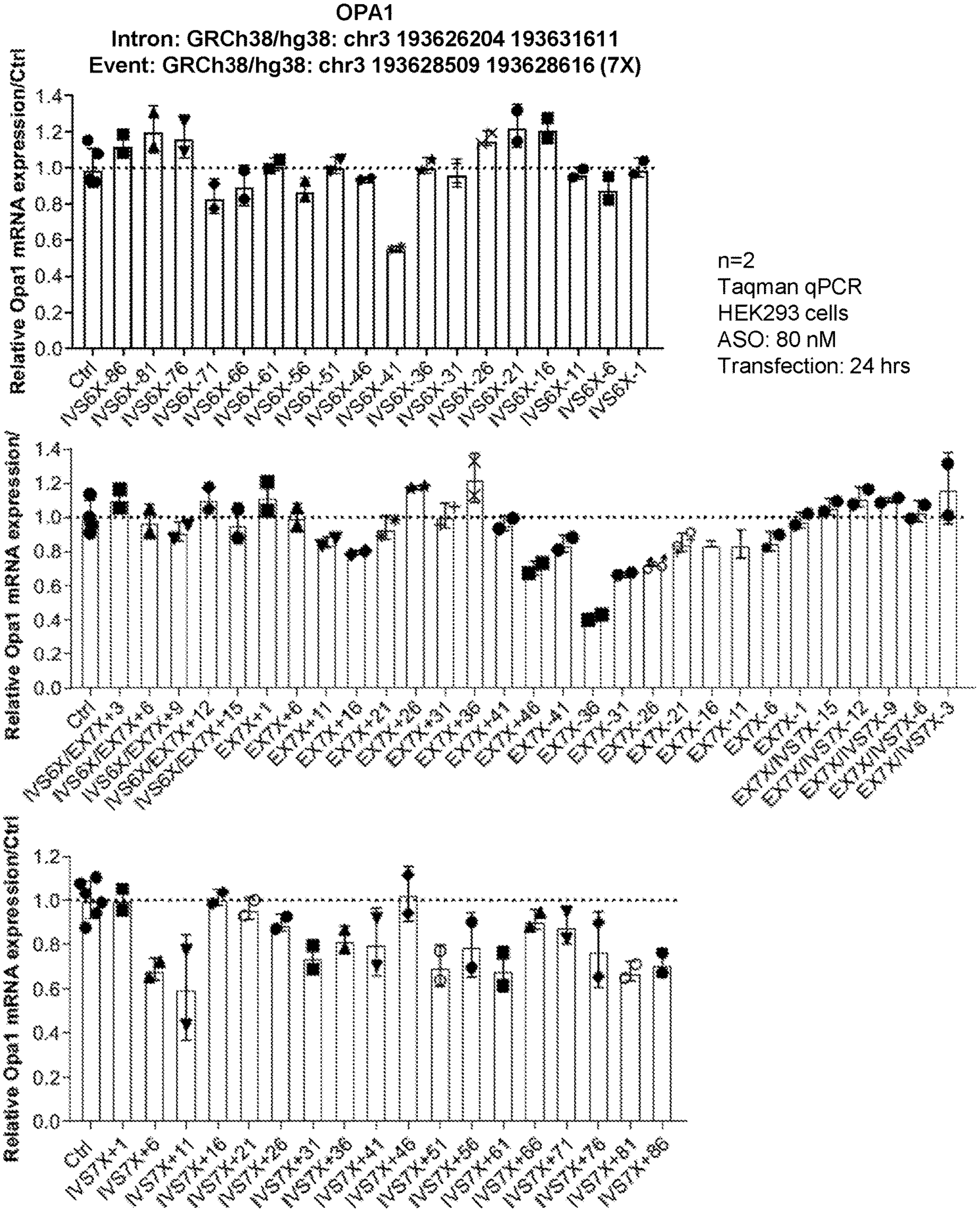
FIG. 6 depicts an OPA1 exon 7x (GRCh38/hg38: chr3 193628509 193628616) region ASO walk evaluated by Taqman RT-qPCR. Graphs of fold-change of the OPA1 productive mRNA product relative to Sham are plotted.

ASO walk sequences were evaluated by RT-PCR. HEK293 cells were transfected using Lipofectamine RNAiMax with control ASO treated (Ctrl), or with a 2'-MOE ASO targeting the OPA1 NMD exon regions as described herein. Products corresponding to OPA1 mRNA were quantified and normalized to RPL32 internal control, and fold-change relative to control was plotted. FIG. 6 depicts evaluation via TaqMan qPCR of various exemplary ASO walk along exemplary NMD exon regions. The measurement of the amount of OPA1 mRNA was carried out with HEK293 cells 24 hours after treatment with 80 nM of an exemplary ASO in the absence of cycloheximide, by Taqman qPCR using probes spanning exon 7 and exon 8.

Example 5: NMD Exon Region ASO Microwalk Evaluated by RT-qPCR

Figure 7:
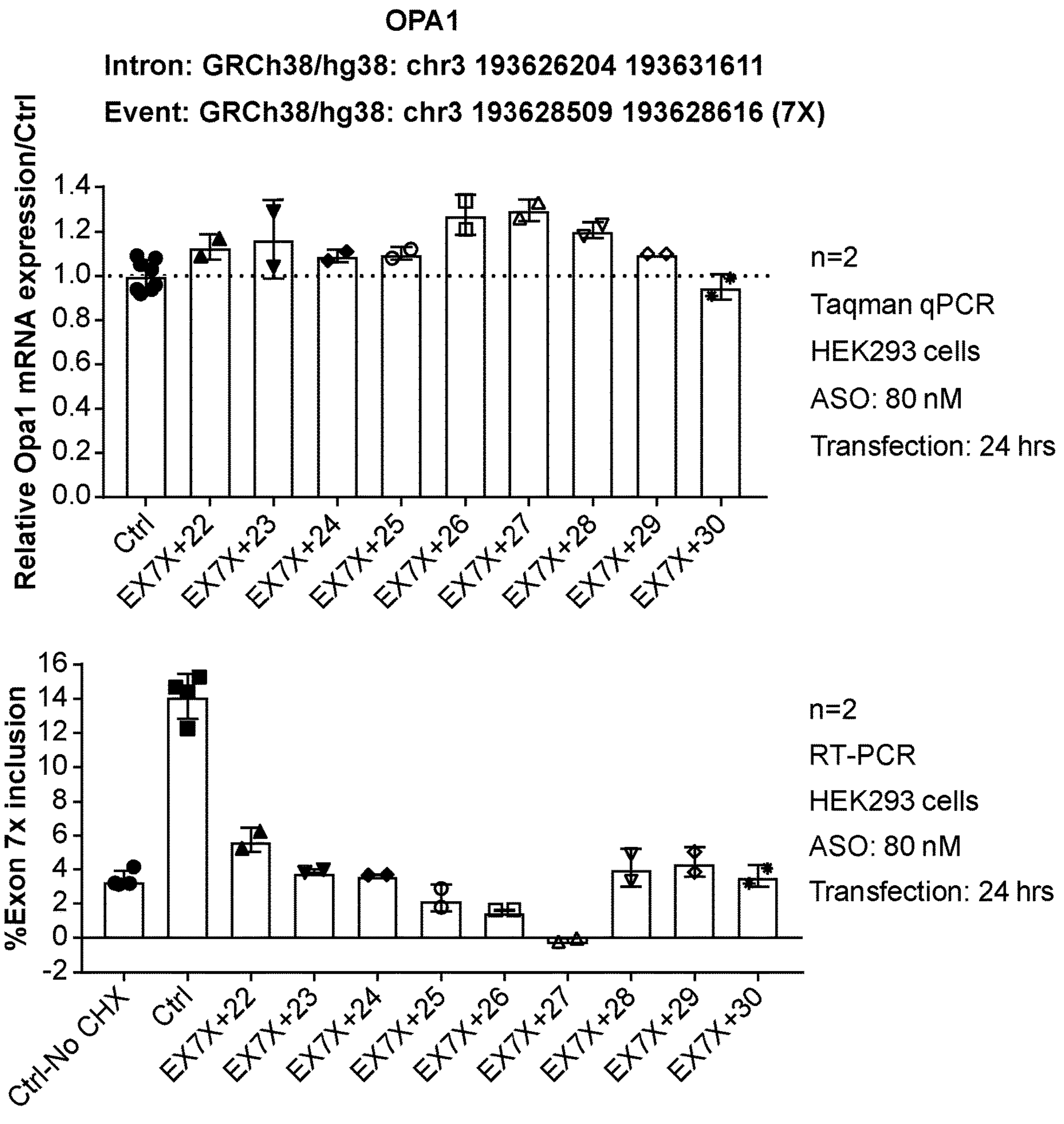
FIG. 7 depicts an OPA1 exon 7x (GRCh38/hg38: chr3 193628509 193628616) region ASO walk evaluated by Taqman RT-qPCR. Graphs of fold-change of the OPA1 productive mRNA product relative to Sham are plotted.

ASO microwalk sequences (across exon 7x) were evaluated by RT-PCR. HEK293 cells were transfected using Lipofectamine RNAiMax with control ASO treated (Ctrl), or with a 2'-MOE ASO targeting the OPA1 NMD exon regions as described herein. Products corresponding to NMD exon inclusion and full-length were quantified and percent NMD exon inclusion was plotted. FIG. 7 depicts evaluation of various exemplary ASO walk along exemplary NMD exon regions. The measurement of the amount of OPA1 mRNA was carried out with HEK293 cells 24 hours after transfection with 80 nM of an exemplary ASO in the absence of cycloheximide, by Taqman qPCR using probes spanning exon 7 and exon 8 (top panel of FIG. 7). qPCR amplification results were normalized to RPL32, and plotted as fold change relative to control. The measurement of exon 7x inclusion was carried out by quantifying exon 7x inclusion based on RT-PCR using probes spanning exon 7 and exon 8 (bottom panel of FIG. 7).

Example 6: Dose-Dependent Effect of Selected ASO in CXH-Treated Cells

PAGE can be used to show SYBR-safe-stained RT-PCR products of mock-treated (Sham, RNAiMAX alone), or treated with 2'-MOE ASOs targeting NMD exons at 30 nM, 80 nM, and 200 nM concentrations in mouse or human cells by RNAiMAX transfection. Products corresponding to NMD exon inclusion and full-length are quantified and percent NMD exon inclusion can be plotted. The full-length products can also be normalized to HPRT internal control and fold-change relative to Sham can be plotted.

Example 7: Intravitreal (IVT) Injection of Selected ASOs

PAGEs of SYBR-safe-stained RT-PCR products of mice from PBS-injected (1 μL) (−) or ASOs or Cep290 (negative control ASO; Gerard et al, *Mol. Ther. Nuc. Ac.,* 2015) 2'-MOE ASO-injected (1 μL) (+) at 10 mM concentration. Products corresponding to NMD exon inclusion and full-length (are quantified and percent NMD exon inclusion can be plotted Full-length products can be normalized to GAPDH internal control and fold-change of ASO-injected relative to PBS-injected can plotted.

Example 8: Intracerebroventricular (ICV) Injection of Selected ASOs

PAGEs of SYBR-safe-stained RT-PCR products of mice from uninjected (−, no ASO control), or 300 μg of Cep290 (negative control ASO; Gerard et al, *Mol. Ther. Nuc. Ac.,* 2015), 2'-MOE ASO-injected brains. Products corresponding to NMD exon inclusion and full-length can be quantified and percent NMD exon inclusion can be plotted. Taqman PCR can be performed using two different probes spanning NMD exon junctions and the products can be normalized to GAPDH internal control and fold-change of ASO-injected relative to Cep290-injected brains can be plotted.

Example 9: OPA1 Non-Productive Splicing Event Identification and Validation

Figure 1A:
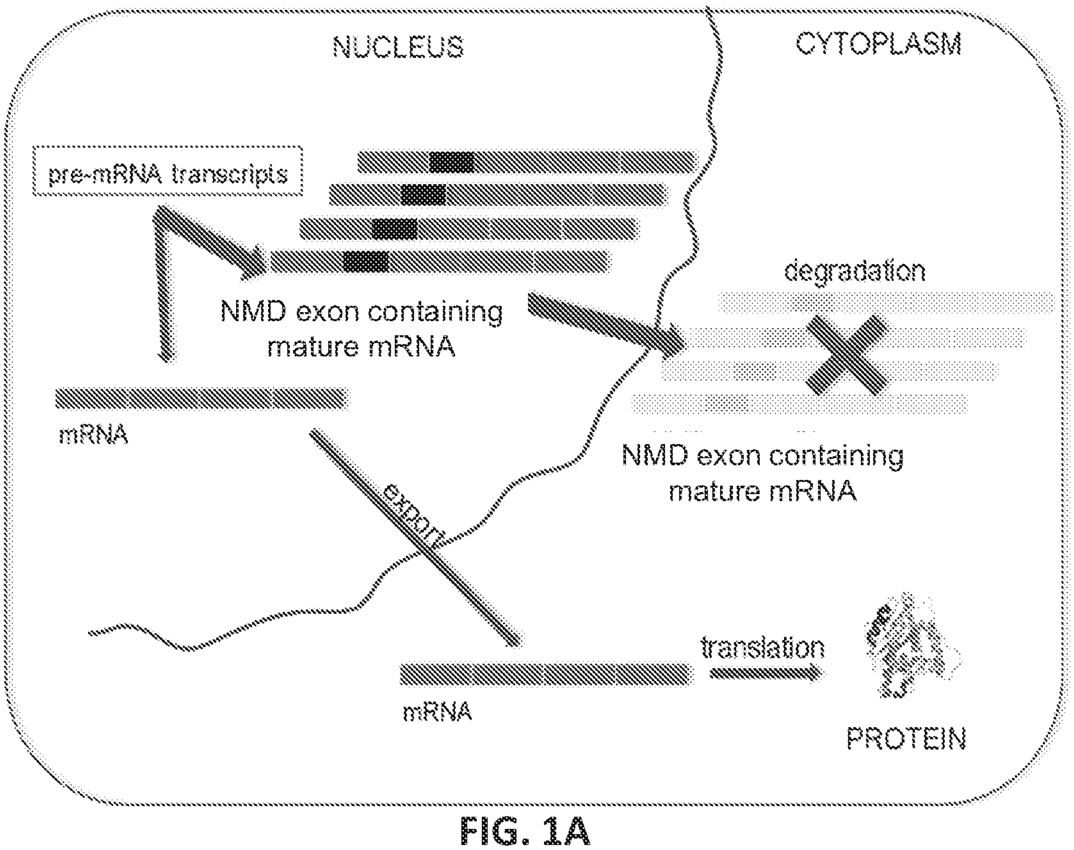
FIGS. 1A-1C depict a schematic representation of a target mRNA that contains a non-sense mediated mRNA decay-inducing exon (NMD exon mRNA) and therapeutic agent-mediated exclusion of the nonsense-mediated mRNA decay-inducing exon to increase expression of the full-length target protein or functional RNA.
Figure 1B:
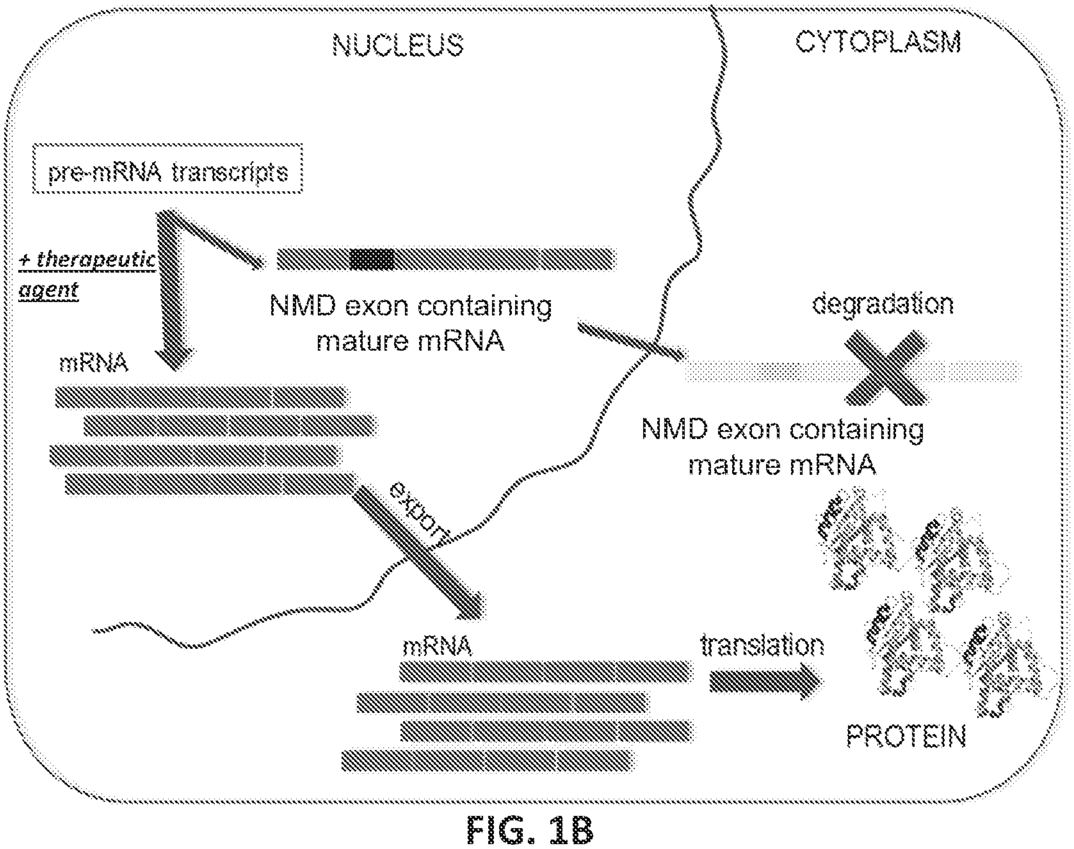
Figure 1C:
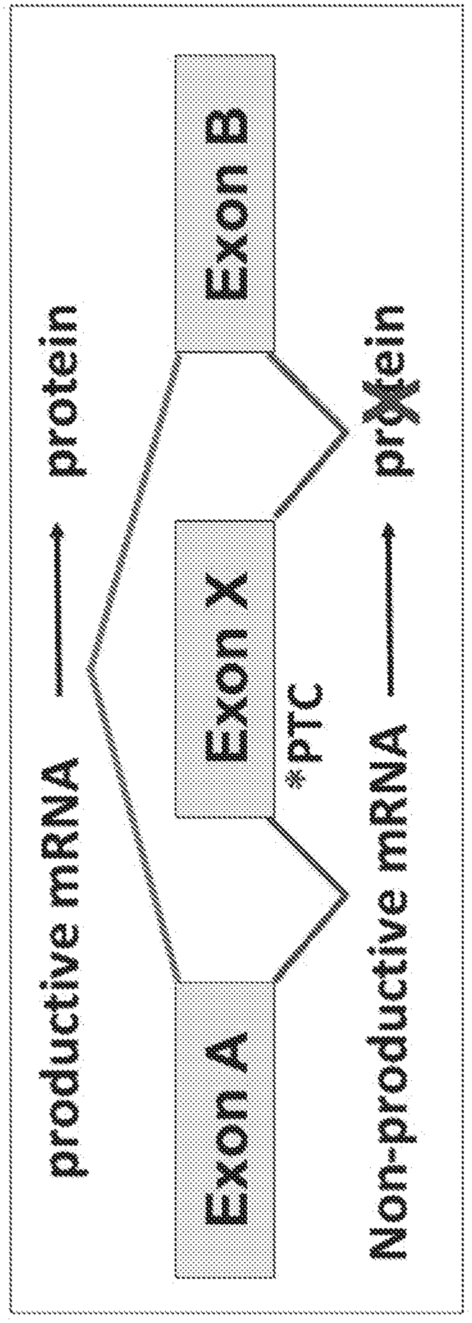
Figure 8:
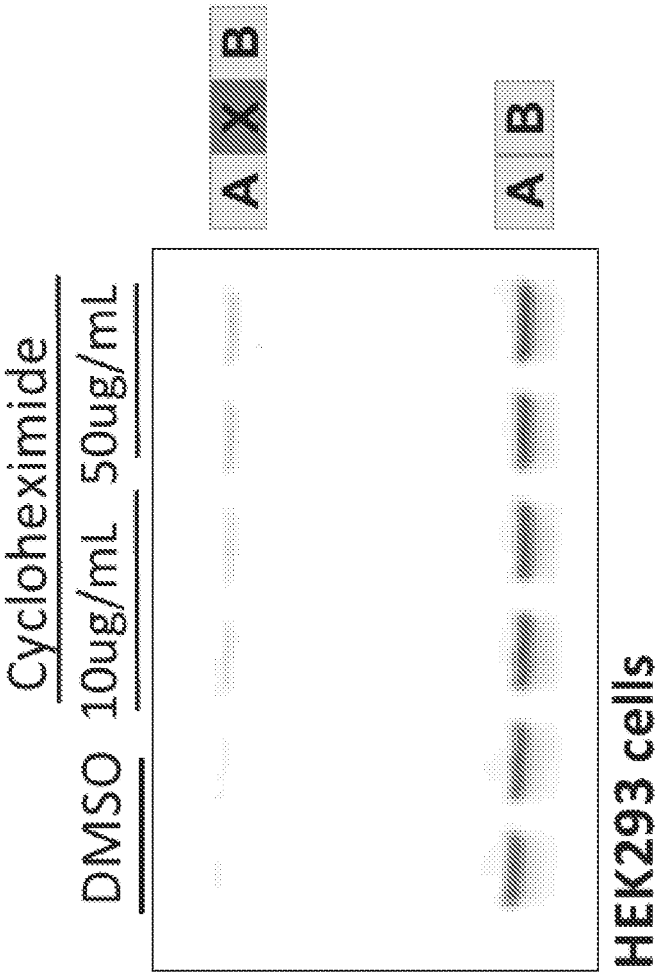
FIG. 8 illustrates expression of OPA1 transcripts containing the NMD exon in HEK293 cells treated with increasing amounts of cycloheximide.

A novel nonsense mediated decay (NMD) exon inclusion event (Exon X) was identified in the OPA1 gene which leads to the introduction of a premature termination codon (PTC) resulting in a non-productive mRNA transcript degraded by NMD, as diagramed in FIG. 1D. As NMD is a translation-dependent process, the protein synthesis inhibitor cycloheximide (CHX) was used to evaluate the true abundance of the event. FIG. 8 shows an increase in OPA1 transcripts containing the NMD exon in HEK293 cells with increasing CHX dose. Other ocular cell lines also validated for the presence of the NMD exon (ARPE-19, Y79).

Example 10: OPA1 NMD Event is Conserved in Primate Eyes

Figure 9A:
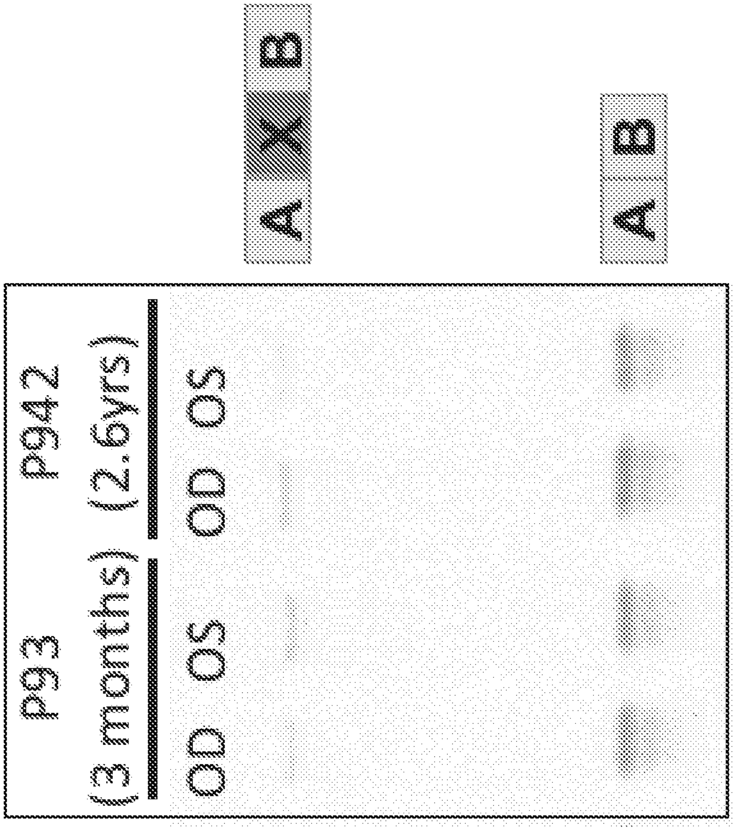
FIG. 9A illustrates RT-PCR data from the posterior segment of the eye of *Chlorocebus sabaeus* (green monkey) at postnatal data P93 (3 months) and postnatal day P942 (2.6 years).
Figure 9B:
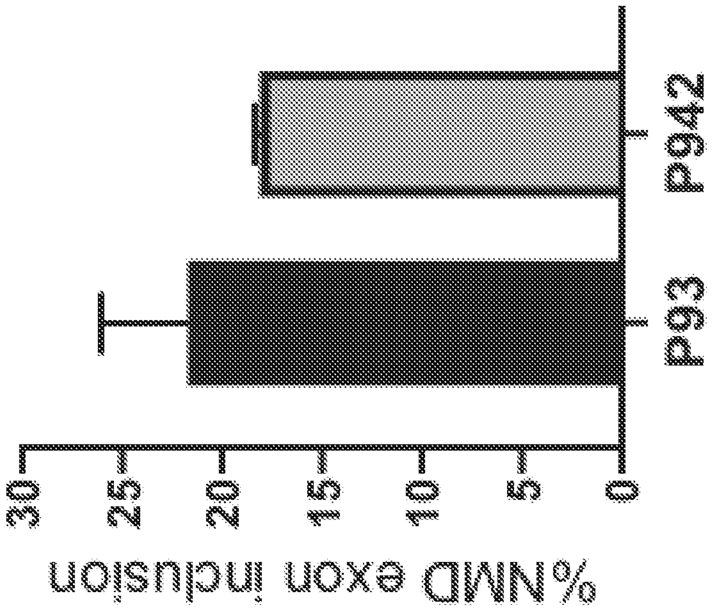
FIG. 9B illustrates quantification of the NMD exon abundance from FIG. 9A.

FIG. 9A shows reverse transcription PCR data from the posterior segment of the eye of *Chlorocebus sabaeus* (green monkey) at postnatal data P93 (3 months) and postnatal day P942 (2.6 years) for the right eye (OD) and left eye (OS). FIG. 9B shows quantification of the NMD exon abundance at 3 months and 2.6 years of age (N=1/age). Data represents average of right eye and left eye values for each animal. The abundance of the event may be higher in vivo, given that NMD is presumed active in the tissue.

Figure 10A:
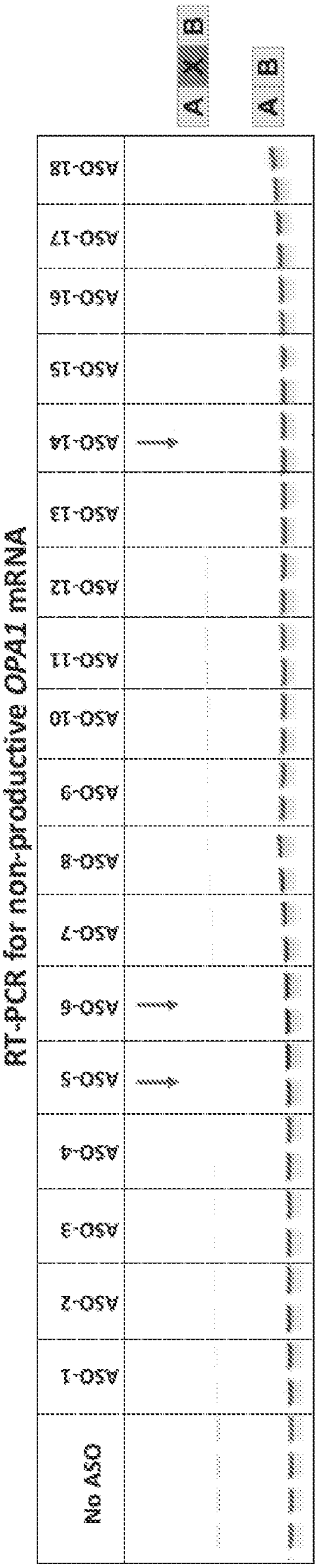
FIG. 10A illustrates RT-PCR of the productive and non-productive OPA1 mRNA after treatment of HEK293 cells with various ASOs and cycloheximide.
Figure 10B:
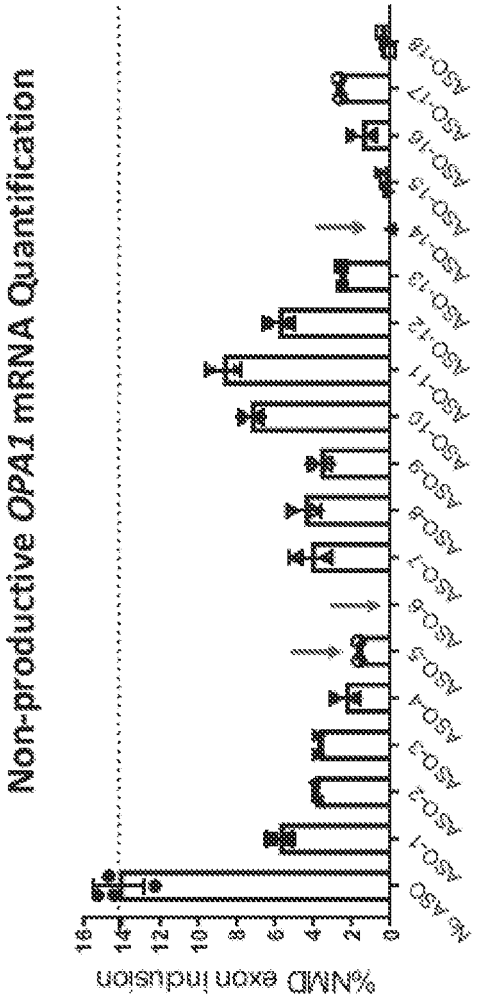
FIG. 10B illustrates quantification of the data in FIG. 10A.
Figure 11:
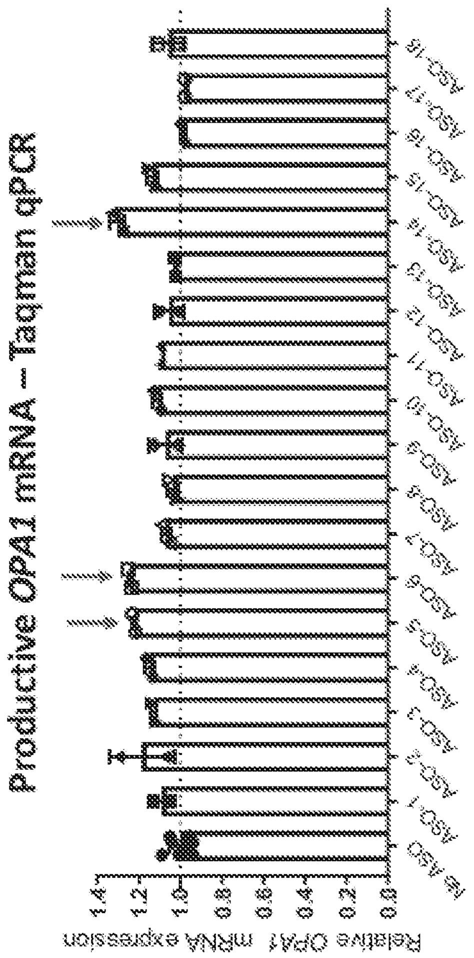
FIG. 11 illustrates expression of productive OPA1 mRNA by quantitative PCR in HEK293 cells treated with various ASOs and not treated with cycloheximide.

Example 11: OPA1 Antisense Oligonucleotides Reduce Non-Productive Splicing and Increase Productive OPA1 mRNA Levels In Vitro Exemplary antisense oligomers (ASOs) were transfected at 80 nM dose into HEK293 cells using Lipofectamine RNAiMax as a transfection agent. To assess the effect on the NMD exon, cells were treated with CHX (50 μg/ml, 3 hrs.) 21 hours after transfection. RNA was isolated for RT-PCR using probes spanning exon 7 and exon 8, as shown in FIG. 10A, and quantified in FIG. 10B. To assess levels of productive OPA1 mRNA expression, non-cycloheximide treated cells were used for Taqman qPCR using probes spanning exon 23 and exon 24, and mRNA expression of OPA1 was normalized to RPL32, as shown in FIG. 11. Arrows highlight ASOs that reduce non-productive splicing and increase OPA1 mRNA expression by at least 20%. Among these, ASO-14 produces the most increase in OPA1 mRNA (30%).

Figure 12A:
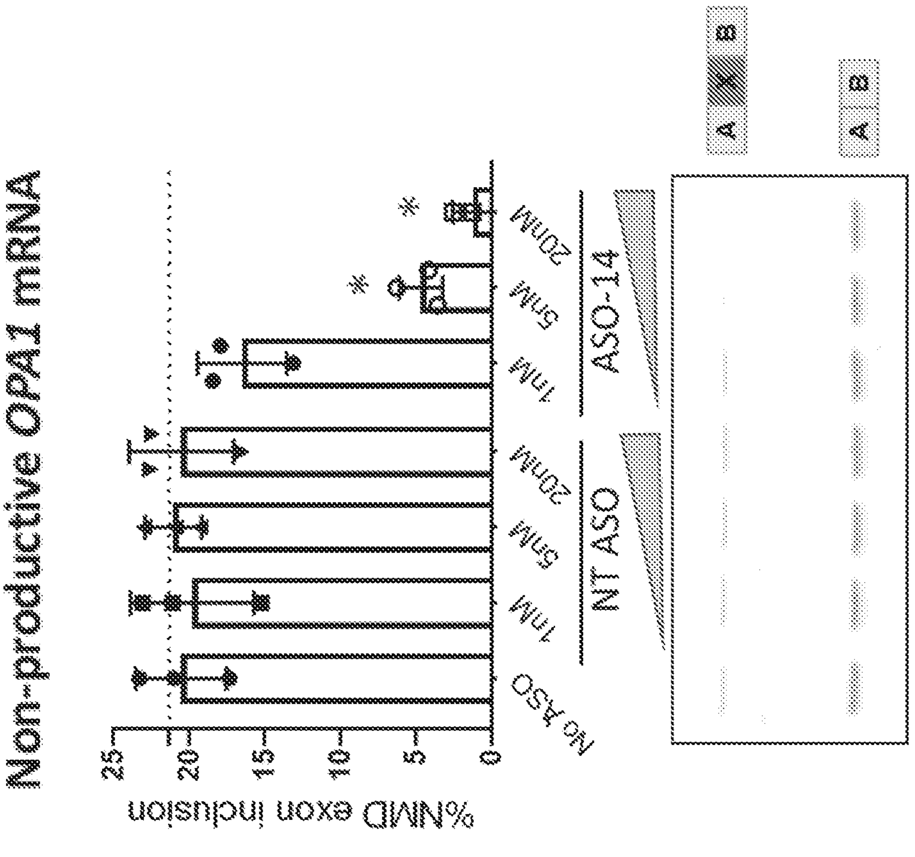
FIG. 12A illustrates RT-PCR for non-productive OPA1 mRNAs in HEK293 cells after treatment with ASO-14 and cycloheximide.
Figure 12B:
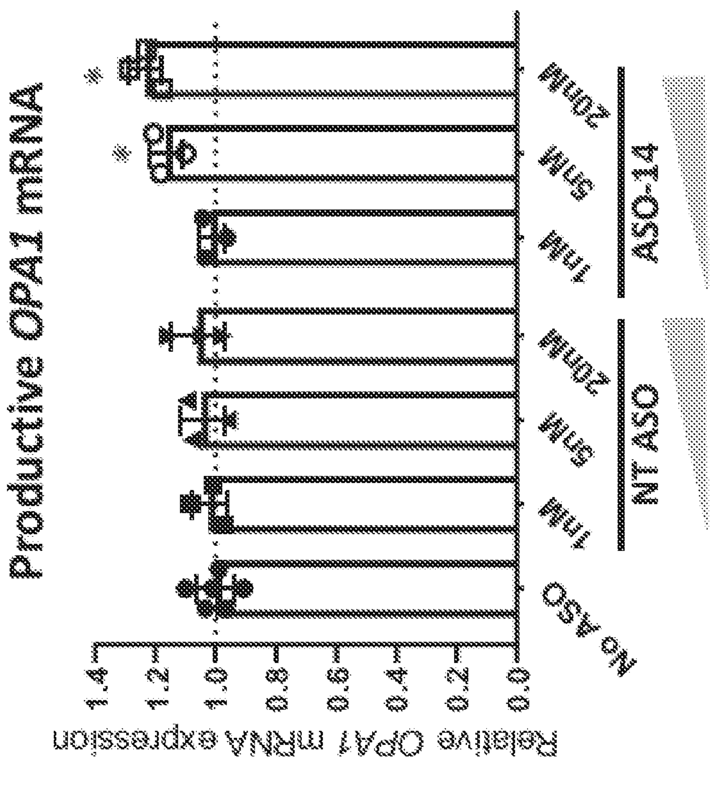
FIG. 12B illustrates quantification of productive OPA1 mRNAs in HEK293 cells after treatment with ASO-14 in the absence of cycloheximide.
Figure 12C:
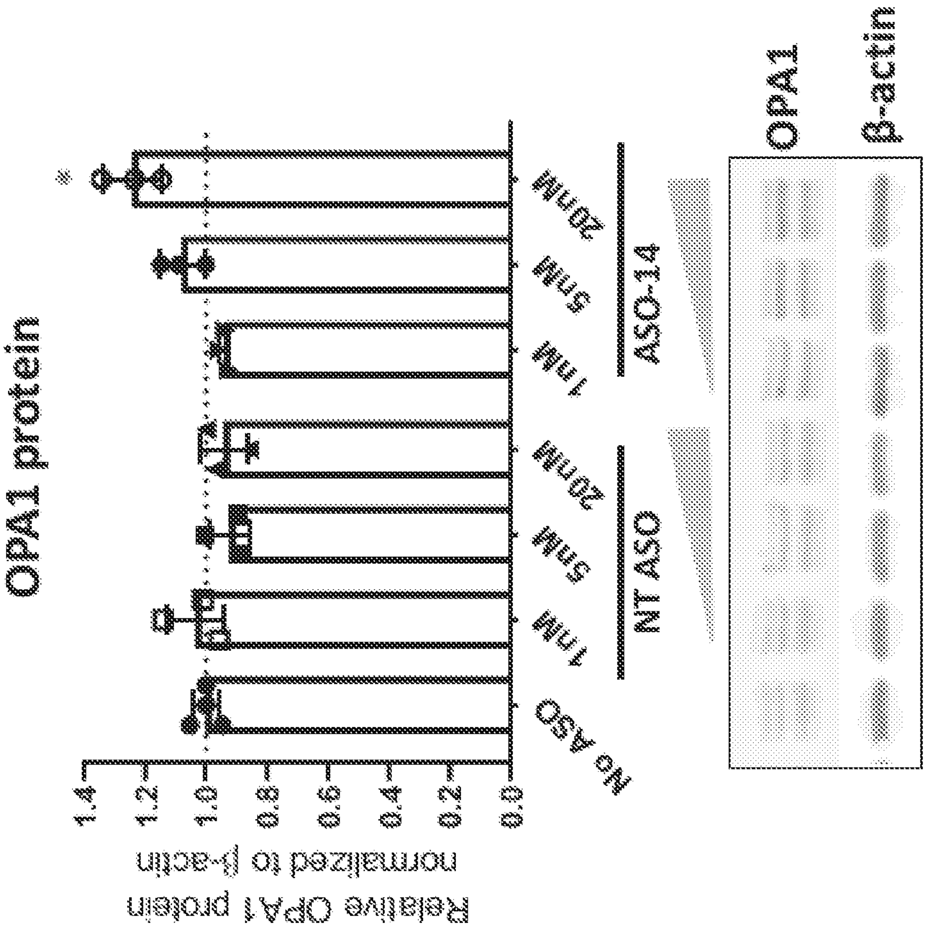
FIG. 12C illustrates protein expression of OPA1 in HEK293 cells after treatment with ASO-14 in the absence of cycloheximide.

Example 12: ASO-14 Decreases Non-Productive OPA1 mRNA and Increases OPA1 Expression in a Dose-Dependent Manner In Vitro HEK293 cells were transfected with different doses of ASO-14 or non-targeting (NT) ASO. RNA was isolated 24 hours after transfection and analyzed for impact on non-productive OPA1 mRNA (FIG. 12A) and OPA1 mRNA expression (FIG. 12B) similarly to in Example 11. For protein analysis, cells were lysed with RIPA buffer 48 hours after transfection and western blots were probed with antibodies targeting OPA1 and β-actin, as shown in FIG. 12C. Multiple bands correspond to different isoforms of OPA1. Data represent the average of three independent experiments (* $P<0.05$ by one-way ANOVA compared to "NO ASO" group). The Non-targeting ASO targets an unrelated gene.

Figure 13A:
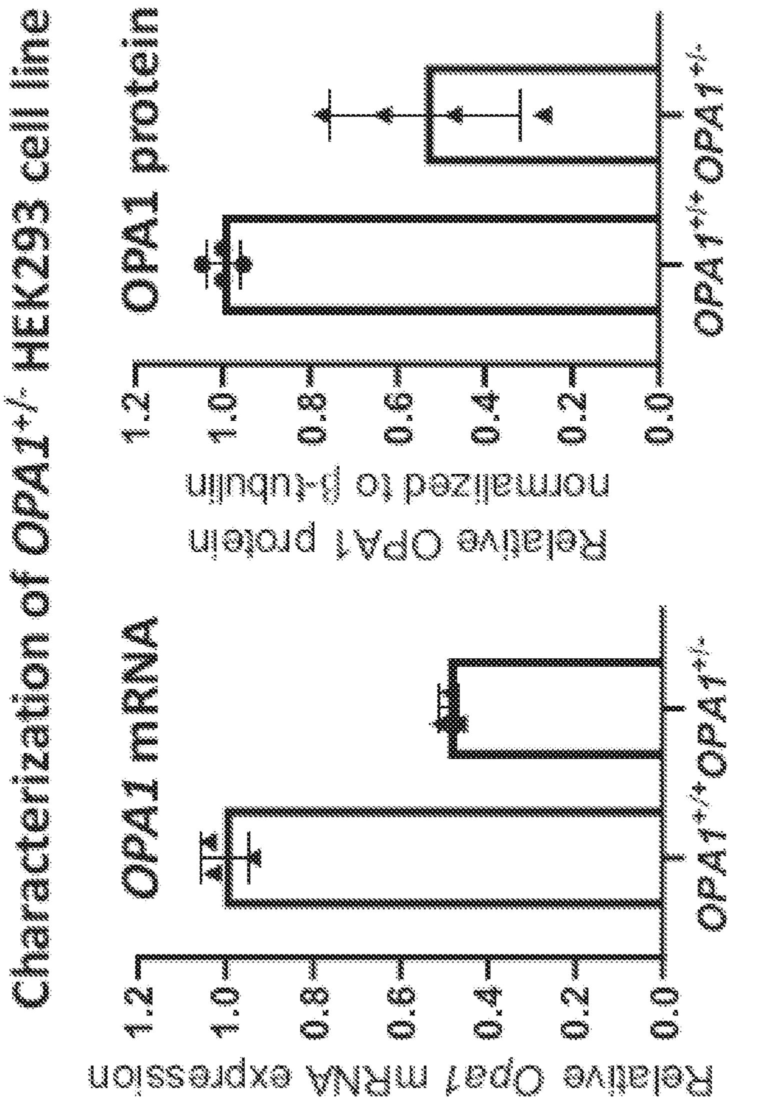
FIG. 13A illustrates mRNA and protein levels of OPA1 gene in OPA1 haploinsufficient (OPA1+/−) HEK293 cells.
Figure 13B:
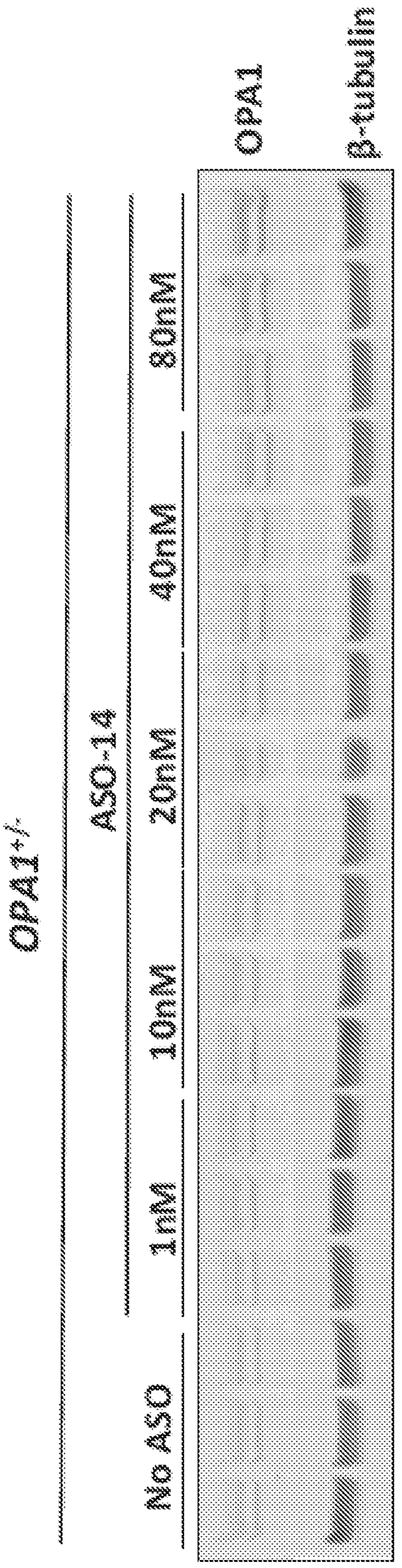
FIG. 13B illustrates OPA1 protein expression in the OPA1 haploinsufficient (OPA1+/−) HEK293 cells after treatment with ASO-14.
Figure 13C:
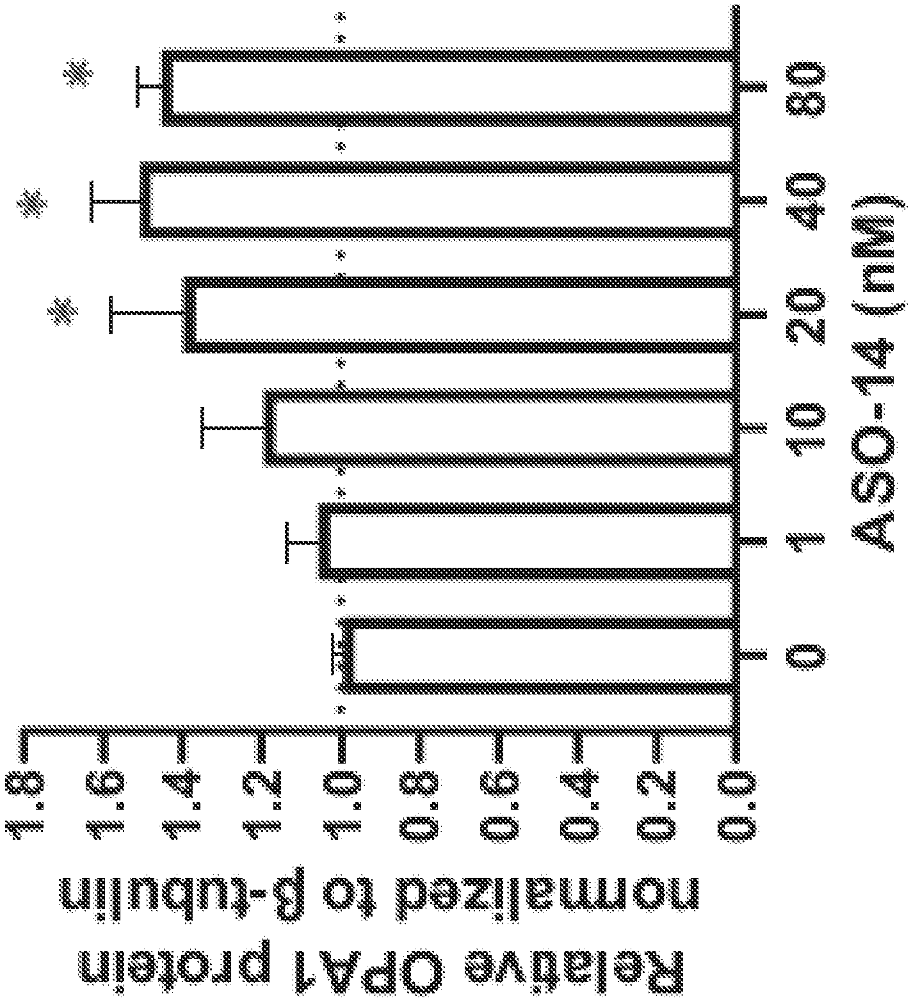
FIG. 13C illustrates quantification of OPA1 protein expression in the OPA1 haploinsufficient (OPA1+/−) HEK293 cells after treatment with ASO-14.

Example 13: ASO-14 Increases OPA1 Expression in an OPA1 Haploinsufficient (OPA1+/−) Cell Line OPA1 haploinsufficient (OPA1+/−) HEK293 cells were generated using CRISPR-Cas9 gene editing. Similar to ADOA patient cells, OPA1+/−HEK293 cells show approximately 50% mRNA and protein levels of that observed in OPA1+/+ cells (FIG. 13A). The OPA1+/−HEK293 cells were transfected with different doses of ASO-14 as indicated in FIG. 13B, and total protein was isolated 72 hours after transfection. Western blots were probed with antibodies targeting OPA1 and β-tubulin, a representative blot is shown in FIG. 13B and quantification of two independent experiments is shown in FIG. 13C (* $P<0.05$ by one-way ANOVA compared to "No ASO" group). ASO-14 increases OPA1 protein levels in OPA1+/−HEK293 cells by 50%, which translates to 75% of wild-type levels.

Figure 14A:
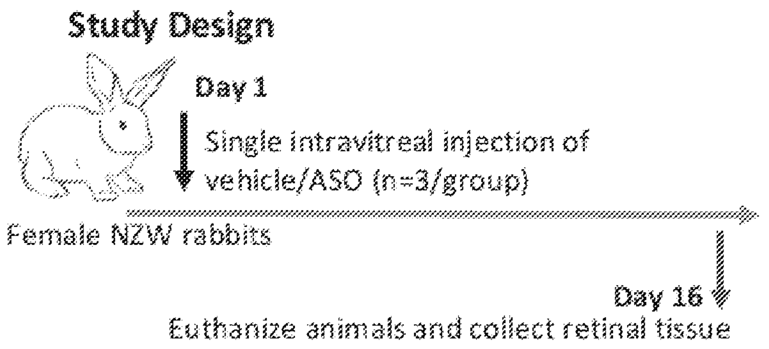
FIG. 14A illustrates study design for the in vivo rabbit experiment of Example 14.
Figure 14B:
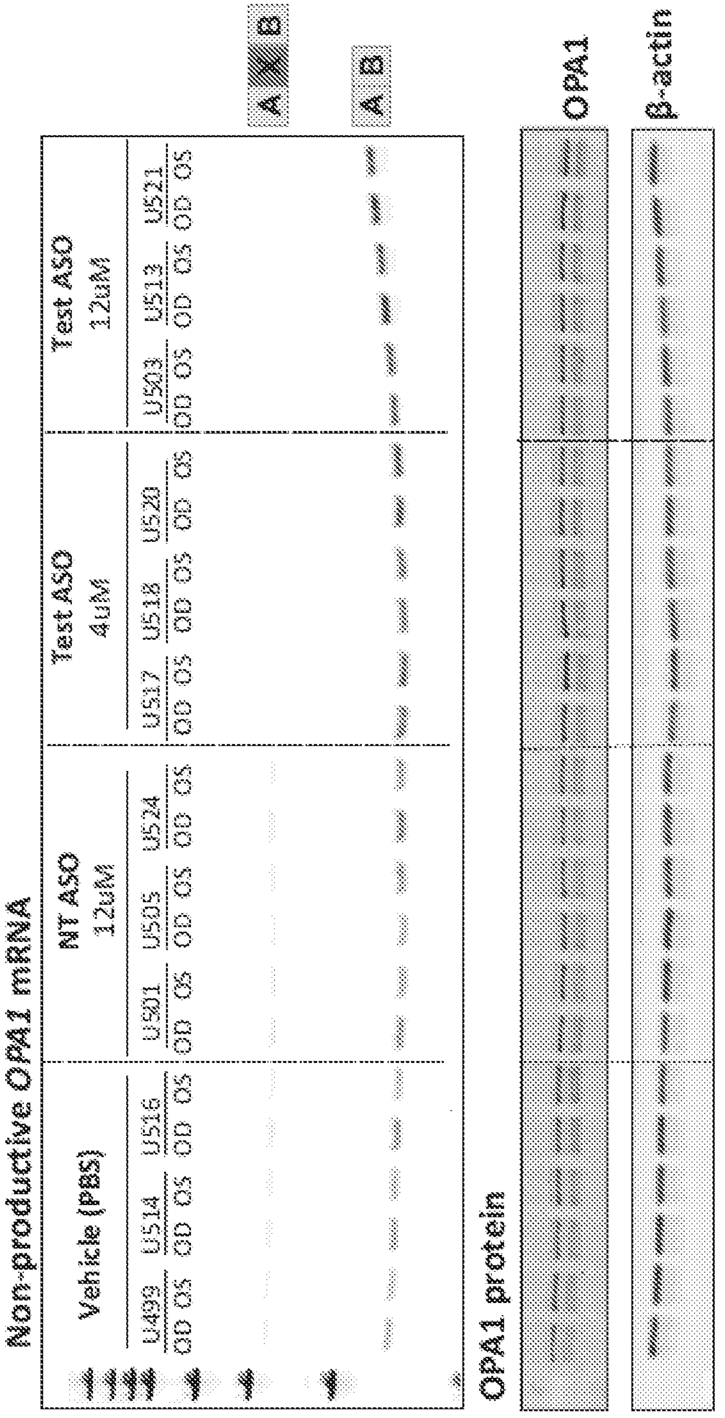
FIG. 14B illustrates levels of productive and non-productive OPA1 mRNA and protein.
Figure 14C:
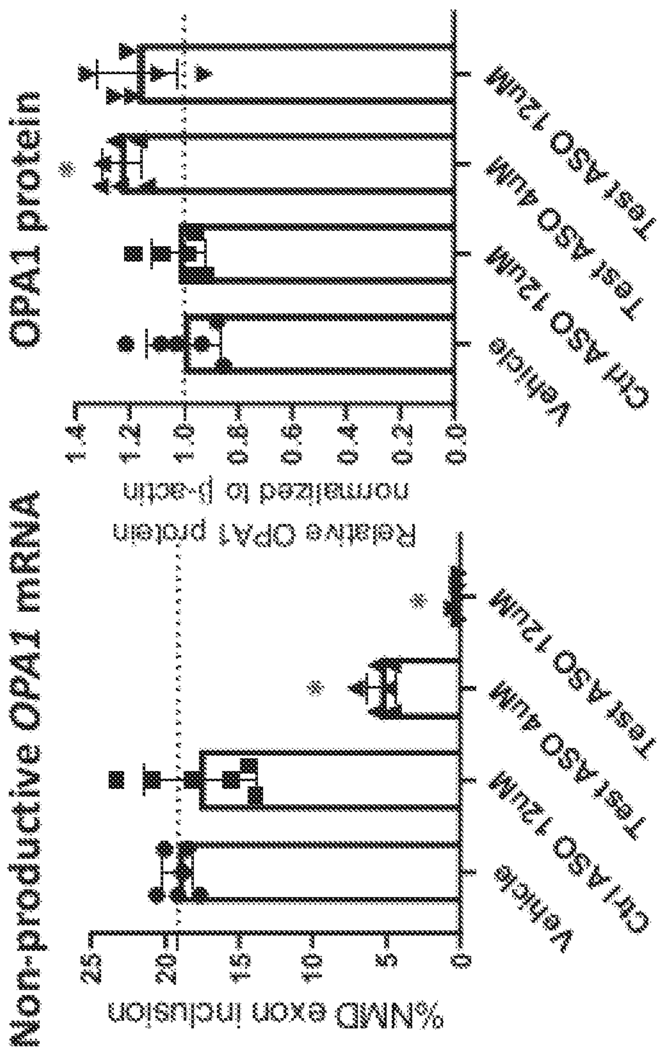
FIG. 14C illustrates quantification of the data from FIG. 14B.

Example 14: Exemplary OPA1 ASOs Decrease Non-Productive Splicing and Increase OPA1 Expression in Wild-Type Rabbit Retinae Following Intravitreal Injection Female New Zealand White (NZW) adult rabbits were injected with either vehicle, non-targeting (NT), or test, antisense oligonucleotides. Animals were euthanized after 15 days to obtain retinal tissue. FIG. 14A outlines the study design, (*Final concentration in the vitreous calculated assuming vitreal volume in the rabbit as 1.5 mL). FIG. 14B shows levels of productive and non-productive OPA1 mRNA and protein, and FIG. 14C shows quantification of this data (* $P<0.05$ by one-way ANOVA compared to Vehicle group). OD: oculus dextrus (right eye), OS: oculus sinister (left eye).

It was also found that the antisense oligonucleotides were well-tolerated in wild-type rabbit for up to 28 days after intravitreal injection.

Figure 16A:
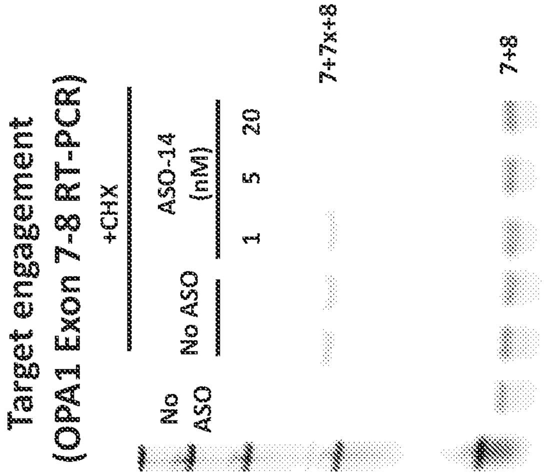
FIG. 16A illustrates RT-PCR results for OPA1 mRNAs using probes spanning exon 7 and exon 8 in HEK293 cells after treatment with ASO-14 and cycloheximide.
Figure 16B:
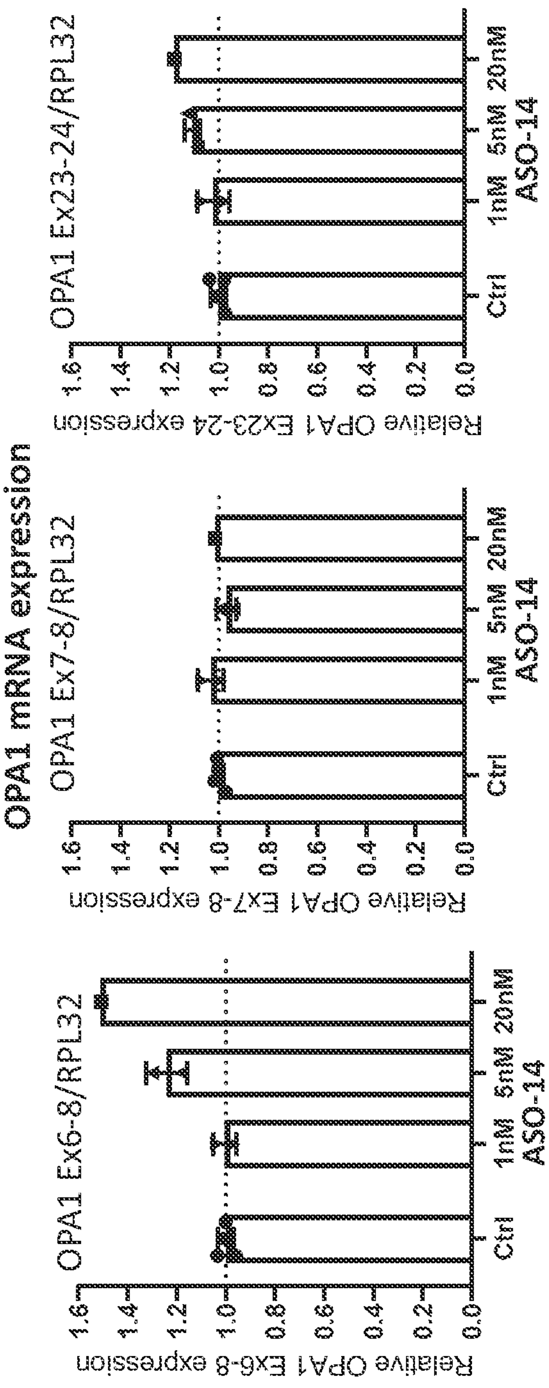
FIG. 16B illustrates quantification of OPA1 mRNAs in HEK293 cells after treatment with ASO-14 in the absence of cycloheximide based on qPCR using probes spanning exons 6 and 8, probes spanning exons 7 and 8, or probes spanning exons 23 and 24.
Figure 16C:
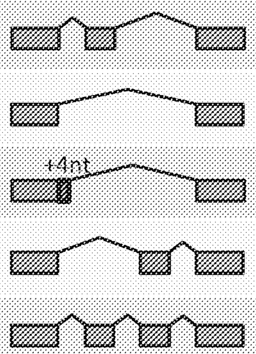
FIG. 16C illustrates sequencing data on the relative amount of various OPA1 mRNA transcripts in HEK293 cells transfected with ASO-14.

Example 15: ASO-14 Modulates Inclusion of Both Exon 7 and Exon 7x in OPA1 mRNA Transcript HEK293 cells were transfected with different doses of ASO-14 or no ASO, in the presence or absence of cycloheximide. RNA was isolated 24 hours after transfection and analyzed for impact on OPA1 mRNA splicing and OPA1 mRNA expression similarly to in Example 11. FIG. 16A shows gel image of PCR products from RT-PCR reaction using probes spanning exon 7 and 8. As shown in the figure, the dose of ASO-14 increased from 1 nM, 5 nM, to 20 nM, the amount of transcripts having exon 7x between exons 7 and 8 ("7+7x+8") gradually decreased, as compared to relatively stable amount of transcripts lacking exon 7x between exons 7 and 8 ("7+8"). FIG. 16B shows plots summarizing the relative amount of various OPA1 mRNA transcripts quantified by qPCR reactions using different pairs of probes: "Ex6-8," probes spanning exons 6 and 8; "Ex7-8," probes spanning exons 7 and 8; and "Ex23-24," probes spanning exons 23 and 24. Results were normalized to RPL32 as an internal control. FIG. 16C shows a chart summarizing the quantification of various OPA1 mRNA transcripts based on sequencing of the RNA extracts from the treated HEK293 cells in the absence of cycloheximide. As suggested by the figures, ASO-14 appeared to induce reduction in OPA1 exon 7x inclusion, increase in OPA1 Ex6-8 transcripts (transcripts having exon 6 and exon 8 in tandem, thus lacking exon 7 and exon 7x), modest decrease or no change in OPA1 Ex7-8 transcripts (transcripts having exon 7 and exon 8 in tandem, thus lacking exon 7x).

Figure 17A:
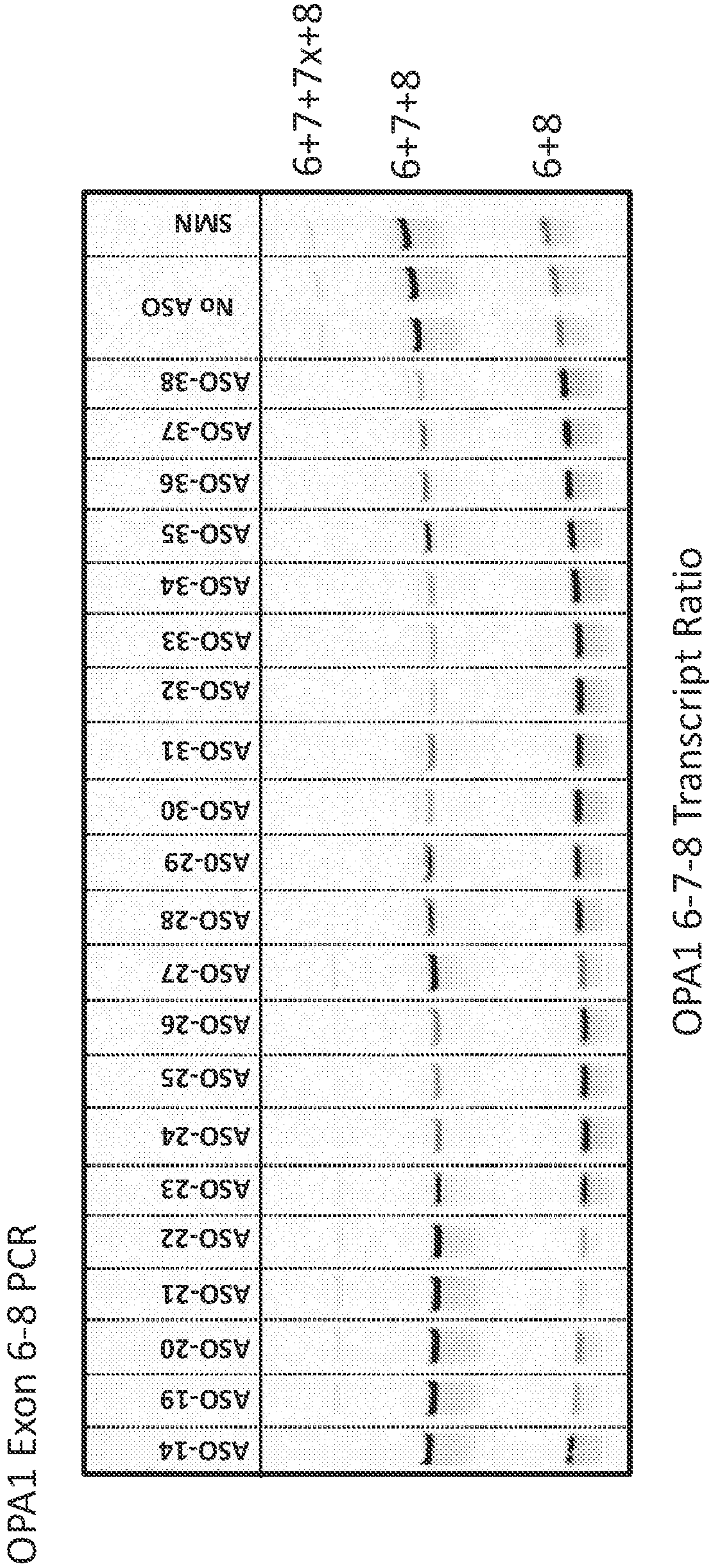
FIG. 17A illustrates RT-PCR results for OPA1 mRNAs using probes spanning exon 6 and exon 8 in HEK293 cells after treatment with various exemplary OPA1 ASOs.
Figure 17B:
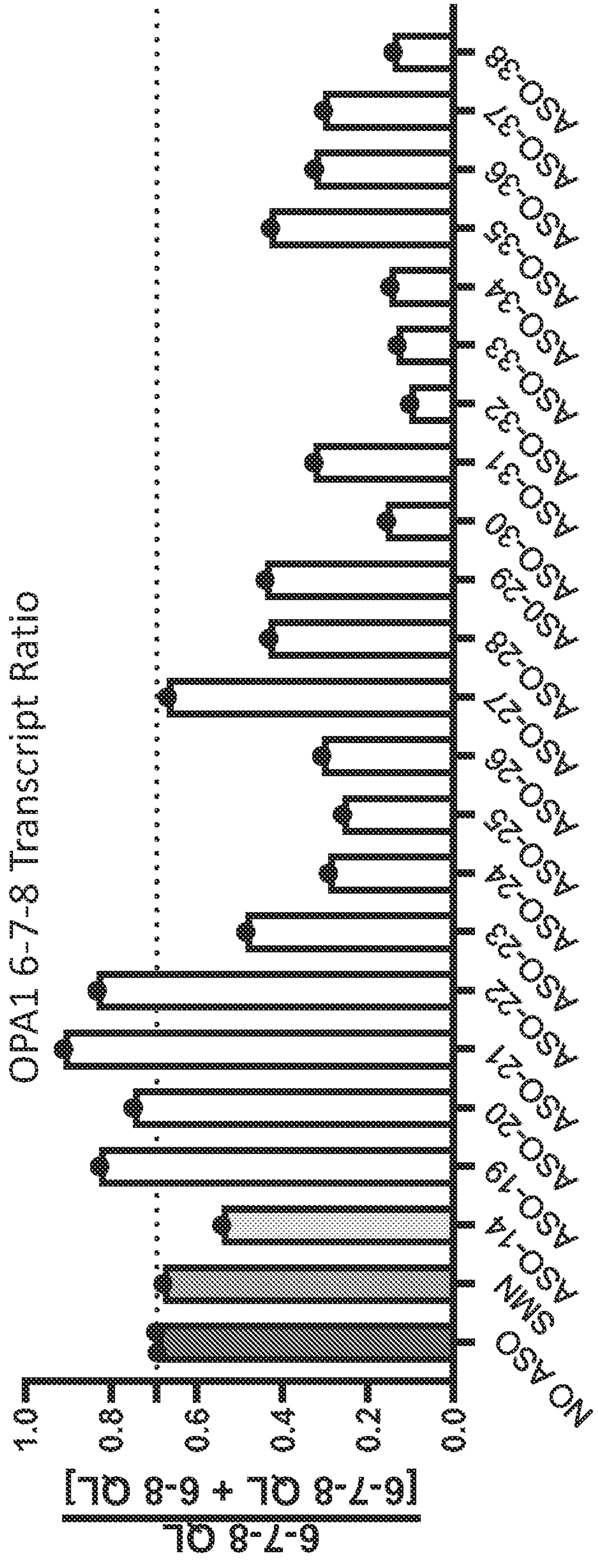
FIG. 17B illustrates relative ratio of OPA1 mRNA transcripts having exons 6, 7, and 8 in tandem ("6-7-8") over the total amount of "6-7-8" transcripts and transcripts having exons 6 and 8 in tandem ("6-8"), in HEK293 cells after treatment with various exemplary OPA1 ASOs.
Figure 17C:
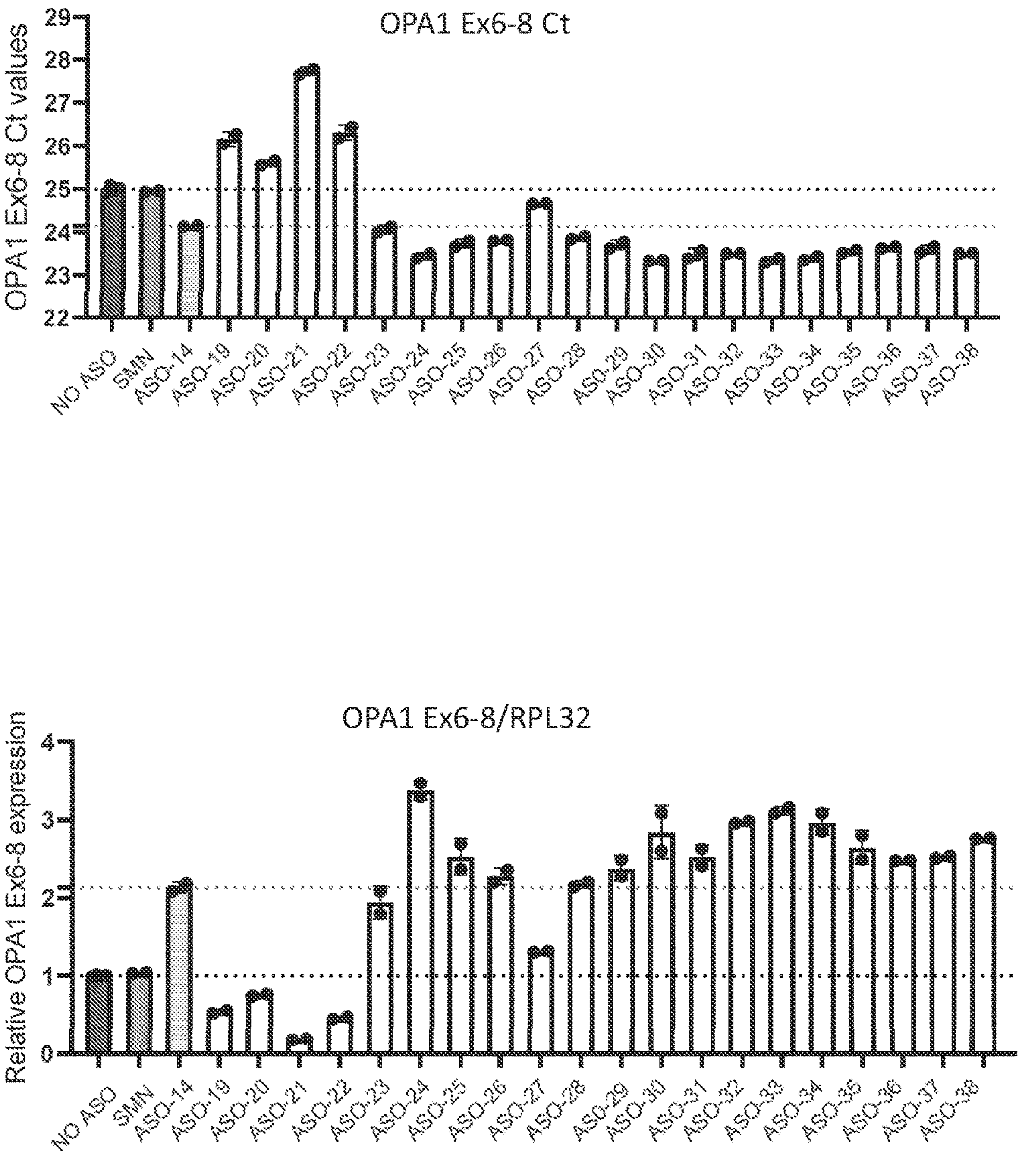
FIGS. 17C and 17D illustrate quantification of OPA1 mRNAs using probes spanning exons 6 and 8, and probes spanning exons 7 and 8, respectively, in HEK293 cells after treatment with various exemplary OPA1 ASOs.
Figure 17D:
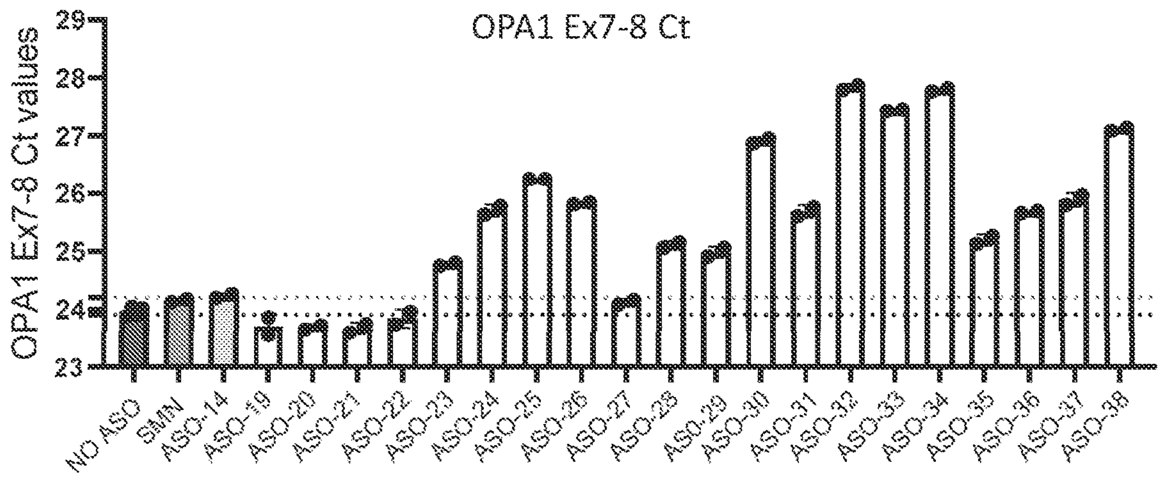
Figure 17D:
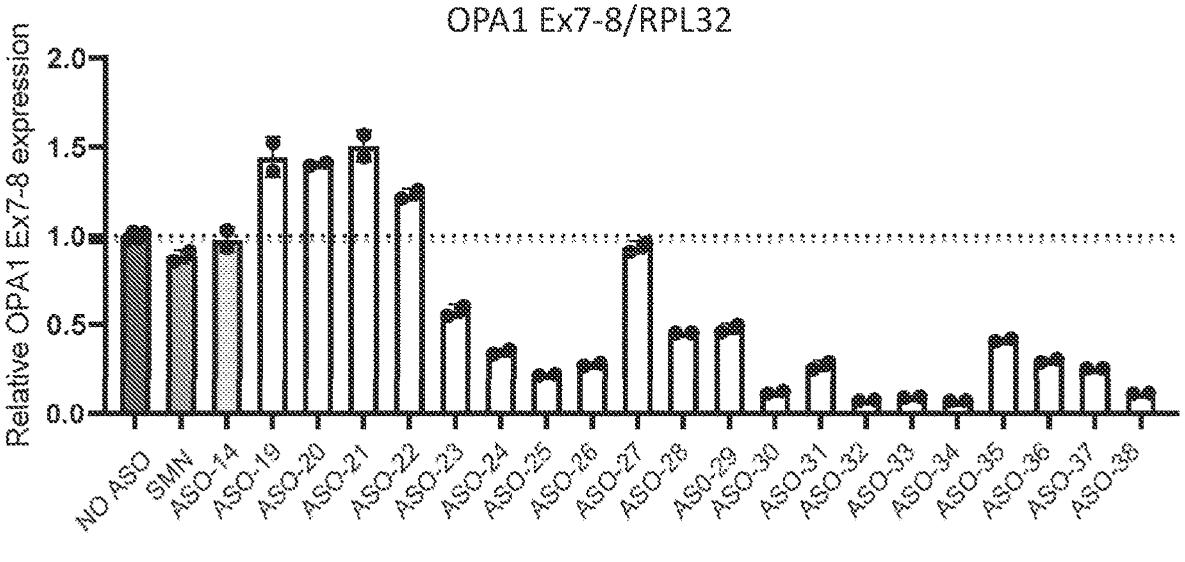

Example 16: Exemplary OPA1 Antisense Oligomers Modulate Inclusion of Exon 7, Exon 7x, or Both in OPA1 mRNA Transcript HEK293 cells were transfected with different exemplary OPA1 modified 2'MOE-PS (2' methoxyethyl and phosphorothioate) ASOs. Each well of HEK 293 cells (about 100, 000 cells/well) were treated with an exemplary ASO at 80 nM final concentration in the presence of 0.9 μL of Lipofectamine® RNAiMax in the absence of cycloheximide. The cells were harvested 24 hours after transfection and RNA was isolated and analyzed for impact on OPA1 mRNA splicing and OPA1 mRNA expression similarly to in Example 11. FIG. 17A shows gel image of PCR products from RT-PCR reaction using probes spanning exon 6 and 8, and FIG. 17B is a plot summarizing the relative ratio of the amount of transcripts having exons 6, 7, and 8 in tandem ("6-7-8") over the total amount of "6-7-8" transcripts and transcripts having exons 6 and 8 in tandem ("6-8"). As shown in the figures, certain ASOs, such as ASO-19, ASO-20, ASO-21, ASO-22, induced increase in the relative amount of "6-7-8" transcripts, suggesting an increase in the inclusion of exon 7 in mature OPA1 mRNA transcripts. Some ASOs, such as ASO-23, ASO-24, ASO-25, ASO-26, ASO-28, ASO-29, ASO-30, ASO-31, ASO-32, ASO-33, ASO-34, ASO-35, ASO-36, ASO-37, and ASO-38, in contrast, induced reduction in the relative amount of "6-7-8" transcripts, suggesting a reduction in the inclusion of exon 7 in mature OPA1 mRNA transcript. FIGS. 17C and 17D show the Ct values for the qPCR reaction (upper plots) for, and quantification of the relative amount (bottom plots) of, OPA1 transcripts having exons 6 and 8 ("Ex6-8") and OPA1 transcripts having exons 7 and 8 ("Ex7-8"), respectively. Cells treated with ASO-29, ASO20, ASO-21, and ASO-22 showed reduced amount of "Ex6-8" transcripts and increased amount of "Ex7-8" transcripts, consistent with the suggestion that these ASOs promote the inclusion of exon 7 in OPA1 mature mRNA transcripts. Cells treated with ASO-23, ASO-24, ASO-25, ASO-26, ASO-28, ASO-29, ASO-30, ASO-31, ASO-32, ASO-33, ASO-34, ASO-35, ASO-36, ASO-37, and ASO-38 showed increase in the amount of "Ex6-8" transcripts and decrease in the amount of "Ex7-8" transcripts, consistent with the suggestion that these ASOs promote the exclusion of exon 7 from OPA1 mature mRNA transcripts.

Figure 18A:
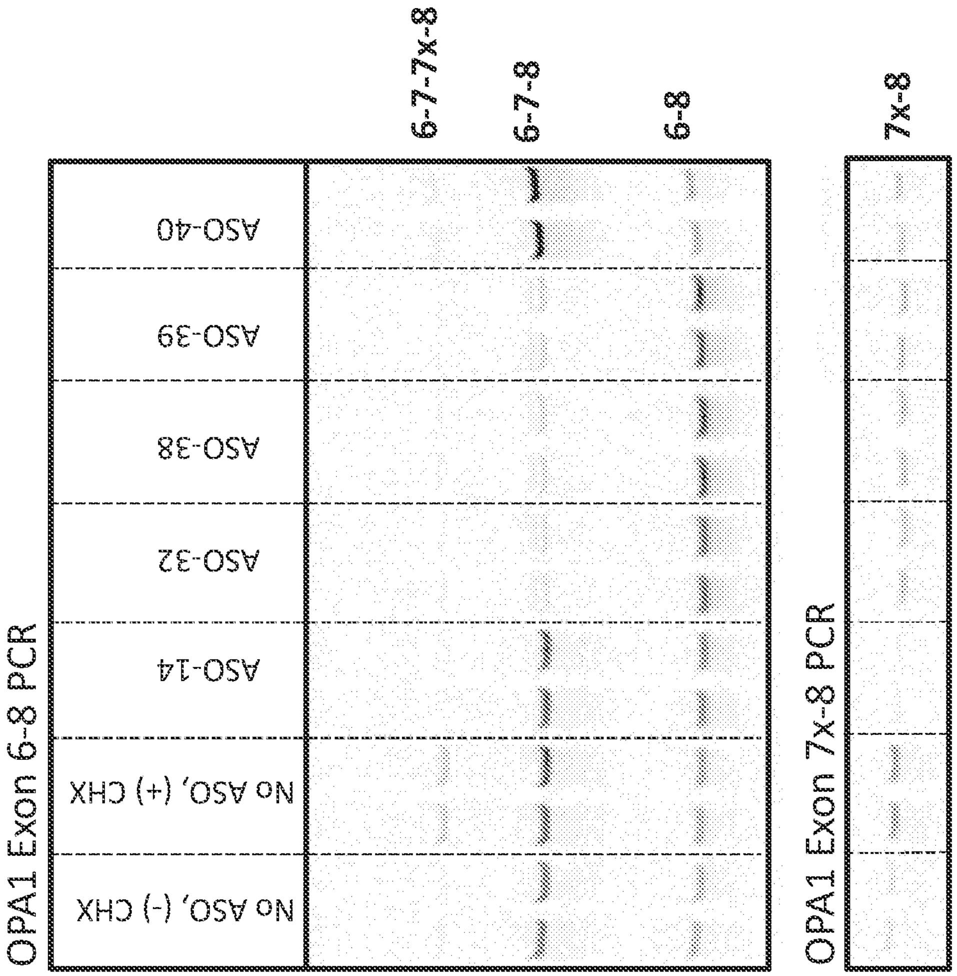
FIG. 18A illustrates RT-PCR results for OPA1 mRNAs using probes spanning exon 6 and exon 8 ("Exon 6-8 PCR"), or probes spanning exon 7x and exon 8 ("Exon 7x-8 PCR"), in HEK293 cells after treatment with various exemplary OPA1 ASOs and treatment with cycloheximide.

Example 17: Exemplary OPA1 Antisense Oligomers Modulate Inclusion of Exon 7, Exon 7x, or Both in OPA1 mRNA Transcript and Modulate Expression Level of OPA1 Protein HEK293 cells were transfected with different exemplary OPA1 modified 2'MOE-PS (2' methoxyethyl and phosphorothioate) ASOs. Each well of HEK 293 cells (about 50,000 cells/well) were treated with an exemplary ASO at 80 nM final concentration in the presence of 0.9 μL of Lipofectamine® RNAiMax. Here, the cells were harvested 72 hours after transfection to test ASO's effect on OPA1 mRNA and protein expression. The cells were treated with cycloheximide (50 μg/mL) for 3 hours prior to harvest for mRNA analysis. FIG. 18A shows gel image of PCR products from RT-PCR reaction using probes spanning exon 6 and 8. As shown in the figure, ASO-14 induced reduction in the amount of transcripts having exons 6, 7, 7x, and 8 in tandem ("6-7-7x-8"). ASO-32, ASO-38, and ASO-39 induced significant reduction in the amount of "6-7-8" transcripts, and modest reduction in the amount of "6-7-7x-8" transcripts, whereas ASO-40 induced increase in the amount of "6-7-8" transcripts. These data suggest that ASO-14 promotes exclusion of exon 7x from OPA1 mRNA transcript, ASO-32, ASO-38, and ASO-39 promote exclusion of exon 7 from OPA1 mRNA transcript, and they also promote exclusion of exon 7x from OPA1 mRNA transcript. In contrast, the data suggest that ASO-40 promotes inclusion of exon 7 in OPA1 mRNA transcript.

Figure 18B:
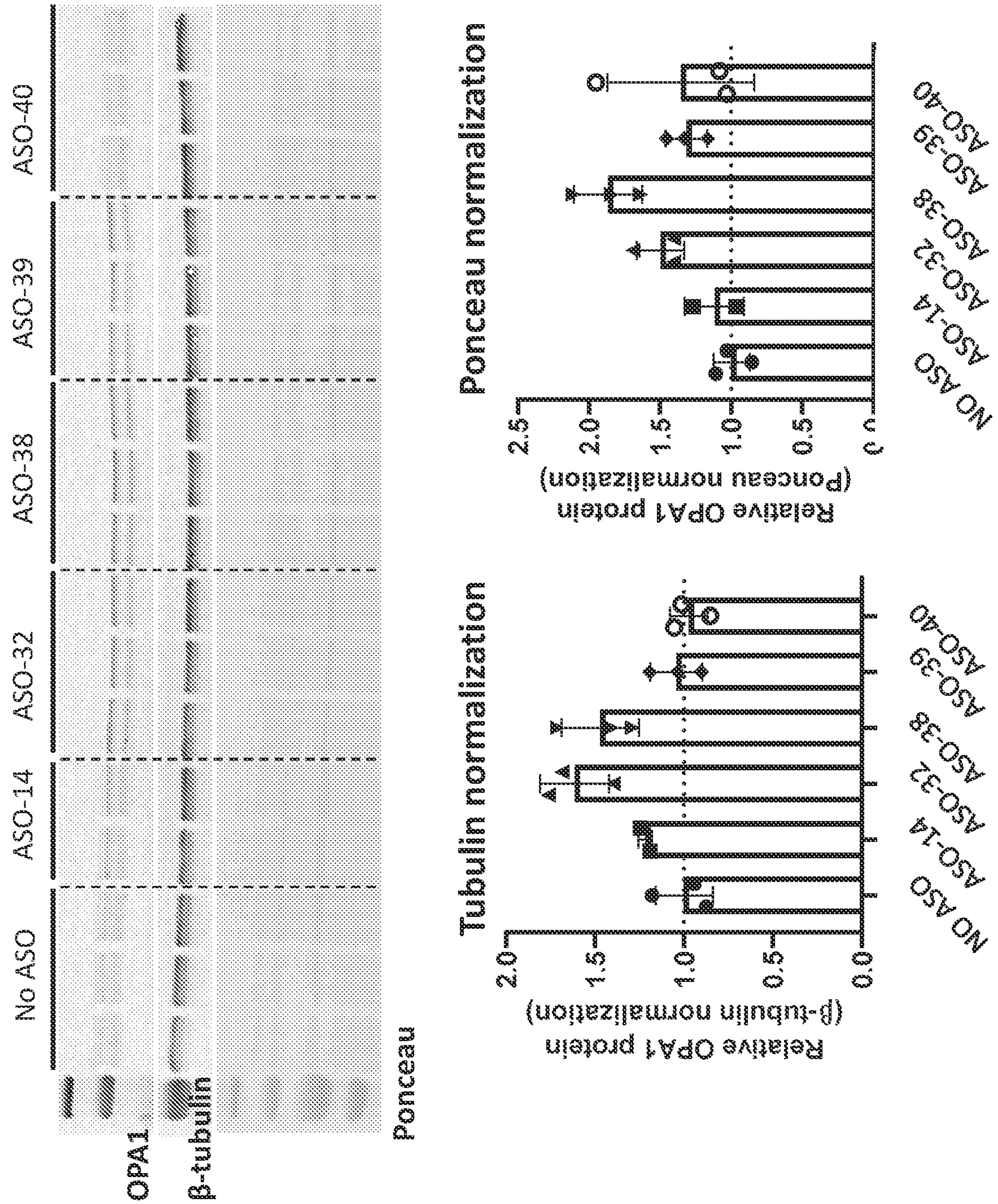
FIG. 18B illustrates expression level of OPA1 protein in HEK293 cells after treatment with various exemplary OPA1 ASOs.

FIG. 18B shows image of Western blot using antibody against OPA1 protein and antibody against β-tubulin protein in the cells after treatment with different ASOs or no ASO (control), as well as Ponceau staining image of the same blot. FIG. 18B also shows plots summarizing the amount of OPA1 protein under different treatment conditions as normalized relative to the amount of β-tubulin or Ponceau staining intensity. The data suggest that ASO-14, ASO-32, ASO-38, and ASO-39 all may induce increase in OPA1 protein expression, whereas ASO-40 may not significantly change the expression level of OPA1 protein.

Dose response of ASO-32 and ASO-38 were also tested along with ASO-14. ASO treatment, cell harvest, and RNA isolation and analysis were conducted similarly to the experiment above in this example. Each well of HEK293 cells (about 50,000 cells/well) were treated with either 20 nM or 80 nM of ASO-14, ASO-32, ASO-38, or no ASO.

Figure 18C:
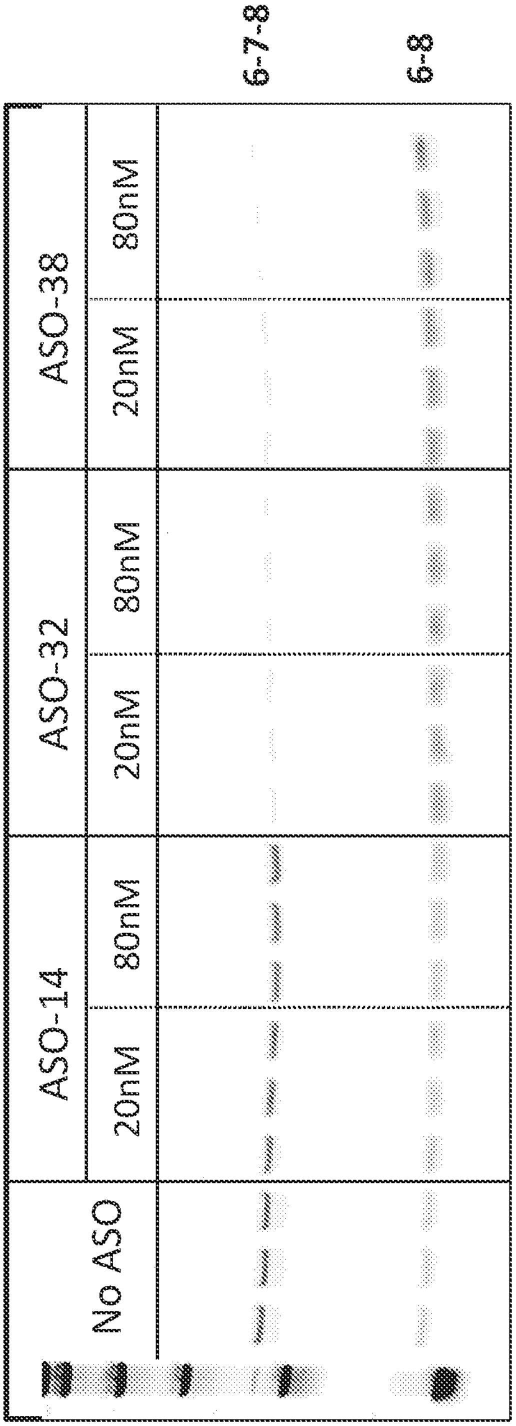
FIG. 18C illustrates dose response in OPA1 mRNAs using probes spanning exon 6 and exon 8 in HEK293 cells after treatment with various exemplary OPA1 ASOs.
Figure 18D:
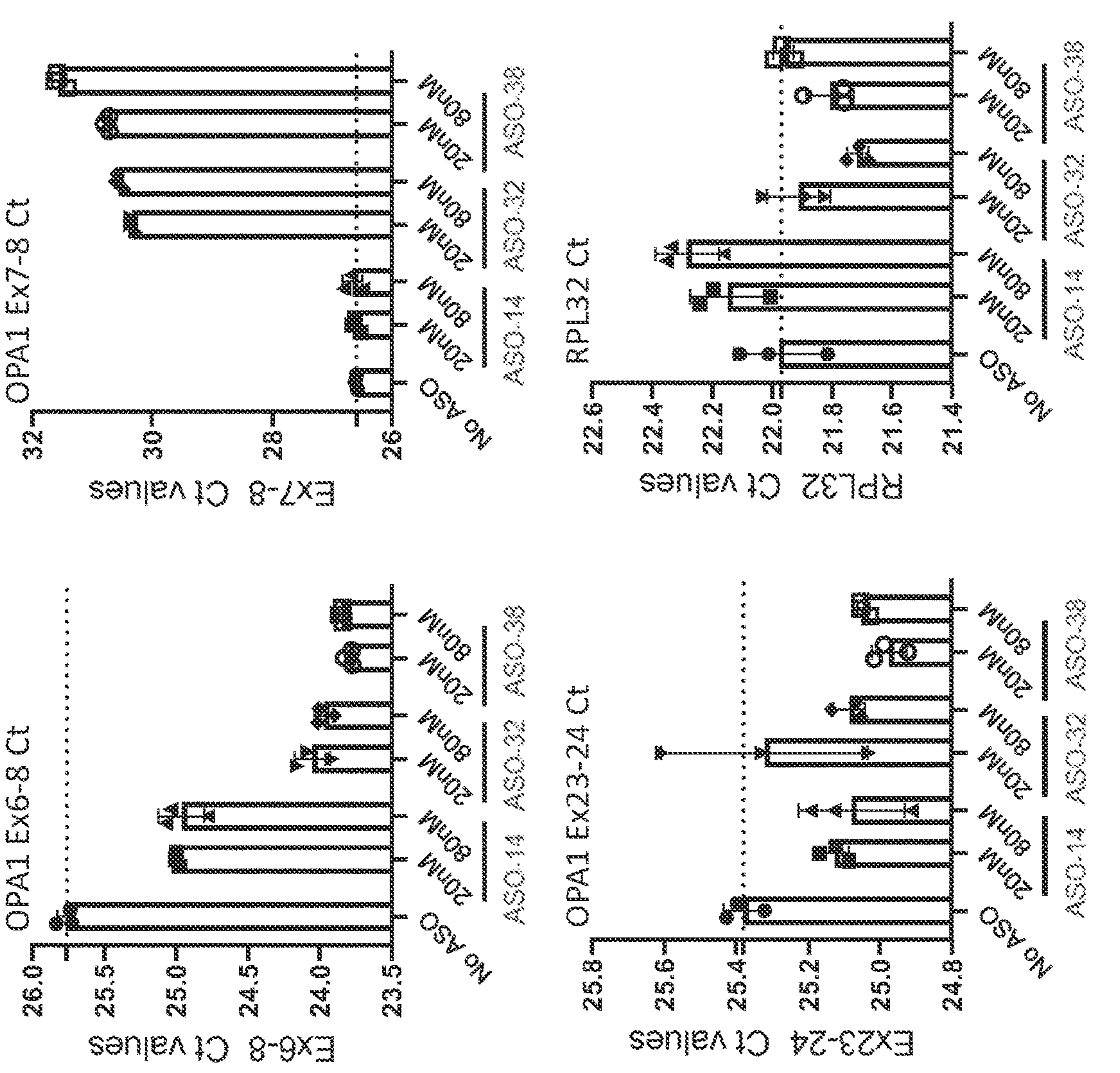
FIGS. 18D and 18E illustrate quantification of the dose response in OPA1 mRNAs using probes spanning exons 6 and 8, probes spanning exons 7 and 8, probes spanning exons 23 and 24, respectively, in HEK293 cells after treatment with various exemplary OPA1 ASOs.
Figure 18E:
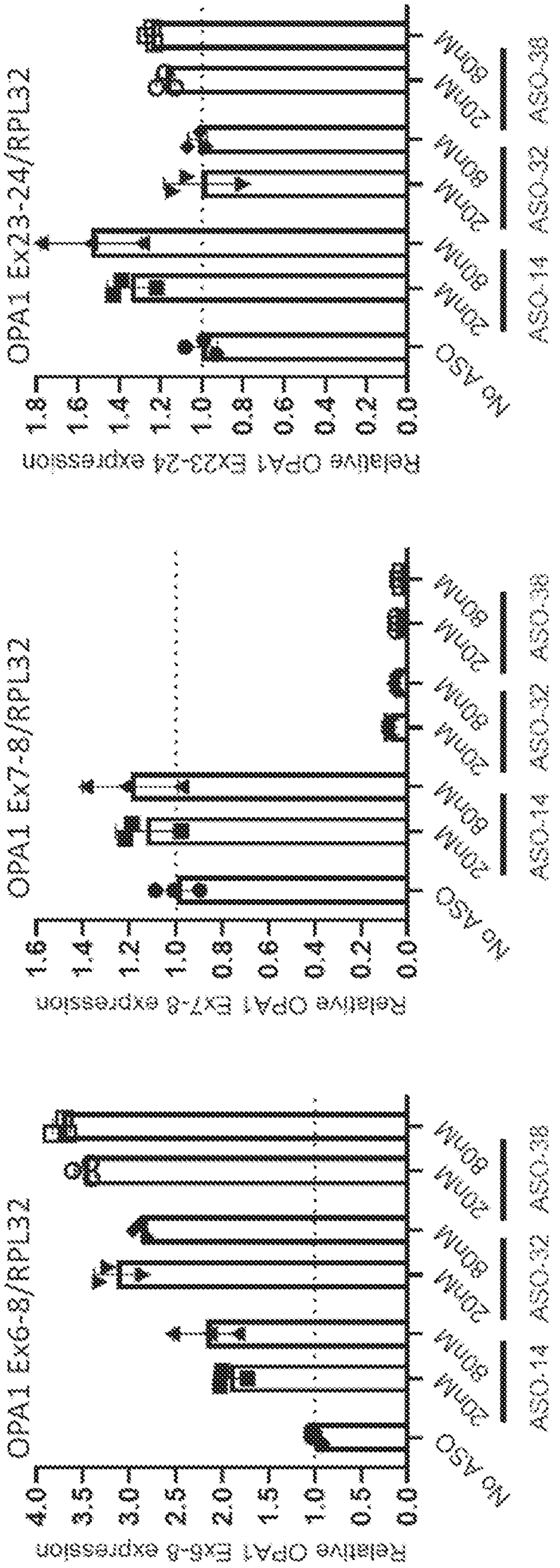
Figure 18F:
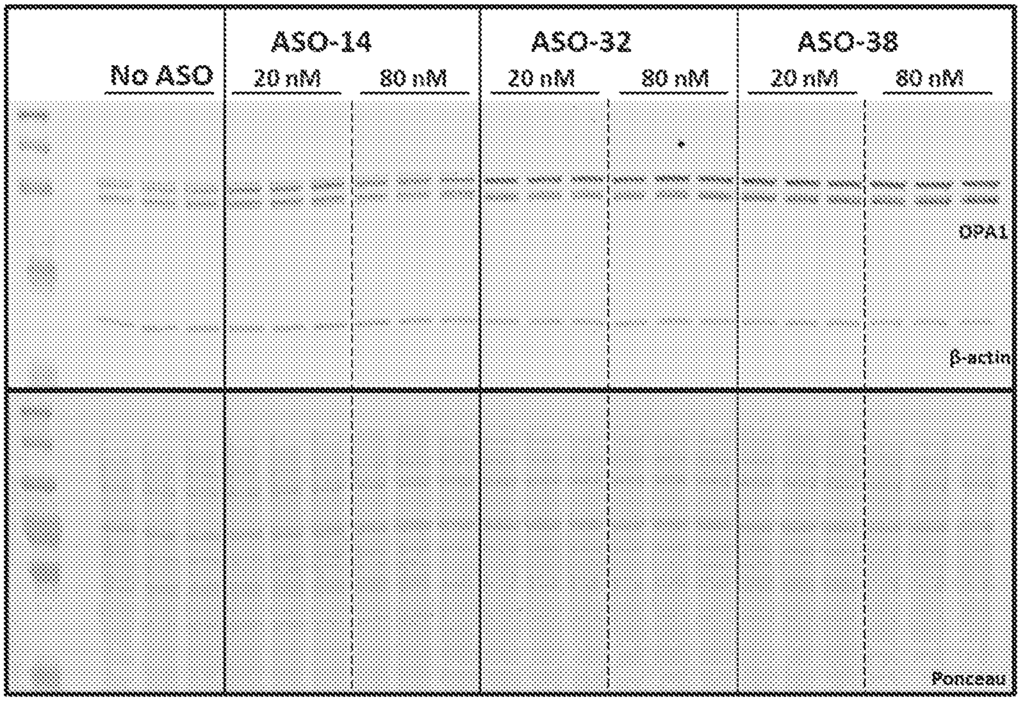
FIG. 18F illustrates dose response in expression level of OPA1 protein in HEK293 cells after treatment with various exemplary OPA1 ASOs.
Figure 18F:
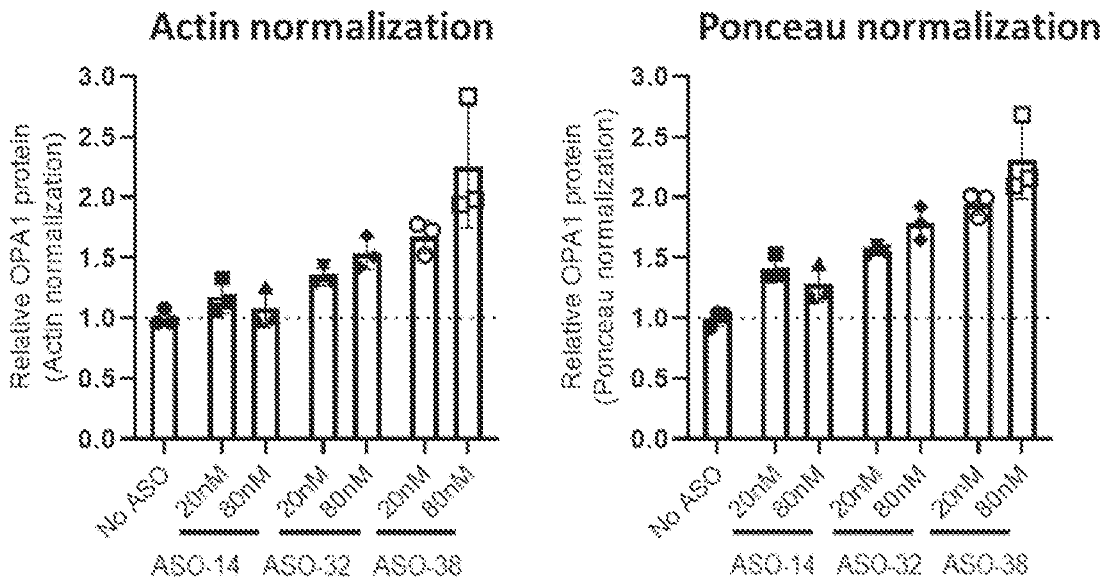

FIG. 18C shows gel image of products from RT-PCR reaction using probes spanning exon 6 and 8. FIG. 18D shows quantification of qPCR Ct values for reactions under different experimental conditions using probes spanning exons and 8 ("Ex6-8"), probes spanning exons 7 and 8 ("Ex7-8"), and probes spanning exons 23 and 24 ("Ex23-24"), and FIG. 18E shows quantification of relative amount of the corresponding transcripts. The data show consistent observation that ASO-32 and ASO-38 promote exclusion of exon 7 from mature OPA1 mRNA transcripts. FIG. 18F shows the data on the OPA1 expression level after treatment of ASO-14, ASO-32, or ASO-38. Consistently, ASO-32 and ASO-38 increased OPA1 protein level.

Example 18: ASO Microwalk Evaluated by RT-qPCR

In one experiment, microwalk was conducted to test ASOs that have sequences listed in Table 7. Briefly, about 30,000 HEK293 cells per well were treated gymnotically with 20 NM one of the 20 exemplary ASOs (free uptake) listed in Table 7 for 72 hours. After the treatment, the cells were harvested for analysis. RT-PCR reactions were conducted for products corresponding to Exon 7 or Exon 7x inclusion and full-length.

Figure 19B:
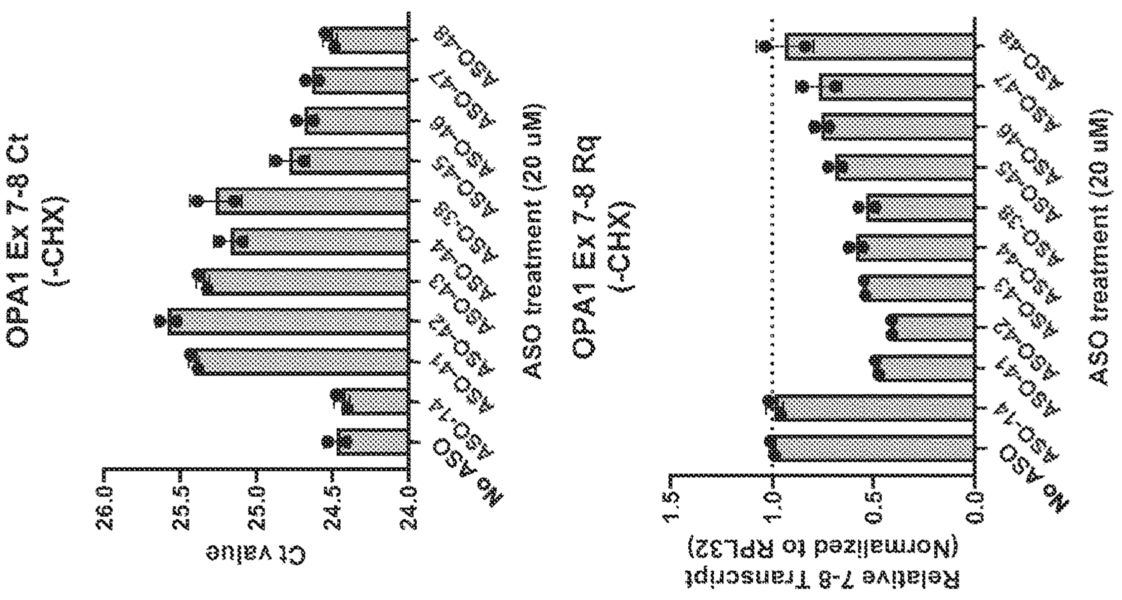
FIGS. 19A-19D illustrate RT-PCR results for OPA1 mRNAs using probes spanning exon 6 and exon 8 ("Exon 6-8"), or probes spanning exon 7x and exon 8 ("Exon 7-8"), in HEK293 cells after treatment with various exemplary OPA1 ASO 18-mers and treatment with or without cycloheximide.
Figure 19A:
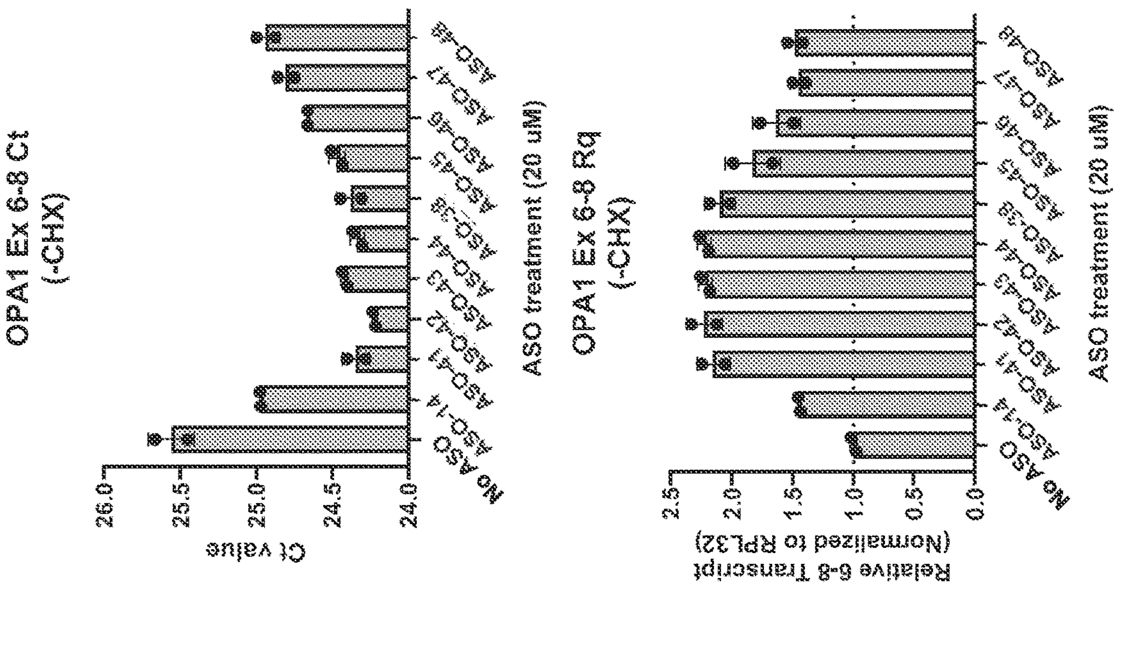
Figure 19D:
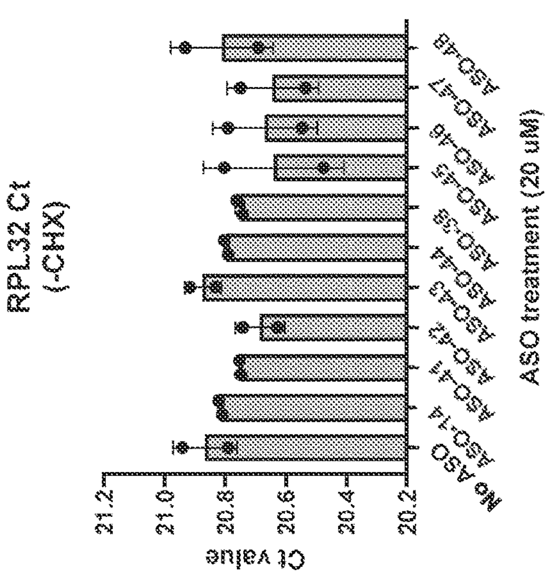
Figure 19C:
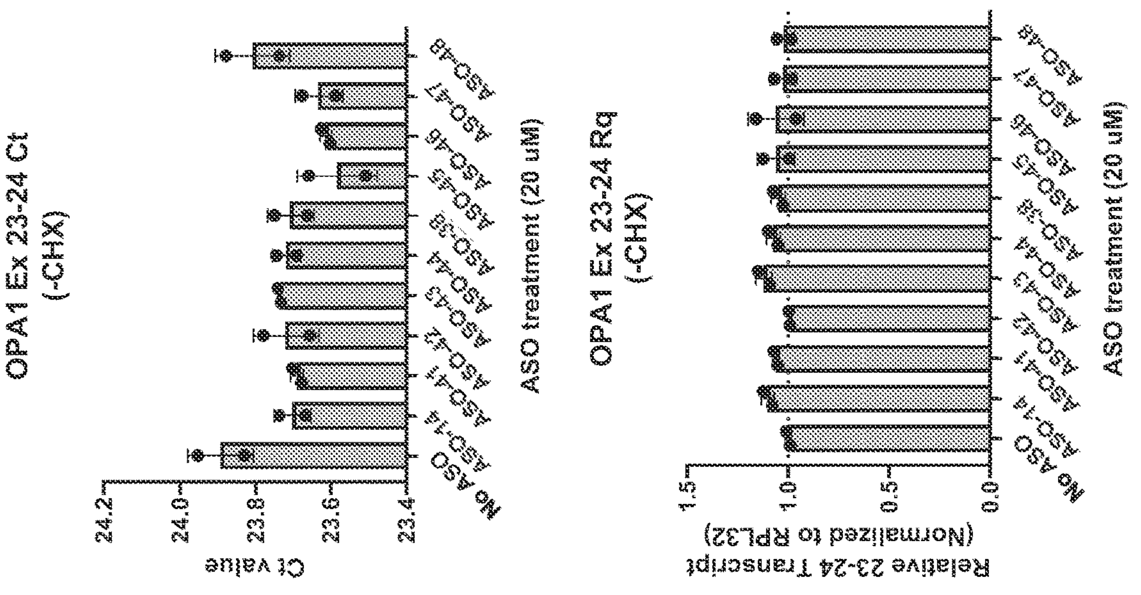
Figure 20B:
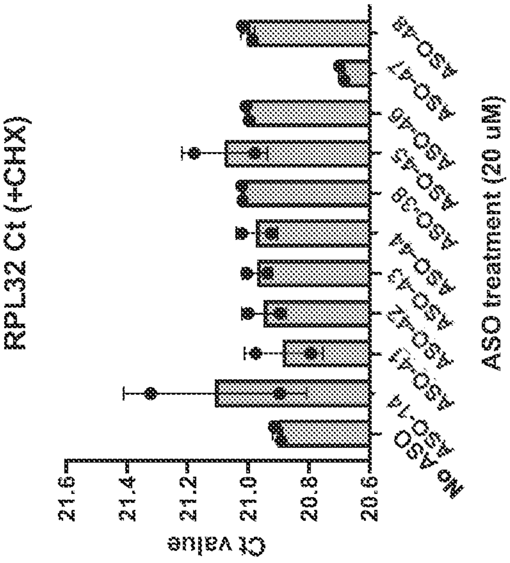
FIGS. 20A-20B illustrate RT-PCR results for OPA1 mRNAs using probes spanning exon 6 and exon 8 ("Exon 6-8"), or probes spanning exon 7x and exon 8 ("Exon 7x-8"), in HEK293 cells after treatment with various exemplary OPA1 ASO 18-mers and treatment with or without cycloheximide.
Figure 20A:
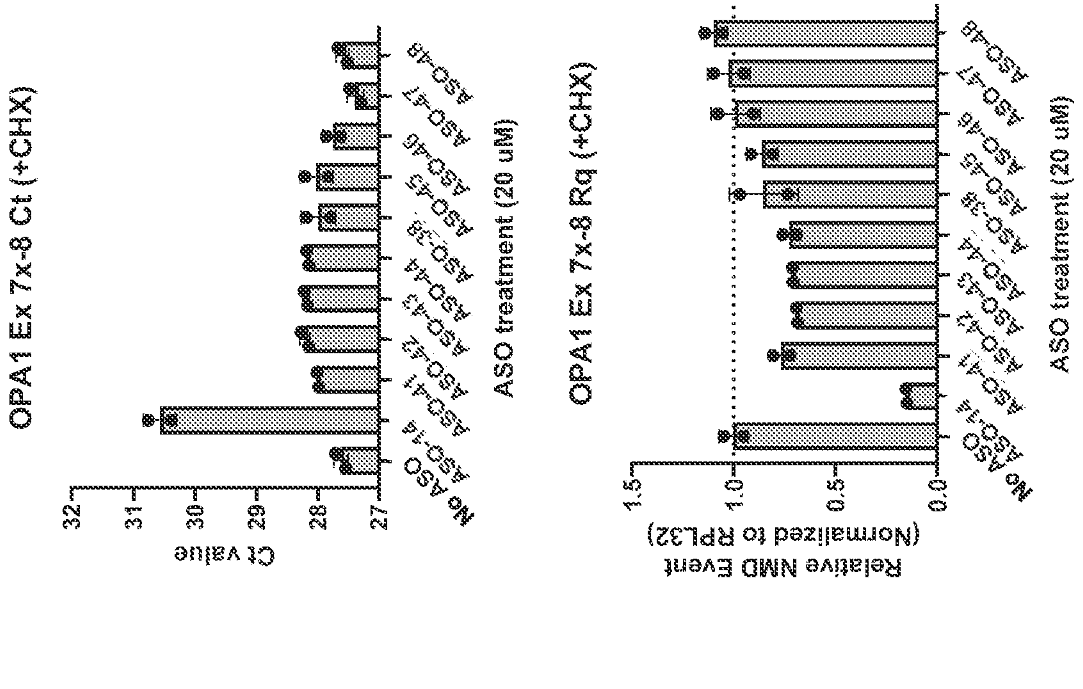

FIGS. 19A-20B demonstrate data from experiments with some of the 18-mers (named ASO-41 to ASO-48) listed in Table 7. FIGS. 19A-19B show the Ct values for the qPCR reaction (upper plots) for, and quantification of the relative amount (lower plots; normalized to Ct value of RPL32 qPCR product) of, OPA1 transcripts having exons 6 and 8 ("Ex6-8") and OPA1 transcripts having exons 7 and 8 ("Ex7-8"), respectively. FIG. 19C shows the Ct values for the qPCR reaction (upper plots) for, and quantification of the relative amount (lower plots; normalized to Ct value of RPL32 qPCR product) of, OPA1 transcripts having exons 23 and 24 ("Ex23-24"), and FIG. 19D shows the Ct values for RPL32 transcripts as a loading control. These data demonstrate that cells treated with ASO-41 to ASO-47 all showed increased amount of "Ex6-8" transcripts and decreased amount of "Ex7-8" transcripts, suggesting these ASOs promote exclusion of Exon 7 from OPA1 transcripts. No cycloheximide was applied to the cells that were subject to these analyses for Exon 7 inclusion. FIG. 20A shows the Ct values for the qPCR reaction (upper plots) for, and quantification of the relative amount (lower plots; normalized to Ct value of RPL32 qPCR product) of, OPA1 transcripts having exons 7x and 8 ("Ex7x-8"), and FIG. 20B shows the Ct values for RPL32 transcripts as a loading control. These data demonstrate that cells treated with ASO-41 to ASO-44 all showed decreased amount of "Ex7x-8" transcripts, suggesting these ASOs promote exclusion of Exon 7x from OPA1 transcripts. Cycloheximide was applied to the cells for these analyses for Exon 7x inclusion.

Figure 21B:
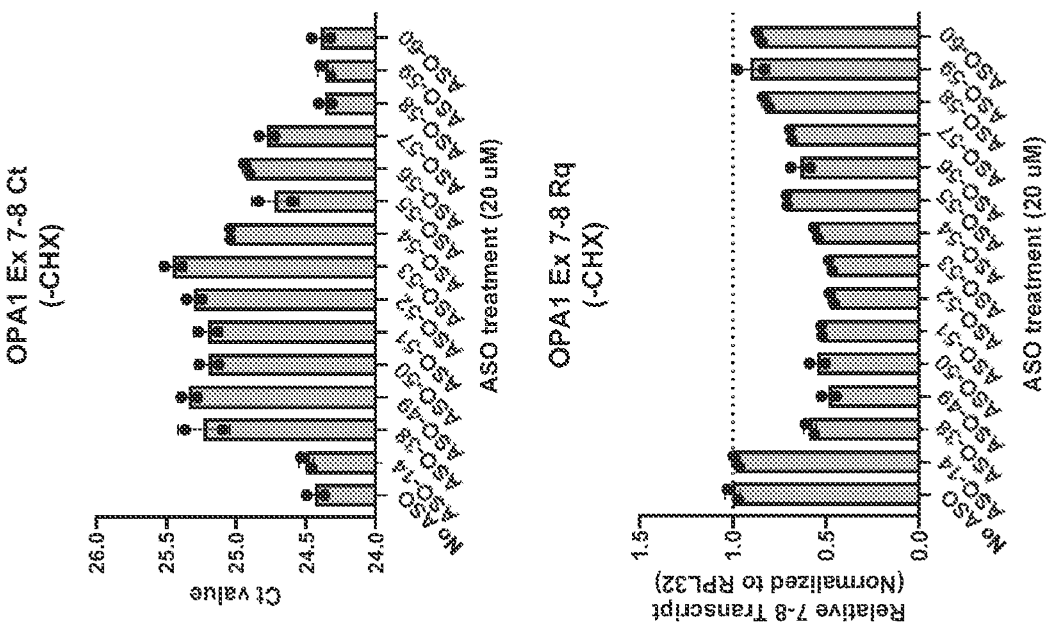
FIGS. 21A-21D illustrate RT-PCR results for OPA1 mRNAs using probes spanning exon 6 and exon 8 ("Exon 6-8"), or probes spanning exon 7x and exon 8 ("Exon 7-8"), in HEK293 cells after treatment with various exemplary OPA1 ASO 16-mers and treatment with or without cycloheximide.
Figure 21A:
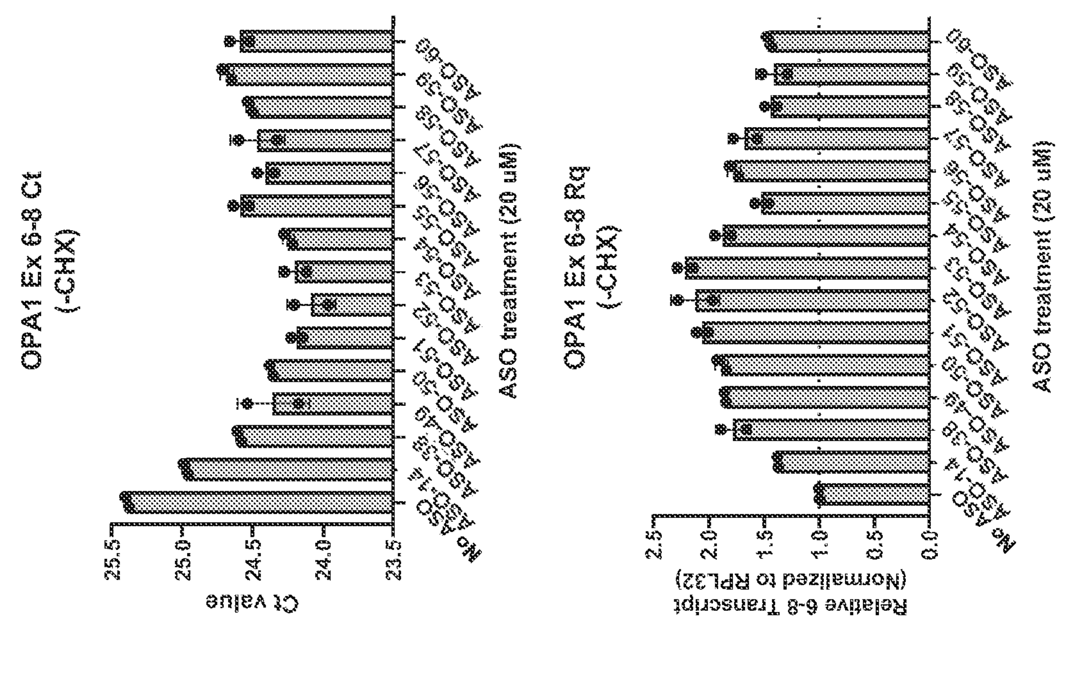
Figure 21D:
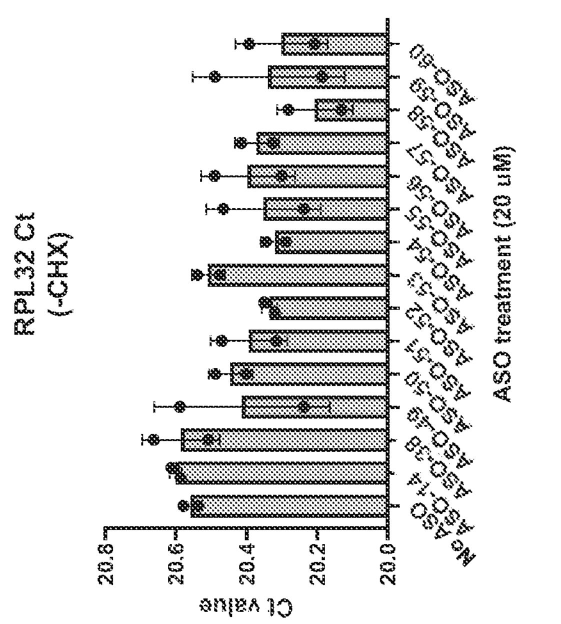
Figure 21C:
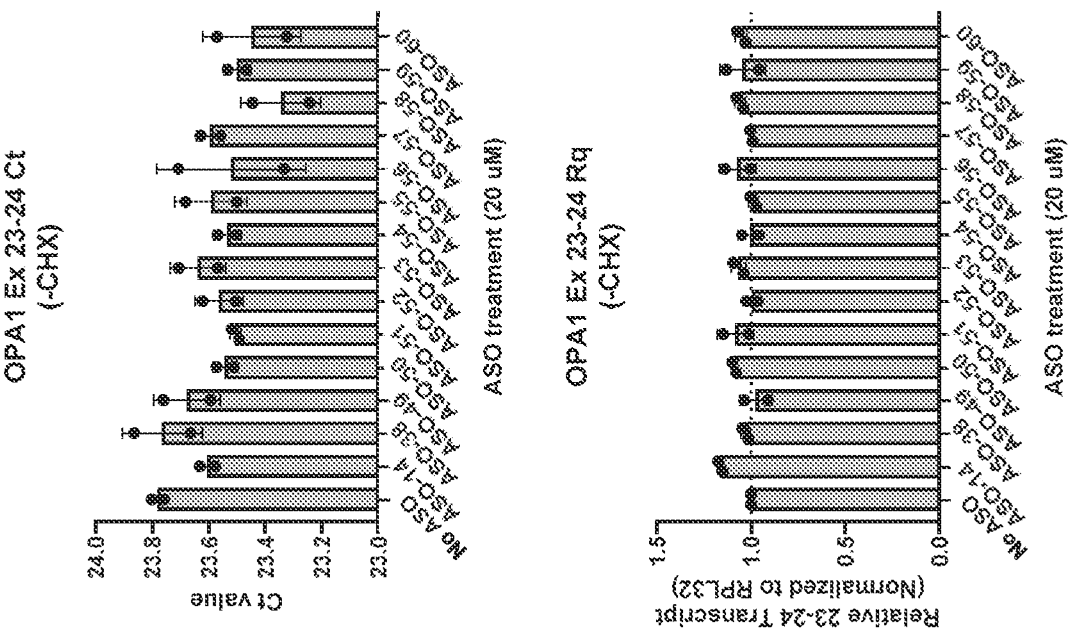
Figure 22C:
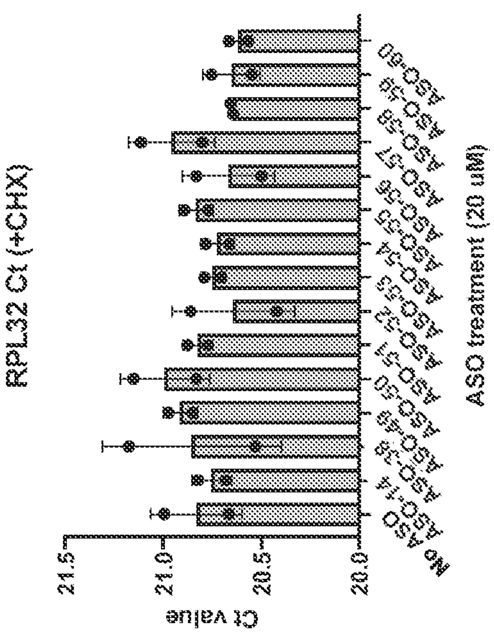
FIGS. 22A-22C illustrate RT-PCR results for OPA1 mRNAs using probes spanning exon 6 and exon 8 ("Exon 6-8"), or probes spanning exon 7x and exon 8 ("Exon 7x-8"), in HEK293 cells after treatment with various exemplary OPA1 ASO 15-mers and treatment with or without cycloheximide.
Figure 22A:
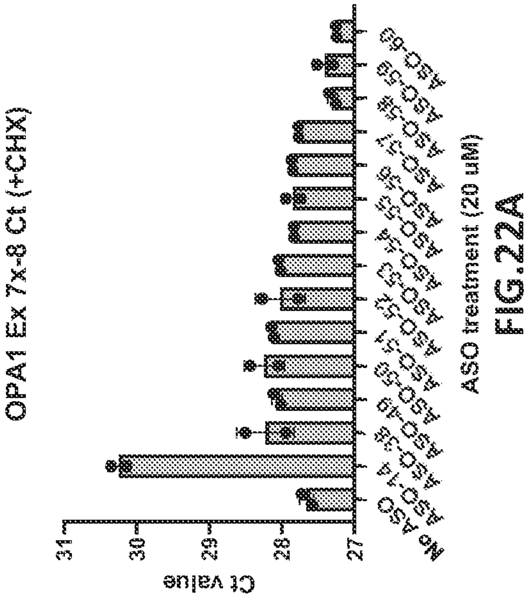
Figure 22B:
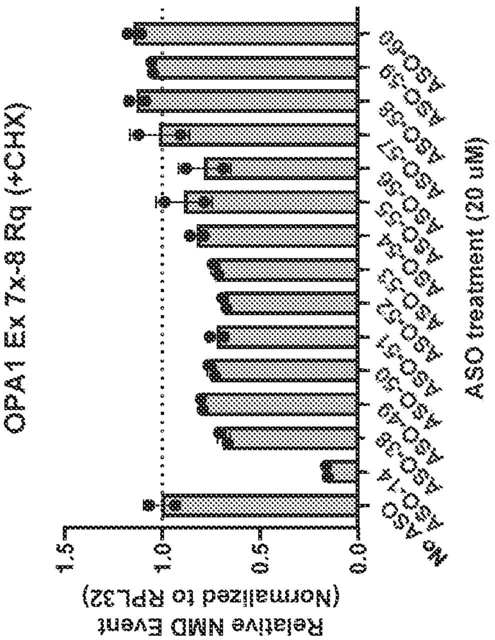

FIGS. 21A-22C demonstrate data from experiments with some of the 16-mers (named ASO-49 to ASO-60) listed in Table 7. FIGS. 21A-21B show the Ct values for the qPCR reaction (upper plots) for, and quantification of the relative amount (lower plots; normalized to Ct value of RPL32 qPCR product) of, OPA1 transcripts having exons 6 and 8 ("Ex6-8") and OPA1 transcripts having exons 7 and 8 ("Ex7-8"), respectively. FIG. 21C shows the Ct values for the qPCR reaction (upper plots) for, and quantification of the relative amount (lower plots; normalized to Ct value of RPL32 qPCR product) of, OPA1 transcripts having exons 23 and 24 ("Ex23-24"), and FIG. 21D shows the Ct values for RPL32 transcripts. These data demonstrate that cells treated with ASO-49 to ASO-60 all showed increased amount of "Ex6-8" transcripts and decreased amount of "Ex7-8" transcripts, suggesting these ASOs promote exclusion of Exon 7 from OPA1 transcripts. No cycloheximide was applied to the cells that were subject to these analyses for Exon 7 inclusion. FIG. 22A shows the Ct values for the qPCR reaction (upper plots) for, and quantification of the relative amount (lower plots; normalized to Ct value of RPL32 qPCR product) of, OPA1 transcripts having exons 7x and 8 ("Ex7x-8"), and FIG. 22C shows the Ct values for RPL32 transcripts as a loading control. These data demonstrate that cells treated with ASO-49 to ASO-56 all showed decreased amount of "Ex7x-8" transcripts, suggesting these ASOs promote exclusion of Exon 7x from OPA1 transcripts. Cycloheximide was applied to the cells for these analyses for Exon 7x inclusion.

Figure 23A:
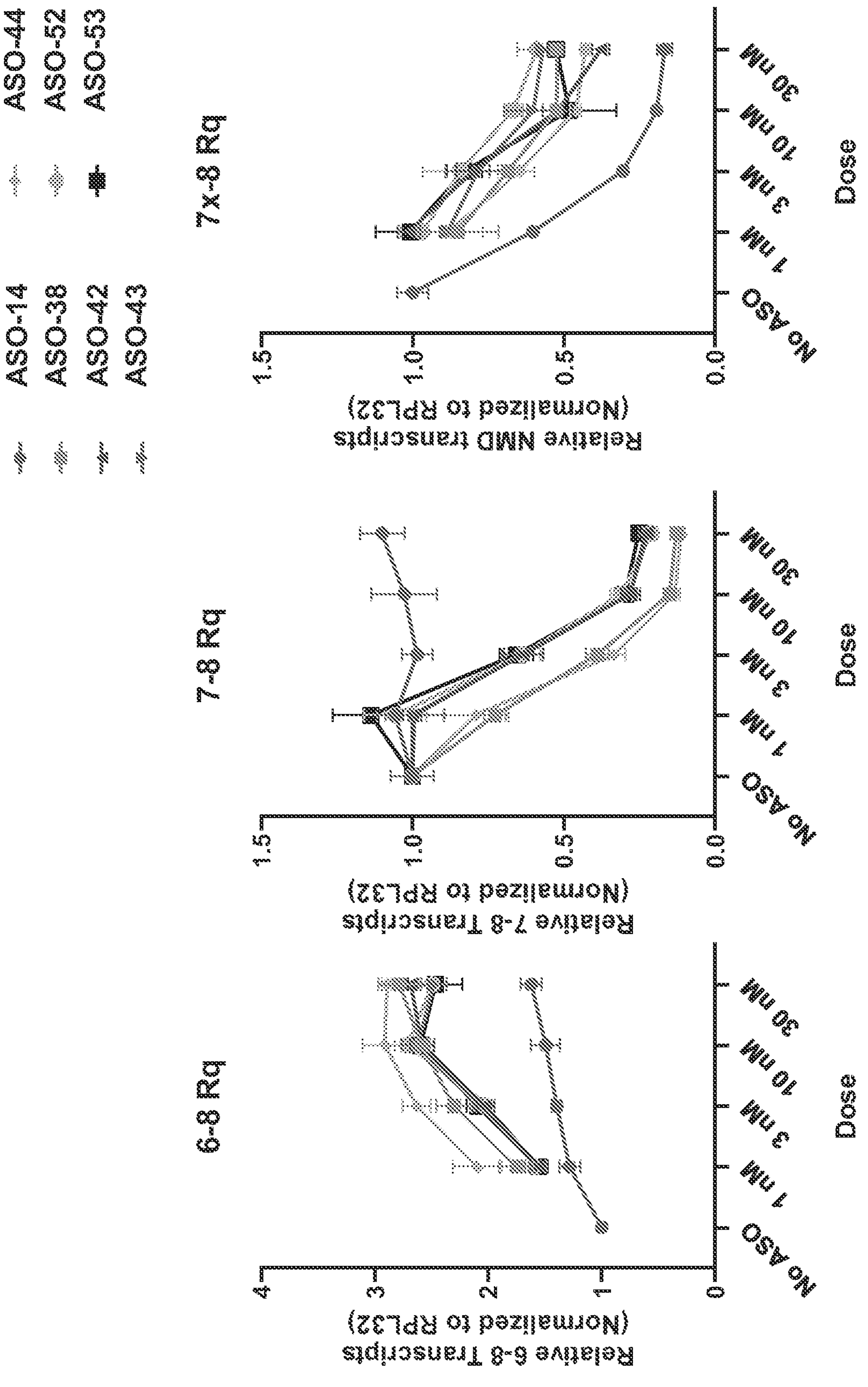
FIGS. 23A-23B illustrate dose response in OPA1 mRNAs having Exon 6 and Exon 8 ("6-8"), having Exon 7 and Exon 8 ("7-8"), or having Exon 7x and Exon 8 ("7x-8") in HEK293 cells after treatment with different concentrations of various exemplary OPA1 ASOs.
Figure 23B:
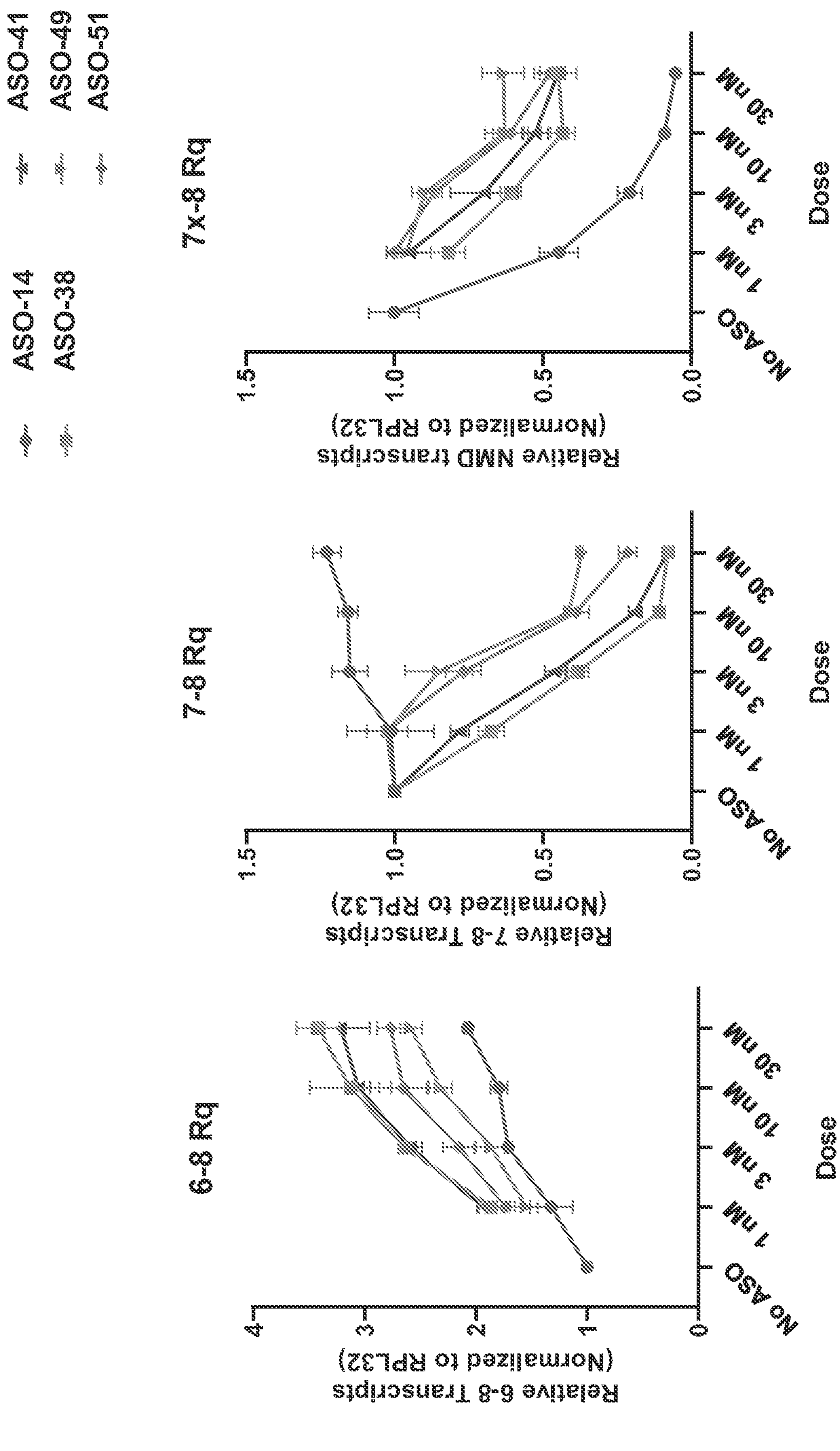

Another experiment was conducted to assess transfection dose response relationship with select ASOs among the ASOs tested above in the microwalk analyses. Briefly, 100,000 HEK293 cells per well were transfected with 1, 3, 10, or 30 nM of an exemplary ASO with 0.45 μL lipofectamine for 24 hours. Cells were later harvested for qPCR analysis as above. FIGS. 23A-23B show plots depicting the dose response curves of relative amounts of different OPA1 transcripts versus the transfection concentration of exemplary ASOs, ASO-14, 38, 41, 42, 43, 44, 49, 51, 52, and 53. The plots show that as a general trend, in cells treated with ASOs like ASO-38, 41, 42, 43, 44, 49, 51, 52, or 53, the amount of OPA1 transcripts having Exon 6 and 8 ("6-8") increased, while the amounts of OPA1 transcripts having Exon 7 and 8 ("7-8") and OPA1 transcripts having Exon 7x and 8 ("7x-8") decreased, as concentration of the exemplary ASO increased. In contrast, in cells treated with ASO-14, while "7x-8" decreased and "6-8" transcripts increased, "7-8" transcripts did not significantly change. These data suggest that ASO-38, 41, 42, 43, 44, 49, 51, 52, and 53 may all promote exclusion of both Exon 7 and Exon 7x, while ASO-14 may promote exclusion of Exon 7x

TABLE 5

Exemplary OPA1 ASO sequences

| SEQ ID NO.: | Sequence (5'-3') | Coordinates GRCh38/hg38: chr3 Oligo Start | Oligo End |
|---|---|---|---|
| 6 | AGGCCATTCTGAAATTCT | 193628406 | 193628423 |
| 7 | CATTGAGGCCATTCTGAA | 193628411 | 193628428 |
| 8 | TAAGGCATTGAGGCCATT | 193628416 | 193628433 |

TABLE 5-continued

Exemplary OPA1 ASO sequences

| SEQ ID NO.: | Sequence (5'-3') | Coordinates GRCh38/hg38: chr3 Oligo Start | Oligo End |
|---|---|---|---|
| 9 | CCTATTAAGGCATTGAGG | 193628421 | 193628438 |
| 10 | TTCTTCCTATTAAGGCAT | 193628426 | 193628443 |
| 11 | AGTATTTCTTCCTATTAA | 193628431 | 193628448 |
| 12 | TTTCAAGTATTTCTTCCT | 193628436 | 193628453 |
| 13 | AAAAATTTCAAGTATTTC | 193628441 | 193628458 |
| 14 | AATTTAAAAATTTCAAGT | 193628446 | 193628463 |
| 15 | GCCCTAATTTAAAAATTT | 193628451 | 193628468 |
| 16 | ACCAAGCCCTAATTTAAA | 193628456 | 193628473 |
| 17 | ACAAAACCAAGCCCTAAT | 193628461 | 193628478 |
| 18 | TCCTCACAAAACCAAGCC | 193628466 | 193628483 |
| 19 | CTAGCTCCTCACAAAACC | 193628471 | 193628488 |
| 20 | CTTTACTAGCTCCTCACA | 193628476 | 193628493 |
| 21 | AAAACCTTTACTAGCTCC | 193628481 | 193628498 |
| 22 | AGAGAAAAACCTTTACTA | 193628486 | 193628503 |
| 23 | CTGAAAGAGAAAAACCTT | 193628491 | 193628508 |
| 24 | AAGCTGAAAGAGAAAAAC | 193628494 | 193628511 |
| 25 | CTAAAGCTGAAAGAGAAA | 193628497 | 193628514 |
| 26 | AAGCTAAAGCTGAAAGAG | 193628500 | 193628517 |
| 27 | AACAAGCTAAAGCTGAAA | 193628503 | 193628520 |
| 28 | AGAAACAAGCTAAAGCTG | 193628506 | 193628523 |
| 29 | CGCAGAAACAAGCTAAAG | 193628509 | 193628526 |
| 30 | TCCTCCGCAGAAACAAGC | 193628514 | 193628531 |
| 31 | CGGAATCCTCCGCAGAAA | 193628519 | 193628536 |
| 32 | AAGAGCGGAATCCTCCGC | 193628524 | 193628541 |
| 33 | GGAGAAAGAGCGGAATCC | 193628529 | 193628546 |
| 34 | CTGATGGAGAAAGAGCGG | 193628534 | 193628551 |
| 35 | TGAAACTGATGGAGAAAG | 193628539 | 193628556 |
| 36 | GGCTATGAAACTGATGGA | 193628544 | 193628561 |
| 37 | TCCAGGGCTATGAAACTG | 193628549 | 193628566 |
| 38 | ACAATTCCAGGGCTATGA | 193628554 | 193628571 |
| 39 | TTTCTACAATTCCAGGGC | 193628559 | 193628576 |
| 40 | GAGCTTTTCTACAATTCC | 193628564 | 193628581 |
| 41 | AACCAGAGCTTTTCTACA | 193628569 | 193628586 |
| 42 | CTTGAAACCAGAGCTTTT | 193628574 | 193628591 |
| 43 | ATGGTCTTGAAACCAGAG | 193628579 | 193628596 |
| 44 | TATCAATGGTCTTGAAAC | 193628584 | 193628601 |
| 45 | ATGGATATCAATGGTCTT | 193628589 | 193628606 |

TABLE 5-continued

| Exemplary OPA1 ASO sequences | | | |
|---|---|---|---|
| SEQ | | Coordinates GRCh38/hg38: chr3 | |
| ID NO.: | Sequence (5'-3') | Oligo Start | Oligo End |
| 46 | CAGAAATGGATATCAATG | 193628594 | 193628611 |
| 47 | CCTGACAGAAATGGATAT | 193628599 | 193628616 |
| 48 | CACCCTGACAGAAATGGA | 193628602 | 193628619 |
| 49 | ACTCACCCTGACAGAAAT | 193628605 | 193628622 |
| 50 | AAAACTCACCCTGACAGA | 193628608 | 193628625 |
| 51 | TTTAAAACTCACCCTGAC | 193628611 | 193628628 |
| 52 | AAATTTAAAACTCACCCT | 193628614 | 193628631 |
| 53 | AATAAATTTAAAACTCAC | 193628617 | 193628634 |
| 54 | CATGAAATAAATTTAAAA | 193628622 | 193628639 |
| 55 | TGCATCATGAAATAAATT | 193628627 | 193628644 |
| 56 | TTGTTTGCATCATGAAAT | 193628632 | 193628649 |
| 57 | ATATATTGTTTGCATCAT | 193628637 | 193628654 |
| 58 | GTTCAATATATTGTTTGC | 193628642 | 193628659 |
| 59 | CTGTTGTTCAATATATTG | 193628647 | 193628664 |
| 60 | ATGTCCTGTTGTTCAATA | 193628652 | 193628669 |
| 61 | AGTTCATGTCCTGTTGTT | 193628657 | 193628674 |
| 62 | GAACAAGTTCATGTCCTG | 193628662 | 193628679 |
| 63 | AACAAGAACAAGTTCATG | 193628667 | 193628684 |
| 64 | CTTACAACAAGAACAAGT | 193628672 | 193628689 |
| 65 | AGCCACTTACAACAAGAA | 193628677 | 193628694 |
| 66 | AATTCAGCCACTTACAAC | 193628682 | 193628699 |
| 67 | GATAAAATTCAGCCACTT | 193628687 | 193628704 |
| 68 | TTACTGATAAAATTCAGC | 193628692 | 193628709 |
| 69 | GTGCTTTACTGATAAAAT | 193628697 | 193628714 |
| 70 | TTGATGTGCTTTACTGAT | 193628702 | 193628719 |
| 71 | TGGAGAAAGAGCGGAATC | 193628530 | 193628547 |
| 72 | ATGGAGAAAGAGCGGAAT | 193628531 | 193628548 |
| 73 | GATGGAGAAAGAGCGGAA | 193628532 | 193628549 |
| 74 | TGATGGAGAAAGAGCGGA | 193628533 | 193628550 |
| 75 | ACTGATGGAGAAAGAGCG | 193628535 | 193628552 |
| 76 | AACTGATGGAGAAAGAGC | 193628536 | 193628553 |
| 77 | AAACTGATGGAGAAAGAG | 193628537 | 193628554 |
| 78 | GAAACTGATGGAGAAAGA | 193628538 | 193628555 |
| 79 | ATGAAACTGATGGAGAAA | 193628540 | 193628557 |
| 80 | TATGAAACTGATGGAGAA | 193628541 | 193628558 |
| 81 | CTATGAAACTGATGGAGA | 193628542 | 193628559 |

TABLE 5-continued

Exemplary OPA1 ASO sequences

| SEQ ID NO.: | Sequence (5'-3') | Coordinates GRCh38/hg38: chr3 Oligo Start | Oligo End |
|---|---|---|---|
| 82 | GCTATGAAACTGATGGAG | 193628543 | 193628560 |
| 83 | GGGCTATGAAACTGATGG | 193628545 | 193628562 |
| 84 | AGGGCTATGAAACTGATG | 193628546 | 193628563 |
| 85 | CAGGGCTATGAAACTGAT | 193628547 | 193628564 |
| 86 | CCAGGGCTATGAAACTGA | 193628548 | 193628565 |
| 87 | CTGATGGAGAAAGAGCGGAATC | 193628530 | 193628551 |
| 88 | CTGATGGAGAAAGAGCGGAA | 193628532 | 193628551 |
| 89 | AACTGATGGAGAAAGAGCGGAA | 193628532 | 193628553 |
| 90 | AACTGATGGAGAAAGAGCGG | 193628534 | 193628553 |
| 91 | GAAACTGATGGAGAAAGAGCGG | 193628534 | 193628555 |
| 92 | GGCTATGAAACTGATGGAGAAA | 193628540 | 193628561 |
| 93 | GGCTATGAAACTGATGGAGA | 193628542 | 193628561 |
| 94 | AGGGCTATGAAACTGATGGAGA | 193628542 | 193628563 |
| 95 | AGGGCTATGAAACTGATGGA | 193628544 | 193628563 |
| 96 | CCAGGGCTATGAAACTGATGGA | 193628544 | 193628565 |
| 97 | TTCTTACCCATTTAATTA | 193655041 | 193655059 |
| 98 | TGCTTCTTACCCATTTAA | 193655044 | 193655062 |
| 99 | TAATGCTTCTTACCCATT | 193655047 | 193655065 |
| 100 | AGATAATGCTTCTTACCC | 193655050 | 193655068 |
| 101 | CAGATAATGCTTCTTACC | 193655051 | 193655069 |
| 102 | CCCTTCAGATAATGCTTC | 193655056 | 193655074 |
| 103 | CTACTCCCTTCAGATAAT | 193655061 | 193655079 |
| 104 | AGCTCCTACTCCCTTCAG | 193655066 | 193655084 |
| 105 | TTCACAGCTCCTACTCCC | 193655071 | 193655089 |
| 106 | TAAAATTCACAGCTCCTA | 193655076 | 193655094 |
| 107 | AAATCTAAAATTCACAGC | 193655081 | 193655099 |
| 108 | GAATAAAATCTAAAATTC | 193655086 | 193655104 |
| 109 | GATGGGAATAAAATCTAA | 193655091 | 193655109 |
| 110 | GCTGTGATGGGAATAAAA | 193655096 | 193655114 |
| 111 | TAGAGGCTGTGATGGGAA | 193655101 | 193655119 |
| 112 | AAAGATAGAGGCTGTGAT | 193655106 | 193655124 |
| 113 | AAAAGAAAGATAGAGGCT | 193655111 | 193655129 |
| 114 | GACCTAAAAGAAAGATAG | 193655116 | 193655134 |
| 115 | ATAAAGACCTAAAAGAAA | 193655121 | 193655139 |
| 116 | GAGATATAAAGACCTAAA | 193655126 | 193655144 |
| 117 | GGCTGTGATGGGAATAAA | 193655097 | 193655115 |
| 118 | AGGCTGTGATGGGAATAA | 193655098 | 193655116 |

TABLE 5-continued

| Exemplary OPA1 ASO sequences | | | |
|---|---|---|---|
| SEQ | | Coordinates GRCh38/hg38: chr3 | |
| ID NO.: | Sequence (5'-3') | Oligo Start | Oligo End |
| 119 | GAGGCTGTGATGGGAATA | 193655099 | 193655117 |
| 120 | AGAGGCTGTGATGGGAAT | 193655100 | 193655118 |
| 121 | ATAGAGGCTGTGATGGGA | 193655102 | 193655120 |
| 122 | GATAGAGGCTGTGATGGG | 193655103 | 193655121 |
| 123 | AGATAGAGGCTGTGATGG | 193655104 | 193655122 |
| 124 | AAGATAGAGGCTGTGATG | 193655105 | 193655123 |
| 125 | TAGAGGCTGTGATGGGAATAAA | 193655097 | 193655119 |
| 126 | ATAGAGGCTGTGATGGGAATAA | 193655098 | 193655120 |
| 127 | GATAGAGGCTGTGATGGGAATA | 193655099 | 193655121 |
| 128 | AGATAGAGGCTGTGATGGGAAT | 193655100 | 193655122 |
| 129 | AAGATAGAGGCTGTGATGGGAA | 193655101 | 193655123 |
| 130 | GAGGCTGTGATGGGAATAAA | 193655097 | 193655117 |
| 131 | AGAGGCTGTGATGGGAATAA | 193655098 | 193655118 |
| 132 | TAGAGGCTGTGATGGGAATA | 193655099 | 193655119 |
| 133 | ATAGAGGCTGTGATGGGAAT | 193655100 | 193655120 |
| 134 | GATAGAGGCTGTGATGGGAA | 193655101 | 193655121 |
| 135 | AGATAGAGGCTGTGATGGGA | 193655102 | 193655122 |
| 136 | AAGATAGAGGCTGTGATGGG | 193655103 | 193655123 |
| 137 | CTGTGATGGGAATAAA | 193655097 | 193655113 |
| 138 | GCTGTGATGGGAATAA | 193655098 | 193655114 |
| 139 | GGCTGTGATGGGAATA | 193655099 | 193655115 |
| 140 | AGGCTGTGATGGGAAT | 193655100 | 193655116 |
| 141 | GAGGCTGTGATGGGAA | 193655101 | 193655117 |
| 142 | AGAGGCTGTGATGGGA | 193655102 | 193655118 |
| 143 | TAGAGGCTGTGATGGG | 193655103 | 193655119 |
| 144 | ATAGAGGCTGTGATGG | 193655104 | 193655120 |
| 145 | GATAGAGGCTGTGATG | 193655105 | 193655121 |
| 146 | AGATAGAGGCTGTGAT | 193655106 | 193655122 |
| 147 | AAGATAGAGGCTGTGA | 193655107 | 193655123 |
| 148 | AGGCTGTGATGTGAATAA | 193655099 | 193655116 |
| 149 | AGAGGCTGTGATGTGAAT | 193655101 | 193655118 |
| 150 | TAGAGGCTGTGATGTGAA | 193655102 | 193655119 |
| 151 | GATAGAGGCTGTGATTGG | 193655104 | 193655121 |
| 152 | GGCTGTGATGTGAATA | 193655100 | 193655115 |
| 153 | GAGGCTGTGATGTGAA | 193655102 | 193655117 |
| 154 | TAGAGGCTGTGATTGG | 193655104 | 193655119 |

TABLE 5-continued

Exemplary OPA1 ASO sequences

| SEQ ID NO.: | Sequence (5'-3') | Coordinates GRCh38/hg38: chr3 Oligo Start | Oligo End |
|---|---|---|---|
| 155 | ATGAAACTGATGGAGA | 193628542 | 193628557 |
| 156 | CTATGAAACTGATGGA | 193628544 | 193628559 |
| 157 | GGCTATGAAACTGATG | 193628546 | 193628561 |
| 158 | GAAACTGATGGAGA | 193628542 | 193628555 |
| 159 | ATGAAACTGATGGA | 193628544 | 193628557 |
| 160 | CTATGAAACTGATG | 193628546 | 193628559 |
| 161 | GGCTATGAAACTGA | 193628548 | 193628561 |
| 162 | TAGAGGCTGTGATGGGAATAAAAT | 193655096 | 193655119 |
| 163 | ATAGAGGCTGTGATGGGAATAAAA | 193655097 | 193655120 |
| 164 | ATAGAGGCTGTGATGGGAATAAAAT | 193655096 | 193655120 |
| 165 | AAAGATAGAGGCTGTGATGGGAATA | 193655100 | 193655124 |
| 166 | GGCTATGAAACTGATGGAGAA | 193628541 | 193628561 |
| 167 | GGCTATGAAACTGATGGAGAAAGA | 193628538 | 193628561 |
| 168 | AGGGCTATGAAACTGATGGAGAAAG | 193628539 | 193628563 |
| 169 | CATTTAATTAAATTATAT | 193655033 | 193655051 |
| 170 | CCATTTAATTAAATTATA | 193655034 | 193655052 |
| 171 | CCCATTTAATTAAATTAT | 193655035 | 193655053 |
| 172 | ACCCATTTAATTAAATTA | 193655036 | 193655054 |
| 173 | TACCCATTTAATTAAATT | 193655037 | 193655055 |
| 174 | TTACCCATTTAATTAAAT | 193655038 | 193655056 |
| 175 | CTTACCCATTTAATTAAA | 193655039 | 193655057 |
| 176 | TCTTACCCATTTAATTAA | 193655040 | 193655058 |
| 177 | GATAGAGGCTGTGATGG | 193655104 | 193655122 |
| 178 | GGCTGTGAAACTGATGGA | 89481662 | 89481679 |
| 179 | GGCTGTGAAACTGATGGAGA | 89481660 | 89481679 |
| 180 | GCTATGAAACTGATGG | 193628545 | 193628560 |
| 181 | TATGAAACTGATGG | 193628545 | 193628558 |
| 182 | GCTATGAAACTGAT | 193628547 | 193628560 |
| 183 | GCTGTGAAACTGATGGAGAA | 89481659 | 89481678 |
| 184 | GGGCTGTGAAACTGATGGAG | 89481661 | 89481680 |
| 185 | TGTGAAACTGATGGAGAA | 89481659 | 89481676 |
| 186 | CTGTGAAACTGATGGAGA | 89481660 | 89481677 |
| 187 | GCTGTGAAACTGATGGAG | 89481661 | 89481678 |
| 188 | GGGCTGTGAAACTGATGG | 89481663 | 89481680 |
| 189 | TGAAACTGATGGAGAA | 89481659 | 89481674 |
| 190 | GTGAAACTGATGGAGA | 89481660 | 89481675 |
| 191 | TGTGAAACTGATGGAG | 89481661 | 89481676 |

TABLE 5-continued

Exemplary OPA1 ASO sequences

| SEQ ID NO.: | Sequence (5'-3') | Coordinates GRCh38/hg38: chr3 Oligo Start | Oligo End |
|---|---|---|---|
| 192 | CTGTGAAACTGATGGA | 89481662 | 89481677 |
| 193 | GCTGTGAAACTGATGG | 89481663 | 89481678 |
| 194 | GGCTGTGAAACTGATG | 89481664 | 89481679 |
| 195 | GGGCTGTGAAACTGAT | 89481665 | 89481680 |
| 196 | CGGTCCAGGAATGAC | 193593285 | 193593303 |
| 197 | CCGGTCCAGGAATGA | 193593286 | 193593304 |
| 198 | CCCGGTCCAGGAATG | 193593287 | 193593305 |
| 199 | TCCCGGTCCAGGAAT | 193593288 | 193593306 |
| 200 | CTCCCGGTCCAGGAA | 193593289 | 193593307 |
| 201 | GCTCCCGGTCCAGGA | 193593290 | 193593308 |
| 202 | GGCTCCCGGTCCAGG | 193593291 | 193593309 |
| 203 | CGGGAGCCCCCGTGT | 193593318 | 193593336 |
| 204 | GCGGGAGCCCCCGTG | 193593319 | 193593337 |
| 205 | CGCGGGAGCCCCCGT | 193593320 | 193593338 |
| 206 | ACGCGGGAGCCCCCG | 193593321 | 193593339 |
| 207 | CACGCGGGAGCCCCC | 193593322 | 193593340 |
| 208 | CCACGCGGGAGCCCC | 193593323 | 193593341 |
| 209 | GCCACGCGGGAGCCC | 193593324 | 193593342 |
| 210 | GGCCACGCGGGAGCC | 193593325 | 193593343 |
| 211 | CGGCCACGCGGGAGC | 193593326 | 193593344 |
| 212 | ACGGCCACGCGGGAG | 193593327 | 193593345 |
| 213 | GACGGCCACGCGGGA | 193593328 | 193593346 |
| 214 | AGACGGCCACGCGGG | 193593329 | 193593347 |
| 215 | GCTAGGGAGGGATGGTTA | 193625988 | 193626006 |
| 216 | TGTAAGCTAGGGAGGGAT | 193625993 | 193626011 |
| 217 | ACAGATGTAAGCTAGGGA | 193625998 | 193626016 |
| 218 | AAGGAACAGATGTAAGCT | 193626003 | 193626021 |
| 219 | CAACAAAGGAACAGATGT | 193626008 | 193626026 |
| 220 | GGGTGCAACAAAGGAACA | 193626013 | 193626031 |
| 221 | ACCAAGGGTGCAACAAAG | 193626018 | 193626036 |
| 222 | GTTAAACCAAGGGTGCAA | 193626023 | 193626041 |
| 223 | ATAATGTTAAACCAAGGG | 193626028 | 193626046 |
| 224 | GGAGAATAATGTTAAACC | 193626033 | 193626051 |
| 225 | GGGGAGGAGAATAATGTT | 193626038 | 193626056 |
| 226 | AAATTGGGGAGGAGAATA | 193626043 | 193626061 |
| 227 | AGAGGAAATTGGGGAGGA | 193626048 | 193626066 |

TABLE 5-continued

Exemplary OPA1 ASO sequences

| SEQ ID NO.: | Sequence (5'-3') | Coordinates GRCh38/hg38: chr3 Oligo Start | Oligo End |
|---|---|---|---|
| 228 | GGAGAAGAGGAAATTGGG | 193626053 | 193626071 |
| 229 | AATGAGGAGAAGAGGAAA | 193626058 | 193626076 |
| 230 | TTCACAATGAGGAGAAGA | 193626063 | 193626081 |
| 231 | ACGAGTTCACAATGAGGA | 193626068 | 193626086 |
| 232 | CTGCCACGAGTTCACAAT | 193626073 | 193626091 |
| 233 | AGACCCTGCCACGAGTTC | 193626078 | 193626096 |
| 234 | CAAGCAGACCCTGCCACG | 193626083 | 193626101 |
| 235 | CTCACCAAGCAGACCCTG | 193626088 | 193626106 |
| 236 | GAGCTCACCAAGCAGACC | 193626091 | 193626109 |
| 237 | AGAATGAGCTCACCAAGC | 193626096 | 193626114 |
| 238 | GTAAGAGAATGAGCTCAC | 193626101 | 193626119 |
| 239 | TTGTTGTAAGAGAATGAG | 193626106 | 193626124 |
| 240 | ATTTGTTGTTGTAAGAGA | 193626111 | 193626129 |
| 241 | CTTGAATTTGTTGTTGTA | 193626116 | 193626134 |
| 242 | ATGCTCTTGAATTTGTTG | 193626121 | 193626139 |
| 243 | TCTTCATGCTCTTGAATT | 193626126 | 193626144 |
| 244 | CTTCCTCTTCATGCTCTT | 193626131 | 193626149 |
| 245 | GCGCGCTTCCTCTTCATG | 193626136 | 193626154 |
| 246 | GCTCTGCGCGCTTCCTCT | 193626141 | 193626159 |
| 247 | GGCCAGCGGCTCTGCGCG | 193626149 | 193626167 |
| 248 | ATATTGGCCAGCGGCTCT | 193626154 | 193626172 |
| 249 | GTGCTATATTGGCCAGCG | 193626159 | 193626177 |
| 250 | AGCTCGTGCTATATTGGC | 193626164 | 193626182 |
| 251 | GGCATAGCTCGTGCTATA | 193626169 | 193626187 |
| 252 | TGTTGGGCATAGCTCGTG | 193626174 | 193626192 |
| 253 | GCTTCTGTTGGGCATAGC | 193626179 | 193626197 |
| 254 | CTTGCGCTTCTGTTGGGC | 193626184 | 193626202 |
| 255 | CACCTTGCGCTTCTGTTG | 193626187 | 193626205 |
| 256 | TCCATCACCTTGCGCTTC | 193626192 | 193626210 |
| 257 | AACCATCCATCACCTTGC | 193626197 | 193626215 |
| 258 | CCTTAAACCATCCATCAC | 193626202 | 193626220 |
| 259 | AGCCCCCTTAAACCATCC | 193626207 | 193626225 |
| 260 | TCGGTAGCCCCCTTAAAC | 193626212 | 193626230 |
| 261 | ATGTATCGGTAGCCCCCT | 193626217 | 193626235 |
| 262 | TGTGAATGTATCGGTAGC | 193626222 | 193626240 |
| 263 | ATTAGTGTGAATGTATCG | 193626227 | 193626245 |
| 264 | GGCTGATTAGTGTGAATG | 193626232 | 193626250 |

TABLE 5-continued

| Exemplary OPA1 ASO sequences | | | |
|---|---|---|---|
| SEQ | | Coordinates GRCh38/hg38: chr3 | |
| ID NO.: | Sequence (5'-3') | Oligo Start | Oligo End |
| 265 | GAAATGGCTGATTAGTGT | 193626237 | 193626255 |
| 266 | TGGCAGAAATGGCTGATT | 193626242 | 193626260 |
| 267 | GATCTTGGCAGAAATGGC | 193626247 | 193626265 |
| 268 | GACATGATCTTGGCAGAA | 193626252 | 193626270 |
| 269 | GAGGTGACATGATCTTGG | 193626257 | 193626275 |
| 270 | AGATTGAGGTGACATGAT | 193626262 | 193626280 |
| 271 | TGAACAGATTGAGGTGAC | 193626267 | 193626285 |
| 272 | GTCCATGAACAGATTGAG | 193626272 | 193626290 |
| 273 | TTGGAGTCCATGAACAGA | 193626277 | 193626295 |
| 274 | TGTATTTGGAGTCCATGA | 193626282 | 193626300 |
| 275 | TTTCTTGTATTTGGAGTC | 193626287 | 193626305 |

TABLE 6

| Exemplary OPA1 ASO sequences | | | | |
|---|---|---|---|---|
| SEQ | | | Coordinates: GRCh38/hg38: chr3 | |
| ID NO | Region | Sequence (5'-3') | Oligo Start | Oligo End |
| 215 | OPA1-IVS6-86 | GCTAGGGAGGGATGGTTA | 193625988 | 193626006 |
| 216 | OPA1-IVS6-81 | TGTAAGCTAGGGAGGGAT | 193625993 | 193626011 |
| 217 | OPA1-IVS6-76 | ACAGATGTAAGCTAGGGA | 193625998 | 193626016 |
| 218 | OPA1-IVS6-71 | AAGGAACAGATGTAAGCT | 193626003 | 193626021 |
| 227 | OPA1-IVS6-26 | AGAGGAAATTGGGGAGGA | 193626048 | 193626066 |
| 228 | OPA1-IVS6-21 | GGAGAAGAGGAAATTGGG | 193626053 | 193626071 |
| 229 | OPA1-IVS6-16 | AATGAGGAGAAGAGGAAA | 193626058 | 193626076 |
| 230 | OPA1-IVS6-11 | TTCACAATGAGGAGAAGA | 193626063 | 193626081 |
| 231 | OPA1-IVS6-6 | ACGAGTTCACAATGAGGA | 193626068 | 193626086 |
| 232 | OPA1-IVS6-1 | CTGCCACGAGTTCACAAT | 193626073 | 193626091 |
| 233 | OPA1-IVS6-EX7 + 5 | AGACCCTGCCACGAGTTC | 193626078 | 193626096 |
| 234 | OPA1-IVS6-EX7 + 10 | CAAGCAGACCCTGCCACG | 193626083 | 193626101 |
| 235 | OPA1-IVS6-EX7 + 15 | CTCACCAAGCAGACCCTG | 193626088 | 193626106 |
| 236 | OPA1-EX7 + 1 | GAGCTCACCAAGCAGACC | 193626091 | 193626109 |
| 237 | OPA1-EX7 + 6 | AGAATGAGCTCACCAAGC | 193626096 | 193626114 |
| 238 | OPA1-EX7 + 11 | GTAAGAGAATGAGCTCAC | 193626101 | 193626119 |
| 239 | OPA1-EX7 + 16 | TTGTTGTAAGAGAATGAG | 193626106 | 193626124 |
| 240 | OPA1-EX7 + 21 | ATTTGTTGTTGTAAGAGA | 193626111 | 193626129 |
| 241 | OPA1-EX7 + 26 | CTTGAATTTGTTGTTGTA | 193626116 | 193626134 |

TABLE 6-continued

| Exemplary OPA1 ASO sequences | | | | |
|---|---|---|---|---|
| SEQ | | | Coordinates: GRCh38/hg38: chr3 | |
| ID NO | Region | Sequence (5'-3') | Oligo Start | Oligo End |
| 242 | OPA1-EX7 + 31 | ATGCTCTTGAATTTGTTG | 193626121 | 193626139 |
| 250 | OPA1-EX7 − 21 | AGCTCGTGCTATATTGGC | 193626164 | 193626182 |
| 267 | OPA1-IVS7 + 46 | GATCTTGGCAGAAATGGC | 193626247 | 193626265 |

TABLE 7

| Exemplary OPA1 ASO sequences | | | | |
|---|---|---|---|---|
| SEQ | | | Coordinates: GRCh38/hg38: chr3 | |
| ID NO | Region | Sequence (5'-3') | Oligo Start | Oligo End |
| 280 | OPA1-EX7 + 27 | TCTTGAATTTGTTGTTGT | 193626117 | 193626135 |
| 281 | OPA1-EX7 + 28 | CTCTTGAATTTGTTGTTG | 193626118 | 193626136 |
| 282 | OPA1-EX7 + 29 | GCTCTTGAATTTGTTGTT | 193626119 | 193626137 |
| 283 | OPA1-EX7 + 30 | TGCTCTTGAATTTGTTGT | 193626120 | 193626138 |
| 284 | OPA1-EX7 + 32 | CATGCTCTTGAATTTGTT | 193626122 | 193626140 |
| 285 | OPA1-EX7 + 33 | TCATGCTCTTGAATTTGT | 193626123 | 193626141 |
| 286 | OPA1-EX7 + 34 | TTCATGCTCTTGAATTTG | 193626124 | 193626142 |
| 287 | OPA1-EX7 + 35 | CTTCATGCTCTTGAATTT | 193626125 | 193626143 |
| 288 | OPA1-EX7 + 26 | TGAATTTGTTGTTGTA | 193626116 | 193626132 |
| 289 | OPA1-EX7 + 27 | TTGAATTTGTTGTTGT | 193626117 | 193626133 |
| 290 | OPA1-EX7 + 28 | CTTGAATTTGTTGTTG | 193626118 | 193626134 |
| 291 | OPA1-EX7 + 29 | TCTTGAATTTGTTGTT | 193626119 | 193626135 |
| 292 | OPA1-EX7 + 30 | CTCTTGAATTTGTTGT | 193626120 | 193626136 |
| 293 | OPA1-EX7 + 31 | GCTCTTGAATTTGTTG | 193626121 | 193626137 |
| 294 | OPA1-EX7 + 32 | TGCTCTTGAATTTGTT | 193626122 | 193626138 |
| 295 | OPA1-EX7 + 33 | ATGCTCTTGAATTTGT | 193626123 | 193626139 |
| 296 | OPA1-EX7 + 34 | CATGCTCTTGAATTTG | 193626124 | 193626140 |
| 297 | OPA1-EX7 + 35 | TCATGCTCTTGAATTT | 193626125 | 193626141 |
| 298 | OPA1-EX7 + 36 | TTCATGCTCTTGAATT | 193626126 | 193626142 |
| 299 | OPA1-EX7 + 37 | CTTCATGCTCTTGAAT | 193626127 | 193626143 |

Example 19: ASO-14 Mediates ATP Upregulation in OPA1 Haploinsufficient HEK293 Cell Line The ATP levels generated through mitochondrial oxidative phosphorylation and glycolytic pathway were measured in HEK293 cell lysates using a commercially available kit (Cat #ab83355, Abcam; USA) according to the manufacturer's instructions. Briefly, about $3\times10^5$ OPA1+/+(wildtype) and OPA1+/— HEK293 cells were plated in a T-25 flask and treated with 10 μM ASO-14. For the ATP test, 96-hrs after treatment, cells were harvested, and two aliquots of cell suspension were prepared. One aliquot was processed for deproteinizing using commercially available kit (Cat #ab204708, Abcam; USA) to remove residual protein for executing ATP fluorescence assay to measure total ATP level. The second aliquot was used for BCA assay (Cat #23225, Thermo Fisher; USA) to measure total protein level. ATP level was then calculated by normalizing the measured total ATP level to the measured total protein level.

Figure 24A:
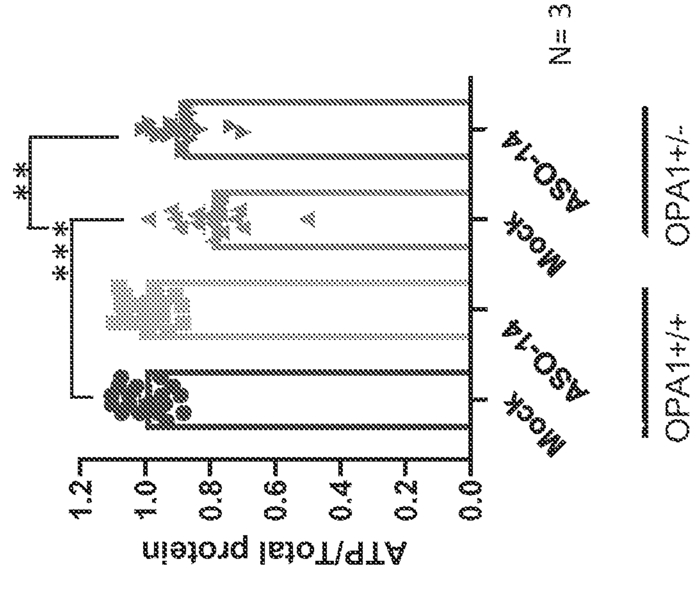
FIG. 24A is a histogram that demonstrates ATP level was reduced in mock-treated OPA1+/−HEK293 cells as compared to OPA1+/+HEK293 cells, and ASO-14 treatment of OPA1+/−HEK293 cells increased the ATP level in the cells.

FIG. 24A summarizes the ATP level measured under each condition. In the mock group, untreated OPA1+/−HEK293 cells were found to have 0.79±0.02 ATP level as compared to untreated OPA1+/+HEK293 cells. There was about 20% ATP deficit in OPA1+/−HEK293 cells. In comparison, OPA1+/−HEK293 cells treated with ASO-14 had ATP levels 0.88±0.01, significantly higher than the mock-treated OPA1+/−HEK293 cells, suggesting that treatment of ASO-14 reduced the deficit by about 50%. Data were collected from three independent experiments. (Statistics: Ordinary one-way ANOVA; *P<0.0001; P<0.0080).

Figure 24B:
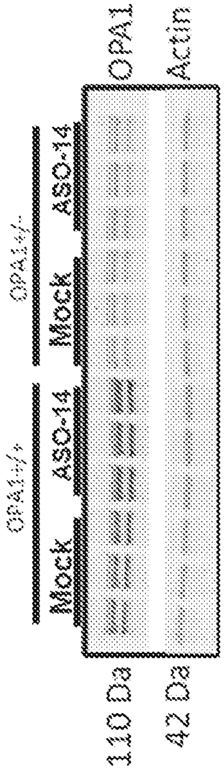
FIGS. 24B-24C demonstrate the OPA1 protein was increased by ASO-14 in OPA1+/+HEK293 cells.
Figure 24C:
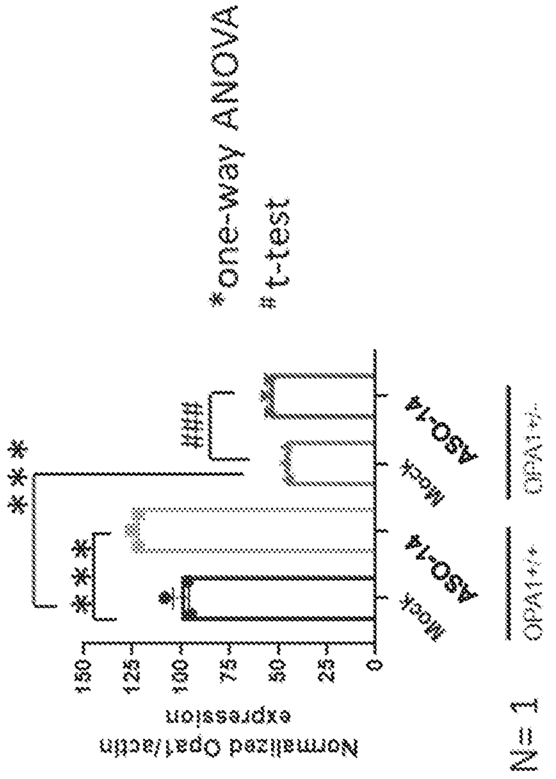

FIGS. 24B-24C demonstrate the OPA1 protein under each condition. 96 hours after treatment with ASO-14 or no treatment (mock), cells were lysed with RIPA buffer and immunoblot blot was probed with antibodies targeting OPA1 and β-actin. The data show that treatment of ASO-14 unregulated about 18% OPA1 protein in OPA1+/− cells. FIG. 24B shows the immunoblot gel images. Multiple bands on the immunoblot image represent various isoforms of OPA1. FIG. 24C summarizes quantification of the immunoblot results. Untreated (mock) OPA1+/−HEK293 cells were found to have 46±0.5% OPA1 protein level as compared to untreated (mock) OPA1+/+HEK293 cells. OPA1+/+ cells treated with ASO-14 had OPA1 levels 123.2±1.3 of untreated OPA1+/+ cells. OPA1+/− cells treated with ASO-14 had OPA1 levels 54.54±0.6% of untreated OPA1+/+ cells. Statistics performed with corresponding mock. *** P<0.0001, by Ordinary one-Way ANOVA and ###P<0.0001, by Welch's t test. Data represent average of three technical replicates.

Example 20: Exemplary Antisense Oligomers Restore OPA1 Expression in Cells with OPA1 Mutations from Diagnosed Patients This example examines OPA1 mRNA and protein levels in cells with mutations in OPA1 gene from patients diagnosed with Autosomal dominant optic atrophy (ADOA), as well as effects of exemplary antisense oligomer ASO-14 on OPA1 mRNA and protein levels, and mitochondrial bioenergetics in the patient cells.

Figure 25B:
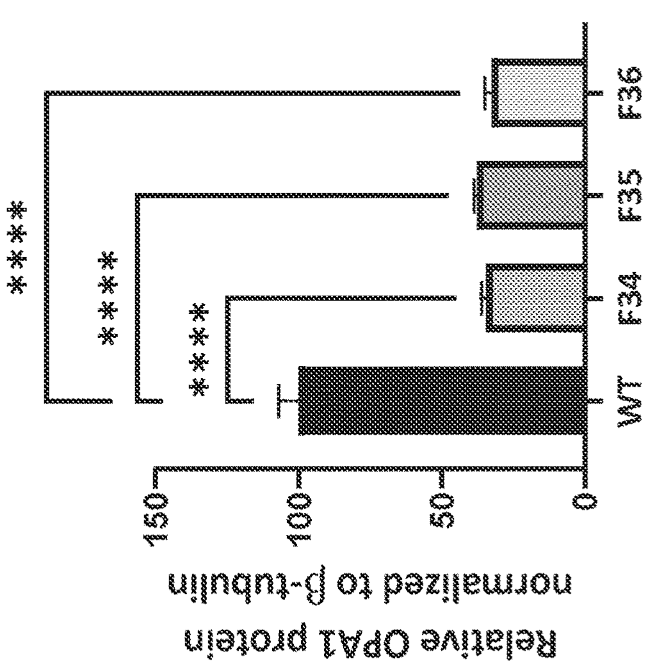
FIGS. 25A-25B show histograms that demonstrate mRNA (FIG. 25A) and protein expression (FIG. 25B) of OPA1 gene were reduced in fibroblast cells from diagnosed patients that have haploinsufficient mutation in OPA1 gene as compared to wildtype (WT) fibroblast cells.
Figure 25A:
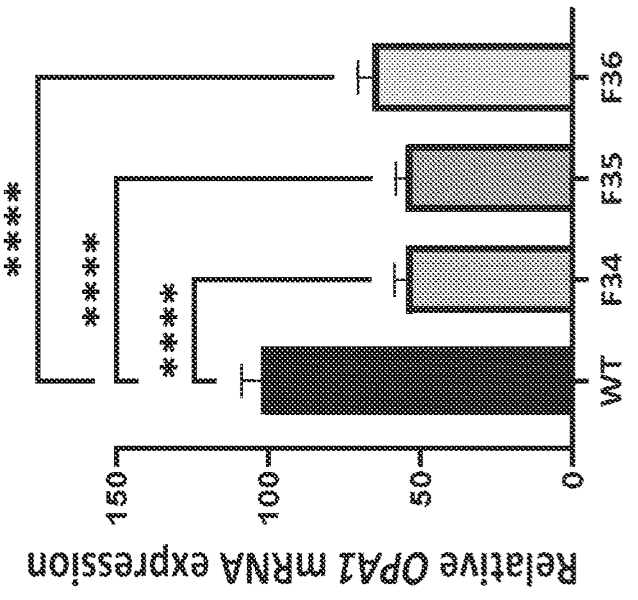
Figure 25C:
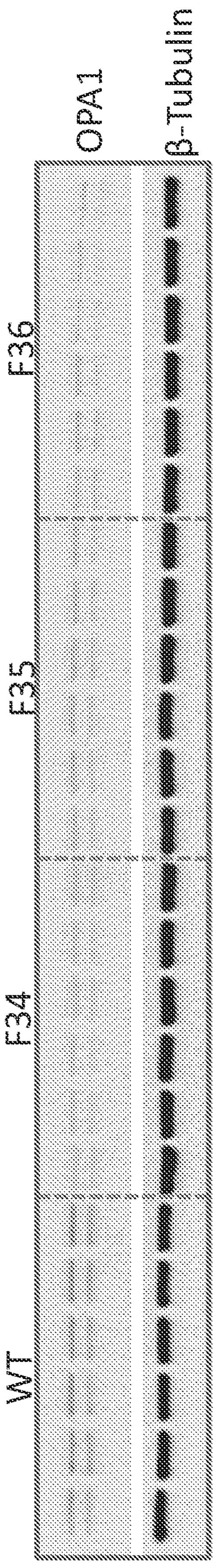
FIG. 25C shows a representative immunoblot image of OPA protein expression level in diseased fibroblast cells.

FIGS. 25A-25C summarize mRNA and protein expression of OPA1 gene in fibroblast cells from diagnosed patients that have haploinsufficient mutation in OPA1 gene: F34 (OPA1 canonical splice mutation at c.1608+1delGTGAGG); F35 (OPA1 frameshift mutation at c.2873_2876del); F36 (OPA1 frameshift mutation at c.635_636delAA). mRNA expression level of OPA1 gene in patient cells is about 50% to 60% of the mRNA level in wildtype (WT) cells (FIG. 25A); OPA1 protein level in patient cells is about 30% to about 40% of the protein level in WT cells (FIG. 25B). Histograms in FIGS. 25A-25B show mean±SEM of 3 independent experiments; one-way ANOVA compared to WT group (**P<0.0001). FIG. 25**C shows a representative immunoblot image of OPA protein expression level in diseased fibroblast cells.

Figure 26D:
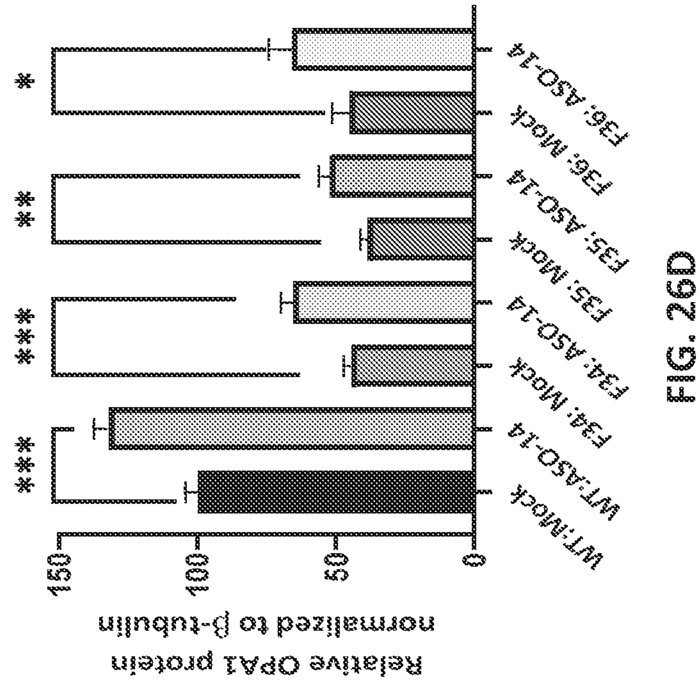

FIGS. 26A-26D demonstrate the effects of exemplary antisense oligomer, ASO-14, on OPA1 NMD exon inclusion, mRNA level, and protein level in wildtype (WT) fibroblast cells and fibroblast cells from diagnosed patients that have haploinsufficient mutation in OPA1 gene. The fibroblast cells were transfected with ASO-14 (40 nM), and RNA was isolated 24 hrs after transfection and analyzed. For non-productive OPA1 mRNA measurement, cells were treated with cycloheximide (50 μg/mL) for 3 hrs. prior to RNA isolation. Immunoblot was performed 72 hrs. post transfection with antibodies targeting OPA1 and β-tubulin. As shown in FIG. 26A, ASO-14 significantly decreased inclusion of NMD exon (exon 7x), measured by level of non-productive OPA1 mRNA, in WT cells and all diseased cells to lower than 20% level of the normalized level in WT cells. There was a trend of increase in total OPA1 mRNA level in all types of cells by the treatment of ASO-14 (FIG. 26B). Histograms in FIGS. 26A-26B show mean±SEM of 2-3 independent experiments; one-way ANOVA vs. Mock for respective cell line (*P<0.05; *P<0.001; P<0.0001). Correspondingly, OPA1. protein level was significantly increased by the treatment of ASO-14 in all types of cells (FIGS. 26C-26D). FIG. 26C shows representative immunoblot images of OPA1 protein and loading control β-Tubulin under all types of conditions; FIG. 26**D shows the statistical summary of the OPA1 protein levels, the histograms show mean±SEM of 3 independent experiments; unpaired t-test vs. Mock for respective cell line (*P<0.05,  P<0.01, *<0.001).

FIGS. 27A-27E demonstrate that patient fibroblast cells (cell lines F35 and F36) show deficiencies in mitochondrial bioenergetics. FIG. 27A shows representative time courses of the oxygen consumption rate of WT cells, F35 cells, and F36 cells at baseline level and when challenged sequentially with oligomycin, FCCP, rotenone and antimycin A. Patient fibroblast cells, F35 and F36 cells, were found to have reduced basal oxygen consumption rate (FIG. 27B), ATP linked respiration (FIG. 27C), maximal respiration (FIG. 27D), and spare respiratory capacity (FIG. 27E), as compared to WT fibroblast cells. Units in FIGS. 27B-27E are pmol/min/cells, data normalized to wild-type (WT). Histograms in FIGS. 27B-27E show mean±SEM of >18 individual measurements from 2 independent experiments; one-way ANOVA vs. WT ( P<0.01; ** P<0.0001).

Figure 28A:
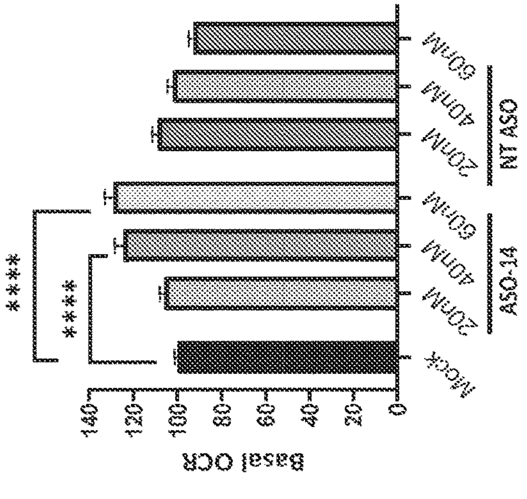
Figure 28B:
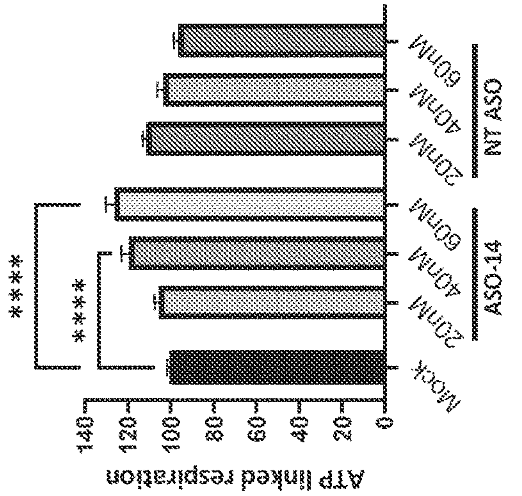
Figure 28C:
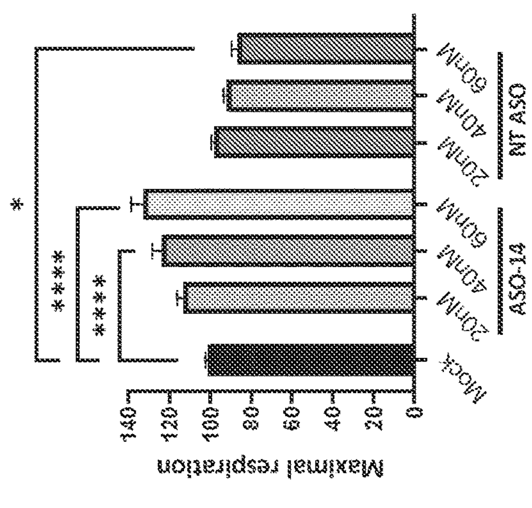
Figure 28D:
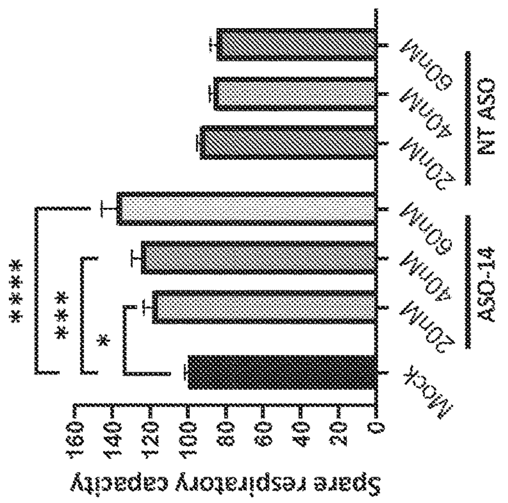
Figure 29A:
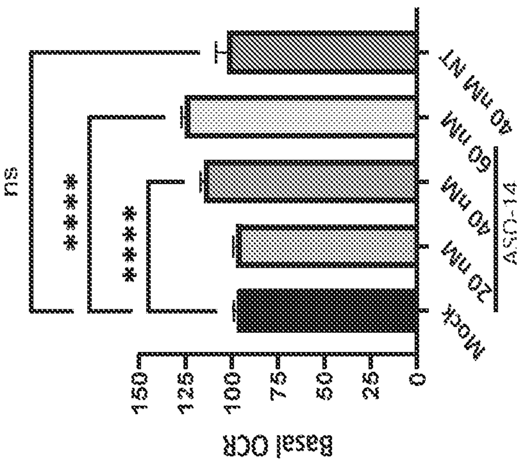
Figure 29B:
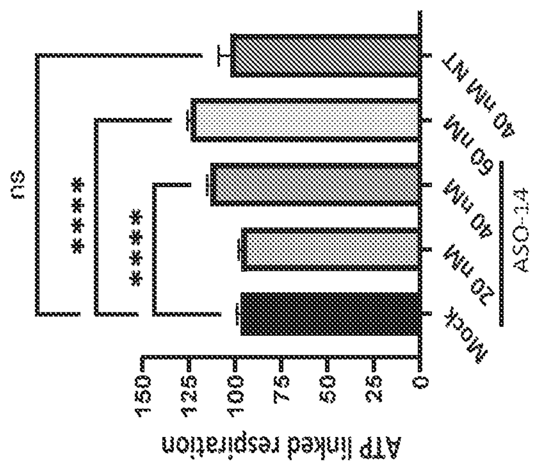
Figure 29C:
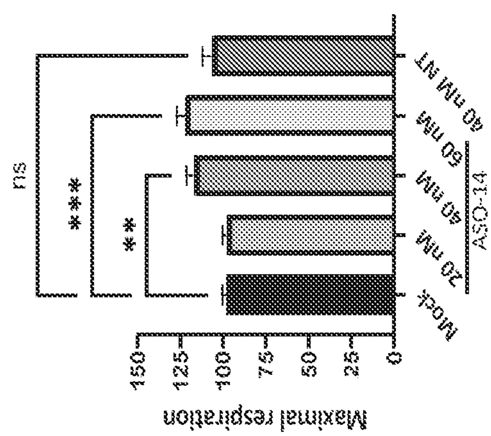
Figure 29D:
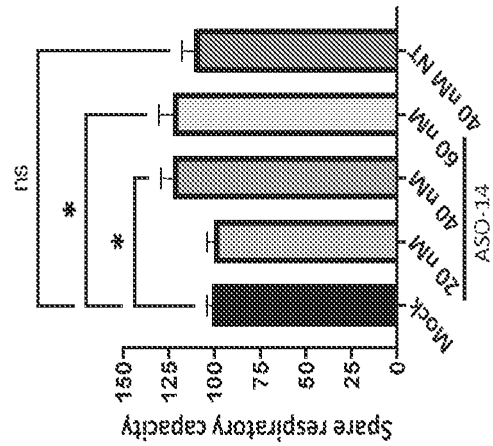

FIGS. 28A-28D demonstrate that ASO-14 increased mitochondrial energetics in F35 patient cell line. As shown in the figures, treatment with 40 nM or 60 nM ASO-14 increased basal oxygen consumption rate (FIG. 28A), ATP linked respiration (FIG. 28B), maximal respiration (FIG. 28C), and spare respiratory capacity (FIG. 28D) of F35 patient cells in a dose-dependent manner. Treatment with 20 nM ASO-14 also significantly increased spare respiratory capacity (FIG. 28D). In contrast, non-targeting ASO (NT ASO, targeting an unrelated gene) did not significantly alter the parameters at any of the tested concentrations. Units in the figures are pmol/min/cells; the Oxygen Consumption Rates (OCR) are normalized to total cell count and plotted to Mock (No ASO). The histograms show mean±SEM of >20 individual measurements from at least 3 independent experiments; one-way ANOVA vs. Mock (*P<0.05; *P<0.001; **P<0.0001).

FIGS. 29A-29D demonstrate that ASO-14 increased mitochondrial energetics in F36 patient cell line. As shown in the figures, ASO-14 also increased basal oxygen consumption rate (FIG. 29A), ATP linked respiration (FIG. 29B), maximal respiration (FIG. 29C), and spare respiratory capacity (FIG. 29D) of F36 patient cells in a dose-dependent manner from 20 nM, 40 nM, to 60 nM. In contrast, non-targeting ASO did not significantly alter the parameters at 40 nM. Units in the figures are pmol/min/cells; the Oxygen Consumption Rates (OCR) are normalized to total cell count and plotted to Mock (No ASO). The histograms show mean±SEM of >20 individual measurements from 2-5 independent experiments; one-way ANOVA vs. Mock (*P<0.05;  P<0.01; *P<0.001 **** P<0.0001).

The experiments in F35 and F36 cells suggest that the dose-dependent improvement in mitochondrial bioenergetics by ASO-14 is mutation-independent.

The foregoing preclinical data support the TANGO disease modifying approach in ADOA. As demonstrated by the data, the exemplary antisense oligomer, ASO-14, reduced non-productive exon inclusion, increased total OPA1 mRNA and protein expression in all three patient fibroblast cell lines; increased ASO-14 dose increased mitochondrial respiration in two fibroblast cell lines. The data further suggest that the ASO mediated increase in OPA1 protein expression is disease modifying in ADOA in a mutation-independent manner.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the present disclosure may be employed in practicing the present disclosure. It is intended that the following claims define the scope of the present disclosure and that methods and structures within the scope of these claims and their equivalents be covered thereby.

The invention claimed is:

1. A method of treating a disease or condition in a subject in need thereof, the method comprising administering to the subject a pharmaceutical composition that comprises:

(a) a pharmaceutically acceptable excipient; and (b) (i) a therapeutic agent, wherein the therapeutic agent comprises an antisense oligomer that comprises the sequence set forth in any one of SEQ ID NO: 36, 92-96, or 166-168, and wherein the antisense oligomer comprises a 2'-O-methoxyethyl moiety; or (ii) a vector encoding an antisense oligomer that comprises the sequence set forth in any one of SEQ ID NO: 36, 92-96, or 166-168, wherein the disease or condition is Optic atrophy type I or autosomal dominant optic atrophy (ADOA).

2. The method of claim 1, wherein the pharmaceutical composition comprises the therapeutic agent, and wherein the antisense oligomer comprises a backbone modification.

3. The method of claim 2, wherein the backbone modification comprises a phosphorothioate linkage or a phosphorodiamidate linkage.

4. The method of claim 1, wherein the pharmaceutical composition comprises the therapeutic agent, and wherein the antisense oligomer comprises a phosphorothioate linkage.

5. The method of claim 1, wherein the pharmaceutical composition comprises the therapeutic agent, and wherein each nucleoside of the antisense oligomer comprises a 2'-O-methoxyethyl moiety.

6. The method of claim 1, wherein the antisense oligomer comprises the sequence of SEQ ID NO: 36, and wherein the antisense oligomer is from 18 to 50 nucleobases in length.

7. The method of claim 6, wherein the antisense oligomer is from 18 to 20 nucleobases in length.

8. The method of claim 7, wherein the antisense oligomer consists of the sequence of SEQ ID NO: 36.

9. The method of claim 1, wherein the antisense oligomer comprises the sequence of SEQ ID NO: 93 or 95, and wherein the antisense oligomer is from 20 to 50 nucleobases in length.

10. The method of claim 1, wherein the antisense oligomer consists of the sequence of SEQ ID NO: 36.

11. The method of claim 1, wherein the pharmaceutical composition comprises the therapeutic agent, wherein the antisense oligomer consists of the sequence of SEQ ID NO: 36, wherein the antisense oligomer comprises a phosphorothioate linkage, and wherein the antisense oligomer comprises a 2'-O-methoxyethyl moiety.

12. The method of claim 9, wherein the antisense oligomer consists of the sequence of SEQ ID NO: 93 or 95.

13. The method of claim 1, wherein the antisense oligomer promotes exclusion of a non-sense mediated RNA decaying inducing exon (NMD exon) from the OPA1 pre-mRNA in a cell contacted with the therapeutic agent by at least 1.1-fold as compared to a corresponding cell that is not contacted with the therapeutic agent.

14. The method of claim 13, wherein the antisense oligomer increases a level of a processed mRNA that is processed from the OPA1 pre-mRNA and that lacks the NMD exon in the cell contacted with the therapeutic agent, and wherein the level of the processed mRNA in the cell contacted with the therapeutic agent is increased by at least 1.1-fold as compared to the corresponding cell that is not contacted with the therapeutic agent.

15. The method of claim 13, wherein the antisense oligomer increases expression of an OPA1 protein in the cell contacted with the therapeutic agent, and wherein the level of the OPA1 protein in the cell contacted with the therapeutic agent is increased by at least 1.1-fold as compared to the corresponding cell that is not contacted with the therapeutic agent.

16. The method of claim 1, wherein the subject has (i) a first allele encoding a functional OPA1 protein, and (ii) a second allele from which an OPA1 protein is not produced or produced at a reduced level, or a second allele encoding a nonfunctional OPA1 protein or a partially functional OPA1 protein.

17. The method of claim 16, wherein the second allele comprises a loss-of-function mutation in the OPA1 gene.

18. The method of claim 1, wherein the disease or condition is Optic atrophy type 1.

19. The method of claim 1, wherein the disease or condition is autosomal dominant optic atrophy (ADOA).

20. The method of claim 1, wherein the subject is a human.

21. The method of claim 1, wherein the pharmaceutical composition is administered by oral administration, synovial injection, or intravitreal injection.

22. The method of claim 1, wherein the pharmaceutical composition is administered by intravitreal injection.

23. The method of claim 1, wherein the antisense oligomer comprises the sequence of SEQ ID NO: 166.

24. The method of claim 23, wherein the antisense oligomer consists of the sequence of SEQ ID NO: 166.

25. The method of claim 23, wherein the pharmaceutical composition comprises the therapeutic agent, wherein the antisense oligomer consists of the sequence of SEQ ID NO: 166, wherein the antisense oligomer comprises a phosphorothioate linkage, and wherein the antisense oligomer comprises a 2'-O-methoxyethyl moiety.

26. The method of claim 1, wherein the antisense oligomer comprises the sequence of SEQ ID NO: 166, and wherein the antisense oligomer is from 21 to 50 nucleobases in length.

27. The method of claim 26, wherein the antisense oligomer consists of the sequence of SEQ ID NO: 166.

28. The method of claim 1, wherein the antisense oligomer comprises the sequence of SEQ ID NO: 92, 94, or 96, and wherein the antisense oligomer is from 22 to 50 nucleobases in length.

29. The method of claim 28, wherein the antisense oligomer consists of the sequence of SEQ ID NO: 92, 94, or 96.

30. The method of claim 1, wherein the antisense oligomer comprises the sequence of SEQ ID NO: 167, and wherein the antisense oligomer is from 24 to 50 nucleobases in length.

31. The method of claim 30, wherein the antisense oligomer consists of the sequence of SEQ ID NO: 167.

32. The method of claim 1, wherein the antisense oligomer comprises the sequence of SEQ ID NO: 168, and wherein the antisense oligomer is from 25 to 50 nucleobases in length.

33. The method of claim 32, wherein the antisense oligomer consists of the sequence of SEQ ID NO: 168.

34. A composition comprising (i) an agent, wherein the agent comprises an antisense oligomer that comprises the sequence set forth in any one of SEQ ID NO: 36, 92-96, or 166-168, wherein the antisense oligomer comprises a backbone modification, a sugar moiety modification, or a combination thereof; or (ii) a vector encoding the agent, wherein the agent comprises an antisense oligomer that comprises the sequence set forth in any one of SEQ ID NO: 36, 92-96, or 166-168.

35. The composition of claim 34, wherein the composition comprises the agent, and wherein the antisense oligomer comprises a backbone modification.

36. The composition of claim 35, wherein the backbone modification comprises a phosphorothioate linkage or a phosphorodiamidate linkage.

37. The composition of claim 35, wherein the antisense oligomer comprises a phosphorothioate linkage.

38. The composition of claim 34, wherein the composition comprises the agent, and wherein each nucleoside of the antisense oligomer comprises a 2'-O-methoxyethyl moiety.

39. The composition of claim 34, wherein the antisense oligomer comprises the sequence of SEQ ID NO: 36, wherein the antisense oligomer is from 18 to 50 nucleobases in length.

40. The composition of claim 39, wherein the antisense oligomer is from 18 to 20 nucleobases in length.

41. The composition of claim 39, wherein the antisense oligomer is 18 nucleobases in length.

42. The composition of claim 34, wherein the antisense oligomer comprises the sequence of SEQ ID NO: 36.

43. The composition of claim 42, wherein the antisense oligomer consists of the sequence of SEQ ID NO: 36.

44. The composition of claim 42, wherein the composition comprises the agent, wherein the antisense oligomer consists of the sequence of SEQ ID NO: 36, wherein the antisense oligomer comprises a phosphorothioate linkage, and wherein the antisense oligomer comprises a 2'-O-methoxyethyl moiety.

45. The composition of claim 34, wherein the antisense oligomer comprises the sequence of SEQ ID NO: 92.

46. The composition of claim 45, wherein the antisense oligomer consists of the sequence of SEQ ID NO: 92.

47. The composition of claim 45, wherein the composition comprises the agent, wherein the antisense oligomer consists of the sequence of SEQ ID NO: 92, wherein the antisense oligomer comprises a phosphorothioate linkage, and wherein the antisense oligomer comprises a 2'-O-methoxyethyl moiety.

48. The composition of claim 34, wherein the composition comprises the vector, and wherein the vector is a viral vector.

49. The composition of claim 34, wherein the antisense oligomer comprises the sequence of SEQ ID NO: 93 or 95, and wherein the antisense oligomer is from 20 to 50 nucleobases in length.

50. The composition of claim 49, wherein the antisense oligomer consists of the sequence of SEQ ID NO: 93 or 95.

51. The composition of claim 34, wherein the antisense oligomer comprises the sequence of SEQ ID NO: 166, and wherein the antisense oligomer is from 21 to 50 nucleobases in length.

52. The composition of claim 51, wherein the antisense oligomer consists of the sequence of SEQ ID NO: 166.

53. The composition of claim 34, wherein the antisense oligomer comprises the sequence of SEQ ID NO: 92, 94, or 96, and wherein the antisense oligomer is from 22 to 50 nucleobases in length.

54. The composition of claim 53, wherein the antisense oligomer consists of the sequence of SEQ ID NO: 92, 94, or 96.

55. The composition of claim 34, wherein the antisense oligomer comprises the sequence of SEQ ID NO: 167, and wherein the antisense oligomer is from 24 to 50 nucleobases in length.

56. The composition of claim 55, wherein the antisense oligomer consists of the sequence of SEQ ID NO: 167.

57. The composition of claim 34, wherein the antisense oligomer comprises the sequence of SEQ ID NO: 168, and wherein the antisense oligomer is from 25 to 50 nucleobases in length.

58. The composition of claim 57, wherein the antisense oligomer consists of the sequence of SEQ ID NO: 168.

* * * * *

SEQUENCE LISTING

```
Sequence total quantity: 607
SEQ ID NO: 1              moltype = DNA  length = 111668
FEATURE                   Location/Qualifiers
source                    1..111668
                          mol_type = genomic DNA
                          organism = Homo sapiens
SEQUENCE: 1
ataaacaaac attataaaat aatgtggatt taatcattaa caaacaattt caagttcttg  60
cacagtttca caaaggttaa tgtgacccaa agcttcacct ttataaagac aactctcgaa  120
tctgtattgc aagccccatc tccctgtgga actccaaagc ttgatttcta actgccacct  180
gaataaccca ttcacacttc agcaccaatc atcattccaa agccagcatt atcatcccct  240
tgtaatcagc ttttctatat ttgtgactgt tactaataat gtcaattgac tttggcttca  300
accccattat cttttgattc ctcttcctag tttcttcatt tagcttttca ttgttttaaa  360
tactccgaag tatcctttca aagaatctct cacttcttcc cattaccagg ctttggttaa  420
gggccctcac acttgacttt ctcaacagcc ccctatccag tcttcctgac cctcagtttc  480
cctctttaca aattcatcct tttctgtttc tccaggatta tcttttttga gcccacttta  540
tgacactata gtctgcctct gtgggtagta actgttgcta cccattactt ggtcctcagc  600
ttgtactacc tcacattaat gtttaccttt tatgtatgtc tgtcttccta accaaaccat  660
ggttagttga gggtgggaac tgtggtttac tctttttaaa aaaatatatc ctcaggcctg  720
gcacggtggc tgatgcctgt aatcctagca ctttggaagg ttgaggcagg cagattactt  780
gaggtcagga gtttgaaacc agcctggcca aaatggtgaa accccgtctc tactaaaata  840
caaaaactta gccaggcatg gtggcatgca cctgtaatcc cagctactca ggagactgag  900
gcaggagaat cacttaaacc tgggaggtgg aggttacagt gagccgagat tgtgccactg  960
cgctccagcc tgggcgacaa agtgagactc tgtctcaaaa caaacaaaca aacaaacaaa  1020
aaccaaatat atatatatgt gtgtgtgtgt gtgtatataa tttgtgtgtg tatatatatg  1080
tatttatatc ctcgactagg gttcatagga agtgactgta aatgtttgtt aataaggatt  1140
ataacatgct tttctgaggg ctggggagag tttgataatg atgatggtgc aaacatgtat  1200
gacttcagct aattattggc ttctccagga aaccacaaag agtagtgtta aggaacttgg  1260
agatctccca agaagaactt tgcaaaagct tttatgtata aatttaaata taaaacttat  1320
gaaatcaatt ttaaacattt ccatttccat taacatctct cattaccttc ctttctgaaa  1380
atttctgatt cgttggataa ttctgaaaag ggtccctttt cctgctaagg taaatattta  1440
gagttttacc tggtgaattg ctcaattccc agctgaactg gaaaatttag tttaaagtag  1500
taaaattatt tcatgacttc tggatcagaa aaatattttt aacatgtttt tacaagtaat  1560
taatacacaa gttcagagta taaaagggtt tacaataaat gtaagcctcc ctcccactca  1620
tgacccacta acttcaagtc cttccttgac tctgcccttc actagggctt atcaactcaa  1680
atattttcgt gggttaggca tgtaacataa atgagtaatg caagtatgtc tgttgtataa  1740
tgtcatatta aattgtattc atataattta ttcatataat tttacttgcc tacttgcata  1800
cttgtgttct tttgccaaaa aaaaaaaaaa aaaaagctct ttctcattgt tttggaaatg  1860
gctgaccctc tcagtccttc attttctctc acttttcata ttgtaatcat ccagcaggtt  1920
cttcctgctc actgcacaga caaaatcatt tcactgagac cagggcatcg cagtagaaaa  1980
agagtttaac tgattcaaga ccagcctatg caggagaact ggagttgtca ctcaaatcaa  2040
tcttcctgaa ggctctgagg ttagaggttt ttatggacaa tttagtgggc aaggggtagg  2100
gaatggatgc tgctgattgg ttggggatga aataatagga aaacattcct tgtgtgctga  2160
gtccacctct gggcggggcc acaggatcac ttgagtcatg agtcataagt ctcgatgggg  2220
tgagtctgaa atataccgca aaaaagcagt cttagattct atagtaatga tgttatctat  2280
aggagcaatt ggggaagtca taagatttgt gagttctggc cacattgatt cctgagcagt  2340
aagggactat agaaaccata cctacgtctt agcacagttc aggcccctct catgatcctg  2400
ttctcttggc ctttcttaca aaggtggttt ttggttcctg agcaacgagg gagttagctt  2460
taggaaggga ctattataat cctttctttc aagttaaact ataaactaca ttcctcccca  2520
aagttcattt ggcttaagtc caggaatgag caaggacagc ttggaggtca gaagcaagat  2580
ggagtcaact atgtcaggtt cctcttgtca taattttgcc aaggcagttt caatataagt  2640
agtggttgtt tttcctctta atttttacta agaaaagtag aagcacaagc ttcatgataa  2700
acagtaattg atgtgttcaa tttcagaaag atgaaggagt gtgaactacc ggagaggaca  2760
tgagtgcctg aaggataaaa ctactacttg gctcctggtt ccgagacatt ttttgtatat  2820
aagaattgaa ggttgatgtt gttaggcatc ctgatatttt tatgtgattt tttaaaatgt  2880
gaaatttgtt gatttttatt tggcaacaaa tgtagcattt ttttgcttgt ttgtttttga  2940
gacggagtct cgatctgtcg ctcaggctgg agtgcagtgg cacaatctca gctcactgca  3000
acctctgcct cctgggttca agcaattttt ctgcctcagc ctccgagtag ctggctaatt  3060
tttttatttt tagtagagac agggtttcac catattggcc aggctggtct caaactcctg  3120
acctcgtgat ctgccttcct cggcctccca aagtgctggg attacaggca taagccgcca  3180
tgcccagccc aaatgtagtg ttatttttaa aacactgcat aggccaacac tgtctaaacc  3240
aaacaaaaca ggtctgtggg ctgaatttgg tccaatggtt gcagtttatt atacaacagt  3300
ttgccctttt ttcatggcaa cactatgtat ctatgggaga tcattcctta tcaggacata  3360
cagacctaaa gcataggttt tcatggctag tacggatgta atttatgtgt ctagttccta  3420
tacatggaca tttatactga ttccaatctt ttcccatttc atacagtgca gaaataaaca  3480
tcatcatgca tacatctttg catacatggg aatgattcca caggataaat gcctagaagt  3540
```

-continued agaactgcaa aacaagggct tcataaaaca tatgataacc atatataaat ggtgatggtg 3600
gttagtttct cctttttta tggttaaagt cttttatccc taatttttct tttttgttgt 3660
tgttgttaaa gtctcttggt ttctcttatt ttattttcta aaataacaag gaagtaacga 3720
ttacaaagac actttttgta caaccctaca atcccaggaa gatctacagt ttgcacaggt 3780
tggtacagca aattgctctc tggacctgcc attgaaacag tcaccacaat aaataaagaa 3840
aattctaaga gtcctgcatt tgggaagttt actatcaatg gctaggtcta ctcttggtgg 3900
tattgtgagt gcatgggtcc agacttatga ttctgacaat taagggaaaa ggaattgtct 3960
ttatgctctg tgtatttgtg tatgtgtgtg gcatgggtgg ggggcgggta gtggggagga 4020
ggtgaaaggt ccctgaagta aagaggatgc acaggaccct tttattttag tccctaaaaa 4080
ttggcttcat aaccgttcac aggccacatc cctttacgg gccctggttt ccttacaaaa 4140
cataaaaggt ttgtgttgga aggggaaagg agtatttaaa gtgatggagg agaggagctc 4200
aagatggctg agatctgggc ctgtccaaca ttgagaaatt tgggagggga gccatcaaag 4260
aagcctggga gcagcagttc cagggaaaaa ggagaatgtg atggccagag agccaaaaga 4320
aaaagtagtt gaaggagtgc tcagcactag gcatctgaac tgaatgctgt ggcaggctca 4380
ctggccacaa acaataggga gctggtggag gccttgacga ggaccatttc aacaaactgg 4440
tgggcttaaa atccggaaga aacagttgaa caaatcattt tgacgccttt tataaaccac 4500
acaagcttat tccaaacccg ttactggcct aactgattta agtccctttc ccatctgatc 4560
ctcagagatt ctaagggact tagcctatcc atgactcttc gtcctgcttc tcacctccca 4620
tgattgccct aacgatgtga aagtgctttc aaacaaagat gcccaagaaa gaaggtaggc 4680
aaatgtgcaa gcattagttt gtagtacgct attactgtat ttcaccttgc actctctagt 4740
ttccttcgtg ctccctcaat atccaactct taataaattc atggctcccg gtgagcattc 4800
atcaattctc attccacgcc tttagccctt cccgttcccg cccaactctc gctccctccc 4860
ctggccaaat ctctaacctg caaggctaat tccgaattcc aaatcggaag caagagggcg 4920
gggccccgtg agaggcgatg gattgctcca gtccgttccc gacgcactgt gcgcatgcgc 4980
tggtcctccg cggaccgttc gtgctgcccg cctagaaagg gtgaagtggt tgtttccgtg 5040
acggactgag tacgggtgcc tgtcaggctc ttgcggaagt ccatgcgcca ttgggagggc 5100
ctcggccgcg gctctgtgcc cttgctgctg agggccactt cctgggtcat tcctggaccg 5160
ggagccgggc tggggctcac acgggggctc ccgcgtggcc gtctcggcgc ctgcgtgacc 5220
tccccgccgg cgggatgtgg cgactacgtc gggccgctgt ggcctggtaa gtgcaggctc 5280
taatctggcc ccgttaattc tggggcctct tgagagtggg gctgtcttat ctctatctcc 5340
aaaaatgtgc aggtgactct caggccaggc cgacggcagt tggagaattc ccagatgttc 5400
ttgaggaccc agaatgacag gagccctggc tgggcttacg ttcggagccg gcttcaatac 5460
tggccctttt ctctggccct acccaacccg aaaattctgg acgcctctca atcttggccc 5520
gtctctattg tccttttgtc tctgcccttt acacccttgt gtcttcagtg ttctgtctgt 5580
ctctggttgc ctcttttgcc ttttttctgt cctctccctg ccaggtttgg ctctgtccat 5640
gagtcacctc tctccacatt tctcctaact ctcggtgtct tctttttctt ccatttccac 5700
gccatgtgta cattgcatct tcaggtacct gggctcttct atcggggaaa ggggcgtccg 5760
tctctttccc tagcccgctg atagaagtca gaactagagc aatgacgcac acggtgtcag 5820
agacggtgat tcgagatgcc ctttcaatag cagctttttt ctgtgtttcg ggagggagac 5880
ttacttttg atgcaaggtc gtgaacgtgg caccaccttt ctaatctcaa tcattgttgc 5940
cctggggtgg tttaattcta aatagaaaat catagaaatc ttttcatttc tgtgcgttac 6000
tatatgcatt gtaatgagat taaattggat tttataggaa attttgttct agtatcatta 6060
gataccttca agcttagctc attgttgcag gcatttgata ggaagtaaga tgcatcaagc 6120
aaaattggaa aaacgtggtt ttcctgaatt aacttctaag cagttgtttt gaatttttc 6180
cagaccttt taagtggtat agataattta tcgtgtttat aaggaatgga atgcattcgt 6240
tagtttgttt ttgttttgtt ttgagacgga gtcttgctct gtcgtccagg ctggagtgca 6300
gtagcgctat ctcggctcac tgcaacctcc gcctcccagg ttcaagcaat tctcctgtct 6360
ccgcctccgg agtagctgga attacaggca cgcgccagca cgcctagcta atttttgtat 6420
ttttagtaga gagggggttt caccattttg gccaggctgg tctcgaactc ctgacctcat 6480
gtgatccacc ctcctcgact tcccaaagtg ctgggattac aaccgtgagc caccgcgccc 6540
ggcccaattt gttttatata ggttaactgg agtccaaaat acagaactag atgagataac 6600
aatagttaac agtgttagtc agttagaatt attgcatagg tatttttaat ctcatggaat 6660
tttagtcttt gagtaagttc acagcccttg gtattaaagt aagttattta caacccttgc 6720
atttctactt ctcaatattt agtgaggaaa catatctgat tttctttaaa taaaaagaga 6780
aaagactgca gaagatagca ttctctgttg gagcaattaa gatgtataag aagaactaca 6840
aagacggagt tttaaaacaa actgatttat aagtggtatt tatttaattg gctgtcattg 6900
ggctaaatta tttctaaagt taccatggat gccattgagt catggcttaa aaatgtctcc 6960
tggtgatggc acagtttagc tacctaaaga agtagagatg tgggaagcca gaagccccaa 7020
gctctgcagt ttttctttg ctatagttcc tttgcatgtt gtgaaagaat acagttaaat 7080
tcctgctccc taacagatga gagcataagc atttctttgg gcatacatat gtaaatacat 7140
gctcatggac atgtgaaaag atcaatacta acatttgggt gcaataaata attgtgtaaa 7200
attattttta aaagaattac atattaggaa atgatatatt gattaaaagt gatagtcaat 7260
gaacaagaga gtagatttct gggggaaacc tattttgcat catacttgat ttttagtttt 7320
gactgaatat tgaagtctat attcaaaatt cttttccttt agaactgtaa aggcattgct 7380
gcattttctt ctaatgtaat tgtttattgc tgctgagaat tcttatgaca atctgatttt 7440
ttcatcttca tgattatctt gtttttccct tcatggaatc tgttagggtc ttgactttat 7500
cctttatcct aaatttctca aggcttggac caggtgtggg tttggttttg ttttcttttg 7560
ctactcattt gacttggcac actcagtggg cctttccctt tatctttctt catttctgag 7620
acgtttttct ctcttatttt ttattatctt cctttcattt ttcctgtcct ttttctttct 7680
agacatctct taggaggata gtggtcctct tagattgata tgttatgtcc gtgatttcca 7740
aagtaagatt tgtactcgtc gtctgttaaa aggaaaagca tacatatacc ctatgtatat 7800
atgcacactt ttttattttt aaattatata tgtatctgta ctaattattt acattgtaag 7860
tcaaccctaa cataatctta aaggataaga tacaaaacat actgcatcta gaagcttcag 7920
tactttcttc ctgaatccca gtagatcctt ttgttcatcc cacgggatgc attccgcccc 7980
catcctccca ctccctttgg ataccacatt accacagctc tgcatcactt aactttcctc 8040
ttatgttttt cacctttttt tttttttttt ttttgcattt tatgtcctgg ggaatttcct 8100
taattcattt catggtttta ctgttgattt ttttaatatt ggccatcgca actttttcttt 8160
tcttttcctt tcctttcctt tcctttcctt tccttttctt ttcttttctt ttcttttctt 8220
aattttcttt tcttttcttt tcttttctgt tcttttcttt tcttttcttt tcttttcttt 8280

```
cacacaggat cttggcgtgt tgtccaggct ggcctcgaac tcctgggctc aggtaatcct  8340
ctcaccttgg cctcccaaaa tgccaggatt acaggcgtgc gccactgcat ttggcggcaa  8400
cttaattttt ttatttttat ttttcctttt agaggacacc tagcactgag cattgcaact  8460
tttcatttcc atgaactttt aagaaaactc ttaaagacat gtttaattct gtacactttc  8520
tattgttctt tgattgctgt ttttgaataa caacaaggag tacgccttag catttttgatg  8580
gtatcctctt aatagtcgca ataatagtcc ccttggcgct ctgtatactc tcaagtctta  8640
aatgttttgt atgcagctgt acgttgacag ttgaatggtc tcgctccaag tggatcagca  8700
agaacataaa gaatcattta actggtacag gctgcggctt gtgaattccc tattaacacc  8760
aaagaagacg tgtgagactc cgtactgaaa ctaaagacga cttgtgagtt ccacactgag  8820
atcaaataag tctttatgat ggtgacagag agtggtgtca acgcctaaag ttttggttaa  8880
tctctctaaa ttgaggggct gaccaaaagg gggaacttaa ctgtattaga cataattttg  8940
agaaacatgg gtatgtggat ggtaatggag gaaatgggtg tagatgagat tgcctaggga  9000
gagtgagaag taggttaggt ctaagccttg atgagttccc aacatttcca agggtagttg  9060
aggatactga aaatgagtgg ccagtgagat agaggtaaag ctagagactg cccaggggag  9120
aggaattttc aacaatgagg aggtgtcaac attgtcaggt attgctgaga ggtcagataa  9180
aaccagaatt gagcaaaatg gccattggaa gcctatggtg ccctccgtaa gagctgtttc  9240
gctgaagtga tagaaacgga aatcaggctg ggcacagtgg ctcactcctg taatcccagc  9300
actttgggag gccgaggtgg gcggatcacc tgaggttagg agttcgagac cagcctggcc  9360
aacatggtga aaccctgtct ctactaaaaa tacaaaaagt agccaggtgt ggtggcaggt  9420
ccctgtaatc ccagctactc aggaggctga ggcaggagaa tcgcttgagc cccagaggcg  9480
gaggttgcag tgagcagaga tcgagccact gcactccaac ctgggtgaca gagcaagact  9540
ccgtttcaaa aaaaaaaaaa aaaaaagaaa tggaaatcag gatggtttgg cttttatttt  9600
aataaaatag ctagagcagg gaaatggggt actttttttc cccttttaa gatgagacat  9660
agccaggtgc agtggcttac acctgtaatc ccaacacttt gaaagggagg gtcgcttgag  9720
ctcaggagtt tgagaccagc ctaggcaaca tagcaagacc ttgtctctac taaaattcaa  9780
aaaaaattaa ctgggcatgc tggcacacac ctctagtccc agctatttat gaagctgagg  9840
caggaggatc acacttgagc ccagatacgt ggggctgcag tgagccctga taatgccatt  9900
gcactccacg ttgggcaaca gagcaagact tcgtctcaaa aataaataaa taccctgtct  9960
caaaaataaa aaataaatat gggaggagag atttgactta gattcctcaa agggcaggag  10020
gaaagagaat tccaaacagt gattcacctt taatgggaga aagatcgctt aatttttacat  10080
gaggaagaag aggattggtg gagatacagt aggtgaacag tttttgtatg aggaagttga  10140
acatgtgtca ttctaatagc ttccattctc tgtgaagtag agggcaaggt catctactga  10200
gagttgggga ggtcaagaga gataaggggga gattagaaga gctcttctag cagagagtgg  10260
aagaatgaat tgctaagaga gatgaagtag gattgttaag tagttttgag ggccctgttg  10320
agatgtgctt ccagttgggt gtgattttct ccagtagtgc tttatttccc tgggtacagg  10380
cagagagaaa aacaataagg ctcatgtagg gtttgtattt tgttggacaa gtcaaacaga  10440
aaagtcagag gacgagggag tttagaatgt ttgcaaaaga gttattgaaa cgatgaaccg  10500
cataatctaa ggtggtaagt gggtgaatag ataaggagga tgtgaatagg taaggagaag  10560
aaagaaatat cagattattg attattgatg gcgactctct aatacagcta ttatgccatt  10620
ttaaccgatt aagaaactaa ggctttagaa aattcataat ttgccctaac tgcacagcta  10680
gtaagcagtg gaaatgtgat tggaaccaga gttcttctga ctcaatagac taaatggatg  10740
taaggatgta gttgaaagaa gggtgagcta aacgttgtgg aaccatgagc tctttctctg  10800
gttgatatcc ctctctgtaa gtgataacat gggtcacgct ggataaaacc ttgtggtgat  10860
tggtgacttt cctttgtcct tcctcctgtg cctagtctgg cgagtatctg cctttccctt  10920
tcctttctca ttgctgccac ctaactttag gctcttcccc ttacatctgg gtaactgaaa  10980
taagatcacc tttttgttcc ccttctgatt tactttgacc taacattatc tttactattt  11040
tctttaaatt aatgtttcat tagtcttatt ctactcagga actctgtagt tccccattgc  11100
ctacgaaaaa aagttaagcc tcagccttat attcagtgac tcttcaattg gatattcagt  11160
ccagttttac tcctcctatg agccttctat gccagctcct tgggtctctt gccctttcat  11220
tgtctcagct ctgcaccctt ctttctcttt tttattcttt tttttttttg tactttttttg  11280
gttttctttt tggtttcttt ttttgtttta tttattaaac ctccatcaca cttcatccta  11340
tggagttttg aaccacagca aggtgcagta tcatcctggg gctctggagg aagtggcagg  11400
gagtccaaaa tgtcacctta gcttcttatc tggggccaca tgtatttctg catctgctgc  11460
ttcccacact cttgcccaca agtgtcgctt gtggaaataa tttgagattt actgtctggc  11520
tgaccctagt ttcaatctct tttccaccat ttgctaatca ttctaccttg ggcaaaacat  11580
agaattaaaa gaaaacttca gacaagttaa atttgatgga gtttaattga gcaaagaaaa  11640
aaaatgatcc acaaattggg cagtctccag aatcaccgca gattcagaga gactccaggg  11700
gtgcctcgtg gtcagaacaa atttatagac agaaaaggta aagtgaccta caggaatcag  11760
aattgagaca tagaaacagt gagattggtt acagctcggc gtttgcctta tttgaacgca  11820
gtttgaacac tcagcagtct atgagtggtt gaagtatggc cgctgggatt ggccaacact  11880
cagctgttat tacagatgca tactactaag ttaggttttc gattttgtct gcctatttga  11940
gctaggttac agttcgtcca caaggactca aatataaaag tacggagtcc tcttcgggcc  12000
atatttagtt cgctttaaca attccccctt ttggtcagcc cctcaattta gagagattga  12060
ccaaaacttt aggcgttgac accactctct gtcaccatca taaagactta tttggtctca  12120
gtgtggaact cacaagtcgt ctttagtttc agtatggagt ctcacacatc ttctttggtg  12180
ttaataggga attcacaagt tgcaactttg taccagctaa atgattcttt atgttcttgc  12240
tgatccagtt ggagtaagac cattcaactg tcaatgtaca gctgcataca aaacatttaa  12300
gacttgagag tatacagtgc accaagggga ctattattat gactgttaag aggacaccgt  12360
caaaatgcta aggtgtactc cttaataaaa gttcttatga aatgaactga accaaatcag  12420
ccaagttaag gttcagacaa tataagcagt tcagcagtat tggggtctga ttggtcagag  12480
tcttcagttg gagtatgata gtgattaagg atcatagttc gctgtaaagt agcttgactt  12540
aaagaggtgc tcgttttcat tgttaccttg ttaatacaag tcataataac ttgaaaacct  12600
gctagaagag atataaagat tagaaaccct tggaaaaccc aagcttgcca ttcaccactt  12660
aggatgcctg caaaccaact gttagttgct cctataaaca tatcgtgggt tcctttctct  12720
tgagagattt ctttattgta cttggtggca gtgtctaagg aaacagcagt atcagccacc  12780
ttttaaatta agctttttgt agtaacagaa tcaggggagg gattagtaca aaattcagtt  12840
ttgtttaaca ccaaacatag gcctccagct tgagcaaaaa gaagatctaa gactgcatga  12900
tcttccatta agtgttttcg ttgaatatgt atgttgtcat gtgcctttct gagagtagct  12960
tctacccatc tgaaaccctg ggaggtctga ttggctacca aatccaagaa ttttcccaat  13020
```

-continued

```
atacaaatta gttttaaatt ccgtacaaat ggtacttcac taccaccaag agtgagcccc  13080
caggaacccc agtggaatct ttccccggta gaaactagct tatcctcgtc tatttcgagg  13140
ctagtgctaa tttcagttat tgatcatttt ggcctccaag tataagggct atcatgagaa  13200
ttttcagggg aagcaattcg aaaggcagga gcaggccagg ccagataaca agaaccaaac  13260
caaccaagga ggcagaacag aatatgcaga ttctccacag acccaataga gaccctcagg  13320
ggttggaaaa gggggccacc tagttgtatt tgagcaggga tcattcaggt ttgttcgacc  13380
atgaatctgt agctcctgaa taacatccag tgggaaattt acttttctat ggccccttg   13440
tagtgtgttg taagggtgta taaccacatc tagtaaaaag agaccctact ggatatacaa  13500
gcaatcactt gtactaacat aagtaattcc caaatcttga gtatgtgatg cctgcaagca  13560
caatatacgt tttgtaggca tcatttggat ttgtttttta tatttggtgt gatcgacttt  13620
atcagttgaa aaagagtgtt gtttttagtg agtgtaggaa agcaagtact agtgatgttt  13680
agagtatcaa gaatagcttt ccattcttcc cttggggttt cagggtgact cattgggaaa  13740
cgtggagggg cactggcacc cttggaatca tttcctgatt ttttggcatt agcccacaaa  13800
cccaacagtt accctggttt tgtgctagag cataagcttg agctgaagcc atccactgat  13860
tatggtccca tggattttca tgtaaggaaa aggaaaggat tagggaaaaa aataaggaaa  13920
acagaaaaac acataaggct ttcatggtgg tagagaagtc ttgatctgtg atctagggaa  13980
agctgtctgt aaccaggatg ctgtctgctt ctgggaagag atttccctgg tcagctttac  14040
cttaaagtct ccaacgggta tatagtacca ggagtctgag ggggcccttt tgaattgtga  14100
gatgtggacc catggttcaa agccctgaag cttctctgca ctgtgggtgg taagaaggac  14160
ttggtatggt cccatccaac gaggttcaag agtgatcttc ttctgatgtc atttccggaa  14220
ggcccagtct ccaaattcca gaccatggag ggtttgattg tcctcagttg gtggatcttg  14280
aaatgcttcc tttacctggt ggaagtatac tttggcgtaa tacattaaag ccttgcagta  14340
tttagtcata tcagagttta agagagcagg agaagcatga gatgctatta ttagggacat  14400
gggcctccca gtgactattt cataaggggt caatttatgt tttccaacag gattgaatct  14460
gattgccatt aaaaccaaaa ggtagtacct ttggccaagg caactcaatt gattcagtta  14520
acttggacag tttcagtttt caaatgccat ttgttcttc aagctttcct gaagactgag   14580
ggtaataagg acaatggtaa tgcaactgtg tcagtaacac cttatttaac tgctttataa  14640
cttgctcagt aaaatgagtt cctctatcac tggagacttt tagagggatc cccataaag   14700
gaaaaacatt ttctaataat ttcttagcta tggtcacagc atcagctttc ctacatggga  14760
aggcctttat ccaaccagaa aacatgcaaa ctattacaag aacatactga taccccattg  14820
agggtggtaa ctgaatgaag tccatctgta aatgttcaaa tggtccatca ggtggtggaa  14880
atatactgcc tctagttttt ctgggattat gagtttgaca agtcaaacat tgattataag  14940
ccattttagt aatgtcagaa tagtcacccc accagtattt tttcataatt tggatcactt  15000
tgtctgttcc atgatgagct gtggagagct ttcaataatg gaagcttcaa agattcagga  15060
aggaccaggc ggccgtccgg gccctttgtg agtctttgct tcacgttaaa tttacatcct  15120
tttagatacc agttttgttt ttgcaaatca gatgcgttgc actgtttatt aaataggtca  15180
tcgtaaggaa attggcttgg attaatctta tggagttcat tcagattgcg tatcttgatg  15240
gttccagcac tagctgattg agcataaaaa tctgctaaag catttcactg atatttgggt  15300
tcatttctac aagtatgagc ttcagtctta ataacagcaa tctgcatttg taacaggata  15360
gcagaaagga gctcatctgt ttggagtcca tttttgatgg ggatcccact agaggtgaga  15420
aaccttcgta gtttccatat catgccaaaa tcacgtacta ctccaaaagc atgtctacta  15480
tccgtaaata tttactgact tgtccttagc tgtgtgacat gttcaggtaa gggcagaaag  15540
ttctgcaggt tgggctgact tgacttgaag agttcgcttc tctattaact catttttgggt  15600
ggtaacagca tatcctgact gatatttttt tttctgagtt tttggcatag gacccatcaa  15660
caaaaagtgt taattcagga ttatccagtg gagtatcttg tatagcaaca cgagggggcca  15720
ctatttctga tactacactc acaccgttgt ggtcttcacc atcatcaggc agagataaca  15780
gagtagcagc attaagtaga ttacagcctt ttagatgaag ataagaagga gataggagaa  15840
gtaattcata agatgttagt ctactcactg aaaaatgctg ggtttgattg gaatttaata  15900
gactttccac agcgtgtggg acttgcaaat taagttcatt tcctaaaacc agatctgatg  15960
aagcttctac cagcttggct gctgctactg cttttaaaca attaggatat gccttagaga  16020
ctgggcctaa ttgcaggcta tagtatgcag tggtcctatg tttagcaccg tgttcctgat  16080
tattacattc atgaacaaac aaagtgaaag gtttagtgta atttggaagt cctaaagctg  16140
ggggctgttg taaggccaac ttcatttggc taaaagcctg ctcatgactg tcttcccaag  16200
gtaaaggctc tggtacagca tttttagtga gctcatacag tggtgaagct attaaggaaa  16260
aatttggaac ccaggatctg caatatcctg caagcctaag aaagcctttt gtcttttggt  16320
tgcaggtcga ggaaaacttt aaataggttt tatcctctca ggtaagaggg aaatcccttc  16380
agcagccaag tcatgtccca aatagtggac tttttctttt gaaaattgaa gttttggcca  16440
ggcatggtgg ctaacgcctg taatcccagc actttgggag gctgaggcag gcggatcacc  16500
tgaggtcggg agttcaagga cagcctgacc aacatggaga aaccctgtct ctactaaaaa  16560
tacaaaatta gccaggcgtg gtggtgcatg cctgtaatcc cagctactcg ggaggctgag  16620
gcaggagaat cgcttgaacc caggaggcag aggttgtggt gagccagtat cacaccattg  16680
cactccagcc tgggcaacaa gagtgaaact ccatctcaaa aaaaaaaaaa aagaaaaaag  16740
aaaagaaaaa attgaagttt ttccattgaa gccctgtgac ctttatatgc aagttgctgt  16800
aaaaggtaaa ctgagtcaat ttccgggcac tccttaatag gagagcataa caataagtta  16860
tctacatact gaatgagagt agaattttga ggaaactgta gtgtcattaa ctcctgatgc  16920
agtgcctggg gaaaatatga aggggcttca gtaaaccctt gtggcattac actccaggtg  16980
tattgctgat ttttccaagt aaaggcaaac aagtattgac tttctttatg gaatgctaga  17040
gaaggctgag ccaagatcta ttactgtgga caacttggaa tcagtgggta cattaggtta  17100
taaagtatta ggatttggga ctacaggaaa tcttggtatt acaattttat taattgcctg  17160
taaatctgga acaaatctcc agtctcatcc attttgtttt ttaactggta ggattggagt  17220
gttacagggg ctggtgcatg gaattatgag tccttgttta attaaatctt ctacaattgg  17280
tgagagccct taaattgctt caggttttag tggatattgt ggtaattagg caaaggttta  17340
gaatgatctg ttagtacttt tataggttct acacttttaa ttcttcctat atcagttggg  17400
aagaggccca taaacattag gtgttttcga aagatcaggg gtattacagg cttgagtttc  17460
gatcttatca atttctgcct gtagacagca taacaattct agttcaggag aatcaggaaa  17520
actcttaaga ttatttctgt ttctgaggaa aattttaggt gccctttttag ctttgaaagt  17580
aaatcttgcc ctaccaagtt tactggaaca gtatcacgta gtaaaaaact gtgtttttct  17640
gaaagggggc tcagagttaa ttggatgggt tcagatatgg gaacctctgg aacttgattt  17700
gaaacccctg tcacagaaat gaccttttta ctctaaggga tttgttggct tattaaggtg  17760
```

```
gggtttatgg tagatagagt agccctggta tccataagga ctatacacaa ctccctattt  17820
attttaacct ctgtttcccc atgttccttt aaaggtatta cggggagcaa tccactggag  17880
aatcccttag agcctccttt aagttgaata ttgtcaggag gactaaggtc tcttgggctc  17940
cctctagtgg tgaaacagtt tggcctagag ggaggtttat cagccgacaa tccctttcc  18000
agtgccctgg ttgtttgcaa tacaggcaga catcttgggg taaagaaatt cttgttctgg  18060
gacctcttga tttgattttt ttaatatata attttaaaaa tattttccaa agtgtgactt  18120
aaaaaaattt tttttatta tactttaagt tttagggtac atgtgcacaa cgtgcaggtt  18180
tgttacatat gtatacatgt gccatgttgg tgtgctgcac ccattaactc atcatttaca  18240
ttaggtatat ctcctaatgc tatccctccc ccctccccca accccacaac aggccccagt  18300
gtgtgatgtt ccccttcctg tgtccaagtg ttctcactgt tcagttccca cctacgagtg  18360
agaacatgcg gtgtttggtt ttttgtcctt gtgatagttt gctgagaatg atggtttcca  18420
gcttcatcca tgtccctaca aaggacatta actcatcatt ttttatggct ccatagtatt  18480
ccatggtgta tatatgccac attttcttaa tccagtctat cattgttgga catttgtgtt  18540
ggttccaagt ctttgctatt gtgaatagtg ctgcaataaa catacgtgtg catgtgtctt  18600
tatagcagca tgatttataa tcctttgggt atatacccag taatgggatg gctgggtcaa  18660
acggtatttc tagttctaga tccctgagga attgccacac tgacttccac aatggttgaa  18720
ctagtttaca gtcccaccaa cagtgtaaaa gtgttcctat ttctccacat cctctccagc  18780
acctgttgtt tcctgacttt ttaatgattg ccattctaac tggtgtgagt tggtatctca  18840
ttgtggtttt gatttgcatt tctctgatgg ccagtgatga tgagcatttt ttcatgtgtc  18900
ttttggctgc ataaatgtct tcttttgaga agtgtctgtt catatccttc acccacttgt  18960
tgatggggtt gtttgttttt ctcttgtaag tttgtttgag ttctttgtag attctggata  19020
ttagcccttt gtcagatgag aagtttcaga aattttctcc cattctgtag gttgcctgtt  19080
cactctgatg gtagtttctt ttgctgtgca gaagctcttt actttaatga gatcccattt  19140
gtcaattttg gcttttgttg ccattgcttt tggtgtttta gacatgaagt ccttggccat  19200
gcctatgtcc tgaatggtat tgcctaggtt ttcttctagg atttttatgg ttttaggtct  19260
aaattaagtc tttaatctat cttgaattaa tttttgtata aggtgtaagg aagggatcca  19320
gtttcagctt tctacatatg gctagccagt tttcccagca ccatttatta aatagggaat  19380
cgtttccccg tttcttgttt ttgtcaggtt tgtcaaagat cagatagttg tagatatgcg  19440
gcgttatttc tgagggctct gttctgttcc attggcctat atctctgttt tggtaccagt  19500
accatgctgt tttggtgact gtagccttgt atagtttgaa gtcaggtagc gtgatgcctc  19560
cagctttgtt ctttggctta ggattgactt ggcaatgcag gctctttttt ggttccatat  19620
gaactttaaa gtagtttttt ccaattctgt gaagaaagtc tttggtagct tgatggggat  19680
ggcattgaat ctataaatta ccctgggcag tatggccatt ttcacgatat tgattcttcc  19740
tacccatgag catggaatgt tcttccattt gtttgtatcc tcttttattt ccttgagcag  19800
tggtttgtag ttctccttga agaggtcttt cacatccctt gtatgttgga ttcctaggta  19860
ttttattctc tttgaagcaa ttgtgaatga gagttcactc atgatttggc tctctgtttg  19920
tctgttattg gtatataaga atgctctctt ttgttctttg ttagtcttgc tagcggtcta  19980
tcaattttgt tgatcttttc gaaaaaccag ttactggatt cattgatttt ttgaagggtt  20040
ttttgtgtct ctatctcctt cagttctgct ctggtcttat ttatttcttg ccttctgctg  20100
gcttttgaat gtgtttgctc ttgcttctct agttctttta attgtgacgt tagggtgtca  20160
attttagatc tttcctactt tctcttgtgg gcatttagtg ctataaattt ccctctacac  20220
actgctttga atgtgtccca gagattctgg tatgttgtgt ctttgttctc attggtttca  20280
aagaacatct ttacttctgc cttcatttcg ttatgtaccc agtagtcatt caggagcagg  20340
ttgttcagtt tccatgtagt tgagcagttt tgagtgagtt tcttaatcct gagttctagt  20400
ttgattccac tgtggtctga gagacagttt gttataattt gtattctttt acattttctg  20460
aggagagctt tatttccaac tatgtggtca attttggaat aagtgcagtg tggtgctaag  20520
aagaacgtat gttctgttga tttggggtgg agagttctgt agatgtgtat taggtccgct  20580
tggtgcagag ctgagttgaa ttcctggata tccttgttaa ctttctgtct cgttggtctg  20640
tctaatgttg acagtggggt gttaaagtct cccattattg ttgtgtggga gtctgagtct  20700
ctttgtaggt cactcagggc ttgctttatg aatctgggtg ctcctgtatt ggttgcatat  20760
atatttagga tagttagctc ttcttgttga attgatccct ttaccattat gtaatggcct  20820
tctttgtctc ttttgatctt tgttggttta aagtctgttt taccagagac taggattgaa  20880
acccctgcct ttttttgttt tccatttgct tggtagatct tcctccatcc ctttattttg  20940
agcctatgtg tgactctgca cgtgagatgg gtttcctgaa tacagcacac tgatgggtct  21000
tgactcttta tccaatttgc cagtccgtgt cttttaattg gagcatttag cccatttaca  21060
tttaaggtta atattgttat gtgtgaattt gatcctgtca ttctctcaac atttgcttgt  21120
ctgtaaagga ttttatttct ccttcactta tgaagcttag tttggctgga tatgaaattc  21180
tgggttgaaa attcttttct ttaagaatgt tgaatattgg cctccactct cttctggcgt  21240
gtagagtttc tgccgagaga tcagctgttg gtctgatggg cttccctttg tgggtaacct  21300
gacctttctc tctagctgcc attaacattt tttccttcat ttcaactttg gtgaatctga  21360
caattatgtg tcttggagtt gctcttttcg aggagtatct ttgtggcatt ctctgtgttt  21420
cctgaatttg aatgttggcc tgccttgcta gattggggaa gttctcctgg ataatatcct  21480
gcagagtgtt ttccaacttg gttccattct tcccgtcact ttcaggtaca ccaatcagac  21540
gtagatttgg tcttttcaca tagtcccata tttcttggag gctttgttcg tttcttttta  21600
ttcttttttc tctaaacttc tcttcccgct tcatttcatt gatttgatct tccatcactg  21660
ataccctttc ttccagttga tcgaatcggc tactgaggct tgtgcatccg tcacgtagtt  21720
ctcgtgcctt ggttttcagc tccatcaggt cctttaagga cttctctgca ttagttattc  21780
tagttagccg ttcgtcgaat ttttttcaag gtttttaact tctttgccat gggttcgaac  21840
ttcctccttt agcttggata gtttgattgt ctgaagtctt cttctctcag ctcgtcaaag  21900
tcattctctg tccagctttg ttccgttgct ggtgaggagc tgcattcctt tggaggagga  21960
gaggtgctct gatttttaga attttcagta tttttgctct gtttcttccc catctttgtg  22020
gttttgtcta cctttggtct ttgatgatgg tgatgtacag atgggttttt ggtgtggatg  22080
tcctttctgt ttgttagttt tccttctaac agtcaggacc ctcagctgca ggtctattgg  22140
agtttgctgg aggtccactc cagaccatgt ttgcctgggt atcagcagcg gaggctgcag  22200
aacaacgaat attggtgaac agcagatgtt gctgcctgat cgttcctctg gaagttttgt  22260
ctcagagggg tacccggcca tgtgaggtgt cagtctgccc ctactggggg gtgcctccca  22320
gttaggctat tcgggggtca gggacccact tgaggaggca gtctgtctgt tctcagatct  22380
caagctgtgt gctgggagaa ccactgctct cttccaagct gtcagacagg gacatttaag  22440
tctgcagagg tttctgctgc cttttgttcg gctatgccct gcctgcagag gtggagtcta  22500
```

```
cagaggaagg caggcctcct tgagctgcag tgggctccac ccagttcgag cttcccagct  22560
gcttttttta cctgctcaag cctccgcaat ggcgggcacc cctcccccag cctcgctgcc  22620
accttgcagt ttgatctcag actgctgtgc tagcaatgag cgaggctcca tgggcatagg  22680
acccgctgag ccaggcgcgg gatatagtct cctggtgtgc tgtttgctaa gaccatcgga  22740
aaagcgcagt attagggtgg gagtgaccca attttccagg tgctgtctgt caccccttc  22800
cttggctagg aaagggaatt ccctgacccc ttgtgcttcc tgggtgaggc gatgcctcgc  22860
cctgctttgg ctcatgctcg gtgcgctgca cccactgtcc tgcacccact gtctgacaat  22920
ccccagtgag atgaacccag tacctcagtt ggaaatgcag aaatcacccg ttttctgcgt  22980
cgctcaagct gggagctgta gactggagct gttcctattt ggccatcttg gaaccgcccg  23040
attgtgattt aaaatgagaa cgagatggtc cctttggttc ctggtccctg taactgttgc  23100
aattgaaggg gcataagctt attagccttt tgaggttttt tttgctctag agtcttctca  23160
aaatgcttag ctaggttggg cacgatggct cacgcctgta atcccagcac tttggaaggc  23220
caaggtggga ggatcacgag gtcaggagat caagaccatc ctggctaaga tggtgaaatc  23280
ccatctctac taaaaataca cagattagct gggcatggtg gcacacgcct gtagtcgcag  23340
ctactcggga ggctgaggca agagaattgc ttgaacctgg gaggcagagg ttgcagtgag  23400
ccgagattgc gccactacac tctagcctgg gtgacagagc aagactccac ctcaaaaaaa  23460
aaaaaaaaaa aaaaaaaagt tcagctaagg ccaccaattc agtcacatct ctaacttccc  23520
attgcaactt atgtttttta gttaaactgc taagttcagg atggagtcca tttataagta  23580
aagcagttaa tgctgtttca gcccctgcag ggaatactcc ttgctgtact ttgagcccag  23640
gatgtttcac aaatatttct aagcgacttc tgtaatctga aactggttca tcttttcttt  23700
tcttttttt ttgcttacaa gattgtatga tggaccaatt ttttgtggaa aaattttagg  23760
aactgaatgt taaaaggttt tcagcgattt ttctagctat ttttggtcct tcttgtgagg  23820
agctcttaga gggcccttta aaatgtcctc ctcaggtttg tcccattctg ctgctgccat  23880
ccatttctga gcttcaccag cccccagtat catatgaata aattggtaaa ttcatgaagt  23940
cctggatcgt aagctcctat taggattcta aattcctcag taaatttttg agacttttcc  24000
cttggaccag ggaagtcctt cacaatgggg ctaagctcag ttttagacca tggagtgaaa  24060
gtagttacag caggcaggcc tggctgatat aaggtctcac tttgtaagac atctgtctaa  24120
cttccttttt tttttttttt ttttttaaa tcatcttcag ggtgaaagtg taatttaaca  24180
aaaagtttag tggactcaga gtatgtaggt agagatggac aaagaaggaa cagtccgagt  24240
tagatcagtc aaagtacagt cctctttctt catgtccttg gtctgttgct taagcttttc  24300
atttggtttt tgcaaagaat cttttaagga ggcacttttt gattcactta gtcttttgga  24360
ggcctttgcg tatccatgag acaatacatc ccactgtatt tgtgggggct ttgatcccct  24420
ttttctaata tgccttgcaa acaattttat ccaaattaaa acttctccat tgtggccatt  24480
ttaattctaa gttttcttta gtgaggttaa cccattttac tgaaaatgca catgttctgg  24540
gcccataatt tttatacgta aaattagctg gagtccctga agatggagtc ccagactcct  24600
tggattgaga tgatcccatt attaaataag gtacttatca gaggtctgag gcctctaact  24660
gaatccaatc cagttaatta tcaaatccaa tttgatcttg gatccagtcc aggctaagta  24720
ttgcttgagt aaactcggag agctcaaaac acaagttagt ggagctcgga atctgagaga  24780
aaactcaccc atgacctcca gttacaatca agagaccagt gagagcaacg gcctcagtgg  24840
gtacctcacc aggtcacctg gtgttccagg gggttgccag agtttttctt caaatcccac  24900
ttctgacacc agatctgtta aaagaaaact tcagacaagt taaatttgat ggagtttaat  24960
taagcaagga aaataaacac tttgcaaatc aggcagcctc cagaattgaa tgcagtttga  25020
acacttagca gtctattagt gcttgaagta tggccactgg gattggccaa cactcagcta  25080
ttattacaga tgcatactac tcaggttttc cattttgtct gcctattgtg ctaggttatg  25140
gtttgtccac aagaacacaa atatagaagt atggagtcct tctcaggcca tatttagttt  25200
gctttaacaa tacttaaaaa aaaaatttgt aaaataagga tacttaacct tactcggtgt  25260
ttctgagagt taacatttat atagttatgc tgtagtgaaa acagctagcg taatgtctgg  25320
tatgtatagg aacacaagag ataccgcttt tcccatatcc ccataccatt cttcacagca  25380
ttgctcctgt cttccttgat tcctcctcct ccttctttgt tttttttttg tttgtttgtt  25440
tgtttttttt tggaggtgga gtctcactct gttgcccagg ctggagtgca gtggtgtgat  25500
ctcagcttac tgcaacctct gcctcctggg ttcaagtgat tctcctgcct cagcctcctg  25560
aatagctggg attacaggca cacaccaaca cactcagcta atttttgtat ttttagtagg  25620
gatggggttt caccatgttg gccaggctgg tcttgaactc ctgacctcag gtgattcacc  25680
cacctcagcc tcccaaagtg ctgggattac aggtgtgagc caccacaccc tgcctccttc  25740
ttaagaagtt tccagtccct tgtaattaaa ggaattaata ttttttaact acttagaatc  25800
agactggccc tgattattag taagcaacta atagtaagca agcaactatg tatgcaacta  25860
tgagtgtatg ttaagatatg gttgttggta acctttcatt ctcttcagga agaagaagag  25920
ggtggagctc tacagtcaat gtgtacattt aaattctgtt ccctttcgag ctttttttgct  25980
actttcattc ttctggggat ccaggtgctt gagttgggat tgattaactt ccttaatttc  26040
cacccctgtg ctgtcaggat cgggagacat agatgaaggt gttctaaact gctagaaatt  26100
ttgttttttga aagcaaaagt ttgcatgcat ttttgtttc aactttttact tacagtgaat  26160
agtagttaat aaaataagtc cctgcctttt ctctctttgg tttcaattcc tgagaccagg  26220
atcatagccc acatattaga gtggagtccc actgctttgg tttgaatcat gcctttgttt  26280
cttatgtcag tgtgactttg ggcaagttat ttaagtcttt gcaccacatt ttcctcatct  26340
gtaaaatgag gataatacta gtactttcta catgggattg ttagcaggat taaatgagat  26400
agcacatact gtaaccatgt ctggcacata gtcaatggtt agtaaatgtg aactattgtg  26460
tgacattgtg gttagtcacg tatggggctg tgtttccttt agtatattgc tcttttaatg  26520
tcatttcctt tgtactgtta ccctctctga tctttcttcc atattcattt ttctttcagt  26580
gaggtctgcc agtctttagt gaaacacagc tctggaataa aaggaagttt accactacaa  26640
aaactacatc tggtttcacg aagcatttat cattcacatc atcctacctt aaagcttcaa  26700
cgaccccaat taaggacatc ctttcagcag ttctcttctc tgacaaacct tcctttacgt  26760
aaactgaaat tctctccaat taaatatggc taccagcctc gcaggaattt ttggccagca  26820
agattagcta cgagactctt aaaacttcgc tatctcatac taggatcggc tgttgggggt  26880
ggctacacag ccaaaaaggt gaacttgaca ttcctcctgg ttttccaatt attatatcat  26940
gattaagttt ctatagcata aatcattttt gtgtagtgga atacaattgg atgtttaaac  27000
atttattttg tgtctctacc atggactaga ttgttttaat gatgctaata ggaagatgcc  27060
tttagaatct tagttataat tacaggaaat taaaatggcc tagtggaagg agcacagggc  27120
tgggaatagg aacacctagg tttgattttg agcttagaca tttagtagca cagatgtgaa  27180
agtcaggtgg cattctcaca caagcacttc ttggcaggtc tgggaccaga ggcaaggcgt  27240
```

```
cctgtctccc agtctgtctt ccttctaccc cacagtaata tttagggcaa aattatgaaa  27300
cctgtttgaa ataggagtat attctgaatt tttacatttt ccatatttaa cagaggagtg  27360
ttaacttgtt ttatatgctt gtttgctgag accacttaat tttgtttctt aaaagttttg  27420
aacataatac attattctta gtagattaat gtgttttaat taaataattt ttctttacat  27480
gtttatttgg catgcagagc atctgattga cacactttct tgtcttttag actttgatc  27540
agtggaaaga tatgataccg gaccttagtg aatataaatg gattgtgcct gacattgtgt  27600
gggaaattga tgagtatatc gattttggtt tgtatcatga acattaaaat acttttttg  27660
gtcatctcga ggaaagagaa atagtttatt gagatagttt cttaacttat gaacctaata  27720
tatcacggtt ttattttaat gatataagta atagaatatc aatgaaaaaa tctgtataaa  27780
agaaataccc agtagcccat aattttacca cagctgccac taactgtttg gagcattttc  27840
ttttaattat acttactata tgtggttagt atctttttaa cttatcgatt gagacaggat  27900
cttgctctgt cactcaggct gaagtgcggt cttggaatca taactcactg cagccctgaa  27960
ctggctaaag tagtccttcc gactctgcct cccaagtagc cgggactaca tgtgtgtgcc  28020
accatgcccg actgattttt taatttcttg tagagatgaa gtctcactat gttgcccagg  28080
ctagtctcaa attccttagc tcaaacctct cacctcagcc tctcaaagca ctgagattac  28140
aagtgtgagc cactatgcct ggcttgagtt tttttctttt aattttttc ttttcatgaa  28200
tactaccaca gaatagtatt ttagttccct ttttaaaaat tatgtaatca tggtgaatat  28260
tcactttggt attttgtctt ttgctaccta acatattttg tcagcatttc catgctgcca  28320
agtagccttt ctattaataa tatcattttc tgcattatgt aatgttgccc agagcatatt  28380
tattgtgacc cacctagcta gctccttttg attggatacc ttggttatct ctaccttttg  28440
tagccaagtt ctttaaaagt ctgttagtat ccagggtaat ttcttttctt agttggccac  28500
tgccctccct ttttcaatag gtggatgaga aaaaagtata ttggatcgct atgattgcca  28560
gtaattcatg gtgatcttta agaaatatat tttcatcaaa tttttttaaa acctttgtca  28620
gatttcttag tttaggtgta tgtggaggtg gaattaatct atacttgcac ttattcacag  28680
aatttataaa gataaaactg ttctatgttg acgaatccat ttgcaaaaaa agcacacttt  28740
caaattgttc ttctaatatt aatgaggaga gctttcaaat tgatgtattt gccagtacca  28800
cagcgtagtg gctgagagcc tgtattctgg agctggactg cctgggctgg aacccgggct  28860
cctccacttc cttgctgtgt accttagttt ctcatctgta aatggtgttg ataatagtag  28920
ctgttttgta gggttgtcat gaggattaaa caagttaata ctttagccct ttataagaat  28980
agtatctgac atattttctt agtttcatac tctatatgtt ttgatctttt ccagagaaaa  29040
ttagaaaagc ccttcctagt tcagaagacc ttgtaaagtt agcaccagac tttgacaaga  29100
ttgttgaaag ccttagctta ttgaaggact tttttacctc aggtaaggaa gaagctgttt  29160
gatctaattt aaaaatttaa gaaccatgga ggaaaaatac atggattatt tgtttattcc  29220
catttttttta aaattaaaat atttagtacc aatgaaaaac aggacatttt ttaaaaagat  29280
aaacacaaag ttttgttaca caatggtttt aatctttgtg tagcccagta aaatgacagt  29340
tcctaagcac ttaaacatac ttggctttta tgtgagggga aaaatgtatc acttgttctt  29400
gacaagtaga tgagacttcc tatgtatttg cttttcataa gtggttggac caatttggtg  29460
gttttaaaac aaatttaagt atgatagacc ataatgagta gcatttatta agtttaatcc  29520
tggcatattt gcccaattat tgccctatcg taatatgaaa tctgagatct cagacatctt  29580
tgtttgctca tttctgttaa attttacatt tctatttccc cttttgctga tttttcacag  29640
gtcacaaatt ggttagtgaa gtcataggag cttctgacct acttctcttg ttaggtgtgt  29700
aaacagacat ttttgctgac cttaacatgc cttttaaatg cttctaataa actagttgca  29760
aataaaattg cagaccaaat ttataatgct gcttatgctg aattttaaaa ccccagaact  29820
atattaggca aactcattat cctttaggtg gaaataataa aataattatt ttgtgataac  29880
actaaaattc ttaaatatgt atgtgtatta taagattaaa gctattaaaa gaaaatttac  29940
ttagcaaaaa tattttcttg aaatagatct aattgttttt gataattgaa atgaaaagta  30000
attttagttt gtctcatctg ccctgtcatg gttgacattt aaatttgttt tccggccggg  30060
cgcggtggct catgcctgta atcccagcat tttgggaggc caaggcaggc ggatcatgag  30120
gtcaggagat cgagaccatc ctggctaaca cggtgaaacc ccatctctac taaaaataca  30180
aaaaatttgc cgggcgtggt ggcacacgcc tgtagtccta gctactcggg aggctgaggc  30240
aggagaattg cttgaaccca ggaggcggag gttgcagtga gccaagatcg cgccactgca  30300
ctccagcctg ggcgacagag ggagactctg ccccccaccc ccaaaaaaaa aaagaaaaga  30360
aaaaaaaatt gttttcctgc tatacatggt ctgtaatgcc agtggtatgt ggctgaactg  30420
taagtactct catgtaaaat aatccttacc aaagattgtc ttattttttt attgtaattt  30480
tcagttatat atttttaatt gttaggttaa acatatgctg cgattgctat agttagtttt  30540
ttttttattt tctgcacagg ttatcagtca tgttccttaa aataagaata aaggcgattt  30600
gattctttga atctgagttg ctctaaaaat ccattcacct tttcattgac tcgatgtaat  30660
ttgaaattca gcttaggctg ttgacatcac tggagaatgt aaagggttgc atatttatct  30720
ttaaggttct ccggaagaaa cggcgtttag agcaacagat cgtggatctg aaagtgacaa  30780
gcattttaga aaggtaagtg taaaagagaa ttgttcatgt aggtagtctt gaaagatttt  30840
ttaaagtttt tacttctttg gaagatttta aaatgataac atctgagaag caaatacaaa  30900
aacatccaag tagagatatc gttactaatc ttagtgcaaa gtacaaggta ttacgtggca  30960
gttctggaaa tataattgag aagcccattt ctttcacata tgtccagtga agcattagtt  31020
tcgagggttg tccccaagaa agagttgtgt tgttaagtgt gtggggggag aaaggctcgt  31080
ttagacaagg caagcggact tcttttcttt ccctaggacc tctcatactg taatatactc  31140
atgcgcattg tgaatttcca aggagtcaaa gcatacagtg ttttcccaaa ttatttatca  31200
acagaaccct tttgctcatg gaacgtcgta tagggactag atttcacttt ggggaaacta  31260
gaaagggaat aggaattggg ttattaggaa ataaatcaat tccctgatat tgatagttaa  31320
caaagttatg tatggggtta tttatggtat gttattttca acacatattc attaacaaaa  31380
tccatatgaa agttatagga gaattgctga ggtagaataa catactttgt ttgtatttat  31440
aatactcata tatttacctg acgttttctg agtcttcact tttttcattc ttttggaatt  31500
ggtaaaataa ctgattcctt gaaagttttt ttctaaataa tacctagata atagatttat  31560
agaaaaaata ttgtatgaat gttttaacat tcatgtaata tggaacatgt aatttttata  31620
ctggaggtta ttatagtttt aatacatcaa agaaataatg tttattttgg aagcagaaag  31680
aagaaataat ttctatgaat aggttttcat ctctttcctt gttcttcaac tttgaacttt  31740
ttatattcca aattttaatt atatttcaaa agatttttttt cttttgcctt ttaattttat  31800
cttttggaga aaaatgtatg tcaaaatgta tgtacgtgta tttgtctttt gatttgatct  31860
tttttgaccc tcttttgcat tgacattatt ttaaccaaag gacactcttg attgttcatg  31920
ctactggggg aaaaaaaaat aagtagaaat tagcctaata gttgtggctt attttgagtg  31980
```

```
aaggccttag cccttaaggc aattaaattt actgtggaga gaagagctaa tctaatgggg  32040
agaaggagcc tttgttacag gtgtggtagt gtggttcttt gagtgacaag atttctgttt  32100
gccagattgg ttaggagaag tctgtgtgtc tgctttctct cttatggcct aggatcactg  32160
tggtgaatga aaaacctgtc tcagggcctg actcagataa ttcccttaaa acccggctaa  32220
ggtcatagat gaataatcag taattgaaca gaagctctgc aatagaaaag aagccagata  32280
attatttttg gaaatttaat tatatttaca gattttattt tatacagtag acatggaatt  32340
aaatttatta cattatgttc taatttactc tttgcttgtt ttgatttgct tgtttgacaa  32400
tacatgtcct tgtaaactat ttccttttaa ctttttctca atttatggtg cttattttcc  32460
ccattaaaga cttaccaatt tttttttaa ctatttgtta cacatactga atctagagtt  32520
gtaattaagc tactttcatt actggttaag tcaaattata gcaaatgcta ctataaaaat  32580
ttactatcca aaaatgtgtc tcaagcccca actgatggtt tcaaattctg ttattaataa  32640
tatgcagcat tgtgtttgca aagcttggct gttacttgtg atgcttgaga atgatgagtc  32700
actcagctaa actgagtgat tttgagactt gtgtacaaat tgatggttga atgtaagcat  32760
gcaaagagag accttagctt agcagtaccc tttttgaaat cactctgaca tcaagtttga  32820
aaatgtgggc aataatcaga ggtggtaagg tggccaggct ttagctgaat actttttttaa  32880
ctggttcagt ctgagggctg aaagccccag atttaaacag tatttagaat ttgaagcagt  32940
caagtattag tttaatggtt gtcaggtttg taacaaagtt tctggctaga cttctactag  33000
aaatgtaaaa gtgcatgtga atcagctttt taaaaaagta ataataattg aaaaacattt  33060
ctacaactag aactaaagaa aagatttgtc ctttctaata ggaaaacaca tctggagaag  33120
tgctggcaac tagcagaaca gttaggacca ttcagaatca actgaagtga aagtgacggg  33180
gagctgaggg gaacacagat agtttgactt cagtcagaca gaataaacat gatgaaccga  33240
taacctgtga ttcccagcct ggggttacta ctggagtttt aggtgtcctg gaaagttata  33300
ataccggtct tcaaaaagtc tacagaaagc atagatttcc acataatgct gcacaggcta  33360
acgaattaat caagtttctt tggtttggcc tggatttata tccattcagt ttgtggacac  33420
tactgaatta tttatgtcat gttgatcaaa agttctgata tgatttgatt aatgaaacat  33480
tgaaaaaaat agtaaaacca accattttta accttacact actatcttga ggtatgattg  33540
acatacatta aaaccacctc ttaataaatg cttcttgtta atcaaaaatt tgaaaacgta  33600
tgtccactgg aggaaaaaag acatagccct ggatgtgaac tgaatattac tgagactcgg  33660
agaccttcag aactacctga agatgaatcg aagtgctgcc tactttagag aattggacta  33720
atttaatttg ggagtcagca gattgctgta tatcagtcat catatatacc ggtgacaaga  33780
ccacttagtt cattcccttt tttagattct gtaagattat tgtgttccag tgaaattgat  33840
ttgcaaaatg agacatttta ttttctgtgc ttttgttcta tcatgtttct gattggtcat  33900
aagcatctca cagaagtaag aaatatggcg attcagaagg caacaagcac atttataatt  33960
tatagaaaat atttgaagga ctttttcatg gcccaaatca tgaaaagtag tagtattgtt  34020
ttaagtataa ttattaaatt ataatacatt aatgttcttt cttgcaacat attactctca  34080
ttcttttttt tttttttttt ttttgagacg gagtctcact ctgtcacccg gctggagtac  34140
agtggtacga tcttggccca ctgcaacctc tgcctcccgg gttcaagcga ttctcctgcc  34200
tcagcctccc aagtagctgg gattacaggc tcctgccacc acgcctagct aatttttgta  34260
tttttagtag agacagggtt tcaccaggtt ggccaggatg gtcttgatct cttgacctca  34320
tggtccgtcc acctctgcct cccaaagtgt tgggattaca ggcgtgagcc acccagcagt  34380
ctgattctta attttatagt ttatgttgta cctccccagc tgaagtatct cttttctttt  34440
ttcccgcgtg tttagtgttc actcatcttt atagcatagc tcaattgtca cttcatgaag  34500
ccttccataa cctttgtagc tccattaatt atattcttct gagtgtttaa aacacttgcc  34560
atatgaaaca ctatttactt tggcttacat tcttactatc taatcggcca tttctgttac  34620
taaatctttt tctcagagca cctgggatag tcttgtgtct tagtaaaatc agttgattga  34680
tttaactcgg tagagtagag gctgattaaa gtaaataaat ctggttgatg ccaacaaaat  34740
tttggtcccc tcaatttttt gctctcatta cctgcaaatt ctccctggcc ttcatatttg  34800
gcaaccattg aggagaacaa ggctgtaaaa gtagttcatg tacttgatat tctgaattgg  34860
aattaagcag agttgcttaa gtaggacttg cttttctggg atttcttatg caacaaataa  34920
tgtagtaact ggaaatccaa gttcaagaca ctggcagatt cgatgtcttt tgaggaccct  34980
tggcttcata gatgatgcct tctccctata tccttacata gcaaaagggg ccaggcagct  35040
ctggcctttt tttgtaaggc caataactcc agaaacctca tgacctcatc acctcccaaa  35100
ggccccacct ctcaatacta tcacattgtg aggctaggtt tcaacatatg aattgtggga  35160
gacaaaaatt cagaccatag tataatattt caagattact taaactcttc tctaccaaac  35220
tcattaactt ttaggttagc acagtatttt cattgatatt ttggtttctg gagttattac  35280
taattttctt gatctgatgt tataattaaa aaaaaacagg actttgtacg tgaaatgaga  35340
ctgagataag gaagctgatt cagagatgga gatttaaaaa aagagagatg agagattgag  35400
atctgcagtg tcaaactgac aatagccagg agtcaggaga tattaagaga ctatatcatc  35460
tgtgattgtt aatgattatt tattgttatt tataaatact actgtatttt atatattata  35520
tacattgttt taaaaattat ttttgtacca tttcttgaaa gaaaaatgtc taagcttggg  35580
aaaatattta ttgaaaaatg tggtttgtac atctgaggag tgtatcttgc acagtaggtg  35640
catagatttc ttcctcttcc tgttccacat ggccttagct tagaggctgt gtggccatca  35700
cttggtattt agggtaagac tggtgcacaa aatcaaagac aggtaacctt ggtataagtg  35760
tagtatcatg taaatagctt ttctatgtct aattcttgtt ttcttcctac tttttcagga  35820
ggtcaatttc agttcatttc aactatcttt acataatagt gctttagtaa caggcatgga  35880
aggaaagaga catgtcccta gagtgttttc ttgaaatcta atagatgatt ggagtattta  35940
ccatgcagtt gtgtatatac ataagcagtg aattcgagag gaatttttaa gctgtaaaaa  36000
aaagcattgt gtgccttata gacgcgagtg agaaatgtgg aatatggctg atccaaaggg  36060
aatgagttat ctcaattgat taatcacagt cagttacaga ttgaactctt tgttctactc  36120
tttgcccccct tctcactatt gctcttgact agtcttaaga aagaaatgtg gaatattttc  36180
tcacggcttt gggattttat aaattagaat actagtggta tgtaaataca gcaggtacac  36240
tactgtataa accaacatag gaagccttct ttaaagggaa ttgtttgaga aatttgaaca  36300
cttggataat ttgaataaag gattgtgata aatgatcaaa tgaaagaaaa taaatcaggt  36360
tactcttctt tctgcttgat aaagcaataa tttttttttaa aggtaaaaat tatgagaatg  36420
atgaggatag tagttagcat tgtctttctt tgataggttt gttaatgatc ataaaactga  36480
tttatttaaa gacatgtctt tttataacta ttttatactg ttgtatctgg aaacaaatat  36540
tgaatttcat ttgtcatgtg gaagaaatca actagtttta acctttgatt tataataaat  36600
caaccacttt catttattgt ctaatactgg caatgaacac agcctaatgt atcaaaacta  36660
acagaataaa aattctccaa gttatatcca gactttaaga cactttctaa ttatataaaa  36720
```

taaaatattt tgggcagtca ttttttaact ctgaaactat ttaaaactcc taatttagaa 36780
tatcttaata aatacccatt ttcctctttt tatttttata acttggtaaa aattgagtcc 36840
attgttttcc cagaacgctg ttcttaaaca aatggttacc tccttcatta gaactttact 36900
tttttagga tttctaatta agaaaacatt aggcttgtaa cattgtcaaa tcttggtggt 36960
ctttcttcca cgttttttga ggtcgattat ctaagaggcc atcagttaat aaagctatgc 37020
aggaaatgac atcatgccac atgtgaatat cctgtattaa aaattgtatc aatatactat 37080
tttataatta tgaagtggaa tgaattttag aaatagaaaa ggtgattttt tgtgcatagg 37140
tccaaactgt gttttgtttt catttcagaa tttcataata actatattgt ctccatatct 37200
taattgtgtt tttttatagc acttttgttt agtaatttgt atatgcttgg ctgtattctc 37260
agaggctgtt tctatttaat gttgtcaaaa cagctcataa aaagtgaaaa ttcggtcaga 37320
ctagttattt gatattatat atgaaatcaa aacaacctga aacattatct tttaatttaa 37380
ataaagaacc ccaaatttta atcaaatgta tgcaaaggca catagaatat atgacttaat 37440
gtacaacctt tattaacttg atgatggaaa cctgttccta gggaccttta cttgaataaa 37500
tgaaatatca agaaaaaata ctaacttaag aataataatt taataagtaa gtaagctatt 37560
atgatcttca atcagtcctg agagaatcat ggttgagaat tagaaaattt agaccagtaa 37620
gatcaacact gttaaaaaaa aaaaaaaatc agtatttttt ctccatattt tttatatatc 37680
tggatcattt tatttagcac ttattattgc actttccttt tcacttttta aactatgctg 37740
ttttattttt ctgagacatc tgatttactg aggaggaaaa tggaaatgcg gtacagagcc 37800
caagggtatg acggctttaa atgagtttcc atttctgttt taagttaacc atccctccct 37860
agcttacatc tgttcctttg ttgcaccctt ggtttaacat tattctcctc cccaatttcc 37920
tcttctcctc attgtgaact cgtggcaggg tctgcttggt gagctcattc tcttacaaca 37980
acaaattcaa gagcatgaag aggaagcgcg cagagccgct ggccaatata gcacgagcta 38040
tgcccaacag aagcgcaagg tgatggatgg tttaaggggg ctaccgatac attcacacta 38100
atcagccatt tctgccaaga tcatgtcacc tcaatctgtt catggactcc aaatacaaga 38160
aattaatttg acaaagtgaa aatataaaag atgcatcata taaatatgta acttttctgg 38220
agtgggtagt ataggtaaag ccaaaagaaa caaattcaag cagaggaatt ttggtttctg 38280
aaaattaggt tgtctgtagg gtccctgtat ttatacttag aacaaaatta ggaatttctg 38340
tttatgtggt ccagttattg agtcacccta agtttgtagg catcttacct acctacttgc 38400
tccccaagtt tttatttcta aaatgaaaag cattgctgta gatgaccagt ttacactaaa 38460
gaataacatt tatttatttg ttttagctaa agtatatgga cagggaacat tcatattctt 38520
gtagaagaaa attattttga cttttgggca aaagcatgta gttcttatac actttgacaa 38580
actcattgcg tacatttttc acattaatca aagtcagcac aaataaattt tcaccttgga 38640
ccacggaggg tttgaacact ggaaatttga tataattctg gttgctaaag aacaagttct 38700
aataaaagct taagtgtata ccaatatgtg gctgttggtg caatcagcag gtccgtaaaa 38760
atatgatttt aatggttagg taatcccaca acggagatcc caaagttcat gtttggaaga 38820
gacttttggg tcaaagtgaa atcagtgtaa tgaatttaaa attatactct gagatcttga 38880
aatcagctaa ttatgttaca tcttattagc tcagaaaagt tttgaagtta tatacaaatg 38940
ctagtcagga aaaaagattc agtcatgtaa ttcttgtaca ttctactatt taaatcaacc 39000
aatattatag attatgattt agtgcagtaa ttctgctggc taaccttatc tcatttggtg 39060
gtggttagta cttcagagta ctcaccatag tttcatttat gttttcagca tcacttcctg 39120
gtttttctca attccatggc tgtggaatca attcatatgt atatttagct tcggtgagca 39180
aaaacatagc tagaaaaaga aaagaagtga gtttcctacc tggttaaatt aaagtcgatg 39240
tgttaagcca aggaggactt cttttgaatg gtactttaac aatccctgtt ctgtatactg 39300
tgaatatatc atttaaatag cctaataaat tggatgctta ggctgagcca cctatacttt 39360
agttttgtta tggaaagaag ggagaggagc aagtatgttc ttatatgtta cttagaaata 39420
agaatgtagc tgtagttaca cattgttctt aagttttttt cgtaagacaa cttgaaatga 39480
gtcccatagg cctgctattt aacattctaa gatatgactt aaggttaatg atgagctttt 39540
gaatctgaca attcaagaga tatccataat gaatactgat tcattttcta cattgctgaa 39600
agctaatgtt cattttaagc ctactttagt agcctttatt tgggcttaga gatgttattc 39660
ctctttctga tatttattgg gttatctgtt taaccctttt atatctccct ttcccgattt 39720
gtaaattaga gactggcaag actttttacc ctgagtagag caccaaacat ggcttgtttc 39780
tgcccacact gtagttacct tgaggggaag taaatgggac tttaaaagca atttatgctc 39840
ttttatagtg aaattatccc tcttactatc ccgaaagact gttaccttac aatatcctcc 39900
actcctttcc ccctgtagtt actatagaga tgacttttcg gttcttcact gccataatga 39960
tcaaaatcct aattcatgag atttttatca ttccaggcat gtgaggttta cttgatgcat 40020
aaaaccgcaa gtacttttg ttgtttttta attgtttttt ctctcttatc ttcttgaaag 40080
tctaagtaga tcatcatttt tgatgtctta ttagtagcaa ctaataaatt ttccctgtat 40140
cttctcagca aaagaactca agcagagaca gaagattaga actaccattg gtagttttgc 40200
ttcctatgga tatgttcaca tacatagaaa tttttacaat gaccttttta tatatgtatt 40260
tcagaatttc agaatggcct caatgcctta ataggaagaa atacttgaaa tttttaaatt 40320
agggcttggt tttgtgagga gctagtaaag gtttttctct ttcagcttta gcttgtttct 40380
gcggaggatt ccgctctttc tccatcagtt tcatagccct ggaattgtag aaaagctctg 40440
gtttcaagac cattgatatc catttctgtc agggtgagtt ttaaatttat ttcatgatgc 40500
aaacaatata ttgaacaaca ggacatgaac ttgttcttgt tgtaagtggc tgaattttat 40560
cagtaaagca catcaaaata aaatataccc caattgctag ttaagaccta gagtgacaga 40620
ttgaaaatag cttgtgttat tctcttaaga aaatatataa aaattatcat ctcatcaatc 40680
tttaatgttt gttttataaa tctaaatgtt tttatattgt ttcctaggaa atattaggtc 40740
taattttttta ctttaccacc agctgtcttt tattttactc ttttttgag acggagtttc 40800
gctcttgttg cttaggctag agtgcagtgg cactatctca gctcactgcg acctctgcct 40860
cccgggttca agcgattctc ctgcctcagt ctcccgagta gctgggatta caggcacatg 40920
ccactacacc aggctaattt tgtattttta gtagagacgg ggtttcttca tgttggtcag 40980
gctggtctcg aactcccgac ctcaggtgat ccgcctgcct cggcctccca gagtgctggg 41040
attacaggca tgagccaccg cacctggcca gctgtctttt aatataacat tatgattaat 41100
tgtgatgttc cattaaacta agcggagagg aaacatgctg gtaaaccatg tgtgagttat 41160
tcattgtacc agaaaggcaa atgatacatt ttatcctaaa attcaaattt ataaacatct 41220
taacacttgt gatcattaaa tactactaat ctagcatata aattatattt gtaggcgggg 41280
cacggtggct cacgcctgta atcccagcac tttgggaggc tgaggtgggc agatcacgag 41340
gtcaggagat cgagaccatc ctggctaaca tggtgaaacc ccatctctac taaaaataca 41400
aaaaaaatta gctgggtgtg ctggcgggca cctgtagtcc cagctacttg ggaggctgag 41460

```
gcaggagaat ggcgtgaccc caggaggcag agcttccagc ctgggcgact ccgtctcaaa  41520
aaaaaagaaa aaagaaatta tatttgtaat attctactaa ccttatatca ttttaacttt  41580
ttatataact ttttatttt accaaattaa gttaaccttt tatagccctt ggcttatact  41640
aaacatccta actttttgt ttaattgtat tagtttttaa gttattgccc cagatgtcaa  41700
gtaatgttgg attttctata ataatttagg atatattgca tgaagtcagt tagtatttac  41760
atttaaaact aaaacaattt atactaatac agtttataca tttcatacta atttagctac  41820
agttggataa atatttaatg gaacaaagta aatcaaagta ccttttcaaa tgaattggaa  41880
attaaatcca cataacaatt ttttatgacc acactattac agtgtgatgg catgccaaat  41940
gatcataatg tggaattatg tatttcttca ttggctttca agattctgtt ctttagtttg  42000
tgggctcctc tccaacttgc ttgtctcctc acagtttagg cgactgttta taattcttgt  42060
ccatcctgca taaacacaca cagtcaaaat gaaaaaaagc ttctatcagc agatctgtgc  42120
ttgctgtaca gaaatgggaa aacaattgaa gtttgcatta tcttttttct aattaccaga  42180
tcgtttttgg agctatttag gcatacgctt ttaaggaaaa aagaaaaaaa gagtgtacct  42240
tttgtttcta acaaaggttg ttatctatat tattgaaata aaaaattggg gatagttatg  42300
acaaagtatt tagaaatagg aattaaaatc ttaaaataac ttttcatagc atggacaaga  42360
cttattaatg tctacctcaa taagcaaatc atttaaaaat ttttcatgta tatttgctgc  42420
catgatgtgt tgtgattgct taaataacca atgaatgaag atcaacaagg atttaaatga  42480
agaagaatat ggatttaact attttctcct gtgaaataag ttcatattta caagttttga  42540
ttttcagaaa ttagacaatt atttttaaag gctgggatga caacttctgc ctcttaccaa  42600
gaagtcaaag cacagttatg tgaattcatc ataaatcaca tcatttttat tatattttgt  42660
atttataatt gtattgtgac tactttaaaa cctgttataa aataaaattg tttttttaata  42720
ttttatttta gaattattag cattaataac aatttgaagt agtttacaca atacctgtga  42780
gttttatttt tgttttatat tgaaattaat tttagttgct ttacttggct tcattgctat  42840
ggatgcattc tctgtgttac gagttagcag atctttcctt ggaactgaat ttaaaagcaa  42900
gcatttggct ccacttaaat ctctgaaaat gcaacttgtt ctttgcattt attacataat  42960
tcgctactta tggtacagaa atggatacaa tacaaaaata tttccttata agatacactg  43020
tgaccaatga gctttttaaa tagctgtaat cagtaacatg tatttgactt ttcaaaacac  43080
atttctggag ggatatcagt gctttatttc cccaaatatc tgaatcccta tgctttagta  43140
caaaacaact tctgaagaat ttagtaacca tatgtgttga tctcttgttt ttctaactag  43200
tctttcataa gaaatgacta gaatagcaac agggaaatga ttgcctttta aggtttttgt  43260
ttctcaatat aaaattttgg tgaaccattt ttattgataa atacaggtat ttttactttc  43320
ttaaatcact tgatttaaaa ttactttgat taaatatgca tataaagtca gttgttttta  43380
actctcaata cttatcaaaa aaatttaact tgctgtacat tctgtataaa cctaattcta  43440
ttcaactaaa attattttaa acatttaggt gtcagacaaa gagaaaattg accaacttca  43500
ggaagaactt ctgcacactc aggtaatcat gatgactaag aaaaactagg gacttttaaa  43560
aattatattc gaatgtaact ttggtgatat ggacatttat tttttcaaca gagcaaaatt  43620
tggaaggtgt aatgatagaa ccttattatt atcgatagat gcaaaagcta attgagaaat  43680
aaggaataaa gacagaacta gataagtatg gagttaactc atttatatgt aaaaacctat  43740
tttgagtgaa tcttatgccc aaaagggaga aagtggcttg tccttatata aacttatgct  43800
tgcattttta cattgataag ctaatacagt taaagaaatt cgagttgagt ctaccacatc  43860
gttctagtgg gctctcagga acctttactt tgcttcgcaa gtctgaaagc agtcagacaa  43920
tgcttatcta aagctctttc tggcactact tagaaaagct attttcttat agttggtgat  43980
aaaattatta ctttaaggac ctattttgtg caatgtaatg agtgggtaac attctagtac  44040
aaaattaccc tatcacagcc aggcacggtg gctcacgcct gtaatcccaa cactttggga  44100
ggccgaagtg ggcggatcac aaggtcagga gatcgagacc atcctggcta acacagtgaa  44160
acccccttctc tactaaaaat acaaaaaatt agctgggcgt ggtggcaggc gcctgtagtc  44220
ccagctactc aggaggctga ggcaggagaa tggtgtgaac ccaggaggcg gagcttgcag  44280
tgagcccaga tggcgccact gcactccagc ctgggcgaca gagcaagact ccatctcaaa  44340
aagaaaaaaa agttacccta ttactcaatc atcagttttt ctatataggt gacactgaca  44400
tgcattaatt aacttatttt ttaaagttca aagagttact atcagctggg catggtgggt  44460
catgcctgta atcccagcac tttgagaggc tgaggcagga ggatcgcttg agcccaggag  44520
tttgagacca gcttgggcaa cccggagaaa ccccgtatct ataaaaattt ttttaaaaat  44580
tagccaggtg tggtggttgt gcctgtagtc ccagcaactg ggaggctaag gcgggaggat  44640
cacttgagcc ccaggaggtc aaggctactg taagccatga ttgctccctg gccaatagag  44700
caagaccctg tctggaagaa aacaaaaaag aataagaaaa agagttaatc ttggatctct  44760
tttttgtgaa aaagtgaaac gactacaagt tgaatatctc ttatctgagg tgcttggggc  44820
cagcgtgttt tggatttcag atttttgaat tagggataat cagtcagtag tatgttttga  44880
gtcacaggtt tctttggtat ctatttattg agtctcaaac ctcactatac gctagactca  44940
cctgtgctct gagtggcact atatctatgt ttttaagggt tcctagccag gtgattccaa  45000
tctgcaacca ggggtaagag tcattggtca caaagcatag cctctggagc acattagaaa  45060
tgcacattct tgaccccatc ccataccttc tgaagaatca gaaactctgg gatgaaactc  45120
agcaatctgt ttttaaatgc cctcaagata attctgatgc attctaaagt ttgagaatta  45180
ttgttctaga gctttgagag acagctcaat agcacatctc ttcaggatgg ctacaaattg  45240
gcatctgtac caaaatgttt ccatccccag aaaatgtaga ccccaaaatt gattttgtgt  45300
ttacaaagaa atgagccagt ggaaattcta ccctcttata tgccttgata caaacccttc  45360
aatttgtgca attgtaattg tcagtcacta ggcactgata gactgtatta tggagaattc  45420
actgggttat ctatatcaat gatgtccaat agaaatatac aagccacctg tgtaattttt  45480
aatttttaca ttaaaaaggg gtaaaaagaa acgtggaatt agttttaata atatatttaa  45540
cccagtctat cccagatagt atcatttcaa catgtgatca gtataaaaaa tatgaatgag  45600
gtattttaca cttacagcac aacctcactt caggccagcc acatttcagg tgcttgataa  45660
ctacatgtgg ctagtagctg ccgtgttaaa caacacagat ctaatcctta gatactacca  45720
gaattttgtt aaatatacta ttactagata taaatgagtg agtttatgta aaaatatgtt  45780
tatagtagag tctagccagt agttctgcct gtctcatact atgtaggtgt tcaattatgt  45840
atgcgttctt ttaatttggc ttgagttgga cttgctgtaa ggatagaacc atgatttcct  45900
gttaattact ttgttcttga aagattccaa taagctaaaa aaattgtaag gaatattttt  45960
tattataaaa ggcatattat aagttggaca taaacattct gctggttgta agaatgggtt  46020
atttttaata gttttctctg tgttgttaat gtttagagaa gaaataaaag ctgggaagac  46080
aaattagaaa ggatcaaatt tatttgagac ggaaaatgtg tagacaagca actacttaca  46140
aaaaaaaaac ctgtttagac atattagtct tctttaaaaa tctgttttta tatgattctt  46200
```

```
tttgatttg gtgttttgtt ttgttttttt gtcaagtagt tgcttggcta cacattttcc  46260
ttctcaatta aatttggtcc tttctgattt gtcttcccag cttttttttgt cttcgccagg  46320
ctggagtgca gtggtgcaat cttggctcgc tgcaacctcc gcctcccggg ttcaagcgat  46380
tctcctgcct cagcctccct agtagctggg actacaggtg cccgccacga cgcctggcta  46440
atttttagta gagacagggt ttcaccatgt tggccagaat gctctcgatc tcttggcatc  46500
gtgatccgtc tgcctcggcc tcccaaagtg ctgggattac aggtgtgagc ctctgcgccc  46560
agcctatatc attttttgaa atagtaatat attatctctg gacatggaaa cataacaaaa  46620
catagaagag tttgagcctc tgacagccct ctattcaaaa ccctgctcct ctactaagtg  46680
accttggtca ggctctcaga tattcctcgc tctttattcc tagtctgtgt aattcctgct  46740
ttatggggtt tttgtgaagg ctaagggagt taatgcgttt gcaccactta ctaaggagtc  46800
tgtcacataa tgcatgcttg ggtactgcta gctattattt tatagcatct taattaaaat  46860
ctaaaataat gtgaagaaag ggaagaattt gaatttttgt taagtggccc tgtaatgtga  46920
agacttaaaa ttttgatata ataggaaata ctcccttcta gaatgtattt aagaactact  46980
tctttaaatt cttacgtttt cactatttca aaataatttt ttcaatgtga gtagcaagga  47040
attttccaag tgaaattctt aattatgata gaaaattaca atgatttcca ctgtttgtaa  47100
gagataatag tcattgttta ttttattcct aatgttttcg tagatgcttt taaaatgtaa  47160
tacattttaa ataggagata tgacttcaag attttggaag attttaattt agacttaata  47220
ctatttgata acccatcttt tgcttatata gttacactta ttattttatt gcagttgaag  47280
tatcagagaa tcttggaacg attagaaaag gagaacaaag aattgagaaa attagtattg  47340
cagaaagatg acaaaggcat tcatcataga aagcttaagg tattctaagt ttgtcttgtt  47400
tattctcaaa attttaccgc ttaacgttgt gtgttcatca gtaccagttt ctaaggagct  47460
gtaaagtatt ctgtcatcct tttctttcta acctaatgtg cttggaggat ggaggatctc  47520
ttcctatatt aagacatttt ataagttgta gtctccaaat acttgtttta tactatgccc  47580
ataaaatctt tacactttta agagttattt cgtgtgaatc agtttatttt tctgaaatat  47640
ctagtttatc tctaggctta acttttacat aaaattttat ataaaatcag aattgttaat  47700
tgatggacat gtaagtgact tatcatcatt gctttacttg tatgccagtg aatgattaga  47760
ccactttctt cagtttttaa aaaattaaca cttttcttct aaggagagct ttcttaggca  47820
tttcaaagaa ctttcgaaaa agtgtgtgct ggtattgtta ctatcagcac attggtgaac  47880
ttatttacca ataaatcaag tcttactatt ccccacccaa ctaaaccaca tgtgctaaat  47940
tgaattgaaa caattattta acttaaatct catataagta agcagagttt atatgtagca  48000
aaactgcagt aaatcatggc atgtacattc tgtagtcaag gtccaaagat aatacagttc  48060
tagcttaaca aacatgcatt agtagctttg actataaatc atgactgcat aaaacagata  48120
acatgactat ttacaagtgg cacttagaac tgagaaaagt catttccaag tgctaatata  48180
tgtagagttt acctcagaaa cagtattttc tctcataaaa tgcagtggca attaacattt  48240
tttgtttatt tttaggctgg tgggttggca attgcttgcc atttaatttt ttctagggat  48300
taagaaatga aaggaccctt aagccatcat tttgctcctg ccttagcatt aaaacttatc  48360
cataattatt aaatgcttga tggtacccct ttttttcagg cctgtgtatt tttttgttca  48420
ttcattcatc aaatttacat gaagcttgtt acacgcaatg caaggcacca cattcatttc  48480
tgattctaca gcaagaaacg atacaggata tttgcccttg ctacactcat atttcagcct  48540
gcccagttgt cagtggatac ttaaccaccc ttactggttt aacagtcttc ctggtttatc  48600
ctttattcag atgcttgctt gcacgtgctc tctgtcctct ctctttctct ctcatgcatg  48660
cctcaaactt agcaaagaat aatttcattg tcagttggtt acctgaccac cttttttttg  48720
cctttttggt gttaatggtc ttttcttgca ttcagtatta gctcatcagt attaagtaat  48780
aatttccatc ttatttaatt agaatgttag gaaatcctga attaatttac tttattaaat  48840
cattgtatct aaataaactg aatgagaaat ggacttttaa tctgtaccgt tttagttttt  48900
acgatgaaga tgtatttatg taatttgaga aaacagtaca atgattatgg aaaaacaatt  48960
tgaatttatc actttttttct cttgacacat ctgttatatt tttttcttta cttttactgt  49020
tttatattat aactttttaa aatttttaca gaaatctttg attgacatgt attctgaagt  49080
tcttgatgtt ctctctgatt atgatgccag ttataatacg caagatcatc tgccacgggt  49140
atgtgaaaaa ttgatagtga acttgccaat tagcaaaaaa agaagcagct tagcttccta  49200
aaaattatgt gtatatatgt acacatacac atatatacat actagatgta ggcatttata  49260
ttttttatgt aatcttacat gttccaagta atgtcttaag caatattatt tgactatttt  49320
agttcattat aaatattaat aaatataagt acattatatt tatgagttac tgtatgtgtt  49380
ataaaggaag atatttggct ttatatgtct taatattagt aatatttaaa tactgaacag  49440
tggattaaat tagccatatg cgtgaaattt aagctaatag aattgaaaat gtgtttgtaa  49500
acagtaaact agctatggaa aagatttatg gaaagttaat aacctggttt tagaaatact  49560
ggtttaaatt agcacaagtt tttaaaataa aaattaggct ataaacagtg gatccagtta  49620
tagttttgct gttcctattt tcaatgtgca cacatgcatc aatcaccatt tttttacgga  49680
ttttaaaata tttttcacc tgtagaaatt ttaaaagact aaaaaactca gagcagcatt  49740
acaaataggt tttaatttta atttggtatc agaaaaatat gaataagtgt tctttgtttt  49800
gtgggaaggt tgttgtggtt ggagatcaga gtgctggaaa gactagtgtg ttggaaatga  49860
ttgcccaagc tcgaatattc ccaagaggat ctggggagat gatgacacgt tctccagtta  49920
aggtaagaac ataggccgtc tcagtgaggt tccttaggag agtaactgct tcagtgagac  49980
ctgttcattg tgttgaaatg aggactttta accaaagaaa gacttgatac atagtgtttg  50040
gaatgatccc tagtgtggaa atcagtagaa ggcacagcca ggaggccagt gtggcaggag  50100
ctgagtgagg ggagagtggt aggagaggat gacagagacc cagttgggag gcctttggat  50160
tttattctga ataagataag agagaagtta agagaatgag aatattggaa gtggagtcaa  50220
tgaatataga taattttcta gttttattgt gacaaaagag cagagaaatg aagcagtagc  50280
aattgaatat tgttgaatta agggaaggtt tttaaccctt ttcctgttta gaaaaaaagt  50340
gcagctcaac accagtgctc atttaatttt acgtaaacac actctctgaa gctgaagcaa  50400
atctgactaa ttttcaatgt gaaaataaaa tataaaaact gttcttagag ttatttctaa  50460
acagtactaa catcagaatc gtcccaatca tcagaatgtc tgttttttaa aagtcagatt  50520
tatcaaatca atcttcggcc aacaactttt tgagaatgat gtaaacatca cacataggaa  50580
ttccgcattt tctaggattt gacattttca gctattgaaa attactatat tttgtaaatg  50640
gacgtaccgc tactaaaaac agaatgcttg aaatagaatg tcttttgttt ccaaagtcag  50700
tacactagag ctatgtgaaa ataatcataa aagtgaagat attttatggc agagttatgt  50760
tggggcaaat gctgcagctg caagcggtgc tggcaaatat tgtcggagca agtgggaaaa  50820
ggattaaaga tgtttatatg ctgattataa tgatctaata aaggggggaa atgatgcaag  50880
agagagggaa aattgcaaga gcaaagttac tgaggtgaag gagattgtga cttggtgtac  50940
```

```
tagtccatat ctgggagcac tgacaatttc tccagggtca caggaagaag gtatggggct  51000
gcagagtctt tcattgaaca gatatttacg gaatgcttaa tatgtaccag tagcattcta  51060
ggcaatatgt tggtaaacag caacaacaaa gaagaacctt gccttaatgg agggtatgtt  51120
ctagtagagg gagacagata atagataata aatataatac ataattgtat agtaggttag  51180
aaggcaatag tgttgtacaa caagaaaaag cagaaccagg caaggagaat gagggtgcca  51240
gagtattcat agattgcatt gataaggtgg catttgaacc aagatttgca gaaagtgagg  51300
gagtagtcct gaggatatcc tgtgttcagc aaggagaata gctgatgcaa agcctctgag  51360
gtggttgtgt ggctgtcatg ttcaaggaac aacaaagagg cctgtgtggt caggtcgggg  51420
tgaagagcta gccatggtcg gggcaaatga tgacattaga ggaataatga agagcgggga  51480
ggaacagatc aataaggcct tataggccat tgtacagact tccgttttaa gtaaaatgga  51540
aagccagtgc aggatttcga gcaaagtaac aaaagtgcct tttaaaaggc tgctcttttg  51600
aaaatagttg tagccaagat gtagaaccag ggagtctagg ctactggagt atccaggtga  51660
tacttgggct agggaagtag cagtgaaact ggtaagaaat ggatagatta taaatgtgtt  51720
ttgaaagtag aattaacagg atttcttgac aggtttgata tggagagggg agagaagaaa  51780
agcaatgggg agagagagag agagtgtcaa tcatcaatga tgcctccagg gtctttagcc  51840
tgaacaaatt gaaggatgta gtttgcatgg aagtctgtca gtggatcagg tttgggggaa  51900
gaagatcagg agttcagttt tggacttgct gagtggtgat aacaagcagt tgggtataca  51960
agtttagaca gaggtgtggg ccagagacat acatttagga gtcatgatca actatctaaa  52020
agtagtattt aaagtcatga tcttactgga gaagatcttc aagggagtga gtagagatag  52080
agaaaacaca gaagcaagca gtatattctg ggcactctga acattaagat gttgagggaa  52140
gagaaaataa caaaggaatg tgtgaaggcc caaccagtat agtaagaggg aaagcagagc  52200
aggacagtgt gcgcaaagtc aggtaaacaa aaagaaaaca tggaggagga gggagtgctc  52260
agtgaggtca catgctgctg atccatcaag gaaggtgaac atagaaacca gtcgttgagt  52320
tcaccagtgg aggcaagaaa ggggaacgtg tggaagtttc cttctgattg cttccgctta  52380
ctcagtgaaa tactaagcca gatgatcagc tgttaattag aaaggagaag agattaaaga  52440
ctgaggcagg aagaaaaagt gaagtctgtt aacagatcgt ggtgactcta ggagtgaatc  52500
agtggagaaa gtcaagtgat attaggatta ctgaggtgga ctgaagtccc tttaagttct  52560
gtggacataa attttaaatg aatcattatg attgtgtttt gttttttca tgtttagctg  52620
gtggggggta ggtgtagaat aattggaaga ttgaaattac caagaattat ggcaagaata  52680
gtgggagaaa gacagtgagg ctgatgctga aatcttcaag aaatgaaatc tgtttacaag  52740
tgcaacaggg tatgggcagc ctagtgtgat tcatctagat tgcacttttg tgggtctagc  52800
tatggattga atcgtgttat gtgttactag ttctgtgtgt ggtactgtgt gactgtacca  52860
gactttacat atccatttta ctaccgatgg gaatttgggg tacatctaac ctagagaaaa  52920
aaacaaaatg aacctcagac tacacctcat atcctgttca ataatcagtt gtaaaaacat  52980
gggagagaaa cctacctttt acattgttac tagcatccta attgtagaag ctgtggatga  53040
tacttcaaga agaaattaat tttgttttgg caggcagggt gtggacaggt ttccttgaaa  53100
cagatgaggc tggtctcttt ccggtttgtc attagtccct tagtgtttac tagagcttct  53160
ccttgaccaa ccctgaattc cagttttttg tttccctaga gcagtgaaag tgccaaaacc  53220
ccagcttagc attttaacct ccttagcagc ttctttctgc ttggtttcct aaaatgtgaa  53280
tgccgtgaaa ggaaattgtg cgcaggatgt agggttttgt tttgttttgg aggtttattt  53340
ctgcagttca tttttctttg ggattgtggc accttaagac gtgactactt aataactcgg  53400
aattccaatc ttgtctactc aacccagtga aactgctaca cattttaagt ttttctcttg  53460
ggcctttgcc ctgtgctaca aatcagcaaa tcctctgatg gaaaatagct aaacagcttt  53520
ccaacagctg tttattgttt ttaaatttag cctgtttagc taatctcagt agaaggaatt  53580
gtatttttaa agtaaaataa ctatagagaa gctagaaagg tgtcaattag gcatttagaa  53640
gttcttgtga aaccactgac tgttaatata cattgctata acatttcttg gctgggtgca  53700
gtggctcatg cctgtaatcc cagcactttg ggaggctgag gagggcggat cacctgaggt  53760
caagagttca agaccagcct ggccaacatg gcgaaaccct gtctctacta aaagtacaaa  53820
aaacttgcca ggtgtggtgg cgggcatctg taatcccagc tactcgggag gctgaggcag  53880
gagaatcacc tgaaaccgcg aagtggaggt tgcagtgagc cgagatcatg ccactgcact  53940
tcagcctggg cgacagaatg agactcggtc tcaaaacaaa caaaaaaaca aacaaaacaa  54000
aatttcttac ccaaatatca ctccttgagt gaagcctgtc gtagctccct tatcatcagt  54060
tccattctct tctgtggcac cctaggtttt gtcactctct tctattatgt ctgtgtatat  54120
ttctcccagc atgtgatgag gtctaaaact gggacagtca gctctgtgtt tccccaccta  54180
caacacctga cacatagttc actctctata gaggttgaat gaatgaattg tcctttacct  54240
aaattcatct ttgaggttaa atgcaaggtt tccttttagt gtttcaagtt ttagagagat  54300
gattttgggc ttagtgctgt gtatagcatt gactggggaa agaaagaggc agcagcattt  54360
taggtcataa gcgatataaa ggaaccagca ttcttgttgg gaaatcacaa catatatgac  54420
atatatacaa acaatacaaa tacaaaatta ttgtcttgtc agaactacca tgttgacagc  54480
ttcagggggt gccccagcag tagtgtgaag ggactcttgg atttgtgcaa tgcagtagcc  54540
ctgtctagac cacatacggg ctgtgggaat taatattact tataaataca tcattacctc  54600
tcagttttct gttactatca ggtgactctg agtgaaggtc ctcaccatgt ggccctattt  54660
aaagatagtt ctcgggagtt tgatcttacc aaagaagaag atgtaagtaa aattcatcta  54720
aggttgatat gtgtaatttt ataacctgga tgagcttata aaagacagtt aaagaatatt  54780
tgtgaattaa gattttctta gattttctta ggattttgtg ttttccatta gcttgcagca  54840
ttaagacatg aaatagaact tcgaatgagg aaaaatgtga aagaaggctg taccgttagc  54900
cctgaggtaa gggttgcaat tcatttcagt gacgttttat ggaaattaaa tgtttatgat  54960
ttcaaataaa tcaaaatcta ggtattgatg tttagattgc tgctatctag atatgtagag  55020
cttttaaaaa aaaatccaaa taatatatca ttttgtgggt aattttccag aataattact  55080
tttaggatca gagaaagaat accatttttg tgagcgtctt atctgaatgg atgagatata  55140
gaatttttag aatacatttc accaaaaaaa attcttgaca aattcccccc aaactttagc  55200
attgttttat ttttattttt cctgagtaga ccatatcctt aaatgtaaaa ggccctggac  55260
tacagaggat ggtgcttgtt gacttaccag gtgtgattaa tgtaagtata tacaaaacat  55320
gtattttatt ttattcttat tgtgtgaagc atttataatg acatttaaaa cctttttctt  55380
taagactgtg acatcaggca tggctcctga cacaaaggaa actattttca gtatcagcaa  55440
agcttacatg cagaatccta atgccatcat actgtgtatt caaggtaaat catatcaaaa  55500
gattttaatg tactgatatg ttttcttctt tagcaatcca agctttgcat taaatagttt  55560
gtgttatgta aacatacaag ataaatgcat ttttgccttc tcttcgtatt catttttatta  55620
gtaaattaaa ttgaagttga aattattttg ataagtttta cataagcatc attgaaattt  55680
```

```
ttatcggcta ggatttcttt ttagtaaata acgtaaatgt attaaaatct ttcttgctat  55740
aatgtagaca caggggtata atttgtactg agttttaaaa gtctacttta catcttaaaa  55800
ttccacagtg tcattttttt attttttca gatggatctg tggatgctga acgcagtatt  55860
gttacagact tggtcagtca aatggaccct catggaagga gaaccatatt cgttttgacc  55920
aaagtagacc tggcagagaa aaatgtagcc agtccaagca gggtgaggtc aaattctttg  55980
ttgcgagaat agattctttg taaaagctcc agctgtgata gggatttgtt atttaaaaaa  56040
acaacaacaa caacaaaaaa acaccttaca actaagattt attacaatga aaggataaag  56100
caaaatcaca aaaggaaatg gtacatggta tgaagtctga aggaaaccag gctcacgttt  56160
ttccactagt tcattcccag tagactctac tgggcacatt taattcctcc agcaacaagc  56220
tgcttgttag agactcagct cctaaggttt tcatcggagg ttagtcattt cggcaccctc  56280
atgtaccaaa attatttcat actcccaaaa ggaaagcata tgttataatt aaaccacatt  56340
acttcagtag tgagccactg ttatataagg aaaggtttat atcagtgtag ggaactgttt  56400
accagttaag ttttcagata ccagccaaag acaggcaggc ctttttaagg acagtagtct  56460
caggcctgct gtgttaaccc ttttctaggt agccaccata acctctgttc tgctttcttt  56520
ttaagggtaa ggcctgccgt ggcattaatg gttctgatat ggagaagggg agaagtgagg  56580
tagaaacaaa tttctgtggc ctcctcccca tctttcttca ttcctttcat ttctttcaac  56640
tctaggatag tgagtttata tttcttctga gatgcaactg aagcttattt cagtcctttt  56700
tgtataaaag attcagcatt agcttaggtg taacttgtct taaaggaggg attctcatcc  56760
cattattaat ctgaatgggc ttcagggggt agaaactcta acatatgtga aaggtctcta  56820
tgcaaatatg catttttctg ggtacatagt cttttttttt ttttagtcac atttagaaat  56880
ggatttttga tcctaaaaga gttgagaagc agtggatcca aatattaaag aagaaggtgg  56940
gaggggagga aggagtaaaa gaagacaatc cagcttggtt agaatttaga tatttgaaga  57000
aagtatggaa aaataataat agctaccatt tattgagtgc ttcatgcctg gcactgtatc  57060
atattgtccc ataatctcac caacctttt gaaaaaatta agttgtttac ttaaggtcgc  57120
ataactacta ggcagcagag caggaattca aactaaggtc tgtctgactt taaagaacta  57180
cacatcattc cgggttttcg atacgtgtgt tttaataata cattttcaat gtagtaaaat  57240
taaatgtatt tttttcaaat agcaatggaa aaacatttta aatgcttttg tgcagattta  57300
tttaactata tacatgtata gcattatttt gctttctaaa ttgtatatta cgcttttaaa  57360
acttatgtaa actatatctc acattaattt ttcccacttt taaaaataga ttcagcagat  57420
aattgaagga aagctcttcc caatgaaagc tttaggttat tttgctgttg taacaggaaa  57480
aggtatgcaa agatggatta taataactta tttttagttt ctgttgtttt caaataataa  57540
agagtaattt tcttgatgaa aatttgacca tcattcttcc ccagggaaca gctctgaaag  57600
cattgaagct ataagagaat atgaagaaga gtttttttcag aattcaaagc tcctaaagta  57660
ggtatcttgt taaaacattt aaacatttta cagtaagaga gtagcttaaa ttgaactgtt  57720
ttcacttaaa acatcaggtt ttataactat tagtttaaca tcggatttct agaattttc  57780
ccaaatagtg aactgtatct aataaacaag tccttagcta ctttttggca gaattgagag  57840
cagtttatca catggtacaa tacatactgg catgcttcct tggacgtggg cactgaaaga  57900
caacatagat atctgcctct tactttattt tacttataaa gtggttttag aaaatcgacg  57960
ctttcacttt taaacgtgta catatttctc ttacagtatt ggggaagatt ggagtggggt  58020
tgtcgaagaa gtatccctag atatatattg acaggagata agataagcaa aaagagctaa  58080
aggccagttg tattactgta tactaaaact ttatatgttg agtttctgga aatagaaaag  58140
tatgtttgtt cctaggttag tacggtaagt caagatagtt cttgcaaacc ataatcttac  58200
gtgctttggg gagtgcactg acaacatata gaactgtgct gtctaatatg gtatcactag  58260
ttttgtgtag ttattaaaat ttaaattagt tggaattaaa ttaatttctg gaagatggct  58320
ttcttcatgt tctttttaaa ggcatggtgg ctcacacctg taatcccagt actttgagag  58380
gccaaggcag gcggatcact tgaggccagg agtttgagac cagcctgtcc aacatggtga  58440
aaccccatct ctactaaaag tacaaaaaaa attagctggg catggcgatg ggcagctgta  58500
accccagcta ctcaggaggc tgaggcggga gaatcgcttg aaccccgagg gggtgggggg  58560
cggaagttgt agtgacccaa tatcacgcca ctgcactcca gcccggacga cagtgcaaga  58620
ttccaattca aaaaaataat aaaataaaat ataacattaa atttaaatta gttaaaattc  58680
aacaaaattc aaaatacagt tcctcagtta cactagccac acatttccag ggctcaataa  58740
cccagtgtgc cagtagctac cgtattggaa tgttttcctc ctcacataaa tttttattga  58800
acagcactgg tatgaaaggt aagagtggct gttagcaagc acattcgcag acttggtggt  58860
agtattgttg tcctttttgt cattttaata tactttagct cttgttattt tttttttaata  58920
ggacaagcat gctaaaggca caccaagtga ctacaagaaa tttaagcctt gcagtatcag  58980
actgcttttg gaaaatggta cgagagtctg ttgaacaaca ggctgatagt ttcaaaggta  59040
agttggattt tttaaagaag caagcaaatt aagacatttt attagctggc aatctttggc  59100
atccatacga ttctgtactt ctttccttta acagttgctt ggtagttcat ttacaattag  59160
acagtatctg gaaaatagaa gaatacaaac cttcagttgt tatacaagaa caagattttt  59220
cctttcagag gaaacatctc tagaaacaca tttgcagagt tcaaacagat gagaacattt  59280
gctagtgctt ggaagtacac aataaactat agagaattct agattcaccc tgttgaggat  59340
gaaggagcag atgtgttggg aagcagagcc ctctgaactt cctttacttg gcaccatttc  59400
ctgaatccca cactttcctg ctcagtgtct tttatcggaa gagaatatat ttgctttctc  59460
ttttcccata tgtaaatcct acctgatcct acctatttat gccagttagt ccctctgcaa  59520
tcttgtatta ctttcatttc cattttacag aagaggaaac agaagacagt tacttaccca  59580
aataacttat cctattaccc agtgtcacac aacatgggta ataggcccag gatttggctg  59640
ttggtggtac aactgcagag tccattctct cagcagctct atggtactaa actacttcag  59700
ctgtgtgcta atggatttaa catggagaaa ctagaatcag ggagaatagt tttgaaagct  59760
attgcaaaaa tgaaattctg agacgttgag atcccagagt actaaggggt cataggcgca  59820
ctctcagaaa ttcagttaat acagaggata tgtattttaa ccactttaac cactacatct  59880
ggaaagaagg agggtcatca aacttgaact tttccttctt cctcagcaac acgttttaac  59940
cttgaaactg aatggaagaa taactatcct cgcctgcggg aacttgaccg ggtaatattt  60000
ggatactcgt gtattttgta tatatcttaa tttaatgttg tttgctaact aaatttatgt  60060
tgagagaaaa atctgataag ctaaagtact ttggttttga ctataactac taatttgtaa  60120
gaatacatct ctaggagcag ttatctcttt cagtaattta aattatttat tatataacat  60180
taaaaatgga ttataagatg tcaaaacaag tgttgaaagt gttttctgag aaggtaatga  60240
atgtgcttta aaggttttgt agaattcgtg tattcctgta atttagtggg aattaaacat  60300
tgtttttcct tgattttaaa atccccatta gttaataaaa cacagcatta atatatagtt  60360
actgatgtac taaattaata tgtattgatg ctttcacata acgtgaacaa gtgttatgtg  60420
```

```
aaaaactgca ttcaaacttg agaaggtaga tatttatgtc agtttctttg tccttatctg  60480
cataatggca ttcctaaaaa aaaacactag aagtgcattt ttgctagtca tgtataatta  60540
aacccaaatt cagcctagtc aaaaacctcc ctttggttat ctctgaaaat catgacaggg  60600
taaatttact gtcttatgga aatcttactt acttgtattt atattgccta gaatgaacta  60660
tttgaaaaag ctaaaaatga aatccttgat gaagttatca gtctgagcca ggttacacca  60720
aaacattggt aagtatttga tattaatctc ttttctgaaa gactttactg tacaggttat  60780
aatgaaatgc taaaacttag attgataaag cagtgattta ttgttgcctt ggctcatagg  60840
caaaaacgta atagtatatt tttttggcaa tatctaacta cttttgtagt ctaaccagtt  60900
gaatttcttc atgttctttt taaatcttga ttctctttgc cttttcttta tcttatacct  60960
aataaatacg taatcatgat ttctgtaaaa tcctttgggc agaagttttg tcaaattata  61020
ctttaggtaa atatcaacct gtcaaaattg atttataaag ggagttggta tatattttca  61080
ggttctccat tctgagtaag aacagttagt gctttctgta acatgtggtt aatatgttgt  61140
atacaaatca cattttgaac ttaatgctat taatacttga aatttttaaa aatagcaagt  61200
aaatgcacct ttttgaaaaa tatgttaatc ttttctaagg caaactgtta ccttcagttt  61260
atattttatg taagtttggc cattcctaaa ttcagtggaa tgagacacgg taaaacaagc  61320
tatgtataaa tagccttgac atttttgtag tcacatgtta attaacaaat tcctcatgca  61380
gaaattatct ttctaatgaa gactgtggta tttttaagaa tttatttttg gagcagagct  61440
atcctcactg ccattcattg taaatatttt ctgtacctag tctattcact cagttaaagg  61500
ttatcaaaag tgagcctaga tagtagtatc tggtctgttt gaattcagca tcactagttt  61560
cctcatttca gtgccctttc ttcctcagtg gtgaaacctc ttctatcttc aagtagtcca  61620
catttgcctg tttttaatct ccgttcctta tccaaaaaaa gagatctaat tgtatctatt  61680
cttgttgatt aatcaaacat tgttatgaca caacttatgt ttgtttattt gtatcttagc  61740
ccagttccat ggctttgtgt cagtcagctt tcaagttaca aagagatata taggtttaca  61800
gattgagtat aatactagtt gccttgctag attgtatgag ggcatttaat gtatataaaa  61860
gtgatatgta aactgtaaca actaataatg ctgtttatgg ggagaaaatg tggtccttct  61920
ataaattaat ttttggtatc atcaaatgga aaggttagtt ttgtttggac agagcaaccc  61980
tgaaatcaaa gtatttcttc actaaagtga gccttgaaga taaatgtaat ttatttaata  62040
caaaggtaac tgaagagaat tgtgagggga cagtgaacgc ataccaccag attgcccatt  62100
gaaaaggcaa cggtcagatc tgggacatct ggctgctaga gatttacttg tgtaagctgc  62160
cggatcatat atgattctct gtgttttcag actgtagagg ctgaaaaaat gttatgttaa  62220
cgcaaatata aatcagagta gcaggtccaa gccttagctg ttcataccac attgaattca  62280
agtacattac accccaaata ttttccacat attttattat tttgacatag ttgatgttgt  62340
cttgaagttt ttattggtat ctttttgctg aataatccta tgtgatattt taggacactg  62400
cctaaaatgt ttacaattat ttaagtcata agactgtttg atctatattt ggttatctgg  62460
aaagtgttaa aagcatttta tgtcataaca tgacagtttg ttatttcctt tagacattcc  62520
actgtccttc agttaagttt taggaaggtt attaggggta tagatttgac atataataca  62580
ttatagtagg aaatactcac tcagcatttt tacgctgtgc ctggttttca agagtgaatc  62640
actgacattc agaaggagat attgatatat cattaacatc atgtgaccag caatgtagac  62700
atatcttttc tagaaggata gctggctagc ttcacagaaa tacatttttt ctaaaaatgc  62760
tactatggta catttttaga aattctcgga cttcagaaat caaagatttg caatatcata  62820
atttgaaatt taaaacatga ataagtgtta aggcagaggc aggaatatgg taagggccac  62880
gagatgagaa caagaaaggc gacacaggta gctgtgtcct gtggctttaa cataaatggg  62940
ggcaagaggc aggagataaa acagtagatg taagcaaaat attgggttta ttaaccatat  63000
tcagaagctt agtgtgtatt ccataagcag taggggggagg gtggtcactg aagaggatta  63060
ggtcaggttt gcattttaga aaggtctttg tagtaggcaa aatggaatac aggcggagaa  63120
aactgtaagc aaggaggcag ttggcttttg caataattta ggcaagatgt gatcatggct  63180
taaacttgga tagtgagtgg tagtacaggt agagaagaga cacttgtgag atacttgaga  63240
ggttacctaa aagatagaat tgacaggatt tagtgattgt gtagataatg aagagtctat  63300
taaataatga gtatgtttat attcagtaat tacattgcta ggaatatatg caaatgatat  63360
atttgacaaa gatgaacaca caagaccttt caccttgatt ttttaaataa atgtgaagaa  63420
atggaaagca atttatgtgt cccatttgga attatatagt atttggttta tatagagcag  63480
attactgctc tatggataga agtagccttt gaaaagtata ggatgttgac atggaaaact  63540
aaatacaata tacttttaga tttaaaaaag ggatttataa aacagtatgt ataattatga  63600
accacttgtg taaatacaca caaatagtta cgtagacata attttttaa taataaaacc  63660
ataaatagtg gttatcttat aaaagaggaa ctatggggta cttcttacat tttctgtatt  63720
ggttgaaatt attatatgga gtataatagt cctctacttt aaaataaaaa aaaatccatt  63780
ttaaaaagaa tttaattaaa gtggaatgta ggtaaagttt ctgtagataa agaaggcaat  63840
aaaactatta cctttattat attttgctaa ttatattttg tgtattagta gaagttatcc  63900
ctggttgatg gcaaaacctg gaatagagaa gtcacctata ataacacaga atatagtcca  63960
ggcacggtgg ctcatgcctg taatcccagc actttgggag gccccctatgg tcggatcact  64020
taagctcagg aattcaagac caacctgggc aacatggtga aaaccctgtc tctaataaat  64080
atacaaaaat tagccaggca tggtggtgca cgcttgtaat cccatctact tgggtggctg  64140
aagtgggaga atcgcttgaa cccaggaagc ggaggttgct gtgagccgag actgtgccac  64200
tgcacttcag cctgggtgac agagtgagac cctgtctgaa aacaaacaaa caaaaaaaaa  64260
aaaccataga atataggctg ggaaaattgt tagatgatag cagcaagcaa taaggtagca  64320
gatgacataa ctagatgaag tggcttcaca gtgtaatggt ttttatatga acattgagaa  64380
ctgatggttc agaagagaga ctggggtgag gaggacttaa cttctacttt ctaactctga  64440
aggccattta actgctgaat agcttcatct cagcagaatt tgaggacaga ggacaatcac  64500
tttccttaag gaaaggtttg gaggtaagaa tagggaaaga gaatgagagt gtaaaatggt  64560
ttgtcatgga accgggtatt acaggagcac aacagaaatt gttgggatgg aggggagcag  64620
tgggagtctg agacagagga cagcagcttg gcgatgaaag gcaggagagg ctgggcaagg  64680
agaagtgata acagctgcat ctgtggatgt caaagcagca acctcccttg agaaagttgc  64740
ctttagcttc tcgggatttg gtaatcagga ttttaaaaag ggtgtcaggg atatggattc  64800
ctggcccaca gactccaggg aaaaataaca gactatgtct cttctgaagc aggatgagaa  64860
aaaagccctg gaggtcagag gctggatcct ggtcttcagt tcaactttca gtaatcttct  64920
tgagattgtg tataaagtgg tatctgaaga ggaggccctg acaggctgct tttcttcatc  64980
ttgctcctta aattctccca ctctctgtca ttaactcagt gactaaattg tctttgtcct  65040
tttgggcccc agtcatatat cctcctcaga ctctgatttc tttactggtt gtaactggaa  65100
agtgacctga aagttagcag tgggaaacca ggatctgtgt tgattgattc agtagactta  65160
```

```
attttacaca aaatgtttag taaatagtct tggagggtag gagatgttga ctctcctcac  65220
cagagaagtt cagctgggct tttggacagc aggatatttc tgctaccctg agatttgtgg  65280
ctatatccta aagggttgag attattctta agaaggatcc cctgataagc agagtttttt  65340
ttttatattg tagtattcta agtttattac ccaaataaat atttccttga gatttcaaat  65400
tgaaatagtt gtattttttt attagtgacc catgttcttt taagatgtct ttcaaggcag  65460
aattttcaac atgattatgc atcttttaca ttgttacctt aatcatgaat tattgaaaaa  65520
ttttatctac agcattctat aacatctctg tgctgtgatc tgataagttg tcatatttat  65580
accaagaaat tttcagtctc agactctccc gtaagcacat gaagtatatg ttaatactag  65640
gcagataagt gtgcatgaaa agatgctcag aattattagt cattagagaa atacaacgta  65700
aaaccacaat gaccactata aacttactaa aatggctaca attttaaatg acagactata  65760
ccaagtgttg gcaaggatgt agaggatcta gaactctcat tctctgctag tggaaatgta  65820
aactgaggca aacatttcaa aaaaaaatta aacatgtaat taccatatga tccaaacatt  65880
ccactcttag gtatttacct aagaggaatg aaagcatgtg ttcataagaa agacttgtac  65940
gtgaattctc atagcagctt tatttgtagt agccaaaagc tggaaacagc ctaagggtct  66000
atcaacacaa gaatggataa acacattcat gcaacataat actacacaga aataaaaaga  66060
agtgaaatat tgctagatgc ggtgtctcac acttgtaatc ccaacacttt gggaggccaa  66120
ggcaagagga ttgcttgagc ccaggagttc aagaccagcc tcagcaacat agtgagaccc  66180
catctctaca aaattttaaa aaattagcca ggcataatgg cgtccacctg tagtcccacc  66240
tactcgggag gataaggtgg gaggatggct tgagcccagg aggttgaggc tccagtgagc  66300
catgaatgtg ccactgtact ccatccagcc tgggcaacta agcaagaccc tgtctcaaaa  66360
aaaaaaaaag tgaaatatta atacatacaa cagcatgatg aacctcaaaa taattatgct  66420
ggagtggaag aacaaagaca aaaaaagagt atatgccaca tgattgcatt tatataaatt  66480
tctagaaaat acaaagtaat cacagtgaca gaaagcagtt ccagtggtta caactttttga  66540
ggatgatgga tgcgttcatt atcttgactg gtgcgattta caggtatata cacatgtgaa  66600
aacttatcaa aattttaaat atgtacagtt tattataagt taatgatact tcagtcaagc  66660
tgtttttaaa aacaatatta tatttagatt tggtgctttt gatacttttt tatttcaggg  66720
aggaaatcct tcaacaatct ttgtgggaaa gagtatcaac tcatgtgatt gaaaacatct  66780
accttccagc tgcgcagacc atgaattcag gaacttttaa caccacagtg gatatcaagc  66840
ttaaacagtg gactgataaa caacttccta ataaagcagt agaggttagg atataattta  66900
attaaatggg taagaagcat tatctgaagg gagtaggagc tgtgaatttt agattttatt  66960
cccatcacag cctctatctt tcttttaggt ctttatatct catttattct ttattcctca  67020
tctctgtttt gggactaacc ttaatgttgc taccagttac tacggttata aaaatttact  67080
aattggtatg atgttggcct gagggtattg gtacttcttc caaagacaat atttaacaag  67140
caaattttgc ttgaatatga aatatttgct tgagtatttg cttgaatgtg aaatattttg  67200
aacattttct gtggattctg tggattatag agattccata aagaaaatac ttaatagatg  67260
aagcatttca tctgagctca gttatactta aattatcatt ttcttaggat cctgacagaa  67320
gattaaacta ggaattatta aaaaacaaaa caaaacaaaa caaaaaacta ccttaaagaa  67380
tctatttctg ctaccatgta tcttggcttt atcacttaat agctgtgtga tcctttgcct  67440
agttgcttaa ctttcctatg tgttttttca tctataaaat ggtgacaata atgttgccta  67500
cctcacagca ttgttataag gattaagtaa gtaattatat gtaaaatact tagacaatgc  67560
ccagcccatg gtaactgctc agggaatgga cctgctgtta ttatggtcct catcatctga  67620
attgatccat catgtacatc accccataaa cagcgattgt tcaagctaag agtcagtgtg  67680
tcctgtgctt gtgtgtgagg ttgctcacaa aattgaagtc aatgttaaaa gtaattttgt  67740
ttttcatacc tatcttaaag gcagtgtcag tttctaatta ttcggatgtg atttcacccc  67800
tttcctatct tgctccagtg ttaacttcct tatctctgtt ctcaatttct tcaagcccct  67860
ttctaagaac tccagcagcc tccctgccta agttgcacgt tgctgagccc tggcagttct  67920
tgacacattt accccctgaag aagttagaga gctgctgcta ccccttcagt agctctcatt  67980
actggcacta acatttttttc tgcgccctgt cccatgatag gatattttca catcctaagg  68040
ttcaagcagt ggaagtggtt atgaaagcat caatttttct ttccactgct gctttctgtc  68100
cctcagcact aggtgtcatg gaaagaatgt agatctggtg agaaggtcag gaaacatgga  68160
tcttaatact caccccacca ctcactccgt atttttggac agtcactttc tttttaaaa  68220
tgagagaggg ctaaaatcca gcattaaaaa gcccacatag ttataagtag attttgttct  68280
tcattatttt tgacactgtg ctcttccttt caccgttcag atcattagga gttagctata  68340
atacaaagct gaatactctt cggctatgtt ttaaagtgtt ggtgcattgc ttcatatctt  68400
tgcttaaaga caaagctatg aagatgactg aatcattaag acatttaaaa ccttttgcag  68460
tgtgaaagaa gcagtcagac tcatgtctta gaggttgaaa taaataaatg aactaacttg  68520
ggtggcaggc ttagaataca taccttatct tgaagagaca gccctgttca gctacagtag  68580
gtggtgtcat gtaggaatat gggtatatcc ttctcagtta gtccaagaga agccgtaaat  68640
gcagactttt atatgaaatc tctcaatttt taaatattag catgcaattt taaaaatgag  68700
aaccgctata catgtctagg aaaacatacc aggaagccat atctgtcccc agcaacccgt  68760
gtgagacctc tacatcatgg tttatatttg ccttttttgtt aatgtagttt cacatatatt  68820
ttctgataag ctgatttatt tatcacatct gtttggcttg agctcgtgtt atttttcatg  68880
ttaaccattg aagtatgtag taataatatg gctttttttc tttcaaataa ttataggttg  68940
cttgggagac cctacaagaa gaattttccc gctttatgac agaaccgaaa gggaaagagc  69000
atgatgacat atttgataaa cttaaagagg ctgttaagga agaaagtatt aaacgacaca  69060
agtggaatga ctttgcggag gacagcttgg tatgttgttt gtatactggg gtatcagcct  69120
catattttta tataacttct caaattgata ctttttcata ggagacttta tatgactaaa  69180
ttacattctg aattaaaaat aatgaagtaa agaaacagat ttatgatctg taatctgccc  69240
tttaatattt ccctgccctt ctaaaatcac ctgttgctgt ttctttcttg gctatcattt  69300
cagaaaaaag taaaactttg cagtaaacag actctgataa acttctacaa attgtcatct  69360
gttagccatt ttatgggcct gtctgtagat aggtgcttct aattttaccc tctgtgataa  69420
tgaaaggaac tacatgcgtt ggttttcagt ggattataaa atgttagacg cctaaaatca  69480
taacaccagc taccatgtat tgaatgctta ctatgtgcca ggaactctgc taggtatttt  69540
gcaagcatta tttgatttaa ttcttaacca ctcctgttat tgtcattgac agagctggga  69600
ttcaagcccc tctctaatgg caaagcctgg ttcctgacac cacctgataa atcttttgtt  69660
atgtagactg ctctcactac caaaatcaaa tctgttaagt gcctgctgtg ctcagagagt  69720
tactagaggt gttgttgaat tacaggattg agcgattttc tgggaaaatg cagagctggt  69780
tgtaattata attttgtttt aaagaagtgt ttgtctttat ggccgggcgt ggtggctcac  69840
acctgtaatc ccagcacttt gggaggccga ggtgggtgga tcacctgagg tccggagttt  69900
```

```
gagaccagcc tgaccaacgt ggataaaccc cgtctctact aaaaatacaa aattaaccag  69960
gcatggtggt gcatgcctgt aatcccagct actcgggagg ctgaggcagg agaattgctt  70020
gaacccagga aggggaggtt gcggttagcc gagatcgtgc cattgcactc cagccaaggc  70080
aacaagagca aaactccgtt ttcaaaaaaa aaaaaaaaaa agaaagaaaa ccatatttat  70140
tcttgttaaa tgccttatta agactggctt actgagaaaa cagcttcatt tttattcatc  70200
caaaaattat aaaatttgga agccaatttt caactgtaat aaataacttt tatgatttta  70260
tagacctttt aaatgtctac cttattactt ttttcgttgc tgttaacact gggaataatg  70320
gttaataatt tttttctcct catttttgaa aaggctaaca tgtaggtcac atggcaaaaa  70380
gcgatgaaca tgatctgaat tattaaaccc tgaattttag gtttctagat gttgcatttc  70440
atgtagttaa atttgtaata ttttgtataa tgtaaatgtg taatattacc cacgcacccc  70500
atatggttag cttgtttaat ttgggccagg agagaatctc cactctttat tttttagata  70560
gcaagctaac aaataagcag gcaagtaaaa gaagcttatg cattttttata ggaaggatat  70620
atttttatgc tggtttatat acatggttat ttttccatat ttactaagct gtcaatttga  70680
ataaaactac taaaatgatg agatgtaaaa caagttggct ttttctcttc ttgttatttt  70740
cagagggtta ttcaacacaa tgctttggaa gaccgatcca tatctgataa acagcaatgg  70800
gatgcagcta tttattttat ggaagaggct ctgcaggctc gtctcaagga tagtaagtgg  70860
agacacggct tattgagttc tgagttcaca gtggtgaagg agtcatccaa ctttagtgaa  70920
catttgtaga aatagattga acatttcaaa gtctttgtca ttaatactat agtcgaatat  70980
tatttgtgga atttttttag tcaactgctt tgtaactact aaaaccaatg aataaaatgg  71040
acacatgatg cttatatgca tttatattct ataaagctat aatgcagaat attttagtgt  71100
gttcgctact gtacttatag gaattttata agcaattata cttttaggta tcttaaacac  71160
atatataatt aaactcttac acatgtgcca tatcagtcat gtgggttttt tcctttattt  71220
caactgcctt catattgata tagcactttg aaatagttaa gaaagcaaga ccattattag  71280
ttataatttg tgtgtgtgta agtgataaaa ttcttgatta attaattttt ttttctagct  71340
gaaaatgcaa ttgaaaacat ggtgggtcca gactggaaaa agaggtggtt atactggaag  71400
aatcggaccc aagaacaggt agaaataaac aagtctctag tcttatgatg atataatttt  71460
gttcatttta attcaggcat taaaatataa cctttttgtg gctctagacc agtctcagga  71520
atattaaatg ttttatatca tactttctaa aatataatga atctttagaa taaagaataa  71580
actacataag aaagtttttt ttaagtgaag tagccatgtt gttaaaagac aagagatgaa  71640
acatgcccct tttgtggttg attacattgt tcatttcaat tccctgtttg aggtaaaaag  71700
gaagattaaa gttatgaaca ggccaggcac ggtgtctcat tcctgtaatc acaacccttt  71760
gggaggccaa gtcagaggaa tcgcttgagt taaggagttc gagaccagcc tgggcaacat  71820
agcaagacct cctctttact aaaagtcaaa aaaaattagc caggtgtggt ggcgcatacc  71880
tgttatccca gctactagtg aggctgaggt gggaaggatt gcttgagcct gggagatcga  71940
agctgcaggg aaaataactt gtgaatagaa aaaaatagta aggttttcag aggatgtaca  72000
atgaatatga ttggcgggaa aagatacaat ttttcttgcc ttatttttatt atcttatcta  72060
tatctaccat taaagtccct acccctcacc tccacccctg ttcattcctt tccgattctt  72120
atagcttctt ttcctatcta gcattcagtc ttataccact gtctcattcc ttgttcattc  72180
cttaaatgaa agaatctaaa tagaatatag aatctaacta cataaattaa tgaaataatg  72240
aagatgaaaa agatttagca tccaatccat tttctttttct tgtttgcttt gttccttgaa  72300
ttcatttaga gaaaggagat caagtaatgg aaaaatagag gagacaaagg gaataaaaat  72360
tgaccaaatg agatgtccct atttctttat tttatatttt cattttcatt ttaaatacag  72420
ttaattgtat aatctatatc ctattttttt cctagtttcc cacatttctt gtttcataag  72480
ttctctatca gatgtgagtc tcaactttcc tcaaaaataat gaagagacag tcttcttttt  72540
ctctgtgttt ctttactatt tttttttttg gtaatgactt ttgtgaaaaa tgagccatta  72600
agagactgaa gcaaagctga ggaagcagac agttagtgat tgggtcatgc atgtgttcag  72660
ggtgcgttgg ttatctctgc tctacagatg ggccgagaga aggaggtctg tcagaagaga  72720
atttctagag atccatccaa ggtttctgac tttgatagag gaagatgcat tgattagaaa  72780
gagctgctgt aagggagata aactgcaaaa gaaaaatggt atctggcctt caagacttag  72840
tgatattagg cctaaagtct ctagaacagt tggtggcaga acttgcctca gcaactgact  72900
ggtggtaaat gtgctttggc caaacactct ctgaaagaag tgattcctgc tcgtaagtta  72960
tttttgtcag gaacttaaac ccatagggga atcccttcaa gagaaagaaa ggaatttgct  73020
ttaaagtcag tgcaaagggt ctgtaagcct agaagaggaa tctggaaacc ctttacagaa  73080
gagccttctc cccacaggat ttcagggcag catgtgtgag acccaggctg actgtagaac  73140
agaggccata atttggaata tagaagggag gggcatctga atcacccggg gaggtgttta  73200
tatatagtgt tttgtttttt cttcaaaagc tagcctcatg tcagactcat tgagtcaagc  73260
tctccttctc tatcctttct atccctccca ctcccagttg aagacaagtg ttttcaacct  73320
catacctgga ggttacagtg agacatggat tctagaagag gttgagaata tccctaggtc  73380
tcacatcgta agttcactta gctgaatgac aggatttggc aggaaaagaa acttaaagat  73440
gagaaatcca ttctctgaaa agtattttgt gcttttgtgt ttcttttgtt ttctaggaaa  73500
attcatccct ttgaaacatt ctcgccttgt ttaagccaaa ctaatggaaa ttttggtcag  73560
gatagatcca agagtagttc tctcttctaa tggccaagtg tggtgacagt caaatgatgg  73620
gtagaaaggg ggaagtaaaa catgaggcag gatgagcttg ggaacaccat taccagcgat  73680
ttcctttcca tctcagactg aatagtacat gtttaagcaa acagtgaact ttctctttat  73740
caaatgctct tttttctgaa gtattagttt tcagagagta ttaattagta gttccattta  73800
caagttaatt gtttgcattt atgtgttaat cttgtctact cagatttcat agctgtgata  73860
gagtttgggg caaaaaaaaa cactcagttt cgtagctgtg gtagattttc tattctagta  73920
atttatttag ggtaatgatt gaatttaaag ctagtttctt ctatcatata caattttgag  73980
tggaggtttg aaaaatgaca agattaattt aacacagtat aagaatcttg ttatcaaaca  74040
taactagtgt aggtaagttt tcctcctttg gtaaagagat tatgaataat tacagataag  74100
agactggaag tgaatttaag aaggacagat acctcacagg agcagtctga agtaccattt  74160
tttatgaaaa agctttttaa aaatcaagct atgcatttta tatttattgg aaaagaaaca  74220
tgtcaacaag tttaagtcct tacagtaatc tcgttcttaa gtatagttct tagatatgaa  74280
gcattttaga acatcagctc ttcctatgca ttcagggtgc tttttcctag attcaaatta  74340
taccctacgg tcaagaaaga aagaaaatac atggtaagat tcctggtgct gtaacttcca  74400
caggaaaaaa catttcagca aaagtaaata cataacaagt agggctaatc cctgggtttt  74460
ctaccctctc ataaggcaaa ttcttctgtg ttcataggcc atttaccata ttcataagcc  74520
ggggtgctgt gttctttctt gtgtttcttt cttgtttgtt gtgattaagc ttgtgttatc  74580
ttttatgcaa tagtaatgta tttattaaaa ttgagactgt ttttcaagca ccaaattatg  74640
```

-continued

```
aaccatctaa acacagtcct tttttaaaca ttttaaagtg tgttcacaat gaaaccaaga  74700
atgaattgga gaagatgttg aaatgtaatg aggagcaccc agcttatctt gcaagtgatg  74760
aaataaccac agtccggaag aaccttgaat cccgaggagt agaagtagat ccaagcttgg  74820
taataaatac tgctgagaag caggaatctg cttccttaat atttgtttct tgcagtaaat  74880
gttactacat gtgttagtta gatatttaag tgcttaattt gacttttgtc acgtgtacat  74940
ttgctgacag taaaagctta gtcattttga ttgcgtgaag agaaggaatt ttattctcag  75000
tattgctttt ttaagagtaa tgctttaatt tgtaaatgga gaaatttact ttggcaagtt  75060
caatggtcaa cagtcagttc atgcaaaatg ggatgaaacc gacctagacc tttgccccac  75120
gtcacgctgt ttcagattgc aaaatagaat ttctgtttaa aaatggcata tatatgtgtt  75180
tttgtgtgtg gtttacagtc aaatgtaact caattagatg tgagtggatt cagaaaaaat  75240
aaaaatgttg tttttattaa attggatatg accattgagt tctttctcca ttgtcctctt  75300
ttgttaatgt gagaataaaa atagtctaca ctttaggcta ctttttgctt accttcatga  75360
tgcttttttt gaggatgaat tttaaaaaat actttcgggc ccacgttttt taaaaactac  75420
attctctact gcttagttaa gatgtaagga attcaaaagc tccttataat attagcttaa  75480
gtgaacacaa ttagaaaaat aagtctagtg gggaaagcaa tcattaacaa atttcaaagc  75540
cacacaaact cttttaaaga ttatgtgcta tttatgtttc tgtacttgag ggatgagtat  75600
acttatttta aattccacca caggtcagaa caagtaaaaa aataaaaata aaattggtaa  75660
aactcaaagc agttatatac atctagcatt atttatatat tgaaaatgag atgaaagcta  75720
atgattacat gagctgtttg agttgaatgt ggatttaggt tttattcttg ttggtcccag  75780
ctctcgttaa caataagtta tattcagttt gacactttta aacgttatgt ggcacgttgg  75840
tgaatacagt aggagggatt ttctcttcag agtggtatag aagagatgtt acgtgatttt  75900
tttttaaac ttttgctca tgtcttaggc aatgaattga ctgtatgtct taattagttt  75960
ctaagaccaa gaaaacctca ggttttttaa gtgacagttt gttcagtgca ctttgcaaag  76020
ctataaaata agtagcaaag taccacgaga agaatattgc atggactaga tatcaggaca  76080
tgtgaattct agtgtatttc cattatatta gctaataata tgtcctttaa taattgatac  76140
cacttttctg acctcactta cctcatctgt caaaaggggt tgatgttttt ctagttaaca  76200
ttattattgt tttgctcaaa aaaggacaga gggtattaaa gaatattgga cactcagagt  76260
atctagtaat aaagtggtag ggatcatatt ggtatggtag cagtaaaatt ttataaacag  76320
aaaggaaatg ttgagttgct agacatgatc tgagaccatc ttaagttcta actctgtttt  76380
tagataaggc tttcaacctc tttctgcatt ggtttcctca cctctaacta ggggaaggta  76440
atacctaccc tgtctactcc acaagatgat tatttgatta tagtaacagc atttgtttaa  76500
atcattgcta atttttaagt acataaactg gtaatgggtc agagtagtag taaatctaat  76560
ctttgcctta aaaaaagtaa gtgaataaaa aaatttgaat aactatgtaa agaataacct  76620
tgcttttgct tttaattaac ttttttggta aatataattt ttgtacaact tctcagtgtg  76680
gttgatcaac atgaagaata tacagtaact ctgggctttc ttttttctca ttttagatta  76740
aggatacttg gcatcaagtt tatagaagac atttttaaa aacagctcta aaccattgta  76800
acctttgtcg aagaggtttt tattactacc aaaggcattt tgtagattct gaggtaaggt  76860
ttccaaaaac aaagagaagt atttttaagc aacagttgtc aaaatatgct taaaagtaaa  76920
ctttagctta agcattaatt ttaagtcctt tgatcatctg gggaaaaaaa gtatgtgtaa  76980
tttataaaga ataatctaac tcttatattt tcaaagatat ttgccacttt gttcgtgata  77040
cgtgcatatt atccccaatg cttataagaa tatgtgaata taaatagtaa aaaaaagtgt  77100
gaatataaat agtaaaaaaa ataaataaat aacaggaaat agtcccttat tccctgacct  77160
gtaagaattt tagttaacat ttttatgtat ttcttttcaa ctttttctgt acatagggag  77220
agagacagag agggaaagag aaagtgtgtg tgtatctgtg tgtgtaacat aaccatccat  77280
ttgcataatg gaaatcatcc tgcaaaacag tttttatcat gcttttttca ggtgtcataa  77340
ttatttcttc atatcactaa atcttgtttt aaataatcat aaagttcttg tattaaaatg  77400
attcataatt taaagtaacc cctaggtggc agcagtctga tatattttca gcattttctt  77460
acaagcaaaa atgcttttaa atatcctttt gataaagctc agttaatcaa caatcttatt  77520
taattgagac ttctaacatg ctgttctttt gttttcagta gatgaacata aatttatatt  77580
taaatgcacc taattaaaag tggcaagttt tttttgcata attttaattg tagagtgaac  77640
ttctttctat agaaacttct gtagaaagaa gaaacttctg tagaaactgc cttctgtaga  77700
ataagcttct ttttaaatac atcactttat tttcacacag ctgaatttta aaaatggctt  77760
gagtacagac tcaaagaaaa gaggttaacc taaggacgta tttaagataa acatggttag  77820
ctgaaactaa atataaatgg agggtatatg ctgtgaattt caacttacat acaatgtaat  77880
gtaatttgct actactcaag cttatttact ttgtcattag aattgaaaca aagctatcta  77940
ggtgtcagac agatataagc caaattatgc agaatttcat ggctccgtac agaaaggatt  78000
ctgtagctta tatctacagt atatgcatta ggtaaatctg agtacttttt aagcttagga  78060
catatctact ggttctagta gttgtatgtg tttacgatga tagttttcat tttaactttg  78120
catctggtaa tcttagttac ttaatatttc agttggaatg caatgatgtg gtcttgtttt  78180
ggcgtataca gcgcatgctt gctatcaccg caaatacttt aaggcaacaa cttacaaata  78240
ctgaaggtaa gccacatagg gactgcagtc ttattttgac attaaaaaat aatagtggta  78300
atatccatat ttaatagaag gatgccaaaa tacttcccaa aagtagattt attagaaaaa  78360
ctggccaggt gtggtagctc atgcctgtaa tctcagcatg ttgagaggcc gaggcaggaa  78420
aaccgcttga ggcctgtagt ttgagaccag cctgggcaac attgtgagac tctatctcta  78480
caaacaataa aataaattag ccgggcatgg tggcacacat ctgtagttct agctacttgg  78540
gaggctgaga tgggaggatc acttgagccc taggattttg aggctacaat gagctatgat  78600
catactactg cactctagcc taggtgacag agtaagacct tgtctcttta aaaaaaaaag  78660
acaaaaatta ttatttgctt ttaaaataaa tcataattgg aaaagatggg tgataaaaca  78720
taccaggagt ttattttcat tgcatgaaac tctgttggga atggactcct aggtatcact  78780
tagttttttg ggaaatctgc acttccatta aagtgtatag cttaagaata tgacattctc  78840
tgagactata taggtttcat gctgataaaa ctactgtata acagagattt tctatgacta  78900
tgaaaagtat tagcaatagt tctaacatga taaaaaattt actctccata tatataggtt  78960
aattttatca tctttattca tttataaaaa cgatgctcct caggtttttt aactttcttt  79020
aaacagttag gcgattagag aaaaatgtta aagaggtatt ggaagatttt gctgaagatg  79080
gtgagaagaa gattaaattg cttactggta aacgcgttca actggcggaa gacctcagtg  79140
agtagttctt actgccctct accttactac ctttccacct ttcccatttc catttgtttg  79200
ttgatccatt taatctcaaa cttacagaaa agttacaagg aactgggctg agcacggtgg  79260
ctcacgcttg taatcccagc actttgggag gccaagatgg gtggaaaaca aggtcagaag  79320
atcaagacca tcctggctaa cacagtgaaa ccccgtctct actaaaaata caaaaaactt  79380
```

```
agccaggtgt ggtggtgggt gcctatagtc ccagctactt gggaggctga ggcaggagaa  79440
tggtgtgaac ccgggaggcg gagcttgcgg tgagccaaga tcctgccact gcactccagc  79500
ctgagcgaca gggcgagatt ctgtctcaaa aaaaaaaaaa aaaaaaaagt tacaaggaat  79560
ttttttcttc tctgaagtat ttgagagtaa gttgctgacc ttaagtccta tcacttccaa  79620
gtaggttcat gtatagttct tagaaacaga ttttctcata gcaaccgaac attgataaat  79680
tacaatatct aattctcaga cccctttcaa gtttcacccg ttgtcccagt attatccctc  79740
catataacaa gatgttccag gctcaatacc tgacccagct tcctttttt gaagaatggt  79800
gtttagaaat ggagacctag aaattatata tgctgttatt ggaatatcac tgttccctgg  79860
tttctcagtg gaaagagcta ggaactaagt gttgtgaatg tttgtgtgtg tgcaggtgaa  79920
tatacacaca ctgacatctg tattcctaaa tcatgtgtat atttatttat taaaaactgt  79980
gagttgatgc tgatacttcc cattttaatc cagcattaca aggtttgttc tagtgttctc  80040
cctttcgata tttgtcactt gctttcctga tagaaaacgg gcttctagta tccttaatat  80100
attttcatat tttggtcagt cctcctatac gtaacccaac ttgaatgaag atatgtcctt  80160
ttccattgca gaaatgttct ttttccccag ctcggactca acactacaca ccaggccacc  80220
acatggcgcc gcacccagca ttgacacttc ttttaccttg tctgggctct gacatccgtg  80280
ccaggttgct cttcgtcatg gagtcccttt tactgagctc tgctctgacg ctttgtgcca  80340
ggtgcctctc catctcatcc ttcccacccg ctagcctctg cccgaccccca gacagattcc  80400
ttcctcacct gaagccagac catgcctttg tggagatacc ctctttaccc tgcctgtgct  80460
tcgccagcct gcaccaggcc accctcctgc acagatactc tcctcagtac tggaccaggc  80520
taccaacagc cccatgtgaa cccattgtaa cccaggtcag gcattaacac ctgcagtagg  80580
ctaccatggc ttccccttcc cacccccta gcttggccct actaataatc actttgtcac  80640
tgtttggggt tgatatttgg ttgtttcttg taggttccta gctttaagat aggattgcat  80700
actaaaattt acttagatct ttgagaactc aaggaaatca gtgaaacatt attgttatta  80760
aataaaaata aaatacctgt agttggtacc tctgtttgag cctgccttgt tacaagtttc  80820
actgacttca gcttcgtgta acaaagtatc tttttctttc aacgtgtact taaatttcct  80880
gtcttattag ttttctgata tctaaaagga aaaaaagcag atatcgttaa taaattagaa  80940
agaagttctg caaatttaaa agtgccttct aagctgagtt gtaggattac agtacaatcc  81000
atagggttat cctgaagaag ccaggcaggg ctcttctgtg ttacaccctg tgcctgcgca  81060
gcatgctcac cccttgccat cagcgcttgc ggccccattc tctccctcta gtaataatct  81120
aagttctgca ttgctttctc ctttcctttt ctttcttcct ttaaatattc ttctttcgag  81180
acatatctca ttttaacttt tattttcatt ttctgtcact tttggttttt ctcatgccac  81240
cttggcaatg tagttaagtt tgtgctaacg tagaagatta gtgctcaaat ctgaattgcc  81300
atttactact agctgtgtca tcttcggcag ggaatctccc agagccttag cttctttatt  81360
tgtaaaatga ctattatagt ggttatttct caggattgtt agaattactt ccgcaaacat  81420
ttgcaagtcc ctggttcata atttcatgct aaattagtac cgttacagga agtggtatat  81480
cattgtcaca gtgtatacaa atatatttct tttatatccc tcgtgatata attatcaaga  81540
cagtgaaaca attcaatgaa ttttaccagc ataacacatt tttaagtgat tggaaaatca  81600
taagtatctt ttcttatgtt tttagtagag gctttgcaac cccattactc tccgctccca  81660
atttgattat ttaaaggaag tggattacta actcagatat gtacactgtc aagccaagtt  81720
ctatgttcta ctgctggttt tcctgagaaa gcagtcatat aactcccttg aaatgattta  81780
ctacttttgt acatataaaa ttataatggt gttaatgtac caaataatgt ccttggaagc  81840
aagggttttg ccagtaactc agctgcatca gtcaccctca aggagatgag ccatgacttt  81900
gttcattagt tggaaaagag tctggagagt gccttttcgt tactgtttat ctttggtctg  81960
acacttggga atagggtcat ggatacttca gccagaaaac tttccaaatt taagttatta  82020
atgtattata aggatcaaag tttctagtat agcctgttca attagaacat agtgtgttgg  82080
ttgattggat ttggagaaag ggaggcaatc aaatttttac tacagtttca gcctgttaca  82140
gaatattgta tagagtgtta aaatgttgat gcattcatat ttttgccagt tttaagcttg  82200
tacgatttta aatcatttcc ttaccttgga gacttccccc ccaccttttt tttttttttt  82260
gagatggagt ctcgctgtgt cgcccaggct agagtgcagt ggcacgatct cggctcactg  82320
caaggtggtt ctcccacctc tgcctcccga gtagctgggg ctacaggcgc ccgccaccat  82380
gcctggctta ttttttgtat ttttagtaga gacggggttt ccccatgtta gccaggatgg  82440
tctcgatctc ctgacctcat gatccgcccg cctcggcctc ccaaagtgct ggaattatag  82500
gcatgagcca ccatgcccag ccctgactgc cctttaagat gagtacataa gtagtagtag  82560
tacatttttc tttcacatcc tggagaagat atactgtgtt cactattgaa atgaaaccat  82620
aaagctagag ttaggaagat tgaagaaatg aaaaaggagc tcacatgatt ttgtctcagg  82680
agaggctctt ccaggattct ttggagatat ggtagattcc atagctggag cagggaaagg  82740
acaggatgag cctgtgggtg tagaaaggaa gggagtgctt gaaagatgat gaggagatgt  82800
cagcaggtca cagaaaccct ctgaaggagg ctccaactgg ccaggctggg gacaatttgg  82860
gccccaaaat aatgacagta acaaattgta actcattgaa tgaaatagga atccatacat  82920
tggtaattat ataaataagg gaataaaacc atgatgcaaa aagggatgtt tatgtcatca  82980
cgcaaaatat gttcacagaa aatatgtact aattaaaaga gggaaaagag taactttaca  83040
gtggatgaag cctggcaatc atcactttaa gcaagtggtc agagttaata ttatcagtaa  83100
tggtcaaatc aaaaccatat gcaagaagac tctaaaatgc aagaagactc ctgaagtact  83160
tcttaccaaa gatgtagaac ttaaattcag tcataacaat acatgagaca aacccaagtt  83220
agagcacagt ctgcaaaata actggcctgt aatcttcaaa tgcatcaaga tcatgaaaga  83280
caaggaaaga gtgaagagct gctccagttg gaagagactt aaaactaaat gcaatgtatg  83340
atcctagatt ggatcttttt gctctaagga cattaatggg ccagttagtg atatttgaag  83400
gggatccgag ggttccattg tagtaatata tcagtgttaa tttttaaatt tttattaggt  83460
tgggattatt ttggaaaata ccattattca tagcgaatac aaagtagaat atttggggat  83520
gataatgcat gattacaaca aatgtttcag gagaaatatg atctttgtag tggtcttgca  83580
acttttctgt aagtctgaaa ttgtttatgc ataaaaggtt aaaaaaaggt taaattttgt  83640
ttttataact aataatggat tagggtcatg tgaaagtact ttagaggaaa tgagactttt  83700
gagaacatca tccctgaaga cgttgaaaca ctgagttacc tcatggataa tttaatagga  83760
tatgcagctg atttttctac cttaatttct tgtttgcagt atctacccat acttagaatt  83820
gtctggtgtt aaaatatgcc cactgggact ttcatgaaat tcttttgatt ttctagaaaa  83880
ttcagtttca aaggattttt taaatagata ttttaagttt ggtgtcaact tagataaaat  83940
ctgtttggag tcccagtgta agttttagta atgtgtccaa tctgtttatt gaaatagtat  84000
aactttagaa tactttcttt ggagagatga agattggtat gttatagttc aattcaaagt  84060
tgttctttct attatgatct attttataat tcataaaatc tatcttatga ttgtcatcat  84120
```

```
aagtgcaatt tgttttttgc cccattctac ctcagaaact aagtatctgg gcatcaataa  84180
caattggtag tagtgtttgc tgctaagcca agtttcacca gtacagtgtg gaattatttt  84240
attgtttttt ctgtgaacat tgtatctgct gttactaggt tattgtgagg tattgggcct  84300
tcatagaaat tgcctggaac ccttgttcac taaagcctgt tacacttttt attctctgtg  84360
cgtgtaatca gagacttatt gatactgaca cattcaaggg gcattattga tcatttagat  84420
tgctctaaga cctaaggagt cttggccgga tgcggtgcct cacgcctgta atcccagcac  84480
tatgggaggc cgaggcgggt ggatcacctg aggtcaggag ttcgagatca gcctggccaa  84540
catggtgaaa ccccgtctct actaaaaatg cgaaaattag ctgggcatgg tggcaggcgc  84600
ctgtaattcc agctactcgg gaggctgaga caggagaatc gcctgaaccc gggaggcaga  84660
ggttgcagtg agccaagact gtgccattgc attccagcct gggtaacaga gcgagactcc  84720
atctcaaaaa aaaaaaaaaa acgaaaaaca aaaacctaag gagtcttttc tccttatttt  84780
acaataaatt ccttttgatt ttgtgtaaaa acttgaaact gtttatgaat gtaaaataac  84840
atttgaatac ttttcttgtg ccagatatta ggttaaatgc tttatgtgaa ttttcatttg  84900
attctcacaa cttttgagtt aggtagttat ttttctcatt ttacagatga aatggagggt  84960
taggaactcg taggtagtag atgctgaagc tgagatttgg gcctgggtct tttcactact  85020
gtgccagaat catttgggag ggagtaaaaa ctcaagcctt tggaaaatat gatgacataa  85080
aattgtcctt tatattgaga agcttccata gttaccagtg tccttcacag ggttgatcgg  85140
aaagacatac atgttagtga tgatgataat gatgaagata atcattatta ccacaggtac  85200
ttcctataat ataagcatct ttcaaattgt atgagaactt tcatagaaca tctgagtaaa  85260
tgaacagtac agtgtgcatg aaaccactaa gcaaaccaag ggaagttaat tttctttata  85320
tgaattgtaa acatgtctct agatatcctt tatcagattc caccatgcgt aagtagtgtc  85380
taagttgccc catatttaga gtttttcaat gaggttgtgt tcctacttag aatcctaaag  85440
ttcagctata acagatatat taataaaatc tgtggaatct ttaattgagc ataatggtgg  85500
ctgttatttt aacttgaggc tttttgttga gctggattgg aagtgcaact tattagaaat  85560
tacagtgtat ttattcctat ttcttgttct ttatgtgaga gaagatatac tttagtagac  85620
tgaatacttc agagctgtat ctcatttacc aataaaatgt gaaaacagtg gtaaattcct  85680
tcacttgggc taccattgta caggcctatt ttaatggtat agtttgatat ccttaatgtt  85740
aaaagcaata tagcttaaag aggctggtaa attagaattt tccaatatcc tcagcttttt  85800
ttcctctcac agttaatttg ctctgctgac tccctacgcg aggtggcaac agctggccct  85860
tttactggag cttgtgggga ttagagagtc gggctcgcag cagcgtgctc ggcctcttgc  85920
ctctgttgac tgttctttat tgtttgatgc ctgagcatct cccagacagc gagcaattgt  85980
ttctggaaac ttaaagtttg tttctcttgg gagtagacaa tgcttttggg gcttgtcttt  86040
gtgtttcttc actttcccag tctcctctta tccttcatcc tgtgctttct cttgataatt  86100
agaaaggagc aaagatacca cctttttatt taggtctgca tgagattcta aaacttagaa  86160
gtataggcta tagatgaaag tttctttttt cagtaagcca cctcagtaac aaatcatgtt  86220
ttaaatgaaa actttgttct tcataatatc atttagtgag agaaaacaaa tgcatgagtg  86280
catttttgaa attatggtac taaaagggag cagcagcaag gtgacctaat actgccattt  86340
taaaagctag gattagaaat gtatcataac tgcttaaatc taaaaagatt ctttcactga  86400
atccaaaata tagttctaat ttataggata gttataagaa atctctatgc catgtggaaa  86460
catgaataaa aagtagtcag aacatagcta aatagaaccc tgaggtaggc agaatgattt  86520
tattcttcac atttagaaaa gaaaacatca aggtaccctg gaacttaatt tctacagtga  86580
cttcacattc cgacacttct cccatacctg ccataccctt gagtgttgtt acggatgaga  86640
atatcgtctg tgaagtagta tgagatggaa attttcctag aaagattatt gtactcggaa  86700
tttggaactg aaaagtgtag aaaggggaag tgatgtgttt aaaactgttt gcggaggtgg  86760
ggctctgcca tgtgtatttt gacaaagcta cacaggtgat tcttgccatc cccgattacc  86820
gtgtacccgc ctgcccctga gctggcactc caaagagttc tttcagtgca tagcaagaca  86880
atttttcatg ctattaattg ggataaaatt gacatacatt catttgtaga gtctgagaca  86940
caacgtcact ttggaaaatt tggtgagcaa tttgaactgc atctgcactg gtgtgttctt  87000
tttgtttctg tagacttaac caaagaaaat gaactttaaa gggactttaa aggcatctgc  87060
actggtgtgt tctttttgtt tctgtagact taaccaaaga aaatgaattt taaaggaaga  87120
gagggtgata ccaagttgta gaattctagg tatgtaggtt cagaggagat ttttttttt  87180
taagaaaaaa aaaaaaaaaa aaaaaaacac ccaatcaaga agaatagagc agggtgtccc  87240
gaagagaacg tgtgagctcg aagcatcccg gcagcatctt tcatatctca gtactgttgc  87300
tctgtttctt gggctcacaa caccatttcc tctctcctgg cttttaacac atctcgaggc  87360
aaccttttcc ctttcttttt atgcacttct ctcactgcgt ctcttctata tcatcatcac  87420
ttcaacctaa cccagtattt ttatcccacc tgcttattta ccttccttca gtgactaaaa  87480
accttactca gatactgcca gtgttgttta attgagcaga atagaggctt ctcactatag  87540
gcaactgtaa atcaatgaaa ataaccattt aaagaagaaa aacattttca tgtctatcac  87600
ggtcgatccc ttctgccaaa gtgatttggt tcattcataa attccccata cctcgtgtgt  87660
tacatattgt actgtacaca tttactgaat gttcgattgt gatcttgtaa tacagactgt  87720
tcattagccc ccttctcttg acttaaaaag ttggggggaa ctaactcttt tcatcccaag  87780
gaaactttct tctactctgt cttgccagaa agttactgct catttctctt gtagagcagc  87840
ttgcctgtgt ggcattcact cctgttctgc ccactccctt cctaatatcg tgcagtctgg  87900
ctttcatcta tatcaaaacc acttattgat agatcaccaa tgatttccta atgccagtct  87960
acccagttca ccaggaaact ttaataactt tttatgttta ttaggaattt ttaagttcat  88020
tggaatacat tcaagtactt tttggaatga ttatatgatg tagaaatgtg tatgtttgag  88080
agacagaaaa attgattttt ttttcctctt cactacagaa taaataatgt atttgtttta  88140
tggtagcaat acttgaactc tttaaggcat cttttcatgg taaatctggc aattttaaaa  88200
atctgggctt tgtaaaataa tttttttat agtaaggcag ttaacacatt aaagcaacta  88260
ggaaagatag tgaagaatta tttttacctt gagtctgtat agatgaagta ggctctgctt  88320
tgtgttggaa cagaacaaac aaacaaaaaa acctgagttg atacaaagat aaagtaatcc  88380
tcaaggaaag tcctctctgt tagagaagtg gttatttaca cacagaattc cacatgacaa  88440
cgcctgagtg gtgtggtttc caggttattg atgagaaaat cgagactcaa aatgggtctt  88500
ttagaatgaa gtacattttt catggcctaa gtctgtcttt aaaagtcacc gttgtggccg  88560
ggtgtggtgg ctcacgcctg taatcccagc actttaggag gccaaggtgg gcggatcaca  88620
aggtcaggag atccagacca tcctggctaa cacagtgaaa ccccgtctct actaaaaata  88680
caaaaaattt agccaggcgt ggtggcgggc gcctgtagtc ccagctgctg gggaggctga  88740
ggcaggagaa tggcgtgaac ctgggaggcg gagcttgcgg tgagccgaga tcgcgccact  88800
gcactccagc ctgggtgaca gagcaagact cgtctcaaaa aaaaaaaaaa aaaaaaaaaa  88860
```

```
agtcactgtt gaagaatatc aataaattag tacaagcgta aaagaacatt ttcttttcta  88920
taatattata catgctgctg gtaatcaaca ctttactagc aagtatattc ttttgcttta  88980
aactcaagtt ttaactgatt aagaataaag acaagaatgt tctctacaat aatgtatgga  89040
ttgaatttgc catttatcat tttaatgtag gttttactta tatactattg tgaaaatact  89100
cttaatgtat tcaaaaggcc agtgcacaat tttttttct tttacttctt ttttttttt  89160
tttttcttt agaaagagtg tcacttgctg cccaggctag agtgcagtgg tgtgatcatg  89220
gctcactgca gccttgaact cctgggctca agtgatctaa tacctttaaa gttgggaata  89280
aactttatct taagcgtttt tatttttaaa ttatgttttt gcatatttga tagaaaaagt  89340
agaatgtagt aattgaaaac ctaatcacaa aacaattcat tggactctgc aacagtatat  89400
aaaaaataaa attaaacgag ataggaaatc ttaagggatt ggtggattga tgcacatgaa  89460
actggtaacc tctgttaagt acagttctcc aggtagttgg agaaattagt taaatgtgaa  89520
gagaatttta attttgcact attttgtaca tttctaaact gtgtctccca cagcccttct  89580
cccccagtga gcacgattca gaattacttt gaaatgttgt agtcttaatt atcctattca  89640
tggaaatgac gaagctaata cacgatgtgc tctatcttaa aagtaacaga tatttcccca  89700
agtaacctac tgctggttgt gatgctgagg gacatttcat gggactgcat ggtcgttgct  89760
catcgtgata ccatcctcag tggttggggg attcacagtg aattctcata tcctgtaact  89820
atgcatcatg gatctatcat ctgaaaataa atcaaaatct ttgttgaact cacagtttcc  89880
acacttgtat cacccattta agattgtttc attgttacct cctgtgtaca gaatatttca  89940
tttcaatttc tcttagaaca gctcattcat ctattctcta gtttcaatat tctgagcagt  90000
agaagtttgc tgttttgatt aacttcagtt agatctcttt tctgggccaa gaattaaagc  90060
cattttatct ttagtctctc cttttgttgg cactgcttca tagactgtgt catatataca  90120
gatctgtctt tagactgatc tttaccaaag tacactactg gaatttgagg gttttttttt  90180
ttaacatcct tttcattatg agagagctag tgtatatgca ttgtgggaaa ttagaaacta  90240
tagatggcaa aattttaaaa aataattgcc accacccaga gattgcactg tagtttaaga  90300
cacttttgaa tgtggtccta gggacataat ttctggaaca catttttcgt gaagaggtct  90360
caggttggct tcttataccc acagctcgtt gtcattgccc ctagttttaa tttcccatcg  90420
ctcagtgggc tagatttttt ttcattttct tcatataaac ttatttcaga aatgttcatt  90480
aagaggaata agcagcatta gtaaaaatga aacctatggt acccattact ttatatagtt  90540
caagtattct ggaagccata ttgtagcata gcatgtactg aaaatcactc tcctttgaac  90600
agtaatccca tacctgtatt tgggacctgg ccttcctttg tgtgcttgtg tattcattat  90660
atccccttc tctcttcaaa gatgctcaag tcattctcat cttaaaacta atgggttgaa  90720
ccttccatgc agtctagtag ctactgtgaa ctctaatctc tattacaaag gttagctctt  90780
tgagtctcac ttctactgaa gttgtttttt tttcccaaga ttactgaaaa tttaagagaa  90840
aataatggcc caggcatgca ttcaggacta gaaaatactt ccatgtacag aaaaccaaac  90900
accacatgtt ctcactcata agtgggaatt gaacattgag aacacatgga cacagggagg  90960
ggaacagcat acgccagggc ctgttggggc gtggggggcg aggggaggga acttagagga  91020
cttaagtgca gcagaccacc atggcacacg tatacctgtg tagcctgcac attctgcaca  91080
tagagcccgc ttttgttttt gtttttgttt ttaagaagaa ataacgggga aaaaaaaggt  91140
ttcaaaactc ataaagaaag agaaagagag ggagggaggg agggaagaaa atgcttccat  91200
gtaactgcat catttggtac tttggagtcc atatcctact tgaaactcta ggatctggcc  91260
ctcacattta tgtagtgctt tattttacag tttacaaaac ttctgcttgt ccatgtgtgt  91320
ctgtaaagtc atatgaggca ttatgcccat tgttcagata gagaaattaa cgttcattga  91380
cataaatggt taagcccatt atgtaaatat ttatggcaaa gctggggcta atcatatgtg  91440
ttacagatag gacttttttt aaagaattgt ttaggtattc tgttcatcat tagtctctgg  91500
gtttgtgttt gtggtaacca tagacaacca agttcatata atttggcttc ttttttatgt  91560
gatttttgat acgtgttaag gatctataac aatgaatttg cctcctaaag aggtacataa  91620
tgttttcatt cctccaaaaa gataattcta ggtttataaa tctatgtatg ctcagtgcca  91680
gttgaatttt gtgattgttc aatagaaaag aaattgtgac ttaaaggtga ttttccagtt  91740
taatggaata aatgaaatta gtttagaagt tatttttatt tttctgagcc tgattctcac  91800
tcagttgtga taaacagcac ctctgtaaga taaactcggt gataaaccga gaacttctga  91860
aatcagccta acatgaatac ctgttcttct tgtgctaagt ttcataatgc tttatcctaa  91920
tacaccattt ttttaagaaa tggaacttgt atttcatttt tgctttcatc tcacctaatt  91980
cataatttta ttaaaaccta cgatttttaa tttctttttt tatgaatttt tagtttggtg  92040
tataaatcag aattacattc tctgatcttt tacttttaaa attacagtga tgaactgact  92100
gtttaagaat cattctcatg attcattcgt ctgttatgcc tccttttttaa agcttcagca  92160
ctgaaggtct tttgacaaac caatatttat aacagtttga cagcaggatg aggaacagcg  92220
tttgtctttg taacagcttg aagaaagacc ctttccagga cccagtcatg cagttacaat  92280
cttgacctct ttcttatgct gggaacatgc atacagcagc acctcccatg tgtttcttg  92340
tcccattgac tgtccattca cttcccatct gttttgcagt cttaaaggaa cagaaggggc  92400
cttcttataa atctgtcttt gcaggtgata aatgatgcct acctctttaa gagctgcctg  92460
ggtggtttc cttttcttag aacatttctg ctttcctcct aactaaatca gggaaaaata  92520
caattttagg aataagagaa aaagaagaaa agatgaattt ttaaagcatt taattgacta  92580
agaatatttt actgatcttt tttaatcttc ccaattaatt gcctaaatca tattttttaa  92640
aatgtattat cgatatttag atttttgtca gggagtaaaa tgaatgtatt cattttgaaa  92700
taatgtaact ctttttgag aaaacaaagc catgtatcat taatgagtta acatataaaa  92760
taacttttta agttttttgt gataatttaa gtgtggagca tcttatgtat tggatacaaa  92820
agtaaaatat ttcagagtaa atcattgtaa tcttatggta aaatctattc atttttaca  92880
tttaaaaaga tgatcataaa tcccataaac atttatgctt ttacttctgt tgctgaaaat  92940
aagtattgta ggaatagata ttgatatcat tgggttttct aagaattcag cagaaataaa  93000
aataatttac tttttctccc atgcagaaat tatttatgca aggttttatg taacaaatat  93060
tgtccctcta tggccctgca gaatattctt aaattactga tttaaaaact attaccagta  93120
taaaatgacc actttagaa tattgtggtg tattatgtga atcagctggc taataatata  93180
tcttctgtgg actagcttgt tagtttgttt attaattccc tggcatattc caaaaggaat  93240
ttgaggcagc ttacatatat cctacgcaaa agataaaact acttaagtga aaaatttggg  93300
ttgaaagaaa aggaaaatcc aggcaagtga aataaagtaa actttcagat aaaattggtg  93360
cccctcaaag tgcatgctca agggttctac gtacaggcag acctcattgt attgcatgtc  93420
actttattgc acttcacagt tattgcattt ttaacaatag aagttttgtg gcaaccctgc  93480
attgaacaag cctgttggca ctattttccc aacagccatg tgctcacctc atgtcactgt  93540
cacattttgg taattcttgc aatatttcaa atttttccat tattattctg tctgtcatgg  93600
```

```
tgatctttga tgtttgtatt gtagctattt tgggtaccac taactgtgcc catattagtc  93660
agtgacctta atcagtaaac gtgtgtattc tggctgttcc accaactaga cattccctgt  93720
ctctctcctc ctcttcaggc ctccctattc cataggacac aacaatattg aaatttggcc  93780
agctaataac cctacaatgg cctctacatg ttcaagtgaa agaaagagtg ccatatttca  93840
ctttaaatca acaactagaa atgattaagc ttagtaaagg aggtttgttg aaagccaaaa  93900
tgggctatta gccaaattgt gaatgcaaaa gaaaagttct tgaaggaaat taaaagtgtt  93960
attccagtga acacacgaat gataaagcag aacagcctta ttgcctgaga cgcaggaagt  94020
ttcactggtc tggatagaag atcaaaccag ccataacatt cccttaagct aaaacctaat  94080
ccagagcaag ttcctaactc tattcaattc tccgaaagct gagaggtgag gaagctgcag  94140
aataaaattt gaagctagca aagtttggtt cataaggttt aagaggaaaa aagccattct  94200
gcaacatgaa agtgcaaggt gctgatgtag cagctgcagc aagttatcaa gaatatctaa  94260
ctaagataat tgatgaaggt gattatacta aacaacagat tcttgatgca gatgaagtag  94320
ctgtctattg gaagacgatg ccatctagta atttaatagc tagagagaag tcaatgccca  94380
gcttcgaggc ttcgaaagag aggctatccc ctcattttgg gtgccaatgc agcaggtgcc  94440
tttaagttga agccaaccta aagaatttac cattctgaaa atcctagggc ccttaaggat  94500
tatgctaagt ctatcctgct tgttttctaa aagtggaaca aaaagcctgg atgacagcac  94560
atctgtttac agcatggttt actgaatatt ataactctcg agacctgctc agaaaagttt  94620
tctttcaaaa tattactgct cattgacaat gcatctggtc aagcaagagt tctgagggag  94680
atgtacaagg agatttatgt tgtttttgtg cctgctagca caacatccat tctgcagccc  94740
atggatcaag gaatactttc aaccttgaag tcttattatt ttaaaaatac gtgtcttaag  94800
gccctagctg ccatagatag tgattcctct gatggattta ggagaaaaaa aaaggaaaag  94860
cttctggaaa ggactcacca ttttagatgc tgttaagacc attcaggatt catgggagga  94920
ggtcagaatg tcaccattaa cagtttggaa gaagttgatt ccaaccctca tggatgactt  94980
tgaagagttt gggacttaag aggaggaagt aactgcagat atggtagaga cagcaataga  95040
actagaatta gttctgttgt aatatgataa aacttgaaca gatgaaacat tgctttttat  95100
ggacaagcaa agaaagtggt ttcttttttc tttttttttt ttttggcagt ctcagtttga  95160
agaaagtggt ttcttgagat ggaatctgtt cctggtgaag atgctgtgaa cattgttgaa  95220
atggcagtaa aggatttaga atattacata aacttagtag ataaagcagc tgcagggttt  95280
gagaagatag tgtcccaatt tttaaagaag aaaaatttga gtaaatttgg gtaaaattta  95340
cccaaaatta cctattgtgg gtaaaatgct atcagacagc atcacatcct actgtgaaat  95400
ctttcatgaa aggaagaatc aatcagtgca gcaaactaca attgttgtct tattttaaga  95460
aattgccata gccaccgtaa cctgcaacag ccaccaccct gatcagtcag cagccatcaa  95520
cgtcagggcc agaccctcca ccagcaaaaa gattatgact tgctgaaggc tcaggtgatc  95580
cttagcattt gttagcaata aagtactttt aaataagtta tgtacattgt ctttttagac  95640
ataatgctat tacacactta atatattaca gtatactgta aacgtaactt aaacgcaccg  95700
gaaaaccaaa aaaccttatg tgactcactt tattgtgata tacgctttat tgtggcagtc  95760
tagaaccaaa cttgcatatc tcccaagtat gctgggactt tgctagaggt aagctgcaaa  95820
tttagccctc agtttcctgg tggctggcag ttacaaaatg gaaagcagag gtcattccat  95880
cattcatggt ggccatcaga caacaacaca gcagttgctt aggagaagca tgggtcttct  95940
tcgtacgcac aactgagaga aatttccctt aaagtggaca ctgagttaga tgatacaatg  96000
aatctaatgg ctacacataa tcatgaaaat catggggccc tttattgtaa tgtttctcat  96060
gcgggctaac atgcgtagtt ctagggaaaa tatgatgctg tccaaacata cagctatttg  96120
gtttggctta tctaaagata aaatacatag tatccagaga aatagatgaa ctgtatgtcc  96180
tccatacagt ctcccataaa tattatttct ttttgcagct gatcctttta gtaaatatca  96240
ggtagccaga agttcaagat tttacactca ttgacattga caagcacctg gaatggtact  96300
accttttttt tttttttttt tttttgagac agagtcttgc tctgtcaccc aggctggagt  96360
gcagtggcat gatcttggct cactacaacc tccgcctcct ggattcaagt gattctcctg  96420
cctcagcctc ccaggtagct gggattacag gcgcccgcca ctacgcccgg ctaatttttg  96480
tatttttagt agagatgggt tttcgccatg ttggccaggg tgatcttgaa ctcctgacct  96540
catgtgatcc acccgcctcg gcctcccaaa gtgctgggat tacaggcgtg agccactgcg  96600
cccagccaag tactattttt attagttaag tcagagccat aatcattata actgagctga  96660
aattagaatt gccatccact taagaaagtt gagtggtcta acaagtataa aagcctaaat  96720
ataaggctaa ttcatgttca tactgaagcc ttttggggaa taggccttaa aatatgtaga  96780
aagtatttga agcggtttta attgtactag ccaaaaggag cctagtagaa atgcttgtgt  96840
tataagagtt tattttttaa aaagctgaat ttatctgacc aggcgcggtg gttcacgcct  96900
gtaatcccag cactttggga ggccaaggca ggtggatcac gaggtcagga gtttgagacc  96960
agcctagcca atatggtgaa accccatcac tactaaaaat acaaaaaaat tggccaggca  97020
tggtgatgcc tgcctgtagt cccagctact ccggaggctg aggcagaaga atcatttgaa  97080
accgggaggc ggaggttgca gtgagccgag attgcgccac tgcactccag cctggacgac  97140
agagcgagac tccatctcaa aaaaaaaaaa agctgaattt atcaacaaat tgctgtggag  97200
tttttatat attcagcagg catcagttgt aatttacctc acagactttc ttaaggttgc  97260
tttctttcta aattatactt tatgggggtc acaaaatagc aatttttaaa taatcacctt  97320
taatgattaa gtattgttta agtcagatca ctcaactatg aatgcatgaa tattcatgga  97380
catctattac atagcaagca gtgctatgct gggccgagtg attttaaatg acagactttt  97440
tggtaagtag agaatttacc caagcagtcc ttgctgttct ccacattaat gctcagaaaa  97500
aatacattat aaaaatgatc tttccaaaat gaattatgaa gccccatgag aatgatatgg  97560
caatttgtgg ttacatattt tactagagga ttaatatcca ataaataaaa agatactaag  97620
gaataaacaa aaaaaattta aaagatgaag tatataatga attagaacaa tacattttaa  97680
tcataagttt taaattagtg tggactttga attctcctgg acagattcct tcattttata  97740
gataaagcta ggactgtgac ttatccagtt atgaggttaa cggcgaatac aacattgtca  97800
tatattttaa atgacacaca ttacaacatg ttctctgctt tataaaaatc atatcaaata  97860
attgccccat agattattaa aggtgttaga ctagggattc ttaaaaaaaa ttttcatcaa  97920
atgtttcttt cattattaat cccatgaagt ccatgttaca gaagattttg tctacaacag  97980
tgcagttaca ttcttctcgt tagaaataca accaccagtt agagttccta atcagtataa  98040
ggaagtagtt gttaggagag gggatgggtt tcttgtccaa atgaagtttt ccatttgagt  98100
ttttgaagta gtgaaactaa cccagcgttt acaggcccca gaaatctggg aacctcagct  98160
ttcaaagtac tgtaccagtc tttaacagtt ttcctggacg tgtgaattga tgcctccttc  98220
tgtaacatgc aggagtgttc tgtctgtctt cattgagtgt taaaaaataa tcatgcctat  98280
ttcaaggaaa aaatctacag aactaagatg cagaagataa gtgctagatt taatcatatt  98340
```

```
ccttcatcta tctgtttggt tcaacctttc atcaactaaa agatgcacct tttttcttgt  98400
gctaactcta agattttagc tacagttttg agaatcttga gtgtagtctc ttgtttacct  98460
tttttccttt ttttgtttcc cccacaccct agattcattt aaatactgaa cttctaaagg  98520
gcaagtatat agtgtagttt aataaaaagc aaaccttttc atgaacaata tatattacat  98580
aataagaagc gttcctttac ttttcagtac tctagtgaat agctttctac agtagaatct  98640
cacttagagg gtgtcttaaa gcttaacacc aagtgctcag gcagcatgtt atacaacagt  98700
tccattaagg tacatttgga tctttggatg tgtggtttgc ttaaagtaca ctgcattagt  98760
aagttggcag cttgctttct ttaaaaacat caaaagtttt aaaaggttta tttcagggca  98820
tgtgttagtg ttttgtgtgt ggttctttgt tcctgttcta aactgttatt aaccactgaa  98880
gtgaaccttc tcccgggttt ggccttttgg tattcacagt gtattcaaaa cctaattaca  98940
gattagtcta tatttgagac ttttagagca agtatcagaa gacccaaaaa gaaaatgaga  99000
gtagcagtat catttcatgt agagataaag agacccaaaa catgaatggg tgtcaagtca  99060
gctgaagaaa agaaaaaaga gaaggaactt cattcactga gacggtttat gagttgggga  99120
ttatgggaat attcatgact caatcaagaa gcacagtgaa ttgatgtttg aaatagctca  99180
tcttttaagt aaacattgga taaatggaaa gtagactcag tattcactac acgtagaaat  99240
agctatttct gtatagcaga aatagcagtt tgttaatccc ttcctgagtt ggtttaattt  99300
accaagtaaa tcacaaattt tattctttat ttgtgaatat ttaattcaaa tatttaatgg  99360
aaatatgagt ttgctttata attagtcatg ctgatccata cacgtatttc tgagagaaag  99420
caatttctaa tggtgaaata gttacaataa tatttttgaa atttgaaagc accgtgatac  99480
tgaagcatta atctgaagga tcggaaagta gggagttttt gttgccaaca tttaacttca  99540
ttgtttatgg ataacttggt tttctgggca gccagatggc acagttagta tacagacatt  99600
cttggaaact tgtatcaaaa tttaaaatga atgaatttat gagaaataat tctgcttatt  99660
atttgtaatg tagctttctt gaaaagcaag aaatcggaat gtagtttcta aagctgcaag  99720
tgaatatgta tacatagcca gctctttcag ccttgataat aaggtgcaac cattaagatg  99780
aagggatttt tttttcccac ttgtgttttt gggcccgagt atcctgatct gtgttgcttg  99840
tctggttcag gtgtgagcca ccagctttct ttgactttca ttatctatgt gtatcttgcc  99900
tcctgttccc aggcttgctc tagctcttct gatcctgtct tcctccctct tgatcactag  99960
tgtagtattc atgaagccag ctaagttagt ttttcccttt gaaaaccaca gcccttatct  100020
tctgtgccat attttgggca acttcgttta tcattgattg accgtacgca gtgatcaggc  100080
cttgttctag acactgaaga ctctgagcat ttttgggccc atttgtact cctgtattgt  100140
tctccagggg cttctccaag tgtgcgtcaa tttagtcttc tcaagagggc atcattttca  100200
tcagaatatg atagcatatt atggagtgtc cggtcatcct taggcataga ctacttagga  100260
ggtgtaactg ttttgttccc tgatttttac tgaaatgggt cttttctttt tttttttttt  100320
ttttttttt ttttttttt ttttttttt tttgagacag agtctcgcta tgtcaccagg  100380
ctggagtgca gtggcatgat ctcagctcac tgcaacctcc gcctcccgat tctccctgaa  100440
atgcgtctta ttttaagtca aaggtaatac ttaaaaaaga ccaaagagac ttaaaataac  100500
agcatttgct tcgtcactat gagctttgtt attatgagtt aacatacagt agcagactgg  100560
gtgtagtagc tcacgccctg taattccagc agtttgtgaa gccgagtggg gaggattgct  100620
tgaggccaag acttcgagac cagcctgggc aacatagtga gaccccccatc ttgacaaaaa  100680
aaattgtttt aaattagcca ggtgtggtgc tgcatgcctg tggtcccagc tacttggaag  100740
gctaaggtag gagaatcgct tgagcctggg aggtcgaggc tgtagtgagc cgtgtttgca  100800
tcactgcact cctgggtgac agtgcaagac tctgcgtcag acaaacaaac atcgtagcag  100860
atgtgtttct taatcagaga agtgtagaca aggctaactc caggctttaa tgtcctcata  100920
tttagcaatg atacctgcaa ggttgtatga gaaccaaatg aaacgccaaa tttggaaata  100980
catagtagat acatcatagc agagtaagcc aggaatgctt ctcaaaggta ggatatcatc  101040
tgtgtcctca tatcacttta tgaagtacat tgtgaaagtg aaagaacaaa gaaataaatg  101100
ttttttagtt aatgtttaaa ggatacattt atcataattg ctcttttaac actcacctcc  101160
agtctcccct ccgttcacac ctcctacccc cattacttcc tggtaactta gttaagtgtc  101220
ctttgtcatt cctgaggttt caaggcatgg tagtactgtg tcctgatatt ctaatcgtaa  101280
atatttaagg gaaattcggc attttttcat tttgtggttt tcatattaaa gtacattaaa  101340
tagtcttttt gcttttattt aggaaaaaaa ctgcttacct gttaatttta gaaaaatctg  101400
attttcattt agaccttaca gggtgagaca cctgcatcag ggtggctctt ggtatctttc  101460
aattcaattg gatcttctct gaatagtctc ttgtagggag tgaggctgct gtaccacctc  101520
cctgcagtag tccatccagc ttaagatggg ggtcaccagt aggccaaaag aatgggtaga  101580
cctggccatg cactgcccta ttgtactcaa atcgtgtatc aaatggagtt ggatttcttc  101640
tcttcataca gtacagcatt tccaagtaga aatatttctc aatgaaatgt ggagagaagc  101700
acccgtttga gattcccgtg tgttgtgtga tttaagttag atggtttttt aagaccacat  101760
tcatttccag cattctaggt aacaatttag aaaatgtctt tctcctaacc tccccacttt  101820
ttaaaaatcc tccaactgat gaactgatgt gaaactttct tacattcact gaaaaaaaaa  101880
aaaaataggt taagctgttt ctaagcaact agatgaatta atttttaaac taagaatgtg  101940
gccttatttt gggaaaacaa gaatatttac ttgtttgtct gctgtttaaa aaatggaagt  102000
cagcctacca aaaaattgag actcaacttc taggagatgg gttaggattt ttttttttaa  102060
gtttctctag tttaatttta tatataaggg gttaatgcta ccttcataat aactattatc  102120
atattttctc aatacatagc ttgattaaaa caactggact cccccccccac cccaccccac  102180
acacacacag attttatatc agtctgaatc taatgcctag aataagaagt gcttcagcca  102240
ggcatagtgg cactcacctg tagtctcagc tactcaggag gctgaggcag caggatcaat  102300
tgagcccagg agtctgagtc tagcctgggc aacatagtga gacctagaag ttttaaatta  102360
ctggaaaaat aatatgaaaa gaataaatta ctggaaaaag aatatgaaaa tgttacgttc  102420
tttatatcca accgtggtag gctttttgga gttcctgcaa tgctaataag aattcataaa  102480
aaggacaatt cttcattttc ttgggtactc atcactaata gctgcctcgc tggtaaaaag  102540
gaatacatgt atcttcaatt gcagattatt tacttttaaa tataaaagat ataaatgtca  102600
aatattaaat gcatcttaca tggttttcct acatagtgaa agtagaatgc ttgccagttt  102660
tgcctctagg tcactcactt tgaaccagcc aacccacctt aattgatcat ttccactaat  102720
atgttaaatt accttaaaag aacaaaaata tttatcatgc ttactataac ctgtgtttta  102780
aaataggagg ccaggcacag tggctcacac ctgtaatccc aggactttgg gaggccaagg  102840
caggaggatc acttgagccc aggtgttcag gaccagcctg ggcaacaaag tgagatccta  102900
tctccacaaa aaaattaaaa ataaaaactt agccaggcgt ggtggcacgt gcctgtggtc  102960
ttagctacgt gggaggccaa ggcgggagga tcacctgagc tcaggaggtt gaggctgcag  103020
taagccctgc caacaccact gcacgccaac ctgggcgaca gagtaggacc cccatctcag  103080
```

```
aatataaaat aaagtaggag gtgcatgtga agtagtatag atcatgactt ttccaatttt  103140
aagaggggat tggcatgtac tatgagcagt tcacatttgt ggaggaaatc tacatttcag  103200
agagtatata tttcatttgg aagtctataa acatgaaaac ctaaaataaa taatgtaaat  103260
ctacctctag tggctctggt atttttaaac ttatttatag ctggcaaagt actttttttgt  103320
atgtattttt atagcaccat tgcacttctc atgtttgttg caagcatctc ccacagcttc  103380
ctttgtcttt taattttatg acatataaat aaaagtatac atttcaatat ggccatattg  103440
attgatcttt tcctttgtaa ctcttactac tttatattta aaaagtcatt tcccagtcta  103500
aggccacctc tattttcttt tagtttttta aaatggtttc attgttttat atttgcctat  103560
gatccagaca ttagtaactg tgggttctta attgggcttc agagaatctg agaattcctt  103620
aaaattctct acataattgt acatgtactt aatacatgct tttttccatg ttaagagtcc  103680
agagtttttg ttagatcctc aaaggggtca gtcagtctct cctcccactt ccaaaaaaatg  103740
tctgagacct actactataa tccatctgga ctttatttgg gtaaaaggtg gtatggtgag  103800
actcatattt ttctttttcc cgcaaatagt taagtatacc aaccatttag taaataatta  103860
cctcctgatt tgtgatacct ttgaaaaata aatgtttttc tttattttta tctccacaga  103920
gaaagttaga gaaattcaag aaaaacttga tgctttcatt gaagctcttc atcaggagaa  103980
ataaattaag tgagtaaaaa ttctctaact gtattggtgc tgactaaata caaaattaca  104040
cttttcttaa tagtttatca ttctgcttca tttacatcct gcttgtcact tatgctgtaa  104100
tttcaatggc atgaatctct gaaactagct tccgaatttc atttgtataa cgttgctttg  104160
aataacttga ttgccttctg gctgaattaa gaatatcctc tagaactcat tttgaataga  104220
acaaaggtga acacagagct aagatattgt ataatatgca ggtgactcat tttctaggtg  104280
taaagaattg agctgtagtt gacattactt tattcttctt gcctatagtc tatcaataat  104340
gatgtgtatg ttaaatattt aacttagaaa gttttctgtt tgacttaatt aaaattttaa  104400
taattgttct taatccttat ctcttttgtt taaaaacatt tagataagtg tttttcctac  104460
ttaatttata tagccttaga atttagtact ccttgaattt actttcttgt ctgattctgc  104520
tttctggcat tagaggcatg ttcctaataa aatacatatt taaggacttt tccttagtag  104580
cataatcaat taattgttgc tgaagaattt taatcagtaa gtcacttgct tgagaggaga  104640
cctcgctctg ccacccaggc tggagtgcag tagtgcaatc actgttcact gcagcctcaa  104700
cctcctgggc tcaagcagtc ctcccacatc agcctctcaa ggaactgggg ccacaggctc  104760
atgccaccat gcccagctaa tttctttaat tttttgtaga gatggggttt caccccgttg  104820
tccaggctgg catttgcttt tataaaagaa gttgaggaaa gaaaaatact gtagttaagt  104880
cattatcact tcaaatattt tgtcactttt gtctgtgacc cttaccctac agacagcctg  104940
cagcaggctc agaactagaa ggagtagaaa tgtaaaaggt tccctccctg gctacgctcg  105000
gttcaggtca gttcagaaaa ggctcttaaa ccaaactacc tactttcctg tcaggaaaat  105060
gtatttgaga aagcagggtg gaaagggaag tacaacttcc atggtacatc attcggaaca  105120
gtgtgccagc aaaggaggag agaaacaaga cctagaaaac ttgaaaataa agctttgtaa  105180
ctttatttca tttgtttctt tagtaagtta agacaggcca gtgcggtggc tcactcctgt  105240
aatcccagca cttagggaga ccaaggcggg cggatcactt gaggtcagga gttggagacc  105300
agcctgacca acatggtgaa accccgtctc taataaaaat acaaaaattg cccaggtgtg  105360
ctggcacatg cctgtaatcc cagctactcg ggagcctgag tcaggagaat cacttgaacc  105420
tggaaggtag tggttgcagt aagcagaaat cgtgccactg cactccagcc tgggcgacag  105480
agcgagactc ttgtctcaaa aaaaaagtga agacagatat atggaaatat acaaaaatac  105540
ataatcatct ttaacacaag ctaaacataa tttttgtgtt ttataagtgt ccgtgttcat  105600
aaatgttttc tatgtctttt gtgtatgaat attttatttt aaaaccatta agtgttacaa  105660
tatcacccta atcatggtgg ttaccgtgaa tacttactat tagaaataaa catctgtagc  105720
gcctccttga tctccccttt agcaccagag cttacatcat agttctattt actgacctgt  105780
gtgtgctttg cggggaaaaa ttgatgaaag ccccggaagc cccgttaaaa agacaagctg  105840
tatttctgtt tttttaacaa aatgaggaag ctgaaagcca gccagtgttt tacataatgg  105900
tgtctctccc ctcagctgat cagtgtgaca tccagagttg ctgttgctgc tacctgtcta  105960
gtctctaaga ccctttttcaa cccttgtgac ttaagactct gtgaactttt acaaagtatc  106020
ttgtgatctg gacagatgat ctgttttgta ccctgcagat gcatttaaaa gaataaatct  106080
ggcagaatgg taaccttgct tcattctgac cattttatca aagttaccaa ggaccctaag  106140
gaatactttc tcaagtatag ttttaacaca taggattcct aattaattgt tattctaata  106200
tttgctgaag gtgtttatat gctatacagt catacacaga ttcttcttca attaatttta  106260
gtatatgctt ttaacttatg tttgataaaa aaattatgcc aatattgtta ggtcggtgat  106320
agactatata agtttagtaa aactagcaaa ggtaagcggt taggcttcaa cattgttgtg  106380
atcatgcagt catcaacttt gtttagaaat tttgcattta tctcccctga cctcagtttg  106440
ttaaatgggt ttatttttac agaatcgtac tcataatcag ctctgcatac atctgaagaa  106500
caaaaacatc aacgtctttt gtccagcctc tttttcttct gctgttccac ctttctaaac  106560
atacaataaa gtcatgggat aaaaataatc gatgtatgtt acgggcgctt taaccatcag  106620
ctgcctctcg aatggaagaa cagtggtaat ggattaacat cctattttgt tgtactaaag  106680
tgacaaatcg gaataatata attggtatgg ccattaggtt cagtccttga agataagaaa  106740
cttgttctct gtttgttgtc ttatttgtgg tggcactcgt ttaatggatt aactgaggtt  106800
gctcaatgtt cagtttcttt tccagaaata caatgctagg tgttttgaaa taaaacttat  106860
atagcaattg tttaaagtta tcaattgtat ataaaatcac agtagcctgc taaatcattg  106920
tatgtgtctg tagtattcta ttcccagaaa ctatttgacc atgataattc agtttatatt  106980
caccacatga aagaaaaatg ggtaacagaa gaacccttaa aacaggttaa tttggattgt  107040
aacgttcagt gaaagaaatt tcaacccttc atagccagcg aagaaatttg ccttggaagc  107100
caagtcagta ccagcttacc tatttgattc agttgctgtt ttctcactct ctatatccat  107160
ttgaaattga tttattttag atgttgtata cttacgttag gctttctgtt aatagtggtt  107220
tttctcctgt tgacagagcc accggattat gacacaggat gaggaagatt aaggataatc  107280
aattgactaa tttcatttag aatattatca aacatttcaa ctaggtatca gaaaaaggct  107340
ttctttcata agactatttt aaatagaaat tatttcaaca attaaagtaa tgttgaccat  107400
ccccctctca gctgaataaa gaaaaattta gttcaattta ttgcaattta attacaatac  107460
taccttcaca acattttcat gtgttttaaa taaatatttt ttaattggct aaaggacatt  107520
caagcaaaga aatgctttct ttacttaaaa tgtctatctc atttgctgcc ttttcactaa  107580
gcctttactt tgttaataaa agtgtccatt gtgtgatgtt tttgatttta cagtttgcta  107640
aatcttattt tcttggagtt gctttttggt aacagcccca ttgctactcc ccattttatt  107700
gttttacatc aatgcatgct tcgttgtgat ccctcaagat gtaacacttg gtatgctcgg  107760
ttgaggatat gaaaaaatac ttccgaaacc aggaattcaa tgtatgtttg ttttatactg  107820
```

```
tttgataaga aaagtaggtc cagccttaag cagcacagat gcgctggtag atgcatagtc  107880
aggaactttt tttatttctt ttaggtctag ggacaggagt gaatagaaag ggaggagagc  107940
tctattatgt tctatacaca gattaggaga tgaccttact gggtacaccc ctctaaccag  108000
tgcttacagg ttaatgcatg ttaatgaata tttttgcagt tgtaaagcat aacaattaca  108060
actacacatc tatttctaaa gaataaaaca ggaccatatt tatttacttc tgtcaactat  108120
agaaagaaag accttcagct gtatttccac agatttctcc caaggaaaag gctaatatta  108180
gtcactactg ttatcacatc cctttgtata agttttaaaa agagatggag ggagatcttc  108240
atttctttga ggagatcagt attgtaacgt atgtgaatag atgataacaa ttaatattac  108300
taaaagtccc acatgagagt cctgacgccc tctccatgcc ccacagtaat gtggcttctt  108360
tcatgggttt ttttttcttc tttttagctg atctcatcct aagcatgctt tatttttcct  108420
tgaaagctag gtatttatca actgcagatg ttattgaaag aaaataaaat tcagtctcaa  108480
gagtaaaccc tgtgtcttgt gtctgtagtt caaaagtcag aaatgattct aatttaaaca  108540
aaaagatact aaatatacag aagttaaatt cgaactagcc acagaatcat ttgtttttat  108600
gtcagaattt gcaaagagtg gagtggacaa agctctgtat ggaagactga acaactgtaa  108660
atagatgata tccaaactta atttggctag gacttcaatt ttaaaaatca gtgtacctag  108720
gcagtgcaca gcacgaaata agtggccctt gcagcttccc cgtttaaccc actgtgctat  108780
agttgcgggt ggaacagtca acctttctag tagtttatga tattgccctc tttgtattcc  108840
cattttctac agttttttcc gcagacttct ttctgcaaat tattcagcct ccaaatgcaa  108900
atgaatgata taaaaataag tagggaacat ggcagagagt ggtgcttccc agcctcacaa  108960
tgtgggaatt tgacatagga tgagagtcag agtataggtt taaaagataa aatctttagt  109020
taataatttt gtatttattt attctagatg tatgtatctg aggaaagaaa tctggtattt  109080
ttgctttcca ataaagggga tcaaagtaat ggtttttctc tcagttctct aagctggtct  109140
atgttatagc tctagcagta tggaaatgtg ctttaaaata tgcttacctt ttgaatgatc  109200
atggctatat gttgttgaga tatttgaaac ttaccttgtt ttcacttgtg cactgtgaat  109260
gaactttgta ttattttttt aaaaccttca cattacgtgt agatattatt gcaacttata  109320
ttttgcctga gcttgatcaa aggtcatttg tgtagatgag taattaaaaa atatttaaat  109380
cacattataa ttctattatt ggagagcatc ttttaaattt ttttctgttt taacgaggga  109440
aagagaaacc tgtataccta gggtcattat ttgaccccat agtataacca gattcatggt  109500
ctaacaagct ctcagtgtgg ctttttctctg aatgcttgaa tttcacatgc cttgcatttc  109560
acagttgtac tccatggtca accggtgctt tttttcacat cgtggtactt gtcaaaacat  109620
tttgttattt tccttggtaa aatatataaa aaaggttttc taatttcact ttgctgccaa  109680
ggctgtcatt ttcattaatg ctgccaacat gttcatatga ggcttactaa gaagttataa  109740
ctaagcttta gaactggaag agactttaat ttcatctacc atctgattat aaactcctgt  109800
tactcacttt gttattcctc cagaactttg ctcataaatg atacctacta attgtcgatc  109860
attggatatg tcaagttagg tagcgtatag gtgtgccttc ttaattcctt cagaagatgc  109920
agaggcaaga acatgtttca atcgtgttag cattggtttt ctttatcagt gctaacagac  109980
tcagtgtgag gccccatact ttattttaaa ctaggtttc atccttgtgt aattcaagtt  110040
cagaatcttc gtgtatcaaa acgtttgaag aatttagtta ctgaagattt aatagagcaa  110100
ttaatttttt tagcatgtct gattgaagaa ttaatatatt tatcaaattg aaatagctac  110160
catgtgccta tagataatac agatgtattt aattatgaag tacgtcttaa aataaccaca  110220
tacccgattt gtgataacta aaacaatcat gtcctgcaca tattagaccc agttaataag  110280
tgtagaaaac ttaagtgttc aaacaaatac tacaaaaatt gttaaaggtt caaaaccagg  110340
agacagtatc aggaaggctt aaatatgggt gatctctagc tggaagaaga cagcttctaa  110400
aactaagggt aggaaaaacc tatatcataa ggcatttgtt taaatttata tcctaaaatg  110460
acagaattga gcttgaaaat tgagagtatg tatgtgattc ctctccaaga cttctcgtga  110520
gttacgtaca tattctgcag aagccgcgtt aaggtgcatt tgtggccaag tcactgacaa  110580
ggaggtaaat actacttata aatgctgtta aatgaaaatc tttttttttt tttttttttt  110640
tttttgagtt ggagtcttgc tctgtcgccc aggctggagt gcagtggcgc gatctcagct  110700
cactgcaagc tccacctccc gggttcaggc cattctcctg cctcagcctc ccgagtagct  110760
gggactacag gcacctgcca ccatgcctgg ctaatttttt gtatttttag tagagatggg  110820
gtttccccat gttagccagg atggtctcaa tctcctgacc tcgtgatcca cccgcctcgg  110880
cctcccaaag tgctgggatc acaggcgtga ttgttactct ttgtgataaa aaattcttgt  110940
tcctgctgtt agtactttta attcattaac ccaggtgtaa actgttcctt tccaagtatt  111000
tgggaaattc agagatctgt ttttgaaaaa actaggccag aggcacccct gaagatctag  111060
tcacagtgca gtgatactgc cagcagcccc ccacagagat atgtcttacg gctgtattaa  111120
gaatataagt tacactcttt aatgttcaga acagaatact cattctgctg cttactcttg  111180
tagttattaa atcacagagc aacaatacgg aagttagaat tttatccatt tgtcagaaaa  111240
tatgctcatg gtttatgtga cctaatactt tccaaaagct cttgagacct ctgatatttg  111300
tgagagaata tgtagggaat aggttaacct cctttttttg ctttggtaaa cttcatctga  111360
gattaggcca aatcatcaga aagcaatact gcctgggctg ctacttacct acctctttga  111420
tattacgtcc ttggcttcac aggcaagacc ttatgacaca tctatttgaa gaaaatacac  111480
agtctctttt gcagaagtct aacctaatga catgtcttga ttatcactga aattcattaa  111540
ggattactag atagtaccag cggtttcccc tccagacaca tgtatgtact gctctccttg  111600
tgacaatgag aactcaagac tttaccattt tctttgcttc agctgccagg aaatgctgaa  111660
attaattt                                                           111668
```

```
SEQ ID NO: 2           moltype = DNA  length = 5409
FEATURE                Location/Qualifiers
source                 1..5409
                       mol_type = other DNA
                       organism = Homo sapiens
SEQUENCE: 2
gtgatggatg gtttaagggg gctaccgata cattcacact aatcagccat ttctgccaag  60
atcatgtcac ctcaatctgt tcatggactc caaatacaag aaattaattt gacaaagtga  120
aaatataaaa gatgcatcat ataaatatgt aacttttctg gagtgggtag tataggtaaa  180
gccaaaagaa acaaattcaa gcagaggaat tttggtttct gaaaattagg ttgtctgtag  240
ggtccctgta tttatactta gaacaaaatt aggaatttct gtttatgtgg tccagttatt  300
gagtcaccct aagtttgtag gcatcttacc tacctacttg ctccccaagt tttatttct  360
aaaatgaaaa gcattgctgt agatgaccag tttacactaa agaataacat ttatttattt  420
```

-continued

```
gttttagcta aagtatatgg acagggaaca ttcatattct tgtagaagaa aattattttg  480
acttttgggc aaaagcatgt agttcttata cactttgaca aactcattgc gtacattttt  540
cacattaatc aaagtcagca caaataaatt ttcaccttgg accacggagg gtttgaacac  600
tggaaatttg atataattct ggttgctaaa gaacaagttc taataaaagc ttaagtgtat  660
accaatatgt ggctgttggt gcaatcagca ggtccgtaaa aatatgattt taatggttag  720
gtaatcccac aacggagatc ccaaagttca tgtttggaag agacttttgg gtcaaagtga  780
aatcagtgta atgaatttaa aattatactc tgagatcttg aaatcagcta attatgttac  840
atcttattag ctcagaaaag ttttgaagtt atatacaaat gctagtcagg aaaaaagatt  900
cagtcatgta attcttgtac attctactat ttaaatcaac caatattata gattatgatt  960
tagtgcagta attctgctgg ctaaccttat ctcatttggt ggtggttagt acttcagagt  1020
actcaccata gtttcattta tgttttcagc atcacttcct ggtttttctc aattccatgg  1080
ctgtggaatc aattcatatg tatatttagc ttcggtgagc aaaaacatag ctagaaaaag  1140
aaaagaagtg agtttcctac ctggttaaat taaagtcgat gtgttaagcc aaggaggact  1200
tcttttgaat ggtactttaa caatccctgt tctgtatact gtgaatatat catttaaata  1260
gcctaataaa ttggatgctt aggctgagcc acctatactt tagttttgtt atggaaagaa  1320
gggagaggag caagtatgtt cttatatgtt acttagaaat aagaatgtag ctgtagttac  1380
acattgttct taagtttttt tcgtaagaca acttgaaatg agtcccatag gcctgctatt  1440
taacattcta agatatgact taaggttaat gatgagcttt tgaatctgac aattcaagag  1500
atatccataa tgaatactga ttcattttct acattgctga aagctaatgt tcattttaag  1560
cctactttag tagcctttat ttgggcttag agatgttatt cctctttctg atatttattg  1620
ggttatctgt ttaacccttt tatatctccc tttcccgatt tgtaaattag agactggcaa  1680
gactttttac cctgagtaga gcaccaaaca tggcttgttt ctgcccacac tgtagttacc  1740
ttgaggggaa gtaaatggga ctttaaaagc aatttatgct cttttatagt gaaattatcc  1800
ctcttactat cccgaaagac tgttacctta caatatcctc cactcctttc cccctgtagt  1860
tactatagag atgacttttc ggttcttcac tgccataatg atcaaaatcc taattcatga  1920
gatttttatc attccaggca tgtgaggttt acttgatgca taaaaccgca agtacttttt  1980
gttgtttttt aattgttttt tctctcttat cttcttgaaa gtctaagtag atcatcattt  2040
ttgatgtctt attagtagca actaataaat tttccctgta tcttctcagc aaaagaactc  2100
aagcagagac agaagattag aactaccatt ggtagttttg cttcctatgg atatgttcac  2160
atacatagaa atttttacaa tgaccttttt atatatgtat ttcagaattt cagaatggcc  2220
tcaatgcctt aataggaaga aatacttgaa atttttaaat tagggcttgg ttttgtgagg  2280
agctagtaaa ggtttttctc tttcagcttt agcttgtttc tgcggaggat tccgctcttt  2340
ctccatcagt ttcatagccc tggaattgta gaaaagctct ggtttcaaga ccattgatat  2400
ccatttctgt cagggtgagt tttaaattta tttcatgatg caaacaatat attgaacaac  2460
aggacatgaa cttgttcttg ttgtaagtgg ctgaatttta tcagtaaagc acatcaaaat  2520
aaaatatacc ccaattgcta gttaagacct agagtgacag attgaaaata gcttgtgtta  2580
ttctcttaag aaaatatata aaaattatca tctcatcaat ctttaatgtt tgttttataa  2640
atctaaatgt ttttatattg tttcctagga aatattaggt ctaatttttt actttaccac  2700
cagctgtctt ttattttact ctttttttga gacggagttt cgctcttgtt gcttaggcta  2760
gagtgcagtg gcactatctc agctcactgc gacctctgcc tcccgggttc aagcgattct  2820
cctgcctcag tctcccgagt agctgggatt acaggcacat gccactacac caggctaatt  2880
ttgtattttt agtagagacg gggtttcttc atgttggtca ggctggtctc gaactcccga  2940
cctcaggtga tccgcctgcc tcggcctccc agagtgctgg gattacaggc atgagccacc  3000
gcacctggcc agctgtcttt taatataaca ttatgattaa ttgtgatgtt ccattaaact  3060
aagcggagag gaaacatgct ggtaaaccat gtgtgagtta ttcattgtac cagaaaggca  3120
aatgatacat tttatcctaa aattcaaatt tataaacatc ttaacacttg tgatcattaa  3180
atactactaa tctagcatat aaattatatt tgtaggcggg gcacggtggc tcacgcctgt  3240
aatcccagca ctttgggagg ctgaggtggg cagatcacga ggtcaggaga tcgagaccat  3300
cctggctaac atggtgaaac cccatctcta ctaaaaatac aaaaaaaatt agctgggtgt  3360
gctggcgggc acctgtagtc ccagctactt gggaggctga ggcaggagaa tggcgtgacc  3420
ccaggaggca gagcttccag cctgggcgac tccgtctcaa aaaaaaagaa aaaagaaatt  3480
atatttgtaa tattctacta accttatatc attttaactt tttatataac tttttttattt  3540
taccaaatta agttaacctt ttatagccct tggcttatac taaacatcct aactttttttg  3600
tttaattgta ttagtttta agttattgcc ccagatgtca agtaatgttg gattttctat  3660
aataatttag gatatattgc atgaagtcag ttagtattta catttaaaac taaaacaatt  3720
tatactaata cagtttatac atttcatact aatttagcta cagttggata aatatttaat  3780
ggaacaaagt aaatcaaagt accttttcaa atgaattgga aattaaatcc acataacaat  3840
tttttatgac cacactatta cagtgtgatg gcatgccaaa tgatcataat gtggaattat  3900
gtatttcttc attggctttc aagattctgt tctttagttt gtgggctcct ctccaacttg  3960
cttgtctcct cacagtttag gcgactgttt ataattcttg tccatcctgc ataaacacac  4020
acagtcaaaa tgaaaaaaag cttctatcag cagatctgtg cttgctgtac agaaatggga  4080
aaacaattga agtttgcatt atcttttttc taattaccag atcgtttttg gagctattta  4140
ggcatacgct tttaaggaaa aaagaaaaaa agagtgtacc ttttgtttct aacaaaggtt  4200
gttatctata ttattgaaat aaaaaattgg ggatagttat gacaaagtat ttagaaatag  4260
gaattaaaat cttaaaataa cttttcatag catggacaag acttattaat gtctacctca  4320
ataagcaaat catttaaaaa tttttcatgt atatttgctg ccatgatgtg ttgtgattgc  4380
ttaaataacc aatgaatgaa gatcaacaag gatttaaatg aagaagaata tggatttaac  4440
tattttctcc tgtgaaataa gttcatattt acaagttttg attttcagaa attagacaat  4500
tatttttaaa ggctgggatg acaacttctg cctcttacca agaagtcaaa gcacagttat  4560
gtgaattcat cataaatcac atcattttta ttatattttg tatttataat tgtattgtga  4620
ctactttaaa acctgttata aaataaaatt gtttttttaat attttatttt agaattatta  4680
gcattaataa caatttgaag tagtttacac aatacctgtg agttttattt ttgttttata  4740
ttgaaattaa ttttagttgc tttacttggc ttcattgcta tggatgcatt ctctgtgtta  4800
cgagttagca gatctttcct tggaactgaa tttaaaagca agcatttggc tccacttaaa  4860
tctctgaaaa tgcaacttgt tctttgcatt tattacataa ttcgctactt atggtacaga  4920
aatggataca atacaaaaat atttccttat aagatacact gtgaccaatg agctttttaa  4980
atagctgtaa tcagtaacat gtatttgact tttcaaaaca catttctgga gggatatcag  5040
tgctttattt ccccaaatat ctgaatccct atgctttagt acaaaacaac ttctgaagaa  5100
tttagtaacc atatgtgttg atctcttgtt tttctaacta gtctttcata agaaatgact  5160
```

```
agaatagcaa cagggaaatg attgcctttt aaggtttttg tttctcaata taaaattttg  5220
gtgaaccatt tttattgata aatacaggta tttttacttt cttaaatcac ttgatttaaa  5280
attactttga ttaaatatgc atataaagtc agttgttttt aactctcaat acttatcaaa  5340
aaaatttaac ttgctgtaca ttctgtataa acctaattct attcaactaa aattatttta  5400
aacatttag                                                          5409

SEQ ID NO: 3           moltype = DNA  length = 24782
FEATURE                Location/Qualifiers
source                 1..24782
                       mol_type = other DNA
                       organism = Homo sapiens
SEQUENCE: 3
gtgagtagtt cttactgccc tctaccttac tacctttcca cctttcccat ttccatttgt  60
ttgttgatcc atttaatctc aaacttacag aaaagttaca aggaactggg ctgagcacgg  120
tggctcacgc ttgtaatccc agcactttgg gaggccaaga tgggtggaaa acaaggtcag  180
aagatcaaga ccatcctggc taacacagtg aaaccccgtc tctactaaaa atacaaaaaa  240
cttagccagg tgtggtggtg ggtgcctata gtcccagcta cttgggaggc tgaggcagga  300
gaatggtgtg aacccgggag gcggagcttg cggtgagcca agatcctgcc actgcactcc  360
agcctgagcg acagggcgag attctgtctc aaaaaaaaaa aaaaaaaaaa agttacaagg  420
aatttttttc ttctctgaag tatttgagag taagttgctg accttaagtc ctatcacttc  480
caagtaggtt catgtatagt tcttagaaac agattttctc atagcaaccg aacattgata  540
aattacaata tctaattctc agaccccttt caagtttcac ccgttgtccc agtattatcc  600
ctccatataa caagatgttc caggctcaat acctgaccca gcttcctttt tttgaagaat  660
ggtgtttaga aatggagacc tagaaattat atatgctgtt attggaatat cactgttccc  720
tggtttctca gtggaaagag ctaggaacta agtgttgtga atgtttgtgt gtgtgcaggt  780
gaatatacac acactgacat ctgtattcct aaatcatgtg tatatttatt tattaaaaac  840
tgtgagttga tgctgatact tcccatttta atccagcatt acaaggtttg ttctagtgtt  900
ctccctttcg atatttgtca cttgctttcc tgatagaaaa cgggcttcta gtatccttaa  960
tatattttca tattttggtc agtcctccta tacgtaaccc aacttgaatg aagatatgtc  1020
cttttccatt gcagaaatgt tctttttccc cagctcggac tcaacactac acaccaggcc  1080
accacatggc gccgcaccca gcattgacac ttcttttacc ttgtctgggc tctgacatcc  1140
gtgccaggtt gctcttcgtc atggagtccc ttttactgag ctctgctctg acgctttgtg  1200
ccaggtgcct ctccatctca tccttcccac ccgctagcct ctgcccgacc ccagacagat  1260
tccttcctca cctgaagcca gaccatgcct ttgtggagat accctcttta ccctgcctgt  1320
gcttcgccag cctgcaccag gccaccctcc tgcacagata ctctcctcag tactggacca  1380
ggctaccaac agccccatgt gaacccattg taacccaggt caggcattaa cacctgcagt  1440
aggctaccat ggcttcccct tcccaccccc ctagcttggc cctactaata atcactttgt  1500
cactgtttgg ggttgatatt tggttgtttc ttgtaggttc ctagctttaa gataggattg  1560
catactaaaa tttacttaga tctttgagaa ctcaaggaaa tcagtgaaac attattgtta  1620
ttaaataaaa ataaaatacc tgtagttggt acctctgttt gagcctgcct tgttacaagt  1680
ttcactgact tcagcttcgt gtaacaaagt atctttttct ttcaacgtgt acttaaattt  1740
cctgtcttat tagttttctg atatctaaaa ggaaaaaaag cagatatcgt taataaatta  1800
gaaagaagtt ctgcaaattt aaaagtgcct tctaagctga gttgtaggat tacagtacaa  1860
tccatagggt tatcctgaag aagccaggca gggctcttct gtgttacacc ctgtgcctgc  1920
gcagcatgct caccccttgc catcagcgct tgcggcccca ttctctccct ctagtaataa  1980
tctaagttct gcattgcttt ctcctttcct tttctttctt cctttaaata ttcttctttc  2040
gagacatatc tcattttaac ttttattttc attttctgtc acttttggtt tttctcatgc  2100
caccttggca atgtagttaa gtttgtgcta acgtagaaga ttagtgctca aatctgaatt  2160
gccatttact actagctgtg tcatcttcgg cagggaatct cccagagcct tagcttcttt  2220
atttgtaaaa tgactattat agtggttatt tctcaggatt gttagaatta cttccgcaaa  2280
catttgcaag tccctggttc ataatttcat gctaaattag taccgttaca ggaagtggta  2340
tatcattgtc acagtgtata caaatatatt tcttttatat ccctcgtgat ataattatca  2400
agacagtgaa acaattcaat gaattttacc agcataacac atttttaagt gattggaaaa  2460
tcataagtat cttttcttat gtttttagta gaggctttgc aaccccatta ctctccgctc  2520
ccaatttgat tatttaaagg aagtggatta ctaactcaga tatgtacact gtcaagccaa  2580
gttctatgtt ctactgctgg ttttcctgag aaagcagtca tataactccc ttgaaatgat  2640
ttactacttt tgtacatata aaattataat ggtgttaatg taccaaataa tgtccttgga  2700
agcaagggtt ttgccagtaa ctcagctgca tcagtcaccc tcaaggagat gagccatgac  2760
tttgttcatt agttggaaaa gagtctggag agtgcctttt cgttactgtt tatctttggt  2820
ctgacacttg ggaatagggt catggatact tcagccagaa aactttccaa atttaagtta  2880
ttaatgtatt ataaggatca aagtttctag tatagcctgt tcaattagaa catagtgtgt  2940
tggttgattg gatttggaga aagggaggca atcaaatttt tactacagtt tcagcctgtt  3000
acagaatatt gtatagagtg ttaaaatgtt gatgcattca tatttttgcc agttttaagc  3060
ttgtacgatt ttaaatcatt tccttacctt ggagacttcc cccccacctt tttttttttt  3120
tttgagatgg agtctcgctg tgtcgcccag gctagagtgc agtggcacga tctcggctca  3180
ctgcaaggtg gttctcccac ctctgcctcc cgagtagctg gggctacagg cgcccgccac  3240
catgcctggc ttattttttg tatttttagt agagacgggg tttccccatg ttagccagga  3300
tggtctcgat ctcctgacct catgatccgc ccgcctcggc ctcccaaagt gctggaatta  3360
taggcatgag ccaccatgcc cagccctgac tgccctttaa gatgagtaca taagtagtag  3420
tagtacattt ttctttcaca tcctggagaa gatatactgt gttcactatt gaaatgaaac  3480
cataaagcta gagttaggaa gattgaagaa atgaaaaagg agctcacatg attttgtctc  3540
aggagaggct cttccaggat tctttggaga tatggtagat tccatagctg gagcagggaa  3600
aggacaggat gagcctgtgg gtgtagaaag gaagggagtg cttgaaagat gatgaggaga  3660
tgtcagcagg tcacagaaac cctctgaagg aggctccaac tggccaggct ggggacaatt  3720
tgggccccaa aataatgaca gtaacaaatt gtaactcatt gaatgaaata ggaatccata  3780
cattggtaat tatataaata agggaataaa accatgatgc aaaaagggat gtttatgtca  3840
tcacgcaaaa tatgttcaca gaaaatatgt actaattaaa agagggaaaa gagtaacttt  3900
acagtggatg aagcctggca atcatcactt taagcaagtg gtcagagtta atattatcag  3960
taatggtcaa atcaaaacca tatgcaagaa gactctaaaa tgcaagaaga ctcctgaagt  4020
```

-continued acttcttacc aaagatgtag aacttaaatt cagtcataac aatacatgag acaaacccaa 4080
gttagagcac agtctgcaaa ataactggcc tgtaatcttc aaatgcatca agatcatgaa 4140
agacaaggaa agagtgaaga gctgctccag ttggaagaga cttaaaacta aatgcaatgt 4200
atgatcctag attggatctt tttgctctaa ggacattaat gggccagtta gtgatatttg 4260
aaggggatcc gagggttcca ttgtagtaat atatcagtgt taatttttaa atttttatta 4320
ggttgggatt attttggaaa ataccattat tcatagcgaa tacaaagtag aatatttggg 4380
gatgataatg catgattaca acaaatgttt caggagaaat atgatctttg tagtggtctt 4440
gcaacttttc tgtaagtctg aaattgttta tgcataaaag gttaaaaaaa ggttaaattt 4500
tgtttttata actaataatg gattagggtc atgtgaaagt actttagagg aaatgagact 4560
tttgagaaca tcatccctga agacgttgaa acactgagtt acctcatgga taatttaata 4620
ggatatgcag ctgatttttc taccttaatt tcttgtttgc agtatctacc catacttaga 4680
attgtctggt gttaaaatat gcccactggg actttcatga aattcttttg attttctaga 4740
aaattcagtt tcaaaggatt ttttaaatag atattttaag tttggtgtca acttagataa 4800
aatctgtttg gagtcccagt gtaagtttta gtaatgtgtc caatctgttt attgaaatag 4860
tataacttta gaatactttc tttggagaga tgaagattgg tatgttatag ttcaattcaa 4920
agttgttctt tctattatga tctattttat aattcataaa atctatctta tgattgtcat 4980
cataagtgca atttgttttt tgccccattc tacctcagaa actaagtatc tgggcatcaa 5040
taacaattgg tagtagtgtt tgctgctaag ccaagtttca ccagtacagt gtggaattat 5100
tttattgttt tttctgtgaa cattgtatct gctgttacta ggttattgtg aggtattggg 5160
ccttcataga aattgcctgg aaccccttgtt cactaaagcc tgttacactt tttattctct 5220
gtgcgtgtaa tcagagactt attgatactg acacattcaa ggggcattat tgatcattta 5280
gattgctcta agacctaagg agtcttggcc ggatgcggtg cctcacgcct gtaatcccag 5340
cactatggga ggccgaggcg ggtggatcac ctgaggtcag gagttcgaga tcagcctggc 5400
caacatggtg aaaccccgtc tctactaaaa atgcgaaaat tagctgggca tggtggcagg 5460
cgcctgtaat tccagctact cgggaggctg agacaggaga atcgcctgaa cccgggaggc 5520
agaggttgca gtgagccaag actgtgccat tgcattccag cctgggtaac agagcgagac 5580
tccatctcaa aaaaaaaaaa aaaacgaaaa acaaaaacct aaggagtctt ttctccttat 5640
tttacaataa attccttttg attttgtgta aaaacttgaa actgtttatg aatgtaaaat 5700
aacatttgaa tacttttctt gtgccagata ttaggttaaa tgctttatgt gaattttcat 5760
ttgattctca caacttttga gttaggtagt tatttttctc atttacaga tgaaatggag 5820
ggttaggaac tcgtaggtag tagatgctga agctgagatt tgggcctggg tcttttcact 5880
actgtgccag aatcatttgg gagggagtaa aaactcaagc ctttggaaaa tatgatgaca 5940
taaaattgtc ctttatattg agaagcttcc atagttacca gtgtccttca cagggttgat 6000
cggaaagaca tacatgttag tgatgatgat aatgatgaag ataatcatta ttaccacagg 6060
tacttcctat aatataagca tctttcaaat tgtatgagaa ctttcataga acatctgagt 6120
aaatgaacag tacagtgtgc atgaaaccac taagcaaacc aagggaagtt aattttcttt 6180
atatgaattg taaacatgtc tctagatatc ctttatcaga ttccaccatg cgtaagtagt 6240
gtctaagttg ccccatattt agagttttc aatgaggttg tgttcctact tagaatccta 6300
aagttcagct ataacagata tattaataaa atctgtggaa tctttaattg agcataatgg 6360
tggctgttat tttaacttga ggctttttgt tgagctggat tggaagtgca acttattaga 6420
aattacagtg tatttattcc tatttcttgt tctttatgtg agagaagata tactttagta 6480
gactgaatac ttcagagctg tatctcattt accaataaaa tgtgaaaaca gtggtaaatt 6540
ccttcacttg ggctaccatt gtacaggcct attttaatgg tatagtttga tatccttaat 6600
gttaaaagca atatagctta aagaggctgg taaattagaa ttttccaata tcctcagctt 6660
tttttcctct cacagttaat ttgctctgct gactccctac gcgaggtggc aacagctggc 6720
ccttttactg gagcttgtgg ggattagaga gtcgggctcg cagcagcgtg ctcggcctct 6780
tgcctctgtt gactgttctt tattgtttga tgcctgagca tctcccagac agcgagcaat 6840
tgtttctgga aacttaaagt ttgtttctct tgggagtaga caatgctttt ggggcttgtc 6900
tttgtgtttc ttcactttcc cagtctcctc ttatccttca tcctgtgctt tctcttgata 6960
attagaaagg agcaaagata ccaccttttt atttaggtct gcatgagatt ctaaaactta 7020
gaagtatagg ctatagatga aagtttcttt tttcagtaag ccacctcagt aacaaatcat 7080
gttttaaatg aaaactttgt tcttcataat atcatttagt gagagaaaac aaatgcatga 7140
gtgcattttt gaaattatgg tactaaaagg gagcagcagc aaggtgacct aatactgcca 7200
ttttaaaagc taggattaga aatgtatcat aactgcttaa atctaaaaag attctttcac 7260
tgaatccaaa atatagttct aatttatagg atagttataa gaaatctcta tgccatgtgg 7320
aaacatgaat aaaaagtagt cagaacatag ctaaatagaa ccctgaggta ggcagaatga 7380
ttttattctt cacatttaga aaagaaaaca tcaaggtacc ctggaactta atttctacag 7440
tgacttcaca ttccgacact tctcccatac ctgccatacc cttgagtgtt gttacggatg 7500
agaatatcgt ctgtgaagta gtatgagatg gaaattttcc tagaaagatt attgtactcg 7560
gaatttggaa ctgaaaagtg tagaaagggg aagtgatgtg tttaaaactg tttgcggagg 7620
tggggctctg ccatgtgtat tttgacaaag ctacacaggt gattcttgcc atccccgatt 7680
accgtgtacc cgcctgcccc tgagctggca ctccaaagag ttctttcagt gcatagcaag 7740
acaatttttc atgctattaa ttgggataaa attgacatac attcatttgt agagtctgag 7800
acacaacgtc actttggaaa atttggtgag caatttgaac tgcatctgca ctggtgtgtt 7860
ctttttgttt ctgtagactt aaccaaagaa aatgaacttt aaagggactt taaaggcatc 7920
tgcactggtg tgttcttttt gtttctgtag acttaaccaa agaaaatgaa ttttaaagga 7980
agagagggtg ataccaagtt gtagaattct aggtatgtag gttcagagga gatttttttt 8040
ttttaagaaa aaaaaaaaaa aaaaaaaaaa cacccaatca agaagaatag agcagggtgt 8100
cccgaagaga acgtgtgagc tcgaagcatc ccggcagcat ctttcatatc tcagtactgt 8160
tgctctgttt cttgggctca caacaccatt tcctctctcc tggcttttaa cacatctcga 8220
ggcaaccttt tccctttctt tttatgcact tctctcactg cgtctcttct atatcatcat 8280
cacttcaacc taacccagta tttttatccc acctgcttat ttaccttcct tcagtgacta 8340
aaaaccttac tcagatactg ccagtgttgt ttaattgagc agaatagagg cttctcacta 8400
taggcaactg taaatcaatg aaaataacca tttaaagaag aaaaacattt tcatgtctat 8460
cacggtcgat cccttctgcc aaagtgattt ggttcattca taaattcccc atacctcgtg 8520
tgttacatat tgtactgtac acatttactg aatgttcgat tgtgatcttg taatacagac 8580
tgttcattag ccccttctc ttgacttaaa aagttggggg gaactaactc ttttcatccc 8640
aaggaaactt tcttctactc tgtcttgcca gaaagttact gctcatttct cttgtagagc 8700
agcttgcctg tgtggcattc actcctgttc tgcccactcc cttcctaata tcgtgcagtc 8760

```
tggctttcat ctatatcaaa accacttatt gatagatcac caatgatttc ctaatgccag  8820
tctacccagt tcaccaggaa actttaataa ctttttatgt ttattaggaa tttttaagtt  8880
cattggaata cattcaagta ctttttggaa tgattatatg atgtagaaat gtgtatgttt  8940
gagagacaga aaaattgatt ttttttttcct cttcactaca gaataaataa tgtatttgtt  9000
ttatggtagc aatacttgaa ctctttaagg catcttttca tggtaaatct ggcaatttta  9060
aaaatctggg ctttgtaaaa taattttttt tatagtaagg cagttaacac attaaagcaa  9120
ctaggaaaga tagtgaagaa ttatttttac cttgagtctg tatagatgaa gtaggctctg  9180
ctttgtgttg gaacagaaca aacaaacaaa aaaacctgag ttgatacaaa gataaagtaa  9240
tcctcaagga aagtcctctc tgttagagaa gtggttattt acacacagaa ttccacatga  9300
caacgcctga gtggtgtggt ttccaggtta ttgatgagaa aatcgagact caaaatgggt  9360
cttttagaat gaagtacatt tttcatggcc taagtctgtc tttaaaagtc accgttgtgg  9420
ccgggtgtgg tggctcacgc ctgtaatccc agcactttag gaggccaagg tgggcggatc  9480
acaaggtcag gagatccaga ccatcctggc taacacagtg aaaccccgtc tctactaaaa  9540
atacaaaaaa tttagccagg cgtggtggcg ggcgcctgta gtcccagctg ctggggaggc  9600
tgaggcagga gaatggcgtg aacctgggag gcggagcttg cggtgagccg agatcgcgcc  9660
actgcactcc agcctgggtg acagagcaag actcgtctca aaaaaaaaaa aaaaaaaaaa  9720
aaaagtcact gttgaagaat atcaataaat tagtacaagc gtaaaagaac attttctttt  9780
ctataatatt atacatgctg ctggtaatca acactttact agcaagtata ttcttttgct  9840
ttaaactcaa gttttaactg attaagaata aagacaagaa tgttctctac aataatgtat  9900
ggattgaatt tgccatttat cattttaatg taggttttac ttatatacta ttgtgaaaat  9960
actcttaatg tattcaaaag gccagtgcac aattttttttt tcttttactt cttttttttt  10020
tttttttttc tttagaaaga gtgtcacttg ctgcccaggc tagagtgcag tggtgtgatc  10080
atggctcact gcagccttga actcctgggc tcaagtgatc taatacctttt aaagttggga  10140
ataaacttta tcttaagcgt ttttattttt aaattatgtt tttgcatatt tgatagaaaa  10200
agtagaatgt agtaattgaa aacctaatca caaaacaatt cattggactc tgcaacagta  10260
tataaaaaat aaaattaaac gagataggaa atcttaaggg attggtggat tgatgcacat  10320
gaaactggta acctctgtta agtacagttc tccaggtagt tggagaaatt agttaaatgt  10380
gaagagaatt ttaattttgc actattttgt acatttctaa actgtgtctc ccacagccct  10440
tctcccccag tgagcacgat tcagaattac tttgaaatgt tgtagtctta attatcctat  10500
tcatggaaat gacgaagcta atacacgatg tgctctatct taaaagtaac agatattttc  10560
ccaagtaacc tactgctggt tgtgatgctg agggacattt catgggactg catggtcgtt  10620
gctcatcgtg ataccatcct cagtggttgg gggattcaca gtgaattctc atatcctgta  10680
actatgcatc atggatctat catctgaaaa taaatcaaaa tctttgttga actcacagtt  10740
tccacacttg tatcacccat ttaagattgt ttcattgtta cctcctgtgt acagaatatt  10800
tcatttcaat ttctcttaga acagctcatt catctattct ctagtttcaa tattctgagc  10860
agtagaagtt tgctgttttg attaacttca gttagatctc ttttctgggc caagaattaa  10920
agccatttta tctttagtct ctccttttgt tggcactgct tcatagactg tgtcatatat  10980
acagatctgt ctttagactg atctttacca aagtacacta ctggaatttg agggtttttt  11040
tttttaacat ccttttcatt atgagagagc tagtgtatat gcattgtggg aaattagaaa  11100
ctatagatgg caaaatttta aaaaataatt gccaccaccc agagattgca ctgtagttta  11160
agacactttt gaatgtggtc ctagggacat aatttctgga acacattttt cgtgaagagg  11220
tctcaggttg gcttcttata cccacagctc gttgtcattg cccctagttt taatttccca  11280
tcgctcagtg ggctagattt tttttcattt tcttcatata aacttatttc agaaatgttc  11340
attaagagga ataagcagca ttagtaaaaa tgaaacctat ggtacccatt actttatata  11400
gttcaagtat tctggaagcc atattgtagc atagcatgta ctgaaaatca ctctcctttg  11460
aacagtaatc ccatacctgt atttgggacc tggccttcct ttgtgtgctt gtgtattcat  11520
tatatcccct ttctctcttc aaagatgctc aagtcattct catcttaaaa ctaatgggtt  11580
gaaccttcca tgcagtctag tagctactgt gaactctaat ctctattaca aaggttagct  11640
ctttgagtct cacttctact gaagttgttt ttttttccca agattactga aaatttaaga  11700
gaaaataatg gcccaggcat gcattcagga ctagaaaata cttccatgta cagaaaacca  11760
aacaccacat gttctcactc ataagtggga attgaacatt gagaacacat ggacacaggg  11820
aggggaacag catacgccag ggcctgttgg ggcgtggggg gcgaggggag ggaacttaga  11880
ggacttaagt gcagcagacc accatggcac acgtatacct gtgtagcctg cacattctgc  11940
acatagagcc cgcttttgtt tttgtttttg tttttaagaa gaaataacgg ggaaaaaaaa  12000
ggtttcaaaa ctcataaaga aagagaaaga gagggaggga gggagggaag aaaatgcttc  12060
catgtaactg catcatttgg tactttggag tccatatcct acttgaaact ctaggatctg  12120
gccctcacat ttatgtagtg ctttatttta cagtttacaa aacttctgct tgtccatgtg  12180
tgtctgtaaa gtcatatgag gcattatgcc cattgttcag atagagaaat taacgttcat  12240
tgacataaat ggttaagccc attatgtaaa tatttatggc aaagctgggg ctaatcatat  12300
gtgttacaga taggactttt tttaaagaat tgtttaggta ttctgttcat cattagtctc  12360
tgggtttgtg tttgtggtaa ccatagacaa ccaagttcat ataatttggc ttctttttta  12420
tgtgattttt gatacgtgtt aaggatctat aacaatgaat ttgcctccta aagaggtaca  12480
taatgttttc attcctccaa aaagataatt ctaggtttat aaatctatgt atgctcagtg  12540
ccagttgaat tttgtgattg ttcaatagaa aagaaattgt gacttaaagg tgattttcca  12600
gtttaatgga ataaatgaaa ttagtttaga agttattttt atttttctga gcctgattct  12660
cactcagttg tgataaacag cacctctgta agataaactc ggtgataaac cgagaacttc  12720
tgaaatcagc ctaacatgaa tacctgttct tcttgtgcta agtttcataa tgctttatcc  12780
taatacacca ttttttttaag aaatggaact tgtatttcat ttttgctttc atctcaccta  12840
attcataatt ttattaaaac ctacgatttt taatttcttt ttttatgaat ttttagtttg  12900
gtgtataaat cagaattaca ttctctgatc ttttactttt aaaattacag tgatgaactg  12960
actgtttaag aatcattctc atgattcatt cgtctgttat gcctcctttt taaagcttca  13020
gcactgaagg tcttttgaca aaccaatatt tataacagtt tgacagcagg atgaggaaca  13080
gcgtttgtct ttgtaacagc ttgaagaaag accctttcca ggacccagtc atgcagttac  13140
aatcttgacc tctttcttat gctgggaaca tgcatacagc agcacctccc atgtgttttc  13200
ttgtcccatt gactgtccat tcacttccca tctgttttgc agtcttaaag gaacagaagg  13260
ggccttctta taaatctgtc tttgcaggtg ataaatgatg cctacctctt taagagctgc  13320
ctgggtggtt ttcctttttct tagaacattt ctgctttcct cctaactaaa tcagggaaaa  13380
atacaatttt aggaataaga gaaaaagaag aaaagatgaa tttttaaagc atttaattga  13440
ctaagaatat tttactgatc ttttttaatc ttcccaatta attgcctaaa tcatattttt  13500
```

-continued

```
taaaatgtat tatcgatatt tagatttttg tcagggagta aaatgaatgt attcattttg  13560
aaataatgta actctttttt gagaaaacaa agccatgtat cattaatgag ttaacatata  13620
aaataacttt ttaagttttt tgtgataatt taagtgtgga gcatcttatg tattggatac  13680
aaaagtaaaa tatttcagag taaatcattg taatcttatg gtaaaatcta ttcatttttt  13740
acatttaaaa agatgatcat aaatcccata aacatttatg cttttacttc tgttgctgaa  13800
aataagtatt gtaggaatag atattgatat cattgggttt tctaagaatt cagcagaaat  13860
aaaaataatt tactttttct cccatgcaga aattatttat gcaaggtttt atgtaacaaa  13920
tattgtccct ctatggccct gcagaatatt cttaaattac tgatttaaaa actattacca  13980
gtataaaatg accactttta gaatattgtg gtgtattatg tgaatcagct ggctaataat  14040
atatcttctg tggactagct tgttagtttg tttattaatt ccctggcata ttccaaaagg  14100
aatttgaggc agcttacata tatcctacgc aaaagataaa actacttaag tgaaaaattt  14160
gggttgaaag aaaaggaaaa tccaggcaag tgaaataaag taaactttca gataaaattg  14220
gtgcccctca aagtgcatgc tcaagggttc tacgtacagg cagacctcat tgtattgcat  14280
gtcactttat tgcacttcac agttattgca tttttaacaa tagaagtttt gtggcaaccc  14340
tgcattgaac aagcctgttg gcactatttt cccaacagcc atgtgctcac ctcatgtcac  14400
tgtcacattt tggtaattct tgcaatattt caaatttttc cattattatt ctgtctgtca  14460
tggtgatctt tgatgtttgt attgtagcta ttttgggtac cactaactgt gcccatatta  14520
gtcagtgacc ttaatcagta aacgtgtgta ttctggctgt tccaccaact agacattccc  14580
tgtctctctc ctcctcttca ggcctcccta ttccatagga cacaacaata ttgaaatttg  14640
gccagctaat aaccctacaa tggcctctac atgttcaagt gaaagaaaga gtgccatatt  14700
tcactttaaa tcaacaacta gaaatgatta agcttagtaa aggaggtttg ttgaaagcca  14760
aaatgggcta ttagccaaat tgtgaatgca aaagaaaagt tcttgaagga aattaaaagt  14820
gttattccag tgaacacacg aatgataaag cagaacagcc ttattgcctg agacgcagga  14880
agtttcactg gtctggatag aagatcaaac cagccataac attcccttaa gctaaaacct  14940
aatccagagc aagttcctaa ctctattcaa ttctccgaaa gctgagaggt gaggaagctg  15000
cagaataaaa tttgaagcta gcaaagtttg gttcataagg tttaagagga aaaaagccat  15060
tctgcaacat gaaagtgcaa ggtgctgatg tagcagctgc agcaagttat caagaatatc  15120
taactaagat aattgatgaa ggtgattata ctaaacaaca gattcttgat gcagatgaag  15180
tagctgtcta ttggaagacg atgccatcta gtaatttaat agctagagag aagtcaatgc  15240
ccagcttcga ggcttcgaaa gagaggctat cccctcattt tgggtgccaa tgcagcaggt  15300
gcctttaagt tgaagccaac ctaaagaatt taccattctg aaaatcctag ggcccttaag  15360
gattatgcta agtctatcct gcttgttttc taaaagtgga acaaaaagcc tggatgacag  15420
cacatctgtt tacagcatgg tttactgaat attataactc tcgagacctg ctcagaaaag  15480
ttttctttca aaatattact gctcattgac aatgcatctg gtcaagcaag agttctgagg  15540
gagatgtaca aggagattta tgttgttttt gtgcctgcta gcacaacatc cattctgcag  15600
cccatggatc aaggaatact ttcaaccttg aagtcttatt attttaaaaa tacgtgtctt  15660
aaggccctag ctgccataga tagtgattcc tctgatggat ttaggagaaa aaaaaaggaa  15720
aagcttctgg aaaggactca ccatttttaga tgctgttaag accattcagg attcatggga  15780
ggaggtcaga atgtcaccat taacagtttg gaagaagttg attccaaccc tcatggatga  15840
ctttgaagag tttgggactt aagaggagga agtaactgca gatatggtag agacagcaat  15900
agaactagaa ttagttctgt tgtaatatga taaaacttga acagatgaaa cattgctttt  15960
tatggacaag caaagaaagt ggtttctttt ttctttttttt ttttttggc agtctcagtt  16020
tgaagaaagt ggtttcttga gatggaatct gttcctggtg aagatgctgt gaacattgtt  16080
gaaatggcag taaaggattt agaatattac ataaacttag tagataaagc agctgcaggg  16140
tttgagaaga tagtgtccca atttttaaag aagaaaaatt tgagtaaatt tgggtaaaat  16200
ttacccaaaa ttacctattg tgggtaaaat gctatcagac agcatcacat cctactgtga  16260
aatctttcat gaaaggaaga atcaatcagt gcagcaaact acaattgttg tcttatttta  16320
agaaattgcc atagccaccg taacctgcaa cagccaccac cctgatcagt cagcagccat  16380
caacgtcagg gccagaccct ccaccagcaa aaagattatg acttgctgaa ggctcaggtg  16440
atccttagca tttgttagca ataaagtact tttaaataag ttatgtacat tgtcttttta  16500
gacataatgc tattacacac ttaatatatt acagtatact gtaaacgtaa cttaaacgca  16560
ccggaaaacc aaaaaacctt atgtgactca ctttattgtg atatacgctt tattgtggca  16620
gtctagaacc aaacttgcat atctcccaag tatgctggga ctttgctaga ggtaagctgc  16680
aaatttagcc ctcagtttcc tggtggctgg cagttacaaa atggaaagca gaggtcattc  16740
catcattcat ggtggccatc agacaacaac acagcagttg cttaggagaa gcatgggtct  16800
tcttcgtacg cacaactgag agaaatttcc cttaaagtgg acactgagtt agatgataca  16860
atgaatctaa tggctacaca taatcatgaa aatcatgggg ccctttattg taatgtttct  16920
catgcgggct aacatgcgta gttctaggga aaatatgatg ctgtccaaac atacagctat  16980
ttggtttggc ttatctaaag ataaaataca tagtatccag agaaatagat gaactgtatg  17040
tcctccatac agtctcccat aaatattatt tctttttgca gctgatcctt ttagtaaata  17100
tcaggtagcc agaagttcaa gattttacac tcattgacat tgacaagcac ctggaatggt  17160
actacctttt tttttttttt tttttttgga gacagagtct tgctctgtca cccaggctgg  17220
agtgcagtgg catgatcttg gctcactaca acctccgcct cctggattca agtgattctc  17280
ctgcctcagc ctcccaggta gctgggatta caggcgcccg ccactacgcc cggctaattt  17340
ttgtattttt agtagagatg ggttttcgcc atgttggcca gggtgatctt gaactcctga  17400
cctcatgtga tccacccgcc tcggcctccc aaagtgctgg gattacaggc gtgagccact  17460
gcgcccagcc aagtactatt tttattagtt aagtcagagc cataatcatt ataactgagc  17520
tgaaattaga attgccatcc acttaagaaa gttgagtggt ctaacaagta taaaagccta  17580
aatataaggc taattcatgt tcatactgaa gccttttggg gaataggcct taaaatatgt  17640
agaaagtatt tgaagcggtt ttaattgtac tagccaaaag gagcctagta gaaatgcttg  17700
tgttataaga gtttattttt taaaaagctg aatttatctg accaggcgcg gtggttcacg  17760
cctgtaatcc cagcactttg ggaggccaag gcaggtggat cacgaggtca ggagtttgag  17820
accagcctag ccaatatggt gaaaccccat cactactaaa aatacaaaaa aattggccag  17880
gcatggtgat gcctgcctgt agtcccagct actccggagg ctgaggcaga agaatcattt  17940
gaaaccggga ggcggaggtt gcagtgagcc gagattgcgc cactgcactc cagcctggac  18000
gacagagcga gactccatct caaaaaaaaa aaaagctgaa tttatcaaca aattgctgtg  18060
gagtttttta tatattcagc aggcatcagt tgtaatttac ctcacagact ttcttaaggt  18120
tgctttcttt ctaaattata ctttatgggg gtcacaaaat agcaattttt aaataatcac  18180
ctttaatgat taagtattgt ttaagtcaga tcactcaact atgaatgcat gaatattcat  18240
```

```
ggacatctat tacatagcaa gcagtgctat gctgggccga gtgattttaa atgacagact  18300
ttttggtaag tagagaattt acccaagcag tccttgctgt tctccacatt aatgctcaga  18360
aaaaatacat tataaaaatg atctttccaa aatgaattat gaagccccat gagaatgata  18420
tggcaatttg tggttacata ttttactaga ggattaatat ccaataaata aaaagatact  18480
aaggaataaa caaaaaaaat ttaaaagatg aagtatataa tgaattagaa caatacattt  18540
taatcataag ttttaaatta gtgtggactt tgaattctcc tggacagatt ccttcatttt  18600
atagataaag ctaggactgt gacttatcca gttatgaggt taacggcgaa tacaacattg  18660
tcatatattt taaatgacac acattacaac atgttctctg ctttataaaa atcatatcaa  18720
ataattgccc catagattat taaaggtgtt agactaggga ttcttaaaaa aaattttcat  18780
caaatgtttc tttcattatt aatcccatga agtccatgtt acagaagatt ttgtctacaa  18840
cagtgcagtt acattcttct cgttagaaat acaaccacca gttagagttc ctaatcagta  18900
taaggaagta gttgttagga gaggggatgg gtttcttgtc caaatgaagt tttccatttg  18960
agtttttgaa gtagtgaaac taacccagcg tttacaggcc ccagaaatct gggaacctca  19020
gctttcaaag tactgtacca gtctttaaca gttttcctgg acgtgtgaat tgatgcctcc  19080
ttctgtaaca tgcaggagtg ttctgtctgt cttcattgag tgttaaaaaa taatcatgcc  19140
tatttcaagg aaaaaatcta cagaactaag atgcagaaga taagtgctag atttaatcat  19200
attccttcat ctatctgttt ggttcaacct ttcatcaact aaaagatgca cctttttttct  19260
tgtgctaact ctaagatttt agctacagtt ttgagaatct tgagtgtagt ctcttgttta  19320
cctttttttcc tttttttgtt tcccccacac cctagattca tttaaatact gaacttctaa  19380
agggcaagta tatagtgtag tttaataaaa agcaaacctt ttcatgaaca atatatatta  19440
cataataaga agcgttcctt tacttttcag tactctagtg aatagctttc tacagtagaa  19500
tctcacttag agggtgtctt aaagcttaac accaagtgct caggcagcat gttatacaac  19560
agttccatta aggtacattt ggatctttgg atgtgtggtt tgcttaaagt acactgcatt  19620
agtaagttgg cagcttgctt tctttaaaaa catcaaaagt tttaaaaggt ttatttcagg  19680
gcatgtgtta gtgttttgtg tgtggttctt tgttcctgtt ctaaactgtt attaaccact  19740
gaagtgaacc ttctcccggg tttggccttt tggtattcac agtgtattca aaacctaatt  19800
acagattagt ctatatttga gacttttaga gcaagtatca gaagacccaa aaagaaaatg  19860
agagtagcag tatcatttca tgtagagata aagagaccca aaacatgaat gggtgtcaag  19920
tcagctgaag aaaagaaaaa agagaaggaa cttcattcac tgagacggtt tatgagttgg  19980
ggattatggg aatattcatg actcaatcaa gaagcacagt gaattgatgt ttgaaatagc  20040
tcatctttta agtaaacatt ggataaatgg aaagtagact cagtattcac tacacgtaga  20100
aatagctatt tctgtatagc agaaatagca gtttgttaat cccttcctga gttggtttaa  20160
tttaccaagt aaatcacaaa ttttattctt tatttgtgaa tatttaattc aaatatttaa  20220
tggaaatatg agtttgcttt ataattagtc atgctgatcc atacacgtat ttctgagaga  20280
aagcaatttc taatggtgaa atagttacaa taatattttt gaaatttgaa agcaccgtga  20340
tactgaagca ttaatctgaa ggatcggaaa gtagggagtt tttgttgcca acatttaact  20400
tcattgttta tggataactt ggttttctgg gcagccagat ggcacagtta gtatacagac  20460
attcttggaa acttgtatca aaatttaaaa tgaatgaatt tatgagaaat aattctgctt  20520
attatttgta atgtagcttt cttgaaaagc aagaaatcgg aatgtagttt ctaaagctgc  20580
aagtgaatat gtatacatag ccagctcttt cagccttgat aataaggtgc aaccattaag  20640
atgaagggat ttttttttcc cacttgtgtt tttgggcccg agtatcctga tctgtgttgc  20700
ttgtctggtt caggtgtgag ccaccagctt tctttgactt tcattatcta tgtgtatctt  20760
gcctcctgtt cccaggcttg ctctagctct tctgatcctg tcttcctccc tcttgatcac  20820
tagtgtagta ttcatgaagc cagctaagtt agtttttccc tttgaaaacc acagccctta  20880
tcttctgtgc catattttgg gcaacttcgt ttatcattga ttgaccgtac gcagtgatca  20940
ggccttgttc tagacactga agactctgag catttttggg cccattttgt actcctgtat  21000
tgttctccag gggcttctcc aagtgtgcgt caatttagtc ttctcaagag ggcatcattt  21060
tcatcagaat atgatagcat attatggagt gtccggtcat ccttaggcat agactactta  21120
ggaggtgtaa ctgttttgtt ccctgatttt tactgaaatg ggtcttttct tttttttttt  21180
tttttttttt tttttttttt tttttttttt ttttttgaga cagagtctcg ctatgtcacc  21240
aggctggagt gcagtggcat gatctcagct cactgcaacc tccgcctccc gattctccct  21300
gaaatgcgtc ttattttaag tcaaaggtaa tacttaaaaa agaccaaaga gacttaaaat  21360
aacagcattt gcttcgtcac tatgagcttt gttattatga gttaacatac agtagcagac  21420
tgggtgtagt agctcacgcc ctgtaattcc agcagtttgt gaagccgagt ggggaggatt  21480
gcttgaggcc aagacttcga gaccagcctg ggcaacatag tgagaccccc atcttgacaa  21540
aaaaaattgt tttaaattag ccaggtgtgg tgctgcatgc ctgtggtccc agctacttgg  21600
aaggctaagg taggagaatc gcttgagcct gggaggtcga ggctgtagtg agccgtgttt  21660
gcatcactgc actcctgggt gacagtgcaa gactctgcgt cagacaaaca aacatcgtag  21720
cagatgtgtt tcttaatcag agaagtgtag acaaggctaa ctccaggctt taatgtcctc  21780
atatttagca atgatacctg caaggttgta tgagaaccaa atgaaacgcc aaatttggaa  21840
atacatagta gatacatcat agcagagtaa gccaggaatg cttctcaaag gtaggatatc  21900
atctgtgtcc tcatatcact ttatgaagta cattgtgaaa gtgaaagaac aaagaaataa  21960
atgtttttta gttaatgttt aaaggataca tttatcataa ttgctctttt aacactcacc  22020
tccagtctcc cctccgttca cacctcctac ccccattact tcctggtaac ttagttaagt  22080
gtcctttgtc attcctgagg tttcaaggca tggtagtact gtgtcctgat attctaatcg  22140
taaatattta agggaaattc ggcatttttt cattttgtgg ttttcatatt aaagtacatt  22200
aaatagtctt tttgctttta tttaggaaaa aaactgctta cctgttaatt tttagaaaaat  22260
ctgattttca tttagacctt acagggtgag acacctgcat cagggtggct cttggtatct  22320
ttcaattcaa ttggatcttc tctgaatagt ctcttgtagg gagtgaggct gctgtaccac  22380
ctccctgcag tagtccatcc agcttaagat gggggtcacc agtaggccaa aagaatgggt  22440
agacctggcc atgcactgcc ctattgtact caaatcgtgt atcaaatgga gttggatttc  22500
ttctcttcat acagtacagc atttccaagt agaaatattt ctcaatgaaa tgtggagaga  22560
agcacccgtt tgagattccc gtgtgttgtg tgatttaagt tagatggttt tttaagacca  22620
cattcatttc cagcattcta ggtaacaatt tagaaaatgt ctttctccta acctccccac  22680
tttttaaaaa tcctccaact gatgaactga tgtgaaactt tcttacattc actgaaaaaa  22740
aaaaaaaata ggttaagctg tttctaagca actagatgaa ttaattttta aactaagaat  22800
gtggccttat tttgggaaaa caagaatatt tacttgtttg tctgctgttt aaaaaatgga  22860
agtcagccta ccaaaaaatt gagactcaac ttctaggaga tgggttagga ttttttttt  22920
taagtttctc tagtttaatt ttatatataa ggggttaatg ctaccttcat aataactatt  22980
```

-continued

```
atcatatttt ctcaatacat agcttgatta aaacaactgg actccccccc caccccaccc  23040
cacacacaca cagattttat atcagtctga atctaatgcc tagaataaga agtgcttcag  23100
ccaggcatag tggcactcac ctgtagtctc agctactcag gaggctgagg cagcaggatc  23160
aattgagccc aggagtctga gtctagcctg ggcaacatag tgagacctag aagttttaaa  23220
ttactggaaa aataatatga aaagaataaa ttactggaaa aagaatatga aaatgttacg  23280
ttctttatat ccaaccgtgg taggcttttt tgagttcctg caatgctaat aagaattcat  23340
aaaaaggaca attcttcatt ttcttgggta ctcatcacta atagctgcct cgctggtaaa  23400
aaggaataca tgtatcttca attgcagatt atttactttt aaatataaaa gatataaatg  23460
tcaaatatta aatgcatctt acatggtttt cctacatagt gaaagtagaa tgcttgccag  23520
ttttgcctct aggtcactca ctttgaacca gccaacccac cttaattgat catttccact  23580
aatatgttaa attaccttaa aagaacaaaa atatttatca tgcttactat aacctgtgtt  23640
ttaaaatagg aggccaggca cagtggctca cacctgtaat cccaggactt tgggaggcca  23700
aggcaggagg atcacttgag cccaggtgtt caggaccagc ctgggcaaca aagtgagatc  23760
ctatctccac aaaaaaatta aaaataaaaa cttagccagg cgtggtggca cgtgcctgtg  23820
gtcttagcta cgtgggaggc caaggcggga ggatcacctg agctcaggag gttgaggctg  23880
cagtaagccc tgccaacacc actgcacgcc aacctgggcg acagagtagg acccccatct  23940
cagaatataa aataaagtag gaggtgcatg tgaagtagta tagatcatga cttttccaat  24000
tttaagaggg gattggcatg tactatgagc agttcacatt tgtggaggaa atctacattt  24060
cagagagtat atatttcatt tggaagtcta taaacatgaa aacctaaaat aaataatgta  24120
aatctacctc tagtggctct ggtattttta aacttattta tagctggcaa agtacttttt  24180
tgtatgtatt tttatagcac cattgcactt ctcatgtttg ttgcaagcat ctcccacagc  24240
ttcctttgtc ttttaatttt atgacatata aataaaagta tacatttcaa tatggccata  24300
ttgattgatc ttttcctttg taactcttac tactttatat ttaaaaagtc atttcccagt  24360
ctaaggccac ctctatttc ttttagtttt ttaaaatggt ttcattgttt tatatttgcc  24420
tatgatccag acattagtaa ctgtgggttc ttaattgggc ttcagagaat ctgagaattc  24480
cttaaaattc tctacataat tgtacatgta cttaatacat gctttttcc atgttaagag  24540
tccagagttt ttgttagatc ctcaaagggg tcagtcagtc tctcctccca cttccaaaaa  24600
atgtctgaga cctactacta taatccatct ggactttatt tgggtaaaag gtggtatggt  24660
gagactcata tttttctttt tcccgcaaat agttaagtat accaaccatt tagtaaataa  24720
ttacctcctg atttgtgata cctttgaaaa ataaatgttt ttctttattt ttatctccac  24780
ag                                                                 24782

SEQ ID NO: 4           moltype = DNA  length = 5409
FEATURE                Location/Qualifiers
source                 1..5409
                       mol_type = other DNA
                       organism = Homo sapiens
SEQUENCE: 4
gtgatggatg gtttaagggg gctaccgata cattcacact aatcagccat ttctgccaag  60
atcatgtcac ctcaatctgt tcatggactc caaatacaag aaattaattt gacaaagtga  120
aaatataaaa gatgcatcat ataaatatgt aacttttctg gagtgggtag tataggtaaa  180
gccaaaagaa acaaattcaa gcagaggaat tttggtttct gaaaattagg ttgtctgtag  240
ggtccctgta tttatactta gaacaaaatt aggaatttct gtttatgtgg tccagttatt  300
gagtcaccct aagtttgtag gcatcttacc tacctacttg ctccccaagt ttttatttct  360
aaaatgaaaa gcattgctgt agatgaccag tttacactaa agaataacat ttatttattt  420
gttttagcta aagtatatgg acagggaaca ttcatattct tgtagaagaa aattattttg  480
acttttgggc aaaagcatgt agttcttata cactttgaca aactcattgc gtacattttt  540
cacattaatc aaagtcagca caaataaatt ttcaccttgg accacggagg gtttgaacac  600
tggaaatttg atataattct ggttgctaaa gaacaagttc taataaaagc ttaagtgtat  660
accaatatgt ggctgttggt gcaatcagca ggtccgtaaa aatatgattt taatggttag  720
gtaatcccac aacggagatc ccaaagttca tgtttggaag agacttttgg gtcaaagtga  780
aatcagtgta atgaatttaa aattatactc tgagatcttg aaatcagcta attatgttac  840
atcttattag ctcagaaaag ttttgaagtt atatacaaat gctagtcagg aaaaaagatt  900
cagtcatgta attcttgtac attctactat ttaaatcaac caatattata gattatgatt  960
tagtgcagta attctgctgg ctaaccttat ctcatttggt ggtggttagt acttcagagt  1020
actcaccata gtttcattta tgttttcagc atcacttcct ggtttttctc aattccatgg  1080
ctgtggaatc aattcatatg tatatttagc ttcggtgagc aaaaacatag ctagaaaaag  1140
aaaagaagtg agtttcctac ctggttaaat taaagtcgat gtgttaagcc aaggaggact  1200
tcttttgaat ggtactttaa caatccctgt tctgtatact gtgaatatat catttaaata  1260
gcctaataaa ttggatgctt aggctgagcc acctatactt tagttttgtt atggaaagaa  1320
gggagaggag caagtatgtt cttatatgtt acttagaaat aagaatgtag ctgtagttac  1380
acattgttct taagtttttt tcgtaagaca acttgaaatg agtcccatag gcctgctatt  1440
taacattcta agatatgact taaggttaat gatgagcttt tgaatctgac aattcaagag  1500
atatccataa tgaatactga ttcattttct acattgctga aagctaatgt tcattttaag  1560
cctactttag tagcctttat ttgggcttag agatgttatt cctctttctg atatttattg  1620
ggttatctgt ttaacccttt tatatctccc tttcccgatt tgtaaattag agactggcaa  1680
gactttttac cctgagtaga gcaccaaaca tggcttgttt ctgcccacac tgtagttacc  1740
ttgaggggaa gtaaatggga ctttaaaagc aatttatgct cttttatagt gaaattatcc  1800
ctcttactat cccgaaagac tgttacctta caatatcctc cactcctttc cccctgtagt  1860
tactatagag atgacttttc ggttcttcac tgccataatg atcaaaatcc taattcatga  1920
gatttttatc attccaggca tgtgaggttt acttgatgca taaaaccgca agtacttttt  1980
gttgtttttt aattgttttt tctctcttat cttcttgaaa gtctaagtag atcatcattt  2040
ttgatgtctt attagtagca actaataaat tttccctgta tcttctcagc aaaagaactc  2100
aagcagagac agaagattag aactaccatt ggtagttttg cttcctatgg atatgttcac  2160
atacatagaa atttttacaa tgaccttttt atatatgtat ttcagaattt cagaatggcc  2220
tcaatgcctt aataggaaga aatacttgaa atttttaaat tagggcttgg ttttgtgagg  2280
agctagtaaa ggtttttctc tttcagcttt agcttgtttc tgcggaggat tccgctcttt  2340
ctccatcagt ttcatagccc tggaattgta gaaaagctct ggtttcaaga ccattgatat  2400
ccatttctgt cagggtgagt tttaaattta tttcatgatg caaacaatat attgaacaac  2460
```

```
aggacatgaa cttgttcttg ttgtaagtgg ctgaatttta tcagtaaagc acatcaaaat  2520
aaaatatacc ccaattgcta gttaagacct agagtgacag attgaaaata gcttgtgtta  2580
ttctcttaag aaaatatata aaaattatca tctcatcaat ctttaatgtt tgttttataa  2640
atctaaatgt ttttatattg tttcctagga aatattaggt ctaatttttt actttaccac  2700
cagctgtctt ttattttact cttttttga gacggagttt cgctcttgtt gcttaggcta  2760
gagtgcagtg gcactatctc agctcactgc gacctctgcc tcccgggttc aagcgattct  2820
cctgcctcag tctcccgagt agctgggatt acaggcacat gccactacac caggctaatt  2880
ttgtattttt agtagagacg gggtttcttc atgttggtca ggctggtctc gaactcccga  2940
cctcaggtga tccgcctgcc tcggcctccc agagtgctgg gattacaggc atgagccacc  3000
gcacctggcc agctgtcttt taatataaca ttatgattaa ttgtgatgtt ccattaaact  3060
aagcggagag gaaacatgct ggtaaaccat gtgtgagtta ttcattgtac cagaaaggca  3120
aatgatacat tttatcctaa aattcaaatt tataaacatc ttaacacttg tgatcattaa  3180
atactactaa tctagcatat aaattatatt tgtaggcggg gcacggtggc tcacgcctgt  3240
aatcccagca ctttgggagg ctgaggtggg cagatcacga ggtcaggaga tcgagaccat  3300
cctggctaac atggtgaaac cccatctcta ctaaaaatac aaaaaaaatt agctgggtgt  3360
gctggcgggc acctgtagtc ccagctactt gggaggctga ggcaggagaa tggcgtgacc  3420
ccaggaggca gagcttccag cctgggcgac tccgtctcaa aaaaaaagaa aaaagaaatt  3480
atatttgtaa tattctacta accttatatc attttaactt tttatataac tttttttattt  3540
taccaaatta agttaacctt ttatagccct tggcttatac taaacatcct aacttttttg  3600
tttaattgta ttagttttta agttattgcc ccagatgtca agtaatgttg gattttctat  3660
aataatttag gatatattgc atgaagtcag ttagtattta catttaaaac taaaacaatt  3720
tatactaata cagtttatac atttcatact aatttagcta cagttggata aatatttaat  3780
ggaacaaagt aaatcaaagt accttttcaa atgaattgga aattaaatcc acataacaat  3840
tttttatgac cacactatta cagtgtgatg gcatgccaaa tgatcataat gtggaattat  3900
gtatttcttc attggctttc aagattctgt tctttagttt gtgggctcct ctccaacttg  3960
cttgtctcct cacagtttag gcgactgttt ataattcttg tccatcctgc ataaacacac  4020
acagtcaaaa tgaaaaaaag cttctatcag cagatctgtg cttgctgtac agaaatggga  4080
aaacaattga agtttgcatt atctttttttc taattaccag atcgtttttg gagctattta  4140
ggcatacgct tttaaggaaa aaagaaaaaa agagtgtacc ttttgtttct aacaaaggtt  4200
gttatctata ttattgaaat aaaaaattgg ggatagttat gacaaagtat ttagaaatag  4260
gaattaaaat cttaaaataa cttttcatag catggacaag acttattaat gtctacctca  4320
ataagcaaat catttaaaaa tttttcatgt atatttgctg ccatgatgtg ttgtgattgc  4380
ttaaataacc aatgaatgaa gatcaacaag gatttaaatg aagaagaata tggatttaac  4440
tattttctcc tgtgaaataa gttcatattt acaagttttg attttcagaa attagacaat  4500
tatttttaaa ggctgggatg acaacttctg cctcttacca agaagtcaaa gcacagttat  4560
gtgaattcat cataaatcac atcattttta ttatattttg tatttataat tgtattgtga  4620
ctactttaaa acctgttata aaataaaatt gttttttaat attttatttt agaattatta  4680
gcattaataa caatttgaag tagtttacac aatacctgtg agttttattt ttgttttata  4740
ttgaaattaa ttttagttgc tttacttggc ttcattgcta tggatgcatt ctctgtgtta  4800
cgagttagca gatctttcct tggaactgaa tttaaaagca agcatttggc tccacttaaa  4860
tctctgaaaa tgcaacttgt tctttgcatt tattacataa ttcgctactt atggtacaga  4920
aatggataca atacaaaaat atttccttat aagatacact gtgaccaatg agctttttaa  4980
atagctgtaa tcagtaacat gtatttgact tttcaaaaca catttctgga gggatatcag  5040
tgctttattt ccccaaatat ctgaatccct atgctttagt acaaaacaac ttctgaagaa  5100
tttagtaacc atatgtgttg atctcttgtt tttctaacta gtctttcata agaaatgact  5160
agaatagcaa cagggaaatg attgcctttt aaggttttg tttctcaata taaaattttg  5220
gtgaaccatt tttattgata aatacaggta tttttacttt cttaaatcac ttgatttaaa  5280
attactttga ttaaatatgc atataaagtc agttgttttt aactctcaat acttatcaaa  5340
aaaatttaac ttgctgtaca ttctgtataa acctaattct attcaactaa aattatttta  5400
aacatttag                                                            5409

SEQ ID NO: 5            moltype = DNA  length = 21301
FEATURE                 Location/Qualifiers
source                  1..21301
                        mol_type = other DNA
                        organism = Homo sapiens
SEQUENCE: 5
gtaagtgcag gctctaatct ggccccgtta attctggggc ctcttgagag tggggctgtc  60
ttatctctat ctccaaaaat gtgcaggtga ctctcaggcc aggccgacgg cagttggaga  120
attcccagat gttcttgagg acccagaatg acaggagccc tggctgggct tacgttcgga  180
gccggcttca atactggccc ttttctctgg ccctacccaa cccgaaaatt ctggacgcct  240
ctcaatcttg gcccgtctct attgtccttt tgtctctgcc ctttacaccc ttgtgtcttc  300
agtgttctgt ctgtctctgg ttgcctcttt tgccttttttt ctgtcctctc cctgccaggt  360
ttggctctgt ccatgagtca cctctctcca catttctcct aactctcggt gtcttctttt  420
tcttccattt ccacgccatg tgtacattgc atcttcaggt acctgggctc ttctatcggg  480
gaaaggggcg tccgtctctt tccctagccc gctgatagaa gtcagaacta gagcaatgac  540
gcacacggtg tcagagacgg tgattcgaga tgccctttca atagcagctt ttttctgtgt  600
ttcgggaggg agacttactt tttgatgcaa ggtcgtgaac gtggcaccac ctttctaatc  660
tcaatcattg ttgccctggg gtggtttaat tctaaataga aaatcataga aatcttttca  720
tttctgtgcg ttactatatg cattgtaatg agattaaatt ggattttata ggaaattttg  780
ttctagtatc attagatacc ttcaagctta gctcattgtt gcaggcattt gataggaagt  840
aagatgcatc aagcaaaatt ggaaaaacgt ggttttcctg aattaacttc taagcagttg  900
ttttgaattt tttccagacc tttttaagtg gtatagataa tttatcgtgt ttataaggaa  960
tggaatgcat tcgttagttt gtttttgttt tgttttgaga cggagtcttg ctctgtcgtc  1020
caggctggag tgcagtagcg ctatctcggc tcactgcaac ctccgcctcc caggttcaag  1080
caattctcct gtctccgcct ccggagtagc tggaattaca ggcacgcgcc agcacgccta  1140
gctaattttt gtatttttag tagagagggg gtttcaccat tttggccagg ctggtctcga  1200
actcctgacc tcatgtgatc caccctcctc gacttcccaa agtgctggga ttacaaccgt  1260
gagccaccgc gcccggccca atttgtttta tataggttaa ctggagtcca aaatacagaa  1320
```

-continued

```
ctagatgaga taacaatagt taacagtgtt agtcagttag aattattgca taggtatttt  1380
taatctcatg gaattttagt ctttgagtaa gttcacagcc cttggtatta aagtaagtta  1440
tttacaaccc ttgcatttct acttctcaat atttagtgag gaaacatatc tgattttctt  1500
taaataaaaa gagaaaagac tgcagaagat agcattctct gttggagcaa ttaagatgta  1560
taagaagaac tacaaagacg gagttttaaa acaaactgat ttataagtgg tatttattta  1620
attggctgtc attgggctaa attatttcta aagttaccat ggatgccatt gagtcatggc  1680
ttaaaaatgt ctcctggtga tggcacagtt tagctaccta aagaagtaga gatgtgggaa  1740
gccagaagcc ccaagctctg cagtttttct tttgctatag ttcctttgca tgttgtgaaa  1800
gaatacagtt aaattcctgc tccctaacag atgagagcat aagcatttct ttgggcatac  1860
atatgtaaat acatgctcat ggacatgtga aaagatcaat actaacattt gggtgcaata  1920
aataattgtg taaaattatt tttaaaagaa ttacatatta ggaaatgata tattgattaa  1980
aagtgatagt caatgaacaa gagagtagat ttctgggga aacctatttt gcatcatact  2040
tgatttttag ttttgactga atattgaagt ctatattcaa aattcttttc ctttagaact  2100
gtaaaggcat tgctgcattt tcttctaatg taattgttta ttgctgctga gaattcttat  2160
gacaatctga tttttcatc ttcatgatta tcttgttttt cccttcatgg aatctgttag  2220
ggtcttgact ttatccttta tcctaaattt ctcaaggctt ggaccaggtg tgggtttggt  2280
tttgttttct tttgctactc atttgacttg gcacactcag tgggcctttc cctttatctt  2340
tcttcatttc tgagacgttt ttctctctta ttttttatta tcttcctttc atttttcctg  2400
tccttttct ttctagacat ctcttaggag gatagtggtc ctcttagatt gatatgttat  2460
gtccgtgatt tccaaagtaa gatttgtact cgtcgtctgt taaaaggaaa agcatacata  2520
taccctatgt atatatgcac acttttttat ttttaaatta tatatgtatc tgtactaatt  2580
atttacattg taagtcaacc ctaacataat cttaaaggat aagatacaaa acatactgca  2640
tctagaagct tcagtacttt cttcctgaat cccagtagat ccttttgttc atcccacggg  2700
atgcattccg cccccatcct cccactccct ttggatacca cattaccaca gctctgcatc  2760
acttaacttt cctcttatgt ttttcacctt tttttttttt tttttttgc attttatgtc  2820
ctggggaatt tccttaattc atttcatggt tttactgttg atttttttaa tattggccat  2880
cgcaactttt cttttctttt cctttccttt cctttccttt cctttccttt tcttttcttt  2940
tcttttcttt tcttaatttt cttttctttt cttttctttt ctgttctttt cttttctttt  3000
cttttctttt ctttcacaca ggatcttggc gtgttgtcca ggctggcctc gaactcctgg  3060
gctcaggtaa tcctctcacc ttggcctccc aaaatgccag gattacaggc gtgcgccact  3120
gcatttggcg gcaacttaat tttttttattt ttatttttcc ttttagagga cacctagcac  3180
tgagcattgc aacttttcat ttccatgaac ttttaagaaa actcttaaag acatgtttaa  3240
ttctgtacac tttctattgt tctttgattg ctgtttttga ataacaacaa ggagtacgcc  3300
ttagcatttt gatggtatcc tcttaatagt cgcaataata gtccccttgg cgctctgtat  3360
actctcaagt cttaaatgtt ttgtatgcag ctgtacgttg acagttgaat ggtctcgctc  3420
caagtggatc agcaagaaca taaagaatca tttaactggt acaggctgcg gcttgtgaat  3480
tccctattaa caccaaagaa gacgtgtgag actccgtact gaaactaaag acgacttgtg  3540
agttccacac tgagatcaaa taagtcttta tgatggtgac agagagtggt gtcaacgcct  3600
aaagttttgg ttaatctctc taaattgagg ggctgaccaa aagggggaac ttaactgtat  3660
tagacataat tttgagaaac atgggtatgt ggatggtaat ggaggaaatg ggtgtagatg  3720
agattgccta gggagagtga gaagtaggtt aggtctaagc cttgatgagt tcccaacatt  3780
tccaagggta gttgaggata ctgaaaatga gtggccagtg agatagaggt aaagctagag  3840
actgcccagg ggagaggaat tttcaacaat gaggaggtgt caacattgtc aggtattgct  3900
gagaggtcag ataaaaccag aattgagcaa aatggccatt ggaagcctat ggtgccctcc  3960
gtaagagctg tttcgctgaa gtgatagaaa cggaaatcag gctgggcaca gtggctcact  4020
cctgtaatcc cagcactttg ggaggccgag gtgggcggat cacctgaggt taggagttcg  4080
agaccagcct ggccaacatg gtgaaaccct gtctctacta aaaatacaaa aagtagccag  4140
gtgtggtggc aggtccctgt aatcccagct actcaggagg ctgaggcagg agaatcgctt  4200
gagccccaga ggcggaggtt gcagtgagca gagatcgagc cactgcactc caacctgggt  4260
gacagagcaa gactccgttt caaaaaaaaa aaaaaaaaaa gaaatggaaa tcaggatggt  4320
ttggctttta ttttaataaa atagctagag cagggaaatg gggtactttt tttcccctt  4380
ttaagatgag acatagccag gtgcagtggc ttacacctgt aatcccaaca ctttgaaagg  4440
gagggtcgct tgagctcagg agtttgagac cagcctaggc aacatagcaa gaccttgtct  4500
ctactaaaat tcaaaaaaaa ttaactgggc atgctggcac acacctctag tcccagctat  4560
ttatgaagct gaggcaggag gatcacactt gagcccagat acgtggggct gcagtgagcc  4620
ctgataatgc cattgcactc cacgttgggc aacagagcaa gacttcgtct caaaaataaa  4680
taaataccct gtctcaaaaa taaaaaataa atatgggagg agagatttga cttagattcc  4740
tcaaagggca ggaggaaaga gaattccaaa cagtgattca cctttaatgg gagaaagatc  4800
gcttaatttt acatgaggaa gaagaggatt ggtggagata cagtaggtga acagtttttg  4860
tatgaggaag ttgaacatgt gtcattctaa tagcttccat tctctgtgaa gtagagggca  4920
aggtcatcta ctgagagttg gggaggtcaa gagagataag gggagattag aagagctctt  4980
ctagcagaga gtggaagaat gaattgctaa gagagatgaa gtaggattgt taagtagttt  5040
tgagggccct gttgagatgt gcttccagtt gggtgtgatt ttctccagta gtgctttatt  5100
tccctgggta caggcagaga gaaaaacaat aaggctcatg tagggtttgt attttgttgg  5160
acaagtcaaa cagaaaagtc agaggacgag ggagtttaga atgtttgcaa aagagttatt  5220
gaaacgatga accgcataat ctaaggtggt aagtgggtga atagataagg aggatgtgaa  5280
taggtaagga gaagaaagaa atatcagatt attgattatt gatggcgact ctctaataca  5340
gctattatgc cattttaacc gattaagaaa ctaaggcttt agaaaattca taatttgccc  5400
taactgcaca gctagtaagc agtggaaatg tgattggaac cagagttctt ctgactcaat  5460
agactaaatg gatgtaagga tgtagttgaa agaagggtga gctaaacgtt gtggaaccat  5520
gagctctttc tctggttgat atccctctct gtaagtgata acatgggtca cgctggataa  5580
aaccttgtgg tgattggtga ctttcctttg tccttcctcc tgtgcctagt ctggcgagta  5640
tctgcctttc cctttccttt ctcattgctg ccacctaact ttaggctctt ccccttacat  5700
ctgggtaact gaaataagat caccttttttg ttccccttct gatttacttt gacctaacat  5760
tatctttact attttcttta aattaatgtt tcattagtct tattctactc aggaactctg  5820
tagttcccca ttgcctacga aaaaaagtta agcctcagcc ttatattcag tgactcttca  5880
attggatatt cagtccagtt ttactcctcc tatgagcctt ctatgccagc tccttgggtc  5940
tcttgccctt tcattgtctc agctctgcac ccttctttct ctttttttatt ctttttttttt  6000
tttgtacttt tttggttttc tttttggttt ctttttttgt tttatttatt aaacctccat  6060
```

```
cacacttcat cctatggagt tttgaaccac agcaaggtgc agtatcatcc tggggctctg  6120
gaggaagtgg cagggagtcc aaaatgtcac cttagcttct tatctggggc cacatgtatt  6180
tctgcatctg ctgcttccca cactcttgcc cacaagtgtc gcttgtggaa ataatttgag  6240
atttactgtc tggctgaccc tagtttcaat ctcttttcca ccatttgcta atcattctac  6300
cttgggcaaa acatagaatt aaaagaaaac ttcagacaag ttaaatttga tggagtttaa  6360
ttgagcaaag aaaaaaaatg atccacaaat tgggcagtct ccagaatcac cgcagattca  6420
gagagactcc aggggtgcct cgtggtcaga acaaatttat agacagaaaa ggtaaagtga  6480
cctacaggaa tcagaattga gacatagaaa cagtgagatt ggttacagct cggcgtttgc  6540
cttatttgaa cgcagtttga acactcagca gtctatgagt ggttgaagta tggccgctgg  6600
gattggccaa cactcagctg ttattacaga tgcatactac taagttaggt tttcgatttt  6660
gtctgcctat ttgagctagg ttacagttcg tccacaagga ctcaaatata aaagtacgga  6720
gtcctcttcg ggccatattt agttcgcttt aacaattccc ccttttggtc agcccctcaa  6780
tttagagaga ttgaccaaaa ctttaggcgt tgacaccact ctctgtcacc atcataaaga  6840
cttatttggt ctcagtgtgg aactcacaag tcgtctttag tttcagtatg gagtctcaca  6900
catcttcttt ggtgttaata gggaattcac aagttgcaac tttgtaccag ctaaatgatt  6960
ctttatgttc ttgctgatcc agttggagta agaccattca actgtcaatg tacagctgca  7020
tacaaaacat ttaagacttg agagtataca gtgcaccaag gggactatta ttatgactgt  7080
taagaggaca ccgtcaaaat gctaaggtgt actccttaat aaaagttctt atgaaatgaa  7140
ctgaaccaaa tcagccaagt taaggttcag acaatataag cagttcagca gtattggggt  7200
ctgattggtc agagtcttca gttggagtat gatagtgatt aaggatcata gttcgctgta  7260
aagtagcttg acttaaagag gtgctcgttt tcattgttac cttgttaata caagtcataa  7320
taacttgaaa acctgctaga agagatataa agattagaaa cccttggaaa acccaagctt  7380
gccattcacc acttaggatg cctgcaaacc aactgttagt tgctcctata aacatatcgt  7440
gggttccttt ctcttgagag atttctttat tgtacttggt ggcagtgtct aaggaaacag  7500
cagtatcagc caccttttaa attaagcttt ttgtagtaac agaatcaggg gagggattag  7560
tacaaaattc agttttgttt aacaccaaac ataggcctcc agcttgagca aaaagaagat  7620
ctaagactgc atgatcttcc attaagtgtt ttcgttgaat atgtatgttg tcatgtgcct  7680
ttctgagagt agcttctacc catctgaaac cctgggaggt ctgattggct accaaatcca  7740
agaattttcc caatatacaa attagtttta aattccgtac aaatggtact tcactaccac  7800
caagagtgag cccccaggaa ccccagtgga atctttcccc ggtagaaact agcttatcct  7860
cgtctatttc gaggctagtg ctaatttcag ttattgatca ttttggcctc caagtataag  7920
ggctatcatg agaattttca ggggaagcaa ttcgaaaggc aggagcaggc caggccagat  7980
aacaagaacc aaaccaacca aggaggcaga acagaatatg cagattctcc acagacccaa  8040
tagagaccct caggggttgg aaaagggggc cacctagttg tatttgagca gggatcattc  8100
aggtttgttc gaccatgaat ctgtagctcc tgaataacat ccagtgggaa atttactttt  8160
ctatggcccc tttgtagtgt gttgtaaggg tgtataacca catctagtaa aaagagaccc  8220
tactggatat acaagcaatc acttgtacta acataagtaa ttcccaaatc ttgagtatgt  8280
gatgcctgca agcacaatat acgttttgta ggcatcattt ggatttgttt tttatatttg  8340
gtgtgatcga ctttatcagt tgaaaaagag tgttgttttt agtgagtgta ggaaagcaag  8400
tactagtgat gtttagagta tcaagaatag ctttccattc ttcccttggg gtttcagggt  8460
gactcattgg gaaacgtgga ggggcactgg caccccttgga atcatttcct gattttttgg  8520
cattagccca caaacccaac agttaccctg gttttgtgct agagcataag cttgagctga  8580
agccatccac tgattatggt cccatggatt ttcatgtaag gaaaaggaaa ggattaggga  8640
aaaaaataag gaaaacagaa aaacacataa ggctttcatg gtggtagaga agtcttgatc  8700
tgtgatctag ggaaagctgt ctgtaaccag gatgctgtct gcttctggga agagatttcc  8760
ctggtcagct ttaccttaaa gtctccaacg ggtatatagt accaggagtc tgagggggcc  8820
cttttgaatt gtgagatgtg gacccatggt tcaaagccct gaagcttctc tgcactgtgg  8880
gtggtaagaa ggacttggta tggtcccatc caacgaggtt caagagtgat cttcttctga  8940
tgtcatttcc ggaaggccca gtctccaaat tccagaccat ggagggtttg attgtcctca  9000
gttggtggat cttgaaatgc ttcctttacc tggtggaagt atactttggc gtaatacatt  9060
aaagccttgc agtatttagt catatcagag tttaagagag caggagaagc atgagatgct  9120
attattaggg acatgggcct cccagtgact atttcataag gggtcaattt atgttttcca  9180
acaggattga atctgattgc cattaaaacc aaaaggtagt acctttggcc aaggcaactc  9240
aattgattca gttaacttgg acagtttcag ttttcaaatg ccatttgttc tttcaagctt  9300
tcctgaagac tgagggtaat aaggacaatg gtaatgcaac tgtgtcagta acaccttatt  9360
taactgcttt ataacttgct cagtaaaatg agttcctcta tcactggaga cttttagagg  9420
gatcccccat aaaggaaaaa cattttctaa taatttctta gctatggtca cagcatcagc  9480
tttcctacat gggaaggcct ttatccaacc agaaaacatg caaactatta caagaacata  9540
ctgataccccc attgagggtg gtaactgaat gaagtccatc tgtaaatgtt caaatggtcc  9600
atcaggtggt ggaaatatac tgcctctagt ttttctggga ttatgagttt gacaagtcaa  9660
acattgatta taagccattt tagtaatgtc agaatagtca ccccaccagt atttttttcat  9720
aatttggatc actttgtctg ttccatgatg agctgtggag agctttcaat aatggaagct  9780
tcaaagattc aggaaggacc aggcggccgt ccgggccctt tgtgagtctt tgcttcacgt  9840
taaatttaca tccttttaga taccagtttt gtttttgcaa atcagatgcg ttgcactgtt  9900
tattaaatag gtcatcgtaa ggaaattggc ttggattaat cttatggagt tcattcagat  9960
tgcgtatctt gatggttcca gcactagctg attgagcata aaaatctgct aaagcatttc  10020
actgatattt gggttcattt ctacaagtat gagcttcagt cttaataaca gcaatctgca  10080
tttgtaacag gatagcagaa aggagctcat ctgtttggag tccatttttg atggggatcc  10140
cactagaggt gagaaacctt cgtagtttcc atatcatgcc aaaatcacgt actactccaa  10200
aagcatgtct actatccgta aatatttact gacttgtcct tagctgtgtg acatgttcag  10260
gtaagggcag aaagttctgc aggttgggct gacttgactt gaagagttcg cttctctatt  10320
aactcatttt gggtggtaac agcatatcct gactgatatt ttttttctg agtttttggc  10380
ataggaccca tcaacaaaaa gtgttaattc aggattatcc agtggagtat cttgtatagc  10440
aacacgaggg gccactattt ctgatactac actcacaccg ttgtggtctt caccatcatc  10500
aggcagagat aacagagtag cagcattaag tagattacag ccttttagat gaagataaga  10560
aggagatagg agaagtaatt cataagatgt tagtctactc actgaaaaat gctgggtttg  10620
attggaattt aatagacttt ccacagcgtg tgggacttgc aaattaagtt catttcctaa  10680
aaccagatct gatgaagctt ctaccagctt ggctgctgct actgctttta aacaattagg  10740
atatgcctta gagactgggc ctaattgcag gctatagtat gcagtggtcc tatgtttagc  10800
```

```
accgtgttcc tgattattac attcatgaac aaacaaagtg aaaggtttag tgtaatttgg  10860
aagtcctaaa gctgggggct gttgtaaggc caacttcatt tggctaaaag cctgctcatg  10920
actgtcttcc caaggtaaag gctctggtac agcattttta gtgagctcat acagtggtga  10980
agctattaag gaaaaatttg gaacccagga tctgcaatat cctgcaagcc taagaaagcc  11040
ttttgtcttt tggttgcagg tcgaggaaaa ctttaaatag gttttatcct ctcaggtaag  11100
agggaaatcc cttcagcagc caagtcatgt cccaaatagt ggactttttc ttttgaaaat  11160
tgaagttttg gccaggcatg gtggctaacg cctgtaatcc cagcactttg ggaggctgag  11220
gcaggcggat cacctgaggt cgggagttca aggacagcct gaccaacatg gagaaaccct  11280
gtctctacta aaaatacaaa attagccagg cgtggtggtg catgcctgta atcccagcta  11340
ctcgggaggc tgaggcagga gaatcgcttg aacccaggag gcagaggttg tggtgagcca  11400
gtatcacacc attgcactcc agcctgggca acaagagtga aactccatct caaaaaaaaa  11460
aaaaaagaaa aaagaaaaga aaaaattgaa gtttttccat tgaagccctg tgacctttat  11520
atgcaagttg ctgtaaaagg taaactgagt caatttccgg gcactcctta ataggagagc  11580
ataacaataa gttatctaca tactgaatga gagtagaatt ttgaggaaac tgtagtgtca  11640
ttaactcctg atgcagtgcc tggggaaaat atgaaggggc ttcagtaaac ccttgtggca  11700
ttacactcca ggtgtattgc tgatttttcc aagtaaaggc aaacaagtat tgactttctt  11760
tatggaatgc tagagaaggc tgagccaaga tctattactg tggacaactt ggaatcagtg  11820
ggtacattag gttataaagt attaggattt gggactacag gaaatcttgg tattacaatt  11880
ttattaattg cctgtaaatc tggaacaaat ctccagtctc atccattttg tttttttaact  11940
ggtaggattg gagtgttaca ggggctggtg catggaatta tgagtccttg tttaattaaa  12000
tcttctacaa ttggtgagag cccttaaatt gcttcaggtt ttagtggata ttgtggtaat  12060
taggcaaagg tttagaatga tctgttagta ctttttatagg ttctacactt ttaattcttc  12120
ctatatcagt tgggaagagg cccataaaca ttaggtgttt tcgaaagatc aggggtatta  12180
caggcttgag tttcgatctt atcaatttct gcctgtagac agcataacaa ttctagttca  12240
ggagaatcag gaaaactctt aagattattt ctgtttctga ggaaaatttt aggtgccctt  12300
ttagctttga aagtaaatct tgccctacca agtttactgg aacagtatca cgtagtaaaa  12360
aactgtgttt ttctgaaagg gggctcagag ttaattggat gggttcagat atgggaacct  12420
ctggaacttg atttgaaacc cctgtcacag aaatgacctt tttactctaa gggatttgtt  12480
ggcttattaa ggtggggttt atggtagata gagtagccct ggtatccata aggactatac  12540
acaactccct atttatttta acctctgttt ccccatgttc ctttaaaggt attacgggga  12600
gcaatccact ggagaatccc ttagagcctc ctttaagttg aatattgtca ggaggactaa  12660
ggtctcttgg gctccctcta gtggtgaaac agtttggcct agagggaggt ttatcagccg  12720
acaatccctt ttccagtgcc ctggttgttt gcaatacagg cagacatctt ggggtaaaga  12780
aattcttgtt ctgggacctc ttgatttgat ttttttaata tataatttta aaaatatttt  12840
ccaaagtgtg acttaaaaaa atttttttttt attatacttt aagttttagg gtacatgtgc  12900
acaacgtgca ggtttgttac atatgtatac atgtgccatg ttggtgtgct gcacccatta  12960
actcatcatt tacattaggt atatctccta atgctatccc tccccccctcc cccaacccca  13020
caacaggccc cagtgtgtga tgttcccctt cctgtgtcca agtgttctca ctgttcagtt  13080
cccacctacg agtgagaaca tgcggtgttt ggttttttgt ccttgtgata gtttgctgag  13140
aatgatggtt tccagcttca tccatgtccc tacaaaggac attaactcat cattttttat  13200
ggctccatag tattccatgg tgtatatatg ccacattttc ttaatccagt ctatcattgt  13260
tggacatttg tgttggttcc aagtctttgc tattgtgaat agtgctgcaa taaacatacg  13320
tgtgcatgtg tctttatagc agcatgattt ataatccttt gggtatatac ccagtaatgg  13380
gatggctggg tcaaacggta tttctagttc tagatccctg aggaattgcc acactgactt  13440
ccacaatggt tgaactagtt tacagtccca ccaacagtgt aaaagtgttc ctatttctcc  13500
acatcctctc cagcacctgt tgtttcctga ctttttaatg attgccattc taactggtgt  13560
gagttggtat ctcattgtgg ttttgatttg catttctctg atggccagtg atgatgagca  13620
tttttcatg tgtcttttgg ctgcataaat gtcttctttt gagaagtgtc tgttcatatc  13680
cttcacccac ttgttgatgg ggttgtttgt ttttctcttg taagtttgtt tgagttcttt  13740
gtagattctg gatattagcc ctttgtcaga tgagaagttt cagaaatttt ctcccattct  13800
gtaggttgcc tgttcactct gatggtagtt tcttttgctg tgcagaagct ctttacttta  13860
atgagatccc atttgtcaat tttggctttt gttgccattg cttttggtgt tttagacatg  13920
aagtccttgg ccatgcctat gtcctgaatg gtattgccta ggttttcttc taggattttt  13980
atggttttag gtctaaatta agtctttaat ctatcttgaa ttaatttttg tataaggtgt  14040
aaggaaggga tccagtttca gctttctaca tatggctagc cagttttccc agcaccattt  14100
attaaatagg gaatcgtttc cccgtttctt gtttttgtca ggtttgtcaa agatcagata  14160
gttgtagata tgcggcgtta tttctgaggg ctctgttctg ttccattggc ctatatctct  14220
gttttggtac cagtaccatg ctgttttggt gactgtagcc ttgtatagtt tgaagtcagg  14280
tagcgtgatg cctccagctt tgttctttgg cttaggattg acttggcaat gcaggctctt  14340
ttttggttcc atatgaactt taaagtagtt ttttccaatt ctgtgaagaa agtctttggt  14400
agcttgatgg ggatggcatt gaatctataa attaccctgg gcagtatggc cattttcacg  14460
atattgattc ttcctaccca tgagcatgga atgttcttcc atttgtttgt atcctctttt  14520
atttccttga gcagtggttt gtagttctcc ttgaagaggt ctttcacatc ccttgtatgt  14580
tggattccta ggtattttat tctctttgaa gcaattgtga atgagagttc actcatgatt  14640
tggctctctg tttgtctgtt attggtatat aagaatgctc tcttttgttc tttgttagtc  14700
ttgctagcgg tctatcaatt ttgttgatct tttcgaaaaa ccagttactg gattcattga  14760
ttttttgaag ggttttttgt gtctctatct ccttcagttc tgctctggtc ttatttattt  14820
cttgccttct gctggctttt gaatgtgttt gctcttgctt ctctagttct tttaattgtg  14880
acgttagggt gtcaatttta gatctttcct actttctctt gtgggcattt agtgctataa  14940
atttccctct acacactgct ttgaatgtgt cccagagatt ctggtatgtt gtgtctttgt  15000
tctcattggt ttcaaagaac atctttactt ctgccttcat ttcgttatgt acccagtagt  15060
cattcaggag caggttgttc agtttccatg tagttgagca gttttgagtg agtttcttaa  15120
tcctgagttc tagtttgatt ccactgtggt ctgagagaca gtttgttata atttgtattc  15180
ttttacattt tctgaggaga gctttatttc caactatgtg gtcaattttg gaataagtgc  15240
agtgtggtgc taagaagaac gtatgttctg ttgatttggg gtggagagtt ctgtagatgt  15300
gtattaggtc cgcttggtgc agagctgagt tgaattcctg gatatccttg ttaactttct  15360
gtctcgttgg tctgtctaat gttgacagtg gggtgttaaa gtctcccatt attgttgtgt  15420
gggagtctga gtctctttgt aggtcactca gggcttgctt tatgaatctg ggtgctcctg  15480
tattggttgc atatatattt aggatagtta gctcttcttg ttgaattgat ccctttacca  15540
```

```
ttatgtaatg gccttctttg tctcttttga tctttgttgg tttaaagtct gttttaccag  15600
agactaggat tgaaacccct gccttttttt gttttccatt tgcttggtag atcttcctcc  15660
atccctttat tttgagccta tgtgtgactc tgcacgtgag atgggtttcc tgaatacagc  15720
acactgatgg gtcttgactc tttatccaat ttgccagtcc gtgtctttta attggagcat  15780
ttagcccatt tacatttaag gttaatattg ttatgtgtga atttgatcct gtcattctct  15840
caacatttgc ttgtctgtaa aggattttat ttctccttca cttatgaagc ttagtttggc  15900
tggatatgaa attctgggtt gaaaattctt ttctttaaga atgttgaata ttggcctcca  15960
ctctcttctg gcgtgtagag tttctgccga gagatcagct gttggtctga tgggcttccc  16020
tttgtgggta acctgacctt tctctctagc tgccattaac attttttcct tcatttcaac  16080
tttggtgaat ctgacaatta tgtgtcttgg agttgctctt ttcgaggagt atctttgtgg  16140
cattctctgt gtttcctgaa tttgaatgtt ggcctgcctt gctagattgg ggaagttctc  16200
ctggataata tcctgcagag tgttttccaa cttggttcca ttcttcccgt cactttcagg  16260
tacaccaatc agacgtagat ttggtctttt cacatagtcc catatttctt ggaggctttg  16320
ttcgtttctt tttattcttt tttctctaaa cttctcttcc cgcttcattt cattgatttg  16380
atcttccatc actgataccc tttcttccag ttgatcgaat cggctactga ggcttgtgca  16440
tccgtcacgt agttctcgtg ccttggtttt cagctccatc aggtccttta aggacttctc  16500
tgcattagtt attctagtta gccgttcgtc gaatttttttt caaggttttt aacttctttg  16560
ccatgggttc gaacttcctc ctttagcttg gatagtttga ttgtctgaag tcttcttctc  16620
tcagctcgtc aaagtcattc tctgtccagc tttgttccgt tgctggtgag gagctgcatt  16680
cctttggagg aggagaggtg ctctgatttt tagaattttc agtatttttg ctctgtttct  16740
tccccatctt tgtggttttg tctacctttg gtctttgatg atggtgatgt acagatgggt  16800
ttttggtgtg gatgtccttt ctgtttgtta gtttccttc taacagtcag gaccctcagc  16860
tgcaggtcta ttggagtttg ctggaggtcc actccagacc atgtttgcct gggtatcagc  16920
agcggaggct gcagaacaac gaatattggt gaacagcaga tgttgctgcc tgatcgttcc  16980
tctggaagtt ttgtctcaga ggggtacccg gccatgtgag gtgtcagtct gcccctactg  17040
gggggtgcct cccagttagg ctattcgggg gtcagggacc cacttgagga ggcagtctgt  17100
ctgttctcag atctcaagct gtgtgctggg agaaccactg ctctcttcca agctgtcaga  17160
cagggacatt taagtctgca gaggtttctg ctgccttttg ttcggctatg ccctgcctgc  17220
agaggtggag tctacagagg aaggcaggcc tccttgagct gcagtgggct ccacccagtt  17280
cgagcttccc agctgctttt tttacctgct caagcctccg caatggcggg cacccctccc  17340
ccagcctcgc tgccaccttg cagttttgatc tcagactgct gtgctagcaa tgagcgaggc  17400
tccatgggca taggacccgc tgagccaggc gcgggatata gtctcctggt gtgctgtttg  17460
ctaagaccat cggaaaagcg cagtattagg gtgggagtga cccaatttc caggtgctgt  17520
ctgtcacccc tttccttggc taggaaaggg aattccctga ccccttgtgc ttcctgggtg  17580
aggcgatgcc tcgccctgct ttggctcatg ctcggtgcgc tgcacccact gtcctgcacc  17640
cactgtctga caatccccag tgagatgaac ccagtacctc agttggaaat gcagaaatca  17700
cccgttttct gcgtcgctca agctgggagc tgtagactgg agctgttcct atttggccat  17760
cttggaaccg cccgattgtg atttaaaatg agaacgagat ggtccctttg gttcctggtc  17820
cctgtaactg ttgcaattga aggggcataa gcttattagc cttttgaggt ttttttgct  17880
ctagagtctt ctcaaaatgc ttagctaggt tgggcacgat ggctcacgcc tgtaatccca  17940
gcactttgga aggccaaggt gggaggatca cgaggtcagg agatcaagac catcctggct  18000
aagatggtga aatcccatct ctactaaaaa tacacagatt agctgggcat ggtggcacac  18060
gcctgtagtc gcagctactc gggaggctga ggcaagagaa ttgcttgaac ctgggaggca  18120
gaggttgcag tgagccgaga ttgcgccact acactctagc ctgggtgaca gagcaagact  18180
ccacctcaaa aaaaaaaaaa aaaaaaaaaa aagttcagct aaggccacca attcagtcac  18240
atctctaact tcccattgca acttatgttt tttagttaaa ctgctaagtt caggatggag  18300
tccatttata agtaaagcag ttaatgctgt ttcagcccct gcagggaata ctccttgctg  18360
tactttgagc ccaggatgtt tcacaaatat ttctaagcga cttctgtaat ctgaaactgg  18420
ttcatctttt cttttctttt ttttttgctt acaagattgt atgatggacc aattttttgt  18480
ggaaaaattt taggaactga atgttaaaag gttttcagcg atttttctag ctatttttgg  18540
tccttcttgt gaggagctct tagagggccc tttaaaatgt cctcctcagg tttgtcccat  18600
tctgctgctg ccatccattt ctgagcttca ccagcccccca gtatcatatg aataaattgg  18660
taaattcatg aagtcctgga tcgtaagctc ctattaggat tctaaattcc tcagtaaatt  18720
tttgagactt ttcccttgga ccagggaagt ccttcacaat ggggctaagc tcagttttag  18780
accatggagt gaaagtagtt acagcaggca ggcctggctg atataaggtc tcactttgta  18840
agacatctgt ctaacttcct ttttttttt ttttttttt taaatcatct tcagggtgaa  18900
agtgtaattt aacaaaaagt ttagtggact cagagtatgt aggtagagat ggacaaagaa  18960
ggaacagtcc gagttagatc agtcaaagta cagtcctctt tcttcatgtc cttggtctgt  19020
tgcttaagct tttcatttgg tttttgcaaa gaatctttta aggaggcact ttttgattca  19080
cttagtcttt tggaggcctt tgcgtatcca tgagacaata catcccactg tatttgtggg  19140
ggctttgatc cccttttttct aatatgcctt gcaaacaatt ttatccaaat taaaacttct  19200
ccattgtggc cattttaatt ctaagttttc tttagtgagg ttaacccatt ttactgaaaa  19260
tgcacatgtt ctgggcccat aatttttata cgtaaaatta gctggagtcc ctgaagatgg  19320
agtcccagac tccttggatt gagatgatcc cattattaaa taaggtactt atcagaggtc  19380
tgaggcctct aactgaatcc aatccagtta attatcaaat ccaatttgat cttggatcca  19440
gtccaggcta agtattgctt gagtaaactc ggagagctca aaacacaagt tagtggagct  19500
cggaatctga gagaaaactc acccatgacc tccagttaca atcaagagac cagtgagagc  19560
aacggcctca gtgggtacct caccaggtca cctggtgttc caggggggttg ccagagtttt  19620
tcttcaaatc ccacttctga caccagatct gttaaaagaa aacttcagac aagttaaatt  19680
tgatggagtt taattaagca aggaaaataa acactttgca aatcaggcag cctccagaat  19740
tgaatgcagt ttgaacactt agcagtctat tagtgcttga agtatggcca ctgggattgg  19800
ccaacactca gctattatta cagatgcata ctactcaggt tttccatttt gtctgcctat  19860
tgtgctaggt tatggtttgt ccacaagaac acaaatatag aagtatggag tccttctcag  19920
gccatattta gtttgcttta acaatactta aaaaaaaaat ttgtaaaata aggatactta  19980
accttactcg gtgtttctga gagttaacat ttatatagtt atgctgtagt gaaaacagct  20040
agcgtaatgt ctggtatgta taggaacaca agagataccg cttttcccat atccccatac  20100
cattcttcac agcattgctc ctgtcttcct tgattcctcc tcctccttct ttgttttttt  20160
tttgtttgtt tgtttgtttt tttttggagg tggagtctca ctctgttgcc caggctggag  20220
tgcagtggtg tgatctcagc ttactgcaac ctctgcctcc tgggttcaag tgattctcct  20280
```

```
gcctcagcct cctgaatagc tgggattaca ggcacacacc aacacactca gctaattttt  20340
gtatttttag tagggatggg gtttcaccat gttggccagg ctggtcttga actcctgacc  20400
tcaggtgatt cacccacctc agcctcccaa agtgctggga ttacaggtgt gagccaccac  20460
accctgcctc cttcttaaga agtttccagt cccttgtaat taaaggaatt aatatttttt  20520
aactacttag aatcagactg gccctgatta ttagtaagca actaatagta agcaagcaac  20580
tatgtatgca actatgagtg tatgttaaga tatggttgtt ggtaaccttt cattctcttc  20640
aggaagaaga agagggtgga gctctacagt caatgtgtac atttaaattc tgttcccttt  20700
cgagcttttt tgctactttc attcttctgg ggatccaggt gcttgagttg ggattgatta  20760
acttccttaa tttccacccc tgtgctgtca ggatcgggag acatagatga aggtgttcta  20820
aactgctaga aattttgttt ttgaaagcaa aagtttgcat gcatttttgt tttcaacttt  20880
tacttacagt gaatagtagt taataaaata agtccctgcc ttttctctct ttggtttcaa  20940
ttcctgagac caggatcata gcccacatat tagagtggag tcccactgct ttggtttgaa  21000
tcatgccttt gtttcttatg tcagtgtgac tttgggcaag ttatttaagt ctttgcacca  21060
cattttcctc atctgtaaaa tgaggataat actagtactt tctacatggg attgttagca  21120
ggattaaatg agatagcaca tactgtaacc atgtctggca catagtcaat ggttagtaaa  21180
tgtgaactat tgtgtgacat tgtggttagt cacgtatggg gctgtgtttc ctttagtata  21240
ttgctctttt aatgtcattt cctttgtact gttaccctct ctgatctttc ttccatattc  21300
a                                                                 21301

SEQ ID NO: 6            moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 6
aggccattct gaaattct                                                18

SEQ ID NO: 7            moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 7
cattgaggcc attctgaa                                                18

SEQ ID NO: 8            moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 8
taaggcattg aggccatt                                                18

SEQ ID NO: 9            moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 9
cctattaagg cattgagg                                                18

SEQ ID NO: 10           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 10
ttcttcctat taaggcat                                                18

SEQ ID NO: 11           moltype = DNA  length = 18
FEATURE                 Location/Qualifiers
misc_feature            1..18
                        note = Description of Artificial Sequence: Synthetic
                         oligonucleotide
```

```
source                  1..18
                        mol_type = other DNA
                        organism = synthetic construct
SEQUENCE: 11
agtatttctt cctattaa                                                18

SEQ ID NO: 12           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 12
tttcaagtat ttcttcct                                                18

SEQ ID NO: 13           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 13
aaaaatttca agtatttc                                                18

SEQ ID NO: 14           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 14
aatttaaaaa tttcaagt                                                18

SEQ ID NO: 15           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 15
gccctaattt aaaaattt                                                18

SEQ ID NO: 16           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 16
accaagccct aatttaaa                                                18

SEQ ID NO: 17           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 17
acaaaaccaa gccctaat                                                18

SEQ ID NO: 18           moltype = DNA  length = 18
FEATURE                 Location/Qualifiers
misc_feature            1..18
                        note = Description of Artificial Sequence: Synthetic
                         oligonucleotide
```

```
source                  1..18
                        mol_type = other DNA
                        organism = synthetic construct
SEQUENCE: 18
tcctcacaaa accaagcc                                              18

SEQ ID NO: 19           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 19
ctagctcctc acaaaacc                                              18

SEQ ID NO: 20           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 20
ctttactagc tcctcaca                                              18

SEQ ID NO: 21           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 21
aaaaccttta ctagctcc                                              18

SEQ ID NO: 22           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 22
agagaaaaac ctttacta                                              18

SEQ ID NO: 23           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 23
ctgaaagaga aaaacctt                                              18

SEQ ID NO: 24           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 24
aagctgaaag agaaaaac                                              18

SEQ ID NO: 25           moltype = DNA  length = 18
FEATURE                 Location/Qualifiers
misc_feature            1..18
                        note = Description of Artificial Sequence: Synthetic
                         oligonucleotide
```

```
source                1..18
                      mol_type = other DNA
                      organism = synthetic construct
SEQUENCE: 25
ctaaagctga aagagaaa                                           18

SEQ ID NO: 26         moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 26
aagctaaagc tgaaagag                                           18

SEQ ID NO: 27         moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 27
aacaagctaa agctgaaa                                           18

SEQ ID NO: 28         moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 28
agaaacaagc taaagctg                                           18

SEQ ID NO: 29         moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 29
cgcagaaaca agctaaag                                           18

SEQ ID NO: 30         moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 30
tcctccgcag aaacaagc                                           18

SEQ ID NO: 31         moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 31
cggaatcctc cgcagaaa                                           18

SEQ ID NO: 32         moltype = DNA  length = 18
FEATURE               Location/Qualifiers
misc_feature          1..18
                      note = Description of Artificial Sequence: Synthetic
                       oligonucleotide
```

```
source                  1..18
                        mol_type = other DNA
                        organism = synthetic construct
SEQUENCE: 32
aagagcggaa tcctccgc                                             18

SEQ ID NO: 33           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 33
ggagaaagag cggaatcc                                             18

SEQ ID NO: 34           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 34
ctgatggaga aagagcgg                                             18

SEQ ID NO: 35           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 35
tgaaactgat ggagaaag                                             18

SEQ ID NO: 36           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 36
ggctatgaaa ctgatgga                                             18

SEQ ID NO: 37           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 37
tccagggcta tgaaactg                                             18

SEQ ID NO: 38           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 38
acaattccag ggctatga                                             18

SEQ ID NO: 39           moltype = DNA  length = 18
FEATURE                 Location/Qualifiers
misc_feature            1..18
                        note = Description of Artificial Sequence: Synthetic
                         oligonucleotide
```

```
source                  1..18
                        mol_type = other DNA
                        organism = synthetic construct
SEQUENCE: 39
tttctacaat tccagggc                                            18

SEQ ID NO: 40           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 40
gagcttttct acaattcc                                            18

SEQ ID NO: 41           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 41
aaccagagct tttctaca                                            18

SEQ ID NO: 42           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 42
cttgaaacca gagctttt                                            18

SEQ ID NO: 43           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 43
atggtcttga aaccagag                                            18

SEQ ID NO: 44           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 44
tatcaatggt cttgaaac                                            18

SEQ ID NO: 45           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 45
atggatatca atggtctt                                            18

SEQ ID NO: 46           moltype = DNA  length = 18
FEATURE                 Location/Qualifiers
misc_feature            1..18
                        note = Description of Artificial Sequence: Synthetic
                         oligonucleotide
```

```
source                  1..18
                        mol_type = other DNA
                        organism = synthetic construct
SEQUENCE: 46
cagaaatgga tatcaatg                                                18

SEQ ID NO: 47           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 47
cctgacagaa atggatat                                                18

SEQ ID NO: 48           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 48
caccctgaca gaaatgga                                                18

SEQ ID NO: 49           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 49
actcaccctg acagaaat                                                18

SEQ ID NO: 50           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 50
aaaactcacc ctgacaga                                                18

SEQ ID NO: 51           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 51
tttaaaactc accctgac                                                18

SEQ ID NO: 52           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 52
aaatttaaaa ctcaccct                                                18

SEQ ID NO: 53           moltype = DNA  length = 18
FEATURE                 Location/Qualifiers
misc_feature            1..18
                        note = Description of Artificial Sequence: Synthetic
                         oligonucleotide
```

```
source                1..18
                      mol_type = other DNA
                      organism = synthetic construct
SEQUENCE: 53
aataaattta aaactcac                                            18

SEQ ID NO: 54         moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 54
catgaaataa atttaaaa                                            18

SEQ ID NO: 55         moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 55
tgcatcatga aataaatt                                            18

SEQ ID NO: 56         moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 56
ttgtttgcat catgaaat                                            18

SEQ ID NO: 57         moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 57
atatattgtt tgcatcat                                            18

SEQ ID NO: 58         moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 58
gttcaatata ttgtttgc                                            18

SEQ ID NO: 59         moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 59
ctgttgttca atatattg                                            18

SEQ ID NO: 60         moltype = DNA  length = 18
FEATURE               Location/Qualifiers
misc_feature          1..18
                      note = Description of Artificial Sequence: Synthetic
                       oligonucleotide
```

```
source                 1..18
                       mol_type = other DNA
                       organism = synthetic construct
SEQUENCE: 60
atgtcctgtt gttcaata                                               18

SEQ ID NO: 61          moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 61
agttcatgtc ctgttgtt                                               18

SEQ ID NO: 62          moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 62
gaacaagttc atgtcctg                                               18

SEQ ID NO: 63          moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 63
aacaagaaca agttcatg                                               18

SEQ ID NO: 64          moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 64
cttacaacaa gaacaagt                                               18

SEQ ID NO: 65          moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 65
agccacttac aacaagaa                                               18

SEQ ID NO: 66          moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 66
aattcagcca cttacaac                                               18

SEQ ID NO: 67          moltype = DNA  length = 18
FEATURE                Location/Qualifiers
misc_feature           1..18
                       note = Description of Artificial Sequence: Synthetic
                        oligonucleotide
```

```
source                  1..18
                        mol_type = other DNA
                        organism = synthetic construct
SEQUENCE: 67
gataaaattc agccactt                                                18

SEQ ID NO: 68           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 68
ttactgataa aattcagc                                                18

SEQ ID NO: 69           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 69
gtgctttact gataaaat                                                18

SEQ ID NO: 70           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 70
ttgatgtgct ttactgat                                                18

SEQ ID NO: 71           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 71
tggagaaaga gcggaatc                                                18

SEQ ID NO: 72           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 72
atggagaaag agcggaat                                                18

SEQ ID NO: 73           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 73
gatggagaaa gagcggaa                                                18

SEQ ID NO: 74           moltype = DNA  length = 18
FEATURE                 Location/Qualifiers
misc_feature            1..18
                        note = Description of Artificial Sequence: Synthetic
                         oligonucleotide
```

```
source                  1..18
                        mol_type = other DNA
                        organism = synthetic construct
SEQUENCE: 74
tgatggagaa agagcgga                                                18

SEQ ID NO: 75           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 75
actgatggag aaagagcg                                                18

SEQ ID NO: 76           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 76
aactgatgga gaaagagc                                                18

SEQ ID NO: 77           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 77
aaactgatgg agaaagag                                                18

SEQ ID NO: 78           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 78
gaaactgatg gagaaaga                                                18

SEQ ID NO: 79           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 79
atgaaactga tggagaaa                                                18

SEQ ID NO: 80           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 80
tatgaaactg atggagaa                                                18

SEQ ID NO: 81           moltype = DNA  length = 18
FEATURE                 Location/Qualifiers
misc_feature            1..18
                        note = Description of Artificial Sequence: Synthetic
                         oligonucleotide
```

```
source                  1..18
                        mol_type = other DNA
                        organism = synthetic construct
SEQUENCE: 81
ctatgaaact gatggaga                                              18

SEQ ID NO: 82           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 82
gctatgaaac tgatggag                                              18

SEQ ID NO: 83           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 83
gggctatgaa actgatgg                                              18

SEQ ID NO: 84           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 84
agggctatga aactgatg                                              18

SEQ ID NO: 85           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 85
cagggctatg aaactgat                                              18

SEQ ID NO: 86           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 86
ccagggctat gaaactga                                              18

SEQ ID NO: 87           moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 87
ctgatggaga aagagcggaa tc                                         22

SEQ ID NO: 88           moltype = DNA  length = 20
FEATURE                 Location/Qualifiers
misc_feature            1..20
                        note = Description of Artificial Sequence: Synthetic
                         oligonucleotide
```

```
source                  1..20
                        mol_type = other DNA
                        organism = synthetic construct
SEQUENCE: 88
ctgatggaga aagagcggaa                                             20

SEQ ID NO: 89           moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 89
aactgatgga gaaagagcgg aa                                          22

SEQ ID NO: 90           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 90
aactgatgga gaaagagcgg                                             20

SEQ ID NO: 91           moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 91
gaaactgatg gagaaagagc gg                                          22

SEQ ID NO: 92           moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 92
ggctatgaaa ctgatggaga aa                                          22

SEQ ID NO: 93           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 93
ggctatgaaa ctgatggaga                                             20

SEQ ID NO: 94           moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 94
agggctatga aactgatgga ga                                          22

SEQ ID NO: 95           moltype = DNA  length = 20
FEATURE                 Location/Qualifiers
misc_feature            1..20
                        note = Description of Artificial Sequence: Synthetic
                         oligonucleotide
```

```
source                 1..20
                       mol_type = other DNA
                       organism = synthetic construct
SEQUENCE: 95
agggctatga aactgatgga                                              20

SEQ ID NO: 96          moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 96
ccagggctat gaaactgatg ga                                           22

SEQ ID NO: 97          moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 97
ttcttaccca tttaatta                                                18

SEQ ID NO: 98          moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 98
tgcttcttac ccatttaa                                                18

SEQ ID NO: 99          moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 99
taatgcttct tacccatt                                                18

SEQ ID NO: 100         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 100
agataatgct tcttaccc                                                18

SEQ ID NO: 101         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 101
cagataatgc ttcttacc                                                18

SEQ ID NO: 102         moltype = DNA  length = 18
FEATURE                Location/Qualifiers
misc_feature           1..18
                       note = Description of Artificial Sequence: Synthetic
                        oligonucleotide
```

```
source                  1..18
                        mol_type = other DNA
                        organism = synthetic construct
SEQUENCE: 102
cccttcagat aatgcttc                                             18

SEQ ID NO: 103          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 103
ctactccctt cagataat                                             18

SEQ ID NO: 104          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 104
agctcctact cccttcag                                             18

SEQ ID NO: 105          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 105
ttcacagctc ctactccc                                             18

SEQ ID NO: 106          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 106
taaaattcac agctccta                                             18

SEQ ID NO: 107          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 107
aaatctaaaa ttcacagc                                             18

SEQ ID NO: 108          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 108
gaataaaatc taaaattc                                             18

SEQ ID NO: 109          moltype = DNA  length = 18
FEATURE                 Location/Qualifiers
misc_feature            1..18
                        note = Description of Artificial Sequence: Synthetic
                         oligonucleotide
```

```
source                  1..18
                        mol_type = other DNA
                        organism = synthetic construct
SEQUENCE: 109
gatgggaata aaatctaa                                             18

SEQ ID NO: 110          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 110
gctgtgatgg gaataaaa                                             18

SEQ ID NO: 111          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 111
tagaggctgt gatgggaa                                             18

SEQ ID NO: 112          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 112
aaagatagag gctgtgat                                             18

SEQ ID NO: 113          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 113
aaaagaaaga tagaggct                                             18

SEQ ID NO: 114          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 114
gacctaaaag aaagatag                                             18

SEQ ID NO: 115          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 115
ataaagacct aaaagaaa                                             18

SEQ ID NO: 116          moltype = DNA  length = 18
FEATURE                 Location/Qualifiers
misc_feature            1..18
                        note = Description of Artificial Sequence: Synthetic
                         oligonucleotide
```

```
source                  1..18
                        mol_type = other DNA
                        organism = synthetic construct
SEQUENCE: 116
gagatataaa gacctaaa                                           18

SEQ ID NO: 117          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 117
ggctgtgatg ggaataaa                                           18

SEQ ID NO: 118          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 118
aggctgtgat gggaataa                                           18

SEQ ID NO: 119          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 119
gaggctgtga tgggaata                                           18

SEQ ID NO: 120          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 120
agaggctgtg atgggaat                                           18

SEQ ID NO: 121          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 121
atagaggctg tgatggga                                           18

SEQ ID NO: 122          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 122
gatagaggct gtgatggg                                           18

SEQ ID NO: 123          moltype = DNA  length = 18
FEATURE                 Location/Qualifiers
misc_feature            1..18
                        note = Description of Artificial Sequence: Synthetic
                         oligonucleotide
```

```
source                  1..18
                        mol_type = other DNA
                        organism = synthetic construct
SEQUENCE: 123
agatagaggc tgtgatgg                                            18

SEQ ID NO: 124          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 124
aagatagagg ctgtgatg                                            18

SEQ ID NO: 125          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 125
tagaggctgt gatgggaata aa                                       22

SEQ ID NO: 126          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 126
atagaggctg tgatgggaat aa                                       22

SEQ ID NO: 127          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 127
gatagaggct gtgatgggaa ta                                       22

SEQ ID NO: 128          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 128
agatagaggc tgtgatggga at                                       22

SEQ ID NO: 129          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 129
aagatagagg ctgtgatggg aa                                       22

SEQ ID NO: 130          moltype = DNA  length = 20
FEATURE                 Location/Qualifiers
misc_feature            1..20
                        note = Description of Artificial Sequence: Synthetic
                         oligonucleotide
```

```
source                  1..20
                        mol_type = other DNA
                        organism = synthetic construct
SEQUENCE: 130
gaggctgtga tgggaataaa                                        20

SEQ ID NO: 131          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 131
agaggctgtg atgggaataa                                        20

SEQ ID NO: 132          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 132
tagaggctgt gatgggaata                                        20

SEQ ID NO: 133          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 133
atagaggctg tgatgggaat                                        20

SEQ ID NO: 134          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 134
gatagaggct gtgatgggaa                                        20

SEQ ID NO: 135          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 135
agatagaggc tgtgatggga                                        20

SEQ ID NO: 136          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 136
aagatagagg ctgtgatggg                                        20

SEQ ID NO: 137          moltype = DNA  length = 16
FEATURE                 Location/Qualifiers
misc_feature            1..16
                        note = Description of Artificial Sequence: Synthetic
                         oligonucleotide
```

```
source                  1..16
                        mol_type = other DNA
                        organism = synthetic construct
SEQUENCE: 137
ctgtgatggg aataaa                                                  16

SEQ ID NO: 138          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 138
gctgtgatgg gaataa                                                  16

SEQ ID NO: 139          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 139
ggctgtgatg ggaata                                                  16

SEQ ID NO: 140          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 140
aggctgtgat gggaat                                                  16

SEQ ID NO: 141          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 141
gaggctgtga tgggaa                                                  16

SEQ ID NO: 142          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 142
agaggctgtg atggga                                                  16

SEQ ID NO: 143          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 143
tagaggctgt gatggg                                                  16

SEQ ID NO: 144          moltype = DNA  length = 16
FEATURE                 Location/Qualifiers
misc_feature            1..16
                        note = Description of Artificial Sequence: Synthetic
                         oligonucleotide
```

```
source                  1..16
                        mol_type = other DNA
                        organism = synthetic construct
SEQUENCE: 144
atagaggctg tgatgg                                                            16

SEQ ID NO: 145          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 145
gatagaggct gtgatg                                                            16

SEQ ID NO: 146          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 146
agatagaggc tgtgat                                                            16

SEQ ID NO: 147          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 147
aagatagagg ctgtga                                                            16

SEQ ID NO: 148          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 148
aggctgtgat gtgaataa                                                          18

SEQ ID NO: 149          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 149
agaggctgtg atgtgaat                                                          18

SEQ ID NO: 150          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 150
tagaggctgt gatgtgaa                                                          18

SEQ ID NO: 151          moltype = DNA  length = 18
FEATURE                 Location/Qualifiers
misc_feature            1..18
                        note = Description of Artificial Sequence: Synthetic
                         oligonucleotide
```

```
source                  1..18
                        mol_type = other DNA
                        organism = synthetic construct
SEQUENCE: 151
gatagaggct gtgattgg                                                18

SEQ ID NO: 152          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 152
ggctgtgatg tgaata                                                  16

SEQ ID NO: 153          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 153
gaggctgtga tgtgaa                                                  16

SEQ ID NO: 154          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 154
tagaggctgt gattgg                                                  16

SEQ ID NO: 155          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 155
atgaaactga tggaga                                                  16

SEQ ID NO: 156          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 156
ctatgaaact gatgga                                                  16

SEQ ID NO: 157          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 157
ggctatgaaa ctgatg                                                  16

SEQ ID NO: 158          moltype = DNA  length = 14
FEATURE                 Location/Qualifiers
misc_feature            1..14
                        note = Description of Artificial Sequence: Synthetic
                         oligonucleotide
```

```
source                  1..14
                        mol_type = other DNA
                        organism = synthetic construct
SEQUENCE: 158
gaaactgatg gaga                                                    14

SEQ ID NO: 159          moltype = DNA  length = 14
FEATURE                 Location/Qualifiers
misc_feature            1..14
                        note = Description of Artificial Sequence: Synthetic
                         oligonucleotide
source                  1..14
                        mol_type = other DNA
                        organism = synthetic construct
SEQUENCE: 159
atgaaactga tgga                                                    14

SEQ ID NO: 160          moltype = DNA  length = 14
FEATURE                 Location/Qualifiers
misc_feature            1..14
                        note = Description of Artificial Sequence: Synthetic
                         oligonucleotide
source                  1..14
                        mol_type = other DNA
                        organism = synthetic construct
SEQUENCE: 160
ctatgaaact gatg                                                    14

SEQ ID NO: 161          moltype = DNA  length = 14
FEATURE                 Location/Qualifiers
misc_feature            1..14
                        note = Description of Artificial Sequence: Synthetic
                         oligonucleotide
source                  1..14
                        mol_type = other DNA
                        organism = synthetic construct
SEQUENCE: 161
ggctatgaaa ctga                                                    14

SEQ ID NO: 162          moltype = DNA  length = 24
FEATURE                 Location/Qualifiers
misc_feature            1..24
                        note = Description of Artificial Sequence: Synthetic
                         oligonucleotide
source                  1..24
                        mol_type = other DNA
                        organism = synthetic construct
SEQUENCE: 162
tagaggctgt gatgggaata aaat                                         24

SEQ ID NO: 163          moltype = DNA  length = 24
FEATURE                 Location/Qualifiers
misc_feature            1..24
                        note = Description of Artificial Sequence: Synthetic
                         oligonucleotide
source                  1..24
                        mol_type = other DNA
                        organism = synthetic construct
SEQUENCE: 163
atagaggctg tgatgggaat aaaa                                         24

SEQ ID NO: 164          moltype = DNA  length = 25
FEATURE                 Location/Qualifiers
misc_feature            1..25
                        note = Description of Artificial Sequence: Synthetic
                         oligonucleotide
source                  1..25
                        mol_type = other DNA
                        organism = synthetic construct
SEQUENCE: 164
atagaggctg tgatgggaat aaaat                                        25

SEQ ID NO: 165          moltype = DNA  length = 25
FEATURE                 Location/Qualifiers
misc_feature            1..25
                        note = Description of Artificial Sequence: Synthetic
                         oligonucleotide
```

```
source                1..25
                      mol_type = other DNA
                      organism = synthetic construct
SEQUENCE: 165
aaagatagag gctgtgatgg gaata                                      25

SEQ ID NO: 166        moltype = DNA  length = 21
FEATURE               Location/Qualifiers
misc_feature          1..21
                      note = Description of Artificial Sequence: Synthetic
                       oligonucleotide
source                1..21
                      mol_type = other DNA
                      organism = synthetic construct
SEQUENCE: 166
ggctatgaaa ctgatggaga a                                          21

SEQ ID NO: 167        moltype = DNA  length = 24
FEATURE               Location/Qualifiers
misc_feature          1..24
                      note = Description of Artificial Sequence: Synthetic
                       oligonucleotide
source                1..24
                      mol_type = other DNA
                      organism = synthetic construct
SEQUENCE: 167
ggctatgaaa ctgatggaga aaga                                       24

SEQ ID NO: 168        moltype = DNA  length = 25
FEATURE               Location/Qualifiers
misc_feature          1..25
                      note = Description of Artificial Sequence: Synthetic
                       oligonucleotide
source                1..25
                      mol_type = other DNA
                      organism = synthetic construct
SEQUENCE: 168
agggctatga aactgatgga gaaag                                      25

SEQ ID NO: 169        moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 169
catttaatta aattatat                                              18

SEQ ID NO: 170        moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 170
ccatttaatt aaattata                                              18

SEQ ID NO: 171        moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 171
cccatttaat taaattat                                              18

SEQ ID NO: 172        moltype = DNA  length = 18
FEATURE               Location/Qualifiers
misc_feature          1..18
                      note = Description of Artificial Sequence: Synthetic
                       oligonucleotide
```

```
source                  1..18
                        mol_type = other DNA
                        organism = synthetic construct
SEQUENCE: 172
acccatttaa ttaaatta                                             18

SEQ ID NO: 173          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 173
tacccattta attaaatt                                             18

SEQ ID NO: 174          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 174
ttacccattt aattaaat                                             18

SEQ ID NO: 175          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 175
cttacccatt taattaaa                                             18

SEQ ID NO: 176          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 176
tcttacccat ttaattaa                                             18

SEQ ID NO: 177          moltype = DNA  length = 17
FEATURE                 Location/Qualifiers
misc_feature            1..17
                        note = Description of Artificial Sequence: Synthetic
                         oligonucleotide
source                  1..17
                        mol_type = other DNA
                        organism = synthetic construct
SEQUENCE: 177
gatagaggct gtgatgg                                              17

SEQ ID NO: 178          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 178
ggctgtgaaa ctgatgga                                             18

SEQ ID NO: 179          moltype = DNA  length = 20
FEATURE                 Location/Qualifiers
misc_feature            1..20
                        note = Description of Artificial Sequence: Synthetic
                         oligonucleotide
```

```
source                  1..20
                        mol_type = other DNA
                        organism = synthetic construct
SEQUENCE: 179
ggctgtgaaa ctgatggaga                                              20

SEQ ID NO: 180          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 180
gctatgaaac tgatgg                                                  16

SEQ ID NO: 181          moltype = DNA  length = 14
FEATURE                 Location/Qualifiers
misc_feature            1..14
                        note = Description of Artificial Sequence: Synthetic
                         oligonucleotide
source                  1..14
                        mol_type = other DNA
                        organism = synthetic construct
SEQUENCE: 181
tatgaaactg atgg                                                    14

SEQ ID NO: 182          moltype = DNA  length = 14
FEATURE                 Location/Qualifiers
misc_feature            1..14
                        note = Description of Artificial Sequence: Synthetic
                         oligonucleotide
source                  1..14
                        mol_type = other DNA
                        organism = synthetic construct
SEQUENCE: 182
gctatgaaac tgat                                                    14

SEQ ID NO: 183          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 183
gctgtgaaac tgatggagaa                                              20

SEQ ID NO: 184          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 184
gggctgtgaa actgatggag                                              20

SEQ ID NO: 185          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 185
tgtgaaactg atggagaa                                                18

SEQ ID NO: 186          moltype = DNA  length = 18
FEATURE                 Location/Qualifiers
misc_feature            1..18
                        note = Description of Artificial Sequence: Synthetic
                         oligonucleotide
```

```
source                 1..18
                       mol_type = other DNA
                       organism = synthetic construct
SEQUENCE: 186
ctgtgaaact gatggaga                                              18

SEQ ID NO: 187         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 187
gctgtgaaac tgatggag                                              18

SEQ ID NO: 188         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 188
gggctgtgaa actgatgg                                              18

SEQ ID NO: 189         moltype = DNA  length = 16
FEATURE                Location/Qualifiers
misc_feature           1..16
                       note = Description of Artificial Sequence: Synthetic
                        oligonucleotide
source                 1..16
                       mol_type = other DNA
                       organism = synthetic construct
SEQUENCE: 189
tgaaactgat ggagaa                                                16

SEQ ID NO: 190         moltype = DNA  length = 16
FEATURE                Location/Qualifiers
misc_feature           1..16
                       note = Description of Artificial Sequence: Synthetic
                        oligonucleotide
source                 1..16
                       mol_type = other DNA
                       organism = synthetic construct
SEQUENCE: 190
gtgaaactga tggaga                                                16

SEQ ID NO: 191         moltype = DNA  length = 16
FEATURE                Location/Qualifiers
misc_feature           1..16
                       note = Description of Artificial Sequence: Synthetic
                        oligonucleotide
source                 1..16
                       mol_type = other DNA
                       organism = synthetic construct
SEQUENCE: 191
tgtgaaactg atggag                                                16

SEQ ID NO: 192         moltype = DNA  length = 16
FEATURE                Location/Qualifiers
misc_feature           1..16
                       note = Description of Artificial Sequence: Synthetic
                        oligonucleotide
source                 1..16
                       mol_type = other DNA
                       organism = synthetic construct
SEQUENCE: 192
ctgtgaaact gatgga                                                16

SEQ ID NO: 193         moltype = DNA  length = 16
FEATURE                Location/Qualifiers
misc_feature           1..16
                       note = Description of Artificial Sequence: Synthetic
                        oligonucleotide
```

```
source                  1..16
                        mol_type = other DNA
                        organism = synthetic construct
SEQUENCE: 193
gctgtgaaac tgatgg                                                   16

SEQ ID NO: 194          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 194
ggctgtgaaa ctgatg                                                   16

SEQ ID NO: 195          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 195
gggctgtgaa actgat                                                   16

SEQ ID NO: 196          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 196
cggtccagga atgac                                                    15

SEQ ID NO: 197          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 197
ccggtccagg aatga                                                    15

SEQ ID NO: 198          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 198
cccggtccag gaatg                                                    15

SEQ ID NO: 199          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 199
tcccggtcca ggaat                                                    15

SEQ ID NO: 200          moltype = DNA  length = 15
FEATURE                 Location/Qualifiers
misc_feature            1..15
                        note = Description of Artificial Sequence: Synthetic
                         oligonucleotide
```

```
source                  1..15
                        mol_type = other DNA
                        organism = synthetic construct
SEQUENCE: 200
ctcccggtcc aggaa                                                    15

SEQ ID NO: 201          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 201
gctcccggtc cagga                                                    15

SEQ ID NO: 202          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 202
ggctcccggt ccagg                                                    15

SEQ ID NO: 203          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 203
cgggagcccc cgtgt                                                    15

SEQ ID NO: 204          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 204
gcgggagccc ccgtg                                                    15

SEQ ID NO: 205          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 205
cgcgggagcc cccgt                                                    15

SEQ ID NO: 206          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 206
acgcgggagc ccccg                                                    15

SEQ ID NO: 207          moltype = DNA  length = 15
FEATURE                 Location/Qualifiers
misc_feature            1..15
                        note = Description of Artificial Sequence: Synthetic
                         oligonucleotide
```

```
source                  1..15
                        mol_type = other DNA
                        organism = synthetic construct
SEQUENCE: 207
cacgcgggag ccccc                                                             15

SEQ ID NO: 208          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 208
ccacgcggga gcccc                                                             15

SEQ ID NO: 209          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 209
gccacgcggg agccc                                                             15

SEQ ID NO: 210          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 210
ggccacgcgg gagcc                                                             15

SEQ ID NO: 211          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 211
cggccacgcg ggagc                                                             15

SEQ ID NO: 212          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 212
acggccacgc gggag                                                             15

SEQ ID NO: 213          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 213
gacggccacg cggga                                                             15

SEQ ID NO: 214          moltype = DNA  length = 15
FEATURE                 Location/Qualifiers
misc_feature            1..15
                        note = Description of Artificial Sequence: Synthetic
                         oligonucleotide
```

```
source                1..15
                      mol_type = other DNA
                      organism = synthetic construct
SEQUENCE: 214
agacggccac gcggg                                                15

SEQ ID NO: 215        moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 215
gctagggagg gatggtta                                             18

SEQ ID NO: 216        moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 216
tgtaagctag ggagggat                                             18

SEQ ID NO: 217        moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 217
acagatgtaa gctaggga                                             18

SEQ ID NO: 218        moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 218
aaggaacaga tgtaagct                                             18

SEQ ID NO: 219        moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 219
caacaaagga acagatgt                                             18

SEQ ID NO: 220        moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 220
gggtgcaaca aaggaaca                                             18

SEQ ID NO: 221        moltype = DNA  length = 18
FEATURE               Location/Qualifiers
misc_feature          1..18
                      note = Description of Artificial Sequence: Synthetic
                       oligonucleotide
```

```
source                  1..18
                        mol_type = other DNA
                        organism = synthetic construct
SEQUENCE: 221
accaagggtg caacaaag                                              18

SEQ ID NO: 222          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 222
gttaaaccaa gggtgcaa                                              18

SEQ ID NO: 223          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 223
ataatgttaa accaaggg                                              18

SEQ ID NO: 224          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 224
ggagaataat gttaaacc                                              18

SEQ ID NO: 225          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 225
ggggaggaga ataatgtt                                              18

SEQ ID NO: 226          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 226
aaattgggga ggagaata                                              18

SEQ ID NO: 227          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 227
agaggaaatt ggggagga                                              18

SEQ ID NO: 228          moltype = DNA  length = 18
FEATURE                 Location/Qualifiers
misc_feature            1..18
                        note = Description of Artificial Sequence: Synthetic
                         oligonucleotide
```

```
source                  1..18
                        mol_type = other DNA
                        organism = synthetic construct
SEQUENCE: 228
ggagaagagg aaattggg                                                18

SEQ ID NO: 229          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 229
aatgaggaga agaggaaa                                                18

SEQ ID NO: 230          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 230
ttcacaatga ggagaaga                                                18

SEQ ID NO: 231          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 231
acgagttcac aatgagga                                                18

SEQ ID NO: 232          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 232
ctgccacgag ttcacaat                                                18

SEQ ID NO: 233          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 233
agaccctgcc acgagttc                                                18

SEQ ID NO: 234          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 234
caagcagacc ctgccacg                                                18

SEQ ID NO: 235          moltype = DNA  length = 18
FEATURE                 Location/Qualifiers
misc_feature            1..18
                        note = Description of Artificial Sequence: Synthetic
                         oligonucleotide
```

```
source                  1..18
                        mol_type = other DNA
                        organism = synthetic construct
SEQUENCE: 235
ctcaccaagc agaccctg                                              18

SEQ ID NO: 236          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 236
gagctcacca agcagacc                                              18

SEQ ID NO: 237          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 237
agaatgagct caccaagc                                              18

SEQ ID NO: 238          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 238
gtaagagaat gagctcac                                              18

SEQ ID NO: 239          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 239
ttgttgtaag agaatgag                                              18

SEQ ID NO: 240          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 240
atttgttgtt gtaagaga                                              18

SEQ ID NO: 241          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 241
cttgaatttg ttgttgta                                              18

SEQ ID NO: 242          moltype = DNA  length = 18
FEATURE                 Location/Qualifiers
misc_feature            1..18
                        note = Description of Artificial Sequence: Synthetic
                         oligonucleotide
```

```
source                  1..18
                        mol_type = other DNA
                        organism = synthetic construct
SEQUENCE: 242
atgctcttga atttgttg                                                      18

SEQ ID NO: 243          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 243
tcttcatgct cttgaatt                                                      18

SEQ ID NO: 244          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 244
cttcctcttc atgctctt                                                      18

SEQ ID NO: 245          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 245
gcgcgcttcc tcttcatg                                                      18

SEQ ID NO: 246          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 246
gctctgcgcg cttcctct                                                      18

SEQ ID NO: 247          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 247
ggccagcggc tctgcgcg                                                      18

SEQ ID NO: 248          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 248
atattggcca gcggctct                                                      18

SEQ ID NO: 249          moltype = DNA  length = 18
FEATURE                 Location/Qualifiers
misc_feature            1..18
                        note = Description of Artificial Sequence: Synthetic
                         oligonucleotide
```

```
source                  1..18
                        mol_type = other DNA
                        organism = synthetic construct
SEQUENCE: 249
gtgctatatt ggccagcg                                                18

SEQ ID NO: 250          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 250
agctcgtgct atattggc                                                18

SEQ ID NO: 251          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 251
ggcatagctc gtgctata                                                18

SEQ ID NO: 252          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 252
tgttgggcat agctcgtg                                                18

SEQ ID NO: 253          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 253
gcttctgttg ggcatagc                                                18

SEQ ID NO: 254          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 254
cttgcgcttc tgttgggc                                                18

SEQ ID NO: 255          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 255
caccttgcgc ttctgttg                                                18

SEQ ID NO: 256          moltype = DNA  length = 18
FEATURE                 Location/Qualifiers
misc_feature            1..18
                        note = Description of Artificial Sequence: Synthetic
                         oligonucleotide
```

```
source                  1..18
                        mol_type = other DNA
                        organism = synthetic construct
SEQUENCE: 256
tccatcacct tgcgcttc                                                18

SEQ ID NO: 257          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 257
aaccatccat caccttgc                                                18

SEQ ID NO: 258          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 258
ccttaaacca tccatcac                                                18

SEQ ID NO: 259          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 259
agccccctta aaccatcc                                                18

SEQ ID NO: 260          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 260
tcggtagccc ccttaaac                                                18

SEQ ID NO: 261          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 261
atgtatcggt agccccct                                                18

SEQ ID NO: 262          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 262
tgtgaatgta tcggtagc                                                18

SEQ ID NO: 263          moltype = DNA  length = 18
FEATURE                 Location/Qualifiers
misc_feature            1..18
                        note = Description of Artificial Sequence: Synthetic
                         oligonucleotide
```

```
source                  1..18
                        mol_type = other DNA
                        organism = synthetic construct
SEQUENCE: 263
attagtgtga atgtatcg                                             18

SEQ ID NO: 264          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 264
ggctgattag tgtgaatg                                             18

SEQ ID NO: 265          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 265
gaaatggctg attagtgt                                             18

SEQ ID NO: 266          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 266
tggcagaaat ggctgatt                                             18

SEQ ID NO: 267          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 267
gatcttggca gaaatggc                                             18

SEQ ID NO: 268          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 268
gacatgatct tggcagaa                                             18

SEQ ID NO: 269          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 269
gaggtgacat gatcttgg                                             18

SEQ ID NO: 270          moltype = DNA  length = 18
FEATURE                 Location/Qualifiers
misc_feature            1..18
                        note = Description of Artificial Sequence: Synthetic
                         oligonucleotide
```

```
source                  1..18
                        mol_type = other DNA
                        organism = synthetic construct
SEQUENCE: 270
agattgaggt gacatgat                                                18

SEQ ID NO: 271          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 271
tgaacagatt gaggtgac                                                18

SEQ ID NO: 272          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 272
gtccatgaac agattgag                                                18

SEQ ID NO: 273          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 273
ttggagtcca tgaacaga                                                18

SEQ ID NO: 274          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 274
tgtatttgga gtccatga                                                18

SEQ ID NO: 275          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 275
tttcttgtat ttggagtc                                                18

SEQ ID NO: 276          moltype = DNA  length = 7155
FEATURE                 Location/Qualifiers
source                  1..7155
                        mol_type = other DNA
                        organism = Homo sapiens
SEQUENCE: 276
gtaagtgtaa aagagaattg ttcatgtagg tagtcttgaa agattttttta aagtttttac  60
ttctttggaa gattttaaaa tgataacatc tgagaagcaa atacaaaaac atccaagtag  120
agatatcgtt actaatctta gtgcaaagta caaggtatta cgtggcagtt ctggaaatat  180
aattgagaag cccatttctt tcacatatgt ccagtgaagc attagtttcg agggttgtcc  240
ccaagaaaga gttgtgttgt taagtgtgtg gggggagaaa ggctcgttta gacaaggcaa  300
gcggacttct tttctttccc taggacctct catactgtaa tatactcatg cgcattgtga  360
atttccaagg agtcaaagca tacagtgttt tcccaaatta tttatcaaca gaaccctttt  420
gctcatggaa cgtcgtatag ggactagatt tcactttggg gaaactagaa agggaatagg  480
aattgggtta ttaggaaata aatcaattcc ctgatattga tagttaacaa agttatgtat  540
ggggttattt atggtatgtt attttcaaca catattcatt aacaaaatcc atatgaaagt  600
tataggagaa ttgctgaggt agaataacat actttgtttg tatttataat actcatatat  660
ttacctgacg ttttctgagt cttcactttt ttcattcttt tggaattggt aaaataactg  720
```

-continued

```
attccttgaa agttttttc taaataatac ctagataata gatttataga aaaaatattg  780
tatgaatgtt ttaacattca tgtaatatgg aacatgtaat ttttatactg gaggttatta  840
tagttttaat acatcaaaga aataatgttt attttggaag cagaaagaag aaataatttc  900
tatgaatagg ttttcatctc tttccttgtt cttcaacttt gaacttttta tattccaaat  960
tttaattata tttcaaaaga ttttttttctt ttgcctttta attttatctt ttggagaaaa  1020
atgtatgtca aaatgtatgt acgtgtattt gtcttttgat ttgatctttt ttgaccctct  1080
tttgcattga cattatttta accaaaggac actcttgatt gttcatgcta ctgggggaaa  1140
aaaaaataag tagaaattag cctaatagtt gtggcttatt ttgagtgaag gccttagccc  1200
ttaaggcaat taaatttact gtggagagaa gagctaatct aatggggaga aggagccttt  1260
gttacaggtg tggtagtgtg gttctttgag tgacaagatt tctgtttgcc agattggtta  1320
ggagaagtct gtgtgtctgc tttctctctt atggcctagg atcactgtgg tgaatgaaaa  1380
acctgtctca gggcctgact cagataattc ccttaaaacc cggctaaggt catagatgaa  1440
taatcagtaa ttgaacagaa gctctgcaat agaaaagaag ccagataatt atttttggaa  1500
atttaattat atttacagat tttattttat acagtagaca tggaattaaa tttattacat  1560
tatgttctaa tttactcttt gcttgttttg atttgcttgt ttgacaatac atgtccttgt  1620
aaactatttc cttttaactt tttctcaatt tatggtgctt attttcccca ttaaagactt  1680
accaattttt tttttaacta tttgttacac atactgaatc tagagttgta attaagctac  1740
tttcattact ggttaagtca aattatagca aatgctacta taaaaattta ctatccaaaa  1800
atgtgtctca agccccaact gatggtttca aattctgtta ttaataatat gcagcattgt  1860
gtttgcaaag cttggctgtt acttgtgatg cttgagaatg atgagtcact cagctaaact  1920
gagtgatttt gagacttgtg tacaaattga tggttgaatg taagcatgca aagagagacc  1980
ttagcttagc agtacccttt ttgaaatcac tctgacatca agtttgaaaa tgtgggcaat  2040
aatcagaggt ggtaaggtgg ccaggcttta gctgaatact tttttaactg gttcagtctg  2100
agggctgaaa gccccagatt taaacagtat ttagaatttg aagcagtcaa gtattagttt  2160
aatggttgtc aggtttgtaa caaagtttct ggctagactt ctactagaaa tgtaaaagtg  2220
catgtgaatc agctttttaa aaaagtaata ataattgaaa aacatttcta caactagaac  2280
taaagaaaag atttgtcctt tctaatagga aaacacatct ggagaagtgc tggcaactag  2340
cagaacagtt aggaccattc agaatcaact gaagtgaaag tgacggggag ctgaggggaa  2400
cacagatagt ttgacttcag tcagacagaa taaacatgat gaaccgataa cctgtgattc  2460
ccagcctggg gttactactg gagttttagg tgtcctggaa agttataata ccggtcttca  2520
aaaagtctac agaaagcata gatttccaca taatgctgca caggctaacg aattaatcaa  2580
gtttctttgg tttggcctgg atttatatcc attcagtttg tggacactac tgaattattt  2640
atgtcatgtt gatcaaaagt tctgatatga tttgattaat gaaacattga aaaaaatagt  2700
aaaaccaacc atttttaacc ttacactact atcttgaggt atgattgaca tacattaaaa  2760
ccacctctta ataaatgctt cttgttaatc aaaaatttga aaacgtatgt ccactggagg  2820
aaaaaagaca tagccctgga tgtgaactga atattactga gactcggaga ccttcagaac  2880
tacctgaaga tgaatcgaag tgctgcctac tttagagaat tggactaatt taatttggga  2940
gtcagcagat tgctgtatat cagtcatcat atataccggt gacaagacca cttagttcat  3000
tcccttttttt agattctgta agattattgt gttccagtga aattgatttg caaaatgaga  3060
cattttattt tctgtgcttt tgttctatca tgtttctgat tggtcataag catctcacag  3120
aagtaagaaa tatggcgatt cagaaggcaa caagcacatt tataatttat agaaaatatt  3180
tgaaggactt tttcatggcc caaatcatga aaagtagtag tattgtttta agtataatta  3240
ttaaattata atacattaat gttctttctt gcaacatatt actctcattc tttttttttt  3300
ttttttttt tgagacggag tctcactctg tcacccggct ggagtacagt ggtacgatct  3360
tggcccactg caacctctgc ctcccgggtt caagcgattc tcctgcctca gcctcccaag  3420
tagctgggat tacaggctcc tgccaccacg cctagctaat ttttgtattt ttagtagaga  3480
cagggtttca ccaggttggc caggatggtc ttgatctctt gacctcatgg tccgtccacc  3540
tctgcctccc aaagtgttgg gattacaggc gtgagccacc cagcagtctg attcttaatt  3600
ttatagttta tgttgtacct ccccagctga agtatctctt ttcttttttc ccgcgtgttt  3660
agtgttcact catctttata gcatagctca attgtcactt catgaagcct tccataacct  3720
ttgtagctcc attaattata ttcttctgag tgtttaaaac acttgccata tgaaacacta  3780
tttactttgg cttacattct tactatctaa tcggccattt ctgttactaa atctttttct  3840
cagagcacct gggatagtct tgtgtcttag taaaatcagt tgattgattt aactcggtag  3900
agtagaggct gattaaagta aataaatctg gttgatgcca acaaaatttt ggtcccctca  3960
attttttgct ctcattacct gcaaattctc cctggccttc atatttggca accattgagg  4020
agaacaaggc tgtaaaagta gttcatgtac ttgatattct gaattggaat taagcagagt  4080
tgcttaagta ggacttgctt ttctgggatt tcttatgcaa caaataatgt agtaactgga  4140
aatccaagtt caagacactg gcagattcga tgtcttttga ggacccttgg cttcatagat  4200
gatgccttct ccctatatcc ttacatagca aaaggggcca ggcagctctg gccttttttt  4260
gtaaggccaa taactccaga aacctcatga cctcatcacc tcccaaaggc cccacctctc  4320
aatactatca cattgtgagg ctaggtttca acatatgaat tgtgggagac aaaaattcag  4380
accatagtat aatatttcaa gattacttaa actcttctct accaaactca ttaactttta  4440
ggttagcaca gtattttcat tgatattttg gtttctggag ttattactaa ttttcttgat  4500
ctgatgttat aattaaaaaa aaacaggact ttgtacgtga aatgagactg agataaggaa  4560
gctgattcag agatggagat ttaaaaaaag agagatgaga gattgagatc tgcagtgtca  4620
aactgacaat agccaggagt caggagatat taagagacta tatcatctgt gattgttaat  4680
gattatttat tgttatttat aaatactact gtattttata tattatatac attgttttaa  4740
aaattatttt tgtaccattt cttgaaagaa aaatgtctaa gcttgggaaa atatttattg  4800
aaaaatgtgg tttgtacatc tgaggagtgt atcttgcaca gtaggtgcat agatttcttc  4860
ctcttcctgt tccacatggc cttagcttag aggctgtgtg gccatcactt ggtatttagg  4920
gtaagactgg tgcacaaaat caaagacagg taaccttggt ataagtgtag tatcatgtaa  4980
atagcttttc tatgtctaat tcttgttttc ttcctacttt ttcaggaggt caatttcagt  5040
tcatttcaac tatctttaca taatagtgct ttagtaacag gcatggaagg aaagagacat  5100
gtccctagag tgttttcttg aaatctaata gatgattgga gtatttacca tgcagttgtg  5160
tatatacata agcagtgaat tcgagaggaa tttttaagct gtaaaaaaaa gcattgtgtg  5220
ccttatagac gcgagtgaga aatgtggaat atggctgatc caaagggaat gagttatctc  5280
aattgattaa tcacagtcag ttacagattg aactctttgt tctactcttt gcccccttct  5340
cactattgct cttgactagt cttaagaaag aaatgtggaa tattttctca cggctttggg  5400
attttataaa ttagaatact agtggtatgt aaatacagca ggtacactac tgtataaacc  5460
```

```
aacataggaa gccttcttta aagggaattg tttgagaaat ttgaacactt ggataatttg  5520
aataaaggat tgtgataaat gatcaaatga aagaaaataa atcaggttac tcttctttct  5580
gcttgataaa gcaataattt tttttaaagg taaaaattat gagaatgatg aggatagtag  5640
ttagcattgt ctttctttga taggtttgtt aatgatcata aaactgattt atttaaagac  5700
atgtcttttt ataactattt tatactgttg tatctggaaa caaatattga atttcatttg  5760
tcatgtggaa gaaatcaact agttttaacc tttgatttat aataaatcaa ccactttcat  5820
ttattgtcta atactggcaa tgaacacagc ctaatgtatc aaaactaaca gaataaaaat  5880
tctccaagtt atatccagac tttaagacac tttctaatta tataaaataa aatattttgg  5940
gcagtcattt tttaactctg aaactattta aaactcctaa tttagaatat cttaataaat  6000
acccattttc ctctttttat ttttataact tggtaaaaat tgagtccatt gttttcccag  6060
aacgctgttc ttaaacaaat ggttacctcc ttcattagaa ctttactttt tttaggattt  6120
ctaattaaga aaacattagg cttgtaacat tgtcaaatct tggtggtctt tcttccacgt  6180
tttttgaggt cgattatcta agaggccatc agttaataaa gctatgcagg aaatgacatc  6240
atgccacatg tgaatatcct gtattaaaaa ttgtatcaat atactatttt ataattatga  6300
agtggaatga attttagaaa tagaaaaggt gattttttgt gcataggtcc aaactgtgtt  6360
ttgttttcat ttcagaattt cataataact atattgtctc catatcttaa ttgtgttttt  6420
ttatagcact tttgtttagt aatttgtata tgcttggctg tattctcaga ggctgtttct  6480
atttaatgtt gtcaaaacag ctcataaaaa gtgaaaattc ggtcagacta gttatttgat  6540
attatatatg aaatcaaaac aacctgaaac attatctttt aatttaaata aagaacccca  6600
aattttaatc aaatgtatgc aaaggcacat agaatatatg acttaatgta caacctttat  6660
taacttgatg atggaaacct gttcctaggg acctttactt gaataaatga aatatcaaga  6720
aaaaatacta acttaagaat aataatttaa taagtaagta agctattatg atcttcaatc  6780
agtcctgaga gaatcatggt tgagaattag aaaatttaga ccagtaagat caacactgtt  6840
aaaaaaaaaa aaaaatcagt attttttctc catatttttt atatatctgg atcattttat  6900
ttagcactta ttattgcact ttccttttca ctttttaaac tatgctgttt tatttttctg  6960
agacatctga tttactgagg aggaaaatgg aaatgcggta cagagcccaa gggtatgacg  7020
gctttaaatg agtttccatt tctgttttaa gttaaccatc cctccctagc ttacatctgt  7080
tcctttgttg cacccttggt ttaacattat tctcctcccc aatttcctct tctcctcatt  7140
gtgaactcgt ggcag                                                    7155

SEQ ID NO: 277          moltype = DNA  length = 111
FEATURE                 Location/Qualifiers
source                  1..111
                        mol_type = other DNA
                        organism = Homo sapiens
SEQUENCE: 277
ggtctgcttg gtgagctcat tctcttacaa caacaaattc aagagcatga agaggaagcg  60
cgcagagccg ctggccaata tagcacgagc tatgcccaac agaagcgcaa g            111

SEQ ID NO: 278          moltype = DNA  length = 5409
FEATURE                 Location/Qualifiers
source                  1..5409
                        mol_type = other DNA
                        organism = Homo sapiens
SEQUENCE: 278
gtgatggatg gtttaagggg gctaccgata cattcacact aatcagccat ttctgccaag  60
atcatgtcac ctcaatctgt tcatggactc caaatacaag aaattaattt gacaaagtga  120
aaatataaaa gatgcatcat ataaatatgt aacttttctg gagtgggtag tataggtaaa  180
gccaaaagaa acaaattcaa gcagaggaat tttggtttct gaaaattagg ttgtctgtag  240
ggtccctgta tttatactta gaacaaaatt aggaatttct gtttatgtgg tccagttatt  300
gagtcaccct aagtttgtag gcatcttacc tacctacttg ctccccaagt tttatttct   360
aaaatgaaaa gcattgctgt agatgaccag tttacactaa agaataacat ttatttattt  420
gttttagcta aagtatatgg acagggaaca ttcatattct tgtagaagaa aattattttg  480
actttttgggc aaaagcatgt agttcttata cactttgaca aactcattgc gtacattttt  540
cacattaatc aaagtcagca caaataaatt ttcaccttgg accacggagg gtttgaacac  600
tggaaatttg atataattct ggttgctaaa gaacaagttc taataaaagc ttaagtgtat  660
accaatatgt ggctgttggt gcaatcagca ggtccgtaaa aatatgattt taatggttag  720
gtaatcccac aacggagatc ccaaagttca tgtttggaag agacttttgg gtcaaagtga  780
aatcagtgta atgaatttaa aattatactc tgagatcttg aaatcagcta attatgttac  840
atcttattag ctcagaaaag ttttgaagtt atatacaaat gctagtcagg aaaaaagatt  900
cagtcatgta attcttgtac attctactat ttaaatcaac caatattata gattatgatt  960
tagtgcagta attctgctgg ctaaccttat ctcatttggt ggtggttagt acttcagagt  1020
actcaccata gtttcattta tgttttcagc atcacttcct ggtttttctc aattccatgg  1080
ctgtggaatc aattcatatg tatatttagc ttcggtgagc aaaaacatag ctagaaaaag  1140
aaaagaagtg agtttcctac ctggttaaat taaagtcgat gtgttaagcc aaggaggact  1200
tcttttgaat ggtactttaa caatccctgt tctgtatact gtgaatatat catttaaata  1260
gcctaataaa ttggatgctt aggctgagcc acctatactt tagttttgtt atggaaagaa  1320
gggagaggag caagtatgtt cttatatgtt acttagaaat aagaatgtag ctgtagttac  1380
acattgttct taagtttttt tcgtaagaca acttgaaatg agtcccatag gcctgctatt  1440
taacattcta agatatgact taaggttaat gatgagcttt tgaatctgac aattcaagag  1500
atatccataa tgaatactga ttcattttct acattgctga aagctaatgt tcattttaag  1560
cctactttag tagcctttat ttgggcttag agatgttatt cctctttctg atatttattg  1620
ggttatctgt ttaacccttt tatatctccc tttcccgatt tgtaaattag agactggcaa  1680
gactttttac cctgagtaga gcaccaaaca tggcttgttt ctgcccacac tgtagttacc  1740
ttgaggggaa gtaaatggga ctttaaaagc aatttatgct cttttatagt gaaattatcc  1800
ctcttactat cccgaaagac tgttacctta caatatcctc cactcctttc cccctgtagt  1860
tactatagag atgacttttc ggttcttcac tgccataatg atcaaaatcc taattcatga  1920
gatttttatc attccaggca tgtgaggttt acttgatgca taaaaccgca agtacttttt  1980
gttgtttttt aattgttttt tctctcttat cttcttgaaa gtctaagtag atcatcattt  2040
```

```
ttgatgtctt attagtagca actaataaat tttccctgta tcttctcagc aaaagaactc  2100
aagcagagac agaagattag aactaccatt ggtagttttg cttcctatgg atatgttcac  2160
atacatagaa atttttacaa tgaccttttt atatatgtat ttcagaattt cagaatggcc  2220
tcaatgcctt aataggaaga aatacttgaa atttttaaat tagggcttgg ttttgtgagg  2280
agctagtaaa ggtttttctc tttcagcttt agcttgtttc tgcggaggat tccgctcttt  2340
ctccatcagt ttcatagccc tggaattgta gaaaagctct ggtttcaaga ccattgatat  2400
ccatttctgt cagggtgagt tttaaattta tttcatgatg caaacaatat attgaacaac  2460
aggacatgaa cttgttcttg ttgtaagtgg ctgaatttta tcagtaaagc acatcaaaat  2520
aaaatatacc ccaattgcta gttaagacct agagtgacag attgaaaata gcttgtgtta  2580
ttctcttaag aaaatatata aaaattatca tctcatcaat ctttaatgtt tgttttataa  2640
atctaaatgt ttttatattg tttcctagga aatattaggt ctaatttttt actttaccac  2700
cagctgtctt ttattttact cttttttga gacggagttt cgctcttgtt gcttaggcta  2760
gagtgcagtg gcactatctc agctcactgc gacctctgcc tcccgggttc aagcgattct  2820
cctgcctcag tctcccgagt agctgggatt acaggcacat gccactacac caggctaatt  2880
ttgtattttt agtagagacg gggtttcttc atgttggtca ggctggtctc gaactcccga  2940
cctcaggtga tccgcctgcc tcggcctccc agagtgctgg gattacaggc atgagccacc  3000
gcacctggcc agctgtcttt taatataaca ttatgattaa ttgtgatgtt ccattaaact  3060
aagcggagag gaaacatgct ggtaaaccat gtgtgagtta ttcattgtac cagaaaggca  3120
aatgatacat tttatcctaa aattcaaatt tataaacatc ttaacacttg tgatcattaa  3180
atactactaa tctagcatat aaattatatt tgtaggcggg gcacggtggc tcacgcctgt  3240
aatcccagca ctttgggagg ctgaggtggg cagatcacga ggtcaggaga tcgagaccat  3300
cctggctaac atggtgaaac cccatctcta ctaaaaatac aaaaaaaatt agctgggtgt  3360
gctggcgggc acctgtagtc ccagctactt gggaggctga ggcaggagaa tggcgtgacc  3420
ccaggaggca gagcttccag cctgggcgac tccgtctcaa aaaaaaagaa aaaagaaatt  3480
atatttgtaa tattctacta accttatatc attttaactt tttatataac tttttttattt  3540
taccaaatta agttaacctt ttatagccct tggcttatac taaacatcct aactttttttg  3600
tttaattgta ttagttttta agttattgcc ccagatgtca agtaatgttg gattttctat  3660
aataatttag gatatattgc atgaagtcag ttagtattta catttaaaac taaaacaatt  3720
tatactaata cagtttatac atttcatact aatttagcta cagttggata aatatttaat  3780
ggaacaaagt aaatcaaagt accttttcaa atgaattgga aattaaatcc acataacaat  3840
tttttatgac cacactatta cagtgtgatg gcatgccaaa tgatcataat gtggaattat  3900
gtatttcttc attggctttc aagattctgt tctttagttt gtgggctcct ctccaacttg  3960
cttgtctcct cacagtttag gcgactgttt ataattcttg tccatcctgc ataaacacac  4020
acagtcaaaa tgaaaaaaag cttctatcag cagatctgtg cttgctgtac agaaatggga  4080
aaacaattga agtttgcatt atcttttttc taattaccag atcgtttttg gagctattta  4140
ggcatacgct tttaaggaaa aaagaaaaaa agagtgtacc ttttgtttct aacaaaggtt  4200
gttatctata ttattgaaat aaaaaattgg ggatagttat gacaaagtat ttagaaatag  4260
gaattaaaat cttaaaataa cttttcatag catggacaag acttattaat gtctacctca  4320
ataagcaaat catttaaaaa tttttcatgt atatttgctg ccatgatgtg ttgtgattgc  4380
ttaaataacc aatgaatgaa gatcaacaag gatttaaatg aagaagaata tggatttaac  4440
tattttctcc tgtgaaataa gttcatattt acaagttttg attttcagaa attagacaat  4500
tatttttaaa ggctgggatg acaacttctg cctcttacca agaagtcaaa gcacagttat  4560
gtgaattcat cataaatcac atcattttta ttatattttg tatttataat tgtattgtga  4620
ctactttaaa acctgttata aaataaaatt gtttttttaat attttatttt agaattatta  4680
gcattaataa caatttgaag tagtttacac aatacctgtg agttttattt ttgttttata  4740
ttgaaattaa ttttagttgc tttacttggc ttcattgcta tggatgcatt ctctgtgtta  4800
cgagttagca gatctttcct tggaactgaa tttaaaagca agcatttggc tccacttaaa  4860
tctctgaaaa tgcaacttgt tctttgcatt tattacataa ttcgctactt atggtacaga  4920
aatggataca atacaaaaat atttccttat aagatacact gtgaccaatg agcttttttaa  4980
atagctgtaa tcagtaacat gtatttgact tttcaaaaca catttctgga gggatatcag  5040
tgctttattt ccccaaatat ctgaatccct atgctttagt acaaaacaac ttctgaagaa  5100
tttagtaacc atatgtgttg atctcttgtt tttctaacta gtctttcata agaaatgact  5160
agaatagcaa cagggaaatg attgcctttt aaggttttttg tttctcaata taaaattttg  5220
gtgaaccatt tttattgata aatacaggta tttttacttt cttaaatcac ttgatttaaa  5280
attactttga ttaaatatgc atataaagtc agttgttttt aactctcaat acttatcaaa  5340
aaaatttaac ttgctgtaca ttctgtataa acctaattct attcaactaa aattatttta  5400
aacatttag                                                          5409
```

```
SEQ ID NO: 279          moltype = DNA  length = 108
FEATURE                 Location/Qualifiers
source                  1..108
                        mol_type = other DNA
                        organism = Homo sapiens
SEQUENCE: 279
ctttagcttg tttctgcgga ggattccgct ctttctccat cagtttcata gccctggaat  60
tgtagaaaag ctctggtttc aagaccattg atatccattt ctgtcagg              108
```

```
SEQ ID NO: 280          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 280
tcttgaattt gttgttgt                                                18
```

```
SEQ ID NO: 281          moltype = DNA  length = 18
```

```
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 281
ctcttgaatt tgttgttg                                                18

SEQ ID NO: 282        moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 282
gctcttgaat ttgttgtt                                                18

SEQ ID NO: 283        moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 283
tgctcttgaa tttgttgt                                                18

SEQ ID NO: 284        moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 284
catgctcttg aatttgtt                                                18

SEQ ID NO: 285        moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 285
tcatgctctt gaatttgt                                                18

SEQ ID NO: 286        moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 286
ttcatgctct tgaatttg                                                18

SEQ ID NO: 287        moltype = DNA  length = 18
FEATURE               Location/Qualifiers
misc_feature          1..18
                      note = Description of Artificial Sequence: Synthetic
                       oligonucleotide
source                1..18
                      mol_type = other DNA
                      organism = synthetic construct
SEQUENCE: 287
cttcatgctc ttgaattt                                                18
```

```
SEQ ID NO: 288          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 288
tgaatttgtt gttgta                                                  16

SEQ ID NO: 289          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 289
ttgaatttgt tgttgt                                                  16

SEQ ID NO: 290          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 290
cttgaatttg ttgttg                                                  16

SEQ ID NO: 291          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 291
tcttgaattt gttgtt                                                  16

SEQ ID NO: 292          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 292
ctcttgaatt tgttgt                                                  16

SEQ ID NO: 293          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 293
gctcttgaat ttgttg                                                  16

SEQ ID NO: 294          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 294
tgctcttgaa tttgtt                                                  16

SEQ ID NO: 295          moltype = DNA  length = 16
```

```
FEATURE                Location/Qualifiers
misc_feature           1..16
                       note = Description of Artificial Sequence: Synthetic
                        oligonucleotide
source                 1..16
                       mol_type = other DNA
                       organism = synthetic construct
SEQUENCE: 295
atgctcttga atttgt                                                 16

SEQ ID NO: 296         moltype = DNA  length = 16
FEATURE                Location/Qualifiers
misc_feature           1..16
                       note = Description of Artificial Sequence: Synthetic
                        oligonucleotide
source                 1..16
                       mol_type = other DNA
                       organism = synthetic construct
SEQUENCE: 296
catgctcttg aatttg                                                 16

SEQ ID NO: 297         moltype = DNA  length = 16
FEATURE                Location/Qualifiers
misc_feature           1..16
                       note = Description of Artificial Sequence: Synthetic
                        oligonucleotide
source                 1..16
                       mol_type = other DNA
                       organism = synthetic construct
SEQUENCE: 297
tcatgctctt gaattt                                                 16

SEQ ID NO: 298         moltype = DNA  length = 16
FEATURE                Location/Qualifiers
misc_feature           1..16
                       note = Description of Artificial Sequence: Synthetic
                        oligonucleotide
source                 1..16
                       mol_type = other DNA
                       organism = synthetic construct
SEQUENCE: 298
ttcatgctct tgaatt                                                 16

SEQ ID NO: 299         moltype = DNA  length = 16
FEATURE                Location/Qualifiers
misc_feature           1..16
                       note = Description of Artificial Sequence: Synthetic
                        oligonucleotide
source                 1..16
                       mol_type = other DNA
                       organism = synthetic construct
SEQUENCE: 299
cttcatgctc ttgaat                                                 16

SEQ ID NO: 300         moltype = DNA  length = 308
FEATURE                Location/Qualifiers
misc_feature           1..308
                       note = Description of Artificial Sequence: Synthetic
                        polynucleotide
source                 1..308
                       mol_type = other DNA
                       organism = synthetic construct
SEQUENCE: 300
atttcagaat ggcctcaatg ccttaatagg aagaaatact tgaaattttt aaattagggc  60
ttggttttgt gaggagctag taaaggtttt tctctttcag ctttagcttg tttctgcgga  120
ggattccgct ctttctccat cagtttcata gccctggaat tgtagaaaag ctctggtttc  180
aagaccattg atatccattt ctgtcagggt gagttttaaa tttatttcat gatgcaaaca  240
atatattgaa caacaggaca tgaacttgtt cttgttgtaa gtggctgaat tttatcagta  300
aagcacat                                                          308

SEQ ID NO: 301         moltype = DNA  length = 258
FEATURE                Location/Qualifiers
misc_feature           1..258
                       note = Description of Artificial Sequence: Synthetic
                        polynucleotide
source                 1..258
                       mol_type = other DNA
                       organism = synthetic construct
```

```
SEQUENCE: 301
attgagcata aaaatctgct aaagcatttc actgatattt gggttcattt ctacaagtat  60
gagcttcagt cttaataaca gcaatctgca tttgtaacag gatagcagaa aggagctcat  120
ctgtttggag tccatttttg atggggatcc cactagaggt gagaaacctt cgtagtttcc  180
atatcatgcc aaaatcacgt actactccaa aagcatgtct actatccgta aatatttact  240
gacttgtcct tagctgtg                                                258

SEQ ID NO: 302          moltype = DNA  length = 110
FEATURE                 Location/Qualifiers
misc_feature            1..110
                        note = Description of Artificial Sequence: Synthetic
                         polynucleotide
source                  1..110
                        mol_type = other DNA
                        organism = synthetic construct
SEQUENCE: 302
gtatttcaga atttcagaat ggcctcaatg ccttaatagg aagaaatact tgaaattttt  60
aaattagggc ttggttttgt gaggagctag taaaggtttt tctctttcag             110

SEQ ID NO: 303          moltype = DNA  length = 151
FEATURE                 Location/Qualifiers
misc_feature            1..151
                        note = Description of Artificial Sequence: Synthetic
                         polynucleotide
source                  1..151
                        mol_type = other DNA
                        organism = synthetic construct
SEQUENCE: 303
gagctagtaa aggtttttct ctttcagctt tagcttgttt ctgcggagga ttccgctctt  60
tctccatcag tttcatagcc ctggaattgt agaaaagctc tggtttcaag accattgata  120
tccatttctg tcagggtgag ttttaaattt a                                 151

SEQ ID NO: 304          moltype = DNA  length = 104
FEATURE                 Location/Qualifiers
misc_feature            1..104
                        note = Description of Artificial Sequence: Synthetic
                         polynucleotide
source                  1..104
                        mol_type = other DNA
                        organism = synthetic construct
SEQUENCE: 304
gtgagtttta aatttatttc atgatgcaaa caatatattg aacaacagga catgaacttg  60
ttcttgttgt aagtggctga attttatcag taaagcacat caaa                   104

SEQ ID NO: 305          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 305
aggccattct gaaattct                                                18

SEQ ID NO: 306          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 306
cattgaggcc attctgaa                                                18

SEQ ID NO: 307          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 307
taaggcattg aggccatt                                                18

SEQ ID NO: 308          moltype = DNA  length = 18
FEATURE                 Location/Qualifiers
```

```
misc_feature           1..18
                       note = Description of Artificial Sequence: Synthetic
                        oligonucleotide
source                 1..18
                       mol_type = other DNA
                       organism = synthetic construct
SEQUENCE: 308
cctattaagg cattgagg                                                18

SEQ ID NO: 309         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 309
ttcttcctat taaggcat                                                18

SEQ ID NO: 310         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 310
agtatttctt cctattaa                                                18

SEQ ID NO: 311         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 311
tttcaagtat ttcttcct                                                18

SEQ ID NO: 312         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 312
aaaaatttca agtatttc                                                18

SEQ ID NO: 313         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 313
aatttaaaaa tttcaagt                                                18

SEQ ID NO: 314         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 314
gccctaattt aaaaattt                                                18
```

```
SEQ ID NO: 315          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 315
accaagccct aatttaaa                                                    18

SEQ ID NO: 316          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 316
acaaaaccaa gccctaat                                                    18

SEQ ID NO: 317          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 317
tcctcacaaa accaagcc                                                    18

SEQ ID NO: 318          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 318
ctagctcctc acaaaacc                                                    18

SEQ ID NO: 319          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 319
ctttactagc tcctcaca                                                    18

SEQ ID NO: 320          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 320
aaaaccttta ctagctcc                                                    18

SEQ ID NO: 321          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 321
agagaaaaac ctttacta                                                    18

SEQ ID NO: 322          moltype = DNA  length = 18
```

```
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 322
ctgaaagaga aaaacctt                                               18

SEQ ID NO: 323         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 323
aagctgaaag agaaaaac                                               18

SEQ ID NO: 324         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 324
ctaaagctga aagagaaa                                               18

SEQ ID NO: 325         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 325
aagctaaagc tgaaagag                                               18

SEQ ID NO: 326         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 326
aacaagctaa agctgaaa                                               18

SEQ ID NO: 327         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 327
agaaacaagc taaagctg                                               18

SEQ ID NO: 328         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 328
cgcagaaaca agctaaag                                               18
```

```
SEQ ID NO: 329          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 329
tcctccgcag aaacaagc                                                18

SEQ ID NO: 330          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 330
cggaatcctc cgcagaaa                                                18

SEQ ID NO: 331          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 331
aagagcggaa tcctccgc                                                18

SEQ ID NO: 332          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 332
ggagaaagag cggaatcc                                                18

SEQ ID NO: 333          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 333
ctgatggaga aagagcgg                                                18

SEQ ID NO: 334          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 334
tgaaactgat ggagaaag                                                18

SEQ ID NO: 335          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 335
ggctatgaaa ctgatgga                                                18
```

```
SEQ ID NO: 336          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 336
tccagggcta tgaaactg                                                18

SEQ ID NO: 337          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 337
acaattccag ggctatga                                                18

SEQ ID NO: 338          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 338
tttctacaat tccagggc                                                18

SEQ ID NO: 339          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 339
gagcttttct acaattcc                                                18

SEQ ID NO: 340          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 340
aaccagagct tttctaca                                                18

SEQ ID NO: 341          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 341
cttgaaacca gagctttt                                                18

SEQ ID NO: 342          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 342
atggtcttga aaccagag                                                18

SEQ ID NO: 343          moltype = DNA  length = 18
```

```
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 343
tatcaatggt cttgaaac                                             18

SEQ ID NO: 344         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 344
atggatatca atggtctt                                             18

SEQ ID NO: 345         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 345
cagaaatgga tatcaatg                                             18

SEQ ID NO: 346         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 346
cctgacagaa atggatat                                             18

SEQ ID NO: 347         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 347
caccctgaca gaaatgga                                             18

SEQ ID NO: 348         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 348
actcaccctg acagaaat                                             18

SEQ ID NO: 349         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 349
aaaactcacc ctgacaga                                             18
```

SEQ ID NO: 350 moltype = DNA length = 18
FEATURE Location/Qualifiers
misc_feature 1..18
note = Description of Artificial Sequence: Synthetic
oligonucleotide
source 1..18
mol_type = other DNA
organism = synthetic construct
SEQUENCE: 350
tttaaaactc accctgac 18

SEQ ID NO: 351 moltype = DNA length = 18
FEATURE Location/Qualifiers
misc_feature 1..18
note = Description of Artificial Sequence: Synthetic
oligonucleotide
source 1..18
mol_type = other DNA
organism = synthetic construct
SEQUENCE: 351
aaatttaaaa ctcaccct 18

SEQ ID NO: 352 moltype = DNA length = 18
FEATURE Location/Qualifiers
misc_feature 1..18
note = Description of Artificial Sequence: Synthetic
oligonucleotide
source 1..18
mol_type = other DNA
organism = synthetic construct
SEQUENCE: 352
aataaattta aaactcac 18

SEQ ID NO: 353 moltype = DNA length = 18
FEATURE Location/Qualifiers
misc_feature 1..18
note = Description of Artificial Sequence: Synthetic
oligonucleotide
source 1..18
mol_type = other DNA
organism = synthetic construct
SEQUENCE: 353
catgaaataa atttaaaa 18

SEQ ID NO: 354 moltype = DNA length = 18
FEATURE Location/Qualifiers
misc_feature 1..18
note = Description of Artificial Sequence: Synthetic
oligonucleotide
source 1..18
mol_type = other DNA
organism = synthetic construct
SEQUENCE: 354
tgcatcatga aataaatt 18

SEQ ID NO: 355 moltype = DNA length = 18
FEATURE Location/Qualifiers
misc_feature 1..18
note = Description of Artificial Sequence: Synthetic
oligonucleotide
source 1..18
mol_type = other DNA
organism = synthetic construct
SEQUENCE: 355
ttgtttgcat catgaaat 18

SEQ ID NO: 356 moltype = DNA length = 18
FEATURE Location/Qualifiers
misc_feature 1..18
note = Description of Artificial Sequence: Synthetic
oligonucleotide
source 1..18
mol_type = other DNA
organism = synthetic construct
SEQUENCE: 356
atatattgtt tgcatcat 18

SEQ ID NO: 357 moltype = DNA length = 18

```
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 357
gttcaatata ttgtttgc                                              18

SEQ ID NO: 358          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 358
ctgttgttca atatattg                                              18

SEQ ID NO: 359          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 359
atgtcctgtt gttcaata                                              18

SEQ ID NO: 360          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 360
agttcatgtc ctgttgtt                                              18

SEQ ID NO: 361          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 361
gaacaagttc atgtcctg                                              18

SEQ ID NO: 362          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 362
aacaagaaca agttcatg                                              18

SEQ ID NO: 363          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 363
cttacaacaa gaacaagt                                              18
```

```
SEQ ID NO: 364          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 364
agccacttac aacaagaa                                                  18

SEQ ID NO: 365          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 365
aattcagcca cttacaac                                                  18

SEQ ID NO: 366          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 366
gataaaattc agccactt                                                  18

SEQ ID NO: 367          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 367
ttactgataa aattcagc                                                  18

SEQ ID NO: 368          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 368
gtgctttact gataaaat                                                  18

SEQ ID NO: 369          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 369
ttgatgtgct ttactgat                                                  18

SEQ ID NO: 370          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 370
tggagaaaga gcggaatc                                                  18

SEQ ID NO: 371          moltype = DNA  length = 18
```

```
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 371
atggagaaag agcggaat                                                18

SEQ ID NO: 372         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 372
gatggagaaa gagcggaa                                                18

SEQ ID NO: 373         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 373
tgatggagaa agagcgga                                                18

SEQ ID NO: 374         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 374
actgatggag aaagagcg                                                18

SEQ ID NO: 375         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 375
aactgatgga gaaagagc                                                18

SEQ ID NO: 376         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 376
aaactgatgg agaaagag                                                18

SEQ ID NO: 377         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 377
gaaactgatg gagaaaga                                                18
```

```
SEQ ID NO: 378          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 378
atgaaactga tggagaaa                                                18

SEQ ID NO: 379          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 379
tatgaaactg atggagaa                                                18

SEQ ID NO: 380          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 380
ctatgaaact gatggaga                                                18

SEQ ID NO: 381          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 381
gctatgaaac tgatggag                                                18

SEQ ID NO: 382          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 382
gggctatgaa actgatgg                                                18

SEQ ID NO: 383          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 383
agggctatga aactgatg                                                18

SEQ ID NO: 384          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 384
cagggctatg aaactgat                                                18

SEQ ID NO: 385          moltype = DNA  length = 18
```

```
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 385
ccagggctat gaaactga                                            18

SEQ ID NO: 386         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 386
ctgatggaga aagagcggaa tc                                       22

SEQ ID NO: 387         moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 387
ctgatggaga aagagcggaa                                          20

SEQ ID NO: 388         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 388
aactgatgga gaaagagcgg aa                                       22

SEQ ID NO: 389         moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 389
aactgatgga gaaagagcgg                                          20

SEQ ID NO: 390         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 390
gaaactgatg gagaaagagc gg                                       22

SEQ ID NO: 391         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 391
ggctatgaaa ctgatggaga aa                                       22
```

```
SEQ ID NO: 392          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 392
ggctatgaaa ctgatggaga                                              20

SEQ ID NO: 393          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 393
agggctatga aactgatgga ga                                           22

SEQ ID NO: 394          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 394
agggctatga aactgatgga                                              20

SEQ ID NO: 395          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 395
ccagggctat gaaactgatg ga                                           22

SEQ ID NO: 396          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 396
ttcttaccca tttaatta                                                18

SEQ ID NO: 397          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 397
tgcttcttac ccatttaa                                                18

SEQ ID NO: 398          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 398
taatgcttct tacccatt                                                18

SEQ ID NO: 399          moltype = DNA  length = 18
```

```
FEATURE              Location/Qualifiers
misc_feature         1..18
                     note = Description of Artificial Sequence: Synthetic
                      oligonucleotide
source               1..18
                     mol_type = other DNA
                     organism = synthetic construct
SEQUENCE: 399
agataatgct tcttaccc                                                  18

SEQ ID NO: 400       moltype = DNA  length = 18
FEATURE              Location/Qualifiers
misc_feature         1..18
                     note = Description of Artificial Sequence: Synthetic
                      oligonucleotide
source               1..18
                     mol_type = other DNA
                     organism = synthetic construct
SEQUENCE: 400
cagataatgc ttcttacc                                                  18

SEQ ID NO: 401       moltype = DNA  length = 18
FEATURE              Location/Qualifiers
misc_feature         1..18
                     note = Description of Artificial Sequence: Synthetic
                      oligonucleotide
source               1..18
                     mol_type = other DNA
                     organism = synthetic construct
SEQUENCE: 401
cccttcagat aatgcttc                                                  18

SEQ ID NO: 402       moltype = DNA  length = 18
FEATURE              Location/Qualifiers
misc_feature         1..18
                     note = Description of Artificial Sequence: Synthetic
                      oligonucleotide
source               1..18
                     mol_type = other DNA
                     organism = synthetic construct
SEQUENCE: 402
ctactccctt cagataat                                                  18

SEQ ID NO: 403       moltype = DNA  length = 18
FEATURE              Location/Qualifiers
misc_feature         1..18
                     note = Description of Artificial Sequence: Synthetic
                      oligonucleotide
source               1..18
                     mol_type = other DNA
                     organism = synthetic construct
SEQUENCE: 403
agctcctact cccttcag                                                  18

SEQ ID NO: 404       moltype = DNA  length = 18
FEATURE              Location/Qualifiers
misc_feature         1..18
                     note = Description of Artificial Sequence: Synthetic
                      oligonucleotide
source               1..18
                     mol_type = other DNA
                     organism = synthetic construct
SEQUENCE: 404
ttcacagctc ctactccc                                                  18

SEQ ID NO: 405       moltype = DNA  length = 18
FEATURE              Location/Qualifiers
misc_feature         1..18
                     note = Description of Artificial Sequence: Synthetic
                      oligonucleotide
source               1..18
                     mol_type = other DNA
                     organism = synthetic construct
SEQUENCE: 405
taaaattcac agctccta                                                  18
```

```
SEQ ID NO: 406          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 406
aaatctaaaa ttcacagc                                                18

SEQ ID NO: 407          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 407
gaataaaatc taaaattc                                                18

SEQ ID NO: 408          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 408
gatgggaata aaatctaa                                                18

SEQ ID NO: 409          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 409
gctgtgatgg gaataaaa                                                18

SEQ ID NO: 410          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 410
tagaggctgt gatgggaa                                                18

SEQ ID NO: 411          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 411
aaagatagag gctgtgat                                                18

SEQ ID NO: 412          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 412
aaaagaaaga tagaggct                                                18

SEQ ID NO: 413          moltype = DNA  length = 18
```

```
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 413
gacctaaaag aaagatag                                                 18

SEQ ID NO: 414          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 414
ataaagacct aaaagaaa                                                 18

SEQ ID NO: 415          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 415
gagatataaa gacctaaa                                                 18

SEQ ID NO: 416          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 416
ggctgtgatg ggaataaa                                                 18

SEQ ID NO: 417          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 417
aggctgtgat gggaataa                                                 18

SEQ ID NO: 418          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 418
gaggctgtga tgggaata                                                 18

SEQ ID NO: 419          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 419
agaggctgtg atgggaat                                                 18
```

SEQ ID NO: 420 moltype = DNA length = 18
FEATURE Location/Qualifiers
misc_feature 1..18
note = Description of Artificial Sequence: Synthetic
oligonucleotide
source 1..18
mol_type = other DNA
organism = synthetic construct
SEQUENCE: 420
atagaggctg tgatggga 18

SEQ ID NO: 421 moltype = DNA length = 18
FEATURE Location/Qualifiers
misc_feature 1..18
note = Description of Artificial Sequence: Synthetic
oligonucleotide
source 1..18
mol_type = other DNA
organism = synthetic construct
SEQUENCE: 421
gatagaggct gtgatggg 18

SEQ ID NO: 422 moltype = DNA length = 18
FEATURE Location/Qualifiers
misc_feature 1..18
note = Description of Artificial Sequence: Synthetic
oligonucleotide
source 1..18
mol_type = other DNA
organism = synthetic construct
SEQUENCE: 422
agatagaggc tgtgatgg 18

SEQ ID NO: 423 moltype = DNA length = 18
FEATURE Location/Qualifiers
misc_feature 1..18
note = Description of Artificial Sequence: Synthetic
oligonucleotide
source 1..18
mol_type = other DNA
organism = synthetic construct
SEQUENCE: 423
aagatagagg ctgtgatg 18

SEQ ID NO: 424 moltype = DNA length = 22
FEATURE Location/Qualifiers
misc_feature 1..22
note = Description of Artificial Sequence: Synthetic
oligonucleotide
source 1..22
mol_type = other DNA
organism = synthetic construct
SEQUENCE: 424
tagaggctgt gatgggaata aa 22

SEQ ID NO: 425 moltype = DNA length = 22
FEATURE Location/Qualifiers
misc_feature 1..22
note = Description of Artificial Sequence: Synthetic
oligonucleotide
source 1..22
mol_type = other DNA
organism = synthetic construct
SEQUENCE: 425
atagaggctg tgatgggaat aa 22

SEQ ID NO: 426 moltype = DNA length = 22
FEATURE Location/Qualifiers
misc_feature 1..22
note = Description of Artificial Sequence: Synthetic
oligonucleotide
source 1..22
mol_type = other DNA
organism = synthetic construct
SEQUENCE: 426
gatagaggct gtgatgggaa ta 22

SEQ ID NO: 427 moltype = DNA length = 22

```
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 427
agatagaggc tgtgatggga at                                            22

SEQ ID NO: 428         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 428
aagatagagg ctgtgatggg aa                                            22

SEQ ID NO: 429         moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 429
gaggctgtga tgggaataaa                                               20

SEQ ID NO: 430         moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 430
agaggctgtg atgggaataa                                               20

SEQ ID NO: 431         moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 431
tagaggctgt gatgggaata                                               20

SEQ ID NO: 432         moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 432
atagaggctg tgatgggaat                                               20

SEQ ID NO: 433         moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 433
gatagaggct gtgatgggaa                                               20
```

```
SEQ ID NO: 434          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 434
agatagaggc tgtgatggga                                                20

SEQ ID NO: 435          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 435
aagatagagg ctgtgatggg                                                20

SEQ ID NO: 436          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 436
ctgtgatggg aataaa                                                    16

SEQ ID NO: 437          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 437
gctgtgatgg gaataa                                                    16

SEQ ID NO: 438          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 438
ggctgtgatg ggaata                                                    16

SEQ ID NO: 439          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 439
aggctgtgat gggaat                                                    16

SEQ ID NO: 440          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 440
gaggctgtga tgggaa                                                    16

SEQ ID NO: 441          moltype = DNA  length = 16
```

```
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 441
agaggctgtg atggga                                                   16

SEQ ID NO: 442          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 442
tagaggctgt gatggg                                                   16

SEQ ID NO: 443          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 443
atagaggctg tgatgg                                                   16

SEQ ID NO: 444          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 444
gatagaggct gtgatg                                                   16

SEQ ID NO: 445          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 445
agatagaggc tgtgat                                                   16

SEQ ID NO: 446          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 446
aagatagagg ctgtga                                                   16

SEQ ID NO: 447          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 447
aggctgtgat gtgaataa                                                 18
```

```
SEQ ID NO: 448          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 448
aggctgtgat gtgaataa                                                18

SEQ ID NO: 449          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 449
aggctgtgat gtgaataa                                                18

SEQ ID NO: 450          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 450
agaggctgtg atgtgaat                                                18

SEQ ID NO: 451          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 451
agaggctgtg atgtgaat                                                18

SEQ ID NO: 452          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 452
agaggctgtg atgtgaat                                                18

SEQ ID NO: 453          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 453
tagaggctgt gatgtgaa                                                18

SEQ ID NO: 454          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 454
tagaggctgt gatgtgaa                                                18

SEQ ID NO: 455          moltype = DNA  length = 18
```

```
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 455
tagaggctgt gatgtgaa                                                18

SEQ ID NO: 456          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 456
gatagaggct gtgattgg                                                18

SEQ ID NO: 457          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 457
gatagaggct gtgattgg                                                18

SEQ ID NO: 458          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 458
gatagaggct gtgattgg                                                18

SEQ ID NO: 459          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 459
agatagaggc tgtgatgg                                                18

SEQ ID NO: 460          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 460
ggctgtgatg tgaata                                                  16

SEQ ID NO: 461          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 461
ggctgtgatg tgaata                                                  16
```

```
SEQ ID NO: 462          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 462
ggctgtgatg tgaata                                                  16

SEQ ID NO: 463          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 463
gaggctgtga tgtgaa                                                  16

SEQ ID NO: 464          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 464
gaggctgtga tgtgaa                                                  16

SEQ ID NO: 465          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 465
gaggctgtga tgtgaa                                                  16

SEQ ID NO: 466          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 466
tagaggctgt gattgg                                                  16

SEQ ID NO: 467          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 467
tagaggctgt gattgg                                                  16

SEQ ID NO: 468          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 468
tagaggctgt gattgg                                                  16

SEQ ID NO: 469          moltype = DNA  length = 16
```

```
FEATURE                Location/Qualifiers
misc_feature           1..16
                       note = Description of Artificial Sequence: Synthetic
                        oligonucleotide
source                 1..16
                       mol_type = other DNA
                       organism = synthetic construct
SEQUENCE: 469
atagaggctg tgatgg                                                  16

SEQ ID NO: 470         moltype = DNA  length = 16
FEATURE                Location/Qualifiers
misc_feature           1..16
                       note = Description of Artificial Sequence: Synthetic
                        oligonucleotide
source                 1..16
                       mol_type = other DNA
                       organism = synthetic construct
SEQUENCE: 470
gatagaggct gtgatg                                                  16

SEQ ID NO: 471         moltype = DNA  length = 16
FEATURE                Location/Qualifiers
misc_feature           1..16
                       note = Description of Artificial Sequence: Synthetic
                        oligonucleotide
source                 1..16
                       mol_type = other DNA
                       organism = synthetic construct
SEQUENCE: 471
agatagaggc tgtgat                                                  16

SEQ ID NO: 472         moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 472
ggctatgaaa ctgatggaga                                              20

SEQ ID NO: 473         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 473
ctatgaaact gatggaga                                                18

SEQ ID NO: 474         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 474
gctatgaaac tgatggag                                                18

SEQ ID NO: 475         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 475
ggctatgaaa ctgatgga                                                18
```

```
SEQ ID NO: 476          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 476
atgaaactga tggaga                                                    16

SEQ ID NO: 477          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 477
atgaaactga tggaga                                                    16

SEQ ID NO: 478          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 478
ctatgaaact gatgga                                                    16

SEQ ID NO: 479          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 479
ctatgaaact gatgga                                                    16

SEQ ID NO: 480          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 480
ggctatgaaa ctgatg                                                    16

SEQ ID NO: 481          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 481
ggctatgaaa ctgatg                                                    16

SEQ ID NO: 482          moltype = DNA  length = 14
FEATURE                 Location/Qualifiers
misc_feature            1..14
                        note = Description of Artificial Sequence: Synthetic
                         oligonucleotide
source                  1..14
                        mol_type = other DNA
                        organism = synthetic construct
SEQUENCE: 482
gaaactgatg gaga                                                      14

SEQ ID NO: 483          moltype = DNA  length = 14
```

```
FEATURE                Location/Qualifiers
misc_feature           1..14
                       note = Description of Artificial Sequence: Synthetic
                        oligonucleotide
source                 1..14
                       mol_type = other DNA
                       organism = synthetic construct
SEQUENCE: 483
atgaaactga tgga                                                      14

SEQ ID NO: 484         moltype = DNA  length = 14
FEATURE                Location/Qualifiers
misc_feature           1..14
                       note = Description of Artificial Sequence: Synthetic
                        oligonucleotide
source                 1..14
                       mol_type = other DNA
                       organism = synthetic construct
SEQUENCE: 484
ctatgaaact gatg                                                      14

SEQ ID NO: 485         moltype = DNA  length = 14
FEATURE                Location/Qualifiers
misc_feature           1..14
                       note = Description of Artificial Sequence: Synthetic
                        oligonucleotide
source                 1..14
                       mol_type = other DNA
                       organism = synthetic construct
SEQUENCE: 485
ggctatgaaa ctga                                                      14

SEQ ID NO: 486         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 486
tagaggctgt gatgggaata aa                                             22

SEQ ID NO: 487         moltype = DNA  length = 24
FEATURE                Location/Qualifiers
misc_feature           1..24
                       note = Description of Artificial Sequence: Synthetic
                        oligonucleotide
source                 1..24
                       mol_type = other DNA
                       organism = synthetic construct
SEQUENCE: 487
tagaggctgt gatgggaata aaat                                           24

SEQ ID NO: 488         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 488
atagaggctg tgatgggaat aa                                             22

SEQ ID NO: 489         moltype = DNA  length = 24
FEATURE                Location/Qualifiers
misc_feature           1..24
                       note = Description of Artificial Sequence: Synthetic
                        oligonucleotide
source                 1..24
                       mol_type = other DNA
                       organism = synthetic construct
SEQUENCE: 489
atagaggctg tgatgggaat aaaa                                           24
```

```
SEQ ID NO: 490          moltype = DNA  length = 25
FEATURE                 Location/Qualifiers
misc_feature            1..25
                        note = Description of Artificial Sequence: Synthetic
                         oligonucleotide
source                  1..25
                        mol_type = other DNA
                        organism = synthetic construct
SEQUENCE: 490
atagaggctg tgatgggaat aaaat                                         25

SEQ ID NO: 491          moltype = DNA  length = 25
FEATURE                 Location/Qualifiers
misc_feature            1..25
                        note = Description of Artificial Sequence: Synthetic
                         oligonucleotide
source                  1..25
                        mol_type = other DNA
                        organism = synthetic construct
SEQUENCE: 491
aaagatagag gctgtgatgg gaata                                         25

SEQ ID NO: 492          moltype = DNA  length = 21
FEATURE                 Location/Qualifiers
misc_feature            1..21
                        note = Description of Artificial Sequence: Synthetic
                         oligonucleotide
source                  1..21
                        mol_type = other DNA
                        organism = synthetic construct
SEQUENCE: 492
ggctatgaaa ctgatggaga a                                             21

SEQ ID NO: 493          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 493
ggctatgaaa ctgatggaga aa                                            22

SEQ ID NO: 494          moltype = DNA  length = 24
FEATURE                 Location/Qualifiers
misc_feature            1..24
                        note = Description of Artificial Sequence: Synthetic
                         oligonucleotide
source                  1..24
                        mol_type = other DNA
                        organism = synthetic construct
SEQUENCE: 494
ggctatgaaa ctgatggaga aaga                                          24

SEQ ID NO: 495          moltype = DNA  length = 25
FEATURE                 Location/Qualifiers
misc_feature            1..25
                        note = Description of Artificial Sequence: Synthetic
                         oligonucleotide
source                  1..25
                        mol_type = other DNA
                        organism = synthetic construct
SEQUENCE: 495
agggctatga aactgatgga gaaag                                         25

SEQ ID NO: 496          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 496
catttaatta aattatat                                                 18

SEQ ID NO: 497          moltype = DNA  length = 18
```

```
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 497
ccatttaatt aaattata                                                18

SEQ ID NO: 498         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 498
cccatttaat taaattat                                                18

SEQ ID NO: 499         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 499
acccatttaa ttaaatta                                                18

SEQ ID NO: 500         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 500
tacccattta attaaatt                                                18

SEQ ID NO: 501         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 501
ttacccattt aattaaat                                                18

SEQ ID NO: 502         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 502
cttacccatt taattaaa                                                18

SEQ ID NO: 503         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 503
tcttacccat ttaattaa                                                18
```

```
SEQ ID NO: 504          moltype = DNA  length = 17
FEATURE                 Location/Qualifiers
misc_feature            1..17
                        note = Description of Artificial Sequence: Synthetic
                         oligonucleotide
source                  1..17
                        mol_type = other DNA
                        organism = synthetic construct
SEQUENCE: 504
gatagaggct gtgatgg                                                 17

SEQ ID NO: 505          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 505
ggctgtgaaa ctgatgga                                                18

SEQ ID NO: 506          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 506
ggctgtgaaa ctgatggaga                                              20

SEQ ID NO: 507          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 507
ctatgaaact gatgga                                                  16

SEQ ID NO: 508          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 508
gctatgaaac tgatgg                                                  16

SEQ ID NO: 509          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 509
ggctatgaaa ctgatg                                                  16

SEQ ID NO: 510          moltype = DNA  length = 14
FEATURE                 Location/Qualifiers
misc_feature            1..14
                        note = Description of Artificial Sequence: Synthetic
                         oligonucleotide
source                  1..14
                        mol_type = other DNA
                        organism = synthetic construct
SEQUENCE: 510
atgaaactga tgga                                                    14

SEQ ID NO: 511          moltype = DNA  length = 14
```

```
FEATURE                  Location/Qualifiers
misc_feature             1..14
                         note = Description of Artificial Sequence: Synthetic
                          oligonucleotide
source                   1..14
                         mol_type = other DNA
                         organism = synthetic construct
SEQUENCE: 511
tatgaaactg atgg                                                           14

SEQ ID NO: 512           moltype = DNA  length = 14
FEATURE                  Location/Qualifiers
misc_feature             1..14
                         note = Description of Artificial Sequence: Synthetic
                          oligonucleotide
source                   1..14
                         mol_type = other DNA
                         organism = synthetic construct
SEQUENCE: 512
ctatgaaact gatg                                                           14

SEQ ID NO: 513           moltype = DNA  length = 14
FEATURE                  Location/Qualifiers
misc_feature             1..14
                         note = Description of Artificial Sequence: Synthetic
                          oligonucleotide
source                   1..14
                         mol_type = other DNA
                         organism = synthetic construct
SEQUENCE: 513
gctatgaaac tgat                                                           14

SEQ ID NO: 514           moltype = DNA  length = 14
FEATURE                  Location/Qualifiers
misc_feature             1..14
                         note = Description of Artificial Sequence: Synthetic
                          oligonucleotide
source                   1..14
                         mol_type = other DNA
                         organism = synthetic construct
SEQUENCE: 514
ggctatgaaa ctga                                                           14

SEQ ID NO: 515           moltype = DNA  length = 20
FEATURE                  Location/Qualifiers
misc_feature             1..20
                         note = Description of Artificial Sequence: Synthetic
                          oligonucleotide
source                   1..20
                         mol_type = other DNA
                         organism = synthetic construct
SEQUENCE: 515
gctgtgaaac tgatggagaa                                                     20

SEQ ID NO: 516           moltype = DNA  length = 20
FEATURE                  Location/Qualifiers
misc_feature             1..20
                         note = Description of Artificial Sequence: Synthetic
                          oligonucleotide
source                   1..20
                         mol_type = other DNA
                         organism = synthetic construct
SEQUENCE: 516
gggctgtgaa actgatggag                                                     20

SEQ ID NO: 517           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 517
tgtgaaactg atggagaa                                                       18
```

```
SEQ ID NO: 518          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 518
ctgtgaaact gatggaga                                                18

SEQ ID NO: 519          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 519
gctgtgaaac tgatggag                                                18

SEQ ID NO: 520          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 520
gggctgtgaa actgatgg                                                18

SEQ ID NO: 521          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 521
tgaaactgat ggagaa                                                  16

SEQ ID NO: 522          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 522
gtgaaactga tggaga                                                  16

SEQ ID NO: 523          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 523
tgtgaaactg atggag                                                  16

SEQ ID NO: 524          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 524
ctgtgaaact gatgga                                                  16

SEQ ID NO: 525          moltype = DNA  length = 16
```

```
FEATURE                Location/Qualifiers
misc_feature           1..16
                       note = Description of Artificial Sequence: Synthetic
                        oligonucleotide
source                 1..16
                       mol_type = other DNA
                       organism = synthetic construct
SEQUENCE: 525
gctgtgaaac tgatgg                                                   16

SEQ ID NO: 526         moltype = DNA  length = 16
FEATURE                Location/Qualifiers
misc_feature           1..16
                       note = Description of Artificial Sequence: Synthetic
                        oligonucleotide
source                 1..16
                       mol_type = other DNA
                       organism = synthetic construct
SEQUENCE: 526
ggctgtgaaa ctgatg                                                   16

SEQ ID NO: 527         moltype = DNA  length = 16
FEATURE                Location/Qualifiers
misc_feature           1..16
                       note = Description of Artificial Sequence: Synthetic
                        oligonucleotide
source                 1..16
                       mol_type = other DNA
                       organism = synthetic construct
SEQUENCE: 527
gggctgtgaa actgat                                                   16

SEQ ID NO: 528         moltype = DNA  length = 15
FEATURE                Location/Qualifiers
misc_feature           1..15
                       note = Description of Artificial Sequence: Synthetic
                        oligonucleotide
source                 1..15
                       mol_type = other DNA
                       organism = synthetic construct
SEQUENCE: 528
cggtccagga atgac                                                    15

SEQ ID NO: 529         moltype = DNA  length = 15
FEATURE                Location/Qualifiers
misc_feature           1..15
                       note = Description of Artificial Sequence: Synthetic
                        oligonucleotide
source                 1..15
                       mol_type = other DNA
                       organism = synthetic construct
SEQUENCE: 529
ccggtccagg aatga                                                    15

SEQ ID NO: 530         moltype = DNA  length = 15
FEATURE                Location/Qualifiers
misc_feature           1..15
                       note = Description of Artificial Sequence: Synthetic
                        oligonucleotide
source                 1..15
                       mol_type = other DNA
                       organism = synthetic construct
SEQUENCE: 530
cccggtccag gaatg                                                    15

SEQ ID NO: 531         moltype = DNA  length = 15
FEATURE                Location/Qualifiers
misc_feature           1..15
                       note = Description of Artificial Sequence: Synthetic
                        oligonucleotide
source                 1..15
                       mol_type = other DNA
                       organism = synthetic construct
SEQUENCE: 531
tcccggtcca ggaat                                                    15
```

```
SEQ ID NO: 532          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 532
ctcccggtcc aggaa                                                    15

SEQ ID NO: 533          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 533
gctcccggtc cagga                                                    15

SEQ ID NO: 534          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 534
ggctcccggt ccagg                                                    15

SEQ ID NO: 535          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 535
cgggagcccc cgtgt                                                    15

SEQ ID NO: 536          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 536
gcgggagccc ccgtg                                                    15

SEQ ID NO: 537          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 537
cgcgggagcc cccgt                                                    15

SEQ ID NO: 538          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 538
acgcgggagc ccccg                                                    15

SEQ ID NO: 539          moltype = DNA  length = 15
```

```
FEATURE                Location/Qualifiers
misc_feature           1..15
                       note = Description of Artificial Sequence: Synthetic
                        oligonucleotide
source                 1..15
                       mol_type = other DNA
                       organism = synthetic construct
SEQUENCE: 539
cacgcgggag ccccc                                                    15

SEQ ID NO: 540         moltype = DNA  length = 15
FEATURE                Location/Qualifiers
misc_feature           1..15
                       note = Description of Artificial Sequence: Synthetic
                        oligonucleotide
source                 1..15
                       mol_type = other DNA
                       organism = synthetic construct
SEQUENCE: 540
ccacgcggga gcccc                                                    15

SEQ ID NO: 541         moltype = DNA  length = 15
FEATURE                Location/Qualifiers
misc_feature           1..15
                       note = Description of Artificial Sequence: Synthetic
                        oligonucleotide
source                 1..15
                       mol_type = other DNA
                       organism = synthetic construct
SEQUENCE: 541
gccacgcggg agccc                                                    15

SEQ ID NO: 542         moltype = DNA  length = 15
FEATURE                Location/Qualifiers
misc_feature           1..15
                       note = Description of Artificial Sequence: Synthetic
                        oligonucleotide
source                 1..15
                       mol_type = other DNA
                       organism = synthetic construct
SEQUENCE: 542
ggccacgcgg gagcc                                                    15

SEQ ID NO: 543         moltype = DNA  length = 15
FEATURE                Location/Qualifiers
misc_feature           1..15
                       note = Description of Artificial Sequence: Synthetic
                        oligonucleotide
source                 1..15
                       mol_type = other DNA
                       organism = synthetic construct
SEQUENCE: 543
cggccacgcg ggagc                                                    15

SEQ ID NO: 544         moltype = DNA  length = 15
FEATURE                Location/Qualifiers
misc_feature           1..15
                       note = Description of Artificial Sequence: Synthetic
                        oligonucleotide
source                 1..15
                       mol_type = other DNA
                       organism = synthetic construct
SEQUENCE: 544
acggccacgc gggag                                                    15

SEQ ID NO: 545         moltype = DNA  length = 15
FEATURE                Location/Qualifiers
misc_feature           1..15
                       note = Description of Artificial Sequence: Synthetic
                        oligonucleotide
source                 1..15
                       mol_type = other DNA
                       organism = synthetic construct
SEQUENCE: 545
gacggccacg cggga                                                    15
```

```
SEQ ID NO: 546          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 546
agacggccac gcggg                                                   15

SEQ ID NO: 547          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 547
gctagggagg gatggtta                                                18

SEQ ID NO: 548          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 548
tgtaagctag ggagggat                                                18

SEQ ID NO: 549          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 549
acagatgtaa gctaggga                                                18

SEQ ID NO: 550          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 550
aaggaacaga tgtaagct                                                18

SEQ ID NO: 551          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 551
caacaaagga acagatgt                                                18

SEQ ID NO: 552          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 552
gggtgcaaca aaggaaca                                                18

SEQ ID NO: 553          moltype = DNA  length = 18
```

```
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 553
accaagggtg caacaaag                                             18

SEQ ID NO: 554          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 554
gttaaaccaa gggtgcaa                                             18

SEQ ID NO: 555          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 555
ataatgttaa accaaggg                                             18

SEQ ID NO: 556          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 556
ggagaataat gttaaacc                                             18

SEQ ID NO: 557          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 557
ggggaggaga ataatgtt                                             18

SEQ ID NO: 558          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 558
aaattgggga ggagaata                                             18

SEQ ID NO: 559          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 559
agaggaaatt ggggagga                                             18
```

```
SEQ ID NO: 560          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 560
ggagaagagg aaattggg                                                18

SEQ ID NO: 561          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 561
aatgaggaga agaggaaa                                                18

SEQ ID NO: 562          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 562
ttcacaatga ggagaaga                                                18

SEQ ID NO: 563          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 563
acgagttcac aatgagga                                                18

SEQ ID NO: 564          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 564
ctgccacgag ttcacaat                                                18

SEQ ID NO: 565          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 565
agaccctgcc acgagttc                                                18

SEQ ID NO: 566          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 566
caagcagacc ctgccacg                                                18

SEQ ID NO: 567          moltype = DNA  length = 18
```

```
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 567
ctcaccaagc agaccctg                                               18

SEQ ID NO: 568          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 568
gagctcacca agcagacc                                               18

SEQ ID NO: 569          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 569
agaatgagct caccaagc                                               18

SEQ ID NO: 570          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 570
gtaagagaat gagctcac                                               18

SEQ ID NO: 571          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 571
ttgttgtaag agaatgag                                               18

SEQ ID NO: 572          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 572
atttgttgtt gtaagaga                                               18

SEQ ID NO: 573          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 573
cttgaatttg ttgttgta                                               18
```

```
SEQ ID NO: 574          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 574
atgctcttga atttgttg                                                18

SEQ ID NO: 575          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 575
tcttcatgct cttgaatt                                                18

SEQ ID NO: 576          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 576
cttcctcttc atgctctt                                                18

SEQ ID NO: 577          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 577
gcgcgcttcc tcttcatg                                                18

SEQ ID NO: 578          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 578
gctctgcgcg cttcctct                                                18

SEQ ID NO: 579          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 579
ggccagcggc tctgcgcg                                                18

SEQ ID NO: 580          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 580
atattggcca gcggctct                                                18

SEQ ID NO: 581          moltype = DNA  length = 18
```

```
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 581
gtgctatatt ggccagcg                                              18

SEQ ID NO: 582         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 582
agctcgtgct atattggc                                              18

SEQ ID NO: 583         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 583
ggcatagctc gtgctata                                              18

SEQ ID NO: 584         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 584
tgttgggcat agctcgtg                                              18

SEQ ID NO: 585         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 585
gcttctgttg ggcatagc                                              18

SEQ ID NO: 586         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 586
cttgcgcttc tgttgggc                                              18

SEQ ID NO: 587         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 587
caccttgcgc ttctgttg                                              18
```

```
SEQ ID NO: 588          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 588
tccatcacct tgcgcttc                                                   18

SEQ ID NO: 589          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 589
aaccatccat caccttgc                                                   18

SEQ ID NO: 590          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 590
ccttaaacca tccatcac                                                   18

SEQ ID NO: 591          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 591
agccccctta aaccatcc                                                   18

SEQ ID NO: 592          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 592
tcggtagccc ccttaaac                                                   18

SEQ ID NO: 593          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 593
atgtatcggt agccccct                                                   18

SEQ ID NO: 594          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 594
tgtgaatgta tcggtagc                                                   18

SEQ ID NO: 595          moltype = DNA  length = 18
```

```
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 595
attagtgtga atgtatcg                                                     18

SEQ ID NO: 596         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 596
ggctgattag tgtgaatg                                                     18

SEQ ID NO: 597         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 597
gaaatggctg attagtgt                                                     18

SEQ ID NO: 598         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 598
tggcagaaat ggctgatt                                                     18

SEQ ID NO: 599         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 599
gatcttggca gaaatggc                                                     18

SEQ ID NO: 600         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 600
gacatgatct tggcagaa                                                     18

SEQ ID NO: 601         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 601
gaggtgacat gatcttgg                                                     18
```

```
SEQ ID NO: 602          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 602
agattgaggt gacatgat                                                18

SEQ ID NO: 603          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 603
tgaacagatt gaggtgac                                                18

SEQ ID NO: 604          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 604
gtccatgaac agattgag                                                18

SEQ ID NO: 605          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 605
ttggagtcca tgaacaga                                                18

SEQ ID NO: 606          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 606
tgtatttgga gtccatga                                                18

SEQ ID NO: 607          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 607
tttcttgtat ttggagtc                                                18
```